(12) United States Patent
Kwon et al.

(10) Patent No.: US 12,098,399 B2
(45) Date of Patent: Sep. 24, 2024

(54) COMPOSITIONS, SYSTEMS, AND METHODS FOR EPIGENETIC REGULATION OF PROPROTEIN CONVERTASE SUBTILISIN/KEXIN TYPE 9 (PCSK9) GENE EXPRESSION

(71) Applicant: Tune Therapeutics, Inc., Seattle, WA (US)

(72) Inventors: Jennifer Kwon, Durham, NC (US); Kendra Congdon, Durham, NC (US)

(73) Assignee: TUNE THERAPEUTICS, INC., Seattle, WA (US)

( * ) Notice: Subject to any disclaimer, the term of this patent is extended or adjusted under 35 U.S.C. 154(b) by 0 days.

(21) Appl. No.: 18/479,758

(22) Filed: Oct. 2, 2023

(65) Prior Publication Data
US 2024/0052328 A1    Feb. 15, 2024

Related U.S. Application Data

(63) Continuation of application No. PCT/US2023/069031, filed on Jun. 23, 2023.

(60) Provisional application No. 63/355,540, filed on Jun. 24, 2022, provisional application No. 63/399,625, filed on Aug. 19, 2022, provisional application No. 63/401,558, filed on Aug. 26, 2022, provisional application No. 63/453,044, filed on Mar. 17, 2023, provisional application No. 63/466,681, filed on May 15, 2023, provisional application No. 63/472,224, filed on Jun. 9, 2023.

(51) Int. Cl.
  *C12N 9/22*     (2006.01)
  *C12N 15/11*    (2006.01)

(52) U.S. Cl.
  CPC .............. *C12N 9/22* (2013.01); *C12N 15/11* (2013.01); *C12N 2310/20* (2017.05)

(58) Field of Classification Search
  CPC ....... C12N 9/22; C12N 15/11; C12N 2310/20
  See application file for complete search history.

(56) References Cited

U.S. PATENT DOCUMENTS

| | | |
|---|---|---|
| 4,501,729 A | 2/1985 | Boucher et al. |
| 4,554,101 A | 11/1985 | Hopp |
| 4,737,323 A | 4/1988 | Martin et al. |
| 5,134,066 A | 7/1992 | Rogers et al. |
| 5,139,941 A | 8/1992 | Muzyczka et al. |
| 5,219,740 A | 6/1993 | Miller et al. |
| 5,593,972 A | 1/1997 | Weiner et al. |
| 5,658,784 A | 8/1997 | Eckner et al. |
| 5,741,683 A | 4/1998 | Zhou et al. |
| 5,773,700 A | 6/1998 | Van Grinsven et al. |
| 5,962,428 A | 10/1999 | Carrano et al. |
| 6,057,152 A | 5/2000 | Samulski et al. |
| 6,204,059 B1 | 3/2001 | Samulski et al. |
| 6,207,453 B1 | 3/2001 | Maass et al. |
| 6,268,213 B1 | 7/2001 | Samulski et al. |
| 6,462,254 B1 | 10/2002 | Vernachio et al. |
| 6,491,907 B1 | 12/2002 | Rabinowitz et al. |
| 6,596,535 B1 | 7/2003 | Carter |
| 6,660,514 B1 | 12/2003 | Zolotukhin et al. |
| 6,951,753 B2 | 10/2005 | Shenk et al. |
| 7,074,596 B2 | 7/2006 | Darzynkiewicz et al. |
| 7,094,604 B2 | 8/2006 | Snyder et al. |
| 7,125,717 B2 | 10/2006 | Carter |
| 7,172,893 B2 | 2/2007 | Rabinowitz et al. |
| 7,201,898 B2 | 4/2007 | Monahan et al. |
| 7,229,823 B2 | 6/2007 | Samulski et al. |
| 7,282,199 B2 | 10/2007 | Gao et al. |
| 7,439,065 B2 | 10/2008 | Ferrari et al. |
| 7,456,683 B2 | 11/2008 | Takano et al. |
| 7,588,772 B2 | 9/2009 | Kay et al. |
| 7,728,118 B2 | 6/2010 | Wood et al. |
| 7,745,651 B2 | 6/2010 | Heyes et al. |
| 7,790,449 B2 | 9/2010 | Gao et al. |
| 7,799,565 B2 | 9/2010 | Maclachlan et al. |
| 7,906,111 B2 | 3/2011 | Wilson et al. |
| 8,278,036 B2 | 10/2012 | Kariko et al. |
| 8,450,107 B1 | 5/2013 | Zhang et al. |
| 8,586,526 B2 | 11/2013 | Gregory et al. |
| 8,697,359 B1 | 4/2014 | Zhang et al. |
| 8,889,356 B2 | 11/2014 | Zhang et al. |
| 8,993,233 B2 | 3/2015 | Zhang et al. |
| 9,139,554 B2 | 9/2015 | Hope et al. |
| 9,458,205 B2 | 10/2016 | Gregory et al. |
| 9,738,879 B2 | 8/2017 | Gersbach et al. |
| 9,828,582 B2 | 11/2017 | Perez-Pinera et al. |
| 9,834,791 B2 | 12/2017 | Zhang et al. |
| 10,011,850 B2 | 7/2018 | Joung et al. |
| 10,266,850 B2 | 4/2019 | Doudna et al. |
| 10,676,726 B2 | 6/2020 | Gersbach et al. |

(Continued)

FOREIGN PATENT DOCUMENTS

| | | |
|---|---|---|
| EP | 2620161 A1 | 7/2013 |
| EP | 3009511 A2 | 4/2016 |

(Continued)

OTHER PUBLICATIONS

Witkowski et al., Biochemistry 38:11643-11650, 1999.*

(Continued)

*Primary Examiner* — Delia M Ramirez
(74) *Attorney, Agent, or Firm* — MORRISON & FOERSTER LLP

(57) ABSTRACT

Provided in some aspects are epigenetic-modifying DNA-targeting systems, such as CRISPR-Cas/guide RNA (gRNA) systems for the transcriptional repression of genes to promote a cellular phenotype that leads to reduction of low-density lipoprotein (LDL). In some embodiments, the epigenetic-modifying DNA-targeting systems bind to or target a target site of at least one gene or regulatory element thereof that regulate LDL. In some embodiments, the systems are multiplexed systems that bind to or target a target site in at least two genes or regulatory elements thereof. Also provided herein are methods and uses related to the provided epigenetic-modifying DNA targeting systems in connection with treatments for cardiovascular disease and familial hypercholesterolemia.

8 Claims, 26 Drawing Sheets

Specification includes a Sequence Listing.

(56) References Cited

U.S. PATENT DOCUMENTS

| | | | |
|---|---|---|---|
| 10,676,735 B2 | 6/2020 | Gersbach et al. |
| 10,704,060 B2 | 7/2020 | Gersbach et al. |
| 10,711,256 B2 | 7/2020 | Gersbach et al. |
| 10,723,692 B2 | 7/2020 | Ansell et al. |
| 10,745,714 B2 | 8/2020 | Gersbach et al. |
| 10,941,395 B2 | 3/2021 | Yin et al. |
| 11,072,782 B2 | 7/2021 | Cathomen et al. |
| 11,155,796 B2 | 10/2021 | Gersbach et al. |
| 11,421,251 B2 | 8/2022 | Gersbach et al. |
| 11,427,817 B2 | 8/2022 | Josephs et al. |
| 2002/0160940 A1 | 10/2002 | Case et al. |
| 2004/0142025 A1 | 7/2004 | Maclachlan et al. |
| 2004/0175727 A1 | 9/2004 | Draghia-Akli et al. |
| 2004/0192593 A1 | 9/2004 | Draghia-Akli et al. |
| 2004/0204345 A1 | 10/2004 | Case et al. |
| 2006/0068395 A1 | 3/2006 | Wood et al. |
| 2006/0211647 A1 | 9/2006 | Khan |
| 2007/0042031 A1 | 2/2007 | Maclachlan et al. |
| 2007/0042462 A1 | 2/2007 | Hildinger |
| 2007/0059795 A1 | 3/2007 | Moore et al. |
| 2007/0192880 A1 | 8/2007 | Muyan et al. |
| 2008/0070299 A1 | 3/2008 | Wood et al. |
| 2008/0090291 A1 | 4/2008 | Wood et al. |
| 2009/0018031 A1 | 1/2009 | Trinklein et al. |
| 2010/0076057 A1 | 3/2010 | Sontheimer et al. |
| 2011/0236353 A1 | 9/2011 | Wilson et al. |
| 2011/0263682 A1 | 10/2011 | De Kimpe et al. |
| 2011/0286957 A1 | 11/2011 | Prieve et al. |
| 2012/0195917 A1 | 8/2012 | Sahin et al. |
| 2012/0207744 A1 | 8/2012 | Mendlein et al. |
| 2013/0323001 A1 | 12/2013 | Ueki et al. |
| 2014/0068797 A1 | 3/2014 | Doudna et al. |
| 2014/0179006 A1 | 6/2014 | Zhang |
| 2014/0186958 A1 | 7/2014 | Zhang et al. |
| 2014/0295557 A1 | 10/2014 | Joung et al. |
| 2014/0309177 A1 | 10/2014 | Perez-Pinera et al. |
| 2014/0315862 A1 | 10/2014 | Kaye |
| 2014/0356956 A1 | 12/2014 | Church et al. |
| 2014/0377868 A1 | 12/2014 | Joung et al. |
| 2015/0024499 A1 | 1/2015 | Brouns et al. |
| 2015/0031089 A1 | 1/2015 | Lindstrom |
| 2015/0044772 A1 | 2/2015 | Zhao |
| 2015/0045413 A1 | 2/2015 | De Visser et al. |
| 2015/0056705 A1 | 2/2015 | Conway et al. |
| 2015/0079064 A1 | 3/2015 | Gersbach et al. |
| 2015/0159178 A1 | 6/2015 | Green et al. |
| 2015/0166980 A1 | 6/2015 | Liu et al. |
| 2016/0002634 A1 | 1/2016 | Sazani et al. |
| 2016/0040189 A1 | 2/2016 | Kennedy et al. |
| 2016/0058889 A1 | 3/2016 | Olson et al. |
| 2016/0177278 A1 | 6/2016 | Wolfe et al. |
| 2016/0201089 A1 | 7/2016 | Gersbach et al. |
| 2016/0281166 A1 | 9/2016 | Bhattacharjee et al. |
| 2017/0198308 A1 | 7/2017 | Qi et al. |
| 2017/0283831 A1 | 10/2017 | Zhang et al. |
| 2017/0327806 A1 | 11/2017 | Joung et al. |
| 2018/0023064 A1 | 1/2018 | Gersbach et al. |
| 2018/0073012 A1 | 3/2018 | Liu et al. |
| 2018/0094238 A1 | 4/2018 | Perez-Pinera et al. |
| 2018/0135109 A1 | 5/2018 | Jayaram et al. |
| 2018/0251735 A1 | 9/2018 | Ko |
| 2018/0291370 A1 | 10/2018 | Gersbach et al. |
| 2018/0305719 A1 | 10/2018 | Perez-Pinera et al. |
| 2018/0320197 A1 | 11/2018 | Gersbach et al. |
| 2018/0334688 A1 | 11/2018 | Gersbach et al. |
| 2018/0353615 A1 | 12/2018 | Gersbach et al. |
| 2019/0032049 A1 | 1/2019 | Naldini et al. |
| 2019/0038776 A1 | 2/2019 | Pyle et al. |
| 2019/0048337 A1 | 2/2019 | Hsu et al. |
| 2019/0062790 A1 | 2/2019 | Doudna et al. |
| 2019/0127713 A1 | 5/2019 | Gersbach et al. |
| 2019/0136229 A1 | 5/2019 | Josephs et al. |
| 2019/0151476 A1 | 5/2019 | Gersbach et al. |
| 2019/0183932 A1 | 6/2019 | Mackall et al. |
| 2019/0194633 A1 | 6/2019 | Gersbach et al. |
| 2019/0248854 A1 | 8/2019 | Tremblay et al. |
| 2019/0264232 A1 | 8/2019 | Hou et al. |
| 2019/0359959 A1 | 11/2019 | Jaenisch et al. |
| 2019/0374655 A1 | 12/2019 | Kabadi et al. |
| 2019/0382798 A1* | 12/2019 | Cowan ............... C12N 9/16 |
| 2020/0002731 A1 | 1/2020 | Frendewey et al. |
| 2020/0080108 A1 | 3/2020 | Jaskula-Ranga et al. |
| 2020/0216810 A1 | 7/2020 | Metelitsa et al. |
| 2020/0260698 A1 | 8/2020 | Kyrychenko et al. |
| 2020/0318139 A1 | 10/2020 | Gersbach et al. |
| 2020/0347105 A1 | 11/2020 | Gersbach et al. |
| 2020/0385695 A1 | 12/2020 | Gersbach et al. |
| 2021/0002665 A1 | 1/2021 | Gersbach et al. |
| 2021/0032654 A1 | 2/2021 | Gersbach et al. |
| 2021/0040460 A1 | 2/2021 | Gersbach et al. |
| 2021/0322577 A1 | 10/2021 | Lande et al. |
| 2022/0098561 A1 | 3/2022 | Gersbach et al. |
| 2022/0177879 A1 | 6/2022 | Gersbach et al. |
| 2022/0184229 A1 | 6/2022 | Gersbach et al. |
| 2022/0195406 A1 | 6/2022 | Gersbach et al. |
| 2022/0305141 A1 | 9/2022 | Gersbach et al. |
| 2022/0307015 A1 | 9/2022 | Gersbach et al. |
| 2022/0364124 A1 | 11/2022 | Gersbach et al. |
| 2022/0396790 A1 | 12/2022 | Gersbach et al. |
| 2023/0032846 A1 | 2/2023 | Gersbach et al. |
| 2023/0047669 A1 | 2/2023 | Josephs et al. |
| 2023/0159927 A1 | 5/2023 | Gersbach et al. |
| 2023/0257723 A1 | 8/2023 | Gersbach et al. |
| 2023/0304000 A1 | 9/2023 | Josephs et al. |

FOREIGN PATENT DOCUMENTS

| | | |
|---|---|---|
| EP | 3209783 A1 | 8/2017 |
| EP | 3995584 A1 | 5/2022 |
| JP | 2015534817 A | 12/2015 |
| JP | 2016521452 A | 7/2016 |
| JP | 2016521975 A | 7/2016 |
| JP | 2016523082 A | 8/2016 |
| KR | 20190134673 A | 12/2019 |
| WO | WO 199118114 A1 | 11/1991 |
| WO | WO 1993024640 A2 | 12/1993 |
| WO | WO 1994016737 A1 | 8/1994 |
| WO | WO 1998053058 A1 | 11/1998 |
| WO | WO 1998053059 A1 | 11/1998 |
| WO | WO 1998053060 A1 | 11/1998 |
| WO | WO 2001083793 A2 | 11/2001 |
| WO | WO 2002016536 A1 | 2/2002 |
| WO | WO 2003016496 A2 | 2/2003 |
| WO | WO 2003042397 A2 | 5/2003 |
| WO | WO 2003072788 A1 | 9/2003 |
| WO | WO 2014144592 A2 | 9/2004 |
| WO | WO 2005033321 A2 | 4/2005 |
| WO | WO 2006110689 A2 | 10/2006 |
| WO | WO 2007019301 A2 | 2/2007 |
| WO | WO 2008070859 A2 | 6/2008 |
| WO | WO 2010053572 A2 | 5/2010 |
| WO | WO 2010075424 A2 | 7/2010 |
| WO | WO 2010144740 A1 | 12/2010 |
| WO | WO 2011126808 A2 | 10/2011 |
| WO | WO 2011141820 A1 | 11/2011 |
| WO | WO 2012170930 A1 | 12/2012 |
| WO | WO 2013049493 A1 | 4/2013 |
| WO | WO 2013098244 A1 | 7/2013 |
| WO | WO 2013143555 A1 | 10/2013 |
| WO | WO 2013176772 A1 | 11/2013 |
| WO | WO 2013182683 A1 | 12/2013 |
| WO | WO 2014018423 A2 | 1/2014 |
| WO | WO 2014059255 A1 | 4/2014 |
| WO | WO 2014065596 A1 | 5/2014 |
| WO | WO 2014081855 A1 | 5/2014 |
| WO | WO 2014089290 A1 | 6/2014 |
| WO | WO 2014093479 A1 | 6/2014 |
| WO | WO 2014093595 A1 | 6/2014 |
| WO | WO 2014093622 A2 | 6/2014 |
| WO | WO 2014093655 A2 | 6/2014 |
| WO | WO 2014093661 A2 | 6/2014 |
| WO | WO 2014093709 A1 | 6/2014 |
| WO | WO 2014093712 A1 | 6/2014 |
| WO | WO 2014152432 A2 | 9/2014 |

(56) References Cited

FOREIGN PATENT DOCUMENTS

| | | |
|---|---|---|
| WO | WO 2014172470 A2 | 10/2014 |
| WO | WO 2014191128 A1 | 12/2014 |
| WO | WO 2014197748 A2 | 12/2014 |
| WO | WO 2014204726 A1 | 12/2014 |
| WO | WO 2014204728 A1 | 12/2014 |
| WO | WO 2015006747 A2 | 1/2015 |
| WO | WO 2015017519 A1 | 2/2015 |
| WO | WO 2015035136 A2 | 3/2015 |
| WO | WO 2015048690 A1 | 4/2015 |
| WO | WO 2015070083 A1 | 5/2015 |
| WO | WO 2015089419 A2 | 6/2015 |
| WO | WO 2015089427 A1 | 6/2015 |
| WO | WO 2015089465 A1 | 6/2015 |
| WO | WO 2015089486 A2 | 6/2015 |
| WO | WO 2015126927 A2 | 8/2015 |
| WO | WO 2015155686 A2 | 10/2015 |
| WO | WO 2015161276 A2 | 10/2015 |
| WO | WO 2016011070 A2 | 1/2016 |
| WO | WO 2016011080 A2 | 1/2016 |
| WO | WO 2016049258 A2 | 3/2016 |
| WO | WO 2016063264 A1 | 4/2016 |
| WO | WO 2016070070 A1 | 5/2016 |
| WO | WO 2016081924 A1 | 5/2016 |
| WO | WO 2016094880 A1 | 6/2016 |
| WO | WO 2016114972 A1 | 7/2016 |
| WO | WO 2016123578 A1 | 8/2016 |
| WO | WO 2016130600 A2 | 8/2016 |
| WO | WO 2016161380 A1 | 10/2016 |
| WO | WO 2016187717 A1 | 12/2016 |
| WO | WO 2017015637 A1 | 1/2017 |
| WO | WO 2017035416 A2 | 3/2017 |
| WO | WO 2017049266 A2 | 3/2017 |
| WO | WO 2017070632 A2 | 4/2017 |
| WO | WO 2017072590 A1 | 5/2017 |
| WO | WO 2017075478 A2 | 5/2017 |
| WO | WO 2017077386 A1 | 5/2017 |
| WO | WO 2017093969 A1 | 6/2017 |
| WO | WO 2017139505 A2 | 8/2017 |
| WO | WO 2017141109 A1 | 8/2017 |
| WO | WO 2017165859 A1 | 9/2017 |
| WO | WO 2017180915 A2 | 10/2017 |
| WO | WO 2017180976 A1 | 10/2017 |
| WO | WO 2017189308 A1 | 11/2017 |
| WO | WO 2017193107 A2 | 11/2017 |
| WO | WO 2017197238 A1 | 11/2017 |
| WO | WO 2018031762 A1 | 2/2018 |
| WO | WO 2018035495 A1 | 2/2018 |
| WO | WO 2018081504 A1 | 5/2018 |
| WO | WO 2018098480 A1 | 5/2018 |
| WO | WO 2018154380 A1 | 8/2018 |
| WO | WO 2018179578 A1 | 10/2018 |
| WO | WO 2019067786 A1 | 4/2019 |
| WO | WO 2019077001 A1 | 4/2019 |
| WO | WO 2019079514 A1 | 4/2019 |
| WO | WO 2019092505 A1 | 5/2019 |
| WO | WO 2019113472 A1 | 6/2019 |
| WO | WO 2019204750 A1 | 10/2019 |
| WO | WO 2019204766 A1 | 10/2019 |
| WO | WO 2020124257 A1 | 6/2020 |
| WO | WO 2020163396 A1 | 8/2020 |
| WO | WO 2020257665 A1 | 12/2020 |
| WO | WO 2021034984 A2 | 2/2021 |
| WO | WO 2021034987 A1 | 2/2021 |
| WO | WO 2021076744 A1 | 4/2021 |
| WO | WO 2021142342 A1 | 7/2021 |
| WO | WO 2021226077 A2 | 11/2021 |
| WO | WO 2021226555 A2 | 11/2021 |
| WO | WO 2021247570 A2 | 12/2021 |
| WO | WO 2021247924 A1 | 12/2021 |
| WO | WO 2022038264 A1 | 2/2022 |
| WO | WO 2022051250 A1 | 3/2022 |
| WO | WO 2022087321 A1 | 4/2022 |
| WO | WO 2022104159 A1 | 5/2022 |
| WO | WO 2022133062 A1 | 6/2022 |
| WO | WO 2022140577 A2 | 6/2022 |
| WO | WO 2022187288 A2 | 9/2022 |
| WO | WO 2022220503 A1 | 10/2022 |
| WO | WO 2023049742 A2 | 3/2023 |
| WO | WO 2023093862 A1 | 6/2023 |
| WO | WO 2023164670 A2 | 8/2023 |
| WO | WO 2023164671 A2 | 8/2023 |
| WO | WO 2023173110 A1 | 9/2023 |
| WO | WO 2023215711 A1 | 11/2023 |
| WO | WO-2023/240076 | 12/2023 |

OTHER PUBLICATIONS

Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
Chen et al., Cell 155:1479-1491, 2013.*
Acosta et al., "Use of two gRNAs for CRISPR/Cas9 improves bi-allelic homologous recombination efficiency in mouse embryonic stem cells," Genesis, 2018, 56(5):e23212 (pp. 1-15).
Adamson et al., "A Multiplexed Single-Cell CRISPR Screening Platform Enables Systematic Dissection of the Unfolded Protein Response," Cell, 2016, 167:1867-1882.e21, 38 pages.
Adler et al., (2012). "Nonviral direct conversion of primary mouse embryonic fibroblasts to neuronal cells," Molecular Therapy Nucleic Acids 1, e32, 10 pages.
Adli, (2018). "The CRISPR tool kit for genome editing and beyond," Nat. Commun, 9:1911, 13 pages.
Ahlenius et al., "FoxO3 regulates neuronal reprogramming of cells from postnatal and aging mice," Proc Natl Acad Sci USA, 2016, 113:8514-8519.
Albuquerque et al., "Mammalian nicotinic acetylcholine receptors: from structure to function," Physiol Rev. 2009, 89:73-120.
Aloia, "Epigenetic Regulation of Cell-Fate Changes That Determine Adult Liver Regeneration After Injury," Front. Cell Dev. Biol., 2021, 9:643055, 8 pages.
Alonso-Camino et al., (2013). "CARbodies: Human Antibodies Against Cell Surface Tumor Antigens Selected From Repertoires Displayed on T Cell Chimeric Antigen Receptors," Mol Ther Nucl Acids, 2:e93, 11 pages.
Amabile et al., "Inheritable Silencing of Endogenous Genes by Hit-and-Run Targeted Epigenetic Editing," Cell, 2016, 167(1):219-232.e14, 29 pages.
Amabile et al., "Permanent Epigenetic Silencing of Human Genes With Artificial Transcriptional Repressors,", Molecular Therapy, 2015, 23(Suppl. 1): S275.
Anders et al., "Differential expression analysis for sequence count data," Genome Biology, 2010, 11:RI06, 12 pages.
Anders et al., "Structural basis of PAM-dependent target DNA recognition by the Cas9 endonuclease," Nature (2014) 513:569-73, 16 pages.
Arechavala-Gomeza et al., "Comparative analysis of antisense oligonucleotide sequences for targeted skipping of exon 51 during dystrophin pre-mRNA splicing in human muscle," Human Gene Therapy, 2007, 18:798-810.
Arnold et al., "Genome-wide quantitative enhancer activity maps identified by STARR-seq," Science, 2013. 339(6123):1074-7.
Asokan et al., "Reengineering a receptor footprint of adeno-associated virus enables selective and systemic gene transfer to muscle," Nat Biotechnol, 2010, 28(1):79-82, 8 pages.
Asokan et al., "The AAV Vector Toolkit: Poised at the Clinical Crossroads," Mol Ther 20(4): 699-708. (2012).
Asrani et al., "Burden of liver diseases in the world," J Hepatol, 2019, 70(1):151-171.
Ayyanathan et al. "Regulated recruitment of HPl to a euchromatic gene induces mitotically heritable, epigenetic gene silencing: a mammalian cell culture model of gene variegation," Genes Dev, 17:1855-1869 (2003).
Azuma et al., (2007). "Robust expansion of human hepatocytes in Fah-/-/Rag2-/-/Il2rg-/-mice" Nat Biotechnol., 25(8):903-910, 18 pages.

(56) References Cited

OTHER PUBLICATIONS

Bae et al., "Cas-OFFinder: a fast and versatile algorithm that searches for potential off-target sites of Cas9 RNA-guided endonucleases," Bioinformatics, 2014, 30:1473-1475.
Baratta et al., "Cellular organization of normal mouse liver: a histological, quantitative immunocytochemical, and fine structural analysis," Histochem Cell Biol, 2009, 131(6):713-726.
Barrangou et al., "CRISPR provides acquired resistance against viruses in prokaryotes," Science, 2007, 315(5819):1709-1712.
Bartsevich et al., "Engineered zinc finger proteins for controlling stem cell fate," Stem Cells 2003, 21:632-637.
Bauer et al., "An erythroid enhancer of BCL 11A subject to genetic variation determines fetal hemoglobin level," Science, 2013, 342:253-257, 10 pages.
Beerli et al., "Engineering polydactyl zinc-finger transcription factors," Nat Biotechnol, 2002, 20:135-141.
Beerli et al., "Positive and negative regulation of endogenous genes by designed transcription factors," Proc Natl Acad Sci USA, 2000, 97:1495-1500.
Beerli et al., "Toward controlling gene expression at will: specific regulation of the erbB-2/HER-2 promoter by using polydactyl zinc finger proteins constructed from modular building blocks," Proc Natl Acad Sci USA, 1998 95:14628-14633.
Beltran et al., "Re-activation of a dormant tumor suppressor gene maspin by designed transcription factors," Oncogene 26, 2007, 2791-2798.
Bender et al. "Independent formation of DnaseI hypersensitive sites in the murine beta-globin locus control region," Blood 95, 3600-3604 (2000).
The ENCODE Project Consortium., "An integrated encyclopedia of DNA elements in the human genome," Nature, 2012, 489: 57-74.
Bernstein et al. The NIH Roadmap Epigenomics Mapping Consortium. Nat Biotechnol 28, 1045-1048 (2010).
Beverley, "Primer: making sense of T-cell memory," Nat. Clin Pract. Rheumatol. 2008, 4, 43-49. Abstract only, 1 page.
Bhakta et al., (2010). "The generation of zinc finger proteins by modular assembly," Methods Mol. Biol., 649:3-30, 25 pages.
Bladen et al., "The Treat-NMD DMD Global Database: analysis of more than 7,000 Duchenne muscular dystrophy mutations," Human Mutation, 2015, 36(4):395-402.
Blakemore et al., "Editing of Human Genes May Begin by Year's End in the U.S." Smithsonian.com, <https://www.smithsonianmag.com/smart-news/editing-human-genes-maybegin-years-end-us-180959532/?no-ist> 2016, 4 pages.
Blancafort et al., "Writing and rewriting the epigenetic code of cancer cells: from engineered proteins to small molecules," Mol. Pharmacol., 2013, 83(3): 563-576.
Blancafort et al., "Scanning the human genome with combinatorial transcription factor libraries," Nat Biotechnol 21, 2003, 269-274.
Bloomfield, (1981). "Quasi-Elastic Light Scattering Applications in Biochemistry and Biology," Ann. Rev. Biophys. Bioeng., 10:421-450.
Boris-Lawrie et al., (1993). "Recent advances in retrovirus vector technology," Cur. Opin. Genet. Develop., 3:102-109.
Boshart et al., "A very strong enhancer is located upstream of an immediate early gene of human cytome galovirus," Cell, 1985, 41:521-530.
Bouhairie et al., (2015). "Familial hypercholesterolemia," Cardiol. Clin., 33(2):169-179, 23 pages.
Boyle et al., "High-resolution mapping and characterization of open chromatin across the genome," Cell, 2008. 132(2): p. 311-22.
Brash et al., (1987). "Strontium phosphate transfection of human cells in primary culture: stable expression of the simian virus 40 large-T-antigen gene in primary human bronchial epithelial cells," Mol. Cell Biol., 7(5):2031-2034.
Briguet et al., "Histological parameters for the quantitative assessment of muscular dystrophy in the mdx-mouse," Neuromuscul. Disord., 2004, 14: 675-682.
Briner et al., "Guide RNA Functional Modules Direct Cas9 Activity and Orthogonality," Molecular Cell, 2014, 56(2): 333-339.
Briner et al., "Lactobacillus buchneri genotyping on the basis of clustered regularly interspaced short palindromic repeat (CRISPR) locus diversity," Appl. Environ. Microbial., 2014, 80(3): 994-1001.
Brunger et al., "CRISPR/Cas9 Editing of Murine Induced Pluripotent Stem Cells for Engineering Inflammation-Resistant Tissues," Arthritis Rheumatol, 2017, 69(5): 1111-1121.
Brunger et al., "Genome Engineering of Stem Cells for Autonomously Regulated, Closed-Loop Delivery of Biologic Drugs," Stem Cell Reports, 2017, 8: 1202-1213.
Bultmann et al., "Targeted transcriptional activation of silent oct4 pluripotency gene by combining designer TALEs and inhibition of epigenetic modifiers," Nucleic Acids Res 40(12), 2012, 5368-5377.
Burns et al., (1993). "Vesicular stomatitis virus G glycoprotein pseudotyped retroviral vectors: concentration to very high titer and efficient gene transfer into mammalian and nonmammalian cells," Proc. Natl. Acad. Sci. USA, 90:8033-8037.
Busskamp et al., "Rapid neurogenesis through transcriptional activation in human stem cells," Mol Syst Biol, 2014, 10: 760, 21 pages.
Carlens et al. (2000). "Ex vivo T lymphocyte expansion for retroviral transduction: influence of serum-free media on variations in cell expansion rates and lymphocyte subset distribution," Exp Hematol, 28(10):1137-46.
Carrillo et al., "The Multiple Sequence Alignment Problem in Biology" SIAM J. Applied Math, 1988, 48(5):1073-1082.
Carroll, "A CRISPR approach to gene targeting," Molecular Therapy, 2012, 20(9):1658-1660.
Carter et al., "Long-range chromatin regulatory interactions in vivo," Nat Genet 32, 623-626 (2002).
Cavalieri et al., (2003). "Human T lymphocytes transduced by lentiviral vectors in the absence of TCR activation maintain an intact immune competence," Blood, 102(2):497-505.
Cencic et al., "Protospacer adjacent motif (PAM)-distal sequences engage CRISPR Cas9 DNA target cleavage," PLoS One, 2014, 9, el09213, 13 pages.
Chakraborty et al. "553. AAV-Mediated Delivery of HSV-Specific Homing Endonucleases to Neurons of the Trigeminal Ganglia for HSV-1 Inhibition." Molecular Therapy 22 (2014), S215.
Chakraborty et al. "A CRISPR/Cas9-Based System for Reprogramming Cell Lineage Specification," Stem Cell Reports 3, 940-947 (2014).
Chamberlain et al., "Progress toward Gene Therapy for Duchenne Muscular Dystrophy," Mol. Ther., 2017, 25: 1125-1131.
Chanda et al., "Generation of induced neuronal cells by the single reprogramming factor ASCL 1," Stem Cell Reports, 2014, 3: 282-296.
Chavez et al., "Comparison of Cas9 activators in multiple species," Nat Methods, 2016, 13(7): 563-67, 16 pages.
Chavez et al. "Highly efficient Cas9-mediated transcriptional programming," Nat Methods 12, 326-328 (2015), 11 pages.
Cheloufi et al., "The histone chaperone CAF-1 safeguards somatic cell identity," Nature, 2015, 528: 218-224, 42 pages.
Chen et al., "Expanding the CRISPR imaging toolset with *Staphylococcus aureus* Cas9 for simultaneous imaging of multiple genomic loci," Nucleic Acids Research, 2016, 44(8):e75, 13 pages.
Chen et al., "Genome-wide CRISPR screen in a mouse model of tumor growth and metastasis," Cell, 2015, 160: 1-15, 16 pages.
Chen et al., "Targeted activation of diverse CRISPR-Cas systems for mammalian genome editing via proximal CRISPR targeting," Nature Communications, 2017, 8: 14958, 12 pages.
Chen et al., "Vitamin D receptor suppresses proliferation and metastasis in renal cell carcinoma cell lines via regulating the expression of the epithelial Ca2+ channel TRPV5," PLoS One, 2018, 13: e0195844, 14 pages.
Chen et al., (2013). "Fusion protein linkers: property, design and functionality," Adv. Drug Deliv. Rev., 65(10):1357-1369.
Chen et al., "Life and death of transcriptional co-activator p300," Epigenetics 6:8,957-961 (2011).
Chen et al., "Two upstream enhancers collaborate to regulate the spatial patterning and timing of MyoD transcription during mouse development," Dev Dyn, 221, 274-288 (2001).
Cheng et al. "Multiplexed activation of endogenous genes by CRISPR-on, an RNA-guided transcriptional activator system," Cell Res 23, 1163-1171 (2013).

(56) References Cited

OTHER PUBLICATIONS

Chew et al., "A multi-functional AAV-CRISPR-Cas9 and its host response," Nat Methods, 2016; 13:868-74, 24 pages.
Chhatwal et al., "Identification of cell-type-specific promoters within the brain using lentiviral vectors," Gene Therapy, 2007, 14(7): 575-583, 16 pages.
Chicaybam et al., (2013). "An efficient low cost method for gene transfer to T lymphocytes," PLoS One, 8(3):e60298, 11 pages.
Childers et al., "Gene therapy prolongs survival and restores function in murine and canine models of myotubular myopathy," Sci Transl Med, 2014, 6: 220ra210, 31 pages.
Cho, S.W. et al., "Targeted genome engineering in human cells with the Cas9 RNA-guided endonuclease," Nat Biotechnol 31, 2013, 230-232.
Choy et al., "Eukaryotic activators function during multiple steps of preinitiation complex assembly," Nature 366, 531-536 (1993).
Chronis et al., "Cooperative Binding of Transcription Factors Orchestrates Reprogramming," Cell, 2017, 168: 442-459 e420, 39 pages.
Chu et al., "SV40 DNA transfection of cells in suspension: analysis of efficiency of transcription and translation of T-antigen," Gene, 1981, 13:197-202.
Chylinski et al., (2013). "The tracrRNA and Cas9 families of type II CRISPR-Cas immunity systems," RNA Biol., 10(5):726-737.
Cong et al., "Multiplex Genome Engineering Using CRISPR/Cas Systems," Science 339, 2013, 819-823, 9 pages.
Cong et al., "Comprehensive interrogation of natural TALE DNA-binding modules and transcriptional repressor domains," Nat Commun 3, 968, 6 pages (2012).
Cooper et al., "Improved induction of immune tolerance to factor IX by hepatic AAV-8 gene transfer," Hum Gene Ther, 2009, 20: 767-776.
Cooper et al., (2003). "T-cell clones can be rendered specific for CD19: toward the selective augmentation of the graft-versus-B-lineage leukemia effect," Blood, 101(4):1637-1644.
Corces et al., "The chromatin accessibility landscape of primary human cancers," Science, 2018, 362(6413): eaav1898, 31 pages.
Cordier et al., "Muscle-specific promoters may be necessary for adeno-associated virus-mediated gene transfer in the treatment of muscular dystrophies," Hum. Gene Ther., 2001, 12:205-215.
Cornu et al., "Quantification of zinc finger nuclease-associated toxicity," Meth Mol Biol, 2010, 649:237-245.
Crawford et al., "Genome-wide mapping of DNase hypersensitive sites using massively parallel signature sequencing (MPSS)," Genome Res. 2006, 16, 123-131.
Crocker et al., "TALE-mediated modulation of transcriptional enhancers in vivo," Nature Methods 10, 762-767 (2013), 15 pages.
D'Alessio et al., "A Systematic Approach to Identify Candidate Transcription Factors that Control Cell Identity," Stem Cell Reports, 2015, 5: 763-775.
Daley et al., "CRISPhieRmix: a hierarchical mixture model for CRISPR pooled screens," Genome Biol, 2018, 19: 159, 13 pages.
Darmanis et al., "A survey of human brain transcriptome diversity at the single cell level," Proc Natl Acad Sci U SA, 2015, 112: 7285-7290.
Datlinger et al., "Pooled CRISPR screening with single-cell transcriptome readout," Nat. Methods, 2017, 14: 297-301, 20 pages.
De Groote et al., "Epigenetic Editing: targeted rewriting of epigenetic marks to modulate expression of selected target genes," Nucleic Acids Res, 2012, vol. 40, No. 21, pp. 10596-10613.
Dean et al., "Inducible transcription of five globin genes in K562 human leukemia cells," Proceedings of the National Academy of Sciences of the United States of America 80, 1983, 5515-5519.
Deconinck et al., "Utrophin-Dystrophin-Deficient Mice as a Model for Duchenne Muscular Dystrophy," Cell, 1997, 90(4): 717-727.
Defesche et al., (2017). "Familial hypercholesterolaemia," Nat. Rev. Dis. Primers, 3:17093, 20 pages.
Deltcheva et al., "CRISPR RNA maturation by trans-encoded small RNA and host factor RNase III," Nature, 2011, 471(7340):602-7, 19 pages.

Delvecchio et al., "Structure of the p300 catalytic core and implications for chromatin targeting and HAT regulation," Nat Struct Mol Biol 20, 2013, 1040-1046.
Dempster et al., "Extracting Biological Insights from the Project Achilles Genome-Scale CRISPR Screens in Cancer Cell Lines," Cold Spring Harbor Laboratory, 2019, 35 pages.
Deng et al., "Reactivation of developmentally silenced globin genes by forced chromatin looping," Cell 158, 2014, 849-860.
Deng et al., (2014). "Highly sensitive electrochemical methyltransferase activity assay," Anal Chem., 86:2117-2123.
Dijkema et al., "Cloning and expression of the chromosomal immune interferon gene of the rat," EMBO J., 1985, 4:761-767.
Ding et al., "Permanent Alteration of PCSK9 With in Vivo CRISPR-Cas9 Genome Editing," Circulation Research, 2014, vol. 115, No. 5, pp. 488-492.
Dirks et al., "Triggered amplification by hybridization chain reaction," Proceedings of the National Academy of Sciences of the United States of America, 2004, 101(43): 15275-15278.
Dixit et al., "Perturb-Seq: Dissecting Molecular Circuits with Scalable Single-Cell RNA Profiling of Pooled Genetic Screens," Cell, 2016, 167: 1853-1866.e17, 32 pages.
Doench et al., "Optimized sgRNA design to maximize activity and minimize off-target effects of CRISPR-Cas9," Nat Biotechnol. (2016) 34:184-91, 35 pages.
Doench et al., "Rational design of highly active sgRNAs for CRISPR-Cas9-mediated gene inactivation," Nat Biotechnol. (2014) 32:1262-7, 17 pages.
Dostie et al. "Chromosome Conformation Capture Carbon Copy (5C): a massively parallel solution for mapping interactions between genomic elements," Genome research 16, 1299-1309 (2006).
Doudna et al., "Genome editing. The new frontier of genome engineering with CRISPR-Cas9," Science 346, 1258096 (2014), 11 pages.
Du et al., "Genetic interaction mapping in mammalian cells using CRISPR interference," Nat Methods, 2017, 14: 577-580, 14 pages.
Duan et al., "Expanding AAV packaging capacity with trans-splicing or overlapping vectors: a quantitative comparison," Molecular Therapy, 2001, 4: 383-391.
Duan et al., "Genome-wide identification of CRISPR/Cas9 off-targets in human genome," Cell research, 2014, 24(8): 1009-12.
Duan, "Systemic AAV Micro-dystrophin Gene Therapy for Duchenne Muscular Dystrophy," Molecular Therapy, 2018, 26(10): 2337-2356.
EBI Accession No. GSP: BCJ39961 (2016), 3 pages.
Egger et al., Epigenetics in human disease and prospects for epigenetic therapy. Nature 429, 457-463 (2004).
Eguchi et al., "Reprogramming cell fate with a genome-scale library of artificial transcription factors," Proc Natl Acad Sci U S A, 2016, 113: E8257-E8266.
ENCODE Project Consortium, "Expanded encyclopedias of DNA elements in the human and mouse genomes," Nature, 2020, 583: 699-710, 27 pages.
Eraslan et al., "Deep learning: new computational modelling techniques for genomics," Nat. Rev. Genet., 2019, 20: 389-403, 15 pages.
Ernsberger, "Role of neurotrophin signalling in the differentiation of neurons from dorsal root ganglia and sympathetic ganglia," Cell Tissue Res, 2009, 336: 349-384.
Ernst et al., "ChromHMM: automating chromatin-state discovery and characterization," Nat. Methods, 2012, 9: 215-216, 3 pages.
Erwin et al., "Synthetic transcription elongation factors license transcription across repressive chromatin," Science, 2017, 358: 1617-1622, 14 pages.
Esvelt et al., "Orthogonal Cas9 proteins for RNA-guided gene regulation and editing," Nat Methods 10, 1116-1121 (2013), 19 pages.
European Patent Office Action for Application No. 17783164.1 dated Mar. 7, 2022 (5 pages).
European Patent Office Extended Search Report for Application No. 17783164.1 dated Oct. 2, 2019 (8 pages).
Fagerlund et al., "The Cpf1 CRISPR-Cas protein expands genome-editing tools," Genome Biology, 2015, 16:251, 3 pages.

(56) References Cited

OTHER PUBLICATIONS

Farasat et al., "A Biophysical Model of CRISPR/Cas9 Activity for Rational Design of Genome Editing and Gene Regulation," PLOS Computational Biology, 2016, 12(1):e1004724, 33 pages.
Farasat, "Sequence-to-Function Models for Efficient Optimization of Metabolic Pathways and Genetic Circuits," Ph.D. Thesis, 2015, 254 pages.
Farzadfard et al., "Tunable and multifunctional eukaryotic transcription factors based on CRISPR/Cas," ACS Synth Biol 2, 604-613 (2013).
FDA approval brings first gene therapy to the United States, <https://www.fda.gov/newsevents/newsroom/pressannouncements/ucm574058.htm> (Aug. 30, 2017), 4 pages.
FDA approves first drug for spinal muscular atrophy, <https://www.fda.gov/newsevents/newsroom/pressannouncements/ucm534611.htm> (Dec. 23, 2016), 3 pages.
FDA approves first-of-its kind targeted RNA-based therapy to treat a rare disease, <https://www.fda.gov/newsevents/newsroom/pressannouncements/ucm616518.htm> (Aug. 10, 2018), 4 pages.
FDA approves novel gene therapy to treat patients with a rare form of inherited vision loss, <https://www.fda.gov/newsevents/newsroom/pressannouncements/ucm589467.htm> (Dec. 18, 2017), 4 pages.
FDA grants accelerated approval to first drug for Duchenne muscular dystrophy, <https://www.fda.gov/newsevents/newsroom/pressannouncements/ucm521263.htm> (Sep. 19, 2016), 3 pages.
Ferretti et al., "Complete genome sequence of an MI strain of *Streptococcus pyogenes*," Proc Natl Acad Sci USA. (2001); 98(8): 4658-63.
Fine et al., "Trans-spliced Cas9 allows cleavage of HBB and CCR5 genes in human cells using compact expression cassettes," Sci Rep. 2015; 5:10777, 9 pages.
Flamm et al., "RNA folding at elementary step resolution," RNA, 2000, 6: 325-338.
Flandin et al., "Lhx6 and Lhx8 coordinately induce neuronal expression of Shh that controls the generation of interneuron progenitors," Neuron, 2011, 70: 939-950.
Fontenot et al., "Regulatory T cell lineage specification by the forkhead transcription factor foxp3," Immunity, 2005, 22, 329-341.
Forget, "Molecular basis of hereditary persistence of fetal hemoglobin," Ann NY Acad Sci, 1998, 850, 38-44.
Frank et al., "HDAC inhibitors cause site-specific chromatin remodeling at PU.1-bound enhancers in K562 cells," Epigenetics Chromatin, 2016, 9: 15, 17 pages.
Friedland et al., "Characterization of *Staphylococcus aureus* Cas9: a smaller Cas9 for all-in-one adeno-associated virus delivery and paired nickase applications," Genome Biology, 2015, 16(16):257, 10 pages.
Friedland et al., "*Staphyloccocus aureus* Cas9: An Alternative Cas9 for Genome Editing Applications," Molecular Therapy, 2015, 23(Suppl. 1):S224, 1 page.
Fu et al., "Landscape of target: guide homology effects on Cas9-mediated cleavage," Nucleic Acids Research, 2014, 42(22): 13778-13787.
Fulco et al., "Activity-by-contact model of enhancer-promoter regulation from thousands of CRISPR perturbations," Nature Genetics, 2019, 51: 1664-1669, 25 pages.
Gaj et al., "Structure-Guided Reprogramming of Serine Recombinase DNA Sequence Specificity," Proc Natl Acad Sci USA, 2011, 108(2): 498-503.
Gaj et al., "ZFN, TALEN, and CRISPR/Cas-based methods for genome engineering," Trends Biotechnol 31, 397-405 (2013).
Gao et al., "Complex transcriptional modulation with orthogonal and inducible dCas9 regulators," Nat Methods, 2016, 13: 1043-1049, 19 pages.
Gao et al., "Comparison of TALE designer transcription factors and the CRISPR/dCas9 in regulation of gene expression by targeting enhancers," Nucleic Acids Res 42, e155 (2014), 14 pages.
Gao et al., "Reprogramming to Pluripotency Using Designer TALE Transcription Factors Targeting Enhancers," Stem Cell Reports, 2013. 1(2): p. 183-97.
Garg et al., "Engineering synthetic TAL effectors with orthogonal target sites," Nucleic Acids Res 40, 2012, 7584-7595.
Garriga-Canut et al. "Synthetic zinc finger repressors reduce mutant huntingtin expression in the brain of R6/2 mice," Proceedings of the National Academy of Sciences of the United States of America 109, E3136-3145 (2012).
Gascon et al., "Direct Neuronal Reprogramming: Achievements, Hurdles, and New Roads to Success," Cell Stem Cell, 2017, 21: 18-34.
Gasiunas et al., "Cas9-crRNA ribonucleoprotein complex mediates specific DNA cleavage for adaptive immunity in bacteria," Proceedings of the National Academy of Sciences of the United States of America, 2012, 109, E2579-2586.
Gasperini et al., "A Genome-wide Framework for Mapping Gene Regulation via Cellular Genetic Screens," Cell, 2018, 176(1-2); 377-390.e19, 36 pages.
Gee et al., "Cellular Reprogramming Genome Editing, and Alternative CRISPR Cas9 Technologies for Precise Gene Therapy of Duchenne Muscular Dystrophy," Stem Cells International, 2017, pp. 1-11.
Gemberling et al., "Transgenic mice for in vivo epigenome editing with CRISPR-based systems," Nat Methods, 2021, 18(8): 965-974, 30 pages.
GenBank Accession No. AAC75803.1 (2018), 3 pages.
Gen Bank Accession No. AIN33136.1 (2014), 2 pages.
Gen Bank Accession No. BAB04055.1 (2017), 2 pages.
Gen Bank Accession No. EOT14076.1 (2013), 2 pages.
GenBank Accession AP006627.1 (2016), 5 pages.
GenBank Accession BA000004.3 (2016), 5 pages.
GenBank Accession AF214528.1 (2000), 2 pages.
GenBank Accession No. BB730912 (2001), 2 pages.
GenBank Accession No. BC010291 (2006), 2 pages.
GenBank Accession No. BC026642.1 (2007), 2 pages.
GenBank Accession No. BI143915 (2011), 2 pages.
GenBank Accession No. NM_020562.1 (2004), 2 pages.
GenBank Accession X51934.1 (1997), 2 pages.
GenBank P38036.2 (2013), 4 pages.
GenBank Accession No. AK019325 (2010), 4 pages.
Gersbach et al., "Targeted plasmid integration into the human genome by an engineered zinc-finger recombinase," Nucleic Acids Res, 2011, 39: 7868-7878.
Gersbach et al., (2014). "Synthetic zinc finger proteins: the advent of targeted gene regulation and genome modification technologies," Acc. Chem. Res., 47(8):2309-18.
Gersbach et al., "Activating human genes with zinc finger proteins, transcription activator-like effectors and CRISPR/Cas9 for gene therapy and regenerative medicine," Expert Opin Ther Targets, 2014. 18(8): p. 835-9.
Gersbach, "Genome engineering: the next genomic revolution," Nat Methods 11, 1009-1011 (2014).
Gerstein et al., "Architecture of the human regulatory network derived from ENCODE data," Nature 489, 91-100 (2012).
Gertz et al., "Transposase mediated construction of RNA-seq libraries," Genome Res 22, 2012, 134-141, 10 pages.
Ghaleh et al., (2020). "Concise review on optimized methods in production and transduction of lentiviral vectors in order to facilitate immunotherapy and gene therapy," Biomed. Pharmacother, 128:110276, 11 pages.
Ghisletti et al., "Identification and characterization of enhancers controlling the inflammatory gene expression program in macrophages," Immunity, 2010, 32: 317-328.
Gilbert et al., "Genome-Scale CRISPR-Mediated Control of Gene Repression and Activation," Cell 159, 647-661 (2014).
Gilbert et al. "CRISPR-mediated modular RNA-guided regulation of transcription in eukaryotes," Cell 154, 442-451 (2013).
Gillespie, "A general method for numerically simulating the stochastic time evolution of coupled chemical reactions," Journal of Computational Physics, 1976, 22: 403-434.
Gilman et al., "Distal CCAAT box deletion in the A gamma globin gene of two black adolescents with elevated fetal A gamma globin," Nucleic Acids Res 16, 1988, 10635-10642.

(56) References Cited

OTHER PUBLICATIONS

Gomaa et al., "Programmable Removal of Bacterial Strains by Use of Genome-Targeting CRISPR-Cas Systems," 2014, mBio 5(1): e00928-13, 9 pages.

Gonda "Aerosols for delivery of therapeutic and diagnostic agents to the respiratory tract," Critical Reviews in Therapeutic Drug Carrier Systems, 1990 6:273-313.

Gong et al., "Molecular insights into DNA interference by CRISPR-associated nuclease-helicase Cas3," Proc Natl Acad Sci U S A, 2014, 111 (46): 16359-64.

Gorman et al., "The Rous sarcoma virus long terminal repeat is a strong promoter when introduced into a variety of eukaryotic cells by DNA-mediated transfection," Proc. Natl. Acad. Sci. U.S.A., 1982, 79:6777-6781.

Gou et al., "A novel approach for the construction of multiple shRNA expression vectors," J Gene Med, 2007, 9(9): p. 751-63.

Gowher et al., (2002). "Molecular enzymology of the catalytic domains of the Dnmt3a and Dnmt3b DNA methyltransferases," J. Biol. Chem., 277(23):20409-20414.

Gowher et al., (2005). "Mechanism of stimulation of catalytic activity of Dnmt3A and Dnmt3B DNA-(cytosine-C5)-methyltransferases by Dnmt3L," J. Biol. Chem., 280(14):13341-13348.

Graham et al., "A new technique for the assay of infectivity of human adenovirus 5 DNA," Virol., 1973, 52:456-467.

Graslund et al., "Exploring strategies for the design of artificial transcription factors: targeting sites proximal to known regulatory regions for the induction of gamma-globin expression and the treatment of sickle cell disease," J Biol Chem 280, 2005, 3707-3714.

Gray et al., "G quadruplexes are genomewide targets of transcriptional helicases XPB and XPD," Nat. Chem. Biol, 2014, 10: 313-318, 21 pages.

Gregorevic et al., "Systemic delivery of genes to striated muscles using adeno-associated viral vectors," Nat Med, 2004, 10:828-834, 16 pages.

Grimmer et al. "Analysis of an artificial zinc finger epigenetic modulator: widespread binding but limited regulation," Nucleic acids research 42, 10856-10868 (2014).

Grissa et al., "CRISPRFinder: a web tool to identify clustered regularly interspaced short palindromic repeats," Nucleic Acids Res., 2007, 35(Web Server issue):W52-57.

Groner et al. "KRAB-zinc finger proteins and KAP1 can mediate long-range transcriptional repression through heterochromatin spreading," PLoS Genet 6, e1000869, 14 pages (2010).

Guo et al., "Directed evolution of an enhanced and highly efficient FokI cleavage domain for zinc finger nucleases," J Mol Biol, 2010, 400:96-107, 21 pages.

Guo et al., "Harnessing accurate non-homologous end joining for efficient precise deletion in CRISPR/Cas9-mediated genome editing," Genome Biology, 2018, 19: 170, 20 pages.

Guschin et al., "A rapid and general assay for monitoring endogenous gene modification," Methods Mol Biol 649,2010,247-256.

Hacein-Bey-Abina et al., "LMO2-associated clonal T cell proliferation in two patients after gene therapy forSCID-X1," Science, 2003, 302: 415-419, 11 pages.

Hakim et al., "Evaluation of Muscle Function of the Extensor Digitorum Longus Muscle Ex vivo and Tibialis Anterior Muscle In situ in Mice," J. Vis. Exp., 2013, 1-8.

Hakim et al., "Systemic gene transfer reveals distinctive muscle transduction profile of tyrosine mutant AAV-1, -6, and -9 in neonatal dogs," Mol. Ther. Methods Clin. Dev., 2014, 1 :14002, 8 pages.

Hamar et al., "Small interfering RNA targeting Fas protects mice against renal ischemia-reperfusion injury," PNAS (2004) 101: 14883-8.

Hardison et al. "Locus control regions of mammalian beta-globin gene clusters: combining phylogenetic analyses and experimental results to gain functional insights," Gene 205, 73-94 (1997).

Harper et al., "Modular flexibility of dystrophin: implications for gene therapy of Duchenne muscular dystrophy," Nat. Med., 2002, 8: 253-261.

Harrow et al., "GENCODE: The reference human genome annotation for The ENCODE Project," Genome Res, 2012, 22: 1760-1774.

Hart et al., "High-Resolution CRISPR Screens Reveal Fitness Genes and Genotype-Specific Cancer Liabilities," Cell, 2015, 163: 1515-1526.

Hathaway et al. "Dynamics and memory of heterochromatin in living cells," Cell 149, 1447-1460 (2012).

Hayward et al., "Whole-genome landscapes of major melanoma subtypes," Nature, 2017, 545: 175-180, 31 pages.

He et al., "Molecular Genetic Mechanisms of Hereditary Spherocytosis: Current Perspectives," Acta Haematol., 2018, 139: 60-66.

Heintzman et al., "Distinct and predictive chromatin signatures of transcriptional promoters and enhancers in the human genome," Nat Genet 39, 2007, 311-318.

Henikoff et al., "Amino acid substitution matrices from protein blocks," Proc. Natl. Acad. Sci. USA, 1992, 89: 10915-9.

Hilton et al., "Enabling functional genomics with genome engineering," Genome Research, 2015, 25(10):1442-1455.

Hilton et al., "Epigenome editing by a CRISPR-Cas9-based acetyltransferase activates genes from promoters and enhancers," Nature Biotechnology, 2015, vol. 33, No. 5, pp. 510-519, 20 pages.

Hoen et al., "Generation and characterization of transgenic mice with the full-length human DMD gene," J. Biol. Chem., 2008, 283: 5899-5907.

Hori et al., "Simple and reproducible hepatectomy in the mouse using the clip technique," World J Gastroenterol, 2012, 18(22): 2767-2774.

Horlbeck et al., "Compact and highly active next-generation libraries for CRISPR-mediated gene repression and activation," eLife, 2016, 5: e19760, 20 pages.

Hotta et al. "Isolation of human iPS cells using EOS lentiviral vectors to select for pluripotency," Nat Methods 6, 370-376 (2009), 9 pages.

Howarth et al., "A monovalent streptavidin with a single femtomolar biotin binding site," Nature methods, 2006, 3(4): 267-273, 15 pages.

Hsu et al., "DNA targeting specificity of RNA-guided Cas9 nucleases," Nature Biotechnology 31, 2013, 827-832, 17 pages.

Hsu et al. "Development and applications of CRISPR-Cas9 for genome engineering," Cell, 2014, 157, 1262-1278.

Hu et al. "Direct activation of human and mouse Oct4 genes using engineered TALE and Cas9 transcription factors," Nucleic Acids Res 42, 4375-4390 (2014).

Huang et al., "Impaired respiratory function in mdx and mdx/utrn+/− mice," Muscle & Nerve, 2011, 43(2): 263-267, 10 pages.

Huang et al., (2009). "Chapter 9: DNA transposons for modification of human primary T lymphocytes," Methods Mol Biol, 506:115-126.

Ifuku et al., "Restoration of Dystrophin Protein Expression by Exon Skipping Utilizing CRISPR-Cas9 in Myoblasts Derived from DMD Patient iPS Cells," Methods Mol Biol, 2018, Chapter 12, pp. 191-217.

Ikonomi et al. "Levels of GATA-1/GATA-2 transcription factors modulate expression of embryonic and fetal hemoglobins," Gene 261, 277-287 (2000).

Inoue et al., "Runx transcription factors in neuronal development," Neural Dev, 2008, 3: 20, 7 pages.

Isaac et al., "Dystrophin And Utrophin "Double Knockout" Dystrophic Mice Exhibit A Spectrum of Degenerative Musculoskeletal Abnormalities," Journal of Orthopaedic Research, 2013, 31 (3):343-349.

Lyombe-Engembe et al., "Efficient Restoration of the Dystrophin Gene Reading Frame and Protein Structure in DMD Myoblasts Using the CinDel Method," Molecular Therapy—Nucleic Acids, 2016, 5:e283, 12 pages.

Jeltsch et al., "Application of DNA methyltransferases in targeted DNA methylation," Appl. Microbiol. Biotechnol., 2007, 75(6): 1233-1240.

Ji et al. "Engineered zinc-finger transcription factors activate OCT4 (POU5F1), SOX2, KLF4, c-MYC (MYC) and miR302/367," Nucleic Acids Res 42, 6158-6167 (2014).

(56) References Cited

OTHER PUBLICATIONS

Jia et al., (2007). "Structure of Dnmt3a bound to Dnmt3L suggests a model for de novo DNA methylation," Nature, 449(7159):248-251, 10 pages.
Jiang et al., "A Cas9-guide RNA complex preorganized for target DNA recognition," Science, 2015, 348, 1477-1481.
Jiang et al., "CRISPR-assisted editing of bacterial genomes," Nat. Biotechnol., 2013, 31 :233-239, 23 pages.
Jimenez et al., "Activation of the beta-globin locus control region precedes commitment to the erythroid lineage," Proceedings of the National Academy of Sciences, 1992, 89: 10618-10622.
Jinek et al., "Structures of Cas9 endonucleases reveal RNA-mediated conformational activation," Science, 2014, 343: 1247997, 28 pages.
Jinek et al., "A programmable dual-RNA-guided DNA endonuclease in adaptive bacterial immunity," Science 337,2012,816-821.
Jinek et al., "RNA-programmed genome editing in human cells." eLife 2, e00471, 2013, 9 pages.
Johnston, (1990). "Biolistic transformation: microbes to mice," Nature, 346:776-777.
Jooss et al., "Transduction of dendritic cells by DNA viral vectors directs the immune response to transgene products in muscle fibers," J. Virol., 1998, 72: 4212-4223.
Tost, "Engineering of the epigenome: synthetic biology to define functional causality and develop innovative therapies," Epigenomics, 2016, 8(2):153-156.
Josephs et al., "Structure and specificity of the RNA-guided endonuclease Cas9 during DNA interrogation, target binding and cleavage," Nucleic Acids Research, 2015, 43(18): 8924-8941.
Jurkowska et al., "Silencing of Gene Expression by Targeted DNA Methylation: Concepts and Approaches," Methods Mol. Biol. 649, 2010, Chapter 9: 149-161.
Kabadi et al., "Engineering Synthetic TALE and CRISPR/Cas9 Transcription Factors for Regulating Gene Expression," Methods, 2014, 69(2): 188-197, 27 pages.
Kabadi et al., "Multiplex CRISPR/Cas9-based genome engineering from a single lentiviral vector," Nucleic Acids Res, 2014. 42(19): p. e147, 11 pages.
Karlin et al., "Applications and statistics for multiple high-scoring segments in molecular sequences," Proc. Natl. Acad. Sci. USA, 1993, 90: 5873-77.
Kasaraneni et al., (2018). "A simple strategy for retargeting lentiviral vectors to desired cell types via a disulfide-bond-forming protein-peptide pair," Sci. Rep., 8(1):10990, 9 pages.
Kearns et al. "Functional annotation of native enhancers with a Cas9-histone demethylase fusion," Nat Methods (2015) 12(5):401-403, 13 pages.
Keil et al., "Brain Transcriptome Databases: A User's Guide," J Neurosci, 2018, 38(10): 2399-2412.
Kempfer et al., "Methods for mapping 3D chromosome architecture," Nat. Rev. Genet., 2020, 21: 207-226.
Keung et al. "Using targeted chromatin regulators to engineer combinatorial and spatial transcriptional regulation," Cell 158, 110-120 (2014).
Keys et al., "A genome-wide screen in the mouse liver reveals sex-specific and cell nonautonomous regulation of cell fitness," bioRxiv preprint doi:https://doi.org/10.1101/2021.01.30.428976, posted Feb. 1, 2021, 58 pages.
Khambata-Ford et al., "Identification of Promoter Regions in the Human Genome by Using a Retroviral Plasmid Library-Based Functional Reporter Gene Assay," Genome Research, 2003, 13: 1765-1774.
Khodakov et al., "Protected DNA strand displacement for enhanced single nucleotide discrimination in double-stranded DNA," Scientific Reports, 2015, 5: 8721, 8 pages.
Khoury et al., "Efficient new cationic liposome formulation for systemic delivery of small interfering RNA silencing tumor necrosis factor alpha in experimental arthritis," Arthritis Rheumatol. (2006) 54: 1867-77.
Khurana et al., "Role of non-coding sequence variants in cancer," Nat. Rev. Genet., 2016, 17: 93-108.
Kim et al., "Epigenetic therapy of Prader-Willi Syndrome," Transl Res, 2019, 208: 105-118, 24 pages.
Kim et al., "Use of the human elongation factor 1-alpha promoter as a versatile and efficient expression system," Gene, 1990, 91:217-223.
Kim et al., "Histone acetylation contributes to chromatin looping between the locus control region and globin gene by influencing hypersensitive site formation," Biochim Biophys Acta 1829, 963-969 (2013), 9 pages.
Klann et al., "Genome-wide annotation of gene regulatory elements linked to cell fitness," bioRxiv doi: 10.1101/2021.03.08.434470. Preprint posted Mar. 9, 2021, 42 pages.
Kleinstiver et al., "Genome-wide specificities of CRISPR-Cas Cpf1 nuclease in human cells," Nature Biotechnology, 2016, 34: 869-874, 14 pages.
Kocak, "Synthetic Transcription Factors and their Effects on Endogenous DNA Methylation in Human Cells," Thesis submitted in partial fulfillment of the requirements for the degree of Master of Science in the Department of Biomedical Engineering in the Graduate School of Duke University, 2013, p. 1-29, 35 pages.
Koerber et al., "DNA shuffling of adeno-associated virus yields functionally diverse viral progeny," Mol Ther, 2008, 16: 1703-1709.
Konermann et al., "Genome-scale transcriptional activation by an engineered CRISPRCas9 complex," Nature 517, 583-588 (2015), 37 pages.
Konermann et al. Optical control of mammalian endogenous transcription and epigenetic states. Nature 500, 472-476 (2013), 16 pages.
Koo et al., "Functional Rescue of Dystrophin Deficiency in Mice Caused by Frameshift Mutations Using Campylobacter jejuni Cas9," Molecular Therapy, 2018 26(6): 1529-1538.
Koopmans et al., "SynGO: An Evidence-Based, Expert-Curated Knowledge Base for the Synapse," Neuron, 2019, 103: 217-234 e214, 23 pages.
Koppanati et al., "Improvement of the mdx mouse dystrophic phenotype by systemic in utero AAV8 delivery of a minidystrophin gene," Gene Ther, 2010, 17: 1355-1362, 15 pages.
Koste et al., (2014). "T-cell receptor transfer into human T cells with ecotropic retroviral vectors," Gene Ther, 21(5):533-538.
Kotin, "Prospects for the use of adeno-associated virus as a vector for human gene therapy," Hum Gene Ther., 1994, 5:793-801.
Kreis et al., "The Multifaceted p21 (Cip1/Waf1/CDKN1A) in Cell Differentiation, Migration and Cancer Therapy," Cancers (Basel), 2019, 11(9): 1220, 23 pages.
Kuhnel et al., "Tumor-specific adenoviral gene therapy: Transcriptional repression of gene expression by utilizing p53-signal transduction pathways," Cancer Gene Ther., 2004, 11(1): 28-40.
Kuscu et al., "Genome-wide analysis reveals characteristics of off-target sites bound by the Cas9 endonuclease," Nat Biotechnol, 2014. 32(7): p. 677-83, 9 pages.
Kwon et al., "Myogenic Progenitor Cell Lineage Specification by CRISPR/Cas9-Based Transcriptional Activators," Stem cell reports, 2020, 14: 755-769.
Kyte et al., "A Simple Method for Displaying the Hydropathic Character of a Protein," J. Mol. Biol., 1982, 157:105-132.
La Russa et al., "The New State of the Art: Cas9 for Gene Activation and Repression," Molecular and Cellular Biology, 2015, 35(22):3800-3809.
Lagace, (2014). "PCSK9 and LDLR degradation: regulatory mechanisms in circulation and in cells," Curr. Opin. Lipidol., 25(5):387-393.
Lai et al., "Partial restoration of cardiac function with b.PDZ nNOS in aged mdx model of Duchenne cardiomyopathy," Hum Mol Genet., 2014, 23(12): 3189-3199.
Lake et al., "Integrative single-cell analysis of transcriptional and epigenetic states in the human adult brain," Nat Biotechnol, 2018, 36: 70-80, 33 pages.
Lambert et al., "The Human Transcription Factors," Cell, 2018, 172: 650-665, 19 pages.

(56) References Cited

OTHER PUBLICATIONS

Landen et al., "Intraperitoneal delivery of liposomal siRNA for therapy of advanced ovarian cancer," Cancer Biol. Ther. (2006) 5(12):1708-13.
Landry et al., "Expression of the leukemia oncogene Lmo2 is controlled by an array of tissue-specific elements dispersed over 100 kb and bound by Tal1/Lmo2, Ets, and Gata factors," Blood, 2009, 113: 5783-5792.
Langmead et al., "Fast gapped-read alignment with Bowtie 2," Nature Methods 9, 357-359 (2012), 8 pages.
Langmead et al., "Ultrafast and memory-efficient alignment of short DNA sequences to the human genome," Genome Biology 10, 2009, R25, 10 pages.
Laumont et al., "Noncoding regions are the main source of targetable tumor-specific antigens," Sci. Transl. Med., 2018, 10(470): eaau5516, 12 pages.
Lawrence et al., "Discovery and saturation analysis of cancer genes across 21 tumour types," Nature, 2014, 505: 495-501, 22 pages.
Lee et al., "Role of satellite cells versus myofibers in muscle hypertrophy induced by inhibition of the myostatin/activin signaling pathway," Proc Natl Acad Sci US A, 2012, 109(35):E2353-60.
Lee, "Regulation of muscle mass by myostatin," Annu Rev Cell Dev Biol 20, 61-86 (2004).
Lei et al., (2017). "Targeted DNA methylation in vivo using an engineered dCas9-MQ1 fusion protein," Nat. Commun, 8:16026, 10 pages.
Lenoir et al., "PICKLES: the database of pooled in-vitro CRISPR knockout library essentiality screens," Nucleic Acids Res, 2018, 46: D776-D780.
Lesnik et al., "Relative thermodynamic stability of DNA, RNA, and DNA: RNA hybrid duplexes: relationship with base composition and structure," Biochemistry, 1995, 34(34): 10807-10815.
Levskaya et al., "Synthetic biology: engineering *Escherichia coli* to see light," Nature, 2005, 438:441-442.
Li et al., "Chimeric DNA methyltransferases target DNA methylation to specific DNA sequences and repress expression of target genes," Nucleic Acids Res., 2007, 35(1): 100-112.
Li et al., "Engineering and Selection of Shuffled AAV Genomes: A New Strategy for Producing Targeted Biological Nano Particles," Mol Ther, 2008, 16: 1252-1260.
Li et al., "Ex vivo cell-based CRISPR/Cas9 genome editing for therapeutic applications," Biomaterials, 2020, 234: 119711, 33 pages.
Li et al., "Precise correction of the dystrophin gene in duchenne muscular dystrophy patient induced pluripotent stem cells by TALEN and CRISPR-Cas9," Stem Cell Reports, 2015, 4: 143-154.
Li et al., "Preservation of muscle force in Mdx3cv mice correlates with low-level expression of a near full-length dystrophin protein," Am. J. Pathol., 2008, 172: 1332-1341.
Li et al., "RSEM: accurate transcript quantification from RNA-Seq data with or without a reference genome," BMC Bioinformatics, 2011, 12: 323, 16 pages.
Li et al., (2017). "Development of fluorescent methods for DNA methyltransferase assay," Methods Appl. Fluoresc., 5:012002, 8 pages.
Li et al., "The role of chromatin during transcription," Cell 128, 707-719 (2007).
Li et al. "Extensive promoter-centered chromatin interactions provide a topological basis for transcription regulation," Cell 148, 84-98 (2012).
Li et al. "The Sequence Alignment/Map format and SAMtools," Bioinformatics 25, 2078-2079 (2009).
Li et al., "Locus control regions," Blood 100, 3077-3086 (2002).
Li et al., "Transcription activator-like effector hybrids for conditional control and rewiring of chromosomal transgene expression," Scientific Reports 2, 2012, 897, 7 pages.
Liang et al., "Engineering biological systems with synthetic RNA molecules," Mol Cell 43, 2011, 915-926.
Lim et al., "Application of CRISPR/Cas9 for the Treatment of Duchenne Muscular Dystrophy," Journal of Personalized Medicine, 2018, 8(4): 1-20.
Lin et al., "Essential Role of the 58-kDa Microspherule Protein in the Modulation of Daxx-dependent Transcriptional Repression as Revealed by Nucleolar Sequestration," J Biol Chem, 2002, 277: 25446-25456.
Liu et al., "Adeno-Associated Virus-Mediated Microdystrophin Expression Protects Young Mdx Muscle From Contraction-Induced Injury," Mol. Ther., 2005, 11: 245-256.
Liu et al., "Monte Carlo simulation for single RNA unfolding by force," Biophysical Journal, 2005, 88(1): 76-84.
Liu et al., (1997). "Design of polydactyl zinc-finger proteins for unique addressing within complex genomes," PNAS, 94(11):5525-5530.
Liu et al., (2016). "Editing DNA Methylation in the Mammalian Genome," Cell, 167:233-247, 32 pages.
Lohmueller et al., "A tunable zinc finger-based framework for Boolean logic computation in mammalian cells," Nucleic Acids Res 40, 2012, 5180-5187.
Love et al., "Moderated estimation of fold change and dispersion for RNA-seq data with DESeq2," Genome biology 15, 550 (2014), 21 pages.
Luo et al., "Repurposing endogenous type I CRISPR-Cas systems for programmable gene repression," Nucleic Acids Research, 2014, 43(1): 674-681.
Ma et al., "Targeted gene suppression by inducing de novo DNA methylation in the gene promoter," Epigenetics Chromatin, 2014, 7(20), 11 pages.
Ma et al., (2014). "Pol III Promoters to Express Small RNAs: Delineation of Transcription Initiation," Molecular Therapy—Nucleic Acids, 3:e161, 11 pages.
Ma et al., (2020). "Nanomaterial-based biosensors for DNA methyltransferase assay," Mater Chem B., 8:3488-3501.
Machinek et al., "Programmable energy landscapes for kinetic control of DNA strand displacement," Nature Communications, 2014, 5: 5324, 9 pages.
MacPherson et al., "Flexible guide-RNA design for CRISPR applications using Protospacer Workbench," Nature Biotechnology, 2015, 33(8), 2 pages.
Maeder et al. "Targeted DNA demethylation and activation of endogenous genes using programmable TALE-TET1 fusion proteins," Nat Biotechnol 31, 1137-1142 (2013), 16 pages.
Maeder et al., "Robust, synergistic regulation of human gene expression using TALE activators," Nat Methods 10, 2013, 243-245, 10 pages.
Maeder et al. "CRISPR RNA-guided activation of endogenous human genes," Nat Methods 10, 977-979 (2013), 9 pages.
Magnenat et al., "3rd In vivo selection of combinatorial libraries and designed affinity maturation of polydactyl zinc finger transcription factors for ICAM-1 provides new insights into gene regulation," J Mol Biol 341, 635-649 (2004).
Maheshri et al., "Directed evolution of adeno-associated virus yields enhanced gene delivery vectors," Nat Biotechnol, 2006, 24: 198-204.
Makarova et al., "An updated evolutionary classification of CRISPR-Cas systems," Nature Reviews Microbiology, 2015, 13:722-736, 31 pages.
Makarova et al., "Evolution and classification of the CRISPR-Cas systems," Nature Reviews Microbiology, 2011, pp. 467-477, 23 pages.
Makarova et al., (2015). "Annotation and Classification of CRISPR-Cas Systems," Methods Mol. Biol, 1311:47-75, 27 pages.
Mali et al. "CAS9 transcriptional activators for target specificity screening and paired nickases for cooperative genome engineering," Nat Biotechnol 31, 833-838 (2013), 17 pages.
Mali et al. "RNA-guided human genome engineering via Cas9," Science 339, 823-826 (2013), 8 pages.
Mamchaoui, K. et al., "Immortalized pathological human myoblasts: towards a universal tool for the study of neuromuscular disorders," Skelet Muscle 1, 2011, 1-11.
Maniatis et al., "Regulation of inducible and tissue-specific gene expression," Science, 1987, 236:1237-45.

(56) References Cited

OTHER PUBLICATIONS

Mann et al., "Improved antisense oligonucleotide induced exon skipping in the mdx mouse model of muscular dystrophy," J. Gene Med., 2002, 4: 644-654.
Manning et al., "What has the mdx mouse model of duchenne muscular dystrophy contributed to our understanding of this disease?" Journal of Muscle Research and Cell Motility, 2015, 36:155-167.
Manuri et al., (2010). "piggyBac transposon/transposase system to generate CD19-specific T cells for the treatment of B-lineage malignancies," Hum Gene Ther, 21(4):427-437.
Maruyama et al., "Epigenetic Regulation of Cell Type-Specific Expression Patterns in the Human Mammary Epithelium," PLoS Genetics, 2011, 7(4): e1001369, 15 pages.
Mastellos et al., "Inducing and characterizing liver regeneration in mice: Reliable models, essential "readouts" and critical perspectives," Curr Protoc Mouse Biol., 2013, 3(3): 141-170, 36 pages.
Mathews et al., "Expanded sequence dependence of thermodynamic parameters improves prediction of RNA secondary structure," Journal of Molecular Biology, 1999, 288(5): 911-940.
Matsushita et al., "Adeno-associated virus vectors can be efficiently produced without helper virus," Gene Therapy, 1998, 5:938-945.
Maurano et al., "Systematic localization of common disease-associated variation in regulatory DNA," Science, 2012, 337: 1190-1195, 15 pages.
Mavrothalassitis et al., (2000). "Proteins of the ETS family with transcriptional repressor activity," Oncogene, 19:6524-6532.
Maxwell et al., "A detailed cell-free transcription-translation-based assay to decipher CRISPR protospacer-adjacent motifs," Methods, 2018, 143: 48-57, 28 pages.
McCarty et al, "Self-complementary recombinant adeno-associated virus (scAAV) vectors promote efficient transduction independently of DNA synthesis," Gene Ther. 2001, 8:1248-54.
McDowell et al., "A Structural and functional cross-talk between a distant enhancer and the epsilon-globin gene promoter shows interdependence of the two elements in chromatin," Molecular and cellular biology 19, 7600-7609 (1999).
McGreevy et al., "Animal models of Duchenne muscular dystrophy: from basic mechanisms to gene therapy," Disease Models Mechanisms, 2015, 8(3): 195-213.
Memedula et al., "Sequential recruitment of HAT and SWI/SNF components to condensed chromatin by VP16," Curr Biol 13, 241-246 (2003).
Mendenhall et al. "Locus-specific editing of histone modifications at endogenous enhancers using programmable TALE-LSD1 fusions," Nat Biotechnol 31, 1133-1136 (2013), 14 pages.
Mertens et al., "Evaluating cell reprogramming, differentiation and conversion technologies in neuroscience," Nat Rev Neurosci, 2016, 17: 424-437, 45 pages.
Mevissen et al., "Molecular basis of Lys11-polyubiquitin specificity in the deubiquitinase Cezanne," Nature, 2016, 538(7625): 402-405, 34 pages.
Meyers et al., "Computational correction of copy number effect improves specificity of CRISPR-Cas9 essentiality screens in cancer cells," Nat. Genet., 2017, 49: 1779-1784, 29 pages.
Miller et al., "Transcriptional landscape of the prenatal human brain," Nature, 2014, 508: 199-206, 36 pages.
Miller et al., (1989). "Improved retroviral vectors for gene transfer and expression," BioTechniques, 7(9):980-990, 14 pages.
Miller, (1990). "Retrovirus packaging cells," Human Gene Therapy, 1:5-14.
Miller et al., "A TALE nuclease architecture for efficient genome editing," Nat Biotechnol 29, 2011, 143-148, 8 pages.
Milone et al., (2018). "Clinical use of lentiviral vectors," Leukemia, 32(7):1529-1541.
Min et al., "CRISPR Correction of Duchene Muscular Dystrophy," Annual Review of Medicine, Epub Oct. 2018, 70: 239-255.
Mittler et al. "A novel docking site on Mediator is critical for activation by VP 16 in mammalian cells," EMBO J 22, 6494-6504 (2003).

Mizushima et al., "pEF-BOS, a powerful mammalian expression vector," Nucl. Acids. Res., 1990, 18:5322.
Mojica et al., "Short motif sequences determine the targets of the prokaryotic CRISPR defence system," Microbiology, 2009, 155: 733-740.
Mok et al., (1999). "Stabilized plasmid-lipid particles: factors influencing plasmid entrapment and transfection properties," Biochimica et Biophysica Acta, 1419(2):137-150.
Montalbano et al., "High-Throughput Approaches to Pinpoint Function within the Noncoding Genome," Mol. Cell, 2017, 68: 44-59.
Moon et al., (2019). "Recent advances in the CRISPR genome editing tool set," Exp. Mol. Med. 51(11):130, 11 pages.
Morris et al., "Dissecting engineered cell types and enhancing cell fate conversion via CellNet," Cell, 2014, 158: 889-902.
Morrissey et al., "Activity of stabilized short interfering RNA in a mouse model of hepatitis B virus replication," Hepatol. (2005) 41: 1349-56.
Muir et al., "Engraftment potential of dermal fibroblasts following in vivo myogenic conversion in immunocompetent dystrophic skeletal muscle," Mol. Ther. Methods Clin. Dev., 2014, 1 :14025, 10 pages.
Murphy et al., "The in vitro transcription of the 7SK RNA gene by RNA polymerase III is dependable only on the presence of an upstream promoter," Cell, 1987, 51:81-87.
Murray et al., "Codon usage in plant genes," Nucl. Acids Res., 1989, 17:477-498.
Muzycka, "Use of adeno-associated virus as a general transduction vector for mammalian cells," Curr. Top. Microbiol. Immunol., 1992, 158:97-129.
Myslinski et al., "An unusually compact external promoter for RNA polymerase III transcription of the human H1RNA gene," Nucleic Acids Res, 2001, 29:2502-2509.
Najm et al., "Orthologous CRISPR-Cas9 enzymes for combinatorial genetic screens," Nat Biotechnol, 2018, 36: 179-189, 31 pages.
Naldini, "Gene therapy returns to centre stage," Nature, 2015, 526: 351-360.
Nam et al., "Cas5d protein processes pre-crRNA and assembles into a Cascade-like interference complex in Subtype I-C/Dvulg CRISPR-Cas system," Structure, 2012, 20:1574-1584.
NCBI Reference Sequence NG_028016.2 (2013), 26 pages.
NCBI Reference Sequence NM_004020.2 (2010), 6 pages.
NCBI Reference Sequence XM011532697.1 (2015), 3 pages.
Nelson et al., "In vivo genome editing improves muscle function in a mouse model of Duchenne muscular dystrophy," Science, 2016, 351, 403-7.
Nelson et al., "Local and Systemic Gene Editing in a Mouse Model of Duchenne Muscular Dystrophy," Molecular Therapy, 2016, 24(Supp 1):S191.
Nguyen et al., "Transcriptional Enhancers in the Regulation of T Cell Differentiation," Front. Immunol., 2015, 6: 462, 12 pages.
Nikfarjam et al., "A Model of Partial Hepatectomy in Mice," Journal of Investigative Surgery, 2004, 17(5): 291-294.
Nishimasu et al., "Crystal structure of Cas9 in complex with guide RNA and target DNA," Cell, 2014, 156:935-49.
Nissim et al., "Multiplexed and Programmable Regulation of Gene Networks with an Integrated RNA and CRISPR/Cas Toolkit in Human Cells," Mol Cell 54, 698-710 (2014).
Nordhoff et al., "Comparative analysis of human, bovine, and murine Oct-4 upstream promoter sequences," Mamm Genome 12, 309-317 (2001).
Nunez et al., "Genome-wide programmable transcriptional memory by CRISPR-based epigenome editing," Cell, 2021, 184(9): p. 2503-2519.
O'Brien et al., "GT-Scan: identifying unique genomic targets," Bioinformatics, 2014, 30: 2673- 2675.
O'Connell et al., "Programmable RNA recognition and cleavage by CRISPR/Cas9," Nature, 2014, 516: 263-266, 23 pages.
Odom et al., "Microutrophin Delivery Through rAAV6 Increases Lifespan and Improves Muscle Function in Dystrophic Dystrophin/Utrophin-deficient Mice," Molecular Therapy, 2008, 16(9):1539-1545.

(56) References Cited

OTHER PUBLICATIONS

O'Geen et al., "Ezh2-dCas9 and KRAB-dCas9 enable engineering of epigenetic memory in a context-dependent manner," Epigenetics Chromatin, 2019, 12: 26, 20 pages.
Ogryzko et al., "The transcriptional coactivators p300 and CBP are histone acetyltransferases," Cell 87, 953-959 (1996).
Ohshima et al., "Nucleotide sequence of mouse genomic loci including a gene or pseudogene for U6 (4.85) nuclear RNA," Nucleic Acids Res, 1981, 9:5145-5158.
Okkenhaug et al., "PI3K in lymphocyte development, differentiation and activation," Nat. Rev. Immunol., 2003, 3(4): 317-330.
Ong et al., "Enhancer function: new insights into the regulation of tissue-specific gene expression Nature reviews," Genetics 12, 283-293 (2011), 20 pages.
Orlando et al., "Promoter capture Hi—C-based identification of recurrent noncoding mutations in colorectal cancer," Nat. Genet., 2018, 50: 1375-1380, 23 pages.
Osakabe et al., "FLAG-NLS-SpCas9-2A-GFBSD2 [Binary vector pEgP526-2A-GFBSD2]," National Center for Biotechnology Information, Genbank Entry, Retrieved from the Internet on Sep. 18, 2017 <https://www.ncbi.nlm.nih.gov/protein/BAV01234>, 2 pages.
Ousterout et al., "Correction of dystrophin expression in cells from duchenne muscular dystrophy patients through genomic excision of exon 51 by zinc finger nucleases," Molecular Therapy 23, 2015, 523-532.
Ousterout et al., "Multiplex CRISPR/Cas9-based genome editing for correction of dystrophin mutations that cause Duchenne muscular dystrophy," Nature Communications, 2015, 6:6244, 13 pages.
Ousterout et al., "Reading frame correction by targeted genome editing restores dystrophin expression in cells from Duchenne muscular dystrophy patients," Mol Ther, 2013, 21:1718-1726.
Paez-Espino et al., "CRISPR immunity drives rapid phage genome evolution in *Streptococcus thermophilus*," mBio, 2015, 6(2): e00262-15, 9 pages.
Pang et al., "Induction of human neuronal cells by defined transcription factors," Nature, 2011, 476: 220-223, 17 pages.
Parekh et al., "Mapping Cellular Reprogramming via Pooled Overexpression Screens with Paired Fitness and Single-Cell RNA-Sequencing Readout," Cell Systems, 2018, 7: 548-555.e548, 17 pages.
Park et al., "Cas-Designer: a web-based tool for choice of CRISPR-Cas9 target sites," Bioinformatics, 2015, 31 (24):4014-4016.
Park et al., "Multi-Parametric MRI at 14T for Muscular Dystrophy Mice Treated with AAV Vector-Mediated Gene Therapy," PLoS One, 2015, 10(4): e0124914, 24 pages.
Park et al., (2011). "Treating cancer with genetically engineered T cells," Trends Biotechnol, 29(11):550-557, 15 pages.
Park et al., "Phenotypic alteration of eukaryotic cells using randomized libraries of artificial transcription factors," Nat Biotechnol 21, 2003, 1208-1214.
Penczek et al., "Three-dimensional reconstruction of single particles embedded in ice," Ultramicroscopy, 1992, 40, 33-53.
Perez-Pinera et al., "Gene targeting to the ROSA26 locus directed by engineered zinc finger nucleases," Nucleic Acids Research, 2012, 40:3741-3752.
Perez-Pinera et al., "RNA-guided gene activation by CRISPR-Cas9-based transcription factors," Nat Methods, 2013, 10:973-976, 12 pages.
Perez-Pinera et al., "Synergistic and tunable human gene activation by combinations of synthetic transcription factors," Nature Methods, vol. 10, No. 3, pp. 239-242, Feb. 3, 2013, including pp. 1/12-12-12 of Supplementary Material, 11 pages.
Peterson et al., (2008). "PCSK9 function and physiology," J. Lipid Res., 49:1595-1599.
Piacentino et al., "X-Linked Inhibitor of Apoptosis Protein-Mediated Attenuation of Apoptosis, Using a Novel Cardiac-Enhanced Adeno-Associated Viral Vector," Human Gene Therapy, 2012, 23:635-646.
Pinello et al., "Analyzing CRISPR genome-editing experiments with CRISPResso," Nat Biotechnol, 2016, 34(7) :695-697, 6 pages.
Poh et al., (2016). "DNA Methyltransferase Activity Assays: Advances and Challenges," Theranostics, 6(3):369-391.
Poirier et al., (2008). "The proprotein convertase PCSK9 induces the degradation of low density lipoprotein receptor (LDLR) and its closest family members VLDLR and ApoER2," J. Biol. Chem., 283:2363-2372.
Polstein et al., "A light-inducible CRISPR-Cas9 system for control of endogenous gene activation," Nature Chemical Biology, 2015, 11: 198-200, 10 pages.
Polstein et al., "Genome-wide specificity of DNA-binding, gene regulation, and chromatin remodeling by TALE- and CRISPR/Cas9-based transcriptional activators," Genome Res, 2015, 13 pages.
Povero et al., "Lipid-induced toxicity stimulates hepatocytes to release angiogenic microparticles that require Vanin-1 for uptake by endothelial cells," Sci Signal, 2013, 6(296): ra88, 36 pages.
Prykhozhij et al., "CRISPR MultiTargeter: A Web Tool to Find Common and Unique CRISPR Single Guide RNA Targets in a Set of Similar Sequences," PLoS One, 2015, 10(3): e0119372, 18 pages.
Puccini et al., "Colorectal cancer: epigenetic alterations and their clinical implications," Biochim Biophys Acta Rev Cancer. 1868(2): 439-448 (2017), 25 pages.
Qi et al., "Repurposing CRISPR as an RNA-guided platform for sequence-specific control of gene expression," Cell 152, 2013, 1173-1183.
Quinlan et al., "BEDTools: a flexible suite of utilities for comparing genomic features," Bioinformatics 26, 841-842 (2010).
Rackham et al., "A predictive computational framework for direct reprogramming between human cell types," Nature Genetics, 2016, 48: 331-335.
Rada-Iglesias et al., "A unique chromatin signature uncovers early developmental enhancers in humans," Nature 470, 279-283 (2011), 17 pages.
Raeburn et al., "Techniques for drug delivery to the airways, and the assessment of lung function in animal models," J. Pharmacol. Toxicol. Meth., 1992, 27:143-159.
Rahdar et al., "Synthetic CRISPR RNA-Cas9-Guided Genome Editing in Human Cells," Proceedings to the National Academy of Sciences of USA, 2015, vol. 112, No. 51, pp. E7110-E7117.
Rajagopal et al., "High-throughput mapping of regulatory DNA," Nat. Biotechnol, 2016, 34: 167-174, 22 pages.
Ramachandran et al., "Nitric Oxide Signaling Pathway in Duchenne Muscular Dystrophy Mice: Upregulation of L-arginine Transport," Biochem. J., 2012, 449: 133-142, 25 pages.
Ran et al., "Genome engineering using the CRISPR-Cas9 system," Nature Protocols, 2013, 8(11): 2281-2308, 49 pages.
Ran et al., "In vivo genome editing using *Staphylococcus aureus* Cas9," Nature 520, 2015, 186-91, 28 pages.
Ratcliff et al., "A novel single-molecule study to determine protein protein-protein association constants," Journal of the American Chemical Society, 2001, 123(24): 5632-5635.
Rauscher et al., "GenomeCRISPR—a database for high-throughput CRISPR/Cas9 screens," Nucleic Acids Res, 2017, 45: D679-D686.
Rebar et al., "Induction of angiogenesis in a mouse model using engineered transcription factors," Nat Med 8, 2002, 1427-1432.
Reynolds et al. "NuRD-mediated deacetylation of H3K27 facilitates recruitment of Polycomb Repressive Complex 2 to direct gene repression," The EMBO journal 31, 593-605 (2012).
Rheinbay et al., "Analyses of non-coding somatic drivers in 2,658 cancer whole genomes," Nature, 2020, 578: 102-111, 11 pages.
Rhodes et al., "G-quadruplexes and their regulatory roles in biology," Nucleic Acids Res, 2015, 43: 8627-8637.
Riley, "PD-1 signaling in primary T cells," Immunological Reviews, 2009, 229: 114-125, 19 pages.
Riordan et al., "Application of CRISPR/Cas9 for biomedical discoveries," Cell & Bioscience, 2015, 5(1):11 pages.
Rivenbark, et al. "Epigenetic reprogramming of cancer cells via targeted DNA methylation," Epigenetics 7, 350-360 (2012).
Rmilah et al., "Understanding the marvels behind liver regeneration," Wiley Interdiscip Rev Dev Biol., 2019, 8(3): e340, 46 pages.
Roadmap Epigenomics Consortium, "Integrative analysis of 111 reference human epigenomes," Nature, 2015, 518: 317-330, 32 pages.

(56) References Cited

OTHER PUBLICATIONS

Robinson-Hamm et al., "Gene therapies that restore dystrophin expression for the treatment of Duchenne muscular dystrophy," Human Genetics, 2016, 135(9): 1029-1040, 22 pages.
Rodriguez et al., "Clustering by fast search and find of density peaks," Science, 2014, 344(6191): 1492-1496.
Roudaut et al., "Restriction of calpain3 expression to the skeletal muscle prevents cardiac toxicity and corrects pathology in a murine model of limb-girdle muscular dystrophy," Circulation, 2013, 128: 1094-1104, 18 pages.
Rousseau et al., "Endonucleases: tools to correct the dystrophin gene" The Journal of Gene Medicine, 2011, vol. 13, pp. 522-537.
Rutkauskas et al., "Directional R-loop formation by the CRISPR-Cas surveillance complex cascade provides efficient off-target site rejection," Cell Reports, 2015, 10, 1534-1543.
Sagal et al., "Proneural transcription factor Atoh1 drives highly efficient differentiation of human pluripotent stem cells into dopaminergic neurons," Stem Cells Transl Med, 2014, 3: 888-898.
Salmon et al., "Production and titration of lentiviral vectors," Curr Protoc Hum Genet Chapter, 2007, 12: Unit 12 10, 24 pages.
Sanson et al., "Optimized libraries for CRISPR-Cas9 genetic screens with multiple modalities," Nat Commun, 2018, 9: 5416, 15 pages.
Santa Lucia et al., "Improved nearest-neighbor parameters for predicting DNA duplex stability," Biochemistry, 1996, 35(11): 3555-3562.
Scarpa et al., (1991). "Characterization of recombinant helper retroviruses from moloney-based vectors in ecotropic and amphotropic packaging cell lines," Virology, 180:849-852.
Schellenberger et al., (2009). "A recombinant polypeptide extends the in vivo half-life of peptides and proteins in a tunable manner," Nature Biotechnology, 27(12):1186-1190. 7 pages.
Schmidt et al., "GenomeRNAi: a database for cell-based and in vivo RNAi phenotypes, 2013 update," Nucleic Acids Res, 2013, 41: D1021-6.
Schreck et al., "DNA hairpins destabilize duplexes primarily by promoting melting rather than by inhibiting hybridization," Nucleic Acids Research, 2015, 43(13): 6181-6190.
Schreck et al., "DNA hairpins primarily promote duplex melting rather than by inhibiting hybridization," 2014, arXiv preprint arXiv: 1408.4401, 19 pages.
Schultz et al., "Recombinant adeno-associated virus transduction and integration," Molecular Therapy 16, 2008, 1189-1199.
Schultz et al., "3rd SETDBI: a novel KAP-I-associated histone H3, lysine 9-specific methyltransferase that contributes to HPI-mediated silencing of euchromatic genes by KRAB zinc-finger proteins," Genes & development 16, 919-932 (2002).
Segal et al., "Genome Engineering at the Dawn of the Golden Age," Annu. Rev. Genomics Hum. Genet., 2013, 14: 135-158.
Semenova et al., "The Cas6e ribonuclease is not required for interference and adaptation by the E.coli type I-E CRISPR-Cas system," Nucleic Acids Res, 2015, 43(12):6049-61.
Sengupta et al., "Super-Enhancer-Driven Transcriptional Dependencies in Cancer," Trends Cancer Res, 2017, 3: 269-281, 19 pages.
Serra et al., "Predicting thermodynamic properties of RNA," Methods in Enzymology, 1995, 259: 242-261.
Seto et al., "Gene Replacement Therapies for Duchenne Muscular Dystrophy Using Adeno-Associated Viral Vectors," Current Gene Therapy, 2012, 12:139-151, 28 pages.
Shalem et al., "Genome-scale CRISPR-Cas9 knockout screening in human cells," Science, 2014, 343: 84-87, 10 pages.
Sharma et al., "In vivo genome editing of the albumin locus as a platform for protein replacement therapy," Blood, 2015, 126: 1777-1784.
Sharma et al., (2013). "Efficient Sleeping Beauty DNA Transposition From DNA Minicircles," Molec Ther Nucl Acids, 2(2):e74, 10 pages.
Shen et al., "Combinatorial CRISPR-Cas9 screens for de novo mapping of genetic interactions," Nat Methods, 2017, 14: 573-576, 19 pages.

Shen et al., "Massively parallel cis-regulatory analysis in the mammalian central nervous system," Genome Research, 2015, 26(2): 238-255.
Shin et al., "Microdystrophin Ameliorates Muscular Dystrophy in the Canine Model of Duchenne Muscular Dystrophy," Mol. Ther., 2013, 21: 750-757.
Shlyakhtenko et al., "Silatrane-based surface chemistry for immobilization of DNA, protein-DNA complexes and other biological materials," Ultramicroscopy, 2003, 97: 279-287.
Siddique et al., "Targeted methylation and gene silencing of VEGF-A in human cells by using a designed Dnmt3aDnmt3L single-chain fusion protein with increased DNA methylation activity," J. Mol. Biol., 2013, 425(3): 479-491.
Simpson, "Contacts between *Escherichia coli* RNA polymerase and thymines in the lac UV5 promoter," Proc. Natl. Acad. Sci. USA, 1979, 76: 3233-3237.
Singh et al. "Protein Engineering Approaches in the Post-Genomic Era," Current Protein and Peptide Science, 2018;19(1):5-15.
Skene et al., "Genetic identification of brain cell types underlying schizophrenia," Nat Genet, 2018, 50: 825-833, 24 pages.
Smith et al., "Myostatin inhibitors as therapies for muscle wasting associated with cancer and other disorders," Curr Opin Support Palliat Care, 2013, 7, 352-60.
Snowden et al., "Gene-specific targeting of H3K9 methylation is sufficient for initiating repression in vivo," Curr Biol 12, 2159-2166 (2002).
Song et al., "Non-immunogenic utrophin gene therapy for the treatment of muscular dystrophy animal models," Nature Medicine, 2019, 25(10): 1505-1511, 36 pages.
Song et al., "DNase-seq: a high-resolution technique for mapping active gene regulatory elements across the genome from mammalian cells," Cold Spring Harbor protocols 2010, pdb prot5384 (2010), 13 pages.
Song et al., "Open chromatin defined by DNaseI and FAIRE identifies regulatory elements that shape cell-type identify," Genome Res 21, 2011, 1757-1767.
Soutschek et al., "Therapeutic silencing of an endogenous gene by systemic administration of modified siRNAs," Nature (2004) 432: 173-8.
Spitz et al., "Transcription factors: from enhancer binding to developmental control," Nat. Rev. Genet. 2012, 13, 613-626.
Sripathy et al., "The KAP1 corepressor functions to coordinate the assembly of de novo HPI-demarcated microenvironments of heterochromatin required for KRAB zinc finger protein-mediated transcriptional repression," Molecular and Cellular Biology 26, 8623-8638 (2006).
Stemmer et al., "CCTop: An Intuitive, Flexible and Reliable CRISPR/Cas9 Target Prediction Tool," PLoS One, 2015, 10(4):e0124633, 11 pages.
Stephens, "False discovery rates: a new deal," Biostatistics, 2017, 18: 275-294.
Stepper et al., "Efficient targeted DNA methylation with chimeric dCas9-Dnmt3a-Dnmt3L methyltransferase," Nucleic Acids Res., 2017, 45(4): 1703-1713.
Sternberg et al., "Conformational Control of DNA Target Cleavage by CR1SPR-Cas9," Nature, 2015, vol. 527, No. 7576, pp. 110-113, 21 pages.
Sternberg et al., "DNA interrogation by the CRISPR RNA-guided endonuclease Cas9," Nature, 2014, 507, 62-67, 16 pages.
Stolzenburg et al., "Targeted silencing of the oncogenic transcription factor SOX2 in breast cancer," Nucleic Acids Res., 2012, 40(14): 6725-6740.
Su et al., "In vitro and in vivo mRNA delivery using lipid-enveloped pH-responsive polymer nanoparticles," Mol. Pharmaceutics, 2011, 8, 774-787, 26 pages.
Su et al. "Identification of biologically relevant enhancers in human erythroid cells," J Biol Chem 288, 8433-8444 (2013).
Sugimoto et al., "Thermodynamic parameters to predict stability of RNA/DNA hybrid duplexes," Biochemistry, 1995, 34: 11211-11216.
Sugimoto et al., "Thermodynamics-structure relationship of single mismatches in RNA/DNA duplexes," Biochemistry, 2000, 39: 11270-11281.

(56) References Cited

OTHER PUBLICATIONS

Sun et al., "Phage mutations in response to CRISPR diversification in a bacterial population," Environmental microbiology, 2013, 15(2): 463-470.
Sur et al., "The role of enhancers in cancer," Nat. Rev. Cancer., 2016, 16: 483-493.
Suzuki et al., "In vivo genome editing via CRISPR/Cas9 mediated homology-independent targeted integration," Nature, 2016, 540: 144-149, 44 pages.
Szczelkun et al., "Direct observation of R-loop formation by single RNA-guided Cas9 and Cascade effector complexes," Proceedings of the National Academy of Sciences, 2014, 11(27):9798-9803, 6 pages.
Szymczak et al., "Correction of multi-gene deficiency in vivo using a single 'self-cleaving' 2A peptide-based retroviral vector," Nature Biotechnology, 2004, 22(5): 589-594.
Tabebordbar et al., "In vivo gene editing in dystrophic mouse muscle and muscle stem cells," Science, 2016, 351, 407-11.
Takahashi et al., "A decade of transcription factor-mediated reprogramming to pluripotency," Nature Reviews, 2016, 17: 183-193.
Takahashi et al. "Induction of pluripotent stem cells from adult human fibroblasts by defined factors," Cell 1131, 861-872 (2007).
Takami et al., "Complete Genome Sequence of the Alkaliphilic Bacterium Bacillus halodurans and Genomic Sequence Comparison with Bacillus subtilis," Nucleic Acids Research, 2000, 28(21): 4317-4331.
Takeshima et al., "Mutation spectrum of the dystrophin gene in 442 Duchene/Becker muscular dystrophy cases from one Japanese referral center," Journal of Human Genetics, 2010, 55: 379-388.
Tam et al., "Benefits and limitations of genome-wide association studies," Nat. Rev. Genet., 2019, 20: 467-484.
Tan et al., "Rationally engineered *Staphylococcus aureus* Cas9 nucleases with high genome-wide specificity," Proc. Nat. Acad. Sci. USA, 2019, 116(46): 20969-20976.
Tanenbaum et al., "A Protein-Tagging System for Signal Amplification in Gene Expression and Fluorescence Imaging," Cell, 2014, pp. 635-646.
Teratani-Ota et al., "Induction of specific neuron types by overexpression of single transcription factors," In Vitro Cell Dev Biol Anim, 2016, 52(9): 961-973, 21 pages.
Thakore et al. "Abstract 385. Inhibiting the Myostatin Signaling Pathway using CRISPR/Cas9-Based Repressors." Molecular Therapy 24 (2016): S153.
Thakore et al., "Editing the epigenome: technologies for programmable transcription and epigenetic modulation," Nat Methods. 2016; 13:127-37, 27 pages.
Thakore et al., "Highly specific epigenome editing by CRISPR-Cas9 repressors for silencing of distal regulatory elements," Nat Methods, 2015, 12, 1143-9, 22 pages.
Thakore et al., "RNA-guided transcriptional silencing in vivo with *S. aureus* CRISPR-Cas9 repressors," Nature Communications, 2018, 9(1):1674, 9 pages.
Theodorou et al., "A high throughput embryonic stem cell screen identifies Oct-2 as a bifunctional regulator of neuronal differentiation," Genes Dev, 2009, 23: 575-588.
Thomson et al., "Human herpesvirus 6 (HHV-6) is a helper virus for adeno-associated virus type 2 (AAV-2) and the AAV-2 rep gene homologue inHHV-6 can mediate AAV-2 DNA replication and regulate gene expression," Virol., 1994, 204:304-311.
Thorgeirsson et al., "A variant associated with nicotine dependence, lung cancer and peripheral arterial disease," Nature, 2008, 452: 638-642, 14 pages.
Thurman et al. "The accessible chromatin landscape of the human genome," Nature 489, 75-82 (2012).
Tian et al., "CRISPR Interference-Based Platform for Multimodal Genetic Screens in Human iPSC-Derived Neurons," Neuron, 2019, 104: 239-255 e212, 30 pages.
Tinsley et al., "Amelioration of the dystrophic phenotype of mdx mice using a truncated utrophin transgene," Nature, 1996, 384(6607): 349-353.
Tone et al., "Smad3 and NFAT cooperate to induce Foxp3 expression through its enhancer," Nat. Immunol., 2008, 9, 194-202.
Tracy, "Human DNA sequence from clone RP11-34D15 on chromosome 10, complete sequence," Genbank entry, National Center for Biotechnology Information, <https://www.ncbi.nlm.nih.gov/nucleotide/AL139819.8> 2012, 27 pages.
Trinklein et al., "Identification and functional analysis of human transcriptional promoters," Genome Research, 2003, 13(2): 308-312.
Truong et al., "Development of an intein-mediated split-Cas9 system for gene therapy," Nucleic Acids Res. 2015; 43: 6450-6458.
Tsai et al., "GUIDE-seq enables genome-wide profiling of off-target cleavage by CRISPR-Cas nucleases," Nature Biotechnology, 2015, 33(2): 187-197, 23 pages.
Tsuchiya et al., "The "Spanning Protocol": A new DNA extraction method for efficient single-cell genetic diagnosis," Journal of Assisted Reproduction Genetics, 2005, 22(11-12):407-14.
Tsunemoto et al., "Diverse reprogramming codes for neuronal identity," Nature, 2018, 557: 375-380, 41 pages.
Tuan et al., "Transcription of the hypersensitive site HS2 enhancer in erythroid cells," Proceedings of the National Academy of Sciences of the United States of America 89, 11219-11223 (1992).
Tycko et al., "Screening *S. aureus* CRISPR-Cas9 Paired Guide RNAs for Efficient Targeted Deletion in Duchenne Muscular Dystrophy," Editas, Poster presented on May 5, 2016, 1 page.
Tyle, "Iontophoretic Devices for Drug Delivery," Pharm. Res., 1986, 3: 318-326.
Uchida et al, "In Vivo Messenger RNA Introduction into the Central Nervous System Using Polyplex Nanomicelle," PLoS One, 2013, 8: e56220, 8 pages.
Uetsuki et al., "Isolation and characterization of the human chromosomal gene for polypeptide chain elongation factor-I alpha," J. Biol. Chem., 1989, 264:5791-5798.
United States Patent Office Action for U.S. Appl. No. 15/549,842 dated May 17, 2019 (28 pages).
United States Patent Office Action for U.S. Appl. No. 15/549,842 dated Oct. 10, 2019 (14 pages).
United States Patent Office Action for U.S. Appl. No. 15/746,653 dated Jun. 28, 2019 (22 pages).
United States Patent Office Action for U.S. Appl. No. 16/093,272 dated Mar. 14, 2023 (9 pages).
United States Patent Office Action for U.S. Appl. No. 16/322,234 dated Mar. 1, 2022 (24 pages).
United States Patent Office Action for U.S. Appl. No. 16/322,234 dated Nov. 7, 2022 (25 pages).
United States Patent Office Action for U.S. Appl. No. 17/471,935 dated Jun. 2, 2023 (23 pages).
United States Patent Office Notice of Allowance for U.S. Appl. No. 15/549,842 dated Jan. 30, 2020 (7 pages).
United States Patent Office Notice of Allowance for U.S. Appl. No. 15/746,653 dated Jan. 10, 2020 (5 pages).
Urrutia, "KRAB-containing zinc-finger repressor proteins," Genome Biol., 2003, 4(10): 231, 8 pages.
Vakoc et al. "Proximity among distant regulatory elements at the beta-globin locus requires GATA-1 and FOG-1," Molecular Cell 17, 453-462 (2005).
Valanti et al., (2020). "Advances in biological therapies for dyslipidemias and atherosclerosis," Metabolism, 116:154461, 10 pages.
Van Arensbergen et al., "Genome-wide mapping autonomous promoter activity in human cells," Nature Biotechnology, 2017, 35(2): 145-153, 26 pages.
Van der Oost et al., "Unravelling the structural and mechanistic basis of CRISPR-Cas systems," Nature Reviews Microbiology, 2014, 12: 479-492, 14 pages.
Van Deutekom et al., "Advances in Duchenne muscular dystrophy gene therapy," Nat. Rev. Genet., 2003, 4: 774-783.
Van Tedeloo et al., (2000). "High-level transgene expression in primary human T lymphocytes and adult bone marrow CD34+ cells via electroporation-mediated gene delivery," Gene Therapy, 7(16):1431-1437.
Vaquerizas et al., "A census of human transcription factors: function, expression and evolution," Nat Rev Genet, 2009, 10: 252-263.

(56) References Cited

OTHER PUBLICATIONS

Veltrop et al., "A dystrophic Duchenne mouse model for testing human antisense oligonucleotides," PLoS One, 2018, 13(2): e0193289, 18 pages.
Verhoeyen et al., (2009). "Ch 8: Lentiviral vector gene transfer into human T cells," Methods Mol Biol, 506:97-114.
Verkhusha et al., "GFP-like flourescent proteins and chromoproteins of the class Anthozoa," Protein Structures: Kaleidoscope of Structural Properties and Functions, 2003, 405-439.
Verma et al., "Gene therapy—promises, problems and prospects," Nature, 1997, vol. 389, pp. 239-242.
Vierbuchen et al., "Direct lineage conversions: unnatural but useful?" Nat Biotechnol, 2011, 29:892-907, 39 pages.
Vierbuchen et al., "Molecular roadblocks for cellular reprogramming," Mol Cell, 2012, 47: 827-838.
Vierbuchen et al., "Direct conversion of fibroblasts to functional neurons by defined factors," Nature 463, 2010, 1035-1041, 22 pages.
Visel et al. "ChIP-seq accurately predicts tissue-specific activity of enhancers," Nature 457, 854-858 (2009), 16 pages.
Voss et al., "The role of enhancers in the regulation of cell-type-specific transcriptional control," Trends Biochem Sci., 1986, 11:287.
Wada et al., "Codon usage tabulated from the GenBank genetic sequence data," Nucl. Acids Res., 1990, 18: 2367-2411.
Wagner et al., "A phase 1/11 trial of MYO-029 in adult subjects with muscular dystrophy," Ann Neurol 63, 561-71 (2008).
Wang et al., "Construction and analysis of compact muscle-specific promoters for AAV vectors," Gene Ther, 2008, 15: 1489-1499.
Wang et al., "Gene Essentiality Profiling Reveals Gene Networks and Synthetic Lethal Interactions with Oncogenic Ras," Cell, 2017, 168: 890-903.e15, 30 pages.
Wang et al., "Genetic screens in human cells using the CRISPR-Cas9 system," Science, 2014, 343: 80-84, 12 pages.
Wang et al., "Identification and characterization of essential genes in the human genome," Science, 2015, 350: 1096-1101.
Wang et al., "Systemic human minidystrophin gene transfer improves functions and life span of dystrophin and dystrophin/utrophin-deficient mice," J. Orthop. Res., 2009, 27: 421-426.
Wang et al., "Unbiased detection of off-target cleavage by CRISPR-Cas9 and TALENs using integrase-defective lentiviral vectors," Nature Biotechnology, 2015, 33(2): 175-8, 5 pages.
Wang et al., (2012). "Phenotypic and functional attributes of lentivirus modified CD19-specific human CD8+ central memory T cells manufactured at clinical scale," J. Immunother, 35(9):689-701, 28 pages.
Wang et al., "Epstein-Barr virus nuclear protein 2 interacts with p300, CBP, and PCAF histone acetyltransferases inactivation of the LMPI promoter," Proc Natl Acad Sci US A 97, 430-435 (2000).
Wang et al. "Genome-wide mapping of HATs and HDACs reveals distinct functions inactive and inactive genes," Cell 138, 1019-1031 (2009).
Wapinski et al., "Hierarchical mechanisms for direct reprogramming of fibroblasts to neurons," Cell, 2013, 155: 621-635.
Ward et al., (2019). "Statin Toxicity," Circ. Res., 124:328-350, 45 pages.
Watkins et al., "Thermodynamic contributions of single internal rA.dA, rC.dC, rG.dG and rU.dT mismatches in RNA/DNA duplexes," Nucleic Acids Research, 2011, 39(5): 1894-1902.
Wei et al., "Targeting Regnase-1 programs long-lived effector T cells for cancer therapy," Nature, 2019, 576(7787): 471-476, 46 pages.
Westendorp et al., "E2F7 represses a network of oscillating cell cycle genes to control S-phase progression," Nucleic Acids Res, 2012, 40: 3511-3523.
Wherry, "T cell exhaustion," Nat. Immunology, 2011, 12: 492-499.
Whisstock et al., "Prediction of protein function from protein sequence," Q_ Rev. Biophysics., 2003, 36(3): 307-340.
Wienert et al., "Editing the genome to introduce a beneficial naturally occurring mutation associated with increased fetal globin," Nat Commun 6, 2015, 7085, 8 pages.

Wiggins et al., "High flexibility of DNA on short length scales probed by atomic force microscopy," Nature Nanotechnology, 2006, 1(2): 137-141.
Wiles et al., "CRISPR-Cas9 mediated genome editing and guide RNA design," Mammalian Genome, 2015, 26(9):501-510.
Willmann et al., "Mammalian animal models for Duchenne muscular dystrophy," Neuromuscular Disorders, 2009, 19(4): 241-249.
Wood, "Neuromuscular disease: CRISPR/Cas9 gene-editing platform corrects mutations associated with Duchenne muscular dystrophy," Nature Reviews Neurology, 2015, 11 (4): 184.
Wright et al., (2006). "Standardized reagents and protocols for engineering zinc finger nucleases by modular assembly," Nat. Protoc., 1(3):1637-1652.
Wright et al., (2015). "Rational design of a split-Cas9 enzyme complex," PNAS, 112(10):2984-2989.
Wu et al., "Induction of anion exchanger-1 translation and its opposite roles in the carcinogenesis of gastric cancer cells and differentiation of K562 cells," Oncogene, 2010, 29: 1987-1996. Abstract only, 1 page.
Wu et al. "Genome-wide binding of the CRISPR endonuclease Cas9 in mammalian cells," Nat Biotechnol 32, 670-676 (2014), 20 pages.
Wylie et al., "Distinct transcriptomes define rostral and caudal serotonin neurons," J Neurosci, 2010, 30: 670-684.
Xie et al., "Multiplexed Engineering and Analysis of Combinatorial Enhancer Activity in Single Cells," Mol. Cell, 2017, 66: 285-299. e5, 21 pages.
Xie et al., "sgRNAcas9: a software package for designing CRISPR sgRNA and evaluating potential off-target cleavage sites," PLoS One, 2014, 9(6): e100448, 9 pages.
Xu et al., "Recent advances in neuroepigenetic editing," Curr Opin Neurobiol, 2019, 59: 26-33.
Xue et al., "Synthetic mRNAs Drive Highly Efficient iPS Cell Differentiation to Dopaminergic Neurons," Stem Cells Transl Med, 2019, 8: 112-123.
Yang et al., "Determination of protein-DNA binding constants and specificities from statistical analyses of single molecules: MutS-DNA interactions," Nucleic Acids Research, 2005, 33(13):4322-4334.
Yang et al., "Gene Reactivation by 5-Aza-2'-Deoxycytidine-Induced Demethylation Requires SRCAP-Mediated HZA.Z Insertion to Establish Nucleosome Depleted Regions", PLoS Genetics, 2012, vol. 8, Issue 3, e1002604, 12 pages.
Yang et al., "Generation of pure GABAergic neurons by transcription factor programming," Nat Methods, 2017, 14: 621-628, 19 pages.
Yin et al., "Programming biomolecular self-assembly pathways," Nature, 2008, 451(7176): 318-323.
Young et al., "A Single CRISPR-Cas9 Deletion Strategy that Targets the Majority of DMD Patients Restores Dystrophin Function in hiPSC-Derived Muscle Cells," Cell Stem Cell, 2016, 18: 533-540.
Young et al., "Creation of a Novel Humanized Dystrophic Mouse Model of Duchenne Muscular Dystrophy and Application of a CRISPR/Cas9 Gene Editing Therapy," Journal of Neuromuscular Diseases, 2017, 4(2): 139-145, 10 pages.
Youngblood et al., "Chronic virus infection enforces demethylation of the locus that encodes PD-1 in antigen-specific CD8+ T cells," Immunity, 2011, 35: 400-412.
Younossi et al., "Epidemiology of chronic liver diseases in the USA in the past three decades," Gut, 2020, 69(3): 564-568.
Yu et al., "Dystrophin-deficient large animal models: translational research and exon skipping," Am J Transl Res, 2015, 7(8): 1314-1331.
Zenser et al., "A new TAP system for isolation of plant protein complexes and subsequent mass-spec analysis," https://www.sigmaaldrich.com/deepweb/assets/sigmaaldrich/product/documents/388/028/flag_ha_tap_poster.pdf, published 2008, printed as pp. 1/4-4/4.
Zetsche et al., "Cpf1 Is a Single RNA-Guided Endonuclease of a Class 2 CRISPR-Cas System," Cell, 2015, 163(3):759-71.
Zetsche et al., (2015). "A split-Cas9 architecture for inducible genome editing and transcription modulation," Nat. Biotechnol, 33(2):139-142, 6 pages.

(56) References Cited

OTHER PUBLICATIONS

Zhang et al., "Adenovirus-Adeno-Associated Virus Hybrid for Large-Scale Recombinant Adeno-Associated Virus Production," Hum Gene Ther. 2009; 20:922-9.

Zhang et al., "Comprehensive Structure-Function Study of Neurogenin3 Disease-Causing Alleles during Human Pancreas and Intestinal Organoid Development," Dev Cell, 2019, 50(3):367-380.87, 22 pages.

Zhang et al., "Efficient precise knockin with a double cute HOR donor after CRISPR/Cas9-mediated double-stranded DNA cleavage," Genome Biol, 2017 18(35): 18 pages.

Zhang et al., "Myoediting: Toward Prevention of Muscular Dystrophy by Therapeutic Genome Editing," Physiological Reviews, 2018, 98(3): 1205-1240.

Zhang et al., "Propagated Perturbations from a Peripheral Mutation Show Interactions Supporting WW Domain Thermostability," Structure, 2018, 26: 1474-1485, 18 pages.

Zhang et al., "Rapid single-step induction of functional neurons from human pluripotent stem cells," Neuron, 2013, 78: 785-798.

Zhang, (2019). "Development of CRISPR-Cas systems for genome editing and beyond," Q. Rev. Biophys. 52:E6, 31 pages.

Zhang et al. "Efficient construction of sequence-specific TAL effectors for modulating mammalian transcription," Nat Biotechnol 29, 2011, 149-153.

Zhang et al. "Model-based analysis of ChIP-Seq (MACS)," Genome Biology 9, RI37 (2008), 9 pages.

Zhao et al., "High-efficiency transfection of primary human and mouse T lymphocytes using RNA electroporation," Mol. Ther., 2006, 13: 151-159.

Zhao et al., "Intracellular delivery of artificial transcription factors fused to the protein transduction domain of HIV-1 Tat," Protein Expr Purif, 2013, 90(1): 27-33.

Zhao et al., "The LIM-homeobox gene Lhx8 is required for the development of many cholinergic neurons in the mouse forebrain," Proc Natl Acad Sci U S A, 2003, 100: 9005-9010.

Zheng et al., "Role of conserved non-coding DNA elements in the Foxp3 gene in regulatory T-cell fate," Nature, 2010, 463, 808-812, 14 pages.

Zheng et al., "Foxp3 in control of the regulatory T cell lineage," Nat. Immunol. 2007, 8, 457-462.

Zhou et al., "Haploinsufficiency of utrophin gene worsens skeletal muscle inflammation and fibrosis in mdx mice," Journal of the Neurological Sciences, 2008, 264(1): 106-111, 11 pages.

Zhou et al., "High-throughput screening of a CRISPR/Cas9 library for functional genomics in human cells," Nature, 2014,509(7501): 487-491.

Zhu et al., "The role of histone deacetylase 7 (HDAC7) in cancer cell proliferation: regulation on c-Myc," J. Mol. Med, 2011, 89: 279-289.

Zincarelli et al., "Analysis of AAV serotypes 1-9 mediated gene expression and tropism in mice after systemic injection," Mol Ther 16, 1073-80 (2008).

Braliou et al., (2001). "The v-ErbA oncoprotein quenches the activity of an erythroid-specific enhancer," Oncogene, 20(7):775-87.

Broude et al., (2007). "p21 (CDKN1A) is a negative regulator of p53 stability," Cell Cycle, 6(12):1468-1471.

Cortés-Mancera et al., (2022). "Gene-Targeted DNA Methylation: Towards Long-Lasting Reprogramming of Gene Expression?" Adv Exp Med Biol., 1389:515-533.

Kao et al., (2014). "Ectopic DNMT3L triggers assembly of a repressive complex for retroviral silencing in somatic cells," J Virol., 88(18):10680-95.

Li et al., (2006). "The histone methyltransferase SETDB1 and the DNA methyltransferase DNMT3A interact directly and localize to promoters silenced in cancer cells," J. Biol. Chem., 281(28):19489-19500.

Hochstrasser et al., (2014). "CasA mediates Cas3-catalyzed target degradation during CRISPR RNA-guided interference," PNAS, 111(18):6618-23.

Moussa et al., (2021). "Here to stay: Writing lasting epigenetic memories," Cell, 184(9):2281-2283.

Murphy et al., (2016). "The Transcriptional Repressive Activity of KRAB Zinc Finger Proteins Does Not Correlate with Their Ability to Recruit TRIM28," PLoS One, 11(9):e0163555, 19 pages.

O'Geen et al., (2022). "Determinants of heritable gene silencing for KRAB-dCas9+DNMT3 and Ezh2-dCas9+DNMT3 hit-and-run epigenome editing," Nucleic Acids Res, 50(6):3239-3253.

Policarpi et al., (2021). "Epigenetic editing: Dissecting chromatin function in context," Bioessays, 43(5):e2000316, 16 pages.

Tycko et al., (2020). "High-Throughput Discovery and Characterization of Human Transcriptional Effectors," Cell, 183(7):2020-2035, 33 pages.

Alerasool et al., (2020). "An efficient KRAB domain for CRISPRi applications in human cells," Nat Methods, 17:1093-1096, 14 pages.

Fuks, (2005). "DNA methylation and histone modifications: teaming up to silence genes," Current Opinion in Genetics & Development, 15(5):490-495.

Kim et al., (2007). "Zinc-fingers and homeoboxes 1 (ZHX1) binds DNA methyltransferase (DNMT) 3B to enhance DNMT3B-mediated transcriptional repression," Biochemical and Biophysical Research Communications, 355(2):318-323.

Saha et al., (2021). "The NIH Somatic Cell Genome Editing program," Nature, 592:195-204.

Pickar-Oliver et al., (2019). "The next generation of CRISPR-Cas technologies and applications," Nature Reviews Molecular Cell Biology, 20(8):490-507, 41 pages.

Stepper, (2020). "Dissertation: CRISPR-Cas9 fusions for synthetic epigenetics," Von der Fakultat 4: Energie-, Verfahrens- und Biotechnik, Institut für Biochemie und Technische Biochemie der Universität Stuttgart, 152 pages.

Abaandou et al., (2021). "Affecting HEK293 Cell Growth and Production Performance by Modifying the Expression of Specific Genes," Cells, 10:1667, 21 pages.

Adikusuma et al., (2017). "Versatile single-step-assembly CRISPR/Cas9 vectors for dual gRNA expression," PLoS One, 12(12):e0187236, 11 pages.

Cano-Rodriguez et al., (2016). "Epigenetic Editing: On the Verge of Reprogramming Gene Expression at Will," Curr Genet Med Rep, 4:170-179.

Carcagno et al., (2014). "Neurogenin3 restricts serotonergic neuron differentiation to the hindbrain," J Neurosci, 34(46):15223-33.

Das et al., (2016). "Tet-On Systems for Doxycycline-inducible Gene Expression," Current Gene Therapy, 16:156-167.

Kalsner et al., (2015). "Prader-Willi, Angelman, and 15q11-q13 Duplication Syndromes," Pediatric Clinics of North America United States, 62(3):587-606, 25 pages.

Ohta et al., (1999). "Imprinting-Mutation Mechanisms in Prader-Willi Syndrome," The American Journal of Human Genetics, 64(2):397-413.

Orth et al., (2000). "Structural basis of gene regulation by the tetracycline inducible Tet repressor-operator system," natural structural biology, 7(3):215-219.

Yang et al., (2016). "A dual AAV system enables the Cas9-mediated correction of a metabolic liver disease in newborn mice," Nature Biotechnology, 34(3):334-338, 18 pages.

Brezgin et al., "Dead Cas Systems: Types, Principles, and Applications," Int J Mol Sci., 2019, 20:6041, pp. 1-26.

Katzmann et al., "Gene Therapy Targeting PCSK9," Metabolites, 2022, 12:70, pp. 1-13.

Musunuru, "Moving toward genome-editing therapies for cardiovascular diseases," J Clin Invest., 2022, 132(1): e148555, pp. 1-8.

Musunuru et al., "In vivo CRISPR base editing of PCSK9 durably lowers cholesterol in primates," Nature, 2021, 593:429-434.

Walker et al., "CRISPR Gene Editing in Lipid Disorders and Atherosclerosis: Mechanisms and Opportunities," Metabolites, 2021, 11:857, pp. 1-14.

Whittaker et al., "Epigenome Editing Durability Varies Widely Across Cardiovascular Disease Target Genes," Ateriosler Thromb Vasc Biol., 2023, 43(10):2075-2077.

\* cited by examiner

SEQUENCE LISTING

Sequence total quantity: 395

```
SEQ ID NO: 1              moltype = DNA   length = 20
FEATURE                   Location/Qualifiers
misc_feature              1..20
                          note = PCSK9
source                    1..20
                          mol_type = other DNA
                          organism = Synthetic construct
SEQUENCE: 1
gcgcgtaatc tgacgctgtt                                             20

SEQ ID NO: 2              moltype = DNA   length = 20
FEATURE                   Location/Qualifiers
misc_feature              1..20
                          note = PCSK9
source                    1..20
                          mol_type = other DNA
                          organism = Synthetic construct
SEQUENCE: 2
atcagatagg atcgtccgat                                             20

SEQ ID NO: 3              moltype = DNA   length = 20
FEATURE                   Location/Qualifiers
misc_feature              1..20
                          note = PCSK9
source                    1..20
                          mol_type = other DNA
                          organism = Synthetic construct
SEQUENCE: 3
aggtttccgc agcgacgtcg                                             20

SEQ ID NO: 4              moltype = DNA   length = 20
FEATURE                   Location/Qualifiers
misc_feature              1..20
                          note = PCSK9
source                    1..20
                          mol_type = other DNA
                          organism = Synthetic construct
SEQUENCE: 4
gggcgccgcc gttcagttca                                             20

SEQ ID NO: 5              moltype = DNA   length = 20
FEATURE                   Location/Qualifiers
misc_feature              1..20
                          note = PCSK9
source                    1..20
                          mol_type = other DNA
                          organism = Synthetic construct
SEQUENCE: 5
ggtgctagcc ttgcgttccg                                             20

SEQ ID NO: 6              moltype = DNA   length = 20
FEATURE                   Location/Qualifiers
misc_feature              1..20
                          note = PCSK9
source                    1..20
                          mol_type = other DNA
                          organism = Synthetic construct
```

```
SEQUENCE: 6
cattaacgga accccggac                                                        20

SEQ ID NO: 7            moltype = DNA  length = 20
FEATURE                 Location/Qualifiers
misc_feature            1..20
                        note = PCSK9
source                  1..20
                        mol_type = other DNA
                        organism = Synthetic construct
SEQUENCE: 7
aggatcgtcc gatggggctc                                                       20

SEQ ID NO: 8            moltype = DNA  length = 20
FEATURE                 Location/Qualifiers
misc_feature            1..20
                        note = PCSK9
source                  1..20
                        mol_type = other DNA
                        organism = Synthetic construct
SEQUENCE: 8
ccgttaatgt ttaatcagat                                                       20

SEQ ID NO: 9            moltype = DNA  length = 19
FEATURE                 Location/Qualifiers
misc_feature            1..19
                        note = PCSK9
source                  1..19
                        mol_type = other DNA
                        organism = Synthetic construct
SEQUENCE: 9
cgtaatctga cgctgtttg                                                        19

SEQ ID NO: 10           moltype = DNA  length = 20
FEATURE                 Location/Qualifiers
misc_feature            1..20
                        note = PCSK9
source                  1..20
                        mol_type = other DNA
                        organism = Synthetic construct
SEQUENCE: 10
ggtgtgggtg cttgacgcct                                                       20

SEQ ID NO: 11           moltype = DNA  length = 20
FEATURE                 Location/Qualifiers
misc_feature            1..20
                        note = PCSK9
source                  1..20
                        mol_type = other DNA
                        organism = Synthetic construct
SEQUENCE: 11
acccactgca cgctggacag                                                       20

SEQ ID NO: 12           moltype = DNA  length = 20
FEATURE                 Location/Qualifiers
misc_feature            1..20
                        note = PCSK9
source                  1..20
                        mol_type = other DNA
                        organism = Synthetic construct
SEQUENCE: 12
gcacagtaac aacccctggt                                                       20

SEQ ID NO: 13           moltype = DNA  length = 20
FEATURE                 Location/Qualifiers
misc_feature            1..20
                        note = PCSK9
source                  1..20
                        mol_type = other DNA
                        organism = Synthetic construct
SEQUENCE: 13
ccatccattc tttctctagg                                                       20

SEQ ID NO: 14           moltype = DNA  length = 20
FEATURE                 Location/Qualifiers
misc_feature            1..20
                        note = LPA
source                  1..20
                        mol_type = other DNA
```

```
                            organism = Synthetic construct
SEQUENCE: 14
aaggagacat aaaggcaatg                                                    20

SEQ ID NO: 15               moltype = DNA  length = 20
FEATURE                     Location/Qualifiers
misc_feature                1..20
                            note = LPA
source                      1..20
                            mol_type = other DNA
                            organism = Synthetic construct
SEQUENCE: 15
ggcaatgtgg agcagctgag                                                    20

SEQ ID NO: 16               moltype = DNA  length = 20
FEATURE                     Location/Qualifiers
misc_feature                1..20
                            note = LPA
source                      1..20
                            mol_type = other DNA
                            organism = Synthetic construct
SEQUENCE: 16
ggagcagctg aggggggaaa                                                    20

SEQ ID NO: 17               moltype = DNA  length = 20
FEATURE                     Location/Qualifiers
misc_feature                1..20
                            note = LPA
source                      1..20
                            mol_type = other DNA
                            organism = Synthetic construct
SEQUENCE: 17
tgtcaataga tgctgggaag                                                    20

SEQ ID NO: 18               moltype = DNA  length = 20
FEATURE                     Location/Qualifiers
misc_feature                1..20
                            note = LPA
source                      1..20
                            mol_type = other DNA
                            organism = Synthetic construct
SEQUENCE: 18
agtgcaatgt caatagatgc                                                    20

SEQ ID NO: 19               moltype = DNA  length = 20
FEATURE                     Location/Qualifiers
misc_feature                1..20
                            note = LPA
source                      1..20
                            mol_type = other DNA
                            organism = Synthetic construct
SEQUENCE: 19
tttataagac tctatattca                                                    20

SEQ ID NO: 20               moltype = DNA  length = 20
FEATURE                     Location/Qualifiers
misc_feature                1..20
                            note = LPA
source                      1..20
                            mol_type = other DNA
                            organism = Synthetic construct
SEQUENCE: 20
catgtaagtc aacaatgtcc                                                    20

SEQ ID NO: 21               moltype = DNA  length = 20
FEATURE                     Location/Qualifiers
misc_feature                1..20
                            note = LPA
source                      1..20
                            mol_type = other DNA
                            organism = Synthetic construct
SEQUENCE: 21
gtcaacaatg tcctgggatt                                                    20

SEQ ID NO: 22               moltype = DNA  length = 20
FEATURE                     Location/Qualifiers
misc_feature                1..20
                            note = LPA
source                      1..20
```

```
                              mol_type = other DNA
                              organism = Synthetic construct
SEQUENCE: 22
catatacaag attttgaact                                                   20

SEQ ID NO: 23                 moltype = DNA  length = 20
FEATURE                       Location/Qualifiers
misc_feature                  1..20
                              note = LPA
source                        1..20
                              mol_type = other DNA
                              organism = Synthetic construct
SEQUENCE: 23
gcaccgtgac agtcttcacg                                                   20

SEQ ID NO: 24                 moltype = DNA  length = 20
FEATURE                       Location/Qualifiers
misc_feature                  1..20
                              note = MYLIP
source                        1..20
                              mol_type = other DNA
                              organism = Synthetic construct
SEQUENCE: 24
ttggcgggga cccgagctga                                                   20

SEQ ID NO: 25                 moltype = DNA  length = 20
FEATURE                       Location/Qualifiers
misc_feature                  1..20
                              note = MYLIP
source                        1..20
                              mol_type = other DNA
                              organism = Synthetic construct
SEQUENCE: 25
ctgtcgcagc gcaggcagtt                                                   20

SEQ ID NO: 26                 moltype = DNA  length = 20
FEATURE                       Location/Qualifiers
misc_feature                  1..20
                              note = MYLIP
source                        1..20
                              mol_type = other DNA
                              organism = Synthetic construct
SEQUENCE: 26
gctggagtgc ggcgccaccg                                                   20

SEQ ID NO: 27                 moltype = DNA  length = 20
FEATURE                       Location/Qualifiers
misc_feature                  1..20
                              note = MYLIP
source                        1..20
                              mol_type = other DNA
                              organism = Synthetic construct
SEQUENCE: 27
cggcgccacc gcggaggaca                                                   20

SEQ ID NO: 28                 moltype = DNA  length = 20
FEATURE                       Location/Qualifiers
misc_feature                  1..20
                              note = MYLIP
source                        1..20
                              mol_type = other DNA
                              organism = Synthetic construct
SEQUENCE: 28
cagctctgcg gacccttgtc                                                   20

SEQ ID NO: 29                 moltype = DNA  length = 20
FEATURE                       Location/Qualifiers
misc_feature                  1..20
                              note = MYLIP
source                        1..20
                              mol_type = other DNA
                              organism = Synthetic construct
SEQUENCE: 29
ccccgcgcac accaaagaga                                                   20

SEQ ID NO: 30                 moltype = DNA  length = 20
FEATURE                       Location/Qualifiers
misc_feature                  1..20
                              note = MYLIP
```

-continued

```
source                  1..20
                        mol_type = other DNA
                        organism = Synthetic construct
SEQUENCE: 30
cctcgtcaca taacacagca                                                         20

SEQ ID NO: 31           moltype = DNA  length = 20
FEATURE                 Location/Qualifiers
misc_feature            1..20
                        note = MYLIP
source                  1..20
                        mol_type = other DNA
                        organism = Synthetic construct
SEQUENCE: 31
acctccatca gcaccgcgtc                                                         20

SEQ ID NO: 32           moltype = DNA  length = 20
FEATURE                 Location/Qualifiers
misc_feature            1..20
                        note = MYLIP
source                  1..20
                        mol_type = other DNA
                        organism = Synthetic construct
SEQUENCE: 32
ggaggcgaaa gccaacggcg                                                         20

SEQ ID NO: 33           moltype = DNA  length = 20
FEATURE                 Location/Qualifiers
misc_feature            1..20
                        note = MYLIP
source                  1..20
                        mol_type = other DNA
                        organism = Synthetic construct
SEQUENCE: 33
gttgaggcag tcctcgccgt                                                         20

SEQ ID NO: 34           moltype = DNA  length = 20
FEATURE                 Location/Qualifiers
misc_feature            1..20
                        note = ANGLPTL3
source                  1..20
                        mol_type = other DNA
                        organism = Synthetic construct
SEQUENCE: 34
tacattcgtg caagttaaca                                                         20

SEQ ID NO: 35           moltype = DNA  length = 20
FEATURE                 Location/Qualifiers
misc_feature            1..20
                        note = ANGLPTL3
source                  1..20
                        mol_type = other DNA
                        organism = Synthetic construct
SEQUENCE: 35
cctaccaacc ttaccttttc                                                         20

SEQ ID NO: 36           moltype = DNA  length = 20
FEATURE                 Location/Qualifiers
misc_feature            1..20
                        note = ANGLPTL3
source                  1..20
                        mol_type = other DNA
                        organism = Synthetic construct
SEQUENCE: 36
tatatagagt taagaagtct                                                         20

SEQ ID NO: 37           moltype = DNA  length = 20
FEATURE                 Location/Qualifiers
misc_feature            1..20
                        note = ANGLPTL3
source                  1..20
                        mol_type = other DNA
                        organism = Synthetic construct
SEQUENCE: 37
aacgtggaac tgttttcttc                                                         20

SEQ ID NO: 38           moltype = DNA  length = 20
FEATURE                 Location/Qualifiers
misc_feature            1..20
```

```
                        note = ANGLPTL3
source                  1..20
                        mol_type = other DNA
                        organism = Synthetic construct
SEQUENCE: 38
attttcaatt tcaagcaacg                                                    20

SEQ ID NO: 39           moltype = DNA  length = 20
FEATURE                 Location/Qualifiers
misc_feature            1..20
                        note = ANGLPTL3
source                  1..20
                        mol_type = other DNA
                        organism = Synthetic construct
SEQUENCE: 39
attctggagg aaataactag                                                    20

SEQ ID NO: 40           moltype = DNA  length = 20
FEATURE                 Location/Qualifiers
misc_feature            1..20
                        note = ANGLPTL3
source                  1..20
                        mol_type = other DNA
                        organism = Synthetic construct
SEQUENCE: 40
gcaaatcttg attttggctc                                                    20

SEQ ID NO: 41           moltype = DNA  length = 20
FEATURE                 Location/Qualifiers
misc_feature            1..20
                        note = ANGLPTL3
source                  1..20
                        mol_type = other DNA
                        organism = Synthetic construct
SEQUENCE: 41
agccaatggc ctccttcagt                                                    20

SEQ ID NO: 42           moltype = DNA  length = 20
FEATURE                 Location/Qualifiers
misc_feature            1..20
                        note = ANGLPTL3
source                  1..20
                        mol_type = other DNA
                        organism = Synthetic construct
SEQUENCE: 42
taagaccatg tcccaactga                                                    20

SEQ ID NO: 43           moltype = DNA  length = 20
FEATURE                 Location/Qualifiers
misc_feature            1..20
                        note = ANGLPTL3
source                  1..20
                        mol_type = other DNA
                        organism = Synthetic construct
SEQUENCE: 43
agactttgtc cataagacga                                                    20

SEQ ID NO: 44           moltype = DNA  length = 20
FEATURE                 Location/Qualifiers
misc_feature            1..20
                        note = APOC3
source                  1..20
                        mol_type = other DNA
                        organism = Synthetic construct
SEQUENCE: 44
ggggcacccg tccagctccg                                                    20

SEQ ID NO: 45           moltype = DNA  length = 20
FEATURE                 Location/Qualifiers
misc_feature            1..20
                        note = APOC3
source                  1..20
                        mol_type = other DNA
                        organism = Synthetic construct
SEQUENCE: 45
tgacctttgc ccagcgccct                                                    20

SEQ ID NO: 46           moltype = DNA  length = 20
FEATURE                 Location/Qualifiers
```

```
                    misc_feature         1..20
                                         note = APOC3
                    source               1..20
                                         mol_type = other DNA
                                         organism = Synthetic construct
SEQUENCE: 46
tccagatgca gcaagcgggc                                                   20

SEQ ID NO: 47       moltype = DNA  length = 20
FEATURE             Location/Qualifiers
misc_feature        1..20
                    note = APOC3
source              1..20
                    mol_type = other DNA
                    organism = Synthetic construct
SEQUENCE: 47
tagggatgaa ctgagcagac                                                   20

SEQ ID NO: 48       moltype = DNA  length = 20
FEATURE             Location/Qualifiers
misc_feature        1..20
                    note = APOC3
source              1..20
                    mol_type = other DNA
                    organism = Synthetic construct
SEQUENCE: 48
agaagcactt gctagagcta                                                   20

SEQ ID NO: 49       moltype = DNA  length = 20
FEATURE             Location/Qualifiers
misc_feature        1..20
                    note = APOC3
source              1..20
                    mol_type = other DNA
                    organism = Synthetic construct
SEQUENCE: 49
ctgctccagg taatgccctc                                                   20

SEQ ID NO: 50       moltype = DNA  length = 20
FEATURE             Location/Qualifiers
misc_feature        1..20
                    note = APOC3
source              1..20
                    mol_type = other DNA
                    organism = Synthetic construct
SEQUENCE: 50
gggagagttg ggaaatccct                                                   20

SEQ ID NO: 51       moltype = DNA  length = 20
FEATURE             Location/Qualifiers
misc_feature        1..20
                    note = APOC3
source              1..20
                    mol_type = other DNA
                    organism = Synthetic construct
SEQUENCE: 51
aggaagcctc ggagctggac                                                   20

SEQ ID NO: 52       moltype = DNA  length = 20
FEATURE             Location/Qualifiers
misc_feature        1..20
                    note = APOC3
source              1..20
                    mol_type = other DNA
                    organism = Synthetic construct
SEQUENCE: 52
ccctggagat gatataaaac                                                   20

SEQ ID NO: 53       moltype = DNA  length = 20
FEATURE             Location/Qualifiers
misc_feature        1..20
                    note = APOC3
source              1..20
                    mol_type = other DNA
                    organism = Synthetic construct
SEQUENCE: 53
tcataacctg aagaacatgg                                                   20

SEQ ID NO: 54       moltype = DNA  length = 20
```

```
FEATURE                 Location/Qualifiers
misc_feature            1..20
                        note = APOB
source                  1..20
                        mol_type = other DNA
                        organism = Synthetic construct
SEQUENCE: 54
gtccatcgcc agctgcggtg                                               20

SEQ ID NO: 55           moltype = DNA  length = 20
FEATURE                 Location/Qualifiers
misc_feature            1..20
                        note = APOB
source                  1..20
                        mol_type = other DNA
                        organism = Synthetic construct
SEQUENCE: 55
ggcgcccgca ccccatttat                                               20

SEQ ID NO: 56           moltype = DNA  length = 20
FEATURE                 Location/Qualifiers
misc_feature            1..20
                        note = APOB
source                  1..20
                        mol_type = other DNA
                        organism = Synthetic construct
SEQUENCE: 56
cagagcggcc gcgcactcac                                               20

SEQ ID NO: 57           moltype = DNA  length = 20
FEATURE                 Location/Qualifiers
misc_feature            1..20
                        note = APOB
source                  1..20
                        mol_type = other DNA
                        organism = Synthetic construct
SEQUENCE: 57
ctcagcggca gcaaccgaga                                               20

SEQ ID NO: 58           moltype = DNA  length = 20
FEATURE                 Location/Qualifiers
misc_feature            1..20
                        note = APOB
source                  1..20
                        mol_type = other DNA
                        organism = Synthetic construct
SEQUENCE: 58
tcccggtggg aatgcgcggc                                               20

SEQ ID NO: 59           moltype = DNA  length = 20
FEATURE                 Location/Qualifiers
misc_feature            1..20
                        note = APOB
source                  1..20
                        mol_type = other DNA
                        organism = Synthetic construct
SEQUENCE: 59
gcattcccac cgggacctgc                                               20

SEQ ID NO: 60           moltype = DNA  length = 20
FEATURE                 Location/Qualifiers
misc_feature            1..20
                        note = APOB
source                  1..20
                        mol_type = other DNA
                        organism = Synthetic construct
SEQUENCE: 60
gcctcgcggc cctggctggc                                               20

SEQ ID NO: 61           moltype = DNA  length = 20
FEATURE                 Location/Qualifiers
misc_feature            1..20
                        note = APOB
source                  1..20
                        mol_type = other DNA
                        organism = Synthetic construct
SEQUENCE: 61
cccggccaac ctcgtgccgc                                               20
```

```
SEQ ID NO: 62            moltype = DNA   length = 20
FEATURE                  Location/Qualifiers
misc_feature             1..20
                         note = APOB
source                   1..20
                         mol_type = other DNA
                         organism = Synthetic construct
SEQUENCE: 62
agcgccagca gcgcgggcct                                                 20

SEQ ID NO: 63            moltype = DNA   length = 20
FEATURE                  Location/Qualifiers
misc_feature             1..20
                         note = APOB
source                   1..20
                         mol_type = other DNA
                         organism = Synthetic construct
SEQUENCE: 63
ctccctctgc gcccgcagag                                                 20

SEQ ID NO: 64            moltype = RNA   length = 20
FEATURE                  Location/Qualifiers
misc_feature             1..20
                         note = PCSK9
source                   1..20
                         mol_type = other RNA
                         organism = Synthetic construct
SEQUENCE: 64
gcgcgtaatc tgacgctgtt                                                 20

SEQ ID NO: 65            moltype = RNA   length = 20
FEATURE                  Location/Qualifiers
misc_feature             1..20
                         note = PCSK9
source                   1..20
                         mol_type = other RNA
                         organism = Synthetic construct
SEQUENCE: 65
atcagatagg atcgtccgat                                                 20

SEQ ID NO: 66            moltype = RNA   length = 20
FEATURE                  Location/Qualifiers
misc_feature             1..20
                         note = PCSK9
source                   1..20
                         mol_type = other RNA
                         organism = Synthetic construct
SEQUENCE: 66
aggtttccgc agcgacgtcg                                                 20

SEQ ID NO: 67            moltype = RNA   length = 20
FEATURE                  Location/Qualifiers
misc_feature             1..20
                         note = PCSK9
source                   1..20
                         mol_type = other RNA
                         organism = Synthetic construct
SEQUENCE: 67
gggcgccgcc gttcagttca                                                 20

SEQ ID NO: 68            moltype = RNA   length = 20
FEATURE                  Location/Qualifiers
misc_feature             1..20
                         note = PCSK9
source                   1..20
                         mol_type = other RNA
                         organism = Synthetic construct
SEQUENCE: 68
ggtgctagcc ttgcgttccg                                                 20

SEQ ID NO: 69            moltype = RNA   length = 20
FEATURE                  Location/Qualifiers
source                   1..20
                         mol_type = other RNA
                         organism = Synthetic construct
SEQUENCE: 69
cattaacgga accccggac                                                  20

SEQ ID NO: 70            moltype = RNA   length = 20
```

```
                        -continued

FEATURE                 Location/Qualifiers
misc_feature            1..20
                        note = PCSK9
source                  1..20
                        mol_type = other RNA
                        organism = Synthetic construct
SEQUENCE: 70
aggatcgtcc gatggggctc                                               20

SEQ ID NO: 71           moltype = RNA  length = 20
FEATURE                 Location/Qualifiers
misc_feature            1..20
                        note = PCSK9
source                  1..20
                        mol_type = other RNA
                        organism = Synthetic construct
SEQUENCE: 71
ccgttaatgt ttaatcagat                                               20

SEQ ID NO: 72           moltype = RNA  length = 19
FEATURE                 Location/Qualifiers
misc_feature            1..19
                        note = PCSK9
source                  1..19
                        mol_type = other RNA
                        organism = Synthetic construct
SEQUENCE: 72
cgtaatctga cgctgtttg                                                19

SEQ ID NO: 73           moltype = RNA  length = 20
FEATURE                 Location/Qualifiers
misc_feature            1..20
                        note = PCSK9
source                  1..20
                        mol_type = other RNA
                        organism = Synthetic construct
SEQUENCE: 73
ggtgtgggtg cttgacgcct                                               20

SEQ ID NO: 74           moltype = RNA  length = 20
FEATURE                 Location/Qualifiers
misc_feature            1..20
                        note = PCSK9
source                  1..20
                        mol_type = other RNA
                        organism = Synthetic construct
SEQUENCE: 74
acccactgca cgctggacag                                               20

SEQ ID NO: 75           moltype = RNA  length = 20
FEATURE                 Location/Qualifiers
misc_feature            1..20
                        note = PCSK9
source                  1..20
                        mol_type = other RNA
                        organism = Synthetic construct
SEQUENCE: 75
gcacagtaac aacccctggt                                               20

SEQ ID NO: 76           moltype = RNA  length = 20
FEATURE                 Location/Qualifiers
misc_feature            1..20
                        note = PCSK9
source                  1..20
                        mol_type = other RNA
                        organism = Synthetic construct
SEQUENCE: 76
ccatccattc tttctctagg                                               20

SEQ ID NO: 77           moltype = RNA  length = 20
FEATURE                 Location/Qualifiers
misc_feature            1..20
                        note = LPA
source                  1..20
                        mol_type = other RNA
                        organism = Synthetic construct
SEQUENCE: 77
aaggagacat aaaggcaatg                                               20
```

```
SEQ ID NO: 78          moltype = RNA   length = 20
FEATURE                Location/Qualifiers
misc_feature           1..20
                       note = LPA
source                 1..20
                       mol_type = other RNA
                       organism = Synthetic construct
SEQUENCE: 78
ggcaatgtgg agcagctgag                                                   20

SEQ ID NO: 79          moltype = RNA   length = 20
FEATURE                Location/Qualifiers
misc_feature           1..20
                       note = LPA
source                 1..20
                       mol_type = other RNA
                       organism = Synthetic construct
SEQUENCE: 79
ggagcagctg aggggggaaa                                                   20

SEQ ID NO: 80          moltype = RNA   length = 20
FEATURE                Location/Qualifiers
misc_feature           1..20
                       note = LPA
source                 1..20
                       mol_type = other RNA
                       organism = Synthetic construct
SEQUENCE: 80
tgtcaataga tgctgggaag                                                   20

SEQ ID NO: 81          moltype = RNA   length = 20
FEATURE                Location/Qualifiers
misc_feature           1..20
                       note = LPA
source                 1..20
                       mol_type = other RNA
                       organism = Synthetic construct
SEQUENCE: 81
agtgcaatgt caatagatgc                                                   20

SEQ ID NO: 82          moltype = RNA   length = 20
FEATURE                Location/Qualifiers
misc_feature           1..20
                       note = LPA
source                 1..20
                       mol_type = other RNA
                       organism = Synthetic construct
SEQUENCE: 82
tttataagac tctatattca                                                   20

SEQ ID NO: 83          moltype = RNA   length = 20
FEATURE                Location/Qualifiers
misc_feature           1..20
                       note = LPA
source                 1..20
                       mol_type = other RNA
                       organism = Synthetic construct
SEQUENCE: 83
catgtaagtc aacaatgtcc                                                   20

SEQ ID NO: 84          moltype = RNA   length = 20
FEATURE                Location/Qualifiers
misc_feature           1..20
                       note = LPA
source                 1..20
                       mol_type = other RNA
                       organism = Synthetic construct
SEQUENCE: 84
gtcaacaatg tcctgggatt                                                   20

SEQ ID NO: 85          moltype = RNA   length = 20
FEATURE                Location/Qualifiers
misc_feature           1..20
                       note = LPA
source                 1..20
                       mol_type = other RNA
                       organism = Synthetic construct
SEQUENCE: 85
catatacaag attttgaact                                                   20
```

```
SEQ ID NO: 86          moltype = RNA   length = 20
FEATURE                Location/Qualifiers
misc_feature           1..20
                       note = LPA
source                 1..20
                       mol_type = other RNA
                       organism = Synthetic construct
SEQUENCE: 86
gcaccgtgac agtcttcacg                                                  20

SEQ ID NO: 87          moltype = RNA   length = 20
FEATURE                Location/Qualifiers
misc_feature           1..20
                       note = MYLIP
source                 1..20
                       mol_type = other RNA
                       organism = Synthetic construct
SEQUENCE: 87
ttggcgggga cccgagctga                                                  20

SEQ ID NO: 88          moltype = RNA   length = 20
FEATURE                Location/Qualifiers
misc_feature           1..20
                       note = MYLIP
source                 1..20
                       mol_type = other RNA
                       organism = Synthetic construct
SEQUENCE: 88
ctgtcgcagc gcaggcagtt                                                  20

SEQ ID NO: 89          moltype = RNA   length = 20
FEATURE                Location/Qualifiers
misc_feature           1..20
                       note = MYLIP
source                 1..20
                       mol_type = other RNA
                       organism = Synthetic construct
SEQUENCE: 89
gctggagtgc ggcgccaccg                                                  20

SEQ ID NO: 90          moltype = RNA   length = 20
FEATURE                Location/Qualifiers
misc_feature           1..20
                       note = MYLIP
source                 1..20
                       mol_type = other RNA
                       organism = Synthetic construct
SEQUENCE: 90
cggcgccacc gcggaggaca                                                  20

SEQ ID NO: 91          moltype = RNA   length = 20
FEATURE                Location/Qualifiers
misc_feature           1..20
                       note = MYLIP
source                 1..20
                       mol_type = other RNA
                       organism = Synthetic construct
SEQUENCE: 91
cagctctgcg gacccttgtc                                                  20

SEQ ID NO: 92          moltype = RNA   length = 20
FEATURE                Location/Qualifiers
misc_feature           1..20
                       note = MYLIP
source                 1..20
                       mol_type = other RNA
                       organism = Synthetic construct
SEQUENCE: 92
ccccgcgcac accaaagaga                                                  20

SEQ ID NO: 93          moltype = RNA   length = 20
FEATURE                Location/Qualifiers
misc_feature           1..20
                       note = MYLIP
source                 1..20
                       mol_type = other RNA
                       organism = Synthetic construct
SEQUENCE: 93
```

```
cctcgtcaca taacacagca                                                20

SEQ ID NO: 94           moltype = RNA   length = 20
FEATURE                 Location/Qualifiers
misc_feature            1..20
                        note = MYLIP
source                  1..20
                        mol_type = other RNA
                        organism = Synthetic construct
SEQUENCE: 94
acctccatca gcaccgcgtc                                                20

SEQ ID NO: 95           moltype = RNA   length = 20
FEATURE                 Location/Qualifiers
misc_feature            1..20
                        note = MYLIP
source                  1..20
                        mol_type = other RNA
                        organism = Synthetic construct
SEQUENCE: 95
ggaggcgaaa gccaacggcg                                                20

SEQ ID NO: 96           moltype = RNA   length = 20
FEATURE                 Location/Qualifiers
misc_feature            1..20
                        note = MYLIP
source                  1..20
                        mol_type = other RNA
                        organism = Synthetic construct
SEQUENCE: 96
gttgaggcag tcctcgccgt                                                20

SEQ ID NO: 97           moltype = RNA   length = 20
FEATURE                 Location/Qualifiers
misc_feature            1..20
                        note = ANGLPTL3
source                  1..20
                        mol_type = other RNA
                        organism = Synthetic construct
SEQUENCE: 97
tacattcgtg caagttaaca                                                20

SEQ ID NO: 98           moltype = RNA   length = 20
FEATURE                 Location/Qualifiers
misc_feature            1..20
                        note = ANGLPTL3
source                  1..20
                        mol_type = other RNA
                        organism = Synthetic construct
SEQUENCE: 98
cctaccaacc ttaccttttc                                                20

SEQ ID NO: 99           moltype = RNA   length = 20
FEATURE                 Location/Qualifiers
misc_feature            1..20
                        note = ANGLPTL3
source                  1..20
                        mol_type = other RNA
                        organism = Synthetic construct
SEQUENCE: 99
tatatagagt taagaagtct                                                20

SEQ ID NO: 100          moltype = RNA   length = 20
FEATURE                 Location/Qualifiers
misc_feature            1..20
                        note = ANGLPTL3
source                  1..20
                        mol_type = other RNA
                        organism = Synthetic construct
SEQUENCE: 100
aacgtggaac tgttttcttc                                                20

SEQ ID NO: 101          moltype = RNA   length = 20
FEATURE                 Location/Qualifiers
misc_feature            1..20
                        note = ANGLPTL3
source                  1..20
                        mol_type = other RNA
                        organism = Synthetic construct
```

-continued

| | | |
|---|---|---|
| SEQUENCE: 101 | | |
| attttcaatt tcaagcaacg | | 20 |
| | | |
| SEQ ID NO: 102 | moltype = RNA  length = 20 | |
| FEATURE | Location/Qualifiers | |
| misc_feature | 1..20 | |
| | note = ANGLPTL3 | |
| source | 1..20 | |
| | mol_type = other RNA | |
| | organism = Synthetic construct | |
| SEQUENCE: 102 | | |
| attctggagg aaataactag | | 20 |
| | | |
| SEQ ID NO: 103 | moltype = RNA  length = 20 | |
| FEATURE | Location/Qualifiers | |
| misc_feature | 1..20 | |
| | note = ANGLPTL3 | |
| source | 1..20 | |
| | mol_type = other RNA | |
| | organism = Synthetic construct | |
| SEQUENCE: 103 | | |
| gcaaatcttg attttggctc | | 20 |
| | | |
| SEQ ID NO: 104 | moltype = RNA  length = 20 | |
| FEATURE | Location/Qualifiers | |
| misc_feature | 1..20 | |
| | note = ANGLPTL3 | |
| source | 1..20 | |
| | mol_type = other RNA | |
| | organism = Synthetic construct | |
| SEQUENCE: 104 | | |
| agccaatggc ctccttcagt | | 20 |
| | | |
| SEQ ID NO: 105 | moltype = RNA  length = 20 | |
| FEATURE | Location/Qualifiers | |
| misc_feature | 1..20 | |
| | note = ANGLPTL3 | |
| source | 1..20 | |
| | mol_type = other RNA | |
| | organism = Synthetic construct | |
| SEQUENCE: 105 | | |
| taagaccatg tcccaactga | | 20 |
| | | |
| SEQ ID NO: 106 | moltype = RNA  length = 20 | |
| FEATURE | Location/Qualifiers | |
| misc_feature | 1..20 | |
| | note = ANGLPTL3 | |
| source | 1..20 | |
| | mol_type = other RNA | |
| | organism = Synthetic construct | |
| SEQUENCE: 106 | | |
| agactttgtc cataagacga | | 20 |
| | | |
| SEQ ID NO: 107 | moltype = RNA  length = 20 | |
| FEATURE | Location/Qualifiers | |
| misc_feature | 1..20 | |
| | note = APOC3 | |
| source | 1..20 | |
| | mol_type = other RNA | |
| | organism = Synthetic construct | |
| SEQUENCE: 107 | | |
| ggggcacccg tccagctccg | | 20 |
| | | |
| SEQ ID NO: 108 | moltype = RNA  length = 20 | |
| FEATURE | Location/Qualifiers | |
| misc_feature | 1..20 | |
| | note = APOC3 | |
| source | 1..20 | |
| | mol_type = other RNA | |
| | organism = Synthetic construct | |
| SEQUENCE: 108 | | |
| tgacctttgc ccagcgccct | | 20 |
| | | |
| SEQ ID NO: 109 | moltype = RNA  length = 20 | |
| FEATURE | Location/Qualifiers | |
| misc_feature | 1..20 | |
| | note = APOC3 | |
| source | 1..20 | |
| | mol_type = other RNA | |

```
                        organism = Synthetic construct
SEQUENCE: 109
tccagatgca gcaagcgggc                                                     20

SEQ ID NO: 110          moltype = RNA   length = 20
FEATURE                 Location/Qualifiers
misc_feature            1..20
                        note = APOC3
source                  1..20
                        mol_type = other RNA
                        organism = Synthetic construct
SEQUENCE: 110
tagggatgaa ctgagcagac                                                     20

SEQ ID NO: 111          moltype = RNA   length = 20
FEATURE                 Location/Qualifiers
misc_feature            1..20
                        note = APOC3
source                  1..20
                        mol_type = other RNA
                        organism = Synthetic construct
SEQUENCE: 111
agaagcactt gctagagcta                                                     20

SEQ ID NO: 112          moltype = RNA   length = 20
FEATURE                 Location/Qualifiers
misc_feature            1..20
                        note = APOC3
source                  1..20
                        mol_type = other RNA
                        organism = Synthetic construct
SEQUENCE: 112
ctgctccagg taatgccctc                                                     20

SEQ ID NO: 113          moltype = RNA   length = 20
FEATURE                 Location/Qualifiers
misc_feature            1..20
                        note = APOC3
source                  1..20
                        mol_type = other RNA
                        organism = Synthetic construct
SEQUENCE: 113
gggagagttg ggaaatccct                                                     20

SEQ ID NO: 114          moltype = RNA   length = 20
FEATURE                 Location/Qualifiers
misc_feature            1..20
                        note = APOC3
source                  1..20
                        mol_type = other RNA
                        organism = Synthetic construct
SEQUENCE: 114
aggaagcctc ggagctggac                                                     20

SEQ ID NO: 115          moltype = RNA   length = 20
FEATURE                 Location/Qualifiers
misc_feature            1..20
                        note = APOC3
source                  1..20
                        mol_type = other RNA
                        organism = Synthetic construct
SEQUENCE: 115
ccctggagat gatataaaac                                                     20

SEQ ID NO: 116          moltype = RNA   length = 20
FEATURE                 Location/Qualifiers
misc_feature            1..20
                        note = APOC3
source                  1..20
                        mol_type = other RNA
                        organism = Synthetic construct
SEQUENCE: 116
tcataacctg aagaacatgg                                                     20

SEQ ID NO: 117          moltype = RNA   length = 20
FEATURE                 Location/Qualifiers
misc_feature            1..20
                        note = APOB
source                  1..20
```

```
                                mol_type = other RNA
                                organism = Synthetic construct
SEQUENCE: 117
gtccatcgcc agctgcggtg                                                          20

SEQ ID NO: 118          moltype = RNA   length = 20
FEATURE                 Location/Qualifiers
misc_feature            1..20
                        note = APOB
source                  1..20
                        mol_type = other RNA
                        organism = Synthetic construct
SEQUENCE: 118
ggcgcccgca ccccatttat                                                          20

SEQ ID NO: 119          moltype = RNA   length = 20
FEATURE                 Location/Qualifiers
misc_feature            1..20
                        note = APOB
source                  1..20
                        mol_type = other RNA
                        organism = Synthetic construct
SEQUENCE: 119
cagagcggcc gcgcactcac                                                          20

SEQ ID NO: 120          moltype = RNA   length = 20
FEATURE                 Location/Qualifiers
misc_feature            1..20
                        note = APOB
source                  1..20
                        mol_type = other RNA
                        organism = Synthetic construct
SEQUENCE: 120
ctcagcggca gcaaccgaga                                                          20

SEQ ID NO: 121          moltype = RNA   length = 20
FEATURE                 Location/Qualifiers
misc_feature            1..20
                        note = APOB
source                  1..20
                        mol_type = other RNA
                        organism = Synthetic construct
SEQUENCE: 121
tcccggtggg aatgcgcggc                                                          20

SEQ ID NO: 122          moltype = RNA   length = 20
FEATURE                 Location/Qualifiers
misc_feature            1..20
                        note = APOB
source                  1..20
                        mol_type = other RNA
                        organism = Synthetic construct
SEQUENCE: 122
gcattcccac cgggacctgc                                                          20

SEQ ID NO: 123          moltype = RNA   length = 20
FEATURE                 Location/Qualifiers
misc_feature            1..20
                        note = APOB
source                  1..20
                        mol_type = other RNA
                        organism = Synthetic construct
SEQUENCE: 123
gcctcgcggc cctggctggc                                                          20

SEQ ID NO: 124          moltype = RNA   length = 20
FEATURE                 Location/Qualifiers
misc_feature            1..20
                        note = APOB
source                  1..20
                        mol_type = other RNA
                        organism = Synthetic construct
SEQUENCE: 124
cccggccaac ctcgtgccgc                                                          20

SEQ ID NO: 125          moltype = RNA   length = 20
FEATURE                 Location/Qualifiers
misc_feature            1..20
                        note = APOB
```

```
source                      1..20
                            mol_type = other RNA
                            organism = Synthetic construct
SEQUENCE: 125
agcgccagca gcgcgggcct                                                       20

SEQ ID NO: 126              moltype = RNA   length = 20
FEATURE                     Location/Qualifiers
misc_feature                1..20
                            note = APOB
source                      1..20
                            mol_type = other RNA
                            organism = Synthetic construct
SEQUENCE: 126
ctccctctgc gcccgcagag                                                       20

SEQ ID NO: 127              moltype = RNA   length = 106
FEATURE                     Location/Qualifiers
misc_feature                1..106
                            note = PCSK9
source                      1..106
                            mol_type = other RNA
                            organism = Synthetic construct
SEQUENCE: 127
gcgcgtaatc tgacgctgtt gtttaagagc tatgctggaa acagcatagc aagtttaaat          60
aaggctagtc cgttatcaac ttgaaaaagt ggcaccgagt cggtgc                        106

SEQ ID NO: 128              moltype = RNA   length = 106
FEATURE                     Location/Qualifiers
misc_feature                1..106
                            note = PCSK9
source                      1..106
                            mol_type = other RNA
                            organism = Synthetic construct
SEQUENCE: 128
atcagatagg atcgtccgat gtttaagagc tatgctggaa acagcatagc aagtttaaat          60
aaggctagtc cgttatcaac ttgaaaaagt ggcaccgagt cggtgc                        106

SEQ ID NO: 129              moltype = RNA   length = 106
FEATURE                     Location/Qualifiers
misc_feature                1..106
                            note = PCSK9
source                      1..106
                            mol_type = other RNA
                            organism = Synthetic construct
SEQUENCE: 129
aggtttccgc agcgacgtcg gtttaagagc tatgctggaa acagcatagc aagtttaaat          60
aaggctagtc cgttatcaac ttgaaaaagt ggcaccgagt cggtgc                        106

SEQ ID NO: 130              moltype = RNA   length = 106
FEATURE                     Location/Qualifiers
misc_feature                1..106
                            note = PCSK9
source                      1..106
                            mol_type = other RNA
                            organism = Synthetic construct
SEQUENCE: 130
gggcgccgcc gttcagttca gtttaagagc tatgctggaa acagcatagc aagtttaaat          60
aaggctagtc cgttatcaac ttgaaaaagt ggcaccgagt cggtgc                        106

SEQ ID NO: 131              moltype = RNA   length = 106
FEATURE                     Location/Qualifiers
misc_feature                1..106
                            note = PCSK9
source                      1..106
                            mol_type = other RNA
                            organism = Synthetic construct
SEQUENCE: 131
ggtgctagcc ttgcgttccg gtttaagagc tatgctggaa acagcatagc aagtttaaat          60
aaggctagtc cgttatcaac ttgaaaaagt ggcaccgagt cggtgc                        106

SEQ ID NO: 132              moltype = RNA   length = 106
FEATURE                     Location/Qualifiers
misc_feature                1..106
                            note = PCSK9
source                      1..106
                            mol_type = other RNA
                            organism = Synthetic construct
SEQUENCE: 132
```

```
cattaacgga accccgggac gtttaagagc tatgctggaa acagcatagc aagtttaaat    60
aaggctagtc cgttatcaac ttgaaaaagt ggcaccgagt cggtgc                  106

SEQ ID NO: 133          moltype = RNA   length = 106
FEATURE                 Location/Qualifiers
misc_feature            1..106
                        note = PCSK9
source                  1..106
                        mol_type = other RNA
                        organism = Synthetic construct
SEQUENCE: 133
aggatcgtcc gatgggctc gtttaagagc tatgctggaa acagcatagc aagtttaaat    60
aaggctagtc cgttatcaac ttgaaaaagt ggcaccgagt cggtgc                  106

SEQ ID NO: 134          moltype = RNA   length = 106
FEATURE                 Location/Qualifiers
misc_feature            1..106
                        note = PCSK9
source                  1..106
                        mol_type = other RNA
                        organism = Synthetic construct
SEQUENCE: 134
ccgttaatgt ttaatcagat gtttaagagc tatgctggaa acagcatagc aagtttaaat    60
aaggctagtc cgttatcaac ttgaaaaagt ggcaccgagt cggtgc                  106

SEQ ID NO: 135          moltype = RNA   length = 105
FEATURE                 Location/Qualifiers
misc_feature            1..105
                        note = PCSK9
source                  1..105
                        mol_type = other RNA
                        organism = Synthetic construct
SEQUENCE: 135
cgtaatctga cgctgtttgg tttaagagct atgctggaaa cagcatagca agtttaaata    60
aggctagtcc gttatcaact tgaaaaagtg gcaccgagtc ggtgc                   105

SEQ ID NO: 136          moltype = RNA   length = 106
FEATURE                 Location/Qualifiers
misc_feature            1..106
                        note = PCSK9
source                  1..106
                        mol_type = other RNA
                        organism = Synthetic construct
SEQUENCE: 136
ggtgtgggtg cttgacgcct gtttaagagc tatgctggaa acagcatagc aagtttaaat    60
aaggctagtc cgttatcaac ttgaaaaagt ggcaccgagt cggtgc                  106

SEQ ID NO: 137          moltype = RNA   length = 106
FEATURE                 Location/Qualifiers
misc_feature            1..106
                        note = PCSK9
source                  1..106
                        mol_type = other RNA
                        organism = Synthetic construct
SEQUENCE: 137
acccactgca cgctggacag gtttaagagc tatgctggaa acagcatagc aagtttaaat    60
aaggctagtc cgttatcaac ttgaaaaagt ggcaccgagt cggtgc                  106

SEQ ID NO: 138          moltype = RNA   length = 106
FEATURE                 Location/Qualifiers
misc_feature            1..106
                        note = PCSK9
source                  1..106
                        mol_type = other RNA
                        organism = Synthetic construct
SEQUENCE: 138
gcacagtaac aaccctggt gtttaagagc tatgctggaa acagcatagc aagtttaaat    60
aaggctagtc cgttatcaac ttgaaaaagt ggcaccgagt cggtgc                  106

SEQ ID NO: 139          moltype = RNA   length = 106
FEATURE                 Location/Qualifiers
misc_feature            1..106
                        note = PCSK9
source                  1..106
                        mol_type = other RNA
                        organism = Synthetic construct
SEQUENCE: 139
ccatccattc tttctctagg gtttaagagc tatgctggaa acagcatagc aagtttaaat    60
aaggctagtc cgttatcaac ttgaaaaagt ggcaccgagt cggtgc                  106
```

```
SEQ ID NO: 140          moltype = RNA  length = 106
FEATURE                 Location/Qualifiers
misc_feature            1..106
                        note = LPA
source                  1..106
                        mol_type = other RNA
                        organism = Synthetic construct
SEQUENCE: 140
aaggagacat aaaggcaatg gtttaagagc tatgctggaa acagcatagc aagtttaaat    60
aaggctagtc cgttatcaac ttgaaaaagt ggcaccgagt cggtgc                  106

SEQ ID NO: 141          moltype = RNA  length = 106
FEATURE                 Location/Qualifiers
misc_feature            1..106
                        note = LPA
source                  1..106
                        mol_type = other RNA
                        organism = Synthetic construct
SEQUENCE: 141
ggcaatgtgg agcagctgag gtttaagagc tatgctggaa acagcatagc aagtttaaat    60
aaggctagtc cgttatcaac ttgaaaaagt ggcaccgagt cggtgc                  106

SEQ ID NO: 142          moltype = RNA  length = 106
FEATURE                 Location/Qualifiers
misc_feature            1..106
                        note = LPA
source                  1..106
                        mol_type = other RNA
                        organism = Synthetic construct
SEQUENCE: 142
ggagcagctg agggggggaaa gtttaagagc tatgctggaa acagcatagc aagtttaaat   60
aaggctagtc cgttatcaac ttgaaaaagt ggcaccgagt cggtgc                  106

SEQ ID NO: 143          moltype = RNA  length = 106
FEATURE                 Location/Qualifiers
misc_feature            1..106
                        note = LPA
source                  1..106
                        mol_type = other RNA
                        organism = Synthetic construct
SEQUENCE: 143
tgtcaataga tgctgggaag gtttaagagc tatgctggaa acagcatagc aagtttaaat    60
aaggctagtc cgttatcaac ttgaaaaagt ggcaccgagt cggtgc                  106

SEQ ID NO: 144          moltype = RNA  length = 106
FEATURE                 Location/Qualifiers
misc_feature            1..106
                        note = LPA
source                  1..106
                        mol_type = other RNA
                        organism = Synthetic construct
SEQUENCE: 144
agtgcaatgt caatagatgc gtttaagagc tatgctggaa acagcatagc aagtttaaat    60
aaggctagtc cgttatcaac ttgaaaaagt ggcaccgagt cggtgc                  106

SEQ ID NO: 145          moltype = RNA  length = 106
FEATURE                 Location/Qualifiers
misc_feature            1..106
                        note = LPA
source                  1..106
                        mol_type = other RNA
                        organism = Synthetic construct
SEQUENCE: 145
tttataagac tctatattca gtttaagagc tatgctggaa acagcatagc aagtttaaat    60
aaggctagtc cgttatcaac ttgaaaaagt ggcaccgagt cggtgc                  106

SEQ ID NO: 146          moltype = RNA  length = 106
FEATURE                 Location/Qualifiers
misc_feature            1..106
                        note = LPA
source                  1..106
                        mol_type = other RNA
                        organism = Synthetic construct
SEQUENCE: 146
catgtaagtc aacaatgtcc gtttaagagc tatgctggaa acagcatagc aagtttaaat    60
aaggctagtc cgttatcaac ttgaaaaagt ggcaccgagt cggtgc                  106

SEQ ID NO: 147          moltype = RNA  length = 106
```

```
FEATURE              Location/Qualifiers
misc_feature         1..106
                     note = LPA
source               1..106
                     mol_type = other RNA
                     organism = Synthetic construct
SEQUENCE: 147
gtcaacaatg tcctgggatt gtttaagagc tatgctggaa acagcatagc aagtttaaat   60
aaggctagtc cgttatcaac ttgaaaaagt ggcaccgagt cggtgc                 106

SEQ ID NO: 148       moltype = RNA   length = 106
FEATURE              Location/Qualifiers
misc_feature         1..106
                     note = LPA
source               1..106
                     mol_type = other RNA
                     organism = Synthetic construct
SEQUENCE: 148
catatacaag attttgaact gtttaagagc tatgctggaa acagcatagc aagtttaaat   60
aaggctagtc cgttatcaac ttgaaaaagt ggcaccgagt cggtgc                 106

SEQ ID NO: 149       moltype = RNA   length = 106
FEATURE              Location/Qualifiers
misc_feature         1..106
                     note = LPA
source               1..106
                     mol_type = other RNA
                     organism = Synthetic construct
SEQUENCE: 149
gcaccgtgac agtcttcacg gtttaagagc tatgctggaa acagcatagc aagtttaaat   60
aaggctagtc cgttatcaac ttgaaaaagt ggcaccgagt cggtgc                 106

SEQ ID NO: 150       moltype = RNA   length = 106
FEATURE              Location/Qualifiers
misc_feature         1..106
                     note = MYLIP
source               1..106
                     mol_type = other RNA
                     organism = Synthetic construct
SEQUENCE: 150
ttggcgggga cccgagctga gtttaagagc tatgctggaa acagcatagc aagtttaaat   60
aaggctagtc cgttatcaac ttgaaaaagt ggcaccgagt cggtgc                 106

SEQ ID NO: 151       moltype = RNA   length = 106
FEATURE              Location/Qualifiers
misc_feature         1..106
                     note = MYLIP
source               1..106
                     mol_type = other RNA
                     organism = Synthetic construct
SEQUENCE: 151
ctgtcgcagc gcaggcagtt gtttaagagc tatgctggaa acagcatagc aagtttaaat   60
aaggctagtc cgttatcaac ttgaaaaagt ggcaccgagt cggtgc                 106

SEQ ID NO: 152       moltype = RNA   length = 106
FEATURE              Location/Qualifiers
misc_feature         1..106
                     note = MYLIP
source               1..106
                     mol_type = other RNA
                     organism = Synthetic construct
SEQUENCE: 152
gctggagtgc ggcgccaccg gtttaagagc tatgctggaa acagcatagc aagtttaaat   60
aaggctagtc cgttatcaac ttgaaaaagt ggcaccgagt cggtgc                 106

SEQ ID NO: 153       moltype = RNA   length = 106
FEATURE              Location/Qualifiers
misc_feature         1..106
                     note = MYLIP
source               1..106
                     mol_type = other RNA
                     organism = Synthetic construct
SEQUENCE: 153
cggcgccacc gcggaggaca gtttaagagc tatgctggaa acagcatagc aagtttaaat   60
aaggctagtc cgttatcaac ttgaaaaagt ggcaccgagt cggtgc                 106

SEQ ID NO: 154       moltype = RNA   length = 106
FEATURE              Location/Qualifiers
misc_feature         1..106
```

```
                        note = MYLIP
source                  1..106
                        mol_type = other RNA
                        organism = Synthetic construct
SEQUENCE: 154
cagctctgcg gacccttgtc gtttaagagc tatgctggaa acagcatagc aagtttaaat    60
aaggctagtc cgttatcaac ttgaaaaagt ggcaccgagt cggtgc                  106

SEQ ID NO: 155          moltype = RNA   length = 106
FEATURE                 Location/Qualifiers
misc_feature            1..106
                        note = MYLIP
source                  1..106
                        mol_type = other RNA
                        organism = Synthetic construct
SEQUENCE: 155
ccccgcgcac accaaagaga gtttaagagc tatgctggaa acagcatagc aagtttaaat    60
aaggctagtc cgttatcaac ttgaaaaagt ggcaccgagt cggtgc                  106

SEQ ID NO: 156          moltype = RNA   length = 106
FEATURE                 Location/Qualifiers
misc_feature            1..106
                        note = MYLIP
source                  1..106
                        mol_type = other RNA
                        organism = Synthetic construct
SEQUENCE: 156
cctcgtcaca taacacagca gtttaagagc tatgctggaa acagcatagc aagtttaaat    60
aaggctagtc cgttatcaac ttgaaaaagt ggcaccgagt cggtgc                  106

SEQ ID NO: 157          moltype = RNA   length = 106
FEATURE                 Location/Qualifiers
misc_feature            1..106
                        note = MYLIP
source                  1..106
                        mol_type = other RNA
                        organism = Synthetic construct
SEQUENCE: 157
acctccatca gcaccgcgtc gtttaagagc tatgctggaa acagcatagc aagtttaaat    60
aaggctagtc cgttatcaac ttgaaaaagt ggcaccgagt cggtgc                  106

SEQ ID NO: 158          moltype = RNA   length = 106
FEATURE                 Location/Qualifiers
misc_feature            1..106
                        note = MYLIP
source                  1..106
                        mol_type = other RNA
                        organism = Synthetic construct
SEQUENCE: 158
ggaggcgaaa gccaacggcg gtttaagagc tatgctggaa acagcatagc aagtttaaat    60
aaggctagtc cgttatcaac ttgaaaaagt ggcaccgagt cggtgc                  106

SEQ ID NO: 159          moltype = RNA   length = 106
FEATURE                 Location/Qualifiers
misc_feature            1..106
                        note = MYLIP
source                  1..106
                        mol_type = other RNA
                        organism = Synthetic construct
SEQUENCE: 159
gttgaggcag tcctcgccgt gtttaagagc tatgctggaa acagcatagc aagtttaaat    60
aaggctagtc cgttatcaac ttgaaaaagt ggcaccgagt cggtgc                  106

SEQ ID NO: 160          moltype = RNA   length = 106
FEATURE                 Location/Qualifiers
misc_feature            1..106
                        note = ANGPTL3
source                  1..106
                        mol_type = other RNA
                        organism = Synthetic construct
SEQUENCE: 160
tacattcgtg caagttaaca gtttaagagc tatgctggaa acagcatagc aagtttaaat    60
aaggctagtc cgttatcaac ttgaaaaagt ggcaccgagt cggtgc                  106

SEQ ID NO: 161          moltype = RNA   length = 106
FEATURE                 Location/Qualifiers
misc_feature            1..106
                        note = ANGPTL3
source                  1..106
```

```
                         mol_type = other RNA
                         organism = Synthetic construct
SEQUENCE: 161
cctaccaacc ttaccttttc gtttaagagc tatgctggaa acagcatagc aagtttaaat      60
aaggctagtc cgttatcaac ttgaaaaagt ggcaccgagt cggtgc                    106

SEQ ID NO: 162           moltype = RNA   length = 106
FEATURE                  Location/Qualifiers
misc_feature             1..106
                         note = ANGPTL3
source                   1..106
                         mol_type = other RNA
                         organism = Synthetic construct
SEQUENCE: 162
tatatagagt taagaagtct gtttaagagc tatgctggaa acagcatagc aagtttaaat      60
aaggctagtc cgttatcaac ttgaaaaagt ggcaccgagt cggtgc                    106

SEQ ID NO: 163           moltype = RNA   length = 106
FEATURE                  Location/Qualifiers
misc_feature             1..106
                         note = ANGPTL3
source                   1..106
                         mol_type = other RNA
                         organism = Synthetic construct
SEQUENCE: 163
aacgtggaac tgttttcttc gtttaagagc tatgctggaa acagcatagc aagtttaaat      60
aaggctagtc cgttatcaac ttgaaaaagt ggcaccgagt cggtgc                    106

SEQ ID NO: 164           moltype = RNA   length = 106
FEATURE                  Location/Qualifiers
misc_feature             1..106
                         note = ANGPTL3
source                   1..106
                         mol_type = other RNA
                         organism = Synthetic construct
SEQUENCE: 164
attttcaatt tcaagcaacg gtttaagagc tatgctggaa acagcatagc aagtttaaat      60
aaggctagtc cgttatcaac ttgaaaaagt ggcaccgagt cggtgc                    106

SEQ ID NO: 165           moltype = RNA   length = 106
FEATURE                  Location/Qualifiers
misc_feature             1..106
                         note = ANGPTL3
source                   1..106
                         mol_type = other RNA
                         organism = Synthetic construct
SEQUENCE: 165
attctggagg aaataactag gtttaagagc tatgctggaa acagcatagc aagtttaaat      60
aaggctagtc cgttatcaac ttgaaaaagt ggcaccgagt cggtgc                    106

SEQ ID NO: 166           moltype = RNA   length = 106
FEATURE                  Location/Qualifiers
misc_feature             1..106
                         note = ANGPTL3
source                   1..106
                         mol_type = other RNA
                         organism = Synthetic construct
SEQUENCE: 166
gcaaatcttg attttggctc gtttaagagc tatgctggaa acagcatagc aagtttaaat      60
aaggctagtc cgttatcaac ttgaaaaagt ggcaccgagt cggtgc                    106

SEQ ID NO: 167           moltype = RNA   length = 106
FEATURE                  Location/Qualifiers
misc_feature             1..106
                         note = ANGPTL3
source                   1..106
                         mol_type = other RNA
                         organism = Synthetic construct
SEQUENCE: 167
agccaatggc ctccttcagt gtttaagagc tatgctggaa acagcatagc aagtttaaat      60
aaggctagtc cgttatcaac ttgaaaaagt ggcaccgagt cggtgc                    106

SEQ ID NO: 168           moltype = RNA   length = 106
FEATURE                  Location/Qualifiers
misc_feature             1..106
                         note = ANGPTL3
source                   1..106
                         mol_type = other RNA
                         organism = Synthetic construct
```

```
SEQUENCE: 168
taagaccatg tcccaactga gtttaagagc tatgctggaa acagcatagc aagtttaaat    60
aaggctagtc cgttatcaac ttgaaaaagt ggcaccgagt cggtgc                   106

SEQ ID NO: 169          moltype = RNA  length = 106
FEATURE                 Location/Qualifiers
misc_feature            1..106
                        note = ANGPTL3
source                  1..106
                        mol_type = other RNA
                        organism = Synthetic construct
SEQUENCE: 169
agactttgtc cataagacga gtttaagagc tatgctggaa acagcatagc aagtttaaat    60
aaggctagtc cgttatcaac ttgaaaaagt ggcaccgagt cggtgc                   106

SEQ ID NO: 170          moltype = RNA  length = 106
FEATURE                 Location/Qualifiers
misc_feature            1..106
                        note = APOC3
source                  1..106
                        mol_type = other RNA
                        organism = Synthetic construct
SEQUENCE: 170
ggggcacccg tccagctccg gtttaagagc tatgctggaa acagcatagc aagtttaaat    60
aaggctagtc cgttatcaac ttgaaaaagt ggcaccgagt cggtgc                   106

SEQ ID NO: 171          moltype = RNA  length = 106
FEATURE                 Location/Qualifiers
misc_feature            1..106
                        note = APOC3
source                  1..106
                        mol_type = other RNA
                        organism = Synthetic construct
SEQUENCE: 171
tgacctttgc ccagcgccct gtttaagagc tatgctggaa acagcatagc aagtttaaat    60
aaggctagtc cgttatcaac ttgaaaaagt ggcaccgagt cggtgc                   106

SEQ ID NO: 172          moltype = RNA  length = 106
FEATURE                 Location/Qualifiers
misc_feature            1..106
                        note = APOC3
source                  1..106
                        mol_type = other RNA
                        organism = Synthetic construct
SEQUENCE: 172
tccagatgca gcaagcgggc gtttaagagc tatgctggaa acagcatagc aagtttaaat    60
aaggctagtc cgttatcaac ttgaaaaagt ggcaccgagt cggtgc                   106

SEQ ID NO: 173          moltype = RNA  length = 106
FEATURE                 Location/Qualifiers
misc_feature            1..106
                        note = APOC3
source                  1..106
                        mol_type = other RNA
                        organism = Synthetic construct
SEQUENCE: 173
tagggatgaa ctgagcagac gtttaagagc tatgctggaa acagcatagc aagtttaaat    60
aaggctagtc cgttatcaac ttgaaaaagt ggcaccgagt cggtgc                   106

SEQ ID NO: 174          moltype = RNA  length = 106
FEATURE                 Location/Qualifiers
misc_feature            1..106
                        note = APOC3
source                  1..106
                        mol_type = other RNA
                        organism = Synthetic construct
SEQUENCE: 174
agaagcactt gctagagcta gtttaagagc tatgctggaa acagcatagc aagtttaaat    60
aaggctagtc cgttatcaac ttgaaaaagt ggcaccgagt cggtgc                   106

SEQ ID NO: 175          moltype = RNA  length = 106
FEATURE                 Location/Qualifiers
misc_feature            1..106
                        note = APOC3
source                  1..106
                        mol_type = other RNA
                        organism = Synthetic construct
SEQUENCE: 175
ctgctccagg taatgccctc gtttaagagc tatgctggaa acagcatagc aagtttaaat    60
```

```
aaggctagtc cgttatcaac ttgaaaaagt ggcaccgagt cggtgc                  106

SEQ ID NO: 176          moltype = RNA   length = 106
FEATURE                 Location/Qualifiers
misc_feature            1..106
                        note = APOC3
source                  1..106
                        mol_type = other RNA
                        organism = Synthetic construct
SEQUENCE: 176
gggagagttg ggaaatccct gtttaagagc tatgctggaa acagcatagc aagtttaaat   60
aaggctagtc cgttatcaac ttgaaaaagt ggcaccgagt cggtgc                  106

SEQ ID NO: 177          moltype = RNA   length = 106
FEATURE                 Location/Qualifiers
misc_feature            1..106
                        note = APOC3
source                  1..106
                        mol_type = other RNA
                        organism = Synthetic construct
SEQUENCE: 177
aggaagcctc ggagctggac gtttaagagc tatgctggaa acagcatagc aagtttaaat   60
aaggctagtc cgttatcaac ttgaaaaagt ggcaccgagt cggtgc                  106

SEQ ID NO: 178          moltype = RNA   length = 106
FEATURE                 Location/Qualifiers
misc_feature            1..106
                        note = APOC3
source                  1..106
                        mol_type = other RNA
                        organism = Synthetic construct
SEQUENCE: 178
ccctggagat gatataaaac gtttaagagc tatgctggaa acagcatagc aagtttaaat   60
aaggctagtc cgttatcaac ttgaaaaagt ggcaccgagt cggtgc                  106

SEQ ID NO: 179          moltype = RNA   length = 106
FEATURE                 Location/Qualifiers
misc_feature            1..106
                        note = APOC3
source                  1..106
                        mol_type = other RNA
                        organism = Synthetic construct
SEQUENCE: 179
tcataacctg aagaacatgg gtttaagagc tatgctggaa acagcatagc aagtttaaat   60
aaggctagtc cgttatcaac ttgaaaaagt ggcaccgagt cggtgc                  106

SEQ ID NO: 180          moltype = RNA   length = 106
FEATURE                 Location/Qualifiers
misc_feature            1..106
                        note = APOB
source                  1..106
                        mol_type = other RNA
                        organism = Synthetic construct
SEQUENCE: 180
gtccatcgcc agctgcggtg gtttaagagc tatgctggaa acagcatagc aagtttaaat   60
aaggctagtc cgttatcaac ttgaaaaagt ggcaccgagt cggtgc                  106

SEQ ID NO: 181          moltype = RNA   length = 106
FEATURE                 Location/Qualifiers
misc_feature            1..106
                        note = APOB
source                  1..106
                        mol_type = other RNA
                        organism = Synthetic construct
SEQUENCE: 181
ggcgcccgca ccccatttat gtttaagagc tatgctggaa acagcatagc aagtttaaat   60
aaggctagtc cgttatcaac ttgaaaaagt ggcaccgagt cggtgc                  106

SEQ ID NO: 182          moltype = RNA   length = 106
FEATURE                 Location/Qualifiers
misc_feature            1..106
                        note = APOB
source                  1..106
                        mol_type = other RNA
                        organism = Synthetic construct
SEQUENCE: 182
cagagcggcc gcgcactcac gtttaagagc tatgctggaa acagcatagc aagtttaaat   60
aaggctagtc cgttatcaac ttgaaaaagt ggcaccgagt cggtgc                  106
```

```
SEQ ID NO: 183           moltype = RNA   length = 106
FEATURE                  Location/Qualifiers
misc_feature             1..106
                         note = APOB
source                   1..106
                         mol_type = other RNA
                         organism = Synthetic construct
SEQUENCE: 183
ctcagcggca gcaaccgaga gtttaagagc tatgctggaa acagcatagc aagtttaaat    60
aaggctagtc cgttatcaac ttgaaaaagt ggcaccgagt cggtgc                  106

SEQ ID NO: 184           moltype = RNA   length = 106
FEATURE                  Location/Qualifiers
misc_feature             1..106
                         note = APOB
source                   1..106
                         mol_type = other RNA
                         organism = Synthetic construct
SEQUENCE: 184
tcccggtggg aatgcgcggc gtttaagagc tatgctggaa acagcatagc aagtttaaat    60
aaggctagtc cgttatcaac ttgaaaaagt ggcaccgagt cggtgc                  106

SEQ ID NO: 185           moltype = RNA   length = 106
FEATURE                  Location/Qualifiers
misc_feature             1..106
                         note = APOB
source                   1..106
                         mol_type = other RNA
                         organism = Synthetic construct
SEQUENCE: 185
gcattcccac cgggacctgc gtttaagagc tatgctggaa acagcatagc aagtttaaat    60
aaggctagtc cgttatcaac ttgaaaaagt ggcaccgagt cggtgc                  106

SEQ ID NO: 186           moltype = RNA   length = 106
FEATURE                  Location/Qualifiers
misc_feature             1..106
                         note = APOB
source                   1..106
                         mol_type = other RNA
                         organism = Synthetic construct
SEQUENCE: 186
gcctcgcggc cctggctggc gtttaagagc tatgctggaa acagcatagc aagtttaaat    60
aaggctagtc cgttatcaac ttgaaaaagt ggcaccgagt cggtgc                  106

SEQ ID NO: 187           moltype = RNA   length = 106
FEATURE                  Location/Qualifiers
misc_feature             1..106
                         note = APOB
source                   1..106
                         mol_type = other RNA
                         organism = Synthetic construct
SEQUENCE: 187
cccggccaac ctcgtgccgc gtttaagagc tatgctggaa acagcatagc aagtttaaat    60
aaggctagtc cgttatcaac ttgaaaaagt ggcaccgagt cggtgc                  106

SEQ ID NO: 188           moltype = RNA   length = 106
FEATURE                  Location/Qualifiers
misc_feature             1..106
                         note = APOB
source                   1..106
                         mol_type = other RNA
                         organism = Synthetic construct
SEQUENCE: 188
agcgccagca gcgcgggcct gtttaagagc tatgctggaa acagcatagc aagtttaaat    60
aaggctagtc cgttatcaac ttgaaaaagt ggcaccgagt cggtgc                  106

SEQ ID NO: 189           moltype = RNA   length = 106
FEATURE                  Location/Qualifiers
misc_feature             1..106
                         note = APOB
source                   1..106
                         mol_type = other RNA
                         organism = Synthetic construct
SEQUENCE: 189
ctccctctgc gcccgcagag gtttaagagc tatgctggaa acagcatagc aagtttaaat    60
aaggctagtc cgttatcaac ttgaaaaagt ggcaccgagt cggtgc                  106

SEQ ID NO: 190           moltype = DNA   length = 86
FEATURE                  Location/Qualifiers
```

```
misc_feature            1..86
                        note = SpCas9 gRNA scaffold
source                  1..86
                        mol_type = other DNA
                        organism = Synthetic construct
SEQUENCE: 190
gtttaagagc tatgctggaa acagcatagc aagtttaaat aaggctagtc cgttatcaac    60
ttgaaaaagt ggcaccgagt cggtgc                                        86

SEQ ID NO: 191          moltype = RNA  length = 86
FEATURE                 Location/Qualifiers
misc_feature            1..86
                        note = SpCas9 gRNA scaffold
source                  1..86
                        mol_type = other RNA
                        organism = Synthetic construct
SEQUENCE: 191
gtttaagagc tatgctggaa acagcatagc aagtttaaat aaggctagtc cgttatcaac    60
ttgaaaaagt ggcaccgagt cggtgc                                        86

SEQ ID NO: 192          moltype = DNA  length = 195
FEATURE                 Location/Qualifiers
misc_feature            1..195
                        note = KRAB
source                  1..195
                        mol_type = other DNA
                        organism = Synthetic construct
SEQUENCE: 192
cggacactgg tgaccttcaa ggatgtgttt gtggacttca ccagggagga gtggaagctg    60
ctggacactg ctcagcagat cctgtacaga aatgtgatgc tggagaacta taagaacctg   120
gtttccttgg gttatcagct tactaagcca gatgtgatcc tccggttgga agggagaa    180
gagccctggc tggtg                                                   195

SEQ ID NO: 193          moltype = AA  length = 65
FEATURE                 Location/Qualifiers
REGION                  1..65
                        note = KRAB
source                  1..65
                        mol_type = protein
                        organism = Synthetic construct
SEQUENCE: 193
RTLVTFKDVF VDFTREEWKL LDTAQQILYR NVMLENYKNL VSLGYQLTKP DVILRLEKGE    60
EPWLV                                                               65

SEQ ID NO: 194          moltype = DNA  length = 966
FEATURE                 Location/Qualifiers
misc_feature            1..966
                        note = DNMT3A
source                  1..966
                        mol_type = other DNA
                        organism = Synthetic construct
SEQUENCE: 194
acctacgggc tgctgcggcg gcgagaggac tggcccctccc ggctccagat gttcttcgct    60
aataaccacg accaggaatt tgaccctcca aaggtttacc cacctgtccc agctgagaag   120
aggaagccca tccgggtgct gtctctcttt gatggaatcg ctacagggct cctggtgctg   180
aaggacttgg gcattcaggt ggaccgctac attgcctcgg aggtgtgtga ggactccatc   240
acggtgggca tggtcggca ccaggggaag atcatgtacg tcggggacgt ccgcagcgtc   300
acacagaagc atatccagga gtggggccca ttcgatctgg tgattggggg cagtccctgc   360
aatgacctct ccatcgtcaa ccctgctcgc aagggcctct acgagggcac tggccggcc   420
ttctttgagt tctaccgcct cctgcatgat gcgcggcca aggagggaa tgatcgcccc   480
ttcttctggc tctttgaaa tgtggtggcc atggcggtta gtgacaagag gacatctcg   540
cgatttctcg agtccaaccc tgtgatgatt gatgccaaag aagtgtcagc tgcacacagg   600
gcccgctact tctgggtaa ccttcccggt atgaacaggc cgttggcatc cactgtgaat   660
gataagctgg agctgcagga gtgtctggag catggcagga tagccaagtt cagcaaagtg   720
aggaccatta ctacgaggtc aaactccata aagcagggca agaccagca ttttcctgtc   780
ttcatgaatg agaagagga catcttatgg tgcactgaaa tggaaagggg atttggtttc   840
ccagtccact atactgacgt atccaacatg agccgcttgg cgaggcagag actgctgggc   900
cggtcatgga gcgtgccagt catccgccac ctcttcgctc cgctgaagga gtattttgcg   960
tgtgtg                                                             966

SEQ ID NO: 195          moltype = AA  length = 322
FEATURE                 Location/Qualifiers
REGION                  1..322
                        note = DNMT3A
source                  1..322
                        mol_type = protein
                        organism = Synthetic construct
SEQUENCE: 195
TYGLLRRRED WPSRLQMFFA NNHDQEFDPP KVYPPVPAEK RKPIRVLSLF DGIATGLLVL    60
```

```
KDLGIQVDRY IASEVCEDSI TVGMVRHQGK IMYVGDVRSV TQKHIQEWGP FDLVIGGSPC  120
NDLSIVNPAR KGLYEGTGRL FFEFYRLLHD ARPKEGDDRP FFWLFENVVA MGVSDKRDIS  180
RPLESNPVMI DAKEVSAAHR ARYFWGNLPG MNRPLASTVN DKLELQECLE HGRIAKFSKV  240
RTITTRSNSI KQGKDQHFPV FMNEKEDILW CTEMERVFGF PVHYTDVSNM SRLARQRLLG  300
RSWSVPVIRH LFAPLKEYFA CV                                          322

SEQ ID NO: 196          moltype = DNA  length = 1158
FEATURE                 Location/Qualifiers
misc_feature            1..1158
                        note = DNMT3L
source                  1..1158
                        mol_type = other DNA
                        organism = Synthetic construct
SEQUENCE: 196
atggcggcca tcccagccct ggacccagag gccgagccca gcatggacgt gattttggtg   60
ggatccagtg agctctcaag ctccgtttca cccgggacag gcagagatct tattgcatat  120
gaagtcaagg ctaaccagcg aaatatagaa gacatctgca tctgctgcgg aagtctccag  180
gttcacacac agcaccctct gtttgaggga gggatctgcg ccccatgtaa ggacaagttc  240
ctggatgccc tcttcctgta cgacgatgac gggtaccaat cctactgctc catctgctgc  300
tccggagaaa cgctgctcat ctgcggaaac cctgattgca cccatgcta ctgcttcgag  360
tgtgtggata gcctggtcgg ccccgggacc tcggggaagg tgcacgccat gagcaactgg  420
gtgtgctacc tgtgcctgcc gtcctcccga agcgggctgc tgcagcgtcg gaggaagtgg  480
cgcagccagc tcaaggcctt ctacgaccga gagtcggaga atcccttga gatgttcgaa  540
accgtgcctg tgtggaggag acagccagtc cgggtgctgt ccttttttga agacatcaag  600
aaagagctga cgagtttggg cttttttgaa agtggttctg acccgggaca actgaagcat  660
gtggttgatg tcacagacac agtgaggaag gatgtggagg agtggggaac cttcgatctt  720
gtgtacggcg ccacacctcc cctgggccac acctgtgacc gtcctcccag ctggtacctg  780
ttccagttcc accggctcct gcagtacgca cggcccaagc caggcagccc caggcccttc  840
ttctggatgt tcgtggacaa tctggtgctg aacaaggaag acctggacgt cgcatctcgc  900
ttcctggaga tggagccagt caccatccca gatgtccacg gcggatcctt gcagaatgct  960
gtccgcgtgt ggagcaacat cccagccata aggagcaggc actgggtct ggtttcggaa 1020
gaagaattgt ccctgctggc ccagaacaag cagagctcga agctcgcggc caagtggccc 1080
accaagctgt gaagaactg ctttctcccc ctaagagaat atttcaagta ttttttcaaca 1140
gaactcactt cctctttta                                              1158

SEQ ID NO: 197          moltype = AA  length = 386
FEATURE                 Location/Qualifiers
REGION                  1..386
                        note = DNMT3L
source                  1..386
                        mol_type = protein
                        organism = Synthetic construct
SEQUENCE: 197
MAAIPALDPE AEPSMDVILV GSSELSSSVS PGTGRDLIAY EVKANQRNIE DICICCGSLQ   60
VHTQHPLFEG GICAPCKDKF LDALFLYDDD GYQSYCSICC SGETLLICGN PDCTRCYCFE  120
CVDSLVGPGT SGKVHAMSNW VCYLCLPSSR SGLLQRRRKW RSQLKAFYDR ESENPLEMFE  180
TVPVWRRQPV RVLSLFEDIK KELTSLGFLE SGSDPGQLKH VVDVTDTVRK DVEEWGPFDL  240
VYGATPPLGH TCDRPPSWYL FQFHRLLQYA RPKPGSPRPF FWMFVDNLVL NKEDLDVASR  300
FLEMEPVTIP DVHGGSLQNA VRVWSNIPAI RSRHWALVSE EELSLLAQNK QSSKLAAKWP  360
TKLVKNCFLP LREYFKYFST ELTSSL                                      386

SEQ ID NO: 198          moltype = DNA  length = 1629
FEATURE                 Location/Qualifiers
misc_feature            1..1629
                        note = DNMT3A/L v1
source                  1..1629
                        mol_type = other DNA
                        organism = Synthetic construct
SEQUENCE: 198
aaccatgacc aggaatttga ccccccaaag gtttacccac ctgtgccagc tgagaagagg   60
aagcccatcc gcgtgctgtc tctctttgat gggattgcta cagggctcct ggtgctgaag  120
gacctgggca tccaagtgga ccgctacatt gcctccgagg tgtgtgagga ctccatcacg  180
gtgggcatgg tgcggcacca gggaaagatc atgtacgtcg gggacgtccg cagcgtcaca  240
cagaagcata tccaggagtg gggccattc gacctggtga ttgaggcag tccctgcaat  300
gacctctcca ttgtcaaccc tgcccgcaag gacttatatg agggtactgg ccgcctcttc  360
tttgagttct accgcctcct gcatgatgcg cggcccaagg agggagatga tcgcccttc  420
ttctggctct tgagaatgt ggtggccatg ggcgttagtg acaagaggga catctcgcga  480
tttcttgagt ctaaccccgt gatgattgac gccaaagaag tgtctgctgc acacagggcc  540
cgttacttct ggggtaacct tcctggcatg aacaggcctt tggcatccac tgtgaatgat  600
aagctggagc tgcaagagtg tctggagcac ggcagaatac caagttcag caaagtgagg  660
accattacca ccaggtcaaa ctctataaag cagggcaaag accagcattt ccccgtcttc  720
atgaacgaga aggaggacat cctgtggtgc actgaaatgg aaagggtgtt ggcttcccc  780
gtccactaca cagacgtctc caacatgagc cgcttggcgg gcagagact gctgggccga  840
tcgtggagcg tgccggtcat ccgccacctc ttcgctccg tgaaggaata ttttgcttgt  900
gtgtctagcg gcaatagtaa cgctaacagc cgcgggccga gcttcagcag cggcctggtg  960
ccgttaaagc tgcgcggcag ccatatgggc cctatggaga tatacaagac agtgtctgca 1020
tggaagagac agccagtgcg ggtactgagc ctcttcagaa acatcgacaa ggtactaaag 1080
agtttgggct tcttggaaag cggttctggt tctggggag gaacgctgaa gtacgtgaa 1140
gatgtcacaa atgtcgtgag gagagacgtg gagaaatggg gccctttga cctggtgtac 1200
```

```
ggctcgacgc agcccctagg cagctcttgt gatcgctgtc ccggctggta catgttccag    1260
ttccaccgga tcctgcagta tgcgctgcct cgccaggaga gtcagcgcc cttcttctgg     1320
atattcatgg acaatctgct gctgactgag gatgaccaag agacaactac ccgcttcctt    1380
cagacagagg ctgtgaccct ccaggatgtc cgtggcagag actaccagaa tgctatgcgg    1440
gtgtggagca acattccagg gctgaagagc aagcatgcc ccctgacccc aaaggaagaa     1500
gagtatctgc aagcccaagt cagaagcagg agcaagctgg acgccccgaa agttgacctc    1560
ctggtgaaga actgccttct cccgctgaga gagtacttca agtatttttc tcaaaactca    1620
cttcctctt                                                            1629

SEQ ID NO: 199          moltype = AA   length = 543
FEATURE                 Location/Qualifiers
REGION                  1..543
                        note = DNMT3A/L v1
source                  1..543
                        mol_type = protein
                        organism = Synthetic construct
SEQUENCE: 199
NHDQEFDPPK VYPPVPAEKR KPIRVLSLFD GIATGLLVLK DLGIQVDRYI ASEVCEDSIT     60
VGMVRHQGKI MYVGDVRSVT QKHIQEWGPF DLVIGGSPCN DLSIVNPARK GLYEGTGRLF   120
FEFYRLLHDA RPKEGDDRPF FWLFENVVAM GVSDKRDISR FLESNPVMID AKEVSAAHRA   180
RYFWGNLPGM NRPLASTVND KLELQECLEH GRIAKFSKVR TITTRSNSIK QGKDQHFPVF   240
MNEKEDILWC TEMERVFGFP VHYTDVSNMS RLARQRLLGR SWSVPIRHL FAPLKEYFAC    300
VSSGNSNANS RGPSFSSGLV PLSLRGSHMG PMEIYKTVSA WKRQPVRVLS LFRNIDKVLK   360
SLGFLESGSG SGGGTLKYVE DVTNVVRRDV EKWGPFDLVY GSTQPLGSSC DRCPGWYMFQ   420
FHRILQYALP RQESQRPFFW IFMDNLLLTE DDQETTTRFL QTEAVTLQDV RGRDYQNAMR   480
VWSNIPGLKS KHAPLTPKEE EYLQAQVRSR SKLDAPKVDL LVKNCLLPLR EYFKYFSQNS   540
LPL                                                                  543

SEQ ID NO: 200          moltype = DNA   length = 1629
FEATURE                 Location/Qualifiers
misc_feature            1..1629
                        note = DNMT3A/L v2
source                  1..1629
                        mol_type = other DNA
                        organism = Synthetic construct
SEQUENCE: 200
aaccacgatc aggagtttga ccccctaag gtgtacccac ccgtgccagc cgagaagagg      60
aagcccatcc gcgtgctgtc cctgttcgac ggcatcgcca caggcctgct ggtgctgaag    120
gatctgggca tccaggtgga cagatatatc gcctccgagg tgtgcgagga ttctatcacc    180
gtgggcatgg tgaggcacca gggcaagatc atgtacgtgg gcgacgtgcg cagcgtgaca    240
cagaagcaca tccaggagtg gggacccttc gacctggtca tcggaggcag ccctgtaat    300
gacctgtcca tcgtgaaccc tgcaaggaag ggcctgtatg agggaaccgg cagactgttc    360
tttgagttct acaggctgct gcacgacgcc cgccctaagg agggcgatga caggccattc    420
ttttggctgt ttgagaacgt ggtggccatg ggcgtgagcg acaagcggga tatctccaga    480
ttcctggagt ctaatcccgt gatgatcgat gcaaaggagg tgtctgccgc acacagggca    540
aggtacttttt ggggaaatct gcctggcatg aaccgcccac tggccagcac cgtgaacgac    600
aagctggaac tgcaggagtg cctggagcac ggaaggatcg ccaagttctc caaggtgcgg    660
acaatcacca caagatctaa cagcatcaag cagggcaagg atcagcactt ccccgtgttc    720
atgaatgaga aggaggacat cctgtggtgt accgagatgg agcgcgtgtt cggctttcca    780
gtgcactata cagacgtgag caatatgagc cggctggcaa ggcagagact gctgggccgg    840
tcctggtctg tgcagtgat cagacacctg ttcgcccccc tgaaggagta ctttgcctgc    900
gtgtctagcg gcaactctaa tgccaacagc agaggccctt cctttcctc tggcctggtg    960
ccactgtctc tgaggggcag ccacatgggc cccatggaga tctacaagac cgtgtccgcc   1020
tggaagaggc agcctgtgcg cgtgctgtct ctgttccgca acatcgacaa ggtgctgaag   1080
agcctgggct ttctggagag cggatccgga ctggaggag gcaaccctga gtatgtggaa    1140
gatgtgacaa atgtggtgcg gagagatgtg gagaagtggg gccccttcga tctggttac    1200
ggatccaccc agccactggg aagctcctgc gataggtgtc caggatggta tatgttccag   1260
tttcacagaa tcctgcagta cgcactgcca aggcaggaga gccagcgcc tttctttggg    1320
atctttatgg acaatctgct gctgacagag gatgaccaag agacaacctg ccgcttcctg   1380
cagacagagg cagtgaccct gcaggatgtg aggggacggg actatcagaa tgccatgcgg   1440
gtgtggtcta acatccctgg cctgaagagc aagcacgccc ccctgacccc taaggaggag   1500
gagtacctgc aggcccaggt gcggagcaga tccaagctgg atgccctaa ggtgacctg     1560
ctggtgaaga attgtctgct gccactgcgg gagtacttca gtactttag tcagaatagc    1620
ctgccactg                                                            1629

SEQ ID NO: 201          moltype = AA   length = 543
FEATURE                 Location/Qualifiers
REGION                  1..543
                        note = DNMT3A/L v2
source                  1..543
                        mol_type = protein
                        organism = Synthetic construct
SEQUENCE: 201
NHDQEFDPPK VYPPVPAEKR KPIRVLSLFD GIATGLLVLK DLGIQVDRYI ASEVCEDSIT     60
VGMVRHQGKI MYVGDVRSVT QKHIQEWGPF DLVIGGSPCN DLSIVNPARK GLYEGTGRLF   120
FEFYRLLHDA RPKEGDDRPF FWLFENVVAM GVSDKRDISR FLESNPVMID AKEVSAAHRA   180
RYFWGNLPGM NRPLASTVND KLELQECLEH GRIAKFSKVR TITTRSNSIK QGKDQHFPVF   240
MNEKEDILWC TEMERVFGFP VHYTDVSNMS RLARQRLLGR SWSVPIRHL FAPLKEYFAC    300
VSSGNSNANS RGPSFSSGLV PLSLRGSHMG PMEIYKTVSA WKRQPVRVLS LFRNIDKVLK   360
```

```
SLGFLESGSG SGGGTLKYVE DVTNVVRRDV EKWGPFDLVY GSTQPLGSSC DRCPGWYMFQ    420
FHRILQYALP RQESQRPFFW IFMDNLLLTE DDQETTTRFL QTEAVTLQDV RGRDYQNAMR    480
VWSNIPGLKS KHAPLTPKEE EYLQAQVRSR SKLDAPKVDL LVKNCLLPLR EYFKYFSQNS    540
LPL                                                                  543

SEQ ID NO: 202          moltype =    length =
SEQUENCE: 202
000

SEQ ID NO: 203          moltype = AA   length = 6
FEATURE                 Location/Qualifiers
REGION                  1..6
                        note = PAM - SaCas9
source                  1..6
                        mol_type = protein
                        organism = Synthetic construct
SEQUENCE: 203
NNGRRT                                                                 6

SEQ ID NO: 204          moltype = AA   length = 1053
FEATURE                 Location/Qualifiers
REGION                  1..1053
                        note = SaCas9
source                  1..1053
                        mol_type = protein
                        organism = Synthetic construct
SEQUENCE: 204
MKRNYILGLD IGITSVGYGI IDYETRDVID AGVRLFKEAN VENNEGRRSK RGARRLKRRR     60
RHRIQRVKKL LFDYNLLTDH SELSGINPYE ARVKGLSQKL SEEEFSAALL HLAKRRGVHN    120
VNEVEEDTGN ELSTKEQISR NSKALEEKYV AELQLERLKK DGEVRGSINR FKTSDYVKEA    180
KQLLKVQKAY HQLDQSFIDT YIDLLETRRT YYEGPGEGSP FGWKDIKEWY EMLMGHCTYF    240
PEELRSVKYA YNADLYNALN DLNNLVITRD ENEKLEYYEK FQIIENVFKQ KKKPTLKQIA    300
KEILVNEEDI KGYRVTSTGK PEFTNLKVYH DIKDITARKE IIENAELLDQ IAKILTIYQS    360
SEDIQEELTN LNSELTQEEI EQISNLKGYT GTHNLSLKAI NLILDELWHT NDNQIAIFNR    420
LKLVPKKVDL SQQKEIPTTL VDDFILSPVV KRSFIQSIKV INAIIKKYGL PNDIIIELAR    480
EKNSKDAQKM INEMQKRNRQ TNERIEEIIR TTGKENAKYL IEKIKLHDMQ EGKCLYSLEA    540
IPLEDLLNNP FNYEVDHIIP RSVSFDNSFN NKVLVKQEEN SKKGNRTPFQ YLSSSDSKIS    600
YETFKKHILN LAKGKGRISK TKKEYLLEER DINRFSVQKD FINRNLVDTR YATRGLMNLL    660
RSYFRVNNLD VKVKSINGGF TSFLRRKWKF KKERNKGYKH HAEDALIIAN ADFIFKEWKK    720
LDKAKKVMEN QMFEEKQAES MPEIETEQEY KEIFITPHQI KHIKDFKDYK YSHRVDKKPN    780
RELINDTLYS TRKDDKGNTL IVNNLNGLYD KDNDKLKKLI NKSPEKLLMY HHDPQTYQKL    840
KLIMEQYGDE KNPLYKYYEE TGNYLTKYSK KDNGPVIKKI KYYGNKLNAH LDITDDYPNS    900
RNKVVKLSLK PYRFDVYLDN GVYKFVTVKN LDVIKKENYY EVNSKCYEEA KKLKKISNQA    960
EFIASFYNND LIKINGELYR VIGVNNDLLN RIEVNMIDIT YREYLENMND KRPPRIIKTI   1020
ASKTQSIKKY STDILGNLYE VKSKKHPQII KKG                                1053

SEQ ID NO: 205          moltype = AA   length = 1052
FEATURE                 Location/Qualifiers
REGION                  1..1052
                        note = dSaCas9
source                  1..1052
                        mol_type = protein
                        organism = Synthetic construct
SEQUENCE: 205
KRNYILGLAI GITSVGYGII DYETRDVIDA GVRLFKEANV ENNEGRRSKR GARRLKRRRR     60
HRIQRVKKLL FDYNLLTDHS ELSGINPYEA RVKGLSQKLS EEEFSAALLH LAKRRGVHNV    120
NEVEEDTGNE LSTKEQISRN SKALEEKYVA ELQLERLKKD GEVRGSINRF KTSDYVKEAK    180
QLLKVQKAYH QLDQSFIDTY IDLLETRRTY YEGPGEGSPF GWKDIKEWYE MLMGHCTYFP    240
EELRSVKYAY NADLYNALND LNNLVITRDE NEKLEYYEKF QIIENVFKQK KKPTLKQIAK    300
EILVNEEDIK GYRVTSTGKP EFTNLKVYHD IKDITARKEI IENAELLDQI AKILTIYQSS    360
EDIQEELTNL NSELTQEEIE QISNLKGYTG THNLSLKAIN LILDELWHTN DNQIAIFNRL    420
KLVPKKVDLS QQKEIPTTLV DDFILSPVVK RSFIQSIKVI NAIIKKYGLP NDIIIELARE    480
KNSKDAQKMI NEMQKRNRQT NERIEEIIRT TGKENAKYLI EKIKLHDMQE GKCLYSLEAI    540
PLEDLLNNPF NYEVDHIIPR SVSFDNSFNN KVLVKQEEAS KKGNRTPFQY LSSSDSKISY    600
ETFKKHILNL AKGKGRISKT KKEYLLEERD INRFSVQKDF INRNLVDTRY ATRGLMNLLR    660
SYFRVNNLDV KVKSINGGFT SFLRRKWKFK KERNKGYKHH AEDALIIANA DFIFKEWKKL    720
DKAKKVMENQ MFEEKQAESM PEIETEQEYK EIFITPHQIK HIKDFKDYKY SHRVDKKPNR    780
ELINDTLYST RKDDKGNTLI VNNLNGLYDK DNDKLKKLIN KSPEKLLMYH HDPQTYQKLK    840
LIMEQYGDEK NPLYKYYEET GNYLTKYSKK DNGPVIKKIK YYGNKLNAHL DITDDYPNSR    900
NKVVKLSLKP YRFDVYLDNG VYKFVTVKNL DVIKKENYYE VNSKCYEEAK KLKKISNQAE    960
FIASFYNNDL IKINGELYRV IGVNNDLLNR IEVNMIDITY REYLENMNDK RPPRIIKTIA   1020
SKTQSIKKYS TDILGNLYEV KSKKHPQIIK KG                                 1052

SEQ ID NO: 206          moltype = AA   length = 1368
FEATURE                 Location/Qualifiers
REGION                  1..1368
                        note = SpCas9
source                  1..1368
                        mol_type = protein
```

```
                        organism = Synthetic construct
SEQUENCE: 206
MDKKYSIGLD  IGTNSVGWAV  ITDEYKVPSK  KFKVLGNTDR  HSIKKNLIGA  LLFDSGETAE    60
ATRLKRTARR  RYTRRKNRIC  YLQEIFSNEM  AKVDDSFFHR  LEESFLVEED  KKHERHPIFG   120
NIVDEVAYHE  KYPTIYHLRK  KLVDSTDKAD  LRLIYLALAH  MIKFRGHFLI  EGDLNPDNSD   180
VDKLFIQLVQ  TYNQLFEENP  INASGVDAKA  ILSARLSKSR  RLENLIAQLP  GEKKNGLFGN   240
LIALSLGLTP  NFKSNFDLAE  DAKLQLSKDT  YDDDLDNLLA  QIGDQYADLF  LAAKNLSDAI   300
LLSDILRVNT  EITKAPLSAS  MIKRYDEHHQ  DLTLLKALVR  QQLPEKYKEI  FFDQSKNGYA   360
GYIDGGASQE  EFYKFIKPIL  EKMDGTEELL  VKLNREDLLR  KQRTFDNGSI  PHQIHLGELH   420
AILRRQEDFY  PFLKDNREKI  EKILTFRIPY  YVGPLARGNS  RFAWMTRKSE  ETITPWNFEE   480
VVDKGASAQS  FIERMTNFDK  NLPNEKVLPK  HSLLYEYFTV  YNELTKVKYV  TEGMRKPAFL   540
SGEQKKAIVD  LLFKTNRKVT  VKQLKEDYFK  KIECFDSVEI  SGVEDRFNAS  LGTYHDLLKI   600
IKDKDFLDNE  ENEDILEDIV  LTLTLFEDRE  MIEERLKTYA  HLFDDKVMKQ  LKRRRYTGWG   660
RLSRKLINGI  RDKQSGKTIL  DFLKSDGFAN  RNFMQLIHDD  SLTFKEDIQK  AQVSGQGDSL   720
HEHIANLAGS  PAIKKGILQT  VKVVDELVKV  MGRHKPENIV  IEMARENQTT  QKGQKNSRER   780
MKRIEEGIKE  LGSQILKEHP  VENTQLQNEK  LYLYYLQNGR  DMYVDQELDI  NRLSDYDVDH   840
IVPQSFLKDD  SIDNKVLTRS  DKNRGKSDNV  PSEEVVKKMK  NYWRQLLNAK  LITQRKFDNL   900
TKAERGGLSE  LDKAGFIKRQ  LVETRQITKH  VAQILDSRMN  TKYDENDKLI  REVKVITLKS   960
KLVSDFRKDF  QFYKVREINN  YHHAHDAYLN  AVVGTALIKK  YPKLESEFVY  GDYKVYDVRK  1020
MIAKSEQEIG  KATAKYFFYS  NIMNFFKTEI  TLANGEIRKR  PLIETNGETG  EIVWDKGRDF  1080
ATVRKVLSMP  QVNIVKKTEV  QTGGFSKESI  LPKRNSDKLI  ARKKDWDPKK  YGGFDSPTVA  1140
YSVLVVAKVE  KGKSKKLKSV  KELLGITIME  RSSFEKNPID  FLEAKGYKEV  KKDLIIKLPK  1200
YSLFELENGR  KRMLASAGEL  QKGNELALPS  KYVNFLYLAS  HYEKLKGSPE  DNEQKQLFVE  1260
QHKHYLDEII  EQISEFSKRV  ILADANLDKV  LSAYNKHRDK  PIREQAENII  HLFTLTNLGA  1320
PAAFKYFDTT  IDRKRYTSTK  EVLDATLIHQ  SITGLYETRI  DLSQLGGD                1368

SEQ ID NO: 207         moltype = AA    length = 1367
FEATURE                Location/Qualifiers
REGION                 1..1367
                       note = dSpCas9
source                 1..1367
                       mol_type = protein
                       organism = Synthetic construct
SEQUENCE: 207
DKKYSIGLAI  GTNSVGWAVI  TDEYKVPSKK  FKVLGNTDRH  SIKKNLIGAL  LFDSGETAEA    60
TRLKRTARRR  YTRRKNRICY  LQEIFSNEMA  KVDDSFFHRL  EESFLVEEDK  KHERHPIFGN   120
IVDEVAYHEK  YPTIYHLRKK  LVDSTDKADL  RLIYLALAHM  IKFRGHFLIE  GDLNPDNSDV   180
DKLFIQLVQT  YNQLFEENPI  NASGVDAKAI  LSARLSKSRR  LENLIAQLPG  EKKNGLFGNL   240
IALSLGLTPN  FKSNFDLAED  AKLQLSKDTY  DDDLDNLLAQ  IGDQYADLFL  AAKNLSDAIL   300
LSDILRVNTE  ITKAPLSASM  IKRYDEHHQD  LTLLKALVRQ  QLPEKYKEIF  FDQSKNGYAG   360
YIDGGASQEE  FYKFIKPILE  KMDGTEELLV  KLNREDLLRK  QRTFDNGSIP  HQIHLGELHA   420
ILRRQEDFYP  FLKDNREKIE  KILTFRIPYY  VGPLARGNSR  FAWMTRKSEE  TITPWNFEEV   480
VDKGASAQSF  IERMTNFDKN  LPNEKVLPKH  SLLYEYFTVY  NELTKVKYVT  EGMRKPAFLS   540
GEQKKAIVDL  LFKTNRKVTV  KQLKEDYFKK  IECFDSVEIS  GVEDRFNASL  GTYHDLLKII   600
KDKDFLDNEE  NEDILEDIVL  TLTLFEDREM  IEERLKTYAH  LFDDKVMKQL  KRRRYTGWGR   660
LSRKLINGIR  DKQSGKTILD  FLKSDGFANR  NFMQLIHDDS  LTFKEDIQKA  QVSGQGDSLH   720
EHIANLAGSP  AIKKGILQTV  KVVDELVKVM  GRHKPENIVI  EMARENQTTQ  KGQKNSRERM   780
KRIEEGIKEL  GSQILKEHPV  ENTQLQNEKL  YLYYLQNGRD  MYVDQELDIN  RLSDYDVDAI   840
VPQSFLKDDS  IDNKVLTRSD  KNRGKSDNVP  SEEVVKKMKN  YWRQLLNAKL  ITQRKFDNLT   900
KAERGGLSEL  DKAGFIKRQL  VETRQITKHV  AQILDSRMNT  KYDENDKLIR  EVKVITLKSK   960
LVSDFRKDFQ  FYKVREINNY  HHAHDAYLNA  VVGTALIKKY  PKLESEFVYG  DYKVYDVRKM  1020
IAKSEQEIGK  ATAKYFFYSN  IMNFFKTEIT  LANGEIRKRP  LIETNGETGE  IVWDKGRDFA  1080
TVRKVLSMPQ  VNIVKKTEVQ  TGGFSKESIL  PKRNSDKLIA  RKKDWDPKKY  GGFDSPTVAY  1140
SVLVVAKVEK  GKSKKLKSVK  ELLGITIMER  SSFEKNPIDF  LEAKGYKEVK  KDLIIKLPKY  1200
SLFELENGRK  RMLASAGELQ  KGNELALPSK  YVNFLYLASH  YEKLKGSPED  NEQKQLFVEQ  1260
HKHYLDEIIE  QISEFSKRVI  LADANLDKVL  SAYNKHRDKP  IREQAENIIH  LFTLTNLGAP  1320
AAFKYFDTTI  DRKRYTSTKE  VLDATLIHQS  ITGLYETRID  LSQLGGD                 1367

SEQ ID NO: 208         moltype = DNA   length = 4509
FEATURE                Location/Qualifiers
misc_feature           1..4509
                       note = dSpCas9-KRAB
source                 1..4509
                       mol_type = other DNA
                       organism = Synthetic construct
SEQUENCE: 208
ccaaagaaga  agcggaaggt  cggtatccac  ggagtcccag  cagccgacaa  gaagtactcc    60
attgggctcg  ccatcggcac  aaacagcgtc  ggctgggccg  tcattacgga  cgagtacaag   120
gtgccgagca  aaaaattcaa  agttctgggc  aataccgatc  gccacagcat  aaagaagaac   180
ctcattggcg  ccctcctgtt  cgactccggg  gaaaccgccg  aagccacgcg  gctcaaaaga   240
acagcacggc  gcagatatac  ccgcagaaag  aatcggatct  gctacctgca  ggagatcttt   300
agtaatgaga  tggctaaggt  ggatgactct  ttcttccata  ggctggagga  gtccttttttg   360
gtggaggagg  ataaaaagca  cgagcgccac  ccaatctttg  gcaatatcgt  ggacgaggtg   420
gcgtaccatg  aaaagtaccc  aaccatatat  catctgagaa  agaagcttgt  agacagtact   480
gataaggctg  acttgcggtt  gatctatctc  gcgctggcgc  atatgatcaa  atttcgggga   540
cacttcctca  tcgaggggga  cctgaaccca  gacaacagcg  atgtcgacaa  actctttatc   600
caactggttc  agacttacaa  tcagcttttc  gaagagaacc  cgatcaacgc  atccggagtt   660
gacgccaaag  caatcctgag  cgctaggctg  tccaaatccc  ggcggctcga  aaacctcatc   720
gcacagctcc  ctggggagaa  gaagaacggc  ctgtttggta  atcttatcgc  cctgtcactc   780
```

```
gggctgaccc ccaactttaa atctaacttc gacctggccg aagatgccaa gcttcaactg 840
agcaaagaca cctacgatga tgatctcgac aatctgctgg cccagatcgg cgaccagtac 900
gcagacctt ttttggcggc aaagaacctg tcagacgcca ttctgctgag tgatattctg 960
cgagtgaaca cggagatcac caaagctccg ctgagcgcta gtatgatcaa gcgctatgat 1020
gagcaccacc aagacttgac tttgctgaag gcccttgtca gacagcaact gcctgagaag 1080
tacaaggaaa ttttcttcga tcagtctaaa aatggctacg ccggatacat tgacggcgga 1140
gcaagccagg aggaatttta caaatttatt aagcccatct ggaaaaaat ggacggcacc 1200
gaggagctgc tggtaaagct taacagagaa gatctgttgc gcaaacagcg cacttttcgac 1260
aatggaagca tcccccacca gattcacctg ggcgaactgc acgctatcct caggcggcaa 1320
gaggatttct acccctttt gaaagataac agggaaaaga ttgagaaaat cctcacattt 1380
cggatacct actatgtagg cccctcgcc cggggaaatt ccagattcgc gtggatgact 1440
cgcaaatcag aagagaccat cactccctgg aacttcgagg aagtcgtgga taagggggcc 1500
tctgcccagt ccttcatcga aaggatgact aactttgata aaaatctgcc taacgaaaag 1560
gtgcttccta aacactctct gctgtacgag tacttcacag tttataacga gctcaccaag 1620
gtcaaatacg tcacgaagg gatgagaaag ccagcattcc tgtctggaga gcagaagaaa 1680
gctatcgtgg acctcctctt caagacgaac cggaaagtta ccgtgaaaca gctcaaagaa 1740
gactatttca aaaagattga atgtttcgac tctgttgaaa tcagcggagt ggaggatcgc 1800
ttcaacgcat ccctgggaac gtatcacgat ctcctgaaaa tcattaaaga caaggacttc 1860
ctggacaatg aggagaacga ggacattctt gaggacattg tcctcaccct tacgttgttt 1920
gaagataggg agatgattga agaacgcttg aaaacttacg ctcatctctt cgacgacaaa 1980
gtcatgaaac agctcaagag gcgccgatat acaggatggg ggcggctgtc aagaaaactg 2040
atcaagtgga tccgagacaa gcagagtgga aagacaatcc tggattttct taagtccgat 2100
ggatttgcca accggaactt catgcagttg atccatgatg actctctcac ctttaaggag 2160
gacatccaga aagcacaagt ttctggccag ggggacagtc ttcacgagca catcgctaat 2220
cttgcaggta gcccagctat caaaaaggga atactgcaga ccgttaaggt cgtggatgaa 2280
ctcgtcaaag taatgggaag gcataagccc gagaatatcg ttatcgagat ggcccgagag 2340
aaccaaacta cccagaaggg acagaagaac agtagggaaa ggatgaagag gattgaaag 2400
ggtataaaag aactggggtc ccaaatcctt aaggaacacc cagttgaaaa cacccagctt 2460
cagaatgaga agctctacct gtactacctg cagaacggca gggacatgta cgtggatcag 2520
gaactggaca tcaatcggct ctccgactac gacgtggtc ccatcgtgcc ccagtctttt 2580
ctcaaagatg attctattga taataaagtg ttgacaagat ccgataaaaa tagagggaag 2640
agtgataacg tcccctcaga agaagttgtc aagaaaatga aaaattattg gcggcagctg 2700
ctgaacgcca aactgatcac acaacggaag ttcgataatc tgactaaggc tgaacgaggt 2760
ggcctgtctg agttggataa agccggcttc atcaaaaggc agctgttga gacacgccag 2820
atcaccaagc acgtggccca aattctcgat tcacgcatga acaccaagta cgatgaaat 2880
gacaaactga ttcgagaggt gaaagttatt actctgaagt ctaagctggt ctcagatttc 2940
agaaaggact tcagttttta aggtgagaga gatcaacaa attaccacca tgcgcatgat 3000
gcctacctga atgcagtggt aggcactgca cttatcaaaa aatatcccaa gcttgaatct 3060
gaatttgttt acgagacta taagtgtac gatgttagga aagtgatcgc aaagtctgag 3120
caggaaatag gcaaggccac cgctaagtac ttcttttaca gcaatattat gaattttttc 3180
aagaccgaga ttacactggc caatggagag attcggaagc gaccacttat cgaaacaaac 3240
ggagaaacag gagaatcgt gtgggacaag ggtagggatt cgcgacagt ccggaaggtc 3300
ctgtccatgc cgcaggtgaa catcgttaaa agaccgaag aggcttctcc 3360
aaggaaagta tcctcccgaa aaggaacagc gacaagctga tcgcacgcaa aaaagattgg 3420
gaccccaaga aatacggcgg attcgattct cctacagtcg cttacagtgt actggttgtg 3480
gccaaagtgg agaagggaaa gtctaaaaaa ctcaaaagcg tcaaggaact gctgggcatc 3540
acaatcatgg agcgatcaag cttcgaaaaa aaccccatcg actttctcga ggcgaaagga 3600
tataaagagg tcaaaaaga cctcatcatt aagcttccca gtactctct ctttgagctt 3660
gaaaacggcc ggaaacgaat gctcgctagt gcgggcgagc tgcagaaagg taacgagctg 3720
gcactgccct ctaaatacgt taatttcttg tatctggcca gccactatga aaagctcaaa 3780
gggtctcccg aagataatga gcagaagcag ctgttcgtgg aacaacacaa acactacctt 3840
gatgagatca tcgagcaaat aagcgaattc tccaaaagag tgatcctcgc cgacgctaac 3900
ctcgataagg tgcttctgc ttacaataag cacagggata gcccatcag ggagcaggca 3960
gaaaacatta tccacttgtt tactctgacc aacttgggcg cgcctgcagc cttcaagtac 4020
ttcgacacca ccatagacag aaagcggtac acctctacaa aggaggtcct ggacgccaca 4080
ctgattcatc agtcaattac ggggctctat gaaacaagaa tcgacctctc tcagctcggt 4140
ggagacaaaa ggccggcggc cacgaaaaag gccggccagg caaaaaagaa aaaggctagc 4200
gatgctaagt cactgactgc ctggtccgg acactggtga ccttcaagga tgtgttgtgt 4260
gacttcacca gggaggagtg gaagctctg gacactgtc agcagatcct gtacagaaat 4320
gtgatgctgg agaactataa gaacctggtt tccttgggtt atcagcttac taagccagat 4380
gtgatcctcc ggttggagaa gggagaagag ccctggctgg tggagagaga aattcaccaa 4440
gagacccatc ctgattcaga gactgcattt gaaatcaaat catcagttcc gaaaagaaa 4500
cgcaaagtt 4509
```

SEQ ID NO: 209        moltype = AA   length = 1503
FEATURE               Location/Qualifiers
REGION                1..1503
                      note = dSpCas9-KRAB
source                1..1503
                      mol_type = protein
                      organism = Synthetic construct
SEQUENCE: 209
PKKKRKVGIH GVPAADKKYS IGLAIGTNSV GWAVITDEYK VPSKKFKVLG NTDRHSIKKN 60
LIGALLFDSG ETAEATRLKR TARRRYTRRK NRICYLQEIF SNEMAKVDDS FFHRLEESFL 120
VEEDKKHERH PIFGNIVDEV AYHEKYPTIY HLRKKLVDST DKADLRLIYL ALAHMIKFRG 180
HFLIEGDLNP DNSDVDKLFI QLVQTYNQLF EENPINASGV DAKAILSARL SKSRRLENLI 240
AQLPGEKKNG LFGNLIALSL GLTPNFKSNF DLAEDAKLQL SKDTYDDDLD NLLAQIGDQY 300
ADLFLAAKNL SDAILLSDIL RVNTEITKAP LSASMIKRYD EHHQDLTLLK ALVRQQLPEK 360
YKEIFFDQSK NGYAGYIDGG ASQEEFYKFI KPILEKMDGT EELLVKLNRE DLLRKQRTFD 420

```
                                                       -continued
NGSIPHQIHL GELHAILRRQ EDFYPFLKDN REKIEKILTF RIPYYVGPLA RGNSRFAWMT        480
RKSEETITPW NFEEVVDKGA SAQSFIERMT NFDKNLPNEK VLPKHSLLYE YFTVYNELTK        540
VKYVTEGMRK PAFLSGEQKK AIVDLLFKTN RKVTVKQLKE DYFKKIECFD SVEISGVEDR        600
FNASLGTYHD LLKIIKDKDF LDNEENEDIL EDIVLTLTLF EDREMIEERL KTYAHLFDDK        660
VMKQLKRRRY TGWGRLSRKL INGIRDKQSG KTILDFLKSD GFANRNFMQL IHDDSLTFKE        720
DIQKAQVSGQ GDSLHEHIAN LAGSPAIKKG ILQTVKVVDE LVKVMGRHKP ENIVIEMARE        780
NQTTQKGQKN SRERMKRIEE GIKELGSQIL KEHPVENTQL QNEKLYLYYL QNGRDMYVDQ        840
ELDINRLSDY DVDAIVPQSF LKDDSIDNKV LTRSDKNRGK SDNVPSEEVV KKMKNYWRQL        900
LNAKLITQRK FDNLTKAERG GLSELDKAGF IKRQLVETRQ ITKHVAQILD SRMNTKYDEN        960
DKLIREVKVI TLKSKLVSDF RKDFQFYKVR EINNYHHAHD AYLNAVVGTA LIKKYPKLES       1020
EFVYGDYKVY DVRKMIAKSE QEIGKATAKY FFYSNIMNFF KTEITLANGE IRKRPLIETN       1080
GETGEIVWDK GRDFATVRKV LSMPQVNIVK KTEVQTGGFS KESILPKRNS DKLIARKKDW       1140
DPKKYGGFDS PTVAYSVLVV AKVEKGKSKK LKSVKELLGI TIMERSSFEK NPIDFLEAKG       1200
YKEVKKDLII KLPKYSLFEL ENGRKRMLAS AGELQKGNEL ALPSKYVNFL YLASHYEKLK       1260
GSPEDNEQKQ LFVEQHKHYL DEIIEQISEF SKRVILADAN LDKVLSAYNK HRDKPIREQA       1320
ENIIHLFTLT NLGAPAAFKY FDTTIDRKRY TSTKEVLDAT LIHQSITGLY ETRIDLSQLG       1380
GDKRPAATKK AGQAKKKKAS DAKSLTAWSR TLVTFKDVFV DFTREEWKLL DTAQQILYRN       1440
VMLENYKNLV SLGYQLTKPD VILRLEKGEE PWLVEREIHQ ETHPDSETAF EIKSSVPKKK       1500
RKV                                                                    1503

SEQ ID NO: 210              moltype = AA   length = 8
FEATURE                     Location/Qualifiers
REGION                      1..8
                            note = PAM - N. meningitidis Cas9
source                      1..8
                            mol_type = protein
                            organism = Synthetic construct
SEQUENCE: 210
NNNNGATT                                                                  8

SEQ ID NO: 211              moltype = AA   length = 8
FEATURE                     Location/Qualifiers
REGION                      1..8
                            note = PAM - N. meningitidis Cas9
source                      1..8
                            mol_type = protein
                            organism = Synthetic construct
SEQUENCE: 211
NNNNRYAC                                                                  8

SEQ ID NO: 212              moltype = AA   length = 7
FEATURE                     Location/Qualifiers
REGION                      1..7
                            note = PAM - S. thermophilus
source                      1..7
                            mol_type = protein
                            organism = Synthetic construct
SEQUENCE: 212
NNAGAAW                                                                   7

SEQ ID NO: 213              moltype =     length =
SEQUENCE: 213
000

SEQ ID NO: 214              moltype = AA   length = 6
FEATURE                     Location/Qualifiers
REGION                      1..6
                            note = PAM - T. denticola
source                      1..6
                            mol_type = protein
                            organism = Synthetic construct
SEQUENCE: 214
NAAAAC                                                                    6

SEQ ID NO: 215              moltype = AA   length = 4
FEATURE                     Location/Qualifiers
REGION                      1..4
                            note = PAM - Cas12a/Cpf1
source                      1..4
                            mol_type = protein
                            organism = Synthetic construct
SEQUENCE: 215
TTTV                                                                      4

SEQ ID NO: 216              moltype = AA   length = 4
FEATURE                     Location/Qualifiers
REGION                      1..4
                            note = Variant PAM - SpCas9 variant
source                      1..4
```

```
                           mol_type = protein
                           organism = Synthetic construct
SEQUENCE: 216
NGAN                                                                        4

SEQ ID NO: 217             moltype = AA   length = 4
FEATURE                    Location/Qualifiers
REGION                     1..4
                           note = Variant PAM - SpCas9 variant
source                     1..4
                           mol_type = protein
                           organism = Synthetic construct
SEQUENCE: 217
NGNG                                                                        4

SEQ ID NO: 218             moltype = AA   length = 4
FEATURE                    Location/Qualifiers
REGION                     1..4
                           note = Variant PAM - SpCas9 variant
source                     1..4
                           mol_type = protein
                           organism = Synthetic construct
SEQUENCE: 218
NGAG                                                                        4

SEQ ID NO: 219             moltype = AA   length = 4
FEATURE                    Location/Qualifiers
REGION                     1..4
                           note = Variant PAM - SpCas9 variant
source                     1..4
                           mol_type = protein
                           organism = Synthetic construct
SEQUENCE: 219
NGCG                                                                        4

SEQ ID NO: 220             moltype = AA   length = 548
FEATURE                    Location/Qualifiers
REGION                     1..548
                           note = ERF domain
source                     1..548
                           mol_type = protein
                           organism = Synthetic construct
SEQUENCE: 220
MKTPADTGFA FPDWAYKPES SPGSRQIQLW HFILELLRKE EYQGVIAWQG DYGEFVIKDP           60
DEVARLWGVR KCKPQMNYDK LSRALRYYYN KRILHKTKGK RFTYKFNFNK LVLVNYPFID          120
VGLAGGAVPQ SAPPVPSGGS HFRFPPSTPS EVLSPTEDPR SPPACSSSSS SLFSAVVARR          180
LGRGSVSDCS DGTSELEEPL GEDPRARPPG PPDLGAFRGP PLARLPHDPG VFRVYPRPRG          240
GPEPLSPFPV SPLAGPGSLL PPQLSPALPM TPTHLAYTPS PTLPSPMYPSG GGGPSGSGGG         300
SHFSFSPEDM KRYLQAHTQS VYNYHLSPRA FLHYPGLVVP QPQRPDKCPL PPMAPETPPV          360
PSSASSSSSS SSSPFKFKLQ PPPLGRRQRA AGEKAVAGAD KSGGSAGGLA EGAGALAPPP          420
PPPQIKVEPI SEGESEEVEV TDISDEDEED GEVFKTPRAP PAPPKPEPGE APGASQCMPL          480
KLRFKRRWSE DCRLEGGGGP AGGFEDEGED KKVRGEGPGE AGGPLTPRRV SSDLQHATAQ          540
LSLEHRDS                                                                  548

SEQ ID NO: 221             moltype = AA   length = 228
FEATURE                    Location/Qualifiers
REGION                     1..228
                           note = MXI1 domain
source                     1..228
                           mol_type = protein
                           organism = Synthetic construct
SEQUENCE: 221
MERVKMINVQ RLLEAAEFLE RRERECEHGY ASSFPSMPSP RLQHSKPPRR LSRAQKHSSG           60
SSNTSTANRS THNELEKNRR AHLRLCLERL KVLIPLGPDC TRHTTLGLLN KAKAHIKKLE          120
EAERKSQHQL ENLEREQRFL KWRLEQLQGP QEMERIRMDS IGSTISSDRS DSEREEIEVD          180
VESTEFSHGE VDNISTTSIS DIDDHSSLPS IGSDEGYSSA SVKLSFTS                      228

SEQ ID NO: 222             moltype = AA   length = 144
FEATURE                    Location/Qualifiers
REGION                     1..144
                           note = SID4X domain
source                     1..144
                           mol_type = protein
                           organism = Synthetic construct
SEQUENCE: 222
ASPKKKRKVE ASGSGMNIQM LLEAADYLER EREAEHGYA SMLPGSGMNI QMLLEAADYL            60
ERREREAEHG YASMLPGSGM NIQMLLEAAD YLERRREAE HGYASMLPGS GMNIQMLLEA           120
ADYLERRERE AEHGYASMLP SRSR                                                144
```

```
SEQ ID NO: 223              moltype = AA  length = 220
FEATURE                     Location/Qualifiers
REGION                      1..220
                            note = MAD-SID domain
source                      1..220
                            mol_type = protein
                            organism = Synthetic construct
SEQUENCE: 223
MAAAVRMNIQ MLLEAADYLE RREREAEHGY ASMLPYNNKD RDALKRRNKS KKNNSSSRST    60
HNEMEKNRRA HLRLCLEKLK GLVPLGPESS RHTTLSLLTK AKLHIKKLED CDRKAVHQID   120
QLQREQRHLK RQLEKLGIER IRMDSIGSTV SSERSDSDRE EIDVDVESTD YLTGDLDWSS   180
SSVSDSDERG SMQSLGSDEG YSSTSIKRIK LQDSHKACLG                        220

SEQ ID NO: 224              moltype = AA  length = 853
FEATURE                     Location/Qualifiers
REGION                      1..853
                            note = DNMT3B
source                      1..853
                            mol_type = protein
                            organism = Synthetic construct
SEQUENCE: 224
MKGDTRHLNG EEDAGGREDS ILVNGACSDQ SSDSPPILEA IRTPEIRGRR SSSRLSKREV    60
SSLLSYTQDL TGDGDGEDGD GSDTPVMPKL FRETRTRSES PAVRTRNNNS VSSRERHRPS   120
PRSTRGRQGR NHVDESPVEF PATRSLRRRA TASAGTPWPS PPSSYLTIDL TDDTEDTHGT   180
PQSSSTPYAR LAQDSQQGGM ESPQVEADSG DGDSSEYQDG KEFGIGDLVW GKIKGFSWWP   240
AMVVSWKATS KRQAMSGMRW VQWFGDGKFS EVSADKLVAL GLFSQHFNLA TFNKLVSYRK   300
AMYHALEKAR VRAGKTFPSS PGDSLEDQLK PMLEWAHGGF KPTGIEGLKP NNTQPVVNKS   360
KVRRAGSRKL ESRKYENKTR RRTADDSATS DYCPAPKRLK TNCYNNGKDR GDEDQSREQM   420
ASDVANNKSS LEDGCLSCGR KNPVSFHPLF EGGLCQTCRD RFLELFYMYD DDGYQSYCTV   480
CCEGRELLLC SNTSCCRCFC VECLEVLVGT GTAAEAKLQE PWSCYMCLPQ RCHGVLRRRK   540
DWNVRLQAFF TSDTGLEYEA PKLYPAIPAA RRRPIRVLSL FDGIATGYLV LKELGIKVGK   600
YVASEVCEES IAVGTVKHEG NIKYVNDVRN ITKKNIEEWG PFDLVIGGSP CNDLSNVNPA   660
RKGLYEGTGR LFFEFYHLLN YSRPKEGDDR PFFWMFENVV AMKVGDKRDI SRFLECNPVM   720
IDAIKVSAAH RARYFWGNLP GMNRPVIASK NDKLELQDCL EYNRIAKLKK VQTITTKSNS   780
IKQGKNQLFP VVMNGKEDVL WCTELERIFG FPVHYTDVSN MGRGARQKLL GRSWSVPVIR   840
HLFAPLKDYF ACE                                                     853

SEQ ID NO: 225              moltype = AA  length = 852
FEATURE                     Location/Qualifiers
REGION                      1..852
                            note = LSD1
source                      1..852
                            mol_type = protein
                            organism = Synthetic construct
SEQUENCE: 225
MLSGKKAAAA AAAAAAAATG TEAGPGTAGG SENGSEVAAQ PAGLSGPAEV GPGAVGERTP    60
RKKEPPRASP PGGLAEPPGS AGPQAGPTVV PGSATPMETG IAETPEGRRT SRRKRAKVEY   120
REMDESLANL SEDEYYSEEE RNAKAEKEKK LPPPPPQAPP EEENESEPEE PSGVEGAAFQ   180
SRLPHDRMTS QEAACFPDII SGPQQTQKVF LFIRNRTLQL WLDNPKIQLT FEATLQQLEA   240
PYNSDTVLVH RVHSYLERHG LINFGIYKRI KPLPTKKTGK VIIIGSGVSG LAAARQLQSF   300
GMDVTLLEAR DRVGGRVATF RKGNYVADLG AMVVTGLGGN PMAVVSKQVN MELAKIKQKC   360
PLYEANGQAV PKEKDEMVEQ EFNRLLEATS YLSHQLDFNV LNNKPVSLGQ ALEVVIQLQE   420
KHVKDEQIEH WKKIVKTQEE LKELLNKMVN LKEKIKELHQ QYKEASEVKP PRDITAEFLV   480
KSKHRDLTAL CKEYDELAET QGKLEEKLQE LEANPPSDVY LSSRDRQILD WHFANLEFAN   540
ATPLSTLSLK HWDQDDDFEF TGSHLTVRNG YSCVPVALAE GLDIKLNTAV RQVRYTASGC   600
EVIAVNTRST SQTFIYKCDA VLCTLPLGVL KQQPPAVQFV PPLPEWKTSA VQRMGFGNLN   660
KVVLCFDRVF WDPSVNLFGH VGSTTASRGE LFLFWNLYKA PILLALVAGE AAGIMENISD   720
DVIVGRCLAI LKGIFSSSAV PQPKETVVSR WRADPWARGS YSYVAAGSSG NDYDLMAQPI   780
TPGPSIPGAP QPIPRLFFAG EHTIRNYPAT VHGALLSGLR EAGRIADQFL GAMYTLPRQA   840
TPGVPAQQSP SM                                                      852

SEQ ID NO: 226              moltype = AA  length = 22
FEATURE                     Location/Qualifiers
REGION                      1..22
                            note = SunTag GCN4 peptide
source                      1..22
                            mol_type = protein
                            organism = Synthetic construct
SEQUENCE: 226
LLPKNYHLEN EVARLKKLVG ER                                            22

SEQ ID NO: 227              moltype = AA  length = 5
FEATURE                     Location/Qualifiers
REGION                      1..5
                            note = GGSGG linker
source                      1..5
                            mol_type = protein
                            organism = Synthetic construct
SEQUENCE: 227
```

```
GGSGG                                                                       5

SEQ ID NO: 228         moltype = AA  length = 5
FEATURE                Location/Qualifiers
REGION                 1..5
                       note = GGGGS linker
source                 1..5
                       mol_type = protein
                       organism = Synthetic construct
SEQUENCE: 228
GGGGS                                                                       5

SEQ ID NO: 229         moltype = AA  length = 5
FEATURE                Location/Qualifiers
REGION                 1..5
                       note = GGGGG linker
source                 1..5
                       mol_type = protein
                       organism = Synthetic construct
SEQUENCE: 229
GGGGG                                                                       5

SEQ ID NO: 230         moltype = AA  length = 5
FEATURE                Location/Qualifiers
REGION                 1..5
                       note = GGAGG linker
source                 1..5
                       mol_type = protein
                       organism = Synthetic construct
SEQUENCE: 230
GGAGG                                                                       5

SEQ ID NO: 231         moltype = AA  length = 7
FEATURE                Location/Qualifiers
REGION                 1..7
                       note = GGGGSSS linker
source                 1..7
                       mol_type = protein
                       organism = Synthetic construct
SEQUENCE: 231
GGGGSSS                                                                     7

SEQ ID NO: 232         moltype = AA  length = 7
FEATURE                Location/Qualifiers
REGION                 1..7
                       note = GGGGAAA linker
source                 1..7
                       mol_type = protein
                       organism = Synthetic construct
SEQUENCE: 232
GGGGAAA                                                                     7

SEQ ID NO: 233         moltype = AA  length = 80
FEATURE                Location/Qualifiers
REGION                 1..80
                       note = XTEN80
source                 1..80
                       mol_type = protein
                       organism = Synthetic construct
SEQUENCE: 233
GGPSSGAPPP SGGSPAGSPT STEEGTSESA TPESGPGTST EPSEGSAPGS PAGSPTSTEE           60
GTSTEPSEGS APGTSTEPSE                                                      80

SEQ ID NO: 234         moltype = AA  length = 7
FEATURE                Location/Qualifiers
REGION                 1..7
                       note = NLS - SV40
source                 1..7
                       mol_type = protein
                       organism = Synthetic construct
SEQUENCE: 234
PKKKRKV                                                                     7

SEQ ID NO: 235         moltype = AA  length = 9
FEATURE                Location/Qualifiers
REGION                 1..9
                       note = NLS - cMyc
source                 1..9
                       mol_type = protein
```

```
                          organism = Synthetic construct
SEQUENCE: 235
PAAKRVKLD                                                                  9

SEQ ID NO: 236            moltype = AA  length = 11
FEATURE                   Location/Qualifiers
REGION                    1..11
                          note = NLS - cMyc
source                    1..11
                          mol_type = protein
                          organism = Synthetic construct
SEQUENCE: 236
RQRRNELKRS P                                                              11

SEQ ID NO: 237            moltype = AA  length = 38
FEATURE                   Location/Qualifiers
REGION                    1..38
                          note = NLS - hRNPA1 M9
source                    1..38
                          mol_type = protein
                          organism = Synthetic construct
SEQUENCE: 237
NQSSNFGPMK GGNFGGRSSG PYGGGGQYFA KPRNQGGY                                  38

SEQ ID NO: 238            moltype = AA  length = 42
FEATURE                   Location/Qualifiers
REGION                    1..42
                          note = NLS - IBB domain importin-alpha
source                    1..42
                          mol_type = protein
                          organism = Synthetic construct
SEQUENCE: 238
RMRIZFKNKG KDTAELRRRR VEVSVELRKA KKDEQILKRR NV                             42

SEQ ID NO: 239            moltype = AA  length = 8
FEATURE                   Location/Qualifiers
REGION                    1..8
                          note = NLS - myoma T protein
source                    1..8
                          mol_type = protein
                          organism = Synthetic construct
SEQUENCE: 239
VSRKRPRP                                                                   8

SEQ ID NO: 240            moltype = AA  length = 8
FEATURE                   Location/Qualifiers
REGION                    1..8
                          note = NLS - myoma T protein
source                    1..8
                          mol_type = protein
                          organism = Synthetic construct
SEQUENCE: 240
PPKKARED                                                                   8

SEQ ID NO: 241            moltype = AA  length = 8
FEATURE                   Location/Qualifiers
REGION                    1..8
                          note = NLS - human p53
source                    1..8
                          mol_type = protein
                          organism = Synthetic construct
SEQUENCE: 241
PQPKKKPL                                                                   8

SEQ ID NO: 242            moltype = AA  length = 12
FEATURE                   Location/Qualifiers
REGION                    1..12
                          note = NLS - mouse c-abl IV
source                    1..12
                          mol_type = protein
                          organism = Synthetic construct
SEQUENCE: 242
SALIKKKKKM AP                                                             12

SEQ ID NO: 243            moltype = AA  length = 5
FEATURE                   Location/Qualifiers
REGION                    1..5
                          note = NLS - influenza NS1
source                    1..5
```

```
                          mol_type = protein
                          organism = Synthetic construct
SEQUENCE: 243
DRLRR                                                                          5

SEQ ID NO: 244            moltype = AA  length = 7
FEATURE                   Location/Qualifiers
REGION                    1..7
                          note = NLS - influenza NS1
source                    1..7
                          mol_type = protein
                          organism = Synthetic construct
SEQUENCE: 244
PKQKKRK                                                                        7

SEQ ID NO: 245            moltype = AA  length = 10
FEATURE                   Location/Qualifiers
REGION                    1..10
                          note = NLS - hepatitis delta antigen
source                    1..10
                          mol_type = protein
                          organism = Synthetic construct
SEQUENCE: 245
RKLKKKIKKL                                                                    10

SEQ ID NO: 246            moltype = AA  length = 10
FEATURE                   Location/Qualifiers
REGION                    1..10
                          note = NLS - mouse Mx1
source                    1..10
                          mol_type = protein
                          organism = Synthetic construct
SEQUENCE: 246
REKKKFLKRR                                                                    10

SEQ ID NO: 247            moltype = AA  length = 20
FEATURE                   Location/Qualifiers
REGION                    1..20
                          note = NLS - human poly(ADP-ribose) polymerase
source                    1..20
                          mol_type = protein
                          organism = Synthetic construct
SEQUENCE: 247
KRKGDEVDGV DEVAKKKSKK                                                         20

SEQ ID NO: 248            moltype = AA  length = 17
FEATURE                   Location/Qualifiers
REGION                    1..17
                          note = NLS - glucocorticoid
source                    1..17
                          mol_type = protein
                          organism = Synthetic construct
SEQUENCE: 248
RKCLQAGMNL EARKTKK                                                            17

SEQ ID NO: 249            moltype = AA  length = 16
FEATURE                   Location/Qualifiers
REGION                    1..16
                          note = NLS - nucleoplasmin
source                    1..16
                          mol_type = protein
                          organism = Synthetic construct
SEQUENCE: 249
KRPAATKKAG QAKKKK                                                             16

SEQ ID NO: 250            moltype = DNA  length = 20
FEATURE                   Location/Qualifiers
misc_feature              1..20
                          note = gRNA-mousePCSK9-A spacer DNA
source                    1..20
                          mol_type = other DNA
                          organism = Synthetic construct
SEQUENCE: 250
gggaagggat acaggctgga                                                         20

SEQ ID NO: 251            moltype = DNA  length = 20
FEATURE                   Location/Qualifiers
misc_feature              1..20
                          note = gRNA-mousePCSK9-B spacer DNA
```

```
source                      1..20
                            mol_type = other DNA
                            organism = Synthetic construct
SEQUENCE: 251
gtcccgtttg cagcccaatt                                                   20

SEQ ID NO: 252              moltype = DNA  length = 20
FEATURE                     Location/Qualifiers
misc_feature                1..20
                            note = gRNA-mousePCSK9-C spacer DNA
source                      1..20
                            mol_type = other DNA
                            organism = Synthetic construct
SEQUENCE: 252
gagcgtcatt tgacgctgtc                                                   20

SEQ ID NO: 253              moltype = DNA  length = 20
FEATURE                     Location/Qualifiers
misc_feature                1..20
                            note = gRNA-mousePCSK9-D spacer DNA
source                      1..20
                            mol_type = other DNA
                            organism = Synthetic construct
SEQUENCE: 253
ggatcttccg atggggctcg                                                   20

SEQ ID NO: 254              moltype = DNA  length = 20
FEATURE                     Location/Qualifiers
misc_feature                1..20
                            note = gRNA-mousePCSK9-E spacer DNA
source                      1..20
                            mol_type = other DNA
                            organism = Synthetic construct
SEQUENCE: 254
gtgaaggtgg aagccttctg                                                   20

SEQ ID NO: 255              moltype = DNA  length = 20
FEATURE                     Location/Qualifiers
misc_feature                1..20
                            note = gRNA-mousePCSK9-F spacer DNA
source                      1..20
                            mol_type = other DNA
                            organism = Synthetic construct
SEQUENCE: 255
gtggacgcgc aggctgccgg                                                   20

SEQ ID NO: 256              moltype = DNA  length = 20
FEATURE                     Location/Qualifiers
misc_feature                1..20
                            note = gRNA-mousePCSK9-G spacer DNA
source                      1..20
                            mol_type = other DNA
                            organism = Synthetic construct
SEQUENCE: 256
ggggcgagga gaggtgcgcg                                                   20

SEQ ID NO: 257              moltype = DNA  length = 20
FEATURE                     Location/Qualifiers
misc_feature                1..20
                            note = gRNA-mousePCSK9-H spacer DNA
source                      1..20
                            mol_type = other DNA
                            organism = Synthetic construct
SEQUENCE: 257
agtgggtgcc catcggggcg                                                   20

SEQ ID NO: 258              moltype = DNA  length = 20
FEATURE                     Location/Qualifiers
misc_feature                1..20
                            note = gRNA-mousePCSK9-I spacer DNA
source                      1..20
                            mol_type = other DNA
                            organism = Synthetic construct
SEQUENCE: 258
ctactgtgcc ccaccggcgc                                                   20

SEQ ID NO: 259              moltype = RNA  length = 20
FEATURE                     Location/Qualifiers
misc_feature                1..20
```

```
                        note = gRNA-mousePCSK9-A spacer RNA
source                  1..20
                        mol_type = other RNA
                        organism = Synthetic construct
SEQUENCE: 259
gggaagggat acaggctgga                                                    20

SEQ ID NO: 260          moltype = RNA  length = 20
FEATURE                 Location/Qualifiers
misc_feature            1..20
                        note = gRNA-mousePCSK9-B spacer RNA
source                  1..20
                        mol_type = other RNA
                        organism = Synthetic construct
SEQUENCE: 260
gtcccgtttg cagcccaatt                                                    20

SEQ ID NO: 261          moltype = RNA  length = 20
FEATURE                 Location/Qualifiers
misc_feature            1..20
                        note = gRNA-mousePCSK9-C spacer RNA
source                  1..20
                        mol_type = other RNA
                        organism = Synthetic construct
SEQUENCE: 261
gagcgtcatt tgacgctgtc                                                    20

SEQ ID NO: 262          moltype = RNA  length = 20
FEATURE                 Location/Qualifiers
misc_feature            1..20
                        note = gRNA-mousePCSK9-D spacer RNA
source                  1..20
                        mol_type = other RNA
                        organism = Synthetic construct
SEQUENCE: 262
ggatcttccg atggggctcg                                                    20

SEQ ID NO: 263          moltype = RNA  length = 20
FEATURE                 Location/Qualifiers
misc_feature            1..20
                        note = gRNA-mousePCSK9-E spacer RNA
source                  1..20
                        mol_type = other RNA
                        organism = Synthetic construct
SEQUENCE: 263
gtgaaggtgg aagccttctg                                                    20

SEQ ID NO: 264          moltype = RNA  length = 20
FEATURE                 Location/Qualifiers
misc_feature            1..20
                        note = gRNA-mousePCSK9-F spacer RNA
source                  1..20
                        mol_type = other RNA
                        organism = Synthetic construct
SEQUENCE: 264
gtggacgcgc aggctgccgg                                                    20

SEQ ID NO: 265          moltype = RNA  length = 20
FEATURE                 Location/Qualifiers
misc_feature            1..20
                        note = gRNA-mousePCSK9-G spacer RNA
source                  1..20
                        mol_type = other RNA
                        organism = Synthetic construct
SEQUENCE: 265
ggggcgagga gaggtgcgcg                                                    20

SEQ ID NO: 266          moltype = RNA  length = 20
FEATURE                 Location/Qualifiers
misc_feature            1..20
                        note = gRNA-mousePCSK9-H spacer RNA
source                  1..20
                        mol_type = other RNA
                        organism = Synthetic construct
SEQUENCE: 266
agtgggtgcc catcggggcg                                                    20

SEQ ID NO: 267          moltype = RNA  length = 20
FEATURE                 Location/Qualifiers
```

```
misc_feature            1..20
                        note = gRNA-mousePCSK9-I spacer RNA
source                  1..20
                        mol_type = other RNA
                        organism = Synthetic construct
SEQUENCE: 267
ctactgtgcc ccaccggcgc                                                    20

SEQ ID NO: 268          moltype = RNA  length = 106
FEATURE                 Location/Qualifiers
misc_feature            1..106
                        note = gRNA-mousePCSK9-A gRNA
source                  1..106
                        mol_type = other RNA
                        organism = Synthetic construct
SEQUENCE: 268
gggaagggat acaggctgga gtttaagagc tatgctggaa acagcatagc aagtttaaat        60
aaggctagtc cgttatcaac ttgaaaaagt ggcaccgagt cggtgc                      106

SEQ ID NO: 269          moltype = RNA  length = 106
FEATURE                 Location/Qualifiers
misc_feature            1..106
                        note = gRNA-mousePCSK9-B gRNA
source                  1..106
                        mol_type = other RNA
                        organism = Synthetic construct
SEQUENCE: 269
gtcccgtttg cagcccaatt gtttaagagc tatgctggaa acagcatagc aagtttaaat        60
aaggctagtc cgttatcaac ttgaaaaagt ggcaccgagt cggtgc                      106

SEQ ID NO: 270          moltype = RNA  length = 106
FEATURE                 Location/Qualifiers
misc_feature            1..106
                        note = gRNA-mousePCSK9-C gRNA
source                  1..106
                        mol_type = other RNA
                        organism = Synthetic construct
SEQUENCE: 270
gagcgtcatt tgacgctgtc gtttaagagc tatgctggaa acagcatagc aagtttaaat        60
aaggctagtc cgttatcaac ttgaaaaagt ggcaccgagt cggtgc                      106

SEQ ID NO: 271          moltype = RNA  length = 106
FEATURE                 Location/Qualifiers
misc_feature            1..106
                        note = gRNA-mousePCSK9-D gRNA
source                  1..106
                        mol_type = other RNA
                        organism = Synthetic construct
SEQUENCE: 271
ggatcttccg atgggctcg gtttaagagc tatgctggaa acagcatagc aagtttaaat         60
aaggctagtc cgttatcaac ttgaaaaagt ggcaccgagt cggtgc                      106

SEQ ID NO: 272          moltype = RNA  length = 106
FEATURE                 Location/Qualifiers
misc_feature            1..106
                        note = gRNA-mousePCSK9-E gRNA
source                  1..106
                        mol_type = other RNA
                        organism = Synthetic construct
SEQUENCE: 272
gtgaaggtgg aagccttctg gtttaagagc tatgctggaa acagcatagc aagtttaaat        60
aaggctagtc cgttatcaac ttgaaaaagt ggcaccgagt cggtgc                      106

SEQ ID NO: 273          moltype = RNA  length = 106
FEATURE                 Location/Qualifiers
misc_feature            1..106
                        note = gRNA-mousePCSK9-F gRNA
source                  1..106
                        mol_type = other RNA
                        organism = Synthetic construct
SEQUENCE: 273
gtggacgcgc aggctgccgg gtttaagagc tatgctggaa acagcatagc aagtttaaat        60
aaggctagtc cgttatcaac ttgaaaaagt ggcaccgagt cggtgc                      106

SEQ ID NO: 274          moltype = RNA  length = 106
FEATURE                 Location/Qualifiers
misc_feature            1..106
                        note = gRNA-mousePCSK9-G gRNA
source                  1..106
```

```
                        mol_type = other RNA
                        organism = Synthetic construct
SEQUENCE: 274
ggggcgagga gaggtgcgcg gtttaagagc tatgctggaa acagcatagc aagtttaaat    60
aaggctagtc cgttatcaac ttgaaaaagt ggcaccgagt cggtgc                  106

SEQ ID NO: 275          moltype = RNA  length = 106
FEATURE                 Location/Qualifiers
misc_feature            1..106
                        note = gRNA-mousePCSK9-H gRNA
source                  1..106
                        mol_type = other RNA
                        organism = Synthetic construct
SEQUENCE: 275
agtgggtgcc catcggggcg gtttaagagc tatgctggaa acagcatagc aagtttaaat    60
aaggctagtc cgttatcaac ttgaaaaagt ggcaccgagt cggtgc                  106

SEQ ID NO: 276          moltype = RNA  length = 106
FEATURE                 Location/Qualifiers
misc_feature            1..106
                        note = gRNA-mousePCSK9-I gRNA
source                  1..106
                        mol_type = other RNA
                        organism = Synthetic construct
SEQUENCE: 276
ctactgtgcc ccaccggcgc gtttaagagc tatgctggaa acagcatagc aagtttaaat    60
aaggctagtc cgttatcaac ttgaaaaagt ggcaccgagt cggtgc                  106

SEQ ID NO: 277          moltype = DNA  length = 6204
FEATURE                 Location/Qualifiers
misc_feature            1..6204
                        note = dSpCas9-KRAB-DNTM3A/L
source                  1..6204
                        mol_type = other DNA
                        organism = Synthetic construct
SEQUENCE: 277
aaccacgatc aggagtttga ccccctaag gtgtacccac ccgtgccagc cgagaagagg     60
aagcccatcc gcgtgctgtc cctgttcgac ggcatcgcca caggcctgct ggtgctgaag   120
gatctgggca tccaggtgga cagatatatc gcctccggca gtgtgcgagga ttctatcacc   180
gtgggcatgg tgaggcacca gggcaagatc atgtacgtgg cgacgtgcg cagcgtgaca   240
cagaagcaca tccaggagtg gggacccttc gacctggtca tcggaggcag ccctgtaat   300
gacctgtcca tcgtgaaccc tgcaaggaag ggcctgtatg agggaaccgg cagactgttc   360
tttgagttct acaggctgct gcacgacgcc cgccctaagg aggcgatga caggccattc   420
ttttggctgt ttgagaacgt ggtgccatg ggcgtgagcg acaagcggga tatctccaga   480
ttcctggagt ctaatcccgt gatgatcgat gcaaaggagg tgtctgccgc acacagggca   540
aggtactttt ggggaaatct gcctggcatg aaccgcccac tggccagcac cgtgaacgac   600
aagctggac tgcaggagtg cctggagcac gaaaggatcg ccaagttctc caaggtgcgg   660
acaatcacca caagatccaa cagcatcaag cagggcaagg atcagcactt ccccgtgttc   720
atgaatgaga aggaggacat cctgtggtgt accgagatgg agcgcgtgtt cggctttcca   780
gtgcactata cagacgtgag caatatgagc cggctggcaa gcagagact gctgggccgg   840
tcctggtctg tgcagtgat cagacacctg ttcgcccccc tgaaggagta ctttgcccgg   900
gtgtctagcg gcaactctaa tgccaacagc agaggcccctt cctttcctc tggcctggtg   960
ccactgtctc tgagggcag ccacatgggc cccatggaga tctacaagac cgtgtccgcc  1020
tggaagaggc agcctgtgcg cgtgctgtct ctgttccgca acatcgacaa ggtgctgaag  1080
agcctgggct ttctggagag cggatccgga ctctggagga gcaccctga gtatgtggag  1140
gatgtgacaa atgtggtgcg gagagatgtg gagaagtggg gccccttcga tctggtgtac  1200
ggatccaccc agccactggg aagctcctgc gataggtgtc caggatggta tatgttccag  1260
tttcacagaa tcctgcagta cgcactgcca aggcaggaga gccagcgccc ttctcttttgg  1320
atctttatgt acaacctgct gctgacagag gatgaccagg agcaaacaac cgcttcctg  1380
cagacagagg cagtgaccct gcaggatgtg aggggacggg actatcagaa tgccatgcgg  1440
gtgtggtcta acatccctgg cctgaagagc aagcacgccc cctgaccccc taaggaggag  1500
gagtacctgc aggcccaggt gcggagcaga tccaagctgg atgcccctaa ggtgacctg   1560
ctggtgaaga attgtctgct gccactgcgg gagtacttca gtactttag tcagaatagc   1620
ctgccactgg aggcaagcgg atccggaagg gcatctcctg gaatcccaag aagcacccgc   1680
aaccccaaga gaagcggaa ggtgggcatc cacggcgtgc cgccgccga caagaagtac   1740
agcatcggcc tggccatcgg caccaacagc gtgggctggg ccgtgatcac cgacgagtac   1800
aaggtgccca gcaagaagtt caaggtgctg ggcaacaccg accggcacag catcaagaag   1860
aacctgatcg gcgccgcctgc gttcagagc ggcgagaccg ccgaggccac ccggctgttc   1920
cgaccgccc ggcggccggta cacccggcgg aagaaccgga tctgctacct gcaggagatc   1980
ttcagcaacg agatgccaa ggtggacgac agcttcttcc accggctgga ggagagcttc   2040
ctggtggagg aggacaagaa gcacgagcgg caccccatct tcggcaacat cgtggacgag   2100
gtggcctacc acgagaagta ccccaccatc taccacctgc ggaagaagct ggtggacagc   2160
accgacaagg ccgacctgcg gctgatctac ctggccctgg cccacatgat caagttccgg   2220
ggccacttcc tgatcgaggg cgacctgaac cccgacaaca gcgacgtgga caagctgttc   2280
atccagctgg tgcagaccta caaccagctg ttcgaggaga cccccatcaa cgccagcggc   2340
gtggacgcca aggccatcct gagcgcccgg ctgagcaaga gccggcggct ggagaacctg   2400
atcgcccagc tgcccggcga gaagaagaac ggcctgttcg gcaacctgat cgccctgagc   2460
ctgggcctga cccccaactt caagagcaac ttcgacctgg ccgaggacgc caagctgcag   2520
ctgagcaagg acacctacga cgacgacctg gacaacctgc tggcccagat cggcgaccag   2580
```

```
tacgccgacc tgttcctggc cgccaagaac ctgagcgacg ccatcctgct gagcgacatc  2640
ctgcgggtga acaccgagat caccaaggcc ccctgagcg ccagcatgat caagcggtac  2700
gacgagcacc accaggacct gaccctgctg aaggccctgg tgcggcagca gctgcccgag  2760
aagtacaagg agatcttctt cgaccagagc aagaacggct acgccggcta catcgacggc  2820
ggcgccgcc aggaggagtt ctacaagttc atcaagccca tcctggagaa gatggacggc  2880
accgaggagc tgctggtgaa gctgaaccgg gaggacctgc tgcggaagca gcggaccttc  2940
gacaacggca gcatcccca ccagatccac tggggcgagc tgcacgccat cctgcggcgg  3000
caggaggact tctacccctt cctgaaggac aaccgggaga gatcgagaa gatcctgacc  3060
ttccggatcc cctactacgt gggccccctg gcccggggca aagccggtt cgcctggatg  3120
acccggaaga gcgaggagac catcaccccc tggaacttcg aggaggtggt ggacaaggge  3180
gccagcgccc agagcttcat cgagcggatg accaacttcg acaagaacct gcccaacgag  3240
aaggtgctgc ccaagcacag cctgctgtac gagtacttca ccgtgtacaa cgagctgacc  3300
aaggtgaagt acgtgaccga gggcatgcgg aagcccgcct tcctgagcgg cgagcagaag  3360
aaggccatcg tggacctgct gttcaagacc aaccggaaga tgaccgtgca gcagctgaag  3420
gaggactact tcaagaagat cgagtgcttc gacagcgtga agatcagcgg cgtggaggac  3480
cggttcaacg ccagcctggg cacctaccac gacctgctga agatcatcaa ggacaaggac  3540
ttcctggaca acgaggagaa cgaggacatc ctggaggaca tcgtgctgac cctgaccctg  3600
ttcgaggacc gggagatgat cgaggacgg cgtgaagacct acgcccacct gttcgacgac  3660
aaggtgatga gcagctgaa gcggcggcgg tacaccggct ggggccggct gagccggaag  3720
ctgatcaacg gcatccggga caagcagagc ggcaagacca tcctggactt cctgaagagc  3780
gacggcttcg ccaaccggaa cttcatgcag ctgatccacg acgacagcct gaccttcaag  3840
gaggacatcc agaaggccca ggtgagcggc cagggcgaca gcctgcacga gcacatcgcc  3900
aacctggccg gcagccccgc catcaagaag gcatcctgc agaccgtgaa ggtggtggac  3960
gagctggtga aggtcgatggg ccggcacaag cccgagaaca tcgtgatcga gatggccggg  4020
gagaaccaga ccacccagaa gggccagaag aacagccggg agcggatgaa gcggatcgag  4080
gagggcatca aggagctggg cagccagatc actgaaggagc accccgtgga gaaccgtcga  4140
ctgcagaacg agaagctgta cctgtactac ctgcagaacg gccgggacat gtacgtggac  4200
caggagctgg acatcaaccg gctgagcgac tacgacgtgg acgccatcgt gccccagagc  4260
ttcctgaagg acgacagcat cgacaacaag gtgctgaccc ggagcgacaa gaaccggggc  4320
aagagcgaca acgtgcccag cgaggagtg gtgaagaaga tgaagaacta ctggcggcag  4380
ctgctgaacg ccaagctgat cacccagcgg aagttcgaca acctgaccaa ggccgagcgg  4440
ggcggcctga gcgagctgga caaggccggc ttcatcaagc ggcagctggt ggagacccgg  4500
cagatcacca gcacgtggc ccagatcctg gacagccgga tgaacaccaa gtacgacgag  4560
aacgacaagc tgatccggga ggtgaaggtg atcacctga agagcaagct ggtgagcgac  4620
ttccggaagg acttccagtt ctacaaggtg cgggagatca acaactacca ccacgcccac  4680
gacgcctacc tgaacgccgt ggtgggcacc gccctgatca agaagtaccc caagctggag  4740
agcgagttcg tgtacggcga ctacaaggtg tacgacgtgc ggaagatgat cgccaagagc  4800
gagcaggaga tcggcaaggc caccgccaag tacttcttct acagcaacat catgaacttc  4860
ttcaagacgc agatcaccct ggccaacggc gagatccgga agccccct gatcgagacc  4920
aacggcgaga ccggcgagat cgtgtgggac aagggccggg acttcgccac cgtgcgcgaag  4980
gtgctgagca tgccccaggt gaacatcgtg aagaagaccg aggtgcagac cggcggcttc  5040
agcaaggaga gcatcctgcc caagcggaac agcgacaagc tgatcgcccg gaagaaggac  5100
tgggacccca gaagtacgg cggcttcgac agccccaccg tggccctacg tgctgctgg  5160
gtggccaagg tggagaaggg caagagcaag aagctgaaga gcgtgaagga gctgctgggc  5220
atcaccatca tggagcggag cagcttcgag aagaaccca tcgacttcct ggaggccaag  5280
ggctacaagg aggtgaagaa ggacctgatc atcaagctgc ccaagtacag cctgttcgag  5340
ctggaaacg gccggaagcg gatgctggcc agcgccggag agctgcagaa gggcaacgag  5400
ctggccctgc ccagcaagta cgtgaacttc ctgtacctgg ccagccacta cgagaagctg  5460
aagggcagcc ccgaggacaa cgagcagaag cagctgttcg tggagcagca caagcactac  5520
ctggacgaga tcatcgagca gatcagcgag ttcagcaagc gggtgatcct ggccgacgcc  5580
aacctggaca aggtgctgag cgcctacaac aagcaccgg acaagcccat ccgggagcag  5640
gccgagaaca tcatccacct gttcaccctg accaactgg gcgccccgc cgccttcaag  5700
tacttcgaca ccaccatcga ccggaagcgg tacaccagca ccaaggaggt gctggacgcc  5760
accctgatcc accagagcat caccggcctg tacgagaccc ggatcgacct gagccagctg  5820
ggcggcgaca gcggcggcgc tcagcctcgaggccg gagcgacgcg accggaagaag  5880
aagaaggcta gcgatgctaa gtcactgact gcctggtccc ggacactggt gaccttcaag  5940
gatgtgtttg tggacttcac cagggaggag tggaagctgc tggacactgc tcagcagatc  6000
ctgtacagaa atgtgatgct ggagaactat aagaacctgg tttccttggg ttatcagctt  6060
actaagccag atgtgatcct ccggttggag aagggagaag agccctggct ggtggagaga  6120
gaaattcacc aagagaccca tcctgattca gagactgcat ttgaaatcaa atcatcagtt  6180
ccgaaaaaga aacgcaaagt ttag                                         6204
SEQ ID NO: 278      moltype = AA  length = 2067
FEATURE             Location/Qualifiers
REGION              1..2067
                    note = dSpCas9-KRAB-DNTM3A/L
source              1..2067
                    mol_type = protein
                    organism = Synthetic construct
SEQUENCE: 278
NHDQEFDPPK VYPPVPAEKR KPIRVLSLFD GIATGLLVLK DLGIQVDRYI ASEVCEDSIT   60
VGMVRHQGKI MYVGDVRSVT QKHIQEWGPF DLVIGGSPCN DLSIVNPARK GLYEGTGRLF  120
FEFYRLLHDA RPKEGDDRPF FWLFENVVAM GVSDKRDISR FLESNPVMID AKEVSAAHRA  180
RYFWGNLPGM NRPLASTVND KLELQECLEH GRIAKFSKVR TITTRSNSIK QGKDQHPVF   240
MNEKEDILWC TEMERVFGFP VHYTDVSNMS RLARQRLLGR SWSVPVIRHL FAPLKEYFAC  300
VSSGNSNANS RGPSFSSGLV PLSLRGSHMG PMEIYKTVSA WKRQPVRVLS LFRNIDKVLK  360
SLGFLESGSG SGGGTLKYVE DVTNVVRRDV EKWGPFDLVY GSTQPLGSSC DRCPGWYMFQ  420
FHRILQYALP RQESQRPFFW IFMDNLLLTE DDQETTTRFL QTEAVTLQDV RGRDYQNAMR  480
VWSNIPGLKS KHAPLTPKEE EYLQAQVRSR SKLDAPKVDL LVKNCLLPLR EYFKYFSQNS  540
```

```
LPLEASGSGR ASPGIPGSTR NPKKKRKVGI HGVPAADKKY SIGLAIGTNS VGWAVITDEY  600
KVPSKKFKVL GNTDRHSIKK NLIGALLFDS GETAEATRLK RTARRRYTRR KNRICYLQEI  660
FSNEMAKVDD SFFHRLEESF LVEEDKKHER HPIFGNIVDE VAYHEKYPTI YHLRKKLVDS  720
TDKADLRLIY LALAHMIKFR GHFLIEGDLN PDNSDVDKLF IQLVQTYNQL FEENPINASG  780
VDAKAILSAR LSKSRRLENL IAQLPGEKKN GLFGNLIALS LGLTPNFKSN FDLAEDAKLQ  840
LSKDTYDDDL DNLLAQIGDQ YADLFLAAKN LSDAILLSDI LRVNTEITKA PLSASMIKRY  900
DEHHQDLTLL KALVRQQLPE KYKEIFFDQS KNGYAGYIDG GASQEEFYKF IKPILEKMDG  960
TEELLVKLNR EDLLRKQRTF DNGSIPHQIH LGELHAILRR QEDFYPFLKD NREKIEKILT 1020
FRIPYYVGPL ARGNSRFAWM TRKSEETITP WNFEEVVDKG ASAQSFIERM TNFDKNLPNE 1080
KVLPKHSLLY EYFTVYNELT KVKYVTEGMR KPAFLSGEQK KAIVDLLFKT NRKVTVKQLK 1140
EDYFKKIECF DSVEISGVED RFNASLGTYH DLLKIIKDKD FLDNEENEDI LEDIVLTLTL 1200
FEDREMIEER LKTYAHLFDD KVMKQLKRRR YTGWGRLSRK LINGIRDKQS GKTILDFLKS 1260
DGFANRNFMQ LIHDDSLTFK EDIQKAQVSG QGDSLHEHIA NLAGSPAIKK GILQTVKVVD 1320
ELVKVMGRHK PENIVIEMAR ENQTTQKGQK NSRERMKRIE EGIKELGSQI LKEHPVENTQ 1380
LQNEKLYLYY LQNGRDMYVD QELDINRLSD YDVDAIVPQS FLKDDSIDNK VLTRSDKNRG 1440
KSDNVPSEEV VKKMKNYWRQ LLNAKLITQR KFDNLTKAER GGLSELDKAG FIKRQLVETR 1500
QITKHVAQIL DSRMNTKYDE NDKLIREVKV ITLKSKLVSD FRKDFQFYKV REINNYHHAH 1560
DAYLNAVVGT ALIKKYPKLE SEFVYGDYKV YDVRKMIAKS EQEIGKATAK YFFYSNIMNF 1620
FKTEITLANG EIRKRPLIET NGETGEIVWD KGRDFATVRK VLSMPQVNIV KKTEVQTGGF 1680
SKESILPKRN SDKLIARKKD WDPKKYGGFD SPTVAYSVLV VAKVEKGKSK KLKSVKELLG 1740
ITIMERSSFE KNPIDFLEAK GYKEVKKDLI IKLPKYSLFE LENGRKRMLA SAGELQKGNE 1800
LALPSKYVNF LYLASHYEKL KGSPEDNEQK QLFVEQHKHY LDEIIEQISE FSKRVILADA 1860
NLDKVLSAYN KHRDKPIREQ AENIIHLFTL TNLGAPAAFK YFDTTIDRKR YTSTKEVLDA 1920
TLIHQSITGL YETRIDLSQL GGDSGGKRPA ATKKAGQAKK KKASDAKSLT AWSRTLVTFK 1980
DVFVDFTREE WKLLDTAQQI LYRNVMLENY KNLVSLGYQL TKPDVILRLE KGEEPWLVER 2040
EIHQETHPDS ETAFEIKSSV PKKKRKV                                    2067

SEQ ID NO: 279         moltype = DNA   length = 6399
FEATURE                Location/Qualifiers
misc_feature           1..6399
                       note = DNMT3A/L-XTEN80-dSpCas9-KRAB
source                 1..6399
                       mol_type = other DNA
                       organism = Synthetic construct
SEQUENCE: 279
atgaaccacg atcaggagtt tgacccccct aaggtgtacc cacccgtgcc agccgagaag   60
aggaagccca tccgcgtgct gtccctgttc gacggcatcg ccacaggcct gctggtgctg  120
aaggatctgg gcatccaggt ggacagatat atcgcctccg aggtgtgcga ggattctatc  180
accgtgctga tggtgaggca ccagggcaag atcatgtacg tgggcgacgt gcgcagcgtg  240
acacagaagc acatccagga gtggggaccc ttcgacctgg tcatcggagg cagccccctgt 300
aatgacctgt ccatcgtgaa ccctgcaagg aagggcctgt atgagggaac cggcagactg  360
ttctttgagt tctacaggct gctgcacgac gcccgcccta aggagggcga tgacaggcca  420
ttcttttggc tgtttgagaa cgtggtggcc atgggcgtga gcgacaagcg ggatatctcc  480
agattcctgg agtctaatcc cgtgatgatc gatgcaaagg aggtgtctgc cgcacacagg  540
gcaaggtact tttggggaaa tctgcctgga atgaaccgcc cactggccag cacccgtgaac 600
gacaagctgg agctgcagga gtgcctggag cacggaagga tcgccaagtt ctccaaggtg  660
cggacaatca ccacaagatc taacgacatc aagcagggca aggatcagca cttccccgtg  720
ttcatgaatg agaaggagga catcctgtgg tgtaccgaga tggagcgcgt gttcggcttt  780
ccagtgcact atacagacgt gagcaatatg agccggctgg caaggcagag actgctgggc  840
cggtcctggt ctgtgccagt gatcagacac ctgttcgccc cctgaaggag tactttgcc  900
tgcgtgctca gcggcaactc taatgccaac agcagaggcc cttccttttc tctctgctg  960
gtgccactgt ctctgagggg cagccacatg ggcccatgg agatctacaa gaccgtgtcc 1020
gcctggaaga ggcagcctgt gcgcgtgctg tctctgttcc gcaacatcga caaggtgctg 1080
aagagcctgg gctttctgga gagcggatcc ggatctggag gaggcaccct gaagtatgtg 1140
gaggtgtga caaatgtggt gcggagagat gtggagaagt ggggccccct cgatctggtg 1200
tacggatcca cccagccact gggaagctcc tgcgataggt gtccaggatg gtatatgttc 1260
cagtttcaca gaatcctgca gtacgcactg ccaaggcagg agagccagcg ccctttcttt 1320
tggatcttta tggacaacct gctgctgaca gaggatgacc aggagacaac aacccgcttc 1380
ctgcagacag aggcagtgac cctgcaggat gtgagggac gcgactatca gaatgccata 1440
cgggtgtggt ctaacatccc tggcctgaag agcaagcacg ccccctgac ccctaaggaa 1500
gaggagtacc tgcaggccca ggtgcgggagc agatccaagc tggatgcccc taaggtggac 1560
ctgctggtga agaattgtct gctgccactg cgggagtact tcaagtactt tagtcagaat 1620
agcctgccca tgggagggcc gagctctggc gcaccccac caagtggagg gtctcctgcc 1680
gggtcccaa catcactacga agaaggcacc agcgaatccg caagcccga ctgctgccct 1740
ggtacctcca cagaaccatc tgaaggtagt gcgcctggtt ccccagctgg aagccctact 1800
tccaccgaag aaggcacgtc aaccgaacca agtgaaggat ctgcccctgg accagcact  1860
gaaccatctg aggttaaccc caagaagaag cggaaggtgg catccacgg cgtgccgcc  1920
gccgacaaga gtacagcat cggccggcc atcggcagga cagcgtgggg ctgggccgtg  1980
atcaccgaca gtacaaggt gcccagcaag aagttcaagg tgctgggcaa caccgaccgg  2040
cacagcatca gaagaacct gatcggcgcc ctgctgttcg acagcggcga gaccgccgag  2100
gccacccggc tgaagcggac ccgccggcgg gtgtacaccc ggcggaagaa ccggatctgc  2160
tacctgcagg agatcttcag caacgagatg gccaaggtgg acgacagctt cttccaccgg  2220
ctggaggaga gcttcctggt ggaggaggac aagaagcacg agcggcaccc catcttcggc  2280
aacatcgtgg acgaggtggc ctaccacgag aagtacccca tcatctacca cctgcggaag  2340
aagctggtgg acagcaccga caaggccgac ctgcggctga tctacctggc cctggcccac  2400
atgatcaagt tccggggcca cttcctgatc gagggcgacc tgaaccccga caacagcgac  2460
gtggacaagc tgttcatcca gctggtgcag acctacaacc agctgttcga ggagaacccc  2520
atcaacgcca gcggcgtgga cgccaaggcc atcctgagcg cccggctgag caagagccgg  2580
cggctggaga acctgatcgc ccagctgccc ggcgagaaga gaacgggcct gttcggcaac  2640
```

-continued

```
ctgatcgccc tgagcctggg cctgacccca aacttcaaga gcaacttcga cctggccgag 2700
gacgccaagc tgcagctgag caaggacacc tacgacgacg acctggacaa cctgctggcc 2760
cagatcggcg accagtacgc cgacctgttc ctggccgcca agaacctgag cgacgccatc 2820
ctgctgagcg acatcctgcg ggtgaacacc gagatcacca aggccccct gagcgccagc 2880
atgatcaagc ggtacgacga gcaccaccag gacctgaccc tgctgaaggc cctggtgcgg 2940
cagcagctgc ccgagaagta caaggagatc ttcttcgacc agagcaagaa cggctacgcc 3000
ggctacatcg acggcggcgc cagccaggag gagttctaca gttcatcaa gcccatcctg 3060
gagaagatgg acggcaccga ggagctgctg gtgaagctga accggagga cctgctgcgc 3120
aagcacggga ccttcgacaa cggcagcatc ccccaccaga tccacctggg cgagctgcac 3180
gccatcctgc ggcggcagga ggacttctac cccttcctga aggacaaccg ggagaagatc 3240
gagaagatcc tgaccttccg gatcccctac tacgtgggcc cctggcccg ggcaacagc 3300
cggttcgcct ggatgacccg gaagagcgag gagaccatca cccctgga cttcgaggag 3360
gtggtggaca agggcgccag cgcccagagc ttcatcgagc ggatgaccaa cttcgacaag 3420
aacctgccca acgagaaggt gctgcccaag cacagcctgc tgtacgagta cttcaccgtg 3480
tacaacgagc tgaccaaggt gaagtacgtg accgagggca tgcggaagcc cgccttcctg 3540
agcggcgagc agaagaaggc catcgtggac ctgctgttca gaccaaccg gaaggtgacc 3600
gtgaagcagc tgaaggagga ctacttcaag aagatcgagt gcttcgacag cgtggagatc 3660
agcggcgtgg aggaccggtt caacgccagc ctgggcacct accacgacct gctgaagatc 3720
atcaaggaca aggacttcct ggacaacgag gagaacgagg acatcctgga ggacatcgtg 3780
ctgaccctga ccctgttcga ggaccgggag atgatcgagg agcggctgaa gacctacgcc 3840
cacctgttcg acgacaaggt gatgaagcag ctgaagcggc ggcggtacac cggctgggc 3900
cggctgagcc ggaagctgat caacggcatc cgggacaagc agagcggcaa gaccatcctg 3960
gacttcctga agagcgacgg cttcgccaac cggaacttca tgcagctgat ccacgacgac 4020
agcctgacct tcaaggagga catccagaag gcccaggtga gcggcagggc gacagcctg 4080
cacgagcaca tcgccaacct ggccggcagc cccgccatca agaagggcat cctgcagacc 4140
gtgaaggtgg tggacgagct ggtgaaggtg atgggccggc acaagcccga gaacatcgtg 4200
atcgagatgg cccgggagaa ccagaccacc cagaaggcc agaagaacag ccggagcgg 4260
atgaagcgga tcgaggaggg catcaaggag ctgggcagcc agatcctgaa ggagcacccc 4320
gtggagaaca cccagctgca gaacgagaag ctgtacctgt actacctgca gaacggccgg 4380
gacatgtacg tggaccagga gctggacatc aaccggctga gcgactacga cgtggacgcc 4440
atcgtgcccc agagcttcct gaaggacgac agcatcgaca caaggtgct gaccggag 4500
gacaagaacc ggggcaagag cgacaacgtg cccagcgagg aggtggtgaa gaagatgaag 4560
aactactggc ggcagctgct gaacgccaag ctgatcaccc agcggaagtt cgacaacctg 4620
accaaggccg agcggggcgg cctgagcgag ctggacaagg ccggcttcat caagcggcag 4680
ctggtggaga cccggcagat caccaagcac gtggcccaga tcctggacag ccggatgaac 4740
accaagtacg acgagaacga caagctgatc cggagggtga aggtgatcac cctgaagagc 4800
aagctggtga gcgacttccg gaaggacttc cagttctaca aggtgcggga gatcaacaac 4860
taccaccacg cccacgacgc ctacctgaac gccgtggtgg gcaccgccct gatcaagaag 4920
tacccaaagc tggagagcga gttcgtgtac ggcgactaca aggtgtacga cgtgcggaag 4980
atgatcgcca gagcgagca ggagatcggc aaggccaccg ccaagtactt cttctacagc 5040
aacatcatga acttcttcaa gaccgagatc accctggcca acggcgagat ccggaagcgg 5100
cccctgatcg agaccaacgg cgagaccggc gagatcgtgt gggacaaggg ccgggacttc 5160
gccaccgtgc ggaaggtgct gagcatgccc caggtgaaca tcgtgaagaa gaccgaggtg 5220
cagaccggcg gcttcagcaa ggagagcatc ctgcccaagc ggaacagcga caagctgatc 5280
gcccggaaga aggactggga cccaagaag tacggcggct tcgacagccc caccgtggcc 5340
tacagcgtgc tggtggtggc caaggtggag aagggcaaga gcaagaagct gaagagcgtg 5400
aaggagctgc tgggcatcac catcatggag cggagcagct tcgagaagaa ccccatcgac 5460
ttcctggagg ccaagggcta caaggaggtg aagaaggacc tgatcatcaa gctgcccaag 5520
tacagcctgt tcgagctgga aaacggccgg aagcggatgc tggccagcgc cggcgagctg 5580
cagaagggca acgagctggc cctgcccagc aagtacgtga acttcctgta cctggccagc 5640
cactacgaga gctgaagg cagccccgag gacaacgagc agaagcagct gttcgtggag 5700
cagcacaagc actacctgga cgagatcatc gagcagatca gcgagttcag caagcgggtg 5760
atcctgccg acgccaacct ggacaaggtg ctgagcgcct acaacaagca ccgggacaag 5820
cccatccggg agcaggccga gaacatcatc cacctgttca ccctgaccaa cctgggcgcc 5880
cccgccgcct tcaagtactt cgacaccacc atcgaccgga gcgtgaacga cagcaccaag 5940
gaggtgctgg acgccaccct gatccaccag agcatcaccg gcctgtacga gacccggatc 6000
gacctgagcc agctgggcgg cgacagcggc ggcaagcggc cgccgccac caagaaggcc 6060
ggccaggcca agaagaagaa ggctagcgat gctaagtcac tgactgcctg gtcccggaca 6120
ctggtgacct tcaaggatgt gtttgtggac ttcaccaggg aggagtggaa gctgctggac 6180
actgctcagc agatcctgta cagaaatgtg atgctggaga actataagaa cctggtttcc 6240
ttgggttatc agcttactaa gccagatgtg atcctccggt tggagaaggg agaagagccc 6300
tggctggtga gagagaaat tcaccaagag acccatcctg attcagagac tgcatttgaa 6360
atcaaatcat cagttccgaa aaagaaacgc aaagtttag            6399
```

SEQ ID NO: 280         moltype = AA  length = 2132
FEATURE                  Location/Qualifiers
REGION                   1..2132
                          note = DNMT3A/L-XTEN80-dSpCas9-KRAB
source                   1..2132
                          mol_type = protein
                          organism = Synthetic construct
SEQUENCE: 280

```
MNHDQEFDPP KVYPPVPAEK RKPIRVLSLF DGIATGLLVL KDLGIQVDRY IASEVCEDSI  60
TVGMVRHQGK IMYVGDVRSV TQKHIQEWGP FDLVIGGSPC NDLSIVNPAR KGLYEGTGRL 120
FFEFYRLLHD ARPKEGDDRP FFWLFENVVA MGVSDKRDIS RFLESNPVMI DAKEVSAAHR 180
ARYFWGNLPG MNRPLASTVN DKLELQECLE HGRIAKFSKV RTITTRSNSI KQGKDQHFPV 240
FMNEKEDILW CTEMERVFGF PVHYTDVSNM SRLARQRLLG RSWSVPVIRH LFAPLKEYFA 300
CVSSGNSNAN SRGPSFSSGL VPLSLRGSHM GPMEIYKTVS AWKRQPVRVL SLFRNIDKVL 360
KSLGFLESGS GSGGGTLKYV EDVTNVVRRD VEKWGPFDLV YGSTQPLGSS CDRCPGWYMF 420
```

```
QFHRILQYAL PRQESQRPFF WIFMDNLLLT EDDQETTTRF LQTEAVTLQD VRGRDYQNAM  480
RVWSNIPGLK SKHAPLTPKE EEYLQAQVRS RSKLDAPKVD LLVKNCLLPL REYFKYFSQN  540
SLPLGGPSSG APPPSGGSPA GSPTSTEEGT SESATPESGP GTSTEPSEGS APGSPAGSPT  600
STEEGTSTEP SEGSAPGTST EPSEVNPKKK RKVGIHGVPA ADKKYSIGLA IGTNSVGWAV  660
ITDEYKGPVS KFKVLGNTDR HSIKKNLIGA LLFDSGETAE ATRLKRTARR RYTRRKNRIC  720
YLQEIFSNEM AKVDDSFFHR LEESFLVEED KKHERHPIFG NIVDEVAYHE KYPTIYHLRK  780
KLVDSTDKAD LRLIYLALAH MIKFRGHFLI EGDLNPDNSD VDKLFIQLVQ TYNQLFEENP  840
INASGVDAKA ILSARLSKSR RLENLIAQLP GEKKNGLFGN LIALSLGLTP NFKSNFDLAE  900
DAKLQLSKDT YDDDLDNLLA QIGDQYADLF LAAKNLSDAI LLSDILRVNT EITKAPLSAS  960
MIKRYDEHHQ DLTLLKALVR QQLPEKYKEI FFDQSKNGYA GYIDGGASQE EFYKFIKPIL 1020
EKMDGTEELL VKLNREDLLR KQRTFDNGSI PHQIHLGELH AILRRQEDFY PFLKDNREKI 1080
EKILTFRIPY YVGPLARGNS RFAWMTRKSE ETITPWNFEE VVDKGASAQS FIERMTNFDK 1140
NLPNEKVLPK HSLLYEYFTV YNELTKVKYV TEGMRKPAFL SGEQKKAIVD LLFKTNRKVT 1200
VKQLKEDYFK KIECFDSVEI SGVEDRFNAS LGTYHDLLKI IKDKDFLDNE ENEDILEDIV 1260
LTLTLFEDRE MIEEERLKTYA HLFDDKVMKQ LKRRRYTGWG RLSRKLINGI RDKQSGKTIL 1320
DFLKSDGFAN RNFMQLIHDD SLTFKEDIQK AQVSGQGDSL HEHIANLAGS PAIKKGILQT 1380
VKVVDELVKV MGRHKPENIV IEMARENQTT QKGQKNSRER MKRIEEGIKE LGSQILKEHP 1440
VENTQLQNEK LYLYYLQNGR DMYVDQELDI NRLSDYDVDA IVPQSFLKDD SIDNKVLTRS 1500
DKNRGKSDNV PSEEVVKKMK NYWRQLLNAK LITQRKFDNL TKAERGGLSE LDKAGFIKRQ 1560
LVETRQITKH VAQILDSRMN TKYDENDKLI REVKVITLKS KLVSDFRKDF QFYKVREINN 1620
YHHAHDAYLN AVVGTALIKK YPKLESEFVY GDYKVYDVRK MIAKSEQEIG KATAKYFFYS 1680
NIMNFFKTEI TLANGEIRKR PLIETNGETG EIVWDKGRDF ATVRKVLSMP QVNIVKKTEV 1740
QTGGFSKESI LPKRNSDKLI ARKKDWDPKK YGGFDSPTVA YSVLVVAKVE KGKSKKLKSV 1800
KELLGITIME RSSFEKNPID FLEAKGYKEV KKDLIIKLPK YSLFELENGR KRMLASAGEL 1860
QKGNELALPS KYVNFLYLAS HYEKLKGSPE DNEQKQLFVE QHKHYLDEII EQISEFSKRV 1920
ILADANLDKV LSAYNKHRDK PIREQAENII HLFTLTNLGA PAAFKYFDTT IDRKRYTSTK 1980
EVLDATLIHQ SITGLYETRI DLSQLGGDSG GKRPAATKKA GQAKKKKASD AKSLTAWSRT 2040
LVTFKDVFVD FTREEWKLLD TAQQILYRNV MLENYKNLVS LGYQLTKPDV ILRLEKGEEP 2100
WLVEREIHQE THPDSETAFE IKSSVPKKKR KV                                2132

SEQ ID NO: 281           moltype = DNA  length = 6399
FEATURE                  Location/Qualifiers
misc_feature             1..6399
                         note = DNMT3A/L(CRISPROFF)-XTEN80-dSpCas9-KRAB
source                   1..6399
                         mol_type = other DNA
                         organism = Synthetic construct
SEQUENCE: 281
agtaaccatg accaggaatt tgacccccca aaggtttacc cacctgtgcc agctgagaag   60
aggaagccca tccgcgtgct gtctctcttt gatgggattg ctacagggct cctggtgctg  120
aaggacctgg gcatccaagt ggaccgctac attgcctccg aggtgtgtga ggactccatc  180
acggtgggca tggtgcggca ccaggaaaag atcatgtacg tcgggacgt ccgcagcgtc  240
acacagaagc atatccagga gtggggccca ttcgacctgg tgattggaac cagtccctgc  300
aatgacctct ccattgtcaa ccctgcccgc aagggacttt atgagggtac tggccgcctc  360
ttctttgagt tctaccgcct cctgcatgat gcgcggccca aggagggaga tgatcgcccc  420
ttcttctggc tctttgagaa tgtggtgcc atgggcgtta gtgacaagag ggacatctcg   480
cgatttcttg agtctaaccc cgtgatgatt gacgccaaag aagtgtctgc tgcacacagg  540
gcccgttact tctggggtaa ccttcctggc atgaacaggc ctttggcatc cactgtgaat  600
gataagctgg agctgcaaga gtgtctggag cacggcagaa tagccaagtt cagcaaagtg  660
aggaccatta ccaccaggtc aaactctata agcagggca agaccagca tttccccgtc    720
ttcatgaacg agaaggagaa catctgtgtg tgcactgaaa tggaaagtgg gtttggcttc  780
cccgtccact acacagacgt ctccaacatg agccgcttgg cgaggcagag actgctgggc  840
cgatcgtgga gcgtgccggt catccgccac ctcttcgctc cgctaaggga atattttgct  900
tgtgtgtcta gcggcaatag taacgctaac agccgcgggc cgagcttcag cagcggcctg  960
gtgccgttaa gcttgcgcgg cagccatatg ggccctatgg agatatacaa gacagtgtct 1020
gcatggaaga gacagccagt gcgggtactg agcctcttca gaaacatcga caaggtacta 1080
aagagtttgg gcttcttgga aagcggttct ggttctgggg gaggaacgct gaagtacgtg 1140
gaagatgtca caaatgtcgt gaggagagac gtggagaaat ggggcccctt tgacctggtg 1200
tacggctcga cgcagccct aggcagctct cctgatcgct gtccggctg gtacatgttc   1260
cagttccacc ggatcctgca gtatgcgctg cctcgccagg agagtcaggg gccttctc    1320
tggatattca tggacaatct gctgctgact gaggatgacc aagagacaac tacccgcttc  1380
cttcagacag aggctgtgac cctccaggat gtccgtggca gagactacca gaatgctatg  1440
cgggtgtgga gcaacattcc aggctgaag agcaagcatg cgcccctgac cccaaaggaa   1500
gaagatgtatc tgcaagccca agtcagaagc aggagcaagt tggacgcccc gaaagttgac 1560
ctcctggtga agaactgcct tctcccgctg agagagtact tcaagtatttt ttctcaaaac 1620
tcacttcctc ttggagggcc gagctctggc gcaccccac caagtggagg gtctcctgcc   1680
gggtccccaa catctactga gaaggcacc agcgaatccg caacgcccga tcaggccct    1740
ggtacctcca cagaaccatc tgaaggtagt gcgcctggtt ccccagctgg aagccctact  1800
tccaccgaag aaggcacgtc aaccgaacca agtgaaggat ctgcccctgg gaccagcact  1860
gaaccatctg aggttaaccc caagaagaag cggaaggtgg gcatccacgg cgtgcccgcc  1920
gccgacaaga gtacagcat cggcctggcc atcggcacca cagcgtggg ctgggccgtg     1980
atcaccgacg agtacaaggt gcccagcaag aagttcaagg tgctgggcaa caccgaccgg  2040
cacagcatca gaagaacct gatcggcgcc ctgctgttcg acagcggcga gaccgccgag    2100
gccaccagac tgaagcgcac cgcccggcgg cggtacaccc ggatctgca                2160
tacctgcagg agatcttcag caacgagatg gccaaggtgg acgacagctt cttccaccgg  2220
ctggaggaga gcttcctggt ggaggaggac aagaagcacg agcggcaccc catcttcggc  2280
aacatcgtgg acgaggtggc ctaccacgag aagtaccccca ccatctacca cctgcggaag  2340
aagctggtgt acagcaccga caaggccgac ctgcggctga tctacctggc cctggcccac  2400
atgatcaagt tccgggggcca cttcctgatc gagggcgacc tgaaccccga caacagcgac  2460
```

```
gtggacaagc tgttcatcca gctggtgcag acctacaacc agctgttcga ggagaacccc    2520
atcaacgcca gcggcgtgga cgccaaggcc atcctgagcg cccggctgag caagagccgg    2580
cggctggaga acctgatcgc ccagctgccc ggcgagaaga gaacggcct gttcggcaac     2640
ctgatcgccc tgagcctggg cctgaccccc aacttcaaga gcaacttcga cctggccgag    2700
gacgccaagc tgcagctgag caaggacacc tacgacgacg acctggacaa cctgctggcc    2760
cagatcggcg accagtacgc cgacctgttc ctggccgcca agaacctgag cgacgccatc    2820
ctgctgagcg acatcctgcg ggtgaacacc gagatcacca aggcccccct gagcgccagc    2880
atgatcaagc ggtacgacga gcaccaccag gacctgaccc tgctgaaggc cctggtgcgg    2940
cagcagctgc ccgagaagta caaggagatc ttcttcgacc agagcaagaa cggctacgcc    3000
ggctacatcg acggcggcgc cagccaggag gagttctaca agttcatcaa gcccatcctg    3060
gagaagatgg acggcaccga ggagctgctg gtgaagctga accgggagga cctgctgcgg    3120
aagcagcgga ccttcgacaa cggcagcatc cccaccaga tccacctggg cgagctgcac     3180
gccatcctgc ggcggcagga ggacttctac cccttcctga aggacaaccg ggagaagatc    3240
gagaagatcc tgaccttccg gatcccctac tacgtgggcc cctgccccg ggcaacagc      3300
cggttcgcct ggatgacccg gaagagcgag gagaccatca cccccctgaa cttcgaggag    3360
gtggtcgaca agggcgccag cgcccagagc ttcatcgagc ggatgaccaa cttcgacaag    3420
aacctgccca acgagaaggt gctgcccaag cacagcctgc tgtacgagta cttcaccgtg    3480
tacaacgagc tgaccaaggt gaagtacgtg accgagggcg tgcggaagcc cgccttcctg    3540
agcggcgagc agaagaaggc catcgtggac ctgctgttca gaccaaccg gaaggtgacc     3600
gtgaagcagc tgaaggagga ctacttcaag aagatcgagt gcttcgacag cgtggagatc    3660
agcggcgtgg aggaccggtt caacgccagc ctgggcacct accacgacct gctgaagatc    3720
atcaaggaca aggacttcct ggacaacgag gagaacgagg acatcctgga ggacatcgtg    3780
ctgaccctga ccctgttcga ggaccggag atgatcgagg agcggctgaa gacctacgcg    3840
cacctgttcg acgacaaggt gatgaagcag ctgaagcggc ggcggtacac cggctggggc    3900
cggctgagcc ggaagctgat caacggcatc cgggacaagc agagcggcaa gaccatcctg    3960
gacttcctga agagcgacgg cttcgccaac cggaacttca tgcagctgat ccacgacgac    4020
agcctgacct tcaaggagga catccagaag gcccaggtga gcgccaggg cgacagcctg     4080
cacgagcaca tcgccaacct ggccggcagc cccgccatca gaagggcat cctgcagacc    4140
gtgaaggtgg tggacgagct ggtgaaggtg atgggccggc acaagcccga aacatcgtg    4200
atcgagatgg cccggggaga accagaccac cagaaggcca agaagaacac ccgggagcgg    4260
atgaagcgga tcgaggaggg catcaaggag ctgggcagcc agatcctgaa ggagcacccc    4320
gtggagaaca cccagctgca gaacgagaag ctgtacctgt actacctgca gaacggccgg    4380
gacatgtacg tggaccagga gctggacatc aaccggctga gcgactacga cgtggacgcc    4440
atcgtgcccc agagcttcct gaaggacgac agcatcgaca acaaggtgct gaccggagc     4500
gacaagaacc ggggcaagag cgacaacgtg cccagcgagg aggtggtgaa gaagatgaag    4560
aactactggc ggcagctgct gaacgccaag ctgatcaccc agcggaagtt cgacaacctg    4620
accaaggccg agcggggcgg cctgagcgag ctggacaagg ccggcttcat caagcggcag    4680
ctggtggaga cccggcagat caccaagcac gtggcccaga tcctggacag ccggatgaac    4740
accaagtacg acgagaacga caagctgatc cgggaggtga aggtgatcac cctgaagagc    4800
aagctggtga gcgacttccg gaaggacttc cagttctaca aggtgcggga gatcaacaac    4860
taccaccacg cccacgacgc ctacctgaac gccgtggtgg caccgccct gatcaagaag     4920
taccccaagc tggagagcga gttcgtgtac ggcgactaca aggtgtacga cgtgcggaag    4980
atgatcgcca agagcgagca ggagatcggc aaggccaccg ccaagtactt cttctacagc    5040
aacatcatga acttcttcaa gaccgagatc accctgccca acggcgagat ccggaagcgg    5100
cccctgatcg agaccaacgg cgagaccggc gagatcgtgt gggacaaggg ccgggacttc    5160
gccaccgtgc ggaaggtgct gagcatgccc caggtgaaca tcgtgaagaa gaccgaggtg    5220
cagaccggcg gcttcagcaa ggagagcatc ctgcccaagc ggaacagcga caagctgatc    5280
gcccggaaga aggactggga ccccaagaag tacggcggct tcgacagccc caccgtggcc    5340
tacagcgtgc tggtggtggc caaggtggag aaggcaaga gcaagaagct gaagagcgtg     5400
aaggagctgc tgggcatcac catcatggag cggagcagct tcgagaagaa ccccatcgac    5460
ttcctggagg ccaagggcta caaggaggtg aagaaggacc tgatcatcaa gctgcccaag    5520
tacagcctgt tcgagctgga aaacggccgg aagcggatgc tggccagcgc cggcgagctg    5580
cagaagggca cgagctggc cctgccagc aagtacgtga acttcctgta cctggccagc      5640
cactacgaga agctgaaggg cagccccgag gacaacgagc agaagcagct gttcgtggag    5700
cagcacaagc actacctgga cgagatcatc gagcagatca gcgagttcag caagcgggtg    5760
atcctggccg acgccaacct ggacaaggtg ctgagcgcct acaacaagca ccgggacaag    5820
cccatccggg agcaggccga acatcatc cacctgttca ccctgaccaa cctgggcgcc      5880
cccgccgcct caagtacttt cgacaccacc atcgaccgga gcggtacac cagcaccaag    5940
gaggtgctgg acgccaccct gatccaccag agcatcaccg gcctgtacga gacccggatc    6000
gacctgagcc agctgggcgg cgacagcggc ggcaagcggc ccgccgccac caagaaggcc    6060
ggccaggcca agaagaagaa ggctagcgat gctaagtcac tgactgcctg gtcccggaca    6120
ctggtgacct tcaaggatgt gtttgtggac ttcaccaggg aggagtggaa gctgctggac    6180
actgctcagc agatcctgta cagaaatgtg atgctggaga actataagaa cctggtttcc    6240
ttgggttatc agcttactaa gccagatgtg atcctccgtg tggaagggaa agaagaccc     6300
tggcggtgg agagagaaat tcaccaagag acccatcctg attcagagac tgcatttgaa     6360
atcaaatcat cagttccgaa aaagaaacgc aaagtttag                           6399
```

| | | |
|---|---|---|
| SEQ ID NO: 282 | moltype = AA length = 2132 | |
| FEATURE | Location/Qualifiers | |
| REGION | 1..2132 | |
| | note = DNMT3A/L(CRISPROFF)-XTEN80-dSpCas9-KRAB | |
| source | 1..2132 | |
| | mol_type = protein | |
| | organism = Synthetic construct | |

SEQUENCE: 282

```
SNHDQEFDPP KVYPPVPAEK RKPIRVLSLF DGIATGLLVL KDLGIQVDRY IASEVCEDSI    60
TVGMVRHQGK IMYVGDVRSV TQKHIQEWGP FDLVIGGSPC NDLSIVNPAR KGLYEGTGRL   120
FFEFYRLLHD ARPKEGDDRP FFWLFENVVA MGVSDKRDIS RFLESNPVMI DAKEVSAAHR   180
ARYFWGNLPG MNRPLASTVN DKLELQECLE HGRIAKFSKV RTITTRSNSI KQGKDQHFPV   240
```

```
FMNEKEDILW CTEMERVFGF PVHYTDVSNM SRLARQRLLG RSWSVPVIRH LFAPLKEYFA    300
CVSSGNSNAN SRGPSFSSGL VPLSLRGSHM GPMEIYKTVS AWKRQPVRVL SLFRNIDKVL    360
KSLGFLESGS GSGGGTLKYV EDVTNVVRRD VEKWGPFDLV YGSTQPLGSS CDRCPGWYMF    420
QFHRILQYAL PRQESQRPFF WIFMDNLLLT EDDQETTTRF LQTEAVTLQD VRGRDYQNAM    480
RVWSNIPGLK SKHAPLTPKE EEYLQAQVRS RSKLDAPKVD LLVKNCLLPL REYFKYFSQN    540
SLPLGGPSSG APPPSGGSPA GSPTSTEEGT SESATPESGP GTSTEPSEGS APGSPAGSPT    600
STEEGTSTEP SEGSAPGTST EPSEVNPKKK RKVGIHGVPA ADKKYSIGLA IGTNSVGWAV    660
ITDEYKVPSK KFKVLGNTDR HSIKKNLIGA LLFDSGETAE ATRLKRTARR RYTRRKNRIC    720
YLQEIFSNEM AKVDDSFFHR LEESFLVEED KKHERHPIFG NIVDEVAYHE KYPTIYHLRK    780
KLVDSTDKAD LRLIYLALAH MIKFRGHFLI EGDLNPDNSD VDKLFIQLVQ TYNQLFEENP    840
INASGVDAKA ILSARLSKSR RLENLIAQLP GEKKNGLFGN LIALSLGLTP NFKSNFDLAE    900
DAKLQLSKDT YDDDLDNLLA QIGDQYADLF LAAKNLSDAI LLSDILRVNT EITKAPLSAS    960
MIKRYDEHHQ DLTLLKALVR QQLPEKYKEI FFDQSKNGYA GYIDGGASQE EFYKFIKPIL   1020
EKMDGTEELL VKLNREDLLR KQRTFDNGSI PHQIHLGELH AILRRQEDFY PFLKDNREKI   1080
EKILTFRIPY YVGPLARGNS RFAWMTRKSE ETITPWNFEE VVDKGASAQS FIERMTNFDK   1140
NLPNEKVLPK HSLLYEYFTV YNELTKVKYV TEGMRKPAFL SGEQKKAIVD LLFKTNRKVT   1200
VKQLKEDYFK KIECFDSVEI SGVEDRFNAS LGTYHDLLKI IKDKDFLDNE ENEDILEDIV   1260
LTLTLFEDRE MIEERLKTYA HLFDDKVMKQ LKRRRYTGWG RLSRKLINGI RDKQSGKTIL   1320
DFLKSDGFAN RNFMQLIHDD SLTFKEDIQK AQVSGQGDSL HEHIANLAGS PAIKKGILQT   1380
VKVVDELVKV MGRHKPENIV IEMARENQTT QKGQKNSRER MKRIEEGIKE LGSQILKEHP   1440
VENTQLQNEK LYLYYLQNGR DMYVDQELDI NRLSDYDVDA IVPQSFLKDD SIDNKVLTRS   1500
DKNRGKSDNV PSEEVVKKMK NYWRQLLNAK LITQRKFDNL TKAERGGLSE LDKAGFIKRQ   1560
LVETRQITKH VAQILDSRMN TKYDENDKLI REVKVITLKS KLVSDFRKDF QFYKVREINN   1620
YHHAHDAYLN AVVGTALIKK YPKLESEFVY GDYKVYDVRK MIAKSEQEIG KATAKYFFYS   1680
NIMNFFKTEI TLANGEIRKR PLIETNGETG EIVWDKGRDF ATVRKVLSMP QVNIVKKTEV   1740
QTGGFSKESI LPKRNSDKLI ARKKDWDPKK YGGFDSPTVS YSVLVVAKVE KGKSKKLKSV   1800
KELLGITIME RSSFEKNPID FLEAKGYKEV KKDLIIKLPK YSLFELENGR KRMLASAGEL   1860
QKGNELALPS KYVNFLYLAS HYEKLKGSPE DNEQKQLFVE QHKHYLDEII EQISEFSKRV   1920
ILADANLDKV LSAYNKHRDK PIREQAENII HLFTLTNLGA PAAFKYFDTT IDRKRYTSTK   1980
EVLDATLIHQ SITGLYETRI DLSQLGGDSG GKRPAATKKA GQAKKKKASD AKSLTAWSRT   2040
LVTFKDVFVD FTREEWKLLD TAQQILYRNV MLENYKNLVS LGYQLTKPDV ILRLEKGEEP   2100
WLVEREIHQE THPDSETAFE IKSSVPKKKR KV                                 2132

SEQ ID NO: 283            moltype = AA  length = 746
FEATURE                   Location/Qualifiers
REGION                    1..746
                          note = EZH2
source                    1..746
                          mol_type = protein
                          organism = Synthetic construct
SEQUENCE: 283
MGQTGKKSEK GPVCWRKRVK SEYMRLRQLK RFRRADEVKT MFSSNRQKIL ERTETELNQEW    60
KQRRIQPVHI MTSVSSLRGT RECSVTSDLD FPAQVIPLKT LNAVASVPIM YSWSPLQQNF   120
MVEDETVLHN IPYMGDEVLD QDGTFIEELI KNYDGKVHGD RECGFINDEI FVELVNALGQ   180
YNDDDDDDDG DDPDEREEKQ KDLEDNRDDK ETCPPRKFPA DKIFEAISSM FPDKGTAEEL   240
KEKYKELTEQ QLPGALPPEC TPNIDGPNAK SVQREQSLHS FHTLFCRRCF KYDCFLHPFH   300
ATPNTYKRKN TETALDNKPC GPQCYQHLEG AKEFAAALTA ERIKTPPKRP GGRRRGRLPN   360
NSSRPSTPTI SVLESKDTDS DREAGTETGG ENNDKEEEEK KDETSSSEEA NSRCQTPIKM   420
KPNIEPPENV EWSGAEASMF RVLIGTYYDN FCAIARLIGT KTCRQVYEFR VKESSIIAPV   480
PTEDVDTPPR KKKRKHRLWA AHCRKIQLKK DGSSNHVYNY QPCDHPRQPC DSSCPCVIAQ   540
NFCEKFCQCS SECQNRFPGC RCKAQCNTKQ CPCYLAVREC DPDLCLTCGA ADHWDSKNVS   600
CKNCSIQRGS KKHLLLAPSD VAGWGIFIKD PVQKNEFISE YCGEIISQDE ADRRGKVYDK   660
YMCSFLFNLN NDFVVDATRK GNKIRFANHS VNPNCYAKVM MVNGDHRIGI FAKRAIQTGE   720
ELFFDYRYSQ ADALKYVGIE REMEIP                                        746

SEQ ID NO: 284            moltype = AA  length = 910
FEATURE                   Location/Qualifiers
REGION                    1..910
                          note = DNMT3A
source                    1..910
                          mol_type = protein
                          organism = Synthetic construct
SEQUENCE: 284
MPAMPSSGPG DTSSSAAERE EDRKDGEEQE EPRGKEERQE PSTTARKVGR PGRKRKHPPV    60
ESGDTPKDPA VISKSPSMAQ DSGASELLPN GDLEKRSEPQ PEEGSPAGGQ KGGAPAEGEG   120
AAETLPEASR AVENGCCTPK EGRGAPAEAG KEQKETNIES MKMEGSRGRL RGGLGWESSL   180
RQRPMPRLTF QAGDPYYISK RKRDEWLARW KREAEKKAKV IAGMNAVEEN QGPGESQKVE   240
EASPPAVQQP TDPASPTVAT TPEPVGSDAG DKNATKAGDD EPEYEDGRGF GIGELVWGKL   300
RGFSWWPGRI VSWWMTGRSR AAEGTRWVMW FGDGKFSVVC VEKLMPLSSF CSAFHQATYN   360
KQPMYRKAIY EVLQVASSRA GKLFPVCHDS DESDTAKAVE VQNKPMIEWA LGGFQPSGPK   420
GLEPPEEEKN PYKEVYTDMW VEPEAAAYAP PPPAKKPRKS TAEKPKVVKE IDERTRERLV   480
YEVRQKCRNI EDICISCGSL NVTLEHPLFV GGMCQNCKNC FLECAYQYDD DGYQSYCTIC   540
CGGREVLMCG NNNCCRCFCV ECVDLLVGPG AAQAAIKEDP WNCYMCGHKG TYGLLRRRED   600
WPSRLQMFFA NNHDQEFDPP KVYPPVPAEK RKPIRVLSLF DGIATGLLVL KDLGIQVDRY   660
IASEVCEDSI TVGMVRHQGK IMYVGDVRSN TQKHIQEWGP FDLVIGGSPC NDLSIVNPAR   720
KGLYEGTGRL FFEFYRLLHD ARPKEGDDRP FFWLFENVVA MGVSDKRDIS RFLESNPVMI   780
DAKEVSAAHR ARYFWGNLPG MNRPLASTVN DKLELQECLE HGRIAKFSKV RTITTRSNSI   840
KQGKDQHFPV FMNEKEDILW CTEMERVFGF PVHYTDVSNM SRLARQRLLG RSWSVPVIRH   900
LFAPLKEYFA                                                          910
```

-continued

```
SEQ ID NO: 285          moltype = AA  length = 301
FEATURE                 Location/Qualifiers
REGION                  1..301
                        note = Human DNMT3A
source                  1..301
                        mol_type = protein
                        organism = Synthetic construct
SEQUENCE: 285
NHDQEFDPPK VYPPVPAEKR KPIRVLSLFD GIATGLLVLK DLGIQVDRYI ASEVCEDSIT    60
VGMVRHQGKI MYVGDVRSVT QKHIQEWGPF DLVIGGSPCN DLSIVNPARK GLYEGTGRLF   120
FEFYRLLHDA RPKEGDDRPF FWLFENVVAM GVSDKRDISR FLESNPVMID AKEVSAAHRA   180
RYFWGNLPGM NRPLASTVND KLELQECLEH GRIAKFSKVR TITTRSNSIK QGKDQHPVF    240
MNEKEDILWC TEMERVFGFP VHYTDVSNMS RLARQRLLGR SWSVPVIRHL FAPLKEYFAC   300
V                                                                  301

SEQ ID NO: 286          moltype = AA  length = 215
FEATURE                 Location/Qualifiers
REGION                  1..215
                        note = Murine DNMT3L
source                  1..215
                        mol_type = protein
                        organism = Synthetic construct
SEQUENCE: 286
MGPMEIYKTV SAWKRQPVRV LSLFRNIDKV LKSLGFLESG SGSGGGTLKY VEDVTNVVRR    60
DVEKWGPFDL VYGSTQPLGS SCDRCPGWYM FQFHRILQYA LPRQESQRPF FWIFMDNLLL   120
TEDDQETTTR FLQTEAVTLQ DVRGRDYQNA MRVWSNIPGL KSKHAPLTPK EEEYLQAQVR   180
SRSKLDAPKV DLLVKNCLLP LREYFKYFSQ NSLPL                              215

SEQ ID NO: 287          moltype = AA  length = 214
FEATURE                 Location/Qualifiers
REGION                  1..214
                        note = C-terminal human DNM3L
source                  1..214
                        mol_type = protein
                        organism = Synthetic construct
SEQUENCE: 287
MNPLEMFETV PVWRRQPVRV LSLFEDIKKE LTSLGFLESG SDPGQLKHVV DVTDTVRKDV    60
EEWGPFDLVY GATPPLGHTC DRPPSWYLFQ FHRLLQYARP KPGSPRPFFW MFVDNLVLNK   120
EDLDVASRFL EMEPVTIPDV HGGSLQNAVR VWSNIPAIRS RHWALVSEEE LSLLAQNKQS   180
SKLAAKWPTK LVKNCFLPLR EYFKYFSTEL TSSL                               214

SEQ ID NO: 288          moltype = AA  length = 27
FEATURE                 Location/Qualifiers
REGION                  1..27
                        note = Linker
source                  1..27
                        mol_type = protein
                        organism = Synthetic construct
SEQUENCE: 288
SSGNSNANSR GPSFSSGLVP LSLRGSH                                        27

SEQ ID NO: 289          moltype = AA  length = 421
FEATURE                 Location/Qualifiers
REGION                  1..421
                        note = Murine DNMT3L
source                  1..421
                        mol_type = protein
                        organism = Synthetic construct
SEQUENCE: 289
MGSRETPSSC SKTLETLDLE TSDSSSPDAD SPLEEQWLKS SPALKEDSVD VVLEDCKEPL    60
SPSSPPTGRE MIRYEVKVNR RSIEDICLCC GTLQVYTRHP LFEGGLCAPC KDKFLESLFL   120
YDDDGHQSYC TICCSGGTLF ICESPDCTRC YCFECVDILV GPGTSERINA MACWVCFLCL   180
PFSRSGLLQR RKRWRHQLKA FHDQEGAGPM EIYKTVSAWK RQPVRVLSLF RNIDKVLKSL   240
GFLESGSGSG GGTLKYVEDV TNVVRRDVEK WGPFDLVYGS TQPLGSSCDR CPGWYMFQFH   300
RILQYALPRQ ESQRPFFWIF MDNLLLTEDD QETTTRFLQT EAVTLQDVRG RDYQNAMRVW   360
SNIPGLKSKH APLTPKEEEY LQAQVRSRSK LDAPKVDLLV KNCLLPLREY FKYFSQNSLP   420
L                                                                  421

SEQ ID NO: 290          moltype = AA  length = 87
FEATURE                 Location/Qualifiers
REGION                  1..87
                        note = KRAB
source                  1..87
                        mol_type = protein
                        organism = Synthetic construct
SEQUENCE: 290
RTLVTFKDVF VDFTREEWKL LDTAQQILYR NVMLENYKNL VSLGYQLTKP DVILRLEKGE    60
EPWLVEREIH QETHPDSETA FEIKSSV                                       87
```

-continued

```
SEQ ID NO: 291          moltype = AA  length = 15
FEATURE                 Location/Qualifiers
REGION                  1..15
                        note = NLS and linker
source                  1..15
                        mol_type = protein
                        organism = Synthetic construct
SEQUENCE: 291
PKKKRKVGIH GVPAA                                                          15

SEQ ID NO: 292          moltype = AA  length = 8
FEATURE                 Location/Qualifiers
REGION                  1..8
                        note = Flag tag
source                  1..8
                        mol_type = protein
                        organism = Synthetic construct
SEQUENCE: 292
DYKDDDDK                                                                  8

SEQ ID NO: 293          moltype = AA  length = 17
FEATURE                 Location/Qualifiers
REGION                  1..17
                        note = Linker
source                  1..17
                        mol_type = protein
                        organism = Synthetic construct
SEQUENCE: 293
EASGSGRASP GIPGSTR                                                        17

SEQ ID NO: 294          moltype = AA  length = 8
FEATURE                 Location/Qualifiers
REGION                  1..8
                        note = Linker
source                  1..8
                        mol_type = protein
                        organism = Synthetic construct
SEQUENCE: 294
GIHGVPAA                                                                  8

SEQ ID NO: 295          moltype = AA  length = 23
FEATURE                 Location/Qualifiers
REGION                  1..23
                        note = 3 x Flag peptide
source                  1..23
                        mol_type = protein
                        organism = Synthetic construct
SEQUENCE: 295
MDYKDHDGDY KDHDIDYKDD DDK                                                 23

SEQ ID NO: 296          moltype = AA  length = 9
FEATURE                 Location/Qualifiers
REGION                  1..9
                        note = HA tag
source                  1..9
                        mol_type = protein
                        organism = Synthetic construct
SEQUENCE: 296
YPYDVPDYA                                                                 9

SEQ ID NO: 297          moltype = AA  length = 6
FEATURE                 Location/Qualifiers
REGION                  1..6
                        note = poly-histidine tag
source                  1..6
                        mol_type = protein
                        organism = Synthetic construct
SEQUENCE: 297
HHHHHH                                                                    6

SEQ ID NO: 298          moltype = AA  length = 27
FEATURE                 Location/Qualifiers
REGION                  1..27
                        note = Linker
source                  1..27
                        mol_type = protein
                        organism = Synthetic construct
SEQUENCE: 298
```

| KRPAATKKAG QAKKKKASDA KSLTAWS | | 27 |
|---|---|---|

```
SEQ ID NO: 299            moltype = AA   length = 16
FEATURE                   Location/Qualifiers
REGION                    1..16
                          note = Linker
source                    1..16
                          mol_type = protein
                          organism = Synthetic construct
SEQUENCE: 299
SGSETPGTSE SATPES                                                  16

SEQ ID NO: 300            moltype = AA   length = 85
FEATURE                   Location/Qualifiers
REGION                    1..85
                          note = N term Npu Intein
source                    1..85
                          mol_type = protein
                          organism = Synthetic construct
SEQUENCE: 300
CLSYETEILT VEYGLLPIGK IVEKRIECTV YSVDNNGNIY TQPVAQWHDR GEQEVFEYCL   60
EDGSLIRATK DHKFMTVDGQ MLPID                                        85

SEQ ID NO: 301            moltype = DNA   length = 105
FEATURE                   Location/Qualifiers
misc_feature              1..105
                          note = C term Npu Intein
source                    1..105
                          mol_type = other DNA
                          organism = Synthetic construct
SEQUENCE: 301
atcaagattg ctacacggaa atacctggga aagcagaacg tgtacgacat cggcgtggag   60
cgggatcaca acttcgccct gaagaatggc tttatcgcca gcaat                 105

SEQ ID NO: 302            moltype = AA   length = 35
FEATURE                   Location/Qualifiers
REGION                    1..35
                          note = C term Npu Intein
source                    1..35
                          mol_type = protein
                          organism = Synthetic construct
SEQUENCE: 302
IKIATRKYLG KQNVYDIGVE RDHNFALKNG FIASN                             35

SEQ ID NO: 303            moltype = DNA   length = 2598
FEATURE                   Location/Qualifiers
misc_feature              1..2598
                          note = dSpCas9-573-C Intein
source                    1..2598
                          mol_type = other DNA
                          organism = Synthetic construct
SEQUENCE: 303
atgaaacgga cagccgacgg aagcgagttc gagtcaccaa agaagaagcg gaaagtcatc   60
aagattgcta cacggaaata cctgggaaag cagaacgtgt acgacatcgg cgtggagcgg  120
gatcacaact tcgccctgaa gaatggcttt atcgccagca attgtttcga ctctgttgaa  180
atcagcggag tggaggatcg cttcaacgca tccctgggaa cgtatcacga tctcctgaaa  240
atcattaaag acaaggactt cctggacaat gaggagaacg aggacattct tgaggacatt  300
gtcctcaccc ttacgttgtt tgaagatagg gagatgattg aagaacgctt gaaaacttac  360
gctcatctct tcgacgacaa agtcatgaaa cagctcaaga ggcgccgata tacaggatgg  420
gggcggctgt caagaaaact gatcaatggg atccgagaca agcagagtgg aaagacaatc  480
ctggattttc ttaagtccga tggatttgcc aaccggaact tcatgcagtt gatccatgat  540
gactctctca cctttaagga ggacatccag aaagcacaag tttctggcca ggggacagt   600
cttcacgagc acatcgctaa tcttgcaggt agcccagctc aaaagggg aatactgcag   660
accgttaagg tcgtggatga actcgtcaaa gtaatgcgaa gctaagcc cgagaatatc   720
gttatcgaga tggcccgaga aaccaaact acccagaagg acagaagaa cagtaggaa   780
aggatgaaga ggattgaaga gggtataaaa gaactgggt cccaaatcct taggaacac   840
ccagttgaaa acacccagct tcagaatgag aagctctacc tgtactacct gcagaacggc  900
agggacatgt acgtggatca ggaactggac atcaatcggc tctccgacta cgacgtggat  960
gccatcgtgc cccagtcttt tctcaaagat gattctattg ataataagt gttgacaaga 1020
tccgataaaa atagagggaa gagtgataac gtccctcag aagaagttgt caagaaaatg 1080
aaaaattatt ggcggcagct gctgaacgcc aaactgatca cacaacgaa gttcgataat 1140
ctgactaagg ctgaacgagg tggcctgtct gagttgata agccggctt catcaaagg 1200
cagcttgttg agacacgcca gatcaccaag acgtggccc aaattctcga ttcacgcatg 1260
aacaccaagt acgatgaaaa tgacaaactg attcgagagg tgaaagttat tactctgaag 1320
tctaagctgg tctcagattt cagaaaggac tttcagtttt ataaggtgag agatatcaac 1380
aattaccacc atgcgcatga tgcctacctg aatgcagtgg taggcactgc acttatcaaa 1440
aaatatccca agcttgaatc tgaatttgtt acggagact ataaagtgta cgatgttagg 1500
aaaatgatcg caaagtctga gcaggaaata ggcaaggca ccgctaagta cttcttttac 1560
agcaatatta tgaatttttt caagaccgag attacactgg ccaatggaga gattcggaag 1620
```

-continued

```
cgaccactta tcgaaacaaa cggagaaaca ggagaaatcg tgtgggacaa gggtagggat 1680
ttcgcgacag tccggaaggt cctgtccatg ccgcaggtga acatcgttaa aaagaccgaa 1740
gtacagaccg gaggcttctc caaggaaagt atcctcccga aaaggaacag cgacaagctg 1800
atcgcacgca aaaagattg ggaccccaag aaatacggcg gattcgattc tcctacagtc 1860
gcttacagtg tactggttgt ggccaaagtg gagaaaggga agtctaaaaa actcaaaagc 1920
gtcaaggaac tgctgggcat cacaatcatg gagcgatcaa gcttcgaaaa aaacccatc 1980
gactttctcg aggcgaaagg atataaagag gtcaaaaaag acctcatcat taagcttccc 2040
aagtactctc tctttgagct tgaaaacggc cggaaacgaa tgctcgctag tgcgggcgag 2100
ctgcagaaag gtaacgagct ggcactgccc tctaaatacg ttaatttctt gtatctggcc 2160
agccactatg aaaagctcaa agggtctccc gaagataatg agcagaagca gctgttcgtc 2220
gaacaacaca acactacct tgatgagatc atcgagcaaa taagcgaatt ctccaaaaga 2280
gtgatcctcg ccgacgctaa cctcgataag gtgctttctg cttacaataa gcacagggat 2340
aagcccatca gggagcaggc agaaaacatt atccacttgt ttactctgac caacttgggc 2400
gcgcctgcag ccttcaagta cttcgacacc accatagaca gaaagcggta cacctctaca 2460
aaggaggtcc tggacgccac actgattcat cagtcaatta cggggctcta tgaaacaaga 2520
atcgacctct ctcagctcgg tggagacaaa aggccggcgg ccacgaaaaa ggccggccag 2580
gcaaaaaaga aaaagtga                                              2598

SEQ ID NO: 304      moltype = AA   length = 865
FEATURE             Location/Qualifiers
REGION              1..865
                    note = dSpCas9-573-C Intein
source              1..865
                    mol_type = protein
                    organism = Synthetic construct
SEQUENCE: 304
MKRTADGSEF ESPKKKRKVI KIATRKYLGK QNVYDIGVER DHNFALKNGF IASNCFDSVE  60
ISGVEDRFNA SLGTYHDLLK IIKDKDFLDN EENEDILEDI VLTLTLFEDR EMIEERLKTY 120
AHLFDDKVMK QLKRRRYTGW GRLSRKLING IRDKQSGKTI LDFLKSDGFA NRNFMQLIHD 180
DSLTFKEDIQ KAQVSGQGDS LHEHIANLAG SPAIKKGILQ TVKVVDELVK VMGRHKPENI 240
VIEMARENQT TQKGQKNSRE RMKRIEEGIK ELGSQILKEH PVENTQLQNE KLYLYYLQNG 300
RDMYVDQELD INRLSDYDVD AIVPQSFLKD DSIDNKVLTR SDKNRGKSDN VPSEEVVKKM 360
KNYWRQLLNA KLITQRKFDN LTKAERGGLS ELDKAGFIKR QLVETRQITK HVAQILDSRM 420
NTKYDENDKL IREVKVITLK SKLVSDFRKD FQFYKVREIN NYHHAHDAYL NAVVGTALIK 480
KYPKLESEFV YGDYKVYDVR KMIAKSEQEI GKATAKYFFY SNIMNFFKTE ITLANGEIRK 540
RPLIETNGET GEIVWDKGRD FATVRKVLSM PQVNIVKKTE VQTGGFSKES ILPKRNSDKL 600
IARKKDWDPK KYGGFDSPTV AYSVLVVAKV EKGKSKKLKS VKELLGITIM ERSSFEKNPI 660
DFLEAKGYKE VKKDLIIKLP KYSLFELENG RKRMLASAGE LQKGNELALP SKYVNFLYLA 720
SHYEKLKGSP EDNEQKQLFV EQHKHYLDEI IEQISEFSKR VILADANLDK VLSAYNKHRD 780
KPIREQAENI IHLFTLTNLG APAAFKYFDT TIDRKRYTST KEVLDATLIH QSITGLYETR 840
IDLSQLGGDK RPAATKKAGQ AKKKK                                      865

SEQ ID NO: 305      moltype = DNA   length = 255
FEATURE             Location/Qualifiers
misc_feature        1..255
                    note = N term Npu Intein
source              1..255
                    mol_type = other DNA
                    organism = Synthetic construct
SEQUENCE: 305
tgcctgtcct acgagacaga gatcctgaca gtggagtatg gcctgctgcc aatcggcaag  60
atcgtggaga gaggatcga gtgtaccgtg tactctgtgg ataacaatgg caacatctat 120
acacagcccg tggcacagtg gcacgatagg ggagagcagg aggtgttcga gtattgcctg 180
gaggacggca gcctgatcag ggcaaccaag gaccacaagt tcatgacagt ggatggccag 240
atgctgccca tcgac                                                 255

SEQ ID NO: 306      moltype = DNA   length = 20
FEATURE             Location/Qualifiers
misc_feature        1..20
                    note = PCSK9
source              1..20
                    mol_type = other DNA
                    organism = Synthetic construct
SEQUENCE: 306
gtcgaggcgc tcatggttgc                                             20

SEQ ID NO: 307      moltype = DNA   length = 20
FEATURE             Location/Qualifiers
misc_feature        1..20
                    note = PCSK9
source              1..20
                    mol_type = other DNA
                    organism = Synthetic construct
SEQUENCE: 307
ttccagccca gttaggattt                                             20

SEQ ID NO: 308      moltype = DNA   length = 20
FEATURE             Location/Qualifiers
misc_feature        1..20
```

```
                              note = PCSK9
source                        1..20
                              mol_type = other DNA
                              organism = Synthetic construct
SEQUENCE: 308
tcctaactgg gctggaaggc                                                        20

SEQ ID NO: 309                moltype = DNA  length = 20
FEATURE                       Location/Qualifiers
misc_feature                  1..20
                              note = PCSK9
source                        1..20
                              mol_type = other DNA
                              organism = Synthetic construct
SEQUENCE: 309
tcaggagcag ggcgcgtgaa                                                        20

SEQ ID NO: 310                moltype = DNA  length = 20
FEATURE                       Location/Qualifiers
misc_feature                  1..20
                              note = PCSK9
source                        1..20
                              mol_type = other DNA
                              organism = Synthetic construct
SEQUENCE: 310
cagcgacgtc gaggcgctca                                                        20

SEQ ID NO: 311                moltype = DNA  length = 20
FEATURE                       Location/Qualifiers
misc_feature                  1..20
                              note = PCSK9
source                        1..20
                              mol_type = other DNA
                              organism = Synthetic construct
SEQUENCE: 311
ccgtcagctc caggcggtcc                                                        20

SEQ ID NO: 312                moltype = DNA  length = 20
FEATURE                       Location/Qualifiers
misc_feature                  1..20
                              note = PCSK9
source                        1..20
                              mol_type = other DNA
                              organism = Synthetic construct
SEQUENCE: 312
aacctgatcc tccagtccgg                                                        20

SEQ ID NO: 313                moltype = DNA  length = 20
FEATURE                       Location/Qualifiers
misc_feature                  1..20
                              note = PCSK9
source                        1..20
                              mol_type = other DNA
                              organism = Synthetic construct
SEQUENCE: 313
tcatgggcac cgtcagctcc                                                        20

SEQ ID NO: 314                moltype = DNA  length = 20
FEATURE                       Location/Qualifiers
misc_feature                  1..20
                              note = PCSK9
source                        1..20
                              mol_type = other DNA
                              organism = Synthetic construct
SEQUENCE: 314
ccgccggcgt ggaccgcgca                                                        20

SEQ ID NO: 315                moltype = DNA  length = 20
FEATURE                       Location/Qualifiers
misc_feature                  1..20
                              note = PCSK9
source                        1..20
                              mol_type = other DNA
                              organism = Synthetic construct
SEQUENCE: 315
gaaggcaggc cggcgcccta                                                        20

SEQ ID NO: 316                moltype = DNA  length = 20
FEATURE                       Location/Qualifiers
```

```
misc_feature              1..20
                          note = PCSK9
source                    1..20
                          mol_type = other DNA
                          organism = Synthetic construct
SEQUENCE: 316
gcgccttgag ccttgcggtg                                                    20

SEQ ID NO: 317            moltype = DNA  length = 20
FEATURE                   Location/Qualifiers
misc_feature              1..20
                          note = PCSK9
source                    1..20
                          mol_type = other DNA
                          organism = Synthetic construct
SEQUENCE: 317
cccgcacctt ggcgcagcgg                                                    20

SEQ ID NO: 318            moltype = RNA  length = 20
FEATURE                   Location/Qualifiers
misc_feature              1..20
                          note = PCSK9
source                    1..20
                          mol_type = other RNA
                          organism = Synthetic construct
SEQUENCE: 318
gtcgaggcgc tcatggttgc                                                    20

SEQ ID NO: 319            moltype = RNA  length = 20
FEATURE                   Location/Qualifiers
misc_feature              1..20
                          note = PCSK9
source                    1..20
                          mol_type = other RNA
                          organism = Synthetic construct
SEQUENCE: 319
ttccagccca gttaggattt                                                    20

SEQ ID NO: 320            moltype = RNA  length = 20
FEATURE                   Location/Qualifiers
misc_feature              1..20
                          note = PCSK9
source                    1..20
                          mol_type = other RNA
                          organism = Synthetic construct
SEQUENCE: 320
tcctaactgg gctggaaggc                                                    20

SEQ ID NO: 321            moltype = RNA  length = 20
FEATURE                   Location/Qualifiers
misc_feature              1..20
                          note = PCSK9
source                    1..20
                          mol_type = other RNA
                          organism = Synthetic construct
SEQUENCE: 321
tcaggagcag ggcgcgtgaa                                                    20

SEQ ID NO: 322            moltype = RNA  length = 20
FEATURE                   Location/Qualifiers
misc_feature              1..20
                          note = PCSK9
source                    1..20
                          mol_type = other RNA
                          organism = Synthetic construct
SEQUENCE: 322
cagcgacgtc gaggcgctca                                                    20

SEQ ID NO: 323            moltype = RNA  length = 20
FEATURE                   Location/Qualifiers
misc_feature              1..20
                          note = PCSK9
source                    1..20
                          mol_type = other RNA
                          organism = Synthetic construct
SEQUENCE: 323
ccgtcagctc caggcggtcc                                                    20

SEQ ID NO: 324            moltype = RNA  length = 20
```

```
FEATURE                    Location/Qualifiers
misc_feature               1..20
                           note = PCSK9
source                     1..20
                           mol_type = other RNA
                           organism = Synthetic construct
SEQUENCE: 324
aacctgatcc tccagtccgg                                                     20

SEQ ID NO: 325             moltype = RNA  length = 20
FEATURE                    Location/Qualifiers
misc_feature               1..20
                           note = PCSK9
source                     1..20
                           mol_type = other RNA
                           organism = Synthetic construct
SEQUENCE: 325
tcatgggcac cgtcagctcc                                                     20

SEQ ID NO: 326             moltype = RNA  length = 20
FEATURE                    Location/Qualifiers
misc_feature               1..20
                           note = PCSK9
source                     1..20
                           mol_type = other RNA
                           organism = Synthetic construct
SEQUENCE: 326
ccgccggcgt ggaccgcgca                                                     20

SEQ ID NO: 327             moltype = RNA  length = 20
FEATURE                    Location/Qualifiers
misc_feature               1..20
                           note = PCSK9
source                     1..20
                           mol_type = other RNA
                           organism = Synthetic construct
SEQUENCE: 327
gaaggcaggc cggcgcccta                                                     20

SEQ ID NO: 328             moltype = RNA  length = 20
FEATURE                    Location/Qualifiers
misc_feature               1..20
                           note = PCSK9
source                     1..20
                           mol_type = other RNA
                           organism = Synthetic construct
SEQUENCE: 328
gcgccttgag ccttgcggtg                                                     20

SEQ ID NO: 329             moltype = RNA  length = 20
FEATURE                    Location/Qualifiers
misc_feature               1..20
                           note = PCSK9
source                     1..20
                           mol_type = other RNA
                           organism = Synthetic construct
SEQUENCE: 329
cccgcacctt ggcgcagcgg                                                     20

SEQ ID NO: 330             moltype = RNA  length = 106
FEATURE                    Location/Qualifiers
misc_feature               1..106
                           note = PCSK9
source                     1..106
                           mol_type = other RNA
                           organism = Synthetic construct
SEQUENCE: 330
gtcgaggcgc tcatggttgc gtttaagagc tatgctggaa acagcatagc aagtttaaat         60
aaggctagtc cgttatcaac ttgaaaaagt ggcaccgagt cggtgc                       106

SEQ ID NO: 331             moltype = RNA  length = 106
FEATURE                    Location/Qualifiers
misc_feature               1..106
                           note = PCSK9
source                     1..106
                           mol_type = other RNA
                           organism = Synthetic construct
SEQUENCE: 331
ttccagccca gttaggattt gtttaagagc tatgctggaa acagcatagc aagtttaaat         60
```

```
aaggctagtc cgttatcaac ttgaaaaagt ggcaccgagt cggtgc                    106

SEQ ID NO: 332          moltype = RNA   length = 106
FEATURE                 Location/Qualifiers
misc_feature            1..106
                        note = PCSK9
source                  1..106
                        mol_type = other RNA
                        organism = Synthetic construct
SEQUENCE: 332
tcctaactgg gctggaaggc gtttaagagc tatgctggaa acagcatagc aagtttaaat    60
aaggctagtc cgttatcaac ttgaaaaagt ggcaccgagt cggtgc                    106

SEQ ID NO: 333          moltype = RNA   length = 106
FEATURE                 Location/Qualifiers
misc_feature            1..106
                        note = PCSK9
source                  1..106
                        mol_type = other RNA
                        organism = Synthetic construct
SEQUENCE: 333
tcaggagcag ggcgcgtgaa gtttaagagc tatgctggaa acagcatagc aagtttaaat    60
aaggctagtc cgttatcaac ttgaaaaagt ggcaccgagt cggtgc                    106

SEQ ID NO: 334          moltype = RNA   length = 106
FEATURE                 Location/Qualifiers
misc_feature            1..106
                        note = PCSK9
source                  1..106
                        mol_type = other RNA
                        organism = Synthetic construct
SEQUENCE: 334
cagcgacgtc gaggcgctca gtttaagagc tatgctggaa acagcatagc aagtttaaat    60
aaggctagtc cgttatcaac ttgaaaaagt ggcaccgagt cggtgc                    106

SEQ ID NO: 335          moltype = RNA   length = 106
FEATURE                 Location/Qualifiers
misc_feature            1..106
                        note = PCSK9
source                  1..106
                        mol_type = other RNA
                        organism = Synthetic construct
SEQUENCE: 335
ccgtcagctc caggcggtcc gtttaagagc tatgctggaa acagcatagc aagtttaaat    60
aaggctagtc cgttatcaac ttgaaaaagt ggcaccgagt cggtgc                    106

SEQ ID NO: 336          moltype = RNA   length = 106
FEATURE                 Location/Qualifiers
misc_feature            1..106
                        note = PCSK9
source                  1..106
                        mol_type = other RNA
                        organism = Synthetic construct
SEQUENCE: 336
aacctgatcc tccagtccgg gtttaagagc tatgctggaa acagcatagc aagtttaaat    60
aaggctagtc cgttatcaac ttgaaaaagt ggcaccgagt cggtgc                    106

SEQ ID NO: 337          moltype = RNA   length = 106
FEATURE                 Location/Qualifiers
misc_feature            1..106
                        note = PCSK9
source                  1..106
                        mol_type = other RNA
                        organism = Synthetic construct
SEQUENCE: 337
tcatgggcac cgtcagctcc gtttaagagc tatgctggaa acagcatagc aagtttaaat    60
aaggctagtc cgttatcaac ttgaaaaagt ggcaccgagt cggtgc                    106

SEQ ID NO: 338          moltype = RNA   length = 106
FEATURE                 Location/Qualifiers
misc_feature            1..106
                        note = PCSK9
source                  1..106
                        mol_type = other RNA
                        organism = Synthetic construct
SEQUENCE: 338
ccgccggcgt ggaccgcgca gtttaagagc tatgctggaa acagcatagc aagtttaaat    60
aaggctagtc cgttatcaac ttgaaaaagt ggcaccgagt cggtgc                    106
```

```
SEQ ID NO: 339          moltype = RNA   length = 106
FEATURE                 Location/Qualifiers
misc_feature            1..106
                        note = PCSK9
source                  1..106
                        mol_type = other RNA
                        organism = Synthetic construct
SEQUENCE: 339
gaaggcaggc cggcgcccta gtttaagagc tatgctggaa acagcatagc aagtttaaat    60
aaggctagtc cgttatcaac ttgaaaaagt ggcaccgagt cggtgc                   106

SEQ ID NO: 340          moltype = RNA   length = 106
FEATURE                 Location/Qualifiers
misc_feature            1..106
                        note = PCSK9
source                  1..106
                        mol_type = other RNA
                        organism = Synthetic construct
SEQUENCE: 340
gcgccttgag ccttgcggtg gtttaagagc tatgctggaa acagcatagc aagtttaaat    60
aaggctagtc cgttatcaac ttgaaaaagt ggcaccgagt cggtgc                   106

SEQ ID NO: 341          moltype = RNA   length = 106
FEATURE                 Location/Qualifiers
misc_feature            1..106
                        note = PCSK9
source                  1..106
                        mol_type = other RNA
                        organism = Synthetic construct
SEQUENCE: 341
cccgcacctt ggcgcagcgg gtttaagagc tatgctggaa acagcatagc aagtttaaat    60
aaggctagtc cgttatcaac ttgaaaaagt ggcaccgagt cggtgc                   106

SEQ ID NO: 342          moltype = DNA   length = 20
FEATURE                 Location/Qualifiers
misc_feature            1..20
                        note = MYLIP
source                  1..20
                        mol_type = other DNA
                        organism = Synthetic construct
SEQUENCE: 342
gcactgcggc ggcagccggg                                                20

SEQ ID NO: 343          moltype = DNA   length = 20
FEATURE                 Location/Qualifiers
misc_feature            1..20
                        note = MYLIP
source                  1..20
                        mol_type = other DNA
                        organism = Synthetic construct
SEQUENCE: 343
ggcgccaccg cggaggacag                                                20

SEQ ID NO: 344          moltype = DNA   length = 20
FEATURE                 Location/Qualifiers
misc_feature            1..20
                        note = MYLIP
source                  1..20
                        mol_type = other DNA
                        organism = Synthetic construct
SEQUENCE: 344
atgctcatag gatgtattca                                                20

SEQ ID NO: 345          moltype = DNA   length = 20
FEATURE                 Location/Qualifiers
misc_feature            1..20
                        note = MYLIP
source                  1..20
                        mol_type = other DNA
                        organism = Synthetic construct
SEQUENCE: 345
ccacaataaa cacatggtct                                                20

SEQ ID NO: 346          moltype = DNA   length = 20
FEATURE                 Location/Qualifiers
misc_feature            1..20
                        note = MYLIP
source                  1..20
                        mol_type = other DNA
```

```
                        organism = Synthetic construct
SEQUENCE: 346
gggtcccacc agtgacaagg                                                    20

SEQ ID NO: 347          moltype = DNA  length = 20
FEATURE                 Location/Qualifiers
misc_feature            1..20
                        note = MYLIP
source                  1..20
                        mol_type = other DNA
                        organism = Synthetic construct
SEQUENCE: 347
ggactgcctc aaccaggtga                                                    20

SEQ ID NO: 348          moltype = DNA  length = 20
FEATURE                 Location/Qualifiers
misc_feature            1..20
                        note = MYLIP
source                  1..20
                        mol_type = other DNA
                        organism = Synthetic construct
SEQUENCE: 348
cagagtccct gtcgcagcgc                                                    20

SEQ ID NO: 349          moltype = DNA  length = 20
FEATURE                 Location/Qualifiers
misc_feature            1..20
                        note = MYLIP
source                  1..20
                        mol_type = other DNA
                        organism = Synthetic construct
SEQUENCE: 349
ctcagagtga gcgatcgccc                                                    20

SEQ ID NO: 350          moltype = DNA  length = 20
FEATURE                 Location/Qualifiers
misc_feature            1..20
                        note = MYLIP
source                  1..20
                        mol_type = other DNA
                        organism = Synthetic construct
SEQUENCE: 350
ctgagttttcc ctggccgccc                                                   20

SEQ ID NO: 351          moltype = DNA  length = 20
FEATURE                 Location/Qualifiers
misc_feature            1..20
                        note = MYLIP
source                  1..20
                        mol_type = other DNA
                        organism = Synthetic construct
SEQUENCE: 351
gtttccctgg ccgccccggg                                                    20

SEQ ID NO: 352          moltype = RNA  length = 20
FEATURE                 Location/Qualifiers
misc_feature            1..20
                        note = MYLIP
source                  1..20
                        mol_type = other RNA
                        organism = Synthetic construct
SEQUENCE: 352
gcactgcggc ggcagccggg                                                    20

SEQ ID NO: 353          moltype = RNA  length = 20
FEATURE                 Location/Qualifiers
misc_feature            1..20
                        note = MYLIP
source                  1..20
                        mol_type = other RNA
                        organism = Synthetic construct
SEQUENCE: 353
ggcgccaccg cggaggacag                                                    20

SEQ ID NO: 354          moltype = RNA  length = 20
FEATURE                 Location/Qualifiers
misc_feature            1..20
                        note = MYLIP
source                  1..20
```

```
                            mol_type = other RNA
                            organism = Synthetic construct
SEQUENCE: 354
atgctcatag gatgtattca                                               20

SEQ ID NO: 355              moltype = RNA   length = 20
FEATURE                     Location/Qualifiers
misc_feature                1..20
                            note = MYLIP
source                      1..20
                            mol_type = other RNA
                            organism = Synthetic construct
SEQUENCE: 355
ccacaataaa cacatggtct                                               20

SEQ ID NO: 356              moltype = RNA   length = 20
FEATURE                     Location/Qualifiers
misc_feature                1..20
                            note = MYLIP
source                      1..20
                            mol_type = other RNA
                            organism = Synthetic construct
SEQUENCE: 356
gggtcccacc agtgacaagg                                               20

SEQ ID NO: 357              moltype = RNA   length = 20
FEATURE                     Location/Qualifiers
misc_feature                1..20
                            note = MYLIP
source                      1..20
                            mol_type = other RNA
                            organism = Synthetic construct
SEQUENCE: 357
ggactgcctc aaccaggtga                                               20

SEQ ID NO: 358              moltype = RNA   length = 20
FEATURE                     Location/Qualifiers
misc_feature                1..20
                            note = MYLIP
source                      1..20
                            mol_type = other RNA
                            organism = Synthetic construct
SEQUENCE: 358
cagagtccct gtcgcagcgc                                               20

SEQ ID NO: 359              moltype = RNA   length = 20
FEATURE                     Location/Qualifiers
misc_feature                1..20
                            note = MYLIP
source                      1..20
                            mol_type = other RNA
                            organism = Synthetic construct
SEQUENCE: 359
ctcagagtga gcgatcgccc                                               20

SEQ ID NO: 360              moltype = RNA   length = 20
FEATURE                     Location/Qualifiers
misc_feature                1..20
                            note = MYLIP
source                      1..20
                            mol_type = other RNA
                            organism = Synthetic construct
SEQUENCE: 360
ctgagtttcc ctggccgccc                                               20

SEQ ID NO: 361              moltype = RNA   length = 20
FEATURE                     Location/Qualifiers
misc_feature                1..20
                            note = MYLIP
source                      1..20
                            mol_type = other RNA
                            organism = Synthetic construct
SEQUENCE: 361
gtttccctgg ccgccccggg                                               20

SEQ ID NO: 362              moltype = RNA   length = 106
FEATURE                     Location/Qualifiers
misc_feature                1..106
                            note = MYLIP
```

```
source                          1..106
                                mol_type = other RNA
                                organism = Synthetic construct
SEQUENCE: 362
gcactgcggc ggcagccggg gtttaagagc tatgctggaa acagcatagc aagtttaaat    60
aaggctagtc cgttatcaac ttgaaaaagt ggcaccgagt cggtgc                  106

SEQ ID NO: 363                  moltype = RNA   length = 106
FEATURE                         Location/Qualifiers
misc_feature                    1..106
                                note = MYLIP
source                          1..106
                                mol_type = other RNA
                                organism = Synthetic construct
SEQUENCE: 363
ggcgccaccg cggaggacag gtttaagagc tatgctggaa acagcatagc aagtttaaat    60
aaggctagtc cgttatcaac ttgaaaaagt ggcaccgagt cggtgc                  106

SEQ ID NO: 364                  moltype = RNA   length = 106
FEATURE                         Location/Qualifiers
misc_feature                    1..106
                                note = MYLIP
source                          1..106
                                mol_type = other RNA
                                organism = Synthetic construct
SEQUENCE: 364
atgctcatag gatgtattca gtttaagagc tatgctggaa acagcatagc aagtttaaat    60
aaggctagtc cgttatcaac ttgaaaaagt ggcaccgagt cggtgc                  106

SEQ ID NO: 365                  moltype = RNA   length = 106
FEATURE                         Location/Qualifiers
misc_feature                    1..106
                                note = MYLIP
source                          1..106
                                mol_type = other RNA
                                organism = Synthetic construct
SEQUENCE: 365
ccacaataaa cacatggtct gtttaagagc tatgctggaa acagcatagc aagtttaaat    60
aaggctagtc cgttatcaac ttgaaaaagt ggcaccgagt cggtgc                  106

SEQ ID NO: 366                  moltype = RNA   length = 106
FEATURE                         Location/Qualifiers
misc_feature                    1..106
                                note = MYLIP
source                          1..106
                                mol_type = other RNA
                                organism = Synthetic construct
SEQUENCE: 366
gggtcccacc agtgacaagg gtttaagagc tatgctggaa acagcatagc aagtttaaat    60
aaggctagtc cgttatcaac ttgaaaaagt ggcaccgagt cggtgc                  106

SEQ ID NO: 367                  moltype = RNA   length = 106
FEATURE                         Location/Qualifiers
misc_feature                    1..106
                                note = MYLIP
source                          1..106
                                mol_type = other RNA
                                organism = Synthetic construct
SEQUENCE: 367
ggactgcctc aaccaggtga gtttaagagc tatgctggaa acagcatagc aagtttaaat    60
aaggctagtc cgttatcaac ttgaaaaagt ggcaccgagt cggtgc                  106

SEQ ID NO: 368                  moltype = RNA   length = 106
FEATURE                         Location/Qualifiers
misc_feature                    1..106
                                note = MYLIP
source                          1..106
                                mol_type = other RNA
                                organism = Synthetic construct
SEQUENCE: 368
cagagtccct gtcgcagcgc gtttaagagc tatgctggaa acagcatagc aagtttaaat    60
aaggctagtc cgttatcaac ttgaaaaagt ggcaccgagt cggtgc                  106

SEQ ID NO: 369                  moltype = RNA   length = 106
FEATURE                         Location/Qualifiers
misc_feature                    1..106
                                note = MYLIP
source                          1..106
                                mol_type = other RNA
```

```
                        organism = Synthetic construct
SEQUENCE: 369
ctcagagtga gcgatcgccc gtttaagagc tatgctggaa acagcatagc aagtttaaat    60
aaggctagtc cgttatcaac ttgaaaaagt ggcaccgagt cggtgc                  106

SEQ ID NO: 370          moltype = RNA   length = 106
FEATURE                 Location/Qualifiers
misc_feature            1..106
                        note = MYLIP
source                  1..106
                        mol_type = other RNA
                        organism = Synthetic construct
SEQUENCE: 370
ctgagtttcc ctggccgccc gtttaagagc tatgctggaa acagcatagc aagtttaaat    60
aaggctagtc cgttatcaac ttgaaaaagt ggcaccgagt cggtgc                  106

SEQ ID NO: 371          moltype = RNA   length = 106
FEATURE                 Location/Qualifiers
misc_feature            1..106
                        note = MYLIP
source                  1..106
                        mol_type = other RNA
                        organism = Synthetic construct
SEQUENCE: 371
gtttccctgg ccgccccggg gtttaagagc tatgctggaa acagcatagc aagtttaaat    60
aaggctagtc cgttatcaac ttgaaaaagt ggcaccgagt cggtgc                  106

SEQ ID NO: 372          moltype = DNA   length = 20
FEATURE                 Location/Qualifiers
misc_feature            1..20
                        note = APOB
source                  1..20
                        mol_type = other DNA
                        organism = Synthetic construct
SEQUENCE: 372
tgagggcctc ccactctaca                                                20

SEQ ID NO: 373          moltype = DNA   length = 20
FEATURE                 Location/Qualifiers
misc_feature            1..20
                        note = APOB
source                  1..20
                        mol_type = other DNA
                        organism = Synthetic construct
SEQUENCE: 373
ccagagcact gaagacgctt                                                20

SEQ ID NO: 374          moltype = DNA   length = 20
FEATURE                 Location/Qualifiers
misc_feature            1..20
                        note = APOB
source                  1..20
                        mol_type = other DNA
                        organism = Synthetic construct
SEQUENCE: 374
actggaggaa acctagaagc                                                20

SEQ ID NO: 375          moltype = DNA   length = 20
FEATURE                 Location/Qualifiers
misc_feature            1..20
                        note = APOB
source                  1..20
                        mol_type = other DNA
                        organism = Synthetic construct
SEQUENCE: 375
cactgaagac gcttggggaa                                                20

SEQ ID NO: 376          moltype = DNA   length = 20
FEATURE                 Location/Qualifiers
misc_feature            1..20
                        note = APOB
source                  1..20
                        mol_type = other DNA
                        organism = Synthetic construct
SEQUENCE: 376
tgaagaaggc acccctggtc                                                20

SEQ ID NO: 377          moltype = DNA   length = 20
FEATURE                 Location/Qualifiers
```

```
misc_feature            1..20
                        note = APOB
source                  1..20
                        mol_type = other DNA
                        organism = Synthetic construct
SEQUENCE: 377
tgagtgcgcg gccgctctgc                                                    20

SEQ ID NO: 378          moltype = RNA  length = 20
FEATURE                 Location/Qualifiers
misc_feature            1..20
                        note = APOB
source                  1..20
                        mol_type = other RNA
                        organism = Synthetic construct
SEQUENCE: 378
tgagggcctc ccactctaca                                                    20

SEQ ID NO: 379          moltype = RNA  length = 20
FEATURE                 Location/Qualifiers
misc_feature            1..20
                        note = APOB
source                  1..20
                        mol_type = other RNA
                        organism = Synthetic construct
SEQUENCE: 379
ccagagcact gaagacgctt                                                    20

SEQ ID NO: 380          moltype = RNA  length = 20
FEATURE                 Location/Qualifiers
misc_feature            1..20
                        note = APOB
source                  1..20
                        mol_type = other RNA
                        organism = Synthetic construct
SEQUENCE: 380
actggaggaa acctagaagc                                                    20

SEQ ID NO: 381          moltype = RNA  length = 20
FEATURE                 Location/Qualifiers
misc_feature            1..20
                        note = APOB
source                  1..20
                        mol_type = other RNA
                        organism = Synthetic construct
SEQUENCE: 381
cactgaagac gcttggggaa                                                    20

SEQ ID NO: 382          moltype = RNA  length = 20
FEATURE                 Location/Qualifiers
misc_feature            1..20
                        note = APOB
source                  1..20
                        mol_type = other RNA
                        organism = Synthetic construct
SEQUENCE: 382
tgaagaaggc acccctggtc                                                    20

SEQ ID NO: 383          moltype = RNA  length = 20
FEATURE                 Location/Qualifiers
misc_feature            1..20
                        note = APOB
source                  1..20
                        mol_type = other RNA
                        organism = Synthetic construct
SEQUENCE: 383
tgagtgcgcg gccgctctgc                                                    20

SEQ ID NO: 384          moltype = RNA  length = 106
FEATURE                 Location/Qualifiers
misc_feature            1..106
                        note = APOB
source                  1..106
                        mol_type = other RNA
                        organism = Synthetic construct
SEQUENCE: 384
tgagggcctc ccactctaca gtttaagagc tatgctggaa acagcatagc aagtttaaat        60
aaggctagtc cgttatcaac ttgaaaaagt ggcaccgagt cggtgc                      106
```

```
SEQ ID NO: 385              moltype = RNA   length = 106
FEATURE                     Location/Qualifiers
misc_feature                1..106
                            note = APOB
source                      1..106
                            mol_type = other RNA
                            organism = Synthetic construct
SEQUENCE: 385
ccagagcact gaagacgctt gtttaagagc tatgctggaa acagcatagc aagtttaaat   60
aaggctagtc cgttatcaac ttgaaaaagt ggcaccgagt cggtgc                 106

SEQ ID NO: 386              moltype = RNA   length = 106
FEATURE                     Location/Qualifiers
misc_feature                1..106
                            note = APOB
source                      1..106
                            mol_type = other RNA
                            organism = Synthetic construct
SEQUENCE: 386
actggaggaa acctagaagc gtttaagagc tatgctggaa acagcatagc aagtttaaat   60
aaggctagtc cgttatcaac ttgaaaaagt ggcaccgagt cggtgc                 106

SEQ ID NO: 387              moltype = RNA   length = 106
FEATURE                     Location/Qualifiers
misc_feature                1..106
                            note = APOB
source                      1..106
                            mol_type = other RNA
                            organism = Synthetic construct
SEQUENCE: 387
cactgaagac gcttggggaa gtttaagagc tatgctggaa acagcatagc aagtttaaat   60
aaggctagtc cgttatcaac ttgaaaaagt ggcaccgagt cggtgc                 106

SEQ ID NO: 388              moltype = RNA   length = 106
FEATURE                     Location/Qualifiers
misc_feature                1..106
                            note = APOB
source                      1..106
                            mol_type = other RNA
                            organism = Synthetic construct
SEQUENCE: 388
tgaagaaggc accctggtc gtttaagagc tatgctggaa acagcatagc aagtttaaat    60
aaggctagtc cgttatcaac ttgaaaaagt ggcaccgagt cggtgc                 106

SEQ ID NO: 389              moltype = RNA   length = 106
FEATURE                     Location/Qualifiers
misc_feature                1..106
                            note = APOB
source                      1..106
                            mol_type = other RNA
                            organism = Synthetic construct
SEQUENCE: 389
tgagtgcgcg gccgctctgc gtttaagagc tatgctggaa acagcatagc aagtttaaat   60
aaggctagtc cgttatcaac ttgaaaaagt ggcaccgagt cggtgc                 106

SEQ ID NO: 390              moltype = DNA   length = 20
FEATURE                     Location/Qualifiers
misc_feature                1..20
                            note = cPCSK9-C gRNA target site
source                      1..20
                            mol_type = other DNA
                            organism = Synthetic construct
SEQUENCE: 390
aggtttccgc agcggcgtcg                                               20

SEQ ID NO: 391              moltype = RNA   length = 20
FEATURE                     Location/Qualifiers
misc_feature                1..20
                            note = cPCSK9-C gRNA spacer
source                      1..20
                            mol_type = other RNA
                            organism = Synthetic construct
SEQUENCE: 391
aggtttccgc agcggcgtcg                                               20

SEQ ID NO: 392              moltype = RNA   length = 100
FEATURE                     Location/Qualifiers
misc_feature                1..100
                            note = cPCSK9-C full length gRNA
```

```
source                          1..100
                                mol_type = other RNA
                                organism = Synthetic construct
SEQUENCE: 392
aggtttccgc agcggcgtcg gttttagagc tagaaatagc aagttaaaat aaggctagtc   60
cgttatcaac ttgaaaaagt ggcaccgagt cggtgctttt                         100

SEQ ID NO: 393                  moltype = RNA   length = 63
FEATURE                         Location/Qualifiers
misc_feature                    1..63
                                note = 5' UTR (5U4)
source                          1..63
                                mol_type = other RNA
                                organism = Synthetic construct
SEQUENCE: 393
ggagcaattg accgggaagc tcagaataaa cgctcaactt tggccggatc ttctagagcc   60
acc                                                                63

SEQ ID NO: 394                  moltype = RNA   length = 46
FEATURE                         Location/Qualifiers
misc_feature                    1..46
                                note = 3' UTR (3U2)
source                          1..46
                                mol_type = other RNA
                                organism = Synthetic construct
SEQUENCE: 394
tagtaagaat tcaaagaaag tttcttcaca ttctctcgag cgtacg                  46

SEQ ID NO: 395                  moltype = RNA   length = 6433
FEATURE                         Location/Qualifiers
misc_feature                    1..6433
                                note = dCas9-KRAB-DNMT3A/L mRNA
source                          1..6433
                                mol_type = other RNA
                                organism = Synthetic construct
SEQUENCE: 395
ggagcaattg accgggaagc tcagaataaa cgctcaactt tggccggatc ttctagagcc   60
accatgaacc acgatcagga gtttgacccc cctaaggtgt acccaccccgt gccagccgag  120
aagaggaagc ccatccgcgt gctgtccctg ttcgacguga tcgccacagg cctgctggtg   180
ctgaaggatc tgggcatcca ggtggacaga tatatcgcct ccgaggtgtg cgaggattct   240
atcaccgtgg gcatggtgag gcaccagggc aagatcatgt acgtgggcga cgtgcgcagc   300
gtgacacaga agcacatcca ggagtgggga cccttcgacc tggtcatcgg aggcagcccc   360
tgtaatgacc tgtccatcgt gaaccctgca aggaaggcc tgtatgaggg aaccggcagc   420
ctgttctttg agttctacag gctgctgcac gacgcccgcc ctaaggaggg cgatgacagg   480
ccattctttt ggctgtttga aacgtggtg gccatgggcg tgagcgacaa gcgggatatc   540
tccagattcc tggagtctaa tcccgtgatg atcgatgcaa aggaggtgtc tgcccacac   600
agggcaaggt acttttgggg aaatctgcct ggcatgaacc ccactggc cagcaccgtg   660
aacgacaagc tggagctgca ggagtgcctg agcacggaa ggatcgccaa gttctccaag   720
gtgcggacaa tcaccacaag atctaacagc atcaagcagg gcaaggatca gcacttcccc   780
gtgttcatga atgagaagga ggacatcctg tggtgtaccg agatggagcg cgtgttcggc   840
tttccagtgc actatacaga cgtggcaat atgagccggc tggcaaggca gagactgctg   900
ggccggtcct ggtctgtgcc agtgatcaga cacctgttcg cccccctgaa ggagtacttt   960
gcctgcgtgt ctagcggcaa ctcaatgca acagcagag gccttcctt ttcctctggc   1020
ctggtgccac tgtctctgag gggcagccac atggggccca tggagatcta caagaccgtg   1080
tccgcctgga gaggcagcc tgtgcgcgtg ctgtctctgt tccgcaacat cgacaaggtg   1140
ctcaagagcc tgggctttct ggagagcgga tccggatctg aggaggcac cctgaagtat   1200
gtggaggatg tgacaaatgt ggtgcggaga gatgtggaga gtggggccc cttcgatctg   1260
gtgtacggat ccacccagcc actgggaagc tcctgcgata ggtgtccagg atggtatatg   1320
ttccagtttc acagaatcct gcagtacgca cctgcaaggc aggagagcca gcgccctttc   1380
ttttggatct ttatgacaa cctgctgctg acagaggatg accaggagac aaacaacgc   1440
ttcctgcaga cagaggcagt gaccctgcag gatgtgaggg gacgcgacta tcagaatgcc   1500
atgcgggtgt ggtctaacat ccctggcctg aaaagcaagc acgcccccct gacccctaag   1560
gaggaggagt acctgcaggc caggtgcgg agcagatcca gctggatgc ccctaaggtg   1620
gacctgctgg tgaagaattg tctgctgcca ctgcggaagat acttcaagta ctttagtcag   1680
aatagcctgc cactgaggc aagcggatcc ggaagggcat ctcctggaat cccaggaagc   1740
acccgcaacc caagaagaa gcggaaggtg gcatccacg cgtgcccgc gccgacaag   1800
aagtacagca tcgcctggc catcggcacc aacagcgtgg ctgggccgt gatcaccgac   1860
gagtacaagg tgcccagcaa gaagttcaag gtgctgggca caccgaccg gcacagcatc   1920
aagaagaacc tgatcggcgc cctgctgttc gacagcggcg agacggccga ggccacccgg   1980
ctgaagcgga ccgccggcg gcggtacacc cggcggaaga ccggatctg ctacctgcag   2040
gagatcttca gcaacgagat ggccaaggtg gacgacagct tccacccg gctgaggag   2100
agcttcctgg tggaggagga caagaagcac gagcggcacc catcttcgg caacatcgtg   2160
gacgaggtgg cctaccacga agtacccc ccatctacc acctgcggaa gaagctggtg   2220
gacagcaccg acaaggccgg cctgcagctg atctacctgg ccctggccca catgatcaag   2280
ttccggggcc acttcctgat cgagggcgac ctgaacccg acaacagcga cgtgacaag   2340
ctgttcatcc agctggtgca gacctacaac cagctgttcg aggagaaccc catcaacgcc   2400
agcggcgtga cgccaaggc catcctgagc gccggctga caagagccg cggctggag   2460
aacctgatcg cccagctgcc cggcgagaag aagaacggcc tgttcggcaa cctgatcgcc   2520
ctgagcctgg gcctgacccc caacttcaag agcaacttcg acctggccga ggacgccaag   2580
```

```
                                      -continued
ctgcagctga gcaaggacac ctacgacgac gacctggaca acctgctggc ccagatcggc  2640
gaccagtacg ccgacctgtt cctgccgcc  aagaacctga gcgacgccat cctgctgagc  2700
gacatcctgc gggtgaacac cgagatcacc aaggcccccc tgagcgccag catgatcaag  2760
cggtacgacg agcaccacca ggacctgacc ctgctgaagg ccctggtgcg gcagcagctg  2820
cccgagaagt acaaggagat cttcttcgac cagagcaaga acggctacgc cggctacatc  2880
gacggcggcg ccagccagga ggagttctac aagttcatca agcccatcct ggagaagatg  2940
gacggcaccg aggagctgct ggtgaagctg aaccggagg  acctgctgcg gaagcagcgg  3000
accttcgaca acggcagcat cccccaccag atccacctgg gcgagctgca cgccatcctg  3060
cggcggcagg aggacttcta cccttcctg  aaggacaacc gggagaagat cgagaagatc  3120
ctgaccttcc ggatcccta  ctacgtgggc ccctggccc  ggggcaacag ccggttcgcc  3180
tggatgaccc ggaaaagcga ggagaccatc accccctgga acttcgagga ggtggtggac  3240
aagggcgcca gcgcccagag cttcatcgag cggatgacca acttcgacaa gaacctgccc  3300
aacgagaagg tgctgcccaa gcacagcctg ctgtacgagt acttcaccgt gtacaacgag  3360
ctgaccaagg tgaagtacgt gaccgagggc atgcggaagc ccgccttcct gagcggcgag  3420
cagaagaagg ccatcgtgga cctgctgttc aagaccaacc ggaaggtgac cgtgaagcag  3480
ctgaaggagg actacttcaa gaagatcgag tgcttcgaca gcgtggagat cagcggcgtg  3540
gaggaccggt tcaacgccag cctgggcacc taccacgacc tgctgaagat catcaaggac  3600
aaggacttcc tggacaacga ggagaacgag gacatcctgg aggacatcgt gctgaccctg  3660
accctgttcg aggaccggga gatgatcgag gagcggctga agacctacgc ccacctgttc  3720
gacgacaagg tgatgaagca gctgaagcgg cggcggtaca ccggctgggg ccggctgagc  3780
cggaagctga tcaacggcat ccgggacaag cagagcggca agaccatcct ggacttcctg  3840
aaaagcgacg gcttcgccaa ccggaacttc atgcagctga tccacgacga cagcctgacc  3900
ttcaaggagg acatccagaa ggcccaggtg agcggccagg gcgacagcct gcacgagcac  3960
atcgccaacc tggccggcag ccccgccatc aagaagggca tcctgcagac cgtgaaggtg  4020
gtggacgagc tggtgaaggt gatgggccgg cacaagcccg agaacatcgt gatcgagatg  4080
gcccggagaa accagaccac ccagaagggc cagaagaaca gccgggagcg gatgaagcgg  4140
atcgaggagg gcatcaagga gctgggcagc cagatcctga aggagcaccc cgtggagaac  4200
acccagctgc agaacgagaa gctgtacctg tactacctgc agaacggccg ggacatgtac  4260
gtggaccagg agctggacat caaccggctg agcgactacg acgtggacgc catcgtgccc  4320
cagagcttcc tgaaggacga cagcatcgac aacaaggtgc tgacccggag cgacaagaac  4380
cggggcaaga gcgacaacgt gcccagcgag gaggtggtga agaagatgaa gaactactgg  4440
cggcagctgc tgaacgccaa gctgatcacc cagcggaagt tcgacaacct gaccaaggcc  4500
gagcggggcg gcctgagcga gctggacaag gccggcttca tcaagcggca gctggtggag  4560
acccggcaga tcaccaagca cgtggcccag atcctggaca gccggatgaa caccaagtac  4620
gacgagaacg acaagctgat ccgggaggtg aaggtgatca ccctgaaaag caagctggtg  4680
agcgacttcc ggaaggactt ccagttctac aaggtgcggg agatcaacaa ctaccaccac  4740
gcccacgacg cctacctgaa cgccgtggtg ggcaccgccc tgatcaagaa gtaccccaag  4800
ctggagagcg agttcgtgta cggcgactac aaggtgtacg acgtgcggaa gatgatcgcc  4860
aagagcgagc aggagatcgg caaggccacc gccaagtact tcttctacag caacatcatg  4920
aacttcttca agaccgagat caccctggcc aacggcgaga tccggaagcg gccccctgatc  4980
gagaccaacg gcgagaccgg cgagatcgtg tgggacaagg gccgggactt cgccaccgtg  5040
cggaaggtgc tgagcatgcc ccaggtgaac atcgtgaaga agaccgaggt gcagaccggc  5100
ggcttcagca aggagagcat cctgcccaag cggaacagcg acaagctgat cgcccggaag  5160
aaggactggg accccaagaa gtacggcggc ttcgacagcc ccaccgtggc ctacagcgtg  5220
ctggtggtgg ccaaggtgga aagggcaag  agcaagaagc tgaaaagcgt gaaggagctg  5280
ctgggcatca ccatcatgga gcggagcagc ttcgagaaga accccatcga cttcctggag  5340
gccaaggct  acaaggaggt gaagaaggac ctgatcatca agtgcccaa  gtacagcctg  5400
ttcgagctgg agaacggccg gaagcggatg ctgccagcg  ccggcgagct gcagaagggc  5460
aacgagctgg ccctgcccag caagtacgtg aacttcctgt acctggccag ccactacgag  5520
aagctgaagg gcagccccga ggacaacgag cagaagcagc tgttcgtgga gcagcacaag  5580
cactacctgg acgagatcat cgagcagatc agcgagttca gcaagcgggt gatcctggcc  5640
gacgccaacc tggacaaggt gctgagcgcc tacaacaagc accgggacaa gcccatccgg  5700
gagcaggccg agaacatcat ccacctgttc accctgacca acctgggcgc cccgccgcc  5760
ttcaagtact tcgacaccac catcgaccgg aagcggtaca ccagcaccaa ggaggtgctg  5820
gacgccaccc tgatccacca gagcatcacc ggcctgtacg agacccggat cgacctgagc  5880
cagctgggcg gcgacagcgg cggcaagcgg cccgccgcca ccaagaaggc cggccaggcc  5940
aagaagaaga aggctagcga tgctaagtca ctgactgcct ggtcccggac actggtgacc  6000
ttcaaggatg tgtttgtgga cttcaccagg gaggagtgga agctgctgga cactgctcag  6060
cagatcctgt acagaaatgt gatgctggag aactataaga acctggtttc cttgggttat  6120
cagcttacta agccagatgt gatcctccgg ttggagaagg gagaggaacc ctggctggtg  6180
gagagagaaa ttcaccaaga gacccatcct gattcagaga ctgcatttga aatcaaatca  6240
tcagttccga aaaagaaacg caaagtttag taagaattca aagaaagttt cttcacattc  6300
tctcgagcgt acgaaaaaaa aaaaaaaaaa aaaaaaaaa  aaaaaaaaaa aaaaaaaaaa  6360
aaaaaaaaaa aaaaaaaaa  aaaaaaaaaa aaaaaaaaaa aaaaaaaaaa aaaaaaaaaa  6420
aaaaaaaaaa aaa                                                     6433
```

COMPOSITIONS, SYSTEMS, AND METHODS FOR EPIGENETIC REGULATION OF PROPROTEIN CONVERTASE SUBTILISIN/KEXIN TYPE 9 (PCSK9) GENE EXPRESSION

CROSS-REFERENCE TO RELATED APPLICATIONS

This application is a Continuation application of International Application No. PCT/US2023/069031, filed on Jun. 23, 2023, which claims priority from U.S. provisional application No. 63/355,540 filed Jun. 24, 2022, U.S. provisional application No. 63/399,625 filed Aug. 19, 2022, U.S. provisional application No. 63/401,558 filed Aug. 26, 2022, U.S. provisional application No. 63/453,044 filed Mar. 17, 2023, U.S. provisional application No. 63/466,681 filed May 15, 2023, and U.S. provisional application No. 63/472,224 filed Jun. 9, 2023, the contents of which are incorporated by reference in their entireties.

INCORPORATION BY REFERENCE OF SEQUENCE LISTING

The present application is being filed along with a Sequence Listing in electronic format. The Sequence Listing is provided as a file entitled 224742001901SeqList.xml, created Sep. 28, 2023, which is 561,656 bytes in size. The information in the electronic format of the Sequence Listing is incorporated by reference in its entirety.

FIELD

The present disclosure relates in some aspects to epigenetic-modifying DNA-targeting systems, such as CRISPR-Cas/guide RNA (gRNA) systems, for the transcriptional repression of genes to promote a cellular phenotype that leads to reduction of low-density lipoprotein (LDL). In some embodiments, the epigenetic-modifying DNA-targeting systems bind to or target a target site of at least one gene or regulatory element thereof that regulate LDL. In some embodiments, the systems are multiplexed systems that bind to or target a target site in at least two genes or regulatory elements thereof. In some aspects, the present disclosure also provides methods and uses related to the provided epigenetic-modifying DNA targeting systems in connection with treatments for cardiovascular disease and familial hypercholesterolemia.

BACKGROUND

Familial hypercholesterolemia (FH) is a genetic condition resulting in elevated levels of LDL cholesterol in the bloodstream, resulting in increased risk of cardiovascular disease. Current treatments for FH, including administration of statins and antibody therapy, face challenges including toxicity and high cost associated with repeated drug administration. There is a need for new and improved methods to overcome these challenges. The present disclosure addresses these and other needs.

SUMMARY

In some aspects, provided herein is an epigenetic-modifying DNA-targeting system comprising a plurality of DNA-targeting modules for repressing transcription of a plurality of genes that regulate low-density lipoprotein (LDL), wherein the plurality of DNA-targeting modules comprises a first DNA-targeting module for repressing transcription of a first gene of the plurality of genes, and a second DNA-targeting module for repressing transcription of a second gene of the plurality of genes, and wherein each DNA-targeting module comprises a fusion protein comprising: (a) a DNA-binding domain for targeting to a target site of one of the plurality of genes, and (b) at least one transcriptional repressor domain. In some of any of the provided embodiments, the DNA-targeting system does not introduce a genetic disruption or a DNA break. In some of any of the provided embodiments, the fusion protein of each DNA-targeting module comprises a DNA-binding domain selected from: a Clustered Regularly Interspaced Short Palindromic Repeats associated (Cas) protein or a variant thereof; a zinc finger protein (ZFP); a transcription activator-like effector (TALE); a meganuclease; a homing endonuclease; or an I-SceI enzyme or a variant thereof, optionally wherein the DNA-binding domain comprises a catalytically inactive variant of any of the foregoing. In some of any of the provided embodiments, the fusion protein of the first DNA-targeting module comprises a DNA-binding domain for targeting a target site of the first gene or regulatory DNA element thereof, and at least one transcriptional repressor domain; and the fusion protein of the second DNA-targeting module comprises a DNA-binding domain for targeting a target site of the second gene or regulatory DNA element thereof, and at least one transcriptional repressor domain. In some of any of the provided embodiments, any two or more of the DNA-targeting modules comprise the same fusion protein. In some of any of the provided embodiments, the first and second DNA-targeting modules comprise the same fusion protein. In some of any of the provided embodiments, any two or more of the DNA-targeting modules comprise different fusion proteins. In some of any of the provided embodiments, the first and second DNA-targeting modules comprise different fusion proteins.

In some aspects, provided herein is an epigenetic-modifying DNA-targeting system comprising a plurality of DNA-targeting modules for repressing transcription of a plurality of genes that regulate low-density lipoprotein (LDL), comprising: (1) a first DNA-targeting module that reduces transcription of a first gene that regulates low-density lipoprotein (LDL), wherein the first DNA-targeting module comprises a first fusion protein comprising (a) a DNA-binding domain for targeting a target site of the first gene or regulatory DNA element thereof; and (b) at least one transcriptional repressor domain; and (2) a second DNA-targeting module that reduces transcription of a second gene that regulates LDL, wherein the second DNA-targeting module comprises a second fusion protein comprising (a) a DNA-binding domain for targeting a target site of the second gene or regulatory DNA element thereof; and (b) at least one transcriptional repressor domain. In some of any of the provided embodiments, the first DNA-targeting module comprises a first targeting polynucleotide for targeting to the target site of the first gene and the second DNA-targeting module comprises a second targeting polynucleotide for targeting to the target site of the second gene, wherein the first and second targeting polynucleotides complex with the DNA-binding domain of the fusion protein. In some of any of the provided embodiments, the DNA-binding domain is a Clustered Regularly Interspaced Short Palindromic Repeats associated (Cas) protein or variant thereof and the first and second targeting polynucleotides comprise a first gRNA and a second gRNA, respectively.

In some aspects, provided herein is an epigenetic-modifying DNA-targeting system comprising: (a) a fusion protein comprising a Clustered Regularly Interspaced Short Palindromic Repeats associated (Cas) protein or variant thereof and at least one transcriptional repressor domain; and (b) a plurality of guide RNAs (gRNAs) comprising at least a first gRNA and a second gRNA, wherein the first gRNA targets a target site of a first gene that regulates low-density lipoprotein (LDL) and the second gRNA targets a target site of a second gene that regulates LDL.

In some of any of the provided embodiments, the system further comprises a third DNA-targeting module for repressing transcription of a third gene that regulates low-density lipoprotein (LDL). In some of any of the provided embodiments, the system further comprises a third gRNA that targets a target site of a third gene that regulates LDL, optionally wherein the system further comprises a fourth gRNA that targets a target site of a fourth gene that regulates LDL, optionally a fifth gRNA that targets a target site of a fifth gene that regulates LDL, and/or optionally a sixth gRNA that targets a target site of a sixth gene that regulates LDL.

In some of any of the provided embodiments, the first gene and the second gene are independently selected from the group consisting of PCSK9, LPA, MYLIP, ANGPTL3, APOB, and APOC3. In some of any of the provided embodiments, the first gene and the second gene are different. In some of any of the provided embodiments, the first gene and the second gene are: PCSK9 and LPA; PCSK9 and MYLIP; PCSK9 and ANGPTL3; PCSK9 and APOC3; PCSK9 and APOB; LPA and MYLIP; LPA and ANGPTL3; LPA and APOC3; LPA and APOB; MYLIP and ANGPTL3; MYLIP and APOC3; MYLIP and APOB; ANGPTL3 and APOC3; ANGPTL3 and APOB; or APOC3 and APOB. In some of any of the provided embodiments, the first gene, the second gene, and the third gene are each independently selected from the group consisting of PCSK9, LPA, MYLIP, ANGPTL3, APOC3, and APOB. In some of any of the provided embodiments, the first gene, the second gene, and the third gene are different. In some of any of the provided embodiments, the first gene, the second gene, and the third gene are: PCSK9, LPA, and MYLIP; PCSK9, LPA, and ANGPTL3; PCSK9, LPA, and APOC3; PCSK9, LPA, and APOB; PCSK9, MYLIP, and ANGPTL3; PCSK9, MYLIP, and APOC3; PCSK9, MYLIP, and APOB; PCSK9, ANGPTL3, and APOC3; PCSK9, ANGPTL3, and APOB; PCSK9, APOC3, and APOB; LPA, MYLIP, and ANGPTL3; LPA, MYLIP, and APOC3; LPA, MYLIP, and APOB; LPA, ANGPTL3, and APOC3; LPA, ANGPTL3, and APOB; LPA, APOC3, and APOB; MYLIP, ANGPTL3, and APOC3; MYLIP, ANGPTL3, and APOB; MYLIP, APOC3, and APOB; or ANGPTL3, APOC3, and APOB. In some of any of the provided embodiments, at least one gene is PCSK9. In some of any of the provided embodiments, at least two genes are PCSK9 and LPA. In some of any of the provided embodiments, at least three genes are PCSK9, LPA, and MYLIP. In some of any of the provided embodiments, at least three genes are PCSK9, MYLIP, and APOB.

In some of any of the provided embodiments, the target site of each of the plurality of genes is in the gene or a regulatory DNA element thereof. In some of any of the provided embodiments, the regulatory DNA element is an enhancer or a promoter. In some of any of the provided embodiments, the target site of the first gene and the second gene are selected from two different members of the group consisting of (a)-(f): (a) a target site for PCSK9, located within 500 bp of human genome assembly GRCh38 (hg38) genomic coordinates chr1:55,039,548; (b) a target site for LPA, located within 500 bp of the hg38 genomic coordinates chr6:160,664,275; (c) a target site for MYLIP, located within 500 bp of the hg38 genomic coordinates chr6:16,129,086; (d) a target site for ANGPTL3, located within 500 bp of the hg38 genomic coordinates chr1:62,597,520; (e) a target site for APOC3, located within 500 bp of the hg38 genomic coordinates chr11:116,829,907; and (f) a target site for APOB, located within 500 bp of the hg38 genomic coordinates chr2:21,044,073. In some of any of the provided embodiments, the target site of the first gene and the second gene are selected from two different members of the group consisting of (a)-(f): (a) a target site located within 500 bp of a transcriptional start site of PCSK9; (b) a target site located within 500 bp of a transcriptional start site of LPA; (c) a target site located within 500 bp of a transcriptional start site of MYLIP; (d) a target site located within 500 bp of a transcriptional start site of ANGPTL3; (e) a target site located within 500 bp of a transcriptional start site of APOC3; and (f) a target site located within 500 bp of a transcriptional start site of APOB. In some of any of the provided embodiments, the target site of the first gene, the second gene and the third gene are selected from three different members of the group consisting of (a)-(f): (a) a target site for PCSK9, located within 500 bp of human genome assembly GRCh38 (hg38) genomic coordinates chr1:55,039,548; (b) a target site for LPA, located within 500 bp of the hg38 genomic coordinates chr6:160,664,275; (c) a target site for MYLIP, located within 500 bp of the hg38 genomic coordinates chr6:16,129,086; (d) a target site for ANGPTL3, located within 500 bp of the hg38 genomic coordinates chr1:62,597,520; (e) a target site for APOC3, located within 500 bp of the hg38 genomic coordinates chr11:116,829,907; and (f) a target site for APOB, located within 500 bp of the hg38 genomic coordinates chr2:21,044,073. In some of any of the provided embodiments, the target site of the first gene, the second gene and the third gene are selected from three different members of the group consisting of (a)-(f): (a) a target site located within 500 bp of a transcriptional start site of PCSK9; (b) a target site located within 500 bp of a transcriptional start site of LPA; (c) a target site located within 500 bp of a transcriptional start site of MYLIP; (d) a target site located within 500 bp of a transcriptional start site of ANGPTL3; (e) a target site located within 500 bp of a transcriptional start site of APOC3; and (f) a target site located within 500 bp of a transcriptional start site of APOB. In some of any of the provided embodiments, the target site of the first gene and the second gene are selected from two different members of the group consisting of (a)-(f): (a) a target site for PCSK9 having the sequence set forth in any one of SEQ ID NOS:1-13 or 306-317, a contiguous portion thereof of at least 14 nucleotides (nt), or a complementary sequence of any of the foregoing; (b) a target site for LPA having the sequence set forth in any one of SEQ ID NOS:14-23, a contiguous portion thereof of at least 14 nucleotides (nt), or a complementary sequence of any of the foregoing; (c) a target site for MYLIP having the sequence set forth in any one of SEQ ID NOS:24-33 or 342-351, a contiguous portion thereof of at least 14 nucleotides (nt), or a complementary sequence of any of the foregoing; (d) a target site for ANGPTL3 having the sequence set forth in any one of SEQ ID NOS:34-43, a contiguous portion thereof of at least 14 nucleotides (nt), or a complementary sequence of any of the foregoing; (e) a target site for APOC3 having the sequence set forth in any one of SEQ ID NOS:44-53, a contiguous portion thereof of at least 14 nucleotides (nt), or a complementary sequence of any of the foregoing; and (f) a target site for APOB having the sequence set forth in any one of SEQ ID NOS:54-63 or 372-377, a contiguous portion thereof of at least 14 nucleotides (nt), or a complementary sequence of any of the foregoing. In some embodiments, the target site of PCSK9 is (i) set forth in SEQ ID NO:3, (ii) has a contiguous portion of SEQ ID NO:3 of at least 14 nucleotides, or (iii) is a complementary sequence of (i) or (ii). In some of any of the provided embodiments, the target site of the first gene and the second gene are selected from two different members of the group consisting of (a)-(f): (a) a target site of PCSK9 having the sequence set forth in any one of SEQ ID NOS:1-13 or 306-317; (b) a target site of LPA having the sequence set forth in any one of SEQ ID NOS:14-23; (c) a target site of MYLIP having the sequence set forth in any one of SEQ ID NOS:24-33 or 342-351; (d) a target site of ANGPTL3 having the sequence set forth in any one of SEQ ID NOS: 34-43; (e) a target site of APOC3 having the sequence set forth in any one of SEQ ID NOS:44-53; and (f) a target site of APOB having the sequence set forth in any one of SEQ ID NOS:54-63 or 372-377. In some embodiments, the target site of PCSK9 is set forth in SEQ ID NO:3. In some of any of the provided embodiments, the target site of the first gene, the second gene and the third gene are selected from three different members of the group consisting of (a)-(f): (a) a target site of PCSK9 having the sequence set forth in any one of SEQ ID NOS:1-13 or 306-317, a contiguous portion thereof of at least 14 nucleotides (nt), or a complementary sequence of any of the foregoing; (b) a target site of LPA having the sequence set forth in any one of SEQ ID NOS:14-23, a contiguous portion thereof of at least 14 nucleotides (nt), or a complementary sequence of any of the foregoing; (c) a target site of MYLIP having the sequence set forth in any one of SEQ ID NOS:24-33 or 342-351, a contiguous portion thereof of at least 14 nucleotides (nt), or a complementary sequence of any of the foregoing; (d) a target site of ANGPTL3 having the sequence set forth in any one of SEQ ID NOS:34-43, a contiguous portion thereof of at least 14 nucleotides (nt), or a complementary sequence of any of the foregoing; (e) a target site of APOC3 having the sequence set forth in any one of SEQ ID NOS:44-53, a contiguous portion thereof of at least 14 nucleotides (nt), or a complementary sequence of any of the foregoing; and (f) a target site of APOB having the sequence set forth in any one of SEQ ID NOS:54-63 or 372-377, a contiguous portion thereof of at least 14 nucleotides (nt), or a complementary sequence of any of the foregoing. In some embodiments, the target site of PCSK9 is (i) set forth in SEQ ID NO:3, (ii) has a contiguous portion of SEQ ID NO:3 of at least 14 nucleotides, or (iii) is a complementary sequence of (i) or (ii). In some of any of the provided embodiments, the target site of the first gene, the second gene or the third gene are selected from three different members of the group consisting of (a)-(f): (a) a target site of PCSK9 having the sequence set forth in any one of SEQ ID NOS:1-13 or 306-317; (b) a target site of LPA having the sequence set forth in any one of SEQ ID NOS:14-23; (c) a target site of MYLIP having the sequence set forth in any one of SEQ ID NOS:24-33 or 342-351; (d) a target site of ANGPTL3 having the sequence set forth in any one of SEQ ID NOS: 34-43; (e) a target site of APOC3 having the sequence set forth in any one of SEQ ID NOS:44-53; and (f) a target site of APOB having the sequence set forth in any one of SEQ ID NOS:54-63 or 372-377. In some embodiments, the target site of PCSK9 is set forth in SEQ ID NO:3.

In some of any of the provided embodiments, the Cas protein or variant thereof is a variant Cas protein that is a deactivated (dCas) protein. In some of any of the provided embodiments, the dCas protein lacks nuclease activity. In some of any of the provided embodiments, the dCas protein is a dCas9 protein. In some of any of the provided embodiments, the dCas protein is a dCas12 protein.

In some of any of the provided embodiments, the dCas9 protein is a *Staphylococcus aureus* dCas9 (dSaCas9) protein. In some of any of the provided embodiments, the dSaCas9 comprises at least one amino acid mutation selected from D10A and N580A, with reference to numbering of positions of SEQ ID NO:204. In some of any of the provided embodiments, the dSaCas9 protein comprises the sequence set forth in SEQ ID NO:205, or an amino acid sequence that has at least 90%, 91%, 92%, 93%, 94%, 95%, 96%, 97%, 98%, or 99% sequence identity thereto. In some of any of the provided embodiments, the dSaCas9 is set forth in SEQ ID NO:205.

In some of any of the provided embodiments, the dCas9 protein is a *Streptococcus pyogenes* dCas9 (dSpCas9) protein. In some of any of the provided embodiments, the dSpCas9 protein comprises at least one amino acid mutation selected from D10A and H840A, with reference to numbering of positions of SEQ ID NO:206. In some of any of the provided embodiments, the dSpCas9 comprises the sequence set forth in SEQ ID NO:207, or an amino acid sequence that has at least 90%, 91%, 92%, 93%, 94%, 95%, 96%, 97%, 98%, or 99% sequence identity thereto. In some of any of the provided embodiments, the dSpCas9 is set forth in SEQ ID NO:207.

In some of any of the provided embodiments, each gRNA comprises a gRNA spacer sequence that is complementary to the target site of the respective gene. In some of any of the provided embodiments, the first gRNA and the second gRNA are selected from two different members of the group consisting of (a)-(f): (a) a gRNA targeting a target site of PCSK9 comprising a gRNA spacer sequence comprising the sequence set forth in any one of SEQ ID NOS:64-76 or 318-329, or a contiguous portion thereof of at least 14 nt; (b) a gRNA targeting a target site of LPA comprising a gRNA spacer sequence comprising the sequence set forth in any one of SEQ ID NOS:77-86, or a contiguous portion thereof of at least 14 nt; (c) a gRNA targeting a target site of MYLIP comprising a gRNA spacer sequence comprising the sequence set forth in any one of SEQ ID NOS:87-96 or 352-361, or a contiguous portion thereof of at least 14 nt; (d) a gRNA targeting a target site of ANGPTL3 comprising a gRNA spacer sequence comprising the sequence set forth in any one of SEQ ID NOS:97-106, or a contiguous portion thereof of at least 14 nt; (e) a gRNA targeting a target site of APOC3 comprising a gRNA spacer sequence comprising the sequence set forth in any one of SEQ ID NOS:107-116, or a contiguous portion thereof of at least 14 nt; and (f) a gRNA targeting a target site of APOB comprising a gRNA spacer sequence comprising the sequence set forth in any one of SEQ ID NOS:117-126 or 378-383, or a contiguous portion thereof of at least 14 nt. In some embodiments, the gRNA spacer sequence targeting a target site of PCSK9 comprises the sequence set forth in SEQ ID NO:66 or a contiguous portion of at least 14 nt. In some of any of the provided embodiments, the first gRNA, the second gRNA, and the third gRNA are selected from three different members of the group consisting of (a)-(f): (a) a gRNA targeting a target site of PCSK9 comprising a gRNA spacer sequence comprising the sequence set forth in any one of SEQ ID NOS:64-76 or 318-329, or a contiguous portion thereof of at least 14 nt; (b)

a gRNA targeting a target site of LPA comprising a gRNA spacer sequence comprising the sequence set forth in any one of SEQ ID NOS:77-86, or a contiguous portion thereof of at least 14 nt; (c) a gRNA targeting a target site of MYLIP comprising a gRNA spacer sequence comprising the sequence set forth in any one of SEQ ID NOS:87-96 or 352-361, or a contiguous portion thereof of at least 14 nt; (d) a gRNA targeting a target site of ANGPTL3 comprising a gRNA spacer sequence comprising the sequence set forth in any one of SEQ ID NOS:97-106, or a contiguous portion thereof of at least 14 nt; (e) a gRNA targeting a target site of APOC3 comprising a gRNA spacer sequence comprising the sequence set forth in any one of SEQ ID NOS:107-116, or a contiguous portion thereof of at least 14 nt; and (f) a gRNA targeting a target site of APOB comprising a gRNA spacer sequence comprising the sequence set forth in any one of SEQ ID NOS:117-126 or 378-383, or a contiguous portion thereof of at least 14 nt. In some embodiments, the gRNA spacer sequence targeting a target site of PCSK9 comprises the sequence set forth in SEQ ID NO:66 or a contiguous portion of at least 14 nt. In some of any of the provided embodiments, each gRNA independently comprises a spacer sequence between 14 nt and 24 nt, or between 16 nt and 22 nt in length. In some of any of the provided embodiments, each gRNA independently comprises a spacer sequence that is 18 nt, 19 nt, 20 nt, 21 nt, or 22 nt in length. In some of any of the provided embodiments, the first gRNA and the second gRNA are selected from two different members of the group consisting of (a)-(f): (a) a gRNA targeting a target site of PCSK9 comprising the gRNA spacer sequence set forth in any one of SEQ ID NOS:64-76 or 318-329; (b) a gRNA targeting a target site in LPA comprising the gRNA spacer sequence set forth in any one of SEQ ID NOS:77-86; (c) a gRNA targeting a target site in MYLIP comprising the gRNA spacer sequence set forth in any one of SEQ ID NOS:87-96 or 352-361; (d) a gRNA targeting a target site in ANGPTL3 comprising the gRNA spacer sequence set forth in any one of SEQ ID NOS:97-106; (e) a gRNA targeting a target site in APOC3 comprising the gRNA spacer sequence set forth in any one of SEQ ID NOS:107-116; and (f) a gRNA targeting a target site in APOB comprising the gRNA spacer sequence set forth in any one of SEQ ID NOS:117-126 or 378-383. In some embodiments, the gRNA spacer sequence targeting a target site of PCSK9 comprises the sequence set forth in SEQ ID NO:66. In some of any of the provided embodiments, each gRNA further comprises a scaffold sequence set forth in SEQ ID NO:191. In some of any of the provided embodiments, the first gRNA and the second gRNA are selected from two different members of the group consisting of (a)-(f): (a) a gRNA targeting a target site in PCSK9 comprising the sequence set forth in any one of SEQ ID NOS:127-139 or 330-341; (b) a gRNA targeting a target site in LPA comprising the sequence set forth in any one of SEQ ID NOS:140-149; (c) a gRNA targeting a target site in MYLIP comprising the sequence set forth in any one of SEQ ID NOS:150-159 or 362-371; (d) a gRNA targeting a target site in ANGPTL3 comprising the sequence set forth in any one of SEQ ID NOS:160-169; (e) a gRNA targeting a target site in APOC3 comprising the sequence set forth in any one of SEQ ID NOS:170-179; and (f) a gRNA targeting a target site in APOB comprising the sequence set forth in any one of SEQ ID NOS:180-189 or 384-389. In some embodiments, the gRNA targeting a target site of PCSK9 comprises the sequence set forth in SEQ ID NO:129. In some of any of the provided embodiments, the first gRNA and the second gRNA are selected from two different members of the group consisting of (a)-(f): (a) a gRNA targeting a target site in PCSK9 set forth in any one of SEQ ID NOS:127-139 or 330-341; (b) a gRNA targeting a target site in LPA set forth in any one of SEQ ID NOS:140-149; (c) a gRNA targeting a target site in MYLIP set forth in any one of SEQ ID NOS:150-159 or 362-371; (d) a gRNA targeting a target site in ANGPTL3 set forth in any one of SEQ ID NOS:160-169; (e) a gRNA targeting a target site in APOC3 set forth in any one of SEQ ID NOS:170-179; and (f) a gRNA targeting a target site in APOB set forth in any one of SEQ ID NOS:180-189 or 384-389. In some embodiments, the gRNA targeting a target site of PCSK9 is set forth in SEQ ID NO:129. In some of any of the provided embodiments, the first gRNA, the second gRNA, and the third gRNA are selected from three different members of the group consisting of (a)-(f): (a) a gRNA targeting a target site in PCSK9 comprising the sequence set forth in any one of SEQ ID NOS:127-139 or 330-341; (b) a gRNA targeting a target site in LPA comprising the sequence set forth in any one of SEQ ID NOS:140-149; (c) a gRNA targeting a target site in MYLIP comprising the sequence set forth in any one of SEQ ID NOS:150-159 or 362-371; (d) a gRNA targeting a target site in ANGPTL3 comprising the sequence set forth in any one of SEQ ID NOS:160-169; (e) a gRNA targeting a target site in APOC3 comprising the sequence set forth in any one of SEQ ID NOS:170-179; and (f) a gRNA targeting a target site in APOB comprising the sequence set forth in any one of SEQ ID NOS:180-189 or 384-389. In some embodiments, the gRNA targeting a target site of PCSK9 comprises the sequence set forth in SEQ ID NO:129. In some of any of the provided embodiments, the first gRNA, the second gRNA, and the third gRNA are selected from three different members of the group consisting of (a)-(f): (a) a gRNA targeting a target site in PCSK9 set forth in any one of SEQ ID NOS:127-139 or 330-341; (b) a gRNA targeting a target site in LPA set forth in any one of SEQ ID NOS:140-149; (c) a gRNA targeting a target site in MYLIP set forth in any one of SEQ ID NOS:150-159 or 362-371; (d) a gRNA targeting a target site in ANGPTL3 set forth in any one of SEQ ID NOS:160-169; (e) a gRNA targeting a target site in APOC3 set forth in any one of SEQ ID NOS:170-179; and (f) a gRNA targeting a target site in APOB set forth in any one of SEQ ID NOS:180-189 or 384-389. In some embodiments, the gRNA targeting a target site of PCSK9 is set forth in SEQ ID NO:129. In some of any of the provided embodiments, at least one gRNA comprises modified nucleotides for increased stability.

In some of any of the provided embodiments, at least one transcriptional repressor domain is capable of reducing transcription of the gene. In some of any of the provided embodiments, the transcriptional repressor domain is selected from the group consisting of a KRAB domain, a DNMT3A domain, a DNMT3L domain, a DNMT3B domain, a DNMT3A-DNMT3L fusion protein domain, an ERF repressor domain, an Mxi1 repressor domain, a SID4X repressor domain, a Mad-SID repressor domain, an LSD1 repressor domain, an EZH2 repressor domain, a SunTag domain, or a variant or portion of any of the foregoing, or a combination of any of the foregoing. In some of any of the provided embodiments, the transcriptional repressor domain is a KRAB domain, a DNMT3A domain, or a DNMT3L domain, or a combination of any of the foregoing. In some of any of the provided embodiments, at least one transcriptional repressor domain comprises a sequence selected from any one of SEQ ID NOS:193, 195, 197, 199, 201, 220-226, 283, 284, 285, 286, 287, 289 and 290 or a domain thereof, a portion thereof, or an amino acid sequence that has at least 90%, 91%, 92%, 93%, 94%, 95%, 96%, 97%, 98%, or 99% sequence identity to any one of SEQ ID NOS:193, 195, 197, 199, 201, 220-226, 283, 284, 285, 286, 287, 289 and 290.

In some of any of the provided embodiments, the at least one transcriptional repressor domain comprises a KRAB domain or a variant or portion thereof that exhibits transcriptional repressor activity. In some of any of the provided embodiments, the at least one transcriptional repressor domain comprises the sequence set forth in SEQ ID NO:193, a portion thereof, or an amino acid sequence that has at least 90%, 91%, 92%, 93%, 94%, 95%, 96%, 97%, 98%, or 99% sequence identity to SEQ ID NO:193. In some of any of the provided embodiments, the at least one transcriptional repressor domain comprises the sequence set forth in SEQ ID NO:290, a portion thereof, or an amino acid sequence that has at least 90%, 91%, 92%, 93%, 94%, 95%, 96%, 97%, 98%, or 99% sequence identity to SEQ ID NO:290. In some of any above embodiments, the KRAB domain, portion or variant thereof is a sequence that exhibits transcriptional repressor activity.

In some of any of the provided embodiments, the at least one transcriptional repressor domain comprises a DNMT3A domain or a variant or portion thereof that exhibits transcriptional repressor activity. In some embodiments, the DNMT3A domain, or portion thereof, is from a human DNMT3A. In some of any of the provided embodiments, the at least one effector domain comprises the sequence set forth in SEQ ID NO:284, or is a portion thereof, or an amino acid sequence that has at least 90%, 91%, 92%, 93%, 94%, 95%, 96%, 97%, 98%, or 99% sequence identity to SEQ ID NO: 284. In some embodiments, the portion thereof is a catalytically active portion that exhibits transcription repressor activity. In some of any of the provided embodiments, the at least one transcriptional repressor domain comprises the sequence set forth in SEQ ID NO:195, a portion thereof, or an amino acid sequence that has at least 90%, 91%, 92%, 93%, 94%, 95%, 96%, 97%, 98%, or 99% sequence identity to SEQ ID NO: 195. In some embodiments, the at least one effector domain is or includes the catalytically active portion of DNMT3A set forth in SEQ ID NO: 195. In some of any of the provided embodiments, the at least one effector domain comprises the sequence set forth in SEQ ID NO:285, or is a portion thereof, or an amino acid sequence that has at least 90%, 91%, 92%, 93%, 94%, 95%, 96%, 97%, 98%, or 99% sequence identity to SEQ ID NO: 285. In some embodiments, the at least one effector domain is or includes the catalytically active portion of DNMT3A set forth in SEQ ID NO: 285.

In some of any of the provided embodiments, the at least one transcriptional repressor domain comprises a DNMT3L domain or a variant or portion thereof that exhibits transcriptional repressor activity. In some of any of the provided embodiments, the at least one transcriptional repressor domain is a fusion domain comprising a DNMT3A domain, such as any DNMT3A domain or C-terminal portion or variant described above, and a DNMT3L domain or a variant or portion thereof, in which the fusion domain exhibits transcriptional repressor activity. In some embodiments, DNMT3L domain, or the variant or C-terminal portion of a DNMT3L domain, is one that stimulates enhanced transcription repressor activity of DNMT3A. In some embodiments, DNMT3L domain, or the variant or C-terminal portion of a DNMT3L domain, is one that interacts with DNMT3A. In some embodiments, the DNMT3L domain, or C-terminal portion thereof, is from a murine DNMT3L. In some embodiments, the DNMT3L domain, or C-terminal portion thereof, is a human or humanized DNMT3L. In some of any of the provided embodiments, the DNTML domain comprises the sequence set forth in SEQ ID NO:289, a C-terminal portion thereof, or an amino acid sequence that has at least 90%, 91%, 92%, 93%, 94%, 95%, 96%, 97%, 98%, or 99% sequence identity to SEQ ID NO: 289. In some of any of the provided embodiments, the DNMT3L comprises the sequence set forth in SEQ ID NO:286, or an amino acid sequence that has at least 90%, 91%, 92%, 93%, 94%, 95%, 96%, 97%, 98%, or 99% sequence identity to SEQ ID NO: 286. In some embodiments, the DNMT3L domain is or includes the C-terminal portion of DNMT3L set forth in SEQ ID NO: 286. In some of any of the provided embodiments, the DNMT3L domain comprises the sequence set forth in SEQ ID NO:197, a C-terminal portion thereof, or an amino acid sequence that has at least 90%, 91%, 92%, 93%, 94%, 95%, 96%, 97%, 98%, or 99% sequence identity to SEQ ID NO: 197. In some of any of the provided embodiments, the DNMT3L comprises the sequence set forth in SEQ ID NO:287, or an amino acid sequence that has at least 90%, 91%, 92%, 93%, 94%, 95%, 96%, 97%, 98%, or 99% sequence identity to SEQ ID NO: 287. In some embodiments, the DNMT3L domain is or includes the C-terminal portion of DNMT3L set forth in SEQ ID NO: 287.

In some of any of the provided embodiments, the at least one transcriptional repressor domain is a DNMT3A-DNMT3L fusion protein domain or a variant thereof that exhibits transcriptional repressor activity. In some embodiments, the DNMT3A domain is set forth in SEQ ID NO:285 and the DNMT3L domain is set forth in SEQ ID NO: 286, which can be present in any order. In some embodiments, a linker is present between the DNMT3A domain and the DNMT3L domain. In some of any of the provided embodiments, the at least one transcriptional repressor domain comprises the sequence set forth in SEQ ID NO:199 or SEQ ID NO:201, a portion thereof, or an amino acid sequence that has at least 90%, 91%, 92%, 93%, 94%, 95%, 96%, 97%, 98%, or 99% sequence identity to SEQ ID NO: 199 or SEQ ID NO: 201.

In some of any of the provided embodiments, the at least one transcriptional repressor domain is fused to the N-terminus, the C-terminus, or both the N-terminus and the C-terminus, of the DNA-binding domain. In some of any of the provided embodiments, the fusion protein further comprises one or more nuclear localization signals (NLS). In some of any of the provided embodiments, the fusion protein further comprises one or more linkers connecting two or more of: the DNA-binding domain, the at least one transcriptional repressor domain, and the one or more nuclear localization signals.

In some embodiments, the fusion protein is a dCas9-KRAB or a variant thereof.

In some of any of the provided embodiments, the fusion protein comprises the sequence set forth in any one of SEQ ID NOS:209, or an amino acid sequence that has at least 90%, 91%, 92%, 93%, 94%, 95%, 96%, 97%, 98%, or 99% sequence identity to SEQ ID NO: 209. In some embodiments, the fusion protein has the sequence set forth in SEQ ID NO: 209.

In any of the embodiments herein, the fusion protein is a DNMT3A/3L-dCas9-KRAB domain or a variant thereof.

In any of the embodiments herein, the fusion protein comprises the sequence set forth in any one of SEQ ID NOs: 278, 280, or 282, or an amino acid sequence that has at least 90%, 91%, 92%, 93%, 94%, 95%, 96%, 97%, 98%, or 99% sequence identity to any one of SEQ ID NOS: 278, 280, or 282. In some embodiments, the fusion protein comprises the sequence set forth in SEQ ID NO:280. In some embodiments, the fusion protein has the sequence set forth in SEQ ID NO: 278. In some embodiments, the fusion protein has the sequence set forth in SEQ ID NO: 280. In some embodiments, the fusion protein has the sequence set forth in SEQ ID NO: 282.

In some of any of the provided embodiments, each of the DNA-targeting modules reduces expression of each of the respective genes by a log 2 fold-change of at or lesser than −1.0.

In some of any of the provided embodiments, repressed transcription of the plurality of genes in a cell or population of cells leads to a reduction of low-density lipoprotein (LDL). In some of any of the provided embodiments, the reduction of LDL is greater than the reduction of LDL resulting from comparable repressed transcription of any of the individual genes in the plurality of genes alone. In some of any of the provided embodiments, the reduction of LDL occurs extracellularly. In some of any of the provided embodiments, the cell or population of cells is a liver cell or comprises liver cells. In some of any of the provided embodiments, the cell or population of cells is in a subject. In some of any of the provided embodiments, the reduction of LDL occurs in the subject or a fluid, tissue, or organ thereof. In some of any of the provided embodiments, the reduction of LDL occurs in the blood of a subject.

In some aspects, provided herein is an epigenetic-modifying DNA-targeting system for repressing transcription of a gene that regulates low-density lipoprotein, comprising a fusion protein comprising: (a) a DNA-binding domain for targeting to a target site of a gene, and (b) at least one transcriptional repressor domain. In some of any of the provided embodiments, the target site of the gene is in the gene or a regulatory DNA element thereof. In some of any of the provided embodiments, the DNA-targeting system does not introduce a genetic disruption or a DNA break. In some of any of the provided embodiments, the DNA-binding domain is selected from: a Clustered Regularly Interspaced Short Palindromic Repeats associated (Cas) protein or a variant thereof; a zinc finger protein (ZFP); a transcription activator-like effector (TALE); a meganuclease; a homing endonuclease; or an I-SceI enzyme or a variant thereof, optionally wherein the DNA-binding domain comprises a catalytically inactive variant of any of the foregoing. In some of any of the provided embodiments, the DNA-binding domain is a Clustered Regularly Interspaced Short Palindromic Repeats associated (Cas) protein or variant thereof, and the system further comprises a gRNA for targeting the DNA-binding domain to the target site of the gene.

In some aspects, provided herein is an epigenetic-modifying DNA-targeting system comprising: (a) a fusion protein comprising a Clustered Regularly Interspaced Short Palindromic Repeats associated (Cas) protein or variant thereof and at least one transcriptional repressor domain; and (b) a gRNA that targets a target site of a gene that regulates low-density lipoprotein (LDL).

In some of any of the provided embodiments, the target site of the gene is in the gene and/or a regulatory DNA element thereof. In some of any of the provided embodiments, the regulatory DNA element is a promoter or enhancer. In some of any of the provided embodiments, the gene is selected from the group consisting of: PCSK9, LPA, MYLIP, ANGPTL3, APOB, and APOC3. In some of any of the provided embodiments, the target site is selected from: (a) a target site for PCSK9, located within 500 bp of human genome assembly GRCh38 (hg38) genomic coordinates chr1:55,039,548; (b) a target site for LPA, located within 500 bp of the hg38 genomic coordinates chr6:160,664,275; (c) a target site for MYLIP, located within 500 bp of the hg38 genomic coordinates chr6:16,129,086; (d) a target site for ANGPTL3, located within 500 bp of the hg38 genomic coordinates chr1:62,597,520; (e) a target site for APOC3, located within 500 bp of the hg38 genomic coordinates chr11:116,829,907; and (f) a target site for APOB, located within 500 bp of the hg38 genomic coordinates chr2:21,044,073. In some of any of the provided embodiments, the target site is selected from: (a) a target site located within 500 bp of a transcriptional start site of PCSK9; (b) a target site located within 500 bp of a transcriptional start site of LPA; (c) a target site located within 500 bp of a transcriptional start site of MYLIP; (d) a target site located within 500 bp of a transcriptional start site of ANGPTL3; (e) a target site located within 500 bp of a transcriptional start site of APOC3; and (f) a target site located within 500 bp of a transcriptional start site of APOB. In some of any of the provided embodiments, the target site is selected from: (a) a target site for PCSK9 having the sequence set forth in any one of SEQ ID NOS:1-13 or 306-317, a contiguous portion thereof of at least 14 nucleotides (nt), or a complementary sequence of any of the foregoing; (b) a target site for LPA having the sequence set forth in any one of SEQ ID NOS:14-23, a contiguous portion thereof of at least 14 nucleotides (nt), or a complementary sequence of any of the foregoing; (c) a target site for MYLIP having the sequence set forth in any one of SEQ ID NOS:24-33 or 342-351, a contiguous portion thereof of at least 14 nucleotides (nt), or a complementary sequence of any of the foregoing; (d) a target site for ANGPTL3 having the sequence set forth in any one of SEQ ID NOS:34-43, a contiguous portion thereof of at least 14 nucleotides (nt), or a complementary sequence of any of the foregoing; (e) a target site for APOC3 having the sequence set forth in any one of SEQ ID NOS:44-53, a contiguous portion thereof of at least 14 nucleotides (nt), or a complementary sequence of any of the foregoing; and (f) a target site for APOB having the sequence set forth in any one of SEQ ID NOS:54-63 or 372-377, a contiguous portion thereof of at least 14 nucleotides (nt), or a complementary sequence of any of the foregoing. In some embodiments, the target site for PCSK9 has (i) the sequence set forth in SEQ ID NO:3, (ii) a contiguous portion of at least 14 nucleotides set forth in SEQ ID NO:3, or (iii) a complementary sequence of (i) or (ii). In some of any of the provided embodiments, the target site is selected from: (a) a target site of PCSK9 having the sequence set forth in any one of SEQ ID NOS:1-13 or 306-317; (b) a target site of LPA having the sequence set forth in any one of SEQ ID NOS:14-23; (c) a target site of MYLIP having the sequence set forth in any one of SEQ ID NOS:24-33 or 342-351; (d) a target site of ANGPTL3 having the sequence set forth in any one of SEQ ID NOS: 34-43; (e) a target site of APOC3 having the sequence set forth in any one of SEQ ID NOS:44-53; and (f) a target site of APOB having the sequence set forth in any one of SEQ ID NOS:54-63 or 372-377. In some embodiments, the target site for PCSK9 has the sequence set forth in SEQ ID NO:3.

In some of any of the provided embodiments, the Cas protein or variant thereof is a variant Cas protein that is a deactivated (dCas) protein. In some of any of the provided embodiments, the dCas protein lacks nuclease activity. In some of any of the provided embodiments, the dCas protein is a dCas9 protein. In some of any of the provided embodiments, the dCas protein is a dCas12 protein. In some of any of the provided embodiments, the dCas9 protein is a *Staphylococcus aureus* dCas9 (dSaCas9) protein. In some of any of the provided embodiments, the dSaCas9 comprises at least one amino acid mutation selected from D10A and N580A, with reference to numbering of positions of SEQ ID NO:204. In some of any of the provided embodiments, the dSaCas9 protein comprises the sequence set forth in SEQ ID NO:205, or an amino acid sequence that has at least 90%, 91%, 92%, 93%, 94%, 95%, 96%, 97%, 98%, or 99% sequence identity thereto. In some of any of the provided embodiments, the dSaCas9 is set forth in SEQ ID NO:205. In some of any of the provided embodiments, the dCas9 protein is a *Streptococcus pyogenes* dCas9 (dSpCas9) protein. In some of any of the provided embodiments, the dSpCas9 protein comprises at least one amino acid mutation selected from D10A and H840A, with reference to numbering of positions of SEQ ID NO:206. In some of any of the provided embodiments, the dSpCas9 comprises the sequence set forth in SEQ ID NO:207, or an amino acid sequence that has at least 90%, 91%, 92%, 93%, 94%, 95%, 96%, 97%, 98%, or 99% sequence identity thereto. In some of any of the provided embodiments, the dSpCas9 is set forth in SEQ ID NO:207.

In some of any of the provided embodiments, the gRNA comprises a gRNA spacer that is complementary to the target site of the gene. In some of any of the provided embodiments, the gRNA is selected from: (a) a gRNA targeting a target site of PCSK9 comprising a gRNA spacer sequence comprising the sequence set forth in any one of SEQ ID NOS:64-76 or 318-329, or a contiguous portion thereof of at least 14 nt; (b) a gRNA targeting a target site of LPA comprising a gRNA spacer sequence comprising the sequence set forth in any one of SEQ ID NOS:77-86, or a contiguous portion thereof of at least 14 nt; (c) a gRNA targeting a target site of MYLIP comprising a gRNA spacer sequence comprising the sequence set forth in any one of SEQ ID NOS:87-96 or 352-361, or a contiguous portion thereof of at least 14 nt; (d) a gRNA targeting a target site of ANGPTL3 comprising a gRNA spacer sequence comprising the sequence set forth in any one of SEQ ID NOS:97-106, or a contiguous portion thereof of at least 14 nt; (e) a gRNA targeting a target site of APOC3 comprising a gRNA spacer sequence comprising the sequence set forth in any one of SEQ ID NOS:107-116, or a contiguous portion thereof of at least 14 nt; and (f) a gRNA targeting a target site of APOB comprising a gRNA spacer sequence comprising the sequence set forth in any one of SEQ ID NOS:117-126 or 378-383, or a contiguous portion thereof of at least 14 nt. In some embodiments, the gRNA targeting a target site of PCSK9 comprises a gRNA spacer sequence set forth in SEQ ID NO:66 or a contiguous portion thereof of at least 14 nt.

In some of any of the provided embodiments, the gRNA comprises a spacer sequence between 14 nt and 24 nt, or between 16 nt and 22 nt in length. In some of any of the provided embodiments, the gRNA comprises a spacer sequence that is 18 nt, 19 nt, 20 nt, 21 nt, or 22 nt in length. In some of any of the provided embodiments, the gRNA is selected from: (a) a gRNA targeting a target site of PCSK9 comprising the gRNA spacer sequence set forth in any one of SEQ ID NOS:64-76 or 318-329; (b) a gRNA targeting a target site in LPA comprising the gRNA spacer sequence set forth in any one of SEQ ID NOS:77-86; (c) a gRNA targeting a target site in MYLIP comprising the gRNA spacer sequence set forth in any one of SEQ ID NOS:87-96 or 352-361; (d) a gRNA targeting a target site in ANGPTL3 comprising the gRNA spacer sequence set forth in any one of SEQ ID NOS:97-106; (e) a gRNA targeting a target site in APOC3 comprising the gRNA spacer sequence set forth in any one of SEQ ID NOS:107-116; and (f) a gRNA targeting a target site in APOB comprising the gRNA spacer sequence set forth in any one of SEQ ID NOS:117-126 or 378-383. In some embodiments, the gRNA targeting a target site of PCSK9 comprises a gRNA spacer sequence set forth in SEQ ID NO:66. In some of any of the provided embodiments, the gRNA further comprises a scaffold sequence set forth in SEQ ID NO:191. In some of any of the provided embodiments, the gRNA is selected from: (a) a gRNA targeting a target site in PCSK9 comprising the sequence set forth in any one of SEQ ID NOS:127-139 or 330-341; (b) a gRNA targeting a target site in LPA comprising the sequence set forth in any one of SEQ ID NOS:140-149; (c) a gRNA targeting a target site in MYLIP comprising the sequence set forth in any one of SEQ ID NOS:150-159 or 362-371; (d) a gRNA targeting a target site in ANGPTL3 comprising the sequence set forth in any one of SEQ ID NOS:160-169; (e) a gRNA targeting a target site in APOC3 comprising the sequence set forth in any one of SEQ ID NOS:170-179; and (f) a gRNA targeting a target site in APOB comprising the sequence set forth in any one of SEQ ID NOS:180-189 or 384-389. In some embodiments, the gRNA targeting a target site of PCSK9 comprises the sequence set forth in SEQ ID NO:129. In some of any of the provided embodiments, the gRNA is selected from: (a) a gRNA targeting a target site in PCSK9 set forth in any one of SEQ ID NOS:127-139 or 330-341; (b) a gRNA targeting a target site in LPA set forth in any one of SEQ ID NOS:140-149; (c) a gRNA targeting a target site in MYLIP set forth in any one of SEQ ID NOS:150-159 or 362-371; (d) a gRNA targeting a target site in ANGPTL3 set forth in any one of SEQ ID NOS:160-169; (e) a gRNA targeting a target site in APOC3 set forth in any one of SEQ ID NOS:170-179; and (f) a gRNA targeting a target site in APOB set forth in any one of SEQ ID NOS:180-189 or 384-389. In some embodiments, the gRNA targeting a target site of PCSK9 is set forth in SEQ ID NO:129. In some of any of the provided embodiments, the gRNA comprises modified nucleotides for increased stability.

In some of any of the provided embodiments, the at least one transcriptional repressor domain is capable of reducing transcription of the gene. In some of any of the provided embodiments, the transcriptional repressor domain is selected from the group consisting of a KRAB domain, a DNMT3A domain, a DNMT3L domain, a DNMT3B domain, a DNMT3A-DNMT3L fusion protein domain, an ERF repressor domain, an Mxi1 repressor domain, a SID4X repressor domain, a Mad-SID repressor domain, an LSD1 repressor domain, an EZH2 repressor domain, a SunTag domain, or a variant or portion of any of the foregoing, or a combination of any of the foregoing. In some of any of the provided embodiments, the transcriptional repressor domain is a KRAB domain, a DNMT3A domain, or a DNMT3L domain, or a combination of any of the foregoing. In some of any of the provided embodiments, at least one transcriptional repressor domain comprises a sequence selected from any one of SEQ ID NOS:193, 195, 197, 199, 201, 220-226, 283, 284, 285, 286, 287, 289 and 290 or a domain thereof, a portion thereof, or an amino acid sequence that has at least 90%, 91%, 92%, 93%, 94%, 95%, 96%, 97%, 98%, or 99% sequence identity to any one of SEQ ID NOS:193, 195, 197, 199, 201, 220-226, 283, 284, 285, 286, 287, 289 and 290.

In some of any of the provided embodiments, the at least one transcriptional repressor domain comprises a KRAB domain or a variant or portion thereof that exhibits transcriptional repressor activity. In some of any of the provided embodiments, the at least one transcriptional repressor domain comprises the sequence set forth in SEQ ID NO:193, a portion thereof, or an amino acid sequence that has at least 90%, 91%, 92%, 93%, 94%, 95%, 96%, 97%, 98%, or 99% sequence identity to SEQ ID NO: 193. In some of any of the provided embodiments, the at least one transcriptional repressor domain comprises the sequence set forth in SEQ ID NO:290, a portion thereof, or an amino acid sequence that has at least 90%, 91%, 92%, 93%, 94%, 95%, 96%, 97%, 98%, or 99% sequence identity to SEQ ID NO:290. In some of any above embodiments, the KRAB domain, portion or variant thereof is a sequence that exhibits transcriptional repressor activity.

In some of any of the provided embodiments, the at least one transcriptional repressor domain comprises a DNMT3A domain or a variant or portion thereof that exhibits transcriptional repressor activity. In some embodiments, the DNMT3A domain, or portion thereof, is from a human DNMT3A. In some of any of the provided embodiments, the at least one effector domain comprises the sequence set forth in SEQ ID NO:284, or is a portion thereof, or an amino acid sequence that has at least 90%, 91%, 92%, 93%, 94%, 95%, 96%, 97%, 98%, or 99% sequence identity to SEQ ID NO: 284. In some embodiments, the portion thereof is a catalytically active portion that exhibits transcription repressor activity. In some of any of the provided embodiments, the at least one transcriptional repressor domain comprises the sequence set forth in SEQ ID NO:195, a portion thereof, or an amino acid sequence that has at least 90%, 91%, 92%, 93%, 94%, 95%, 96%, 97%, 98%, or 99% sequence identity to SEQ ID NO: 195. In some embodiments, the at least one effector domain is or includes the catalytically active portion of DNMT3A set forth in SEQ ID NO: 195. In some of any of the provided embodiments, the at least one effector domain comprises the sequence set forth in SEQ ID NO:285, or is a portion thereof, or an amino acid sequence that has at least 90%, 91%, 92%, 93%, 94%, 95%, 96%, 97%, 98%, or 99% sequence identity to SEQ ID NO: 285. In some embodiments, the at least one effector domain is or includes the catalytically active portion of DNMT3A set forth in SEQ ID NO: 285.

In some of any of the provided embodiments, the at least one transcriptional repressor domain comprises a DNMT3L domain or a variant or portion thereof that exhibits transcriptional repressor activity. In some of any of the provided embodiments, the at least one transcriptional repressor domain is a fusion domain comprising a DNMT3A domain, such as any DNMT3A domain or C-terminal portion or variant described above, and a DNMT3L domain or a variant or portion thereof, in which the fusion domain exhibits transcriptional repressor activity. In some embodiments, DNMT3L domain, or the variant or C-terminal portion of a DNMT3L domain, is one that stimulates enhanced transcription repressor activity of DNMT3A. In some embodiments, DNMT3L domain, or the variant or C-terminal portion of a DNMT3L domain, is one that interacts with DNMT3A. In some embodiments, the DNMT3L domain, or C-terminal portion thereof, is from a murine DNMT3L. In some embodiments, the DNMT3L domain, or C-terminal portion thereof, is a human or humanized DNMT3L. In some of any of the provided embodiments, the DNTML domain comprises the sequence set forth in SEQ ID NO:289, a C-terminal portion thereof, or an amino acid sequence that has at least 90%, 91%, 92%, 93%, 94%, 95%, 96%, 97%, 98%, or 99% sequence identity to SEQ ID NO: 289. In some of any of the provided embodiments, the DNMT3L comprises the sequence set forth in SEQ ID NO:286, or an amino acid sequence that has at least 90%, 91%, 92%, 93%, 94%, 95%, 96%, 97%, 98%, or 99% sequence identity to SEQ ID NO: 286. In some embodiments, the DNMT3L domain is or includes the C-terminal portion of DNMT3L set forth in SEQ ID NO: 286. In some of any of the provided embodiments, the DNMT3L domain comprises the sequence set forth in SEQ ID NO:197, a C-terminal portion thereof, or an amino acid sequence that has at least 90%, 91%, 92%, 93%, 94%, 95%, 96%, 97%, 98%, or 99% sequence identity to SEQ ID NO: 197. In some of any of the provided embodiments, the DNMT3L comprises the sequence set forth in SEQ ID NO:287, or an amino acid sequence that has at least 90%, 91%, 92%, 93%, 94%, 95%, 96%, 97%, 98%, or 99% sequence identity to SEQ ID NO: 287. In some embodiments, the DNMT3L domain is or includes the C-terminal portion of DNMT3L set forth in SEQ ID NO: 287.

In some of any of the provided embodiments, the at least one transcriptional repressor domain is a DNMT3A-DNMT3L fusion protein domain or a variant thereof that exhibits transcriptional repressor activity. In some embodiments, the DNMT3A domain is set forth in SEQ ID NO:285 and the DNMT3L domain is set forth in SEQ ID NO: 286, which can be present in any order. In some embodiments, a linker is present between the DNMT3A domain and the DNMT3L domain. In some of any of the provided embodiments, the at least one transcriptional repressor domain comprises the sequence set forth in SEQ ID NO:199 or SEQ ID NO:201, a portion thereof, or an amino acid sequence that has at least 90%, 91%, 92%, 93%, 94%, 95%, 96%, 97%, 98%, or 99% sequence identity to SEQ ID NO: 199 or SEQ ID NO: 201.

In some of any of the provided embodiments, the at least one transcriptional repressor domain is fused to the N-terminus, the C-terminus, or both the N-terminus and the C-terminus, of the DNA-binding domain. In some of any of the provided embodiments, the fusion protein further comprises one or more nuclear localization signals (NLS). In some of any of the provided embodiments, the fusion protein further comprises one or more linkers connecting two or more of: the DNA-binding domain, the at least one transcriptional repressor domain, and the one or more nuclear localization signals.

In some embodiments, the fusion protein is a dCas9-KRAB or a variant thereof.

In some of any of the provided embodiments, the fusion protein comprises the sequence set forth in any one of SEQ ID NOS:209, or an amino acid sequence that has at least 90%, 91%, 92%, 93%, 94%, 95%, 96%, 97%, 98%, or 99% sequence identity to SEQ ID NO: 209. In some embodiments, the fusion protein has the sequence set forth in SEQ ID NO: 209.

In any of the embodiments herein, the fusion protein is a DNMT3A/3L-dCas9-KRAB domain or a variant thereof.

In any of the embodiments herein, the fusion protein comprises the sequence set forth in any one of SEQ ID NOs: 278, 280, or 282, or an amino acid sequence that has at least 90%, 91%, 92%, 93%, 94%, 95%, 96%, 97%, 98%, or 99% sequence identity to any one of SEQ ID NOS: 278, 280, or 282. In some embodiments, the fusion protein has the sequence set forth in SEQ ID NO: 278. In some embodiments, the fusion protein has the sequence set forth in SEQ ID NO: 280. In some embodiments, the fusion protein has the sequence set forth in SEQ ID NO: 282.

In any of the embodiments herein, the fusion protein comprises the sequence set forth in SEQ ID NO: 280, or an amino acid sequence that has at least 90%, 91%, 92%, 93%, 94%, 95%, 96%, 97%, 98%, or 99% sequence identity to SEQ ID NO: 280 and a gRNA that targets a target site of PCSK9 comprising the spacer sequence set forth in SEQ ID NO:66. In some embodiments, the gRNA has the sequence set forth in SEQ ID NO: 129.

In some of any of the provided embodiments, the epigenetic-modifying DNA-targeting system reduces expression of a gene by a log 2 fold-change of at or lesser than −1.0. In some of any of the provided embodiments, repressed transcription of the gene in a cell or population of cells leads to a reduction of low-density lipoprotein (LDL). In some of any of the provided embodiments, the reduction of LDL occurs extracellularly. In some of any of the provided embodiments, the cell or population of cells is a liver cell or comprises liver cells. In some of any of the provided embodiments, the cell or population of cells is in a subject. In some of any of the provided embodiments, the reduction of LDL occurs in the subject or a fluid, tissue, or organ thereof. In some of any of the provided embodiments, the reduction of LDL occurs in the blood of a subject.

In some aspects, provided herein is a combination of epigenetic-modifying DNA-targeting systems comprising at least two of the DNA-targeting systems provided herein, wherein each DNA-targeting system represses transcription of a different gene. In some of any of the provided embodiments, each DNA-targeting system represses transcription of a different gene.

In some aspects, provided herein is a guide RNA (gRNA) that targets a target site of a gene that regulates low-density lipoprotein (LDL). In some of any of the provided embodiments, the gene is selected from the group consisting of PCSK9, LPA, MYLIP, ANGPTL3, APOB, and APOC3. In some of any of the provided embodiments, the target site of the gene is in the gene or a regulatory DNA element thereof. In some of any of the provided embodiments, the regulatory DNA element is an enhancer or a promoter. In some of any of the provided embodiments, the target site is selected from the group consisting of: (a) a target site for PCSK9, located within 500 bp of human genome assembly GRCh38 (hg38) genomic coordinates chr1:55,039,548; (b) a target site for LPA, located within 500 bp of the hg38 genomic coordinates chr6:160,664,275; (c) a target site for MYLIP, located within 500 bp of the hg38 genomic coordinates chr6:16,129,086; (d) a target site for ANGPTL3, located within 500 bp of the hg38 genomic coordinates chr1:62,597,520; (e) a target site for APOC3, located within 500 bp of the hg38 genomic coordinates chr11:116,829,907; and (f) a target site for APOB, located within 500 bp of the hg38 genomic coordinates chr2:21,044,073. In some of any of the provided embodiments, the target site is selected from the group consisting of: (a) a target site located within 500 bp of a transcriptional start site of PCSK9; (b) a target site located within 500 bp of a transcriptional start site of LPA; (c) a target site located within 500 bp of a transcriptional start site of MYLIP; (d) a target site located within 500 bp of a transcriptional start site of ANGPTL3; (e) a target site located within 500 bp of a transcriptional start site of APOC3; and (f) a target site located within 500 bp of a transcriptional start site of APOB. In some of any of the provided embodiments, the target site is selected from: (a) a target site for PCSK9 having the sequence set forth in any one of SEQ ID NOS:1-13 or 306-317, a contiguous portion thereof of at least 14 nucleotides (nt), or a complementary sequence of any of the foregoing; (b) a target site for LPA having the sequence set forth in any one of SEQ ID NOS:14-23, a contiguous portion thereof of at least 14 nucleotides (nt), or a complementary sequence of any of the foregoing; (c) a target site for MYLIP having the sequence set forth in any one of SEQ ID NOS:24-33 or 342-351, a contiguous portion thereof of at least 14 nucleotides (nt), or a complementary sequence of any of the foregoing; (d) a target site for ANGPTL3 having the sequence set forth in any one of SEQ ID NOS:34-43, a contiguous portion thereof of at least 14 nucleotides (nt), or a complementary sequence of any of the foregoing; (e) a target site for APOC3 having the sequence set forth in any one of SEQ ID NOS:44-53, a contiguous portion thereof of at least 14 nucleotides (nt), or a complementary sequence of any of the foregoing; and (f) a target site for APOB having the sequence set forth in any one of SEQ ID NOS:54-63 or 372-377, a contiguous portion thereof of at least 14 nucleotides (nt), or a complementary sequence of any of the foregoing. In some embodiments, the target site has (i) the sequence set forth in SEQ ID NO: 3, (ii) a contiguous portion of SEQ ID NO:3 of at least 14 nt, or (iii) a complementary sequence of (i) or (ii). In some of any of the provided embodiments, the target site is selected from: (a) a target site of PCSK9 having the sequence set forth in any one of SEQ ID NOS:1-13 or 306-317; (b) a target site of LPA having the sequence set forth in any one of SEQ ID NOS:14-23; (c) a target site of MYLIP having the sequence set forth in any one of SEQ ID NOS:24-33 or 342-351; (d) a target site of ANGPTL3 having the sequence set forth in any one of SEQ ID NOS: 34-43; (e) a target site of APOC3 having the sequence set forth in any one of SEQ ID NOS:44-53; and (f) a target site of APOB having the sequence set forth in any one of SEQ ID NOS:54-63 or 372-377. In some embodiments, the target site has the sequence set forth in SEQ ID NO: 3. In some of any of the provided embodiments, the gRNA is selected from: (a) a gRNA targeting a target site of PCSK9 comprising a gRNA spacer sequence comprising the sequence set forth in any one of SEQ ID NOS:64-76 or 318-329, or a contiguous portion thereof of at least 14 nt; (b) a gRNA targeting a target site of LPA comprising a gRNA spacer sequence comprising the sequence set forth in any one of SEQ ID NOS:77-86, or a contiguous portion thereof of at least 14 nt; (c) a gRNA targeting a target site of MYLIP comprising a gRNA spacer sequence comprising the sequence set forth in any one of SEQ ID NOS:87-96 or 352-361, or a contiguous portion thereof of at least 14 nt; (d) a gRNA targeting a target site of ANGPTL3 comprising a gRNA spacer sequence comprising the sequence set forth in any one of SEQ ID NOS:97-106, or a contiguous portion thereof of at least 14 nt; (e) a gRNA targeting a target site of APOC3 comprising a gRNA spacer sequence comprising the sequence set forth in any one of SEQ ID NOS:107-116, or a contiguous portion thereof of at least 14 nt; and (f) a gRNA targeting a target site of APOB comprising a gRNA spacer sequence comprising the sequence set forth in any one of SEQ ID NOS:117-126 or 378-383, or a contiguous portion thereof of at least 14 nt. In some embodiments, the gRNA targeting a target site of PCSK9 comprises a gRNA spacer sequence comprising the sequence set forth in SEQ ID NO: 66 or a continuous portion thereof of at least 14 nt. In some of any of the provided embodiments, the gRNA comprises a spacer sequence between 14 nt and 24 nt, or between 16 nt and 22 nt in length. In some of any of the provided embodiments, the gRNA comprises a spacer sequence that is 18 nt, 19 nt, 20 nt, 21 nt, or 22 nt in length. In some of any of the provided embodiments, the gRNA is selected from: (a) a gRNA targeting a target site of PCSK9 comprising the gRNA spacer sequence set forth in any one of SEQ ID NOS:64-76 or 318-329; (b) a gRNA targeting a target site in LPA comprising the gRNA spacer sequence set forth in any one of SEQ ID NOS:77-86; (c) a gRNA targeting a target site in MYLIP comprising the gRNA spacer sequence set forth in any one of SEQ ID NOS:87-96 or 352-361; (d) a gRNA targeting a target site in ANGPTL3 comprising the gRNA spacer sequence set forth in any one of SEQ ID NOS:97-106; (e) a gRNA targeting a target site in APOC3 comprising the gRNA spacer sequence set forth in any one of SEQ ID NOS:107-116; and (f) a gRNA targeting a target site in APOB comprising the gRNA spacer sequence set forth in any one of SEQ ID NOS:117-126 or 378-383. In some embodiments, the gRNA targeting a target site of PCSK9 comprises a gRNA spacer sequence set forth in SEQ ID NO: 66. In some of any of the provided embodiments, the gRNA further comprises a scaffold sequence set forth in SEQ ID NO:191. In some of any of the provided embodiments, the gRNA is selected from: (a) a gRNA targeting a target site in PCSK9 comprising the sequence set forth in any one of SEQ ID NOS:127-139 or 330-341; (b) a gRNA targeting a target site in LPA comprising the sequence set forth in any one of SEQ ID NOS:140-149; (c) a gRNA targeting a target site in MYLIP comprising the sequence set forth in any one of SEQ ID NOS:150-159 or 362-371; (d) a gRNA targeting a target site in ANGPTL3 comprising the sequence set forth in any one of SEQ ID NOS:160-169; (e) a gRNA targeting a target site in APOC3 comprising the sequence set forth in any one of SEQ ID NOS:170-179; or (f) a gRNA targeting a target site in APOB comprising the sequence set forth in any one of SEQ ID NOS:180-189 or 384-389. In some embodiments, the gRNA targeting a target site in PCSK9 comprises the sequence set forth in SEQ ID NO: 129. In some of any of the provided embodiments, the gRNA is selected from: (a) a gRNA targeting a target site in PCSK9 set forth in any one of SEQ ID NOS:127-139 or 330-341; (b) a gRNA targeting a target site in LPA set forth in any one of SEQ ID NOS:140-149; (c) a gRNA targeting a target site in MYLIP set forth in any one of SEQ ID NOS:150-159 or 362-371; (d) a gRNA targeting a target site in ANGPTL3 set forth in any one of SEQ ID NOS:160-169; (e) a gRNA targeting a target site in APOC3 set forth in any one of SEQ ID NOS:170-179; or (f) a gRNA targeting a target site in APOB set forth in any one of SEQ ID NOS:180-189 or 384-389. In some embodiments, the gRNA targeting a target site in PCSK9 is set forth in SEQ ID NO: 129 In some of any of the provided embodiments, the gRNA comprises modified nucleotides for increased stability.

In some aspects, provided herein is a plurality of gRNAs comprising at least a first gRNA and a second gRNA, wherein the first gRNA targets a target site of a first gene that regulates low-density lipoprotein (LDL) and the second gRNA targets a target site of a second gene that regulates LDL. In some of any of the provided embodiments, the plurality of gRNAs comprises a third gRNA that targets a target site of a third gene that regulates LDL, and optionally the plurality of gRNAs further comprises a fourth gRNA that targets a target site of a fourth gene that regulates LDL, optionally a fifth gRNA that targets a target site of a fifth gene that regulates LDL, and/or optionally a sixth gRNA that targets a target site of a sixth gene that regulates LDL. In some of any of the provided embodiments, each gRNA is selected from any gRNA provided herein. In some of any of the provided embodiments, the first gene and the second gene are independently selected from the group consisting of PCSK9, LPA, MYLIP, ANGPTL3, APOB, and APOC3. In some of any of the provided embodiments, the first gene and the second gene are different. In some of any of the provided embodiments, the first gene and the second gene are: PCSK9 and LPA; PCSK9 and MYLIP; PCSK9 and ANGPTL3; PCSK9 and APOC3; PCSK9 and APOB; LPA and MYLIP; LPA and ANGPTL3; LPA and APOC3; LPA and APOB; MYLIP and ANGPTL3; MYLIP and APOC3; MYLIP and APOB; ANGPTL3 and APOC3; ANGPTL3 and APOB; or APOC3 and APOB. In some of any of the provided embodiments, the first gene, the second gene, and the third gene are each independently selected from the group consisting of PCSK9, LPA, MYLIP, ANGPTL3, APOC3, and APOB. In some of any of the provided embodiments, the first gene, the second gene, and the third gene are different. In some of any of the provided embodiments, the first gene, the second gene, and the third gene are: PCSK9, LPA, and MYLIP; PCSK9, LPA, and ANGPTL3; PCSK9, LPA, and APOC3; PCSK9, LPA, and APOB; PCSK9, MYLIP, and ANGPTL3; PCSK9, MYLIP, and APOC3; PCSK9, MYLIP, and APOB; PCSK9, ANGPTL3, and APOC3; PCSK9, ANGPTL3, and APOB; PCSK9, APOC3, and APOB; LPA, MYLIP, and ANGPTL3; LPA, MYLIP, and APOC3; LPA, MYLIP, and APOB; LPA, ANGPTL3, and APOC3; LPA, ANGPTL3, and APOB; LPA, APOC3, and APOB; MYLIP, ANGPTL3, and APOC3; MYLIP, ANGPTL3, and APOB; MYLIP, APOC3, and APOB; or ANGPTL3, APOC3, and APOB. In some of any of the provided embodiments, at least one gene is PCSK9. In some of any of the provided embodiments, at least two genes are PCSK9 and LPA. In some of any of the provided embodiments, at least three genes are PCSK9, LPA, and MYLIP. In some of any of the provided embodiments, the target site of each of the plurality of genes is in the gene or a regulatory DNA element thereof.

In some aspects, provided herein is a Cas-guide RNA (gRNA) combination comprising: (a) a Clustered Regularly Interspaced Short Palindromic Repeats associated (Cas) protein or variant thereof; and (b) any gRNA or plurality of gRNAs provided herein. In some of any of the provided embodiments, the Cas protein or variant thereof is a variant Cas protein that is a deactivated (dCas) protein. In some of any of the provided embodiments, the dCas protein lacks nuclease activity. In some of any of the provided embodiments, the dCas protein is a dCas9 protein. In some of any of the provided embodiments, the dCas protein is a dCas12 protein. In some of any of the provided embodiments, the dCas9 protein is a *Staphylococcus aureus* dCas9 (dSaCas9) protein. In some of any of the provided embodiments, the dSaCas9 comprises at least one amino acid mutation selected from D10A and N580A, with reference to numbering of positions of SEQ ID NO:204. In some of any of the provided embodiments, the dSaCas9 protein comprises the sequence set forth in SEQ ID NO:205, or an amino acid sequence that has at least 90%, 91%, 92%, 93%, 94%, 95%, 96%, 97%, 98%, or 99% sequence identity thereto. In some of any of the provided embodiments, the dSaCas9 is set forth in SEQ ID NO:205. In some of any of the provided embodiments, the dCas9 protein is a *Streptococcus pyogenes* dCas9 (dSpCas9) protein. In some of any of the provided embodiments, the dSpCas9 protein comprises at least one amino acid mutation selected from D10A and H840A, with reference to numbering of positions of SEQ ID NO:206. In some of any of the provided embodiments, the dSpCas9 comprises the sequence set forth in SEQ ID NO:207, or an amino acid sequence that has at least 90%, 91%, 92%, 93%, 94%, 95%, 96%, 97%, 98%, or 99% sequence identity thereto. In some of any of the provided embodiments, the dSpCas9 is set forth in SEQ ID NO:207.

In some aspects, provided herein is a polynucleotide encoding any epigenetic-modifying DNA-targeting system, combination of epigenetic-modifying DNA-targeting systems, gRNA, plurality of gRNAs, or Cas-gRNA combination provided herein, or a portion or a component of any of the foregoing. In some aspects, provided herein is a polynucleotide encoding any epigenetic-modifying DNA-targeting system provided herein. In some aspects, provided herein is a polynucleotide encoding at least one DNA-targeting module of any epigenetic-modifying DNA-targeting system provided herein. In some aspects, provided herein is a polynucleotide encoding the fusion protein and the at least first gRNA and second gRNA of any epigenetic-modifying DNA-targeting system provided herein. In some aspects, provided herein is a polynucleotide encoding the fusion protein of any epigenetic-modifying DNA-targeting system provided herein. In some aspects, provided herein is a polynucleotide encoding the fusion protein and gRNA of any epigenetic-modifying DNA-targeting system provided herein. In some aspects, provided herein is a polynucleotide encoding any combination of epigenetic-modifying DNA-targeting systems provided herein. In some aspects, provided herein is a polynucleotide encoding any gRNA provided herein. In some aspects, provided herein is a polynucleotide encoding any plurality of gRNAs provided herein. In some aspects, provided herein is a polynucleotide encoding any Cas-gRNA combination provided herein.

In some aspects, provided herein is a plurality of polynucleotides encoding any epigenetic-modifying DNA-targeting system, combination of epigenetic-modifying DNA-targeting systems, plurality of gRNAs, or Cas-gRNA combination provided herein, or a portion or a component of any of the foregoing. In some aspects, provided herein is a plurality of polynucleotides encoding any epigenetic-modifying DNA-targeting system provided herein. In some aspects, provided herein is a plurality of polynucleotides encoding at least one DNA-targeting module of any epigenetic-modifying DNA-targeting system provided herein. In some aspects, provided herein is a plurality of polynucleotides encoding the fusion protein and the at least first gRNA and second gRNA of any epigenetic-modifying DNA-targeting system provided herein. In some aspects, provided herein is a plurality of polynucleotides encoding the fusion protein of any epigenetic-modifying DNA-targeting system provided herein. In some aspects, provided herein is a plurality of polynucleotides encoding the fusion protein and gRNA of any epigenetic-modifying DNA-targeting system provided herein. In some aspects, provided herein is a plurality of polynucleotides encoding any combination of epigenetic-modifying DNA-targeting systems provided herein. In some aspects, provided herein is a plurality of polynucleotides encoding any plurality of gRNAs provided herein. In some aspects, provided herein is a plurality of polynucleotides encoding any Cas-gRNA combination provided herein.

In some aspects, provided herein is a vector comprising any polynucleotide provided herein. In some aspects, provided herein is a vector comprising any plurality of polynucleotides provided herein. In some of any of the provided embodiments, the vector is a viral vector. In some of any of the provided embodiments, the vector is an adeno-associated virus (AAV) vector. In some of any of the provided embodiments, the vector is selected from among AAV1, AAV2, AAV3, AAV4, AAV5, AAV6, AAV7, AAV8, and AAV9. In some of any of the provided embodiments, the vector is a lentiviral vector. In some of any of the provided embodiments, the vector is a non-viral vector. In some of any of the provided embodiments, the non-viral vector is selected from: a lipid nanoparticle, a liposome, an exosome, or a cell penetrating peptide. In some of any of the provided embodiments, the non-viral vector is a lipid nanoparticle. In some of any of the provided embodiments, the vector exhibits hepatocyte tropism. In some of any of the provided embodiments, the vector comprises one vector, or two or more vectors. In some aspects, provided herein is a lipid nanoparticle comprising any polynucleotide or plurality of polynucleotides provided herein.

In some aspects, provided herein is a method of decreasing transcription of at least two genes in a cell or population of cells, the method comprising administering to a cell or population of cells any epigenetic-modifying DNA-targeting system, any combination of epigenetic-modifying DNA-targeting systems, any gRNA, any plurality of gRNAs, any Cas-gRNA combination, any polynucleotide, any plurality of polynucleotides, or any vector or lipid nanoparticle provided herein, or a portion or a component of any of the foregoing. In some of any of the provided embodiments, the at least two genes are epigenetically modified. In some of any of the provided embodiments, the transcription of each of the at least two genes is decreased in comparison to a comparable cell or population of cells not subjected to the method. In some of any of the provided embodiments, the transcription of each of the at least two genes is reduced by at least about 1.2-fold, 1.25-fold, 1.3-fold, 1.4-fold, 1.5-fold, 1.6-fold, 1.7-fold, 1.75-fold, 1.8-fold, 1.9-fold, 2-fold, 2.5-fold, 3-fold, 4-fold, or 5-fold. In some of any of the provided embodiments, the reduced transcription of each of the at least two genes leads to a reduction of low-density lipoprotein (LDL). In some of any of the provided embodiments, the reduction of LDL resulting from reduced transcription each of the at least two genes is greater than the reduction of LDL resulting from comparable reduced transcription of any individual gene of the at least two genes alone.

In some aspects, provided herein is a method of reducing LDL, the method comprising introducing into a cell or population of cells any epigenetic-modifying DNA-targeting system, any combination of epigenetic-modifying DNA-targeting systems, any gRNA, any plurality of gRNAs, any Cas-gRNA combination, any polynucleotide, any plurality of polynucleotides, or any vector or lipid nanoparticle provided herein or a portion or a component of any of the foregoing. In some of any of the provided embodiments, the cell or population of cells is a liver cell or comprises liver cells. In some of any of the provided embodiments, the cell or population of cells is in a subject and the method is carried out in vivo. In some of any of the provided embodiments, LDL is reduced in the subject or a fluid, tissue, or organ thereof. In some of any of the provided embodiments, LDL is reduced in the blood of a subject. In some of any of the provided embodiments, the subject is a human. In some of any of the provided embodiments, the subject has or is suspected of having a disease, condition, or disorder. In some embodiments, the disease, condition, or disorder is a cardiovascular disease. In some of any of the provided embodiments, the subject has or is suspected of having one or more of: elevated levels of low-density lipoprotein in the blood, increased risk of cardiovascular disease, increased risk of early-onset cardiovascular disease, a mutation affecting cholesterol biosynthesis, a loss-of-function mutation in a low-density lipoprotein receptor (LDLR) gene, a loss-of-function mutation in APOB, a gain-of-function mutation in PCSK9, and familial hypercholesterolemia. In some of any of the provided embodiments, the subject has is or is suspected of having familial hypercholesterolemia.

In some aspects, provided herein is a pharmaceutical composition comprising any epigenetic-modifying DNA-targeting system, any combination of epigenetic-modifying DNA-targeting systems, any gRNA, any plurality of gRNAs, any Cas-gRNA combination, any polynucleotide, any plurality of polynucleotides, or any vector or lipid nanoparticle provided herein, or a portion or a component of any of the foregoing. In some of any of the provided embodiments, the pharmaceutical composition is for use in treating a disease, condition, or disorder in a subject. In some embodiments, the disease, condition or disorder is a cardiovascular disease. In some of any of the provided embodiments, use of the pharmaceutical composition is for the manufacture of a medicament for treating a disease, condition, or disorder in a subject. In some embodiments, the disease, condition or disorder is a cardiovascular disease. In some of any of the provided embodiments, the subject has or is suspected of having a disease, condition, or disorder. In some embodiments, the disease, condition or disorder is a cardiovascular disease. In some of any of the provided embodiments, the subject has or is suspected of having one or more of: elevated levels of low-density lipoprotein in the blood, increased risk of cardiovascular disease, increased risk of early-onset cardiovascular disease, a mutation affecting cholesterol biosynthesis, a loss-of-function mutation in a low-density lipoprotein receptor (LDLR) gene, a loss-of-function mutation in APOB, a gain-of-function mutation in PCSK9, and familial hypercholesterolemia. In some of any of the provided embodiments, the subject has is or is suspected of having familial hypercholesterolemia. In some of any of the provided embodiments, the pharmaceutical composition is to be administered to the subject in vivo. In some of any of the provided embodiments, the pharmaceutical composition is targeted to, or is to be administered to the liver of the subject. In some of any of the provided embodiments, following administration of the pharmaceutical composition, the expression of at least two genes is reduced in cells of the subject. In some of any of the provided embodiments, following administration of the pharmaceutical composition, the expression of at least two genes is reduced in liver cells of the subject. In some of any of the provided embodiments, the at least two genes are selected from the group consisting of: PCSK9, LPA, MYLIP, ANGPTL3, APOB, and APOC3.

In some aspects, provided herein is a method for treating a disease, condition, or disorder associated with elevated low-density lipoprotein (LDL) in a subject in need thereof, comprising administering to the subject any epigenetic-modifying DNA-targeting system, any combination of epigenetic-modifying DNA-targeting systems, any gRNA, any plurality of gRNAs, any Cas-gRNA combination, any polynucleotide, any plurality of polynucleotides, any vector or lipid nanoparticle, or any pharmaceutical composition provided herein, or a portion or a component of any of the foregoing. In some of any of the provided embodiments, the subject has or is suspected of having one or more of: elevated levels of low-density lipoprotein in the blood, increased risk of cardiovascular disease, increased risk of early-onset cardiovascular disease, a mutation affecting cholesterol biosynthesis, a loss-of-function mutation in a low-density lipoprotein receptor (LDLR) gene, a loss-of-function mutation in APOB, a gain-of-function mutation in PCSK9, and familial hypercholesterolemia. In some aspects the disease, condition or disorder associated with elevated LDL is a cardiovascular disease.

In some aspects, provided herein is a method for treating a familial hypercholesterolemia in a subject, comprising administering to the subject any epigenetic-modifying DNA-targeting system, any combination of epigenetic-modifying DNA-targeting systems, any gRNA, any plurality of gRNAs, any Cas-gRNA combination, any polynucleotide, any plurality of polynucleotides, any vector or lipid nanoparticle, or any pharmaceutical composition provided herein, or a portion or a component of any of the foregoing.

In some of any of the provided embodiments, the administration is a single dose infusion to the subject. In some of any of the provided embodiments, the administration is repeated at least once. In some embodiments, the administration is repeated a plurality of times at regular intervals. In some embodiments, the administration is a multiple dose administration comprising at least a first dose and a second dose. In some embodiments, the first dose and the second dose are the same. In some embodiments, the second dose is lower than the first dose. In some embodiments, the second dose is 25% to 75% of the first dose. In some embodiments, the second dose is about 30%, about 40%, about 50%, about 60% or about 70%, or a percentage between any of the foregoing, of the first dose. In some embodiments, the second dose is higher than the first dose. In some embodiments, the second dose is 150% to 500% of the first dose. In some embodiments, the second dose is about 200%, about 300%, about 400% or about 500%, or a percentage between any of the foregoing, of the first dose. In some of any of the embodiments, any lipid nanoparticle provided herein is administered to the subject.

In some of any of the embodiments, the pharmaceutical composition is for single dose infusion to the subject. In some of any of the embodiments, the pharmaceutical composition is for repeated dose administration. In some embodiments, the pharmaceutical composition is for repeated dose administration a plurality of times at regular intervals. In some embodiments, the administration is a multiple dose administration comprising at least a first dose and a second dose. In some embodiments, the first dose and the second dose are the same. In some embodiments, the second dose is lower than the first dose. In some embodiments, the second dose is 25% to 75% of the first dose. In some embodiments, the second dose is about 30%, about 40%, about 50%, about 60% or about 70%, or a percentage between any of the foregoing, of the first dose. In some embodiments, the second dose is higher than the first dose. In some embodiments, the second dose is 150% to 500% of the first dose. In some embodiments, the second dose is about 200%, about 300%, about 400% or about 500%, or a percentage between any of the foregoing, of the first dose. In some of any of the embodiments, the pharmaceutical composition comprises any lipid nanoparticle provided herein.

BRIEF DESCRIPTION OF THE DRAWINGS

FIG. 3A shows results from qRT-PCR to assess expression of PCSK9 mRNA in transfected Huh cells on day 3, day 7, day 14, day 21, day 30, day 40, day 50, and day 62 post-transfection. FIG. 3B shows results from qRT-PCR to assess expression of PCSK9 mRNA in transfected Huh cells on day 120 post-transfection. Dots represent expression levels for experimental replicates, bars represent mean of expression from experimental replicates. Expression is shown as fold change with respect to cells expressing the non-targeting gRNA. FIG. 3C shows results from qRT-PCR to assess PCSK9 mRNA expression levels in Huh cells transfected with dSpCas9-KRAB-DNMT3A/L and a non-targeting gRNA (NT) or gRNA PCSK9-C from day 3 through day 180 post-transfection. Dots represent individual time points and error bars represent mean of expression from experimental replicates. FIG. 3D shows the % methylation of CpGs in the PCSK9 promoter in Huh cells transfected with dSpCas9-KRAB-DNMT3A/L and a non-targeting gRNA (NT) or gRNA PCSK9-C. The methylation profiles are shown for cells expressing the non-targeting gRNA (NT) at day 103 post-transfection and for cells expressing PCSK9-C at day 21 and day 103 post-transfection. The shaded bar indicates the location of the target site for gRNA PCSK9-C in the PCSK9 promoter. FIG. 3E shows the methylation profiles of CpG islands 1-22 at the PCSK9 promoter for Huh cells expressing the non-targeting gRNA (NT) at day 103 post-transfection and for cells expressing PCSK9-C at day 21 and day 103 post-transfection. The shaded bar indicates the location of the target site for gRNA PCSK9-C in the PCSK9 promoter.

FIG. 4A shows results from qRT-PCR to assess expression of Cynomolgus PCSK9 (cPCSK9) mRNA levels in transfected hepatocytes at day 3 and day 14 post-transfection. mRNA expression is shown as fold change with respect to cells expressing the non-targeting gRNA. FIG. 4B shows PCSK9 protein levels as measured by ELISA in transfected hepatocytes at day 3 and day 14 post-transfection. Dots represent values for experimental replicates, bars represent mean values for experimental replicates.

FIG. 9A shows ALT levels for each NHP at various timepoints spanning 14 days pre-infusion through 28 days post-infusion. FIG. 9B shows AST levels for each NHP at various timepoints spanning 14 days pre-infusion through 28 days post-infusion.

FIG. 10A shows average ALT levels at various timepoints spanning 0-120 days post-infusion. FIG. 10B shows average AST levels at various timepoints spanning 0-120 days post-infusion.

FIG. 12A shows LDL-C levels as % of baseline at numerous time points spanning 28 days after the initial infusion. FIG. 12B shows ALT levels for each NHP at various timepoints spanning 14 days pre-infusion through 28 days post-infusion. FIG. 12C shows AST levels for each NHP at various timepoints spanning 14 days pre-infusion through 28 days post-infusion.

DETAILED DESCRIPTION

Figure 1:
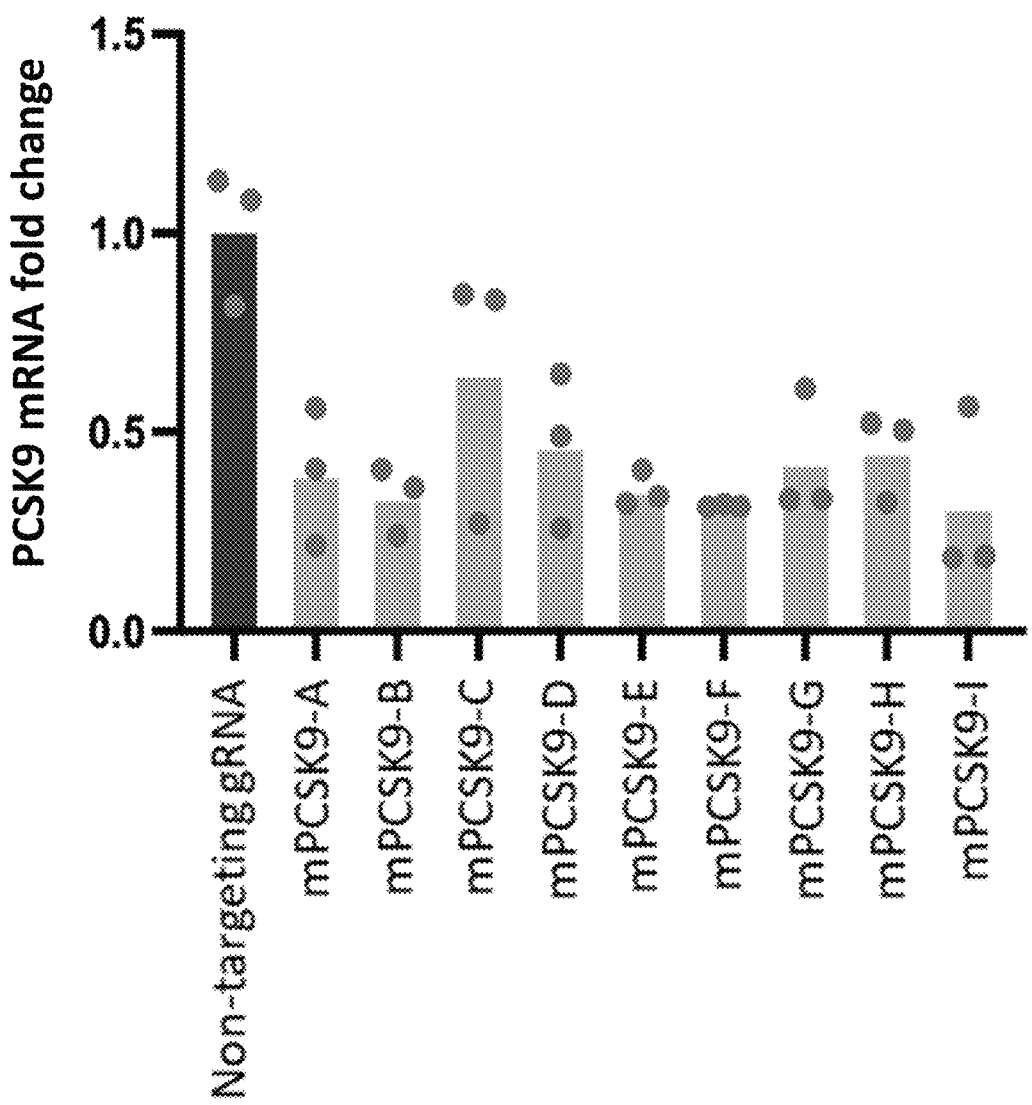
FIG. 1 shows results from qRT-PCR to assess expression of PCSK9 mRNA in murine liver (AML12) cells transfected with dSpCas9-KRAB-DNMT3A/L and a non-targeting gRNA (negative control) or PCSK9-targeting gRNAs. Dots represent expression levels for experimental replicates, bars represent mean of expression from experimental replicates. Expression is shown as fold change with respect to cells expressing the non-targeting gRNA.

Provided herein is an epigenetic-modifying DNA-targeting system comprising one or more, such as a plurality of, DNA-targeting modules for repressing transcription of one or more, such as a plurality of, genes that regulate low-density lipoprotein (LDL). In some embodiments, provided epigenetic-modifying DNA-targeting systems for repressing transcription of a gene that regulates low-density lipoprotein includes fusion proteins comprising: (a) a DNA-binding domain for targeting to a target site of a gene that regulates LDL, and (b) at least one transcriptional repressor domain. In some embodiments, the gene associated with regulation of LDL includes PCSK9, LPA, MYLIP, ANGLPTL3, APOC3, and APOB, or any combination thereof. Also provided herein are epigenetic-modifying DNA-targeting systems that are multiplexed with a plurality of targeting modules such that the system is able to target a combination of such genes. In some embodiments, each module of the DNA-targeting system represses transcription of a different gene. Also provided herein are methods of using the epigenetic-modifying DNA-targeting systems for reducing LDL in a subject. In some embodiments, the methods can be used in therapies for reducing LDL, such as for treatment of Familial Hypercholestorolemia (FH).

FH is a genetic disorder of cholesterol metabolism that is characterized by abnormally elevated blood serum levels of low-density lipoprotein (LDL) cholesterol, which can lead to early-onset cardiovascular disease and death. Unless stated otherwise, reference to LDL throughout this disclosure refers to LDL cholesterol (LDL-C) as this form is a standard measure of LDL and LDL-attributable cardiovascular disease risk. FH is a relatively common disorder, affecting approximately 1 in 250 individuals world-wide. FH can result from mutations in a number of genes, several of which play a role in LDL cholesterol metabolism (Konstantina Valanti, E. et al., Metabolism 116: 154461 (2020); Defesche, J. C. et al. Nat. Rev. Dis. Primers 3: 17093 (2017); Bouhairie, V. E. et al. Cardiol. Clin. 33(2):169-179 (2015)).

The most common form of FH is an autosomal dominant disorder resulting from loss-of-function mutations in the gene that encodes the LDL receptor (LDLR), accounting for 85-90% of all FH cases. LDLR is a cell-surface receptor that mediates endocytosis of LDL, including in liver cells, thus reducing the concentration of circulating LDL. Loss-of-function LDLR mutations result in a decreased capacity to clear LDL from the bloodstream, and consequently elevated levels of circulating LDL.

Loss-of-function mutations in Apolipoprotein B (ApoB) are also associated with FH, accounting for approximately 5-10% of FH cases. ApoB acts as a protein component of LDL, and binds LDLR to facilitate endocytosis of LDL. FH-causing ApoB mutations commonly disrupt the ability of ApoB to bind LDLR, thus reducing the rate of LDL clearance from the bloodstream.

Rare gain-of-function mutations in proprotein convertase subtilisin/kexin type 9 (PCSK9) are have also been associated with FH. PCSK9 negatively regulates cell surface expression of LDLR by binding to the epidermal growth factor-like repeat A (EGF-A) domain of LDLR and targeting LDLR for lysosomal degradation. Mutations resulting in increased PCSK9 activity thus decrease the ability of cells to express LDLR at the cell surface, resulting in elevated circulating LDL. Conversely, loss-of-function PCSK9 mutations are associated with lowered LDL levels and protection from cardiovascular disease (Lagace, T. A. Curr. Opin. Lipidol. 25(5):387-393 (2014); Peterson, A. S. et al. J. Lipid Res. 49(6):1152-1156 (2008); Bouhairie, V. E. et al. Cardiol. Clin. 33(2):169-179 (2015)).

Lipoprotein(a) (LPA) is an LDL-like particle identified as an independent risk factor for FH and cardiovascular disease. Elevated LPA affects approximately 20% of the general population, and is more prevalent in individuals with FH (30-50% of individuals with FH have elevated LPA), creating an added risk for cardiovascular disease.

The understanding of FH as a genetic disorder affecting cholesterol metabolism has led to a number of approaches for treating the disease (Bouhairie et al.). FH is typically treated initially with statins, a class of lipid-lowering medications also known as HMG-CoA reductase inhibitors, which reduce cholesterol synthesis. Statin therapy can reduce LDL in FH patients. However, for a number of FH patients, statins do not sufficiently reduce LDL, and/or the risk of negative cardiovascular events, including for patients with additional independent risk factors for cardiovascular disease, including elevated LPA levels. However, statins alone may be ineffective for certain FH patients, and are associated with a range of toxic side effects, including statin-associated muscle symptoms (Ward, N. C. et al. Circ. Res. 124:328-350 (2019)).

Combination therapies, typically comprising a statin and a secondary non-statin treatment, are required to sufficiently lower LDL in FH patients for whom statins alone are not effective (Bouhairie, V. E. et al. Cardiol. Clin. 33(2):169-179 (2015)). Some patients may additionally require a third treatment if statins and a secondary treatment are not effective. Secondary non-statin treatments may include ezetimibe, bile-acid sequestrants (such as colesevelam, colestipol, and cholestyramine), niacin, and fibrates. Such treatments are associated with a number of side effects, including gastrointestinal and metabolic dysregulation, as well as interference with other medications, including statins themselves.

LDL apheresis, in which LDL is removed from the blood of a patient in a clinical setting, is another potential treatment for FH patients, particularly those with homozygous loss-of-function LDLR mutations, and for whom the above-described treatments are not effective. The cost and intensive nature of LDL apheresis is disadvantageous, with LDL apheresis typically requiring a 3 hour treatment session every 1-2 weeks.

PCSK9 monoclonal antibodies have emerged as a promising secondary non-statin treatment to supplement statin treatment for FH. PCKS9 antibodies inhibit binding of PCKS9 to LDLR, thus reducing LDLR degradation and increasing LDL clearance. However, PCKS9 antibodies incur significant time commitment and cost, requiring injection once every 2 to 4 weeks.

In summary, current therapies for FH face a number of challenges. First-line treatment with statins alone can be ineffective for many patients, while combination therapies are complicated by toxic side-effects, high cost, or inconvenient treatment schedules. There is a need for alternative FH therapies that effectively reduce LDL and that exhibit reduced treatment outcomes, such as greater or more sustained efficacy.

Provided embodiments herein relate to leveraging engineered DNA-binding systems to target genetic mechanisms contributing to regulation of LDL, including for treatment of cardiovascular disease and FH. An understanding of the genetic risk factors of FH, combined with emerging technologies for targeted modulation of gene expression in vivo, present new opportunities for treating the disease. Sequence-specific DNA-binding systems found in nature, such as zinc-fingers, transcription-activator-like effectors, and CRISPR/Cas systems can now be engineered to target one or more genes for activation or repression in vivo (Adli, M. Nat. Commun. 9, 1911 (2018)). The provided embodiments also relate to engineering the DNA-binding systems to target more than one gene, thus eliminating the need for a combination therapy that would previously be required to do so, and the costs and inconvenience associated with such combination therapies.

The provided embodiments relate to targeted repression of one or more genes in liver cells to promote a phenotype that reduces LDL the blood, such as by increased expression of LDLR and/or increased LDL uptake. In aspects, the provided embodiments include introducing into a liver cell epigenetic modifications using effector domains that are repressors of transcription (i.e. transcriptional repressor domains), which can be directed to regions of a target gene (e.g. regulatory elements such as promoters or enhancers) for transcriptional repression and reduced expression of the target gene. For instance, provided herein are epigenetic-modifying DNA binding systems combining a DNA-binding domain (e.g. a dCas and gRNA combination) and an effector domain, in which the effector domain is able to target a target site of the gene or a regulatory element thereof to precisely repress or reduce transcription of the gene by epigenetic regulation. Transcriptional repression, leading to reduced gene expression, increases the capacity of the cell to clear LDL from the blood. Moreover, the epigenetic modification of the cell does not modify DNA at the sequence level, thereby avoiding safety concerns with gene editing approaches.

The ability to epigenetically control the capacity of liver cells to clear LDL provides an advantageous approach for treating FH and cardiovascular disease, eliminating the need for other therapies or combinations of therapies which can be ineffective, toxic, expensive, or inconvenient. In addition, the ability to target multiple genes for repression allows for reduction of LDL via more than one mechanism with a single treatment, thereby avoiding the need for complicated schedules and toxicity associated with some combination therapies. Epigenetic repression of genes may provide a long-lasting solution to reducing LDL, with the potential for administration schedules that are less intensive than current therapies.

In particular, among provided embodiments herein is an epigenetic-modifying DNA-targeting system for repressing transcription of a gene or a plurality of genes that regulates LDL, such as any described herein, in which the epigenetic-modifying DNA-targeting system comprises a fusion protein comprising: (a) at least one DNA-binding domain for targeting to a target site of a gene, and (b) at least one transcriptional repressor domain capable of repressing or reducing transcription of the gene. In some embodiments, the provided epigenetic-modifying DNA-targeting systems are for multiplexed targeted repression of a plurality of different genes that regulate LDL, in which the system contains a plurality of DNA-targeting modules each for repressing transcription of a different gene that regulates LDL. In some embodiments, the epigenetic-modifying DNA-targeting system comprises a plurality of DNA-targeting modules for repressing transcription of a plurality of genes that regulate LDL, wherein each DNA-targeting module comprises a fusion protein comprising: (a) a DNA-binding domain for targeting to a target site of one of the plurality of genes, and (b) at least one transcriptional repressor domain. In some embodiments, at least two different genes that regulate LDL are targeted for repression, wherein the plurality of DNA-targeting modules comprises a first DNA-targeting module for repressing transcription of a first gene of the plurality of genes, and a second DNA-targeting module for repressing transcription of a second gene of the plurality of genes. Also provided herein are polynucleotides encoding the DNA-targeting systems or fusion proteins of the DNA-targeting systems, vectors, and compositions containing the same.

In some embodiments of the provided epigenetic-modifying DNA-targeting system, the DNA binding domain is a nuclease-inactive Clustered Regularly Interspaced Short Palindromic Repeats associated (Cas) protein or variant thereof, such as a dead Cas (dCas, e.g. dCas9), and the DNA-targeting system further includes at least one gRNA that can complex with the Cas. In some embodiments, the DNA-binding domain is a nuclease-inactive Clustered Regularly Interspaced Short Palindromic Repeats associated (Cas) protein or variant thereof complexed with a guide RNA (gRNA). In such systems, the gRNA has a spacer sequence that is capable of hybridizing to the target site of the gene. Also provided herein are related gRNAs, including Cas/gRNA combinations, polynucleotides, compositions and methods involving or related to the epigenetic-modifying DNA targeting systems.

In some embodiments of the provided epigenetic-modifying DNA-targeting system, the DNA-binding domain is a protein domain that is engineered for sequence-specific binding to the target site. For example, in some embodiments, the DNA-binding domain is a zinc-finger (ZFN)-based DNA-binding domain, or transcription activator-like effector DNA-binding domain, as described herein.

Also provided herein are methods of using the epigenetic-modifying DNA-targeting system for modulating transcription or a phenotype of liver cells. Also provided herein are methods of using the epigenetic-modifying DNA-targeting systems for reducing LDL in a subject. In some embodiments, the methods can be used in therapies for reducing LDL, such as for treatment of FH.

Hence, in some embodiments, the DNA-targeting systems comprise synthetic transcription factors that are able to modulate, such as reduce or repress, transcription of a gene in a targeted manner. In provided embodiments, the provided epigenetic-modifying DNA-targeting system reduces transcription of the gene or plurality of genes, and thereby promotes an LDL-reducing phenotype. The provided embodiments can be used to target multiple genetic mechanisms to reduce LDL in FH patients or patients with cardiovascular disease, while avoiding the toxicity, cost, and inconvenience of current combination therapies. For example, artheoscherotic cardiovascular disease (ASCVD) is a chronic inflammatory disease caused by build-up of LDL plaque in the arteries. ASCVD is responsible for 1 in 4 deaths in the US, hundreds of millions globally, and is the underlying cause of ~50% of all deaths in westernized society. In addition, 75% of acute heart attacks are due to sclerotic plaque rupture. Statins can be used to stabilize but do not reverse atherosclerotic plaques. However, the need for repeated administration and side effects of statin treatments limit uptake and compliance. Combination therapy comprising statins and PCSK9 antibodies is a promising alternative, but LDL levels remain too high in many patients. Gene editing approaches targeting PCSK9 create DNA mutations and can have off-target effects while RNAi based methods have not been proven durable. Thus, improved therapies are needed.

This approach provided herein, therefore, offers substantial clinical solutions to treating FH and cardiovascular disease, such as artheoscherotic cardiovascular disease (ASCVD), by reducing circulating LDL, while circumventing the problems associated with current therapies. In particular, provided embodiments relate to methods for targeted repression of PCSK9 by provided DNA-targeting systems. Results herein demonstrate a surprisingly high sustained level of repression of PCSK9 in serum of about 80% more than 22 weeks after a single transient dose to an animal model provided with a DNA-targeting repressor system specific to the PCSK9 promoter. Results demonstrate that silencing PCSK9 results in reduction of LDL-cholesterol and thus is a therapeutic target for the prevention or treatment of cardiovascular disease and FH. While currently approved PCSK9 inhibitors require repeat administration to maintain efficacy, the provided DNA-targeting systems for targeted repression of PCSK9 offers the potential to durably silence PCSK9 without altering the genetic sequence.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. DNA-Targeting Systems

In some embodiments, provided are DNA-targeting systems capable of specifically targeting a target site in at least one gene (also called a target gene herein) or DNA regulatory element thereof, and reducing transcription of the at least one gene, in which each of the at least one gene encodes a gene product that regulates LDL. In provided embodiments, for each target gene that is targeted, the DNA-targeting systems include a DNA-binding domain that binds to a target site in the gene or regulatory DNA element thereof. In some embodiments, the DNA-targeting systems additionally include at least one effector domain that is able to epigenetically modify one or more DNA bases of the gene or regulatory element thereof, in which the epigenetic modification results in a reduction in transcription of the gene (e.g. inhibits transcription or reduces transcription of the gene compared to the absence of the DNA-targeting system). Hence, the terms DNA-targeting system and epigenetic-modifying DNA-targeting system may be used herein interchangeably. In some embodiments, the DNA-targeting systems include a fusion protein comprising (a) at least one DNA-binding domain capable of being targeted to the target site; and (b) at least one effector domain capable of reducing transcription of the gene. For instance, the at least one effector domain is a transcription repressor domain.

In some embodiments, the DNA-targeting system contains at least one DNA-targeting module, where each DNA-targeting module of the system is a component of the DNA-targeting system that is independently capable of targeting one target site in a target gene as provided. In some embodiments, each DNA-targeting module includes (a) a DNA-binding domain capable of being targeted to a target site of the target gene that regulates LDL and (b) an effector domain capable of reducing transcription of the gene.

In some embodiments, the DNA-targeting system includes a single DNA-targeting module for targeting repression of a single gene. In some embodiments, the DNA-targeting module includes (a) a DNA-binding domain capable of being targeted to a target site of the target gene or regulatory element in which the target gene is encodes a gene product that regulates LDL, and (b) an effector domain capable of reducing transcription of the gene.

In some embodiments, the DNA-targeting system includes a plurality of DNA-targeting modules, in which each DNA-targeting module is for targeting repression of a different gene. In some embodiments, the DNA-targeting systems are multiplexed DNA-targeting systems, i.e. targeted to target sites in more than one gene. Hence, the terms DNA-targeting system may include a multiplexed epigenetic-modifying DNA targeting system that includes more than one DNA-targeting module. A multiplexed epigenetic-modifying DNA targeting system comprises at least 2, at least 3, at least 4, at least 5, at least 6, at least 7, at least 8, at least 9, at least 10, at least 20, at least 30 DNA-targeting modules or any value between any of the foregoing In some embodiments, any two DNA-targeting modules of a DNA-targeting system comprise separate (i.e. non-overlapping) components. In some embodiments, each DNA-targeting modules of a DNA-targeting system comprise separate (i.e. non-overlapping) components. For example, a DNA-targeting system may comprise a first DNA-targeting module comprising a first fusion protein comprising a DNA-binding domain (e.g. a ZFN or TALE-based DNA-binding domain) that targets a first target site, and a second DNA-targeting module comprising a second fusion protein comprising a second DNA-binding domain (e.g. a ZFN or TALE-based DNA-binding domain) that targets a second target site.

In some embodiments, any two DNA-targeting modules of a DNA-targeting system may comprise shared (i.e. overlapping) components. In some embodiments, each DNA-targeting modules of a DNA-targeting system comprise shared (i.e. overlapping) components. For example, a DNA-targeting system may comprise a first DNA-targeting module comprising (a) a fusion protein comprising a Cas protein and a transcriptional repressor domain, and (b) a first gRNA that complexes with the Cas protein and targets a first target site, and a second DNA-targeting module comprising (a) the fusion protein of the first DNA-targeting module, and (b) a second gRNA that complexes with the Cas protein and targets a second target site. It will be understood that providing two or more different gRNAs for a given Cas protein allows different molecules of the same Cas protein to be targeted to the target sites of the two or more gRNAs. Conversely, different Cas protein variants (e.g. SpCas9 and SaCas9) are compatible with different gRNA scaffold sequences and PAMs, as described herein. Thus, it is possible to engineer a single DNA-targeting system comprising multiple non-overlapping CRISPR/Cas-based DNA-targeting modules.

In some aspects, provided herein is an epigenetic-modifying DNA-targeting system comprising a plurality of DNA-targeting modules for repressing transcription of a plurality of genes that regulate low-density lipoprotein (LDL). In some embodiments, the plurality of DNA-targeting modules comprises a first DNA-targeting module for repressing transcription of a first gene of the plurality of genes, and a second DNA-targeting module for repressing transcription of a second gene of the plurality of genes. In some embodiments, each DNA-targeting module comprises a fusion protein comprising: (a) a DNA-binding domain for targeting to a target site of one of the plurality of genes, and (b) at least one transcriptional repressor domain.

In some of any of the provided embodiments, the gene(s) is selected from the group consisting of PCSK9, LPA, MYLIP, ANGPTL3, APOB, and APOC3. In some embodiments, the gene is PCSK9.

In some aspects, provided herein is an epigenetic-modifying DNA-targeting system comprising a plurality of DNA-targeting modules for repressing transcription of a plurality of genes that regulate low-density lipoprotein (LDL), comprising: (1) a first DNA-targeting module that reduces transcription of a first gene that regulates low-density lipoprotein (LDL), wherein the first DNA-targeting module comprises a first fusion protein comprising (a) a DNA-binding domain for targeting a target site of the first gene or regulatory DNA element thereof; and (b) at least one transcriptional repressor domain; and (2) a second DNA-targeting module that reduces transcription of a second gene that regulates LDL, wherein the second DNA-targeting module comprises a second fusion protein comprising (a) a DNA-binding domain for targeting a target site of the second gene or regulatory DNA element thereof; and (b) at least one transcriptional repressor domain.

In some aspects, provided herein is an epigenetic-modifying DNA-targeting system comprising: (a) a fusion protein comprising a Clustered Regularly Interspaced Short Palindromic Repeats associated (Cas) protein or variant thereof and at least one transcriptional repressor domain; and (b) a plurality of guide RNAs (gRNAs) comprising at least a first gRNA and a second gRNA, wherein the first gRNA targets a target site of a first gene that regulates low-density lipoprotein (LDL) and the second gRNA targets a target site of a second gene that regulates LDL.

In some aspects, provided herein is an epigenetic-modifying DNA-targeting system for repressing transcription of a gene that regulates low-density lipoprotein, comprising a fusion protein comprising: (a) a DNA-binding domain for targeting to a target site of a gene, and (b) at least one transcriptional repressor domain.

In some aspects, provided herein is an epigenetic-modifying DNA-targeting system comprising: (a) a fusion protein comprising a Clustered Regularly Interspaced Short Palindromic Repeats associated (Cas) protein or variant thereof and at least one transcriptional repressor domain; and (b) a gRNA that targets a target site of a gene that regulates low-density lipoprotein (LDL).

In aspects of the provided embodiments, a DNA-targeting system provided herein targets a combination of genes or a regulatory elements thereof to reduce transcription of the genes in a liver cell, such as a hepatocyte, in which the reduced transcription modulates one or more activities or functions of liver cells, such as a phenotype of the liver cell. In some embodiments, reduced transcription of the genes results in a reduced expression of the genes, i.e. reduced gene expression, in the liver cell. In some embodiments, the reduced transcription of the gene, such as reduced gene expression, promotes a phenotype that leads to reduction of LDL, such as in a subject (i.e. an enhanced LDL-reducing phenotype).

In some aspects, the cell is a liver cell, such as a hepatocyte. In some aspects, the cell is a hepatocyte. For instance, provided herein is a DNA-targeting system that targets a combination of genes or a regulatory elements thereof to reduce transcription of the genes in a hepatocyte, in which the reduced transcription modulates one or more activities or functions of the hepatocyte, such as a phenotype of the hepatocyte. In some embodiments, reduced transcription of the genes results in a reduction in expression of the genes, i.e. reduced gene expression, in the hepatocyte.

In some aspects, the cell is from a human subject. In some aspects the cell is a cell in a subject (i.e. a cell in vivo).

In some embodiments, the DNA-binding domain comprises or is derived from a CRISPR associated (Cas) protein, zinc finger protein (ZFP), transcription activator-like effectors (TALE), meganuclease, homing endonuclease, I-SceI enzyme, or variants thereof. In some embodiments, the DNA-binding domain comprises a catalytically inactive (e.g. nuclease-inactive or nuclease-inactivated) variant of any of the foregoing. In some embodiments, the DNA-binding domain comprises a deactivated Cas9 (dCas9) protein or variant thereof that is a catalytically inactivated so that it is inactive for nuclease activity and is not able to cleave the DNA.

In some embodiments, the DNA-binding domain comprises or is derived from a Cas protein or variant thereof, such as a nuclease-inactive Cas or dCas (e.g. dCas9, and the DNA-targeting system comprises one or more guide RNAs (gRNAs), such as a combination of gRNAs (e.g. two gRNAs or three gRNAs). In some embodiments, the gRNA comprises a spacer sequence that is capable of targeting and/or hybridizing to the target site. In some embodiments, the gRNA is capable of complexing with the Cas protein or variant thereof. In some aspects, the gRNA directs or recruits the Cas protein or variant thereof to the target site.

In some embodiments, the effector domain comprises a transcription repressor domain, and/or is capable of reducing transcription of the gene. In some embodiments, the effector domain directly or indirectly leads to reduced transcription of the gene. In some embodiments, the effector domain induces, catalyzes or leads to transcription repression. In some embodiments, the effector domain induces transcription repression. In some aspects, the effector domain is selected from a KRAB domain, ERF repressor domain, MXI1 domain, SID4X domain, MAD-SID domain, a DNMT family protein domain (e.g. DNMT3A or DNMT3B), a fusion of one or more DNMT family proteins or domains thereof (e.g. DNMT3A/L, which comprises a fusion of DNMT3A and DNMT3L domains), LSD1, EZH2, a SunTag domain, a partially or fully functional fragment or domain of any of the foregoing, or a combination of any of the foregoing. In some embodiments, the effector domain is KRAB. In some embodiments, the effector domain is DNMT3A/L.

In some embodiments, the fusion protein of the DNA-targeting system comprises a dCas9-KRAB fusion protein. In some embodiments, the fusion protein of the DNA-targeting system comprises a dCas9-KRAB-DNMT3A/L fusion protein. For purposes herein, unless a particular SEQ ID NO is identified or a particular order specified, the term dCas9-KRAB-DNMT3A/L may refer to any orientation of the fusion protein as described above. In some embodiments, the fusion protein of the DNA-targeting system comprises in N- to C-terminal order DNMT3A/L-dCas9-KRAB-fusion protein. In some embodiments, the fusion protein of the DNA-targeting system comprises in N- to C-terminal order KRAB-dCas9-DNMT3A/L-fusion protein.

Exemplary components and features of the DNA-targeting systems are provided below in the following subsections.

A. Target Genes and Target Sites

In some embodiments, the target gene is a gene in which reduced expression of the gene regulates a cellular phenotype. In some embodiments, the target gene is capable of regulating a phenotype in a hepatocyte. In some embodiments, the target gene is capable of regulating the ability of a hepatocyte to reduce levels of LDL in the blood of a subject. In some embodiments, reduced transcription of the gene, such as reduced gene expression, promotes a phenotype in a hepatocyte that leads to reduction of LDL (i.e. an enhanced LDL-reducing phenotype).

In some aspects, the phenotype is one that is characterized by a cell surface phenotype of the cells. In some embodiments, the phenotype comprises increased expression of low-density lipoprotein receptor (LDL-R).

It is understood that a cell that is positive (+) for a particular cell surface marker is a cell that expresses the marker on its surface at a level that is detectable. Likewise, it is understood that a cell that is negative (−) for a particular cell surface marker is a cell that expresses the marker on its surface at a level that is not detectable. Antibodies and other binding entities can be used to detect expression levels of marker proteins to identify or detect a given cell surface marker. Suitable antibodies may include polyclonal, monoclonal, fragments (such as Fab fragments), single chain antibodies and other forms of specific binding molecules. Antibody reagents for cell surface markers above are readily known to a skilled artisan. A number of well-known methods for assessing expression level of surface markers or proteins may be used, such as detection by affinity-based methods, e.g., immunoaffinity-based methods, e.g., in the context of surface markers, such as by flow cytometry. In some embodiments, the label is a fluorophore and the method for detection or identification of cell surface markers on cells (e.g. hepatocytes) is by flow cytometry. In some embodiments, different labels are used for each of the different markers by multicolor flow cytometry. In some embodiments, surface expression can be determined by flow cytometry, for example, by staining with an antibody that specifically binds to the marker and detecting the binding of the antibody to the marker.

In some embodiments, a cell (e.g. hepatocyte) is positive (pos or +) for a particular marker if there is detectable presence on or in the cell of a particular marker, which can be an intracellular marker or a surface marker. In some embodiments, surface expression is positive if staining by flow cytometry is detectable at a level substantially above the staining detected carrying out the same procedures with an isotype-matched control under otherwise identical conditions and/or at a level substantially similar to, or in some cases higher than, a cell known to be positive for the marker and/or at a level higher than that for a cell known to be negative for the marker. In some embodiments, a cell (e.g. a hepatocyte) contacted by a DNA-targeting system described herein, has increased expression for a particular marker (e.g. LDL-R) if the staining is substantially than a similar cell that was not contacted by the DNA-targeting system.

In some embodiments, a cell (e.g. hepatocyte) is negative (neg or −) for a particular marker if there is an absence of detectable presence on or in the cell of a particular marker, which can be an intracellular marker or a surface marker. In some embodiments, surface expression is negative if staining is not detectable by flow cytometry at a level substantially above the staining detected carrying out the same procedures with an isotype-matched control under otherwise identical conditions and/or at a level substantially lower than a cell known to be positive for the marker and/or at a level substantially similar to a cell known to be negative for the marker.

In some aspects, the phenotype is one that is characterized functionally. In some aspects, the phenotype can be characterized by one or more functions of the cells. In some embodiments, the phenotype comprises increased uptake of LDL by the cell. In some embodiments, the phenotype comprises reduced expression of lipoprotein(a) (LPA), an LDL variant, by the cell. In some embodiments, the phenotype comprises reduced LDL in one or more tissues of a subject comprising the cell. In some embodiments, the phenotype comprises reduced LDL in the blood of a subject comprising the cell.

The target genes for modulation by the provided multiplexed epigenetic-modifying DNA-targeting systems herein include any whose transcription and expression are reduced in cells with a particular or desired function or activity, such as cell phenotype (e.g. a phenotype for reducing LDL). Various methods may be utilized to characterize the transcription or expression levels of a gene in a cell (e.g. hepatocyte) such as after the cell has been contacted or introduced with a provided DNA-targeting system and selected for a desired activity or function, such as cell phenotype. In some embodiments, the phenotype can be a phenotype comprising one or more cell surface markers as described above. In some embodiments, the phenotype is increased LDL-R expression. In some embodiments, analyzing the transcription activity or expression of a gene may be by RNA analysis. In some embodiments, the RNA analysis includes RNA quantification. In some embodiments, the RNA quantification occurs by reverse transcription quantitative PCR (RT-qPCR), multiplexed qRT-PCR, fluorescence in situ hybridization (FISH), FlowFISH, RNA-sequencing (RNA-seq) or combinations thereof.

In some embodiments, the gene is one in which expression of the gene in the cell (e.g. hepatocyte), is reduced after having been contacted or introduced with a provided multiplexed epigenetic DNA-targeting system. In some embodiments, the reduction in gene expression in a cell (e.g. hepatocyte) is about a log 2 fold change of less than −1.0. For instance, the log 2 fold change is lesser than at or about −1.5, at or about −2.0, at or about −2.5, at or about −3.0, at or about −4.0, at or about −5.0, at or about −6.0, at or about −7.0, at or about −8.0, at or about −9.0, at or about −10.0 or any value between any of the foregoing compared to the level of the gene in a control cell.

In some embodiments, the gene is selected from the list consisting of: PCSK9, LPA, MYLIP, ANGPTL3, APOC3, and APOB. In some embodiments, the target site comprises a sequence selected from any one of SEQ ID NOS: 1-63, 306-317, 342-351, or 372-377, a contiguous portion thereof of at least 14 nucleotides of any one of SEQ ID NOS: 1-63, 306-317, 342-351, or 372-377, or a complementary sequence of any of the foregoing. In some embodiments, the target site is a contiguous portion of any one of SEQ ID NOS: 1-63, 306-317, 342-351, or 372-377 that is 15, 16, 17, 18 or 19 nucleotides in length, or a complementary sequence of any of the foregoing. In some embodiments, the target site is a sequence having at or at least 80%, 85%, 90%, 91%, 92%, 93%, 94%, 95%, 96%, 97%, 98%, 99%, 99.5%, 99.9%, or 100% sequence identity to all or a contiguous portion of a target site sequence described herein above. In some embodiments, the target site is the sequence set forth in any one of SEQ ID NOS: 1-63, 306-317, 342-351, or 372-377.

In some embodiments, the gene is PCSK9. PCSK9 is a gene that encodes Proprotein convertase subtilisin/kexin type 9 (also known as FH3, HCHOLA3, LDLCQ1, NARC-1, NARC1, PC9, FHCL3). PCSK9 plays a role in regulation of plasma cholesterol homeostasis, and binds low-density lipid receptor family members and promotes their degradation (Poirier et al., J. Biol. Chem. 283:2363-2372 (2008)). In some embodiments the target site for PCSK9 is located within 500 bp of human genome assembly GRCh38 (hg38) genomic coordinates chr1:55,039,548 (e.g., a target site that is +500 of 55,039,548 or −500 of 55,039,548 or positions between the foregoing). In some embodiments, the target site is within 400 bp, 300 bp, 200 bp, 100 bp, 80 bp, 60 bp, 50 bp, 40 bp, 30 bp or 20 bp of genomic coordinates chr1:55,039,548. In some embodiments the target site is located within about 80 bp of the genomic coordinate chr1:55,039,548. In some embodiments, the target site in the region from −40 to +40 of the genomic coordinate chr1:55,039,548. In some embodiments the target site is located within 20 bp of the genomic coordinate chr1:55,039,548. In some embodiments, the gRNA targets a target site in the region from −10 to +10 of the genomic coordinate chr1:55,039,548. In some embodiments, any of such target sites include or span the genomic coordinate chr1:55,039,548, which is a PCSK9 transcription start site (TSS). In some embodiments, the target site is within or overlaps the coordinates chr1: 55,039,538-55, 039,557. In some embodiments, the target site is or includes the coordinates chr1: 55,039,538-55,039,557. In some embodiments, the target site comprises a sequence selected from any one of SEQ ID NOS: 1-13 or 306-317, a contiguous portion thereof of at least 14 nucleotides of any one of SEQ ID NOS: 1-13 or 306-317, or a complementary sequence of any of the foregoing. In some embodiments, the target site is a contiguous portion of any one of SEQ ID NOS: 1-13 or 306-317 that is 15, 16, 17, 18 or 19 nucleotides in length, or a complementary sequence of any of the foregoing. In some embodiments, the target site is a sequence having at or at least 80%, 85%, 90%, 91%, 92%, 93%, 94%, 95%, 96%, 97%, 98%, 99%, 99.5%, 99.9%, or 100% sequence identity to all or a contiguous portion of a target site sequence described herein above. In some embodiments, the target site is the sequence set forth in any one of SEQ ID NOS: 1-13 or 306-317. In some embodiments, the target site is the sequence set forth in SEQ ID NO:3 or a contiguous portion thereof of at least 14 nucleotides of SEQ ID NO:3. In some embodiments, the target site is the sequence set forth in SEQ ID NO:3.

In some embodiments, the gene is LPA. LPA is a gene that encodes Apolipoprotein(a) (also known as AK38, APOA, LP, Lipoprotein(a), Lp(a)). Apolipoprotein(a) is a constituent of lipoprotein(a), which has been identified as a risk factor for cardiovascular disease. In some embodiments, the target site for LPA is located within 500 bp of the hg38 genomic coordinates chr6:160,664,275. In some embodiments, the target site comprises a sequence selected from any one of SEQ ID NOS: 14-23, a contiguous portion thereof of at least 14 nucleotides of any one of SEQ ID NOS: 14-23, or a complementary sequence of any of the foregoing. In some embodiments, the target site is a contiguous portion of any one of SEQ ID NOS: 14-23 that is 15, 16, 17, 18 or 19 nucleotides in length, or a complementary sequence of any of the foregoing. In some embodiments, the target site is a sequence having at or at least 80%, 85%, 90%, 91%, 92%, 93%, 94%, 95%, 96%, 97%, 98%, 99%, 99.5%, 99.9%, or 100% sequence identity to all or a contiguous portion of a target site sequence described herein above. In some embodiments, the target site is the sequence set forth in any one of SEQ ID NOS: 14-23.

In some embodiments, the gene is MYLIP. MYLIP is a gene that encodes myosin regulatory light chain interacting protein (also known as IDOL, MIR, myosin regulatory light chain interacting protein). MYLIP is an E3 ubiquitin-protein ligase that mediates ubiquitination and subsequent proteasomal degradation of myosin regulatory light chain (MRLC), LDLR, VLDLR and LRP8. MYLIP acts as a sterol-dependent inhibitor of cellular cholesterol uptake by mediating ubiquitination and subsequent degradation of LDLR. In some embodiments, the target site for MYLIP is located within 500 bp of the hg38 genomic coordinates chr6:16,129,086. In some embodiments, the target site comprises a sequence selected from any one of SEQ ID NOS: 24-33 or 342-351, a contiguous portion thereof of at least 14 nucleotides of any one of SEQ ID NOS: 24-33 or 342-351, or a complementary sequence of any of the foregoing. In some embodiments, the target site is a contiguous portion of any one of SEQ ID NOS: 24-33 or 342-351 that is 15, 16, 17, 18 or 19 nucleotides in length, or a complementary sequence of any of the foregoing. In some embodiments, the target site is a sequence having at or at least 80%, 85%, 90%, 91%, 92%, 93%, 94%, 95%, 96%, 97%, 98%, 99%, 99.5%, 99.9%, or 100% sequence identity to all or a contiguous portion of a target site sequence described herein above. In some embodiments, the target site is the sequence set forth in any one of SEQ ID NOS: 24-33 or 342-351.

In some embodiments, the gene is ANGPTL3. ANGPTL3 is a gene that encodes Angiopoietin-related protein 3 (also known as ANG-5, ANGPT5, ANL3, FHBL2, angiopoietin like 3). ANGPTL3 is a member of the angiopoietin-like family of secreted factors, and is involved in regulation of lipid and glucose metabolism. In some embodiments, the target site for ANGPTL3 is located within 500 bp of the hg38 genomic coordinates chr1:62,597,520. In some embodiments, the target site comprises a sequence selected from any one of SEQ ID NOS: 34-43, a contiguous portion thereof of at least 14 nucleotides of any one of SEQ ID NOS: 34-43, or a complementary sequence of any of the foregoing. In some embodiments, the target site is a contiguous portion of any one of SEQ ID NOS: 34-43 that is 15, 16, 17, 18 or 19 nucleotides in length, or a complementary sequence of any of the foregoing. In some embodiments, the target site is a sequence having at or at least 80%, 85%, 90%, 91%, 92%, 93%, 94%, 95%, 96%, 97%, 98%, 99%, 99.5%, 99.9%, or 100% sequence identity to all or a contiguous portion of a target site sequence described herein above. In some embodiments, the target site is the sequence set forth in any one of SEQ ID NOS: 34-43.

In some embodiments, the gene is APOC3. APOC3 is a gene that encodes Apolipoprotein C-III (also known as APOCIII, HALP2, apolipoprotein C3, Apo-C3, ApoC-3). APOC3 is a component of triglyceride-rich very low density lipoproteins (VLDL) and high density lipoproteins (HDL) in plasma, and plays a role in triglyceride homeostasis. In some embodiments, the target site for APOC3 is located within 500 bp of the hg38 genomic coordinates chr11:116,829,907. In some embodiments, the target site comprises a sequence selected from any one of SEQ ID NOS: 44-53, a contiguous portion thereof of at least 14 nucleotides of any one of SEQ ID NOS: 44-53, or a complementary sequence of any of the foregoing. In some embodiments, the target site is a contiguous portion of any one of SEQ ID NOS: 44-53 that is 15, 16, 17, 18 or 19 nucleotides in length, or a complementary sequence of any of the foregoing. In some embodiments, the target site is a sequence having at or at least 80%, 85%, 90%, 91%, 92%, 93%, 94%, 95%, 96%, 97%, 98%, 99%, 99.5%, 99.9%, or 100% sequence identity to all or a contiguous portion of a target site sequence described herein above. In some embodiments, the target site is the sequence set forth in any one of SEQ ID NOS: 44-53.

In some embodiments, the gene is APOB. APOB is a gene that encodes Apolipoprotein B-100 (also known as FLDB, LDLCQ4, apoB-100, apoB-48, apolipoprotein B, FCHL2). APOB is a constituent of low density lipoproteins and functions as a recognition signal for the cellular binding and internalization of LDL particles by the apoB/E receptor. In some embodiments, the target site for APOB is located within 500 bp of the hg38 genomic coordinates chr2:21,044,073. In some embodiments, the target site comprises a sequence selected from any one of SEQ ID NOS: 54-63 or 372-377, a contiguous portion thereof of at least 14 nucleotides of any one of SEQ ID NOS: 54-63 or 372-377, or a complementary sequence of any of the foregoing. In some embodiments, the target site is a contiguous portion of any one of SEQ ID NOS: 54-63 or 372-377 that is 15, 16, 17, 18 or 19 nucleotides in length, or a complementary sequence of any of the foregoing. In some embodiments, the target site is a sequence having at or at least 80%, 85%, 90%, 91%, 92%, 93%, 94%, 95%, 96%, 97%, 98%, 99%, 99.5%, 99.9%, or 100% sequence identity to all or a contiguous portion of a target site sequence described herein above. In some embodiments, the target site is the sequence set forth in any one of SEQ ID NOS: 54-63 or 372-377.

In some embodiments, the multiplexed epigenetic-modifying DNA-targeting system targets to or binds to a target site in the gene, such as any described above. In some embodiments, the target site is located in a regulatory DNA element of the gene in the cell (e.g. hepatocyte). In some embodiments, a regulatory DNA element is a sequence to which a gene regulatory protein may bind and affect transcription of the gene. In some embodiments, the regulatory DNA element is a cis, trans, distal, proximal, upstream, or downstream regulatory DNA element of a gene. In some embodiments, the regulatory DNA element is a promoter or enhancer of the gene. In some embodiments, the target site is located within a promoter, enhancer, exon, intron, untranslated region (UTR), 5' UTR, or 3' UTR of the gene. In some embodiments, a promoter is a nucleotide sequence to which RNA polymerase binds to begin transcription of the gene. In some embodiments, a promoter is a nucleotide sequence located within about 100 bp, about 500 bp, about 1000 bp, or more, of a transcriptional start site of the gene. In some embodiments the target site is located within a sequence of unknown or known function that is suspected of being able to control expression of a gene.

In some embodiments, provided herein are multiplexed epigenetic-modifying DNA-targeting systems that target a combination of at least two target genes or regulatory DNA elements thereof described herein.

In some embodiments, provided herein are multiplexed epigenetic-modifying DNA-targeting systems that target a first gene and a second gene. In some embodiments, the first gene is selected from the list consisting of PCSK9, LPA, MYLIP, ANGPTL3, APOC3, and APOB, the second gene is selected from the list consisting of PCSK9, LPA, MYLIP, ANGPTL3, APOC3, and APOB, and the first and second genes are different. In some embodiments, the first gene is PCSK9 and the second gene is selected from the list consisting of LPA, MYLIP, ANGPTL3, APOC3, and APOB. In some embodiments, the first gene is PCSK9 and the second gene is LPA.

In some embodiments, the first gene and second gene are selected from a combination listed in Table 1.

TABLE 1

Combinations of a first gene and a second gene targeted by a multiplexed epigenetic-modifying DNA-targeting system provided herein

| First gene | Second gene |
|---|---|
| PCSK9 | LPA |
| PCSK9 | MYLIP |
| PCSK9 | ANGPTL3 |
| PCSK9 | APOC3 |
| PCSK9 | APOB |
| LPA | MYLIP |
| LPA | ANGPTL3 |
| LPA | APOC3 |
| LPA | APOB |
| MYLIP | ANGPTL3 |
| MYLIP | APOC3 |
| MYLIP | APOB |
| ANGPTL3 | APOC3 |
| ANGPTL3 | APOB |
| APOC3 | APOB |

In some embodiments, provided herein are multiplexed epigenetic-modifying DNA-targeting systems that target a first gene, a second gene, and a third gene. In some embodiments, the first gene is selected from the list consisting of PCSK9, LPA, MYLIP, ANGPTL3, APOC3, and APOB, the second gene is selected from the list consisting of PCSK9, LPA, MYLIP, ANGPTL3, APOC3, and APOB, the third gene is selected from the list consisting of PCSK9, LPA, MYLIP, ANGPTL3, APOC3, and APOB, and the first, second, and third genes are different. In some embodiments, the first gene is PCSK9, the second gene is selected from the list consisting of LPA, MYLIP, ANGPTL3, APOC3, and APOB, the third gene is selected from the list consisting of LPA, MYLIP, ANGPTL3, APOC3, and APOB, and the second gene and third gene are different. In some embodiments, the first gene is PCSK9, the second gene is LPA, and the third gene is selected from the list consisting of MYLIP, ANGPTL3, APOC3, and APOB.

In some embodiments, the first gene, second gene, and third gene are selected from a combination listed in Table 2.

TABLE 2

Combinations of a first gene, second gene, and third gene targeted by a multiplexed epigenetic-modifying DNA-targeting system provided herein

| First gene | Second gene | Third gene |
|---|---|---|
| PCSK9 | LPA | MYLIP |
| PCSK9 | LPA | ANGPTL3 |
| PCSK9 | LPA | APOC3 |
| PCSK9 | LPA | APOB |
| PCSK9 | MYLIP | ANGPTL3 |
| PCSK9 | MYLIP | APOC3 |
| PCSK9 | MYLIP | APOB |
| PCSK9 | ANGPTL3 | APOC3 |
| PCSK9 | ANGPTL3 | APOB |
| PCSK9 | APOC3 | APOB |
| LPA | MYLIP | ANGPTL3 |
| LPA | MYLIP | APOC3 |
| LPA | MYLIP | APOB |
| LPA | ANGPTL3 | APOC3 |
| LPA | ANGPTL3 | APOB |
| LPA | APOC3 | APOB |

TABLE 2-continued

Combinations of a first gene, second gene, and third gene targeted by a multiplexed epigenetic-modifying DNA-targeting system provided herein

| First gene | Second gene | Third gene |
|---|---|---|
| MYLIP | ANGPTL3 | APOC3 |
| MYLIP | ANGPTL3 | APOB |
| MYLIP | APOC3 | APOB |
| ANGPTL3 | APOC3 | APOB |

B. CRISPR-Based DNA-Targeting Systems

Provided herein are multiplexed epigenetic-targeting DNA-targeting systems based on CRISPR/Cas systems, i.e. CRISPR/Cas-based DNA-targeting systems, that are able to bind to a target site in a target gene, or to target sites in a combination of target genes. In some embodiments, the CRISPR/Cas DNA-binding domain is nuclease inactive, such as includes a dCas (e.g. dCas9) so that the system binds to the target site in a target gene without mediating nucleic acid cleavage at the target site. The CRISPR/Cas-based DNA-targeting systems may be used to modulate expression of a target gene in a cell, such as a hepatocyte. In some embodiments, the target gene may include any as described herein, including any described above in Section I.A. In some embodiments, the target site of the target gene may include any as described herein, including any described above in Section I.A. In some embodiments, the CRISPR/Cas-based DNA-targeting system can include any known Cas enzyme, and generally a nuclease-inactive or dCas. In some embodiments, the CRISPR/Cas-based DNA-targeting system includes a fusion protein of a nuclease-inactive Cas protein or a variant thereof and an effector domain that reduces transcription of a gene (e.g. a transcriptional repressor), and at least one gRNA.

The CRISPR system (also known as CRISPR/Cas system, or CRISPR-Cas system) refers to a conserved microbial nuclease system, found in the genomes of bacteria and archaea, that provides a form of acquired immunity against invading phages and plasmids. Clustered Regularly Interspaced Short Palindromic Repeats (CRISPR), refers to loci containing multiple repeating DNA elements that are separated by non-repeating DNA sequences called spacers. Spacers are short sequences of foreign DNA that are incorporated into the genome between CRISPR repeats, serving as a 'memory' of past exposures. Spacers encode the DNA-targeting portion of RNA molecules that confer specificity for nucleic acid cleavage by the CRISPR system. CRISPR loci contain or are adjacent to one or more CRISPR-associated (Cas) genes, which can act as RNA-guided nucleases for mediating the cleavage, as well as non-protein coding DNA elements that encode RNA molecules capable of programming the specificity of the CRISPR-mediated nucleic acid cleavage.

In Type II CRISPR/Cas systems with the Cas protein Cas9, two RNA molecules and the Cas9 protein form a ribonucleoprotein (RNP) complex to direct Cas9 nuclease activity. The CRISPR RNA (crRNA) contains a spacer sequence that is complementary to a target nucleic acid sequence (target site), and that encodes the sequence specificity of the complex. The trans-activating crRNA (tracrRNA) base-pairs to a portion of the crRNA and forms a structure that complexes with the Cas9 protein, forming a Cas/RNA RNP complex.

Naturally occurring CRISPR/Cas systems, such as those with Cas9, have been engineered to allow efficient programming of Cas/RNA RNPs to target desired sequences in cells of interest, both for gene-editing and modulation of gene expression. The tracrRNA and crRNA have been engineered to form a single chimeric guide RNA molecule, commonly referred to as a guide RNA (gRNA), for example as described in WO 2013/176772, WO 2014/093661, WO 2014/093655, Jinek, M. et al. Science 337(6096):816-21 (2012), or Cong, L. et al. Science 339(6121):819-23 (2013). The spacer sequence of the gRNA can be chosen by a user to target the Cas/gRNA RNP complex to a desired locus, e.g. a desired target site in the target gene.

Cas proteins have also been engineered to be catalytically inactivated or nuclease inactive to allow targeting of Cas/gRNA RNPs without inducing cleavage at the target site. Mutations in Cas proteins can reduce or abolish nuclease activity of the Cas protein, rendering the Cas protein catalytically inactive. Cas proteins with reduced or abolished nuclease activity are referred to as deactivated Cas (dCas), or nuclease-inactive Cas (iCas) proteins, as referred to interchangeably herein. An exemplary deactivated Cas9 (dCas9) derived from S. pyogenes contains silencing mutations of the RuvC and HNH nuclease domains (D10A and H840A), for example as described in WO 2013/176772, WO 2014/093661, Jinek, M. et al. Science 337(6096):816-21 (2012), and Qi, L. et al. Cell 152(5):1173-83 (2013). Exemplary dCas variants derived from the Cas12 system (i.e. Cpf1) are described, for example in WO 2017/189308 and Zetsche, B. et al. Cell 163(3):759-71 (2015). Conserved domains that mediate nucleic acid cleavage, such as RuvC and HNH endonuclease domains, are readily identifiable in Cas orthologues, and can be mutated to produce inactive variants, for example as described in Zetsche, B. et al. Cell 163(3):759-71 (2015).

dCas-fusion proteins with transcriptional and/or epigenetic regulators have been used as a versatile platform for ectopically regulating gene expression in target cells. These include fusion of a Cas with an effector domain, such as a transcriptional activator or transcriptional repressor. For example, fusing dCas9 with a transcriptional activator such as VP64 (a polypeptide composed of four tandem copies of VP16, a 16 amino acid transactivation domain of the Herpes simplex virus) can result in robust induction of gene expression. Alternatively, fusing dCas9 with a transcriptional repressor such as KRAB (Krüppel associated box) can result in robust repression of gene expression. A variety of dCas-fusion proteins with transcriptional and epigenetic regulators can be engineered for regulation of gene expression, for example as described in WO 2014/197748, WO 2016/130600, WO 2017/180915, WO 2021/226555, WO 2013/176772, WO 2014/152432, WO 2014/093661, WO 2021/247570, Adli, M. Nat. Commun. 9, 1911 (2018), Perez-Pinera, P. et al. Nat. Methods 10, 973-976 (2013), Mali, P. et al. Nat. Biotechnol. 31, 833-838 (2013), Maeder, M. L. et al. Nat. Methods 10, 977-979 (2013), Gilbert, L. A. et al. Cell 154(2):442-451 (2013), and Nunez, J. K. et al. Cell 184(9):2503-2519 (2021).

In some aspects, provided is a DNA-targeting system comprising a fusion protein comprising a DNA-binding domain comprising a nuclease-inactive Cas protein or variant thereof, and an effector domain for reducing transcription or inducing transcriptional repression (i.e. a transcriptional repressor) when targeted to the target gene in the cell (e.g. hepatocyte). In such embodiments, the DNA-targeting system also includes one or more gRNAs, provided in combination or as a complex with the dCas protein or variant thereof, for targeting of the DNA-targeting system to the target site of the target gene. In some embodiments, the fusion protein is guided to a specific target site sequence of the target gene by the guide RNA, wherein the effector domain mediates targeted epigenetic modification to reduce or repress transcription of the target gene. In some embodiments, a combination of gRNAs guides the fusion protein to a combination of target site sequences in a combination of genes, wherein the effector domain mediates targeted epigenetic modification to reduce or repress transcription of the combination of target genes. Any of a variety of effector domains that reduce or repress transcription can be used as described further below.

i. CRISPR-Based DNA-Binding Domains

In some aspects, the DNA-binding domain comprises a CRISPR-associated (Cas) protein or variant thereof, or is derived from a Cas protein or variant thereof. In particular embodiments here, the Cas protein is nuclease-inactive (i.e. is a dCas protein).

In some embodiments, the Cas protein is derived from a Class 1 CRISPR system (i.e. multiple Cas protein system), such as a Type I, Type III, or Type IV CRISPR system. In some embodiments, the Cas protein is derived from a Class 2 CRISPR system (i.e. single Cas protein system), such as a Type II, Type V, or Type VI CRISPR system. In some embodiments, the Cas protein is from a Type V CRISPR system. In some embodiments, the Cas protein is derived from a Cas12 protein (i.e. Cpf1) or variant thereof, for example as described in WO 2017/189308 and Zetsche, B. et al. Cell. 163(3):759-71 (2015). In some embodiments, the Cas protein is derived from a Type II CRISPR system. In some embodiments, the Cas protein is derived from a Cas9 protein or variant thereof, for example as described in WO 2013/176772, WO 2014/152432, WO 2014/093661, WO 2014/093655, Jinek, M. et al. Science 337(6096):816-21 (2012), Mali, P. et al. Science 339(6121):823-6 (2013), Cong, L. et al. Science 339(6121):819-23 (2013), Perez-Pinera, P. et al. Nat. Methods 10, 973-976 (2013), or Mali, P. et al. Nat. Biotechnol. 31, 833-838 (2013). Various CRISPR/Cas systems and associated Cas proteins for use in gene editing and regulation have been described, for example in Moon, S. B. et al. Exp. Mol. Med. 51, 1-11 (2019), Zhang, F. Q. Rev. Biophys. 52, E6 (2019), and Makarova K. S. et al. Methods Mol. Biol. 1311:47-75 (2015).

In some embodiments, the dCas9 protein can comprise a sequence derived from a naturally occurring Cas9 molecule, or variant thereof. In some embodiments, the dCas9 protein can comprise a sequence derived from a naturally occurring Cas9 molecule of S. pyogenes, S. thermophilus, S. aureus, C. jejuni, N. meningitidis, F. novicida, S. canis, S. auricularis, or variant thereof. In some embodiments, the dCas9 protein comprises a sequence derived from a naturally occurring Cas9 molecule of S. aureus. In some embodiments, the dCas9 protein comprises a sequence derived from a naturally occurring Cas9 molecule of S. pyogenes.

Non-limiting examples of Cas9 orthologs from other bacterial strains include but are not limited to: Cas proteins identified in *Acaryochloris marina* MBIC11017; *Acetohalobium arabaticum* DSM 5501; *Acidithiobacillus caldus*; *Acidithiobacillus ferrooxidans* ATCC 23270; *Alicyclobacillus acidocaldarius* LAA1; *Alicyclobacillus acidocaldarius* subsp. *acidocaldarius* DSM 446; *Allochromatium vinosum* DSM 180; *Ammonifex degensii* KC4; *Anabaena variabilis* ATCC 29413; *Arthrospira maxima* CS-328; *Arthrospira* platensis str. Paraca; *Arthrospira* sp. PCC 8005; *Bacillus pseudomycoides* DSM 12442; *Bacillus selenitireducens* MLS10; *Burkholderiales bacterium* 1_1_47; *Caldicelulosiruptor becscii* DSM 6725; *Candidatus Desulforudis audaxviator* MP104C; Caldicellulosiruptor *hydrothermalis* 108; *Clostridium* phage c-st; *Clostridium botulinum* A3 str. Loch Maree; *Clostridium botulinum* Ba4 str. 657; *Clostridium difficile* QCD-63q42; *Crocosphaera watsonii* WH 8501; *Cyanothece* sp. ATCC 51142; *Cyanothece* sp. CCY0110; *Cyanothece* sp. PCC 7424; *Cyanothece* sp. PCC 7822; *Exiguobacterium sibiricum* 255-15; *Finegoldia magna* ATCC 29328; *Ktedonobacter racemifer* DSM 44963; *Lactobacillus delbrueckii* subsp. *bulgaricus* PB2003/044-T3-4; *Lactobacillus salivarius* ATCC 11741; *Listeria innocua; Lyngbya* sp. PCC 8106; *Marinobacter* sp. ELB17; *Methanohalobium evestigatum* Z-7303; *Microcystis phage* Ma-LMMO1; *Microcystis aeruginosa* NIES-843; *Microscilla marina* ATCC 23134; *Microcoleus chthonoplastes* PCC 7420; *Neisseria meningitidis; Nitrosococcus halophilus* Nc4; *Nocardiopsis dassonvillei* subsp. *dassonvillei* DSM 43111; *Nodularia spumigena* CCY9414; *Nostoc* sp. PCC 7120; *Oscillatoria* sp. PCC 6506; *Pelotomaculum_thermopropionicum* SI; *Petrotoga mobilis* SJ95; *Polaromonas naphthalenivorans* CJ2; *Polaromonas* sp. JS666; *Pseudoalteromonas haloplanktis* TAC125; *Streptomyces pristinaespiralis* ATCC 25486; *Streptomyces pristinaespiralis* ATCC 25486; *Streptococcus thermophilus; Streptomyces viridochromogenes* DSM 40736; *Streptosporangium roseum* DSM 43021; *Synechococcus* sp. PCC 7335; and *Thermosipho africanus* TCF52B (Chylinski et al., RNA Biol., 2013; 10(5): 726-737).

In some aspects, the Cas protein is a variant that lacks nuclease activity (i.e. is a dCas protein). In some embodiments, the Cas protein is mutated so that nuclease activity is reduced or eliminated. Such Cas proteins are referred to as deactivated Cas or dead Cas (dCas) or nuclease-inactive Cas (iCas) proteins, as referred to interchangeably herein. In some embodiments, the variant Cas protein is a variant Cas9 protein that lacks nuclease activity or that is a deactivated Cas9 (dCas9, or iCas9) protein.

In some embodiments, the Cas9 protein or a variant thereof is derived from a *Staphylococcus aureus* Cas9 (SaCas9) protein or a variant thereof. In some embodiments, the variant Cas9 is a *Staphylococcus aureus* dCas9 protein (dSaCas9) that comprises at least one amino acid mutation selected from D10A and N580A, with reference to numbering of positions of SEQ ID NO:204. In some embodiments, the variant Cas9 protein comprises the sequence set forth in SEQ ID NO:205, or an amino acid sequence that has at least 90%, 91%, 92%, 93%, 94%, 95%, 96%, 97%, 98%, or 99% sequence identity thereto.

In some embodiments, the Cas9 protein or variant thereof is derived from a *Streptococcus pyogenes* Cas9 (SpCas9) protein or a variant thereof. In some embodiments, the variant Cas9 is a *Streptococcus pyogenes* dCas9 (dSpCas9) protein that comprises at least one amino acid mutation selected from D10A and H840A, with reference to numbering of positions of SEQ ID NO:206. In some embodiments, the variant Cas9 protein comprises the sequence set forth in SEQ ID NO:207, or an amino acid sequence that has at least 90%, 91%, 92%, 93%, 94%, 95%, 96%, 97%, 98%, or 99% sequence identity thereto.

ii. Guide RNAs

In some embodiments, the Cas protein (e.g. dCas9) is provided in combination or as a complex with one or more guide RNA (gRNA). In some aspects, the gRNA is a nucleic acid that promotes the specific targeting or homing of the gRNA/Cas RNP complex to the target site of the target gene, such as any described above. In some embodiments, a target site of a gRNA may be referred to as a protospacer.

Provided herein are gRNAs, such as gRNAs that target or bind to a target gene or DNA regulatory element thereof, such as any described above in Section I.A. In some embodiments, the gRNA is capable of complexing with the Cas protein or variant thereof. In some embodiments, the gRNA comprises a gRNA spacer sequence (i.e. a spacer sequence or a guide sequence) that is capable of hybridizing to the target site, or that is complementary to the target site, such as any target site described in Section I.A or further below. In some embodiments, the gRNA comprises a scaffold sequence that complexes with or binds to the Cas protein.

In some embodiments, the gRNAs provided herein are chimeric gRNAs. In general, gRNAs can be unimolecular (i.e. composed of a single RNA molecule), or modular (comprising more than one, and typically two, separate RNA molecules). Modular gRNAs can be engineered to be unimolecular, wherein sequences from the separate modular RNA molecules are comprised in a single gRNA molecule, sometimes referred to as a chimeric gRNA, synthetic gRNA, or single gRNA. In some embodiments, the chimeric gRNA is a fusion of two non-coding RNA sequences: a crRNA sequence and a tracrRNA sequence, for example as described in WO 2013/176772, or Jinek, M. et al. Science 337(6096):816-21 (2012). In some embodiments, the chimeric gRNA mimics the naturally occurring crRNA:tracrRNA duplex involved in the Type II Effector system, wherein the naturally occurring crRNA:tracrRNA duplex acts as a guide for the Cas9 protein.

In some aspects, the spacer sequence of a gRNA is a polynucleotide sequence comprising at least a portion that has sufficient complementarity with the target gene or DNA regulatory element thereof (e.g. any described in Section I.A) to hybridize with a target site in the target gene and direct sequence-specific binding of a CRISPR complex to the sequence of the target site. Full complementarity is not necessarily required, provided there is sufficient complementarity to cause hybridization and promote formation of a CRISPR complex. In some embodiments, the gRNA comprises a spacer sequence that is complementary, e.g., at least 80%, 85%, 90%, 95%, 98%, 99%, or 100% (e.g., fully complementary), to the target site. The strand of the target nucleic acid comprising the target site sequence may be referred to as the "complementary strand" of the target nucleic acid.

In some embodiments, the gRNA spacer sequence is between about 14 nucleotides (nt) and about 26 nt, or between 16 nt and 22 nt in length. In some embodiments, the gRNA spacer sequence is 14 nt, 15 nt, 16 nt, 17 nt, 18 nt, 19 nt, 20 nt, 21 nt or 22 nt, 23 nt, 24 nt, 25 nt, or 26 nt in length. In some embodiments, the gRNA spacer sequence is 18 nt, 19 nt, 20 nt, 21 nt or 22 nt in length. In some embodiments, the gRNA spacer sequence is 19 nt in length.

A target site of a gRNA may be referred to as a protospacer. In some aspects, the gRNA spacer is designed to target a protospacer with a specific protospacer-adjacent motif (PAM), i.e. a sequence immediately adjacent to the protospacer that contributes to and/or is required for Cas binding specificity. Different CRISPR/Cas systems have different PAM requirements for targeting. For example, in some embodiments, *S. pyogenes* Cas9 uses the PAM 5'-NGG-3' (SEQ ID NO:202), where N is any nucleotide. *S. aureus* Cas9 uses the PAM 5'-NNGRRT-3' (SEQ ID NO:203), where N is any nucleotide, and R is G or A. *N. meningitidis* Cas9 uses the PAM 5'-NNNNGATT-3' (SEQ ID NO:210), where N is any nucleotide. *C. jejuni* Cas9 uses the PAM 5'-NNNNRYAC-3' (SEQ ID NO:211), where N is any nucleotide, R is G or A, and Y is C or T. *S. thermophilus* uses the PAM 5'-NNAGAAW-3'(SEQ ID NO:212), where N is any nucleotide and W is A or T. *F. Novicida* Cas9 uses the PAM 5'-NGG-3'(SEQ ID NO:213), where N is any nucleotide. *T. denticola* Cas9 uses the PAM 5'-NAAAAC-3'(SEQ ID NO:214), where N is any nucleotide. Cas12a (also known as Cpf1) from various species, uses the PAM 5'-TTTV-3' (SEQ ID NO:215). Cas proteins may use or be engineered to use different PAMs from those listed above. For example, variant SpCas9 proteins may use a PAM selected from: 5'-NGG-3' (SEQ ID NO:202), 5'-NGAN-3' (SEQ ID NO:216), 5'-NGNG-3'(SEQ ID NO:217), 5'-NGAG-3'(SEQ ID NO:218), or 5'-NGCG-3'(SEQ ID NO:219). In some embodiments, the PAM sequence for complexing with *S. pyogenes* Cas9 or variant thereof is set forth in SEQ ID NO: 202. In some embodiments, the PAM sequence for complexing with *S. aureus* Cas9 or variant thereof is set forth in SEQ ID NO: 203.

A gRNA spacer sequence may be selected to reduce the degree of secondary structure within the spacer sequence. Secondary structure may be determined by any suitable polynucleotide folding algorithm.

In some embodiments, the gRNA (including the guide sequence) will comprise the base uracil (U), whereas DNA encoding the gRNA molecule will comprise the base thymine (T). While not wishing to be bound by theory, in some embodiments, it is believed that the complementarity of the guide sequence with the target sequence contributes to specificity of the interaction of the gRNA molecule/Cas molecule complex with a target nucleic acid. It is understood that in a guide sequence and target sequence pair, the uracil bases in the guide sequence will pair with the adenine bases in the target sequence. A gRNA spacer sequence herein may be defined by the DNA sequence encoding the gRNA spacer, and/or the RNA sequence of the spacer.

In some embodiments, one, more than one, or all of the nucleotides of a gRNA can have a modification, e.g., to render the gRNA less susceptible to degradation and/or improve bio-compatibility. By way of non-limiting example, the backbone of the gRNA can be modified with a phosphorothioate, or other modification(s). In some cases, a nucleotide of the gRNA can comprise a 2' modification, e.g., a 2-acetylation, e.g., a 2' methylation, or other modification(s).

Methods for designing gRNAs and exemplary targeting domains can include those described in, e.g., International PCT Pub. Nos. WO 2014/197748, WO 2016/130600, WO 2017/180915, WO 2021/226555, WO 2013/176772, WO 2014/152432, WO 2014/093661, WO 2014/093655, WO 2015/089427, WO 2016/049258, WO 2016/123578, WO 2021/076744, WO 2014/191128, WO 2015/161276, WO 2017/193107, and WO 2017/093969.

In some embodiments, a gRNA provided herein targets a target site in a gene in a cell (e.g. hepatocyte) or DNA regulatory element thereof, wherein the gene is selected from the list consisting of: PCSK9, LPA, MYLIP, ANGPTL3, APOC3, and APOB.

In some embodiments, the gRNA targets a target site that comprises a sequence selected from any one of SEQ ID NOS: 1-63, 306-317, 342-351, or 372-377, as shown in Table 3, a contiguous portion thereof of at least 14 nucleotides, a complementary sequence of any of the foregoing, or a sequence having at or at least 80%, 85%, 90%, 91%, 92%, 93%, 94%, 95%, 96%, 97%, 98%, 99%, 99.5%, 99.9%, or 100% sequence identity to any of the foregoing. In some embodiments, the target site is a contiguous portion of any one of SEQ ID NOS:1-63, 306-317, 342-351, or 372-377 that is 14, 15, 16, 17, 18 or 19 nucleotides in length. In some embodiments, the target site is set forth in any one of SEQ ID NOS: 1-63, 306-317, 342-351, or 372-377. In some embodiments, the gRNA targets a target site in a PCSK9 promoter. In some embodiments, the gRNA targets a target site that includes or is set forth in SEQ ID NO:3 or a contiguous portion thereof of at least 14 nucleotides. In some embodiments, the gRNA targets a target site that includes or is set forth in SEQ ID NO:3.

In some embodiments, the gRNA comprises a spacer sequence selected from any one of SEQ ID NOS: 64-126, 318-329, 352-361, or 378-383, as shown in Table 3, or a contiguous portion thereof of at least 14 nt, or a sequence having at or at least 80%, 85%, 90%, 91%, 92%, 93%, 94%, 95%, 96%, 97%, 98%, 99%, 99.5%, 99.9%, or 100% sequence identity to any of the foregoing. In some embodiments, the spacer sequence of the gRNA is a contiguous portion of any one of SEQ ID NOS: 64-126, 318-329, 352-361, or 378-383 that is 14, 15, 16, 17, 18 or 19 nucleotides in length. In some embodiments, the spacer sequence of the gRNA is set forth in any one of SEQ ID NOS: 64-126, 318-329, 352-361, or 378-383. In some embodiments, the spacer sequence of the gRNA includes or is set forth in SEQ ID NO:66 or a contiguous portion thereof of at least 14 nucleotides (e.g. 14, 15, 16, 17, 18 or 19 nucleotides) of SEQ ID NO:66. In some embodiments, the spacer sequence of the gRNA is set forth in SEQ ID NO:66.

In some embodiments, the gRNA further comprises a scaffold sequence. In some embodiments, the scaffold sequence comprises the sequence set forth in SEQ ID NO: 191 (GUUUAAGAGCUAUGCUGGAAACAG-CAUAGCAAGUUUAAAUAAGGCUAGUCCG UUAU-CAACUUGAAAAAGUGGCACCGAGUCGGUGC), or a sequence having at or at least 80%, 85%, 90%, 91%, 92%, 93%, 94%, 95%, 96%, 97%, 98%, 99%, 99.5%, 99.9%, or 100% sequence identity to all or a portion thereof. In some embodiments, the scaffold sequence is set forth in SEQ ID NO: 191. In some embodiments, the scaffold sequence comprises the DNA sequence set forth in SEQ ID NO: 190.

In some embodiments, a gRNA provided herein comprises a spacer sequence selected from any one of SEQ ID NOS: 64-126, 318-329, 352-361, or 378-383, as shown in Table 3. In some embodiments, the gRNA further comprises a scaffold sequence set forth in SEQ ID NO: 191. In some embodiments, the gRNA comprises the sequence selected from any one of SEQ ID NOS: 127-189, 330-341, 362-371, or 384-389, as shown in Table 4, or a sequence having at or at least 80%, 85%, 90%, 91%, 92%, 93%, 94%, 95%, 96%, 97%, 98%, 99%, 99.5%, 99.9%, or 100% sequence identity to any one of SEQ ID NO: 127-189, 330-341, 362-371, or 384-389. In some embodiments, the gRNA is set forth in any one of SEQ ID NOS: 127-189, 330-341, 362-371, or 384-389. In some embodiments, any of the provided gRNA sequences is complexed with or is provided in combination with a Cas9. In some embodiments, the Cas9 is a dCas9. In some embodiments, the dCas9 is a dSpCas9, such as a dSpCas9 set forth in SEQ ID NO: 207, or a variant and/or fusion thereof.

TABLE 3

Genes, target site sequences, and gRNA spacer sequences

| Target Gene | target site (protospacer) sequence | target SEQ ID | gRNA spacer sequence | RNA spacer SEQ ID |
|---|---|---|---|---|
| PCSK9 | GCGCGTAATCTGACGCTGTT | 1 | GCGCGUAAUCUGACGCUGUU | 64 |
| PCSK9 | ATCAGATAGGATCGTCCGAT | 2 | AUCAGAUAGGAUCGUCCGAU | 65 |
| PCSK9 | AGGTTTCCGCAGCGACGTCG | 3 | AGGUUUCCGCAGCGACGUCG | 66 |
| PCSK9 | GGGCGCCGCCGTTCAGTTCA | 4 | GGGCGCCGCCGUUCAGUUCA | 67 |
| PCSK9 | GGTGCTAGCCTTGCGTTCCG | 5 | GGUGCUAGCCUUGCGUUCCG | 68 |
| PCSK9 | CATTAACGGAACCCCCGGAC | 6 | CAUUAACGGAACCCCCGGAC | 69 |
| PCSK9 | AGGATCGTCCGATGGGGCTC | 7 | AGGAUCGUCCGAUGGGGCUC | 70 |
| PCSK9 | CCGTTAATGTTTAATCAGAT | 8 | CCGUUAAUGUUUAAUCAGAU | 71 |
| PCSK9 | CGTAATCTGACGCTGTTTG | 9 | CGUAAUCUGACGCUGUUUG | 72 |
| PCSK9 | GGTGTGGGTGCTTGACGCCT | 10 | GGUGUGGGUGCUUGACGCCU | 73 |
| PCSK9 | ACCCACTGCACGCTGGACAG | 11 | ACCCACUGCACGCUGGACAG | 74 |
| PCSK9 | GCACAGTAACAACCCCTGGT | 12 | GCACAGUAACAACCCCUGGU | 75 |
| PCSK9 | CCATCCATTCTTTCTCTAGG | 13 | CCAUCCAUUCUUUCUCUAGG | 76 |
| LPA | AAGGAGACATAAAGGCAATG | 14 | AAGGAGACAUAAAGGCAAUG | 77 |
| LPA | GGCAATGTGGAGCAGCTGAG | 15 | GGCAAUGUGGAGCAGCUGAG | 78 |
| LPA | GGAGCAGCTGAGGGGGGAAA | 16 | GGAGCAGCUGAGGGGGGAAA | 79 |
| LPA | TGTCAATAGATGCTGGGAAG | 17 | UGUCAAUAGAUGCUGGGAAG | 80 |
| LPA | AGTGCAATGTCAATAGATGC | 18 | AGUGCAAUGUCAAUAGAUGC | 81 |
| LPA | TTTATAAGACTCTATATTCA | 19 | UUUAUAAGACUCUAUAUUCA | 82 |
| LPA | CATGTAAGTCAACAATGTCC | 20 | CAUGUAAGUCAACAAUGUCC | 83 |
| LPA | GTCAACAATGTCCTGGGATT | 21 | GUCAACAAUGUCCUGGGAUU | 84 |
| LPA | CATATACAAGATTTTGAACT | 22 | CAUAUACAAGAUUUUGAACU | 85 |
| LPA | GCACCGTGACAGTCTTCACG | 23 | GCACCGUGACAGUCUUCACG | 86 |
| MYLIP | TTGGCGGGGACCCGAGCTGA | 24 | UUGGCGGGGACCCGAGCUGA | 87 |
| MYLIP | CTGTCGCAGCGCAGGCAGT | 25 | CUGUCGCAGCGCAGGCAGUU | 88 |
| MYLIP | GCTGGAGTGCGGCGCCACCG | 26 | GCUGGAGUGCGGCGCCACCG | 89 |

TABLE 3-continued

Genes, target site sequences, and gRNA spacer sequences

| Target Gene | target site (protospacer) sequence | target SEQ ID | gRNA spacer sequence | RNA spacer SEQ ID |
|---|---|---|---|---|
| MYLIP | CGGCGCCACCGCGGAGGACA | 27 | CGGCGCCACCGCGGAGGACA | 90 |
| MYLIP | CAGCTCTGCGGACCCTTGTC | 28 | CAGCUCUGCGGACCCUUGUC | 91 |
| MYLIP | CCCCGCGCACACCAAAGAGA | 29 | CCCCGCGCACACCAAAGAGA | 92 |
| MYLIP | CCTCGTCACATAACACAGCA | 30 | CCUCGUCACAUAACACAGCA | 93 |
| MYLIP | ACCTCCATCAGCACCGCGTC | 31 | ACCUCCAUCAGCACCGCGUC | 94 |
| MYLIP | GGAGGCGAAAGCCAACGGCG | 32 | GGAGGCGAAAGCCAACGGCG | 95 |
| MYLIP | GTTGAGGCAGTCCTCGCCGT | 33 | GUUGAGGCAGUCCUCGCCGU | 96 |
| ANGLPTL3 | TACATTCGTGCAAGTTAACA | 34 | UACAUUCGUGCAAGUUAACA | 97 |
| ANGLPTL3 | CCTACCAACCTTACCTTTTC | 35 | CCUACCAACCUUACCUUUUC | 98 |
| ANGLPTL3 | TATATAGAGTTAAGAAGTCT | 36 | UAUAUAGAGUUAAGAAGUCU | 99 |
| ANGLPTL3 | AACGTGGAACTGTTTTCTTC | 37 | AACGUGGAACUGUUUUCUUC | 100 |
| ANGLPTL3 | ATTTTCAATTTCAAGCAACG | 38 | AUUUUCAAUUUCAAGCAACG | 101 |
| ANGLPTL3 | ATTCTGGAGGAAATAACTAG | 39 | AUUCUGGAGGAAAUAACUAG | 102 |
| ANGLPTL3 | GCAAATCTTGATTTGGCTC | 40 | GCAAAUCUUGAUUUUGGCUC | 103 |
| ANGLPTL3 | AGCCAATGGCCTCCTTCAGT | 41 | AGCCAAUGGCCUCCUUCAGU | 104 |
| ANGLPTL3 | TAAGACCATGTCCCAACTGA | 42 | UAAGACCAUGUCCCAACUGA | 105 |
| ANGLPTL3 | AGACTTTGTCCATAAGACGA | 43 | AGACUUUGUCCAUAAGACGA | 106 |
| APOC3 | GGGGCACCCGTCCAGCTCCG | 44 | GGGGCACCCGUCCAGCUCCG | 107 |
| APOC3 | TGACCTTTGCCCAGCGCCCT | 45 | UGACCUUUGCCCAGCGCCCU | 108 |
| APOC3 | TCCAGATGCAGCAAGCGGGC | 46 | UCCAGAUGCAGCAAGCGGGC | 109 |
| APOC3 | TAGGGATGAACTGAGCAGAC | 47 | UAGGGAUGAACUGAGCAGAC | 110 |
| APOC3 | AGAAGCACTTGCTAGAGCTA | 48 | AGAAGCACUUGCUAGAGCUA | 111 |
| APOC3 | CTGCTCCAGGTAATGCCCTC | 49 | CUGCUCCAGGUAAUGCCCUC | 112 |
| APOC3 | GGGAGAGTTGGGAAATCCCT | 50 | GGGAGAGUUGGGAAAUCCCU | 113 |
| APOC3 | AGGAAGCCTCGGAGCTGGAC | 51 | AGGAAGCCUCGGAGCUGGAC | 114 |
| APOC3 | CCCTGGAGATGATATAAAAC | 52 | CCCUGGAGAUGAUAUAAAAC | 115 |
| APOC3 | TCATAACCTGAAGAACATGG | 53 | UCAUAACCUGAAGAACAUGG | 116 |

TABLE 3-continued

Genes, target site sequences, and gRNA spacer sequences

| Target Gene | target site (protospacer) sequence | target SEQ ID | gRNA spacer sequence | RNA spacer SEQ ID |
|---|---|---|---|---|
| APOB | GTCCATCGCCAGCTGCGGTG | 54 | GUCCAUCGCCAGCUGCGGUG | 117 |
| APOB | GGCGCCCGCACCCCATTTAT | 55 | GGCGCCCGCACCCCAUUUAU | 118 |
| APOB | CAGAGCGGCCGCGCACTCAC | 56 | CAGAGCGGCCGCGCACUCAC | 119 |
| APOB | CTCAGCGGCAGCAACCGAGA | 57 | CUCAGCGGCAGCAACCGAGA | 120 |
| APOB | TCCCGGTGGGAATGCGCGGC | 58 | UCCCGGUGGGAAUGCGCGGC | 121 |
| APOB | GCATTCCCACCGGGACCTGC | 59 | GCAUUCCCACCGGGACCUGC | 122 |
| APOB | GCCTCGCGGCCCTGGCTGGC | 60 | GCCUCGCGGCCCUGGCUGGC | 123 |
| APOB | CCCGGCCAACCTCGTGCCGC | 61 | CCCGGCCAACCUCGUGCCGC | 124 |
| APOB | AGCGCCAGCAGCGCGGGCCT | 62 | AGCGCCAGCAGCGCGGGCCU | 125 |
| APOB | CTCCCTCTGCGCCCGCAGAG | 63 | CUCCCUCUGCGCCCGCAGAG | 126 |
| PCSK9 | GTCGAGGCGCTCATGGTTGC | 306 | GUCGAGGCGCUCAUGGUUGC | 318 |
| PCSK9 | TTCCAGCCCAGTTAGGATTT | 307 | UUCCAGCCCAGUUAGGAUUU | 319 |
| PCSK9 | TCCTAACTGGGCTGGAAGGC | 308 | UCCUAACUGGGCUGGAAGGC | 320 |
| PCSK9 | TCAGGAGCAGGGCGCGTGAA | 309 | UCAGGAGCAGGGCGCGUGAA | 321 |
| PCSK9 | CAGCGACGTCGAGGCGCTCA | 310 | CAGCGACGUCGAGGCGCUCA | 322 |
| PCSK9 | CCGTCAGCTCCAGGCGGTCC | 311 | CCGUCAGCUCCAGGCGGUCC | 323 |
| PCSK9 | AACCTGATCCTCCAGTCCGG | 312 | AACCUGAUCCUCCAGUCCGG | 324 |
| PCSK9 | TCATGGGCACCGTCAGCTCC | 313 | UCAUGGGCACCGUCAGCUCC | 325 |
| PCSK9 | CCGCCGGCGTGGACCGCGCA | 314 | CCGCCGGCGUGGACCGCGCA | 326 |
| PCSK9 | GAAGGCAGGCCGGCGCCCTA | 315 | GAAGGCAGGCCGGCGCCCUA | 327 |
| PCSK9 | GCGCCTTGAGCCTTGCGGTG | 316 | GCGCCUUGAGCCUUGCGGUG | 328 |
| PCSK9 | CCCGCACCTTGGCGCAGCGG | 317 | CCCGCACCUUGGCGCAGCGG | 329 |
| MYLIP | GCACTGCGGCGGCAGCCGGG | 342 | GCACUGCGGCGGCAGCCGGG | 352 |
| MYLIP | GGCGCCACCGCGGAGGACAG | 343 | GGCGCCACCGCGGAGGACAG | 353 |
| MYLIP | ATGCTCATAGGATGTATTCA | 344 | AUGCUCAUAGGAUGUAUUCA | 354 |
| MYLIP | CCACAATAAACACATGGTCT | 345 | CCACAAUAAACACAUGGUCU | 355 |
| MYLIP | GGGTCCCACCAGTGACAAGG | 346 | GGGUCCCACCAGUGACAAGG | 356 |
| MYLIP | GGACTGCCTCAACCAGGTGA | 347 | GGACUGCCUCAACCAGGUGA | 357 |

TABLE 3-continued

Genes, target site sequences, and gRNA spacer sequences

| Target Gene | target site (protospacer) sequence | target SEQ ID | gRNA spacer sequence | RNA spacer SEQ ID |
|---|---|---|---|---|
| MYLIP | CAGAGTCCCTGTCGCAGCGC | 348 | CAGAGUCCCUGUCGCAGCGC | 358 |
| MYLIP | CTCAGAGTGAGCGATCGCCC | 349 | CUCAGAGUGAGCGAUCGCCC | 359 |
| MYLIP | CTGAGTTTCCCTGGCCGCCC | 350 | CUGAGUUUCCCUGGCCGCCC | 360 |
| MYLIP | GTTTCCCTGGCCGCCCCGGG | 351 | GUUUCCCUGGCCGCCCCGGG | 361 |
| APOB | TGAGGGCCTCCCACTCTACA | 372 | UGAGGGCCUCCCACUCUACA | 378 |
| APOB | CCAGAGCACTGAAGACGCTT | 373 | CCAGAGCACUGAAGACGCUU | 379 |
| APOB | ACTGGAGGAAACCTAGAAGC | 374 | ACUGGAGGAAACCUAGAAGC | 380 |
| APOB | CACTGAAGACGCTTGGGGAA | 375 | CACUGAAGACGCUUGGGGAA | 381 |
| APOB | TGAAGAAGGCACCCCTGGTC | 376 | UGAAGAAGGCACCCCUGGUC | 382 |
| APOB | TGAGTGCGCGGCCGCTCTGC | 377 | UGAGUGCGCGGCCGCUCUGC | 383 |

TABLE 4

Genes and gene-targeting gRNAs

| Target gene | gRNA sequence | SEQ ID |
|---|---|---|
| PCSK9 | GCGCGUAAUCUGACGCUGUUGUUUAAGAGCUAUGCUGGAAACAGCAUAGCAAGUUUAAAUAAGGCUAGUCCGUUAUCAACUUGAAAAAGUGGCACCGAGUCGGUGC | 127 |
| PCSK9 | AUCAGAUAGGAUCGUCCGAUGUUUAAGAGCUAUGCUGGAAACAGCAUAGCAAGUUUAAAUAAGGCUAGUCCGUUAUCAACUUGAAAAAGUGGCACCGAGUCGGUGC | 128 |
| PCSK9 | AGGUUUCCGCAGCGACGUCGGUUUAAGAGCUAUGCUGGAAACAGCAUAGCAAGUUUAAAUAAGGCUAGUCCGUUAUCAACUUGAAAAAGUGGCACCGAGUCGGUGC | 129 |
| PCSK9 | GGGCGCCGCCGUUCAGUUCAGUUUAAGAGCUAUGCUGGAAACAGCAUAGCAAGUUUAAAUAAGGCUAGUCCGUUAUCAACUUGAAAAAGUGGCACCGAGUCGGUGC | 130 |
| PCSK9 | GGUGCUAGCCUUGCGUUCCGGUUUAAGAGCUAUGCUGGAAACAGCAUAGCAAGUUUAAAUAAGGCUAGUCCGUUAUCAACUUGAAAAAGUGGCACCGAGUCGGUGC | 131 |
| PCSK9 | CAUUAACGGAACCCCCGGACGUUUAAGAGCUAUGCUGGAAACAGCAUAGCAAGUUUAAAUAAGGCUAGUCCGUUAUCAACUUGAAAAAGUGGCACCGAGUCGGUGC | 132 |
| PCSK9 | AGGAUCGUCCGAUGGGGCUCGUUUAAGAGCUAUGCUGGAAACAGCAUAGCAAGUUUAAAUAAGGCUAGUCCGUUAUCAACUUGAAAAAGUGGCACCGAGUCGGUGC | 133 |
| PCSK9 | CCGUUAAUGUUUAAUCAGAUGUUUAAGAGCUAUGCUGGAAACAGCAUAGCAAGUUUAAAUAAGGCUAGUCCGUUAUCAACUUGAAAAAGUGGCACCGAGUCGGUGC | 134 |
| PCSK9 | CGUAAUCUGACGCUGUUUGGUUUAAGAGCUAUGCUGGAAACAGCAUAGCAAGUUUAAAUAAGGCUAGUCCGUUAUCAACUUGAAAAAGUGGCACCGAGUCGGUGC | 135 |

TABLE 4-continued

Genes and gene-targeting gRNAs

| Target gene | gRNA sequence | SEQ ID |
|---|---|---|
| PCSK9 | GGUGUGGGUGCUUGACGCCUGUUUAAGAGCUAUGCUGGAAACAGCAU AGCAAGUUUAAAUAAGGCUAGUCCGUUAUCAACUUGAAAAAGUGGCA CCGAGUCGGUGC | 136 |
| PCSK9 | ACCCACUGCACGCUGGACAGGUUUAAGAGCUAUGCUGGAAACAGCAU AGCAAGUUUAAAUAAGGCUAGUCCGUUAUCAACUUGAAAAAGUGGCA CCGAGUCGGUGC | 137 |
| PCSK9 | GCACAGUAACAACCCCUGGUGUUUAAGAGCUAUGCUGGAAACAGCAU AGCAAGUUUAAAUAAGGCUAGUCCGUUAUCAACUUGAAAAAGUGGCA CCGAGUCGGUGC | 138 |
| PCSK9 | CCAUCCAUUCUUUCUCUAGGGUUUAAGAGCUAUGCUGGAAACAGCAU AGCAAGUUUAAAUAAGGCUAGUCCGUUAUCAACUUGAAAAAGUGGCA CCGAGUCGGUGC | 139 |
| LPA | AAGGAGACAUAAAGGCAAUGGUUUAAGAGCUAUGCUGGAAACAGCA UAGCAAGUUUAAAUAAGGCUAGUCCGUUAUCAACUUGAAAAAGUGGC ACCGAGUCGGUGC | 140 |
| LPA | GGCAAUGUGGAGCAGCUGAGGUUUAAGAGCUAUGCUGGAAACAGCAU AGCAAGUUUAAAUAAGGCUAGUCCGUUAUCAACUUGAAAAAGUGGCA CCGAGUCGGUGC | 141 |
| LPA | GGAGCAGCUGAGGGGGAAAGUUUAAGAGCUAUGCUGGAAACAGCA UAGCAAGUUUAAAUAAGGCUAGUCCGUUAUCAACUUGAAAAAGUGGC ACCGAGUCGGUGC | 142 |
| LPA | UGUCAAUAGAUGCUGGGAAGGUUUAAGAGCUAUGCUGGAAACAGCA UAGCAAGUUUAAAUAAGGCUAGUCCGUUAUCAACUUGAAAAAGUGGC ACCGAGUCGGUGC | 143 |
| LPA | AGUGCAAUGUCAAUAGAUGCGUUUAAGAGCUAUGCUGGAAACAGCAU AGCAAGUUUAAAUAAGGCUAGUCCGUUAUCAACUUGAAAAAGUGGCA CCGAGUCGGUGC | 144 |
| LPA | UUUAUAAGACUCUAUAUUCAGUUUAAGAGCUAUGCUGGAAACAGCAU AGCAAGUUUAAAUAAGGCUAGUCCGUUAUCAACUUGAAAAAGUGGCA CCGAGUCGGUGC | 145 |
| LPA | CAUGUAAGUCAACAAUGUCCGUUUAAGAGCUAUGCUGGAAACAGCAU AGCAAGUUUAAAUAAGGCUAGUCCGUUAUCAACUUGAAAAAGUGGCA CCGAGUCGGUGC | 146 |
| LPA | GUCAACAAUGUCCUGGGAUUGUUUAAGAGCUAUGCUGGAAACAGCAU AGCAAGUUUAAAUAAGGCUAGUCCGUUAUCAACUUGAAAAAGUGGCA CCGAGUCGGUGC | 147 |
| LPA | CAUAUACAAGAUUUUGAACUGUUUAAGAGCUAUGCUGGAAACAGCAU AGCAAGUUUAAAUAAGGCUAGUCCGUUAUCAACUUGAAAAAGUGGCA CCGAGUCGGUGC | 148 |
| LPA | GCACCGUGACAGUCUUCACGGUUUAAGAGCUAUGCUGGAAACAGCAU AGCAAGUUUAAAUAAGGCUAGUCCGUUAUCAACUUGAAAAAGUGGCA CCGAGUCGGUGC | 149 |
| MYLIP | UUGGCGGGGACCCGAGCUGAGUUUAAGAGCUAUGCUGGAAACAGCAU AGCAAGUUUAAAUAAGGCUAGUCCGUUAUCAACUUGAAAAAGUGGCA CCGAGUCGGUGC | 150 |
| MYLIP | CUGUCGCAGCGCAGGCAGUUGUUUAAGAGCUAUGCUGGAAACAGCAU AGCAAGUUUAAAUAAGGCUAGUCCGUUAUCAACUUGAAAAAGUGGCA CCGAGUCGGUGC | 151 |
| MYLIP | GCUGGAGUGCGGCGCCACCGGUUUAAGAGCUAUGCUGGAAACAGCAU AGCAAGUUUAAAUAAGGCUAGUCCGUUAUCAACUUGAAAAAGUGGCA CCGAGUCGGUGC | 152 |
| MYLIP | CGGCGCCACCGCGGAGGACAGUUUAAGAGCUAUGCUGGAAACAGCAU AGCAAGUUUAAAUAAGGCUAGUCCGUUAUCAACUUGAAAAAGUGGCA CCGAGUCGGUGC | 153 |
| MYLIP | CAGCUCUGCGGACCCUUGUCGUUUAAGAGCUAUGCUGGAAACAGCAU AGCAAGUUUAAAUAAGGCUAGUCCGUUAUCAACUUGAAAAAGUGGCA CCGAGUCGGUGC | 154 |

TABLE 4-continued

Genes and gene-targeting gRNAs

| Target gene | gRNA sequence | SEQ ID |
|---|---|---|
| MYLIP | CCCCGCGCACACCAAAGAGAGUUUAAGAGCUAUGCUGGAAACAGCAU AGCAAGUUUAAAUAAGGCUAGUCCGUUAUCAACUUGAAAAAGUGGCA CCGAGUCGGUGC | 155 |
| MYLIP | CCUCGUCACAUAACACAGCAGUUUAAGAGCUAUGCUGGAAACAGCAU AGCAAGUUUAAAUAAGGCUAGUCCGUUAUCAACUUGAAAAAGUGGCA CCGAGUCGGUGC | 156 |
| MYLIP | ACCUCCAUCAGCACCGCGUCGUUUAAGAGCUAUGCUGGAAACAGCAU AGCAAGUUUAAAUAAGGCUAGUCCGUUAUCAACUUGAAAAAGUGGCA CCGAGUCGGUGC | 157 |
| MYLIP | GGAGGCGAAAGCCAACGGCGGUUUAAGAGCUAUGCUGGAAACAGCAU AGCAAGUUUAAAUAAGGCUAGUCCGUUAUCAACUUGAAAAAGUGGCA CCGAGUCGGUGC | 158 |
| MYLIP | GUUGAGGCAGUCCUCGCCGUGUUUAAGAGCUAUGCUGGAAACAGCAU AGCAAGUUUAAAUAAGGCUAGUCCGUUAUCAACUUGAAAAAGUGGCA CCGAGUCGGUGC | 159 |
| ANGPTL3 | UACAUUCGUGCAAGUUAACAGUUUAAGAGCUAUGCUGGAAACAGCAU AGCAAGUUUAAAUAAGGCUAGUCCGUUAUCAACUUGAAAAAGUGGCA CCGAGUCGGUGC | 160 |
| ANGPTL3 | CCUACCAACCUUACCUUUUCGUUUAAGAGCUAUGCUGGAAACAGCAU AGCAAGUUUAAAUAAGGCUAGUCCGUUAUCAACUUGAAAAAGUGGCA CCGAGUCGGUGC | 161 |
| ANGPTL3 | UAUAUAGAGUUAAGAAGUCUGUUUAAGAGCUAUGCUGGAAACAGCA UAGCAAGUUUAAAUAAGGCUAGUCCGUUAUCAACUUGAAAAAGUGGC ACCGAGUCGGUGC | 162 |
| ANGPTL3 | AACGUGGAACUGUUUUCUUCGUUUAAGAGCUAUGCUGGAAACAGCAU AGCAAGUUUAAAUAAGGCUAGUCCGUUAUCAACUUGAAAAAGUGGCA CCGAGUCGGUGC | 163 |
| ANGPTL3 | AUUUUCAAUUUCAAGCAACGGUUUAAGAGCUAUGCUGGAAACAGCAU AGCAAGUUUAAAUAAGGCUAGUCCGUUAUCAACUUGAAAAAGUGGCA CCGAGUCGGUGC | 164 |
| ANGPTL3 | AUUCUGGAGGAAAUAACUAGGUUUAAGAGCUAUGCUGGAAACAGCA UAGCAAGUUUAAAUAAGGCUAGUCCGUUAUCAACUUGAAAAAGUGGC ACCGAGUCGGUGC | 165 |
| ANGPTL3 | GCAAAUCUUGAUUUUGGCUCGUUUAAGAGCUAUGCUGGAAACAGCAU AGCAAGUUUAAAUAAGGCUAGUCCGUUAUCAACUUGAAAAAGUGGCA CCGAGUCGGUGC | 166 |
| ANGPTL3 | AGCCAAUGGCCUCCUUCAGUGUUUAAGAGCUAUGCUGGAAACAGCAU AGCAAGUUUAAAUAAGGCUAGUCCGUUAUCAACUUGAAAAAGUGGCA CCGAGUCGGUGC | 167 |
| ANGPTL3 | UAAGACCAUGUCCCAACUGAGUUUAAGAGCUAUGCUGGAAACAGCAU AGCAAGUUUAAAUAAGGCUAGUCCGUUAUCAACUUGAAAAAGUGGCA CCGAGUCGGUGC | 168 |
| ANGPTL3 | AGACUUUGUCCAUAAGACGAGUUUAAGAGCUAUGCUGGAAACAGCAU AGCAAGUUUAAAUAAGGCUAGUCCGUUAUCAACUUGAAAAAGUGGCA CCGAGUCGGUGC | 169 |
| APOC3 | GGGGCACCCGUCCAGCUCCGGUUUAAGAGCUAUGCUGGAAACAGCAU AGCAAGUUUAAAUAAGGCUAGUCCGUUAUCAACUUGAAAAAGUGGCA CCGAGUCGGUGC | 170 |
| APOC3 | UGACCUUUGCCCAGCGCCCUGUUUAAGAGCUAUGCUGGAAACAGCAU AGCAAGUUUAAAUAAGGCUAGUCCGUUAUCAACUUGAAAAAGUGGCA CCGAGUCGGUGC | 171 |
| APOC3 | UCCAGAUGCAGCAAGCGGGCGUUUAAGAGCUAUGCUGGAAACAGCAU AGCAAGUUUAAAUAAGGCUAGUCCGUUAUCAACUUGAAAAAGUGGCA CCGAGUCGGUGC | 172 |
| APOC3 | UAGGGAUGAACUGAGCAGACGUUUAAGAGCUAUGCUGGAAACAGCAU AGCAAGUUUAAAUAAGGCUAGUCCGUUAUCAACUUGAAAAAGUGGCA CCGAGUCGGUGC | 173 |

TABLE 4-continued

Genes and gene-targeting gRNAs

| Target gene | gRNA sequence | SEQ ID |
|---|---|---|
| APOC3 | AGAAGCACUUGCUAGAGCUAGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 174 |
| APOC3 | CUGCUCCAGGUAAUGCCCUCGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 175 |
| APOC3 | GGGAGAGUUGGGAAAUCCCUGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 176 |
| APOC3 | AGGAAGCCUCGGAGCUGGACGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 177 |
| APOC3 | CCCUGGAGAUGAUAUAAAACGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 178 |
| APOC3 | UCAUAACCUGAAGAACAUGGGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 179 |
| APOB | GUCCAUCGCCAGCUGCGGUGGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 180 |
| APOB | GGCGCCCGCACCCCAUUUAUGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 181 |
| APOB | CAGAGCGGCCGCGCACUCACGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 182 |
| APOB | CUCAGCGGCAGCAACCGAGAGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 183 |
| APOB | UCCCGGUGGGAAUGCGCGGCGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 184 |
| APOB | GCAUUCCCACCGGGACCUGCGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 185 |
| APOB | GCCUCGCGGCCCUGGCUGGCGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 186 |
| APOB | CCCGGCCAACCUCGUGCCGCGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 187 |
| APOB | AGCGCCAGCAGCGCGGGCCUGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 188 |
| APOB | CUCCCUCUGCGCCCGCAGAGGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 189 |
| PCSK9 | GUCGAGGCGCUCAUGGUUGCGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 330 |
| PCSK9 | UUCCAGCCCAGUUAGGAUUUGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 331 |
| PCSK9 | UCCUAACUGGGCUGGAAGGCGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 332 |

TABLE 4-continued

Genes and gene-targeting gRNAs

| Target gene | gRNA sequence | SEQ ID |
|---|---|---|
| PCSK9 | UCAGGAGCAGGGCGCGUGAAGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 333 |
| PCSK9 | CAGCGACGUCGAGGCGCUCAGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 334 |
| PCSK9 | CCGUCAGCUCCAGGCGGUCCGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 335 |
| PCSK9 | AACCUGAUCCUCCAGUCCGGGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 336 |
| PCSK9 | UCAUGGGCACCGUCAGCUCCGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 337 |
| PCSK9 | CCGCCGGCGUGGACCGCGCAGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 338 |
| PCSK9 | GAAGGCAGGCCGGCGCCCUAGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 339 |
| PCSK9 | GCGCCUUGAGCCUUGCGGUGGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 340 |
| PCSK9 | CCCGCACCUUGGCGCAGCGGGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 341 |
| MYLIP | GCACUGCGGCGGCAGCCGGGGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 362 |
| MYLIP | GGCGCCACCGCGGAGGACAGGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 363 |
| MYLIP | AUGCUCAUAGGAUGUAUUCAGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 364 |
| MYLIP | CCACAAUAAACACAUGGUCUGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 365 |
| MYLIP | GGGUCCCACCAGUGACAAGGGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 366 |
| MYLIP | GGACUGCCUCAACCAGGUGAGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 367 |
| MYLIP | CAGAGUCCCUGUCGCAGCGCGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 368 |
| MYLIP | CUCAGAGUGAGCGAUCGCCCGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 369 |
| MYLIP | CUGAGUUUCCCUGGCCGCCCGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 370 |
| MYLIP | GUUUCCUGGCCGCCCCGGGUUUAAGAGCUAUGCUGGAAACAGCAU<br>AGCAAGUUUAAAUAAGGCUAGUCCGUUAUCAACUUGAAAAAGUGGCA<br>CCGAGUCGGUGC | 371 |

TABLE 4-continued

Genes and gene-targeting gRNAs

| Target gene | gRNA sequence | SEQ ID |
|---|---|---|
| APOB | UGAGGGCCUCCCACUCUACAGUUUAAGAGCUAUGCUGGAAACAGCAUAGCAAGUUUAAAUAAGGCUAGUCCGUUAUCAACUUGAAAAAGUGGCACCGAGUCGGUGC | 384 |
| APOB | CCAGAGCACUGAAGACGCUUGUUUAAGAGCUAUGCUGGAAACAGCAUAGCAAGUUUAAAUAAGGCUAGUCCGUUAUCAACUUGAAAAAGUGGCACCGAGUCGGUGC | 385 |
| APOB | ACUGGAGGAAACCUAGAAGCGUUUAAGAGCUAUGCUGGAAACAGCAUAGCAAGUUUAAAUAAGGCUAGUCCGUUAUCAACUUGAAAAAGUGGCACCGAGUCGGUGC | 386 |
| APOB | CACUGAAGACGCUUGGGGAAGUUUAAGAGCUAUGCUGGAAACAGCAUAGCAAGUUUAAAUAAGGCUAGUCCGUUAUCAACUUGAAAAAGUGGCACCGAGUCGGUGC | 387 |
| APOB | UGAAGAAGGCACCCCUGGUCGUUUAAGAGCUAUGCUGGAAACAGCAUAGCAAGUUUAAAUAAGGCUAGUCCGUUAUCAACUUGAAAAAGUGGCACCGAGUCGGUGC | 388 |
| APOB | UGAGUGCGCGGCCGCUCUGCGUUUAAGAGCUAUGCUGGAAACAGCAUAGCAAGUUUAAAUAAGGCUAGUCCGUUAUCAACUUGAAAAAGUGGCACCGAGUCGGUGC | 389 |

In some embodiments, a gRNA provided herein targets PCSK9 or a DNA regulatory element thereof. In some embodiments the gRNA targets a target site that is located within 500 bp of human genome assembly GRCh38 (hg38) genomic coordinates chr1:55,039,548 (e.g., a target site that is +500 of 55,039,548 or –500 of 55,039,548 or positions between the foregoing). In some embodiments, the gRNA targets a target site that is within 400 bp, 300 bp, 200 bp, 100 bp, 80 bp, 60 bp, 50 bp, 40 bp, 30 bp or 20 bp of genomic coordinates chr1:55,039,548. In some embodiments the gRNA targets a target site that is located within about 80 bp of the genomic coordinate chr1:55,039,548. In some embodiments, the gRNA targets a target site in the region from –40 to +40 of the genomic coordinate chr1:55,039,548. In some embodiments the gRNA targets a target site that is located within 20 bp of the genomic coordinate chr1:55,039,548. In some embodiments, the gRNA targets a target site in the region from –10 to +10 of the genomic coordinate chr1:55,039,548. In some embodiments, any of such target sites include or span the genomic coordinate chr1:55,039,548, which is a PCSK9 transcription start site (TSS). In some embodiments, the gRNA targets a target site that is within or overlaps the coordinates chr1: 55,039,538-55,039,557. In some embodiments, the target site is or includes the coordinates chr1: 55,039,538-55,039,557. In some embodiments, a provided epigenetic-modifying DNA-targeting system for epigenetic modification of PCSK9, or a multiplexed epigenetic-modifying DNA-targeting system for epigenetic modification of at least two genes including PCSK9, includes any of the aforementioned gRNAs complexed with a Cas protein, such as a Cas9 protein. In some embodiments, the Cas9 is a dCas9. In some embodiments, the dCas9 is a dSpCas9, such as a dSpCas9 set forth in SEQ ID NO: 207, or a variant and/or fusion thereof.

In some embodiments, the gRNA targets a target site in PCSK9 or a DNA regulatory element thereof that comprises the sequence selected from any one of SEQ ID NO:1-13 or 306-317, a contiguous portion thereof of at least 14 nucleotides (e.g. 14, 15, 16, 17, 18 or 19 nucleotides), a complementary sequence of any of the foregoing, or a sequence having at or at least 80%, 85%, 90%, 91%, 92%, 93%, 94%, 95%, 96%, 97%, 98%, 99%, 99.5%, 99.9%, or 100% sequence identity to any of the foregoing. In some embodiments, the gRNA comprises a spacer sequence comprising the sequence selected from any one of SEQ ID NO:64-76 or 318-329, a contiguous portion thereof of at least 14 nt (e.g. 14, 15, 16, 17, 18 or 19 nucleotides), or a sequence having at or at least 80%, 85%, 90%, 91%, 92%, 93%, 94%, 95%, 96%, 97%, 98%, 99%, 99.5%, 99.9%, or 100% sequence identity to any of the foregoing. In some embodiments, the gRNA further comprises a scaffold sequence. In some embodiments, the scaffold sequence comprises the sequence set forth in SEQ ID NO:191, or a sequence having at or at least 80%, 85%, 90%, 91%, 92%, 93%, 94%, 95%, 96%, 97%, 98%, 99%, 99.5%, 99.9%, or 100% sequence identity to SEQ ID NO:191. In some embodiments, the gRNA, including a spacer sequence and a scaffold sequence, comprises the sequence selected from any one of SEQ ID NO:127-139 or 330-341, or a sequence having at or at least 80%, 85%, 90%, 91%, 92%, 93%, 94%, 95%, 96%, 97%, 98%, 99%, 99.5%, 99.9%, or 100% sequence identity to all or a portion thereof. In some embodiments, the gRNA targeting PCSK9 or a DNA regulatory element thereof, is set forth in the sequence selected from any one of SEQ ID NO:127-139 or 330-341. In some embodiments, a provided epigenetic-modifying DNA-targeting system for epigenetic modification of PCSK9, or a multiplexed epigenetic-modifying DNA-targeting system for epigenetic modification of at least two genes including PCSK9, includes any of the aforementioned gRNAs complexed with a Cas protein, such as a Cas9 protein. In some embodiments, the Cas9 is a dCas9. In some embodiments, the dCas9 is a dSpCas9, such as a dSpCas9 set forth in SEQ ID NO: 207, or a variant and/or fusion thereof.

In a particular embodiments, the gRNA targets a target site in the PCSK9 promoter. In some embodiments, the target site is or includes the sequence set forth in SEQ ID NO:3. In some embodiments, a gRNA provided herein comprises a spacer sequence set forth in SEQ ID NO:66. In some embodiments, the gRNA further comprises a scaffold sequence set forth in SEQ ID NO: 191. In some embodiments, the gRNA comprises the sequence set forth in SEQ ID NO:129, or a sequence having at or at least 80%, 85%, 90%, 91%, 92%, 93%, 94%, 95%, 96%, 97%, 98%, 99%, 99.5%, 99.9%, or 100% sequence identity to SEQ ID NO: 129. In some embodiments, the gRNA is set forth in SEQ ID NO: 129. In some embodiments, the gRNA is the gRNA designated PCSK9-C. In some embodiments, the gRNA targeting PCSK9 or a DNA regulatory element thereof, is set forth in the sequence selected from any one of SEQ ID NO:127-139 or 330-341. In some embodiments, a provided epigenetic-modifying DNA-targeting system for epigenetic modification of PCSK9, or a multiplexed epigenetic-modifying DNA-targeting system for epigenetic modification of at least two genes including PCSK9, includes any of the aforementioned gRNAs complexed with a Cas protein, such as a Cas9 protein. In some embodiments, the Cas9 is a dCas9. In some embodiments, the dCas9 is a dSpCas9, such as a dSpCas9 set forth in SEQ ID NO: 207, or a variant and/or fusion thereof.

In some embodiments, a gRNA provided herein targets LPA or a DNA regulatory element thereof. In some embodiments, the gRNA targets a target site that is located within 500 bp of the hg38 genomic coordinates chr6:160,664,275. In some embodiments, the gRNA targets a target site in LPA or a DNA regulatory element thereof that comprises the sequence selected from any one of SEQ ID NO:14-23, a contiguous portion thereof of at least 14 nucleotides (e.g. 14, 15, 16, 17, 18 or 19 nucleotides), a complementary sequence of any of the foregoing, or a sequence having at or at least 80%, 85%, 90%, 91%, 92%, 93%, 94%, 95%, 96%, 97%, 98%, 99%, 99.5%, 99.9%, or 100% sequence identity to any of the foregoing. In some embodiments, the gRNA comprises a spacer sequence comprising the sequence selected from any one of SEQ ID NO:77-86, a contiguous portion thereof of at least 14 nt (e.g. 14, 15, 16, 17, 18 or 19 nucleotides), or a sequence having at or at least 80%, 85%, 90%, 91%, 92%, 93%, 94%, 95%, 96%, 97%, 98%, 99%, 99.5%, 99.9%, or 100% sequence identity to any of the foregoing. In some embodiments, the gRNA further comprises a scaffold sequence. In some embodiments, the scaffold sequence comprises the sequence set forth in SEQ ID NO:191, or a sequence having at or at least 80%, 85%, 90%, 91%, 92%, 93%, 94%, 95%, 96%, 97%, 98%, 99%, 99.5%, 99.9%, or 100% sequence identity to SEQ ID NO:191. In some embodiments, the gRNA, including a spacer sequence and a scaffold sequence, comprises the sequence selected from any one of SEQ ID NO:140-149, or a sequence having at or at least 80%, 85%, 90%, 91%, 92%, 93%, 94%, 95%, 96%, 97%, 98%, 99%, 99.5%, 99.9%, or 100% sequence identity to all or a portion thereof. In some embodiments, the gRNA targeting LPA or a DNA regulatory element thereof, is set forth in the sequence selected from any one of SEQ ID NO:140-149. In some embodiments, a provided epigenetic-modifying DNA-targeting system for epigenetic modification of LPA, or a multiplexed epigenetic-modifying DNA-targeting system for epigenetic modification of at least two genes including LPA, includes any of the aforementioned gRNAs complexed with a Cas protein, such as a Cas9 protein. In some embodiments, the Cas9 is a dCas9. In some embodiments, the dCas9 is a dSpCas9, such as a dSpCas9 set forth in SEQ ID NO: 207, or a variant and/or fusion thereof.

In some embodiments, a gRNA provided herein targets MYLIP or a DNA regulatory element thereof. In some embodiments, the gRNA targets a target site that is located within 500 bp of the hg38 genomic coordinates chr6:16,129,086. In some embodiments, the gRNA targets a target site in MYLIP or a DNA regulatory element thereof that comprises the sequence selected from any one of SEQ ID NO:24-33 or 342-351, a contiguous portion thereof of at least 14 nucleotides (e.g. 14, 15, 16, 17, 18 or 19 nucleotides), a complementary sequence of any of the foregoing, or a sequence having at or at least 80%, 85%, 90%, 91%, 92%, 93%, 94%, 95%, 96%, 97%, 98%, 99%, 99.5%, 99.9%, or 100% sequence identity to any of the foregoing. In some embodiments, the gRNA comprises a spacer sequence comprising the sequence selected from any one of SEQ ID NO:87-96 or 352-361, a contiguous portion thereof of at least 14 nt (e.g. 14, 15, 16, 17, 18 or 19 nucleotides), or a sequence having at or at least 80%, 85%, 90%, 91%, 92%, 93%, 94%, 95%, 96%, 97%, 98%, 99%, 99.5%, 99.9%, or 100% sequence identity to any of the foregoing. In some embodiments, the gRNA further comprises a scaffold sequence. In some embodiments, the scaffold sequence comprises the sequence set forth in SEQ ID NO:191, or a sequence having at or at least 80%, 85%, 90%, 91%, 92%, 93%, 94%, 95%, 96%, 97%, 98%, 99%, 99.5%, 99.9%, or 100% sequence identity to SEQ ID NO:191. In some embodiments, the gRNA, including a spacer sequence and a scaffold sequence, comprises the sequence selected from any one of SEQ ID NO:150-159 or 362-371, or a sequence having at or at least 80%, 85%, 90%, 91%, 92%, 93%, 94%, 95%, 96%, 97%, 98%, 99%, 99.5%, 99.9%, or 100% sequence identity to all or a portion thereof. In some embodiments, the gRNA targeting MYLIP or a DNA regulatory element thereof, is set forth in the sequence selected from any one of SEQ ID NO:150-159 or 362-371. In some embodiments, a provided epigenetic-modifying DNA-targeting system for epigenetic modification of MYLIP, or a multiplexed epigenetic-modifying DNA-targeting system for epigenetic modification of at least two genes including MYLIP, includes any of the aforementioned gRNAs complexed with a Cas protein, such as a Cas9 protein. In some embodiments, the Cas9 is a dCas9. In some embodiments, the dCas9 is a dSpCas9, such as a dSpCas9 set forth in SEQ ID NO: 207, or a variant and/or fusion thereof.

In some embodiments, a gRNA provided herein targets ANGPTL3 or a DNA regulatory element thereof. In some embodiments, the gRNA targets a target site that is located within 500 bp of the hg38 genomic coordinates chr1:62,597,520. In some embodiments, the gRNA targets a target site in ANGPTL3 or a DNA regulatory element thereof that comprises the sequence selected from any one of SEQ ID NO:34-43, a contiguous portion thereof of at least 14 nucleotides (e.g. 14, 15, 16, 17, 18 or 19 nucleotides), a complementary sequence of any of the foregoing, or a sequence having at or at least 80%, 85%, 90%, 91%, 92%, 93%, 94%, 95%, 96%, 97%, 98%, 99%, 99.5%, 99.9%, or 100% sequence identity to any of the foregoing. In some embodiments, the gRNA comprises a spacer sequence comprising the sequence selected from any one of SEQ ID NO:97-106, a contiguous portion thereof of at least 14 nt (e.g. 14, 15, 16, 17, 18 or 19 nucleotides), or a sequence having at or at least 80%, 85%, 90%, 91%, 92%, 93%, 94%, 95%, 96%, 97%, 98%, 99%, 99.5%, 99.9%, or 100% sequence identity to any of the foregoing. In some embodiments, the gRNA further comprises a scaffold sequence. In some embodiments, the scaffold sequence comprises the sequence set forth in SEQ ID NO:191, or a sequence having at or at least 80%, 85%, 90%, 91%, 92%, 93%, 94%, 95%, 96%, 97%, 98%, 99%, 99.5%, 99.9%, or 100% sequence identity to SEQ ID NO:191. In some embodiments, the gRNA, including a spacer sequence and a scaffold sequence, comprises the sequence selected from any one of SEQ ID NO:160-169, or a sequence having at or at least 80%, 85%, 90%, 91%, 92%, 93%, 94%, 95%, 96%, 97%, 98%, 99%, 99.5%, 99.9%, or 100% sequence identity to all or a portion thereof. In some embodiments, the gRNA targeting ANGPTL3 or a DNA regulatory element thereof, is set forth in the sequence selected from any one of SEQ ID NO:160-169. In some embodiments, a provided epigenetic-modifying DNA-targeting system for epigenetic modification of ANGPTL3, or a multiplexed epigenetic-modifying DNA-targeting system for epigenetic modification of at least two genes including ANGPTL3, includes any of the aforementioned gRNAs complexed with a Cas protein, such as a Cas9 protein. In some embodiments, the Cas9 is a dCas9. In some embodiments, the dCas9 is a dSpCas9, such as a dSpCas9 set forth in SEQ ID NO: 207, or a variant and/or fusion thereof.

In some embodiments, a gRNA provided herein targets APOC3 or a DNA regulatory element thereof. In some embodiments, the gRNA targets a target site that is located within 500 bp of the hg38 genomic coordinates chr11:116,829,907. In some embodiments, the gRNA targets a target site in APOC3 or a DNA regulatory element thereof that comprises the sequence selected from any one of SEQ ID NO:44-53, a contiguous portion thereof of at least 14 nucleotides (e.g. 14, 15, 16, 17, 18 or 19 nucleotides), a complementary sequence of any of the foregoing, or a sequence having at or at least 80%, 85%, 90%, 91%, 92%, 93%, 94%, 95%, 96%, 97%, 98%, 99%, 99.5%, 99.9%, or 100% sequence identity to any of the foregoing. In some embodiments, the gRNA comprises a spacer sequence comprising the sequence selected from any one of SEQ ID NO:107-116, a contiguous portion thereof of at least 14 nt (e.g. 14, 15, 16, 17, 18 or 19 nucleotides), or a sequence having at or at least 80%, 85%, 90%, 91%, 92%, 93%, 94%, 95%, 96%, 97%, 98%, 99%, 99.5%, 99.9%, or 100% sequence identity to any of the foregoing. In some embodiments, the gRNA further comprises a scaffold sequence. In some embodiments, the scaffold sequence comprises the sequence set forth in SEQ ID NO:191, or a sequence having at or at least 80%, 85%, 90%, 91%, 92%, 93%, 94%, 95%, 96%, 97%, 98%, 99%, 99.5%, 99.9%, or 100% sequence identity to SEQ ID NO:191. In some embodiments, the gRNA, including a spacer sequence and a scaffold sequence, comprises the sequence selected from any one of SEQ ID NO:170-179, or a sequence having at or at least 80%, 85%, 90%, 91%, 92%, 93%, 94%, 95%, 96%, 97%, 98%, 99%, 99.5%, 99.9%, or 100% sequence identity to all or a portion thereof. In some embodiments, the gRNA targeting APOC3 or a DNA regulatory element thereof, is set forth in the sequence selected from any one of SEQ ID NO:170-179. In some embodiments, a provided epigenetic-modifying DNA-targeting system for epigenetic modification of APOC3, or a multiplexed epigenetic-modifying DNA-targeting system for epigenetic modification of at least two genes including APOC3, includes any of the aforementioned gRNAs complexed with a Cas protein, such as a Cas9 protein. In some embodiments, the Cas9 is a dCas9. In some embodiments, the dCas9 is a dSpCas9, such as a dSpCas9 set forth in SEQ ID NO: 207, or a variant and/or fusion thereof.

In some embodiments, a gRNA provided herein targets APOB or a DNA regulatory element thereof. In some embodiments, the gRNA targets a target site that is located within 500 bp of the hg38 genomic coordinates chr2:21,044,073. In some embodiments, the gRNA targets a target site in APOB or a DNA regulatory element thereof that comprises the sequence selected from any one of SEQ ID NO:54-63 or 372-377, a contiguous portion thereof of at least 14 nucleotides (e.g. 14, 15, 16, 17, 18 or 19 nucleotides), a complementary sequence of any of the foregoing, or a sequence having at or at least 80%, 85%, 90%, 91%, 92%, 93%, 94%, 95%, 96%, 97%, 98%, 99%, 99.5%, 99.9%, or 100% sequence identity to any of the foregoing. In some embodiments, the gRNA comprises a spacer sequence comprising the sequence selected from any one of SEQ ID NO:117-126 or 378-383, a contiguous portion thereof of at least 14 nt (e.g. 14, 15, 16, 17, 18 or 19 nucleotides), or a sequence having at or at least 80%, 85%, 90%, 91%, 92%, 93%, 94%, 95%, 96%, 97%, 98%, 99%, 99.5%, 99.9%, or 100% sequence identity to any of the foregoing. In some embodiments, the gRNA further comprises a scaffold sequence. In some embodiments, the scaffold sequence comprises the sequence set forth in SEQ ID NO:191, or a sequence having at or at least 80%, 85%, 90%, 91%, 92%, 93%, 94%, 95%, 96%, 97%, 98%, 99%, 99.5%, 99.9%, or 100% sequence identity to SEQ ID NO:191. In some embodiments, the gRNA, including a spacer sequence and a scaffold sequence, comprises the sequence selected from any one of SEQ ID NO:180-189 or 384-389, or a sequence having at or at least 80%, 85%, 90%, 91%, 92%, 93%, 94%, 95%, 96%, 97%, 98%, 99%, 99.5%, 99.9%, or 100% sequence identity to all or a portion thereof. In some embodiments, the gRNA targeting APOB or a DNA regulatory element thereof, is set forth in the sequence selected from any one of SEQ ID NO:180-189 or 384-389. In some embodiments, a provided epigenetic-modifying DNA-targeting system for epigenetic modification of APOB, or a multiplexed epigenetic-modifying DNA-targeting system for epigenetic modification of at least two genes including APOB, includes any of the aforementioned gRNAs complexed with a Cas protein, such as a Cas9 protein. In some embodiments, the Cas9 is a dCas9. In some embodiments, the dCas9 is a dSpCas9, such as a dSpCas9 set forth in SEQ ID NO: 207, or a variant and/or fusion thereof.

In some embodiments, provided herein is a combination of gRNAs. In some embodiments, provided herein is a multiplexed epigenetic-modifying DNA-targeting system comprising the combination of gRNAs.

In some embodiments, the combination of gRNAs comprises at least two gRNAs targeting at least two different genes. In some embodiments, the combination of gRNAs comprises a first gRNA targeted to a first gene and a second gRNA targeted to a second gene. In some embodiments, the first gRNA targets a gene selected from the list consisting of PCSK9, LPA, MYLIP, ANGPTL3, APOC3, and APOB, the second gRNA targets a gene selected from the list consisting of PCSK9, LPA, MYLIP, ANGPTL3, APOC3, and APOB, and the first and second gRNAs target different genes. In some embodiments, the first gRNA targets PCSK9 and the second gRNA targets a gene selected from the list consisting of LPA, MYLIP, ANGPTL3, APOC3, and APOB. In some embodiments, the first gRNA targets PCSK9 and the second gRNA targets LPA. In some embodiments, the first gRNA and second gRNA target a combination of two genes selected from the combinations of genes listed in Table 1. In some embodiments, the first gRNA and second gRNA are each independently selected from any of the gRNAs described herein.

In some embodiments, the combination of gRNAs comprises at least three gRNAs targeting at least three different genes. In some embodiments, the combination of gRNAs comprises a first gRNA targeted to a first gene, a second gRNA targeted to a second gene, and a third gRNA targeted to a third gene. In some embodiments, the first gRNA targets a gene selected from the list consisting of PCSK9, LPA, MYLIP, ANGPTL3, APOC3, and APOB, the second gRNA targets a gene selected from the list consisting of PCSK9, LPA, MYLIP, ANGPTL3, APOC3, and APOB, the third gRNA targets a gene selected from the list consisting of PCSK9, LPA, MYLIP, ANGPTL3, APOC3, and APOB, and the first, second, and third gRNA each target a different gene. In some embodiments, the first gRNA targets PCSK9, the second gRNA targets a gene selected from the list consisting of LPA, MYLIP, ANGPTL3, APOC3, and APOB, the third gRNA targets a gene selected from the list consisting of LPA, MYLIP, ANGPTL3, APOC3, and APOB, and the second gRNA and third gRNA target different genes. In some embodiments, the first gRNA targets PCSK9, the second gRNA targets LPA, and the third gRNA targets a gene selected from the list consisting of MYLIP, ANGPTL3, APOC3, and APOB. In some embodiments, the first gRNA, second gRNA, and third gRNA target a combination of three genes selected from the combinations of genes listed in Table 2. In some embodiments, the first gRNA, second gRNA, and third gRNA are each independently selected from any of the gRNAs described herein.

C. Other DNA-Binding Domains

In some of any of the provided embodiments, the DNA-binding domain comprises a zinc finger protein (ZFP); a transcription activator-like effector (TALE); a meganuclease; a homing endonuclease; or an I-SceI enzyme or a variant thereof. In some embodiments, the DNA-binding domain comprises a catalytically inactive variant of any of the foregoing.

In some embodiments, a ZFP, a zinc finger DNA binding protein, or zinc finger DNA binding domain, is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Among the ZFPs are artificial, or engineered, ZFPs, comprising ZFP domains targeting specific DNA sequences, typically 9-18 nucleotides long, generated by assembly of individual fingers. ZFPs include those in which a single finger domain is approximately 30 amino acids in length and contains an alpha helix containing two invariant histidine residues coordinated through zinc with two cysteines of a single beta turn, and having two, three, four, five, or six fingers. Generally, sequence-specificity of a ZFP may be altered by making amino acid substitutions at the four helix positions (—1, 2, 3, and 6) on a zinc finger recognition helix. Thus, for example, the ZFP or ZFP-containing molecule is non-naturally occurring, e.g., is engineered to bind to a target site of choice.

In some embodiments, zinc fingers are custom-designed (i.e. designed by the user), or obtained from a commercial source. Various methods for designing zinc finger proteins are available. For example, methods for designing zinc finger proteins to bind to a target DNA sequence of interest are described, for example in Liu, Q. et al., PNAS, 94(11): 5525-30 (1997); Wright, D. A. et al., Nat. Protoc., 1(3): 1637-52 (2006); Gersbach, C. A. et al., Acc. Chem. Res., 47(8):2309-18 (2014); Bhakta M. S. et al., Methods Mol. Biol., 649:3-30 (2010); and Gaj et al., Trends Biotechnol, 31(7):397-405 (2013). In addition, various web-based tools for designing zinc finger proteins to bind to a DNA target sequence of interest are publicly available. See, for example, the Zinc Finger Tools design web site from Scripps available on the world wide web at scripps.edu/barbas/zfdesign/zfdesignhome.php. Various commercial services for designing zinc finger proteins to bind to a DNA target sequence of interest are also available. See, for example, the commercially available services or kits offered by Creative Biolabs (world wide web at creative-biolabs.com/Design-and-Synthesis-of-Artificial-Zinc-Finger-Proteins.html), the Zinc Finger Consortium Modular Assembly Kit available from Addgene (world wide web at addgene.org/kits/zfc-modular-assembly/), or the CompoZr Custom ZFN Service from Sigma Aldrich (world wide web at sigmaaldrich.com/life-science/zinc-finger-nuclease-technology/custom-zfn.html).

Transcription activator-like effectors (TALEs), are proteins naturally found in *Xanthomonas* bacteria. TALEs comprise a plurality of repeated amino acid sequences, each repeat having binding specificity for one base in a target sequence. Each repeat comprises a pair of variable residues in position 12 and 13 (repeat variable diresidue; RVD) that determine the nucleotide specificity of the repeat. In some embodiments, RVDs associated with recognition of the different nucleotides are HD for recognizing C, NG for recognizing T, NI for recognizing A, NN for recognizing G or A, NS for recognizing A, C, G or T, HG for recognizing T, IG for recognizing T, NK for recognizing G, HA for recognizing C, ND for recognizing C, HI for recognizing C, HN for recognizing G, NA for recognizing G, SN for recognizing G or A and YG for recognizing T, TL for recognizing A, VT for recognizing A or G and SW for recognizing A. In some embodiments, RVDs can be mutated towards other amino acid residues in order to modulate their specificity towards nucleotides A, T, C and G and in particular to enhance this specificity. Binding domains with similar modular base-per-base nucleic acid binding properties can also be derived from different bacterial species. These alternative modular proteins may exhibit more sequence variability than TALE repeats.

In some embodiments, a "TALE DNA binding domain" or "TALE" is a polypeptide comprising one or more TALE repeat domains/units. The repeat domains, each comprising a repeat variable diresidue (RVD), are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. TALE proteins may be designed to bind to a target site using canonical or non-canonical RVDs within the repeat units. See, e.g., U.S. Pat. Nos. 8,586,526 and 9,458,205.

In some embodiments, a TALE is a fusion protein comprising a nucleic acid binding domain derived from a TALE and an effector domain.

Zinc finger and TALE DNA-binding domains can be engineered to bind to a predetermined nucleotide sequence, for example via engineering (altering one or more amino acids) of the recognition helix region of a naturally occurring zinc finger protein, by engineering of the amino acids in a TALE repeat involved in DNA binding (the repeat variable diresidue or RVD region), or by systematic ordering of modular DNA-binding domains, such as TALE repeats or ZFP domains. Therefore, engineered zinc finger proteins or TALE proteins are proteins that are non-naturally occurring. Non-limiting examples of methods for engineering zinc finger proteins and TALEs are design and selection. A designed protein is a protein not occurring in nature whose design/composition results principally from rational criteria. Rational criteria for design include application of substitution rules and computerized algorithms for processing information in a database storing information of existing ZFP or TALE designs (canonical and non-canonical RVDs) and binding data. See, for example, U.S. Pat. Nos. 9,458,205; 8,586,526; 6,140,081; 6,453,242; and 6,534,261; see also WO 98/53058; WO 98/53059; WO 98/53060; WO 02/016536 and WO 03/016496.

D. Effector Domains

In some aspects, the DNA-targeting systems provided herein further include one or more effector domains. In some embodiments, provided herein is a DNA-targeting system comprising a fusion protein comprising: (a) a DNA-binding domain capable of being targeted to a target site in a gene or regulatory DNA element thereof, such as any described above, and (b) at least one effector domain. In some aspects, the effector domain is capable of reducing transcription of the gene or combination of genes. In some aspects, the effector domain comprises a transcription repressor domain.

In some aspects, the effector domain induces, catalyzes, or leads to repressed and/or reduced transcription of a gene when ectopically recruited to the gene or DNA regulatory element thereof.

In some embodiments, the effector domain induces, catalyzes or leads to transcription repression, transcription co-repression, histone modification, histone acetylation, histone deacetylation, nucleosome remodeling, chromatin remodeling, heterochromatin formation, proteolysis, ubiquitination, deubiquitination, phosphorylation, dephosphorylation, splicing, DNA methylation, DNA demethylation, histone methylation, histone demethylation, or DNA base oxidation. In some embodiments, the effector domain induces, catalyzes, or leads to transcription repression or transcription co-repression. In some embodiments, the effector domain induces transcription repression. In some embodiments, the effector domain has one of the aforementioned activities itself (i.e. acts directly). In some embodiments, the effector domain recruits and/or interacts with a protein or polypeptide domain that has one of the aforementioned activities (i.e. acts indirectly).

Gene expression of endogenous mammalian genes, such as human genes, can be achieved by targeting a fusion protein comprising a DNA-binding domain, such as a dCas9, and an effector domain, such as a transcription repression domain, to mammalian genes or regulatory DNA elements thereof (e.g. a promoter or enhancer) via one or more gRNAs. Any of a variety of effector domains for transcriptional repression (e.g. transcription repression domains) are known and can be used in accord with the provided embodiments. Transcription repression domains, as well as transcriptional repression of target genes using Cas fusion proteins with the transcription repression domains, are described, for example, in WO 2014/197748, WO 2017/180915, WO 2021/226077, WO 2013/176772, WO 2014/152432, WO 2014/093661, Adli, M. Nat. Commun. 9, 1911 (2018), and Gilbert, L. A. et al. Cell 154(2): 442-451 (2013).

In some embodiments, the effector domain may comprise a KRAB domain, ERF repressor domain, MXI1 domain, SID4X domain, MAD-SID domain, a DNMT family protein domain (e.g. DNMT3A or DNMT3B), a fusion of one or more DNMT family proteins or domains thereof (e.g. DNMT3A/L, which comprises a fusion of DNMT3A and DNMT3L domains), LSD1, EZH2, a SunTag domain, a partially or fully functional fragment or domain of any of the foregoing, or a combination of any of the foregoing. For example, the fusion protein may be dCas9-KRAB, or dCas9-KRAB-DNMT3A/L. In some embodiments, the fusion protein may be dCas9-KRAB. In some embodiments, the fusion protein may be DNMT3A/L-dCas9-KRAB. In some embodiments, the fusion protein may be KRAB-dCas9-DNMT3A/L.

In some embodiments, the effector domain comprises a transcriptional repressor domain described in WO 2021/226077.

In some embodiments, the effector domain comprises a KRAB domain, or a variant thereof. The KRAB-containing zinc finger proteins make up the largest family of transcriptional repressors in mammals. The Krüppel associated box (KRAB) domain is a transcriptional repressor domain present in many zinc finger protein-based transcription factors. The KRAB domain comprises charged amino acids and can be divided into sub-domains A and B. The KRAB domain recruits corepressors KAP1 (KRAB-associated protein-1), epigenetic readers such as heterochromatin protein 1 (HP1), and other chromatin modulators to induce transcriptional repression through heterochromatin formation. KRAB-mediated gene repression is associated with loss of histone H3-acetylation and an increase in H3 lysine 9 trimethylation (H3K9me3) at the repressed gene promoters. KRAB domains, including in dCas fusion proteins, have been described, for example, in WO 2017/180915, WO 2014/197748, US 2019/0127713, WO 2013/176772, Urrutia R. et al. Genome Biol. 4, 231 (2003), Groner A. C. et al. PLoS Genet. 6, e1000869 (2010). In some embodiments, the effector domain comprises at least one KRAB domain or a variant thereof. In some embodiments, an exemplary KRAB domain is set forth in SEQ ID NO: 193. In some embodiments, the effector domain comprises the sequence set forth in SEQ ID NO: 193, or a portion thereof, or an amino acid sequence that has at least 90%, 91%, 92%, 93%, 94%, 95%, 96%, 97%, 98%, or 99% sequence identity to SEQ ID NO:193. In some embodiments, an exemplary KRAB domain is set forth in SEQ ID NO: 290. In some embodiments, the effector domain comprises the sequence set forth in SEQ ID NO: 290, or a portion thereof, or an amino acid sequence that has at least 90%, 91%, 92%, 93%, 94%, 95%, 96%, 97%, 98%, or 99% sequence identity to SEQ ID NO:290.

In some embodiments, the effector domain comprises at least one ERF repressor domain, or a variant thereof. ERF (ETS2 repressor factor) is a strong transcriptional repressor that comprises a conserved ets-DNA-binding domain, and represses transcription via a distinct domain at the carboxyl-terminus of the protein. ERF repressor domains, including in dCas fusion proteins, have been described, for example, in WO2017180915, WO2014197748, WO2013176772, Mavrothalassitis, G., Ghysdael, J. Proteins of the ETS family with transcriptional repressor activity. Oncogene 19, 6524-6532 (2000). In some embodiments, the effector domain comprises at least one ERF repressor domain or a variant thereof. An exemplary ERF repressor domain is set forth in SEQ ID NO:220. In some embodiments, the effector domain comprises the sequence set forth in SEQ ID NO:220, or a portion thereof, or an amino acid sequence that has at least 90%, 91%, 92%, 93%, 94%, 95%, 96%, 97%, 98%, or 99% sequence identity to any of the foregoing.

In some embodiments, the effector domain comprises at least one MXI1 domain, or a variant thereof. The MXI1 domain functions by antagonizing the myc transcriptional activity by competing for binding to myc-associated factor x (MAX). MXI1 domains, including in dCas fusion proteins, have been described, for example, in WO2017180915, WO2014197748, US20190127713. In some embodiments, the effector domain comprises at least one MXI1 domain or a variant thereof. An exemplary MXI1 domain is set forth in SEQ ID NO:221. In some embodiments, the effector domain comprises the sequence set forth in SEQ ID NO:221, or a portion thereof, or an amino acid sequence that has at least 90%, 91%, 92%, 93%, 94%, 95%, 96%, 97%, 98%, or 99% sequence identity to any of the foregoing.

In some embodiments, the effector domain comprises at least one SID4X domain, or a variant thereof. The mSin3 interacting domain (SID) is present on different transcription repressor proteins. It interacts with the paired amphipathic alpha-helix 2 (PAH2) domain of mSin3, a transcriptional repressor domain that is attached to transcription repressor proteins such as the mSin3 A corepressor. A dCas9 molecule can be fused to four concatenated mSin3 interaction domains (SID4X). SID domains, including in dCas fusion proteins, have been described, for example, in WO2017180915, WO2014197748, WO2014093655. In some embodiments, the effector domain comprises at least one SID domain or a variant thereof. An exemplary SID domain is set forth in SEQ ID NO:222. In some embodiments, the effector domain comprises the sequence set forth in SEQ ID NO:222, or a portion thereof, or an amino acid sequence that has at least 90%, 91%, 92%, 93%, 94%, 95%, 96%, 97%, 98%, or 99% sequence identity to any of the foregoing.

In some embodiments, the effector domain comprises at least one MAD domain, or a variant thereof. The MAD family proteins, Mad1, Mxi1, Mad3, and Mad4, belong to the basic helix-loop-helix-zipper class and contain a conserved N terminal region (termed Sin3 interaction domain (SID)) necessary for repressional activity. MAD-SID domains, including in dCas fusion proteins, have been described, for example, in WO2017180915, WO2014197748, WO2013176772. In some embodiments, the effector domain comprises at least one MAD-SID domain or a variant thereof. An exemplary MAD-SID domain is set forth in SEQ ID NO:223. In some embodiments, the effector domain comprises the sequence set forth in SEQ ID NO:223, or a portion thereof, or an amino acid sequence that has at least 90%, 91%, 92%, 93%, 94%, 95%, 96%, 97%, 98%, or 99% sequence identity to any of the foregoing.

In some embodiments, the effector domain comprises at least one DNMT3 domain, or a variant thereof. In some embodiments, the at least one DNMT3 domain, or a variant thereof, is from a DNMT3 or is a portion or a functionally active variant thereof with DNA methyltransferase activity. The DNMT3A and DNMT3B are two DNA methyltransferases that catalyze de novo methylation, which depending on the site may be associated with transcriptional repression. DNMTs, such as DNMT3s, mediate transfer of a methyl group from the universal methyl donor, S-adenosyl-L-methionine (SAM), to the 5-position of cytosine residues. In some aspects, these DNMT3 DNA methyltransferases induce de novo methylation of a cytosine base to methylated 5-methylcytosine. DNMT3, including in dCas fusion proteins, have been described, for example, in US20190127713, Liu, X. S. et al. Cell 167, 233-247. e17 (2016), Lei, Y. et al. Nat. Commun. 8, 16026 (2017). DNMT3 proteins, such as DNMT3A and DNMT3B, contain an N-terminal part that is naturally involved in regulatory activity and targeting, and a C-terminal catalytic domain termed the MTase C5-type domain. In some embodiments, an effector domain in embodiments provided herein includes a catalytically active portion of a DNMT3A or a DNMT3B that contains a catalytically active C-terminal domain. In particular, isolated catalytic domains of DNMT3a and DNMT3b are catalytically active (see e.g. Gowher and Jeltsch (2002) J. Biol. Chem., 277: 20409).

In some embodiments, the effector domain comprises at least one DNMT3 domain or a variant thereof. In some embodiments, the DNMT3 domain may be an effector domain of DNMT3A or DNMT3B that is catalytically active. In some embodiments, the effector domain may be the full-length of DNMT3A or DNMT3B or a catalytically active portion thereof. In some embodiments, the effector domain is a catalytically active portion that is less than the full-length sequence of DNMT3A or DNMT3B. In some embodiments, a catalytically active portion is a contiguous sequence of amino acids that confers DNA methyltransferase activity, such as by mediating methylation of a cytosine base to methylated 5-methylcytosine. In some embodiments, the contiguous sequence of amino acids is a contiguous C-terminal portion of a DNMT3 protein, such as DNMT3A, or DNMT3B, that is from 280 amino acids to 330 amino acids in length. In some embodiments, the contiguous portion is 280 amino acids, 290 amino acids, 300 amino acids, 310 amino acids, 320 amino acids, or 330 amino acids in length, or is a length of any value between any of the foregoing. In some embodiments, a catalytically active portion of a DNMT, such as a DNMT3, includes a SAM-dependent MTase C5-type domain. In some embodiments, the DNMT3 domain, such as a domain of DNMT3A or DNMT3B, is of human origin.

An exemplary DNMT3A domain is set forth in SEQ ID NO:195 or 285. An exemplary DNMT3B domain is set forth in SEQ ID NO:224. In some embodiments, the effector domain comprises the sequence set forth in SEQ ID NO: 195, SEQ ID NO: 285 or SEQ ID NO: 224, or a portion thereof, or an amino acid sequence that has at least 90%, 91%, 92%, 93%, 94%, 95%, 96%, 97%, 98%, or 99% sequence identity to any of the foregoing.

In some embodiments, the DNMT3A domain is set forth in SEQ ID NO:195, or is a catalytically active portion thereof, or is an amino acid sequence that has at least 90%, 91%, 92%, 93%, 94%, 95%, 96%, 97%, 98%, or 99% sequence identity to SEQ ID NO:195 or the catalytically active portion thereof that exhibits DNA methyltransferase activity. In some embodiments, the DNMT3A domain is set forth in SEQ ID NO:195. In some embodiments, the DNMT3A domain is encoded by the nucleotide sequence set forth in SEQ ID NO: 194.

In some embodiments, the DNMT3A domain is set forth in SEQ ID NO:285, or is a catalytically active portion thereof, or is an amino acid sequence that has at least 90%, 91%, 92%, 93%, 94%, 95%, 96%, 97%, 98%, or 99% sequence identity to SEQ ID NO:285 or the catalytically active portion thereof that exhibits DNA methyltransferase activity. In some embodiments, the DNMT3A domain is set forth in SEQ ID NO:285.

In some embodiments, the effector domain is from DNMT3B or a catalytically active portion or variant thereof that exhibits DNA methyltransferase activity. An exemplary DNMT3B domain is set forth in SEQ ID NO:224, or is a catalytically active portion thereof, or is an amino acid sequence that has at least 90%, 91%, 92%, 93%, 94%, 95%, 96%, 97%, 98%, or 99% sequence identity to SEQ ID NO:224 or the catalytically active portion thereof that exhibits DNA methyltransferase activity. In some embodiments, the catalytically active portion is a contiguous portion of amino acids of SEQ ID NO:224 that includes the SAM-dependent MTase C5-type domain (e.g. corresponding to amino acids 575-853 of SEQ ID NO:224). In some embodiments, the contiguous sequence of amino acids of SEQ ID NO: 224 includes at least 250 amino acids, 275 amino acids, 300 amino acids or 325 amino acids, or any value between any of the foregoing. In some embodiments, the contiguous sequence of amino acids is a contiguous portion of SEQ ID NO:224 that includes amino acids 575-853 and is from 280 amino acids to 330 amino acids in length. In some embodiments, the contiguous portion is 280 amino acids, 290 amino acids, 300 amino acids, 310 amino acids, 320 amino acids, or 330 amino acids in length, or is a length of any value between any of the foregoing.

Any of a variety of assays are known to assess or monitor methyltransferase (MTase) ativity. In some embodiments, exemplary assays to assess DNA methyltransferase activity include, but are not limited to, radio DNA MTase assays, colorimetric DNA MTase activity assays, fluorescent DNA MTase activity assays, chemiluminescent/bioluminescent DNA MTase activity assays, electrochemical DNA MTase activity assays, and elctrogenerated chemiluminescence (ECL) DNA MTase activity assays. Exemplary assays are described in Poh et al. Theranostics, 2016, 6:369-391; Li et al., Methods Appl. Fluoresc., 2017, 5: 012002; Deng et al., Anal Chem., 2014, 86:2117-23; and Ma et al. J Mater Chem B., 2020, 8: 3488-3501.

In some embodiments, the effector domain includes at least one DNMT3L domain, or a variant thereof. The DNMT3L domain or a variant thereof may be a DNMT3L or a portion of DNMT3L, or a variant of DNMT3L or the portion thereof. DNMT3L (DNA (cytosine-5)-methyltransferase 3-like) is a catalytically inactive regulatory factor of DNA methyltransferases that can either promote or inhibit DNA methylation depending on the context. DNMT3L is essential for the function of DNMT3A and DNMT3B; DNMT3L interacts with DNMT3A and DNMT3B and significantly enhances their catalytic activity. For instance, DNMT3L interacts with the catalytic domain of DNMT3A to form a heterodimer, demonstrating that DNMT3L has dual functions of binding an unmethylated histone tail and activating DNA methyltransferase. In some embodiments, reference to a portion or variant of a DNMT3L for purposes herein refers to a sufficient C-terminal sequence portion of DNMT3L that interacts with the catalytic domain of DNMT3A or DNMT3B and is able to stimulate or promote DNA methyltransferase activity of DNMT3A or DNMT3B (see e.g. Jia et al. Nature, 2007, 449:248-251; Gowher et al. J. Biol. Chem., 2005, 280: 13341-13348). In some embodiments, the DNMT3L or portion thereof is of animal origin. In some embodiments, the domain from DNMT3L is of murine origin. In some embodiments, the domain from DNMT3L is of human origin.

In some embodiments, the DNMT3L domain is a DNMT3L, or a C-terminal portion or variant thereof, that interacts with the catalytic domain of DNMT3A to form a heterodimer to provide for a more active DNA methyltransferase. In some embodiments, the effector domain is a fusion domain of a DNMT3A domain and the DNMT3L domain (DNMT3A/3L).

In some embodiments, the DNMT3L domain is a DNMT3L, or a C-terminal portion or variant thereof, that interacts with the catalytic domain of DNMT3B to form a heterodimer to provide for a more active DNA methyltransferase. In some embodiments, the effector domain is a fusion domain of a DNMT3B domain and the DNMT3L domain (DNMT3B/3L).

In some embodiments, the DNMT3L domain is a C-terminal portion of DNMT3L composed of a contiguous C-terminal portion of the full-length DNMT3L that does not include the N-terminal cysteine-rich ATRX-Dnmt3-Dnmt3L (ADD) domain (e.g. corresponding to residues 41-73 of SEQ ID NO: 197 or 75-207 of the sequence set forth in SEQ ID NO:289). In some embodiments, the DNMT3L domain is a contiguous C-terminal portion of DNMT3L that is less than 220 amino acids in length, such as between 100 and 215 amino acids, such as at or about 100, 110, 120, 130, 140, 150, 160, 170, 180, 190, 200, 210 or 215 amino acids in length, or a length between a value of any of the foregoing. In some embodiments, the DNMT3L domain is a contiguous C-terminal portion of DNMT3L that is 205, 206, 207, 208, 209, 210, 211, 212, 213, 214 or 215 amino acids in length.

An exemplary DNMT3L domain is set forth in SEQ ID NO:289, or is a portion thereof, or is an amino acid sequence that has at least 90%, 91%, 92%, 93%, 94%, 95%, 96%, 97%, 98%, or 99% sequence identity to SEQ ID NO:289 or the portion thereof. In some embodiments, the DNMT3L domain is a contiguous C-terminal portion of the full-length DNMT3L set forth in SEQ ID NO: 289 that does not include the N-terminal cysteine-rich ATRX-Dnmt3-Dnmt3L (ADD) domain (corresponding to residues 75-207 of the sequence set forth in SEQ ID NO:289). In some embodiments, the DNMT3L domain is a contiguous C-terminal portion of the full-length DNMT3L set forth in SEQ ID NO: 289 that is less than 220 amino acids in length, such as between 100 and 215 amino acids, such as at or about 100, 110, 120, 130, 140, 150, 160, 170, 180, 190, 200, 210 or 215 amino acids in length, or a length between a value of any of the foregoing. In some embodiments, the DNMT3L domain is a contiguous C-terminal portion of the full-length DNMT3L set forth in SEQ ID NO: 289 that is 205, 206, 207, 208, 209, 210, 211, 212, 213, 214 or 215 amino acids in length.

In some embodiments, the DNMT3L domain is set forth in SEQ ID NO:286, or is a portion thereof, or is an amino acid sequence that has at least 90%, 91%, 92%, 93%, 94%, 95%, 96%, 97%, 98%, or 99% sequence identity to SEQ ID NO:286. In some embodiments, the DNMT3L domain is set forth in SEQ ID NO:286. In some embodiments, the DNMT3L domain does not contain an N-terminal methionine, such as set forth in SEQ ID NO: 286.

In some embodiments, the DNMT3L domain is a human or humanized DNMT3L. Corresponding sequences of human DNMT3L are highly homologous to the DNMT3L derived from mouse and have a sequence identity of at least 90% with the murine sequence. It is within the level of a skilled artisan to humanize a non-human sequence of a DNMT3L domain, such as a domain of a murine DNMT3L. In some embodiments, the effector domain includes a DNMT3L domain that is a humanized variant of the murine DMT3L set forth in SEQ ID NO:289 or a portion thereof that is able to interact with DNMT3A or DNMT3A. In some embodiments, the effector domain includes a DNMT3L domain that is a humanized variant of the murine C-terminal portion of DNMT3L set forth in SEQ ID NO:286.

An exemplary DNMT3L domain of human origin is set forth in SEQ ID NO:197, or is a portion thereof, or is an amino acid sequence that has at least 90%, 91%, 92%, 93%, 94%, 95%, 96%, 97%, 98%, or 99% sequence identity to SEQ ID NO:197 or the portion thereof. In some embodiments, the DNMT3L domain is a contiguous C-terminal portion of the full-length DNMT3L set forth in SEQ ID NO: 197 that does not include the N-terminal cysteine-rich ATRX-Dnmt3-Dnmt3L (ADD) domain (corresponding to residues 41-73 of the sequence set forth in SEQ ID NO:197). In some embodiments, the DNMT3L domain is a contiguous C-terminal portion of the full-length DNMT3L set forth in SEQ ID NO: 197 that is less than 220 amino acids in length, such as between 100 and 215 amino acids, such as at or about 100, 110, 120, 130, 140, 150, 160, 170, 180, 190, 200, 210 or 215 amino acids in length, or a length between a value of any of the foregoing. In some embodiments, the DNMT3L domain is a contiguous C-terminal portion of the full-length DNMT3L set forth in SEQ ID NO: 197 that is 205, 206, 207, 208, 209, 210, 211, 212, 213, 214 or 215 amino acids in length.

An exemplary DNMT3L domain is set forth in SEQ ID NO:197. In some embodiments, a DNMT3L domain comprises the sequence set forth in SEQ ID NO:197, or a portion thereof, or an amino acid sequence that has at least 90%, 91%, 92%, 93%, 94%, 95%, 96%, 97%, 98%, or 99% sequence identity to SEQ ID NO:197. In some embodiments, the DNMT3L domain is encoded by the nucleotide sequence set forth in SEQ ID NO: 196.

In some embodiments, the DNMT3L domain comprises the sequence set forth in SEQ ID NO:287, or is a portion thereof, or is an amino acid sequence that has at least 90%, 91%, 92%, 93%, 94%, 95%, 96%, 97%, 98%, or 99% sequence identity to SEQ ID NO:287.

In some embodiments, the DNMT3L domain is set forth in SEQ ID NO:287. In some embodiments, the DNMT3L domain contains an N-terminal methionine.

In some embodiments, the effector domain comprises a fusion of DNMT3A and DNMT3L (DNMT3A/L). The fusion protein contains DNMT3A and DNMT3L domains that can be any as described above. In some embodiments, the fusion protein contains the DNMT3A domain set forth in SEQ ID NO: 195 and the DNMT3L domain set forth in SEQ ID NO: 289, arranged in any order. In some embodiments, the fusion protein contains the DNMT3A domain set forth in SEQ ID NO: 195 and the DNMT3L domain set forth in SEQ ID NO:286, arranged in any order. In some embodiments, the fusion protein contains the DNMT3A domain set forth in SEQ ID NO:195 and the DNMT3L domain set forth in SEQ ID NO:287, arranged in any order. In some embodiments, the fusion protein contains the DNMT3A domain set forth in SEQ ID NO: 285 and the DNMT3L domain set forth in SEQ ID NO: 289, arranged in any order. In some embodiments, the fusion protein contains the DNMT3A domain set forth in SEQ ID NO: 285 and the DNMT3L domain set forth in SEQ ID NO:286, arranged in any order. In some embodiments, the fusion protein contains the DNMT3A domain set forth in SEQ ID NO:285 and the DNMT3L domain set forth in SEQ ID NO:287, arranged in any order. In some embodiments, the DNMT3A and DNMT3L domains present in a provided fusion protein are separated from each other in the fusion protein by an intervening sequence, such as the DNA-binding domain, another effector domain or a linker. In some embodiments, the domains are either directly linked to each other or they are linked via a linker, such as a peptide linker. In some embodiments, the DNMT3A and DNMT3L domains are connected as a fusion domain via a linker that connects the DNMT3A domain and the DNMT3L domain. Exemplary linkers are described herein. In some embodiments, the linker is the linker set forth in SEQ ID NO: 288.

An exemplary DNMT3A/L fusion domain is set forth in SEQ ID NO:199. In some embodiments, the effector domain comprises the sequence set forth in SEQ ID NO:199, or a portion thereof, or an amino acid sequence that has at least 90%, 91%, 92%, 93%, 94%, 95%, 96%, 97%, 98%, or 99% sequence identity to SEQ ID NO: 199. In some embodiments, the DNMT3A/L fusion domain is encoded by the nucleotide sequence set forth is SEQ ID NO: 198.

An exemplary DNMT3A/L fusion domain is set forth in SEQ ID NO:201. In some embodiments, the effector domain comprises the sequence set forth in SEQ ID NO:201, or a portion thereof, or an amino acid sequence that has at least 90%, 91%, 92%, 93%, 94%, 95%, 96%, 97%, 98%, or 99% sequence identity to SEQ ID NO: 201. In some embodiments, the DNMT3A/L fusion domain is encoded by the nucleotide sequence set forth is SEQ ID NO: 200.

In some embodiments, the effector domain may comprise a LSD1 domain. LSD1 (also known as Lysine-specific histone demethylase 1A) is a histone demethylase that can demethylate lysine residues of histone H3, thereby acting as a coactivator or a corepressor, depending on the context. LSD1, including in dCas fusion proteins, has been described, for example, in WO 2013/176772, WO 2014/152432, and Kearns, N. A. et al. Nat. Methods. 12(5):401-403 (2015). An exemplary LSD1 polypeptide is set forth in SEQ ID NO:225. In some embodiments, the effector domain comprises the sequence set forth in SEQ ID NO:225, or a portion thereof, or an amino acid sequence that has at least 90%, 91%, 92%, 93%, 94%, 95%, 96%, 97%, 98%, or 99% sequence identity to any of the foregoing.

In some embodiments, the effector domain may comprise an EZH2 domain. EZH2 (also known as Histone-lysine N-methyltransferase EZH2) is a Catalytic subunit of the PRC2/EED-EZH2 complex, which methylates 'Lys-9' (H3K9me) and 'Lys-27' (H3K27me) of histone H3, in some aspects leading to transcriptional repression of the affected target gene. EZH2, including in dCas fusion proteins, has been described, for example, in O'Geen, H. et al., Epigenetics Chromatin. 12(1):26 (2019). An exemplary EZH2 polypeptide is set forth in SEQ ID NO:283. In some embodiments, the effector domain comprises the sequence set forth in SEQ ID NO:283, or a portion thereof, or an amino acid sequence that has at least 90%, 91%, 92%, 93%, 94%, 95%, 96%, 97%, 98%, or 99% sequence identity to any of the foregoing.

In some embodiments, the effector domain may comprise a SunTag domain. SunTag is a repeating peptide array, which can recruit multiple copies of an antibody-fusion protein that binds the repeating peptide. The antibody-fusion protein may comprise an additional effector domain, such as a transcription repression domain (e.g. KRAB), to reduce transcription of the target gene. SunTag, including in dCas fusion proteins for gene modulation have been described, for example, in WO 2016/011070 and Tanenbaum, M. et al. Cell. 159(3):635-646 (2014). An exemplary SunTag effector domain includes a repeating GCN4 peptide having the amino acid sequence LLPKNYHLENEVARLKKLVGER (SEQ ID NO: 226) separated by linkers having the amino acid sequence GGSGG (SEQ ID NO: 227). In some embodiments, the effector domain comprises at least one copy of the sequence set forth in SEQ ID NO: 226, or a portion thereof, or an amino acid sequence that has at least 90%, 91%, 92%, 93%, 94%, 95%, 96%, 97%, 98%, or 99% sequence identity to any of the foregoing. In some embodiments, the SunTag effector domain recruits an antibody-fusion protein that comprises KRAB and binds the GCN4 peptide.

E. Fusion Proteins

In some aspects, the DNA-targeting systems provided herein include fusion proteins. In some embodiments, provided herein is a DNA-targeting system that is a fusion protein comprising: (a) a DNA-binding domain capable of being targeted to a target site in a gene or regulatory DNA element thereof in which the gene encodes a gene product that regulates LDL, and (b) at least one effector domain. In some embodiments, provided herein is a DNA-targeting system comprising at least one DNA-targeting module, in which each of the at least one DNA-targeting module comprises a fusion protein comprising: (a) a DNA-binding domain capable of being targeted to a target site in a gene or regulatory DNA element thereof in which the gene encodes a gene product that regulates LDL, and (b) at least one effector domain. In some aspects, the fusion protein comprises at least one of any of the DNA-binding domains described herein, and at least one of any of the effector domains described herein. For instance, in some embodiments, the fusion protein contains a CRISPR-Cas DNA-binding domain, such as described in Section II.B, and at least one effector domain described herein. In some embodiments, the effector domain of a provided fusion protein is a transcriptional repressor domain, such as any described in Section I.D. In some aspects, the fusion protein is targeted to a target site in a gene or regulatory element thereof, and leads to reduced or repressed transcription of the gene. In some aspects, the fusion protein is targeted to target sites in a combination of genes or regulatory elements thereof, and leads to reduced or repressed transcription of each of the genes.

In some embodiments, the DNA-binding domain and effector domain of the fusion protein are heterologous, i.e. the domains are from different species, or at least one of the domains is not found in nature. In some aspects, the fusion protein is an engineered fusion protein, i.e. the fusion protein is not found in nature.

In some embodiments, the at least one effector domain is fused to the N-terminus, the C-terminus, or both the N-terminus and the C-terminus, of the DNA-binding domain or a component thereof. The at least one effector domain may be fused to the DNA-binding domain directly, or via any intervening amino acid sequence, such as a linker sequence or a nuclear localization sequence (NLS).

In some embodiments, the fusion protein of a provided DNA-binding system, or a DNA-targeting module thereof, comprises, from N- to C-terminal order: a transcriptional repressor effector domain and a DNA-binding domain. In some embodiments, the fusion protein of a provided DNA-binding system, or a DNA-targeting module thereof, comprises, from N- to C-terminal order: a DNA-binding domain and a transcriptional repressor effector domain.

In some embodiments, the at least one effector domain of the fusion protein includes more than one effector domains. In some embodiments, the fusion protein includes 2, 3 or 4 effector domains. In some embodiments, at least two of the effector domains of the fusion protein are different. In some embodiments, each of the effector domains of the fusion protein are different. In some embodiments, the at least one effector domain includes two effector domains in which the two effector domains are different. In some embodiments, the effector domains and the DNA-binding domain can be arranged in any order.

In some embodiments, the at least one effector domain of the fusion protein includes two different effector domains. The two different effector domains and the DNA-binding domain can be arranged in any order. In some embodiments, each of the effector domains are N-terminal to the DNA-binding domain in which a first effector domain is fused to the N-terminus of the second effector domain and the second effector domain is fused to the N-terminus of the DNA-binding domain. In some embodiments, the fusion protein of a provided DNA-binding system, or a DNA-targeting module thereof, comprises from N- to C-terminal order: a first transcriptional repressor effector domain, a second transcriptional repressor effector domain and the DNA binding domain. In some embodiments, each of the effector domains are C-terminal to the DNA-binding domain in which a first effector domain is fused to the C-terminus of the DNA-binding domain and the second effector domain is fused to the C-terminus of the first effector domain. In some embodiments, the fusion protein of a provided DNA-binding system, or a DNA-targeting module thereof, comprises from N- to C-terminal order: a DNA-binding domain, a first transcriptional repressor effector domain, and a second transcriptional repressor effector domain. In some embodiments, the DNA-binding domain is between the effector domains, in which one effector domain is fused to the N-terminus of the DNA-binding domain and the other effector domain is fused to the C-terminus of the DNA-binding domain. In some embodiments, the fusion protein of a provided DNA-binding system, or a DNA-targeting module thereof, comprises from N- to C-terminal order: a first transcriptional effector domain, a DNA-binding domain, and a second transcriptional repressor effector domain. In some embodiments, one or more of the components may be fused to eachother directly, or via any intervening amino acid sequence, such as via a linker sequence or a nuclear localization sequence (NLS).

In some embodiments, the fusion protein comprises one or more linkers. In some embodiments, the linker is a peptide linker. In some embodiments, the one or more linkers connect the DNA-binding domain or a component thereof to the at least one effector domain. A linker may be included anywhere in the polypeptide sequence of the fusion protein, for example, between the effector domain and the DNA-binding domain or a component thereof. A linker may be of any length and designed to promote or restrict the mobility of components in the fusion protein. A linker may comprise any amino acid sequence of about 2 to about 100, about 5 to about 80, about 10 to about 60, or about 20 to about 50 amino acids. A linker may comprise an amino acid sequence of at least about 2, 3, 4, 5, 10, 15, 20, 25, or 30 amino acids. A linker may comprise an amino acid sequence of less than about 100, 90, 80, 70, 60, 50, or 40 amino acids. A skilled artisan can readily choose an appropriate linker for the connection of two domains. In some embodiments, the linker is a flexible linker. Flexible linkers are generally composed of small, non-polar or polar residues such as glycine, serine or threonine. In some embodiments, the linker is the Gly$_4$Ser$_{(n)}$ linker, whereby n is an integer of 1 to 10. A linker may include sequential or tandem repeats of an amino acid sequence that is 2 to 20 amino acids in length. Linkers may be rich in amino acids glycine (G), serine (S), and/or alanine (A). Linkers may include, for example, a GS linker. An exemplary GS linker is represented by the sequence GGGGS (SEQ ID NO: 228). A linker may comprise repeats of a sequence, for example as represented by the formula (GGGGS)n, wherein n is an integer that represents the number of times the GGGGS sequence is repeated (e.g. between 1 and 10 times). The number of times a linker sequence is repeated can be adjusted to optimize the linker length and achieve appropriate separation of the functional domains. Other examples of linkers may include, for example, GGGGG (SEQ ID NO: 229), GGAGG (SEQ ID NO: 230), GGGGSSS (SEQ ID NO: 231), or GGGGAAA (SEQ ID NO: 232).

In some embodiments, artificial linker sequences can be used. In some embodiments, the linker is EASGSGRASP-GIPGSTR (SEQ ID NO: 293). In some embodiments, the linker is linker is GIHGVPAA (SEQ ID NO: 294). In some embodiments, the linker is SSGNSNAN-SRGPSFSSGLVPLSLRGSH (SEQ ID NO: 288). In some embodiments, the linker is KRPAATKKAGQAKKKKAS-DAKSLTAWS (SEQ ID NO: 298).

In some embodiments, inclusion of a SunTag linker in the fusion protein leads to enhanced repression of the target gene. In some embodiments, a SunTag linker comprises the sequence set forth in SEQ ID NO:226, or a portion thereof, or an amino acid sequence that has at least 90%, 91%, 92%, 93%, 94%, 95%, 96%, 97%, 98%, or 99% sequence identity to any of the foregoing.

In some embodiments, the linker is an XTEN linker. In some aspects, an XTEN linker is a recombinant polypeptide (e.g., an unstructured recombinant peptide) lacking hydrophobic amino acid residues. Exemplary XTEN linkers are described in, for example, Schellenberger et al., Nature Biotechnology 27, 1186-1190 (2009) or WO 2021/247570. In some embodiments, inclusion of a linker in the fusion protein leads to enhanced repression of the target gene. In some embodiments, a linker comprises the sequence set forth in SEQ ID NO:233, or a portion thereof, or an amino acid sequence that has at least 90%, 91%, 92%, 93%, 94%, 95%, 96%, 97%, 98%, or 99% sequence identity to SEQ ID NO:233. In some aspects, the linker comprises the sequence set forth in SEQ ID NO:233, or a contiguous portion of SEQ ID NO:233 of at least 5, 10, 15, 20, 25, 30, 35, 40, 45, 50, 55, 60, 65, 70 or 75 amino acids. In some aspects, the linker consists of the sequence set forth in SEQ ID NO:233, or a contiguous portion of SEQ ID NO:233 of at least 5, 10, 15, 20, 25, 30, 35, 40, 45, 50, 55, 60, 65, 70 or 75 amino acids. In some embodiments, the linker comprises the sequence set forth in SEQ ID NO:233. In some embodiments, the linker consists of the sequence set forth in SEQ ID NO:233. In some embodiments, a linker comprises the sequence set forth in SEQ ID NO:299, or a portion thereof, or an amino acid sequence that has at least 90%, 91%, 92%, 93%, 94%, 95%, 96%, 97%, 98%, or 99% sequence identity to any of the foregoing. In some aspects, the linker comprises the sequence set forth in SEQ ID NO:299, or a contiguous portion of SEQ ID NO:299 of at least 5, 10, or15 amino acids. In some aspects, the linker consists of the sequence set forth in SEQ ID NO:299, or a contiguous portion of SEQ ID NO:299 of at least 5, 10 or 15 amino acids. In some embodiments, the linker comprises the sequence set forth in SEQ ID NO:299. In some embodiments, the linker consists of the sequence set forth in SEQ ID NO:299. Appropriate linkers may be selected or designed based rational criteria known in the art, for example as described in Chen et al. Adv. Drug Deliv. Rev. 65(10):1357-1369 (2013). In some embodiments, a linker comprises a linker described in WO 2021/247570.

In some embodiments, the fusion protein of the DNA-targeting system, or a DNA-targeting module thereof, comprises one or more nuclear localization signals (NLS). In some embodiments, a fusion protein described herein comprises one or more nuclear localization sequences (NLSs), such as about or more than about 1, 2, 3, 4, 5, 6, 7, 8, 9, 10, or more NLSs. When more than one NLS is present, each may be selected independently of the others, such that a single NLS may be present in more than one copy and/or in combination with one or more other NLSs present in one or more copies. Non-limiting examples of NLSs include an NLS sequence derived from: the NLS of the SV40 virus large T-antigen, having the amino acid sequence PKKKRKV (SEQ ID NO: 234); the NLS from nucleoplasmin (e.g. the nucleoplasmin bipartite NLS with the sequence KRPAATKKAGQAKKKK (SEQ ID NO: 249)); the c-myc NLS having the amino acid sequence PAAKRVKLD (SEQ ID NO: 235) or RQRRNELKRSP (SEQ ID NO: 236); the hRNPA1 M9 NLS having the sequence NQSSNFGPMKGGNFGGRSSGPYGGGGQYFAK-PRNQGGY (SEQ ID NO: 237); the sequence RMRIZFKNKGKDTAELRRRRVEVSVELRKAKKD-EQILKRRNV (SEQ ID NO: 238) of the IBB domain from importin-alpha; the sequences VSRKRPRP (SEQ ID NO: 239) and PPKKARED (SEQ ID NO: 240) of the myoma T protein; the sequence PQPKKKPL (SEQ ID NO: 241) of human p53; the sequence SALIKKKKKMAP (SEQ ID NO: 242) of mouse c-abl IV; the sequences DRLRR (SEQ ID NO: 243) and PKQKKRK (SEQ ID NO: 244) of the influenza virus NS1; the sequence RKLKKKIKKL (SEQ ID NO: 245) of the Hepatitis virus delta antigen; the sequence REKKKFLKRR (SEQ ID NO: 246) of the mouse Mxl protein; the sequence KRKGDEVDGVDEVAKKKSKK (SEQ ID NO: 247) of the human poly(ADP-ribose) polymerase; and the sequence RKCLQAGMNLEARKTKK (SEQ ID NO: 248) of the steroid hormone receptors (human) glucocorticoid. The NLS may comprise a portion of any of the foregoing. In general, the one or more NLSs are of sufficient strength to drive accumulation of the fusion protein in a detectable amount in the nucleus of a eukaryotic cell. In general, strength of nuclear localization activity may derive from the number of NLSs in the fusion protein, the particular NLS(s) used, or a combination of these factors. Detection of accumulation in the nucleus may be performed by any suitable technique. For example, a detectable marker may be fused to the fusion protein, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of the fusion protein (e.g. an assay for altered gene expression activity in a cell transformed with the DNA-targeting system comprising the fusion protein), as compared to a control condition (e.g. an untransformed cell).

In some embodiments, the NLS is linked to the N-terminus or the C-terminus of the DNA-binding domain via a linker. In some embodiments, the NLS is linked to the N-terminus or the C-terminus of an effector domain via a linker. The linker may be any linker as described above. In some embodiments, the linker is GIHGVPAA (SEQ ID NO: 294). In some embodiments, the NLS and linker has the sequence PKKKRKVGIHGVPAA (SEQ ID NO: 291).

In some configurations, the N- or C-terminus of the fusion protein can be linked to a moiety for detection and/or purification. In some aspects, the moiety is or includes a Flag tag DYKDDDDK (SEQ ID NO:292), a 3×Flag tag MDYKDHDGDYKDHDI DYKDDDDK (SEQ ID NO: 295), an HA tag YPYDVPDYA (SEQ ID NO: 296) or a His tag, such as HHHHHH (SEQ ID NO: 297).

I. Split Fusion Proteins

In some embodiments, the fusion protein is a split protein, i.e. comprises two or more separate polypeptide domains that interact or self-assemble to form a functional fusion protein. In some aspects, the split fusion protein comprises a dCas9 and an effector domain. In some aspects, the fusion protein comprises a split dCas9-effector domain fusion protein.

In some embodiments, the split fusion protein is assembled from separate polypeptide domains comprising trans-splicing inteins. Inteins are internal protein elements that self-excise from their host protein and catalyze ligation of flanking sequences with a peptide bond. In some embodiments, the split fusion protein is assembled from a first polypeptide comprising an N-terminal intein and a second polypeptide comprising a C-terminal intein. In some embodiments, the N terminal intein Is the N terminal Npu Intein set forth in SEQ ID NO:300. In some embodiments, the C terminal intein is the C terminal Npu intein set forth in SEQ ID NO:302. In some embodiments, the N terminal intein is the N terminal Npu Intein encoded by the nucleotide sequence set forth in SEQ ID NO:305. In some embodiments, the C terminal intein is the C terminal Npu intein encoded by the nucleotide sequence set forth in SEQ ID NO:301.

In some embodiments, the split fusion protein comprises a split dCas9-effector domain fusion protein assembled from two polypeptides. In an exemplary embodiment, the first polypeptide comprises an effector catalytic domain and an N-terminal fragment of dSpCas9, followed by an N terminal Npu Intein (effector domain-dSpCas9-573N), and the second polypeptide comprises a C terminal Npu Intein, followed by a C-terminal fragment of dSpCas9 (dSpCas9-573C). In some embodiments, the C terminal Npu Intein, followed by a C-terminal fragment of dSpCas9 (dSpCas9-573C) is set forth in SEQ ID NO:304. In some embodiments, the C terminal Npu Intein, followed by a C-terminal fragment of dSpCas9 (dSpCas9-573C) is encoded by the nucleotide sequences set forth in SEQ ID NO:303. The N- and C-terminal fragments of the fusion protein are split at position 573Glu of the dSpCas9 molecule, with reference to SEQ ID NO: 206 (corresponding to residue 572Glu of the dSpCas9 molecule set forth in SEQ ID NO: 207). In some aspects, the N-terminal Npu Intein (SEQ ID NO:300) and C-terminal Npu Intein (set forth in SEQ ID NO:302) may self-excise and ligate the two fragments, thereby forming the full-length dSpCas9-effector domain fusion protein when expressed in a cell.

In some embodiments, the polypeptides of a split protein may interact non-covalently to form a complex that recapitulates the activity of the non-split protein. For example, two domains of a Cas enzyme expressed as separate polypeptides may be recruited by a gRNA to form a ternary complex that recapitulates the activity of the full-length Cas enzyme in complex with the gRNA, for example as described in Wright et al. PNAS 112(10):2984-2989 (2015). In some embodiments, assembly of the split protein is inducible (e.g. light inducible, chemically inducible, small-molecule inducible).

In some aspects, the two polypeptides of a split fusion protein may be delivered and/or expressed from separate vectors, such as any of the vectors described herein. In some embodiments, the two polypeptides of a split fusion protein may be delivered to a cell and/or expressed from two separate AAV vectors, i.e. using a split AAV-based approach, for example as described in WO 2017/197238.

Approaches for the rationale design of split proteins and their delivery, including Cas proteins and fusions thereof, are described, for example, in WO 2016/114972, WO 2017/197238, Zetsche. et al. Nat. Biotechnol. 33(2):139-42 (2015), Wright et al. PNAS 112(10):2984-2989 (2015), Truong. et al. Nucleic Acids Res. 43, 6450-6458 (2015), and Fine et al. Sci. Rep. 5, 10777 (2015).

2 Exemplary Fusion Proteins

In some embodiments, fusion proteins of provided DNA-targeting systems, or DNA-targeting modules thereof, are composed of a DNA-binding domain targeting to a target site in a gene that encodes a gene product that regulates LDL or a regulatory element thereof, and at least one transcriptional repressor effector domain. The DNA-binding domain and transcriptional repressor domain include any as described above. Exemplary fusion proteins are further described below.

In some embodiments, a fusion protein named herein comprises elements of the named fusion protein in any configuration or order, unless a particular SEQ ID NO is identified or a particular order is specified. For example, a dCas9-KRAB fusion protein may comprise a KRAB domain fused to the N- or C-terminus of a dSpCas9 molecule. In another example, a dSpCas9-KRAB-DNMT3A/L fusion protein may comprise dSpCas9, KRAB, and DNMT3A/L in any order. For example, a dSpCas9-KRAB-DNMT3A/L fusion protein may comprise from N-terminal to C-terminal, DNMT3A/L, dSpCas9, and KRAB. In some embodiments, the fusion protein of the DNA-targeting system comprises in N-terminal to C-terminal order dSpCas9-KRAB-DNMT3A/L. In some embodiments, the fusion protein of the DNA-targeting system comprises in N-terminal to C-terminal order DNMT3A/L-dSpCas9-KRAB. A fusion protein named herein may comprise additional elements. For example, a dSpCas9-KRAB-DNMT3A/L fusion protein may comprise one or more linkers, NLS sequences, or other sequences in any combination or order. Similar orientations of fusion proteins are provided in which a different dCas is employed as the DNA-binding domain instead of the exemplary dSpCas9. Any dCas is contemplated included any as described herein. In some embodiments, the DNA-binding domain is a dCas. In some embodiments, the dCas is a dCas9. In some embodiments, the dCas9 is a dSpCas9.

In some aspects, exemplary linkers or NLS sequences can be any described herein. In some aspects, exemplary linkers or NLS sequences can be positioned in any order between the DNA-binding domain (e.g. dSpCas9) and one or more effector domains (e.g., KRAB and DNMT3A/L). In aspects of any of the above embodiments, the NLS can be any as described, such as set forth in Section I.E. In aspects of any of the above embodiments, the linker can be any as described, such as set forth in Section I.E.

In some embodiments, a fusion protein of a DNA-targeting system, or a DNA-targeting module thereof, provided herein comprises a DNA-binding domain and a KRAB domain. In some embodiments, the DNA-binding domain is a catalytically inactive Cas enzyme (dCas). In some embodiments, the Cas is a dCas9, such as a dSaCas9 or a dSpCas9. In some embodiments, the DNA-binding domain is dSpCas9. In some embodiments, the DNA-binding domain is a dSpCas9 set forth in SEQ ID NO: 207 and the KRAB domain is set forth in SEQ ID NO:193. In some embodiments, the DNA-binding domain is a dSpCas9 set forth in SEQ ID NO: 207 and the KRAB domain is set forth in SEQ ID NO:290. In some embodiments, the fusion protein may include one or more linker or NLS sequences, such as at the N- or C-terminus of the fusion protein or between the Cas and the KRAB domain. The linker or NLS can be any as described herein.

In some embodiments, the fusion protein of a DNA-targeting system, or a DNA-targeting module thereof, comprises, from N- to C-terminal order: NLS and/or a linker, dSpCas9 set forth in SEQ ID NO:207, a linker and/or NLS, and a KRAB domain set forth in SEQ ID NO:193. In some embodiments, the fusion protein of a DNA-targeting system, or a DNA-targeting module thereof, comprises, from N- to C-terminal order: NLS and/or a linker, dSpCas9 set forth in SEQ ID NO:207, a linker and/or NLS, and a KRAB domain set forth in SEQ ID NO:290.

In some embodiments, a fusion protein provided herein comprises dCas9 and KRAB. In some embodiments, a fusion protein provided herein comprises dSpCas9-KRAB. In some embodiments, a fusion protein provided herein comprises the sequence set forth in SEQ ID NO: 209, or an amino acid sequence that has at least 90%, 91%, 92%, 93%, 94%, 95%, 96%, 97%, 98%, or 99% sequence identity thereto. In some embodiments, the fusion protein comprises the sequence set forth in SEQ ID NO:209.

In some embodiments, a fusion protein of a DNA-targeting system, or a DNA-targeting module thereof, provided herein comprises a DNA-binding domain, a DNMT3A domain and a DNMT3L domain. In some embodiments, the effector domain is a fusion domain of DNMT3A and DNMT3L (DNMT3A/L domain). In some embodiments, the DNA-binding domain is a catalytically inactive Cas enzyme (dCas). In some embodiments, the Cas is a dCas9, such as a dSaCas9 or a dSpCas9. In some embodiments, the DNA-binding domain is dSpCas9. In some embodiments, the DNA-binding domain is a dSpCas9 set forth in SEQ ID NO:207. In some embodiments, a linker or NLS connects one of the DNMT3A domain or the DNMT3L domain with the DNA-binding domain. In some embodiments, the DNA binding domain is a Cas, and a linker or NLS can be present between the Cas and one or both of the DNMT3A domain and DNMT3L domain. In some embodiments, a fusion protein contains a DNA-binding domain, a DNMT3A domain and a DNMT3L domain, in any order. In some embodiments, a linker connects a DNMT3A domain with a DNMT3L domain. In some embodiments, the DNMT3A domain an DNMT3L domain are connected as a fusion domain. In some embodiments, the fusion domain is the DNMT3A/L domain set forth in SEQ ID NO: 199. In some embodiments, the fusion domain is the DNMT3A/L domain set forth in SEQ ID NO: 201.

In some embodiments, the DNA-targeting system or fusion protein comprises, from N- to C-terminal order: NLS and/or a linker, dSpCas9 set forth in SEQ ID NO:207, a linker and/or NLS, and a DNMT3A/L domain set forth in SEQ ID NO: 199. In some embodiments, the DNA-targeting system or fusion protein comprises, from N- to C-terminal order: NLS and/or a linker, dSpCas9 set forth in SEQ ID NO:207, a linker and/or NLS, and a DNMT3A/L domain set forth in SEQ ID NO: 201.

In some embodiments, the DNA-targeting system or fusion protein comprises, from N- to C-terminal order: NLS and/or a linker, dSpCas9 set forth in SEQ ID NO:207, a linker and/or NLS, and a DNMT3A/L domain set forth in SEQ ID NO:199, and a linker and/or NLS. In some embodiments, the DNA-targeting system or fusion protein comprises, from N- to C-terminal order: NLS and/or a linker, dSpCas9 set forth in SEQ ID NO:207, a linker and/or NLS, and a DNMT3A/L domain set forth in SEQ ID NO:201, and a linker and/or NLS.

In some embodiments, a fusion protein of a DNA-targeting system, or a DNA-targeting module thereof, provided herein comprises a DNA-binding domain, and two effector domains in which one is a KRAB domain and the other is a DNMT3A domain and a DNMT3L domain. In some embodiments, the effector domain composed of the DNMT3A domain and the DNMT3L domain is a fusion domain of DNMT3A and DNMT3L (DNMT3A/L domain). In some embodiments, the DNA-binding domain is a catalytically inactive Cas enzyme (dCas). In some embodiments, the Cas is a dCas9, such as a dSaCas9 or a dSpCas9. In some embodiments, the DNA-binding domain is dSpCas9. In some embodiments, each of the KRAB domain, the DNMT3A domain and the DNMT3L domain are N-terminal to the DNA-binding domain. In some embodiments, each of the KRAB domain, the DNMT3A domain and the DNMT3L domain are C-terminal to the DNA-binding domain. In some embodiments, the DNA-binding domain is between the KRAB domain and one of the DNMT3A or DNMT3L domains. In some embodiments, the fusion domain is the DNMT3A/L domain set forth in SEQ ID NO: 199 or 201. In some embodiments, the KRAB domain is set forth in SEQ ID NO:193. In some embodiments, the KRAB domain is set forth in SEQ ID NO:290. In some embodiments, the DNA-binding domain is a dSpCas9 set forth in SEQ ID NO:207. In some embodiments, the fusion protein may include one or more linker or NLS, such as at the N- or C-terminus of the fusion protein or between the Cas and the KRAB domain or DNMT3A/L domain. The linker or NLS can be any as described herein. In some embodiments, a linker or NLS can be present between the DNMT3A/L domain and the Cas. In some embodiments, a linker or NLS can be present between the Cas and the KRAB domain.

In some embodiments, the fusion protein contains the DNA-binding domain, and the KRAB domain and DNMT3A/3L fusion domain as first and second effector domains. In some embodiments, a first effector domain is fused to the N-terminus of the second effector domain and the second effector domain is fused to the N-terminus of the DNA-binding domain. In some embodiments, a fusion protein provided herein comprises in order: DNMT3A/L-KRAB-dSpCas9. In some embodiments, a fusion protein provided herein comprises in order: KRAB-DNMT3A/L-dSpCas9. In some embodiments, each of the KRAB domain and DNMT3A/3L domain are C-terminal to the DNA-binding domain in which a first effector domain is fused to the C-terminus of the DNA-binding domain and the second effector domain is fused to the C-terminus of the first effector domain. In some embodiments, a fusion protein provided herein comprises in order: dSpCas9-DNMT3A/L-KRAB. In some embodiments, a fusion protein provided herein comprises in order: dSpCas9-KRAB-DNMT3A/L. In some embodiments, the DNA-binding domain is between the KRAB domain and DNMT3A/3L domain, in which one effector domain is fused to the N-terminus of the DNA-binding domain and the other effector domain is fused to the C-terminus of the DNA-binding domain. In some embodiments, a fusion protein provided herein comprises in order: KRAB-dSpCas9-DNMT3A/L. In some embodiments, a fusion protein provided herein comprises in order: DNMT3A/L-dSpCas9-KRAB.

In some embodiments, the fusion protein of a DNA-targeting system, or a DNA-targeting module thereof, comprises, from N- to C-terminal order: a DNMT3A/L fusion domain set forth in SEQ ID NO: 199, an NLS and/or a linker, a dSpCas9 set forth in SEQ ID NO:207, a linker and/or NLS, and a KRAB domain set forth in SEQ ID NO:193. In some embodiments, the fusion protein of a DNA-targeting system, or a DNA-targeting module thereof, comprises, from N- to C-terminal order: a DNMT3A/L fusion domain set forth in SEQ ID NO: 199, an NLS and/or a linker, a dSpCas9 set forth in SEQ ID NO:207, a linker and/or NLS, and a KRAB domain set forth in SEQ ID NO:290.

In some embodiments, the fusion protein of a DNA-targeting system, or a DNA-targeting module thereof, comprises, from N- to C-terminal order: a DNMT3A/L fusion domain set forth in SEQ ID NO: 201, an NLS and/or a linker, a dSpCas9 set forth in SEQ ID NO:207, a linker and/or NLS, and a KRAB domain set forth in SEQ ID NO:193. In some embodiments, the fusion protein of a DNA-targeting system, or a DNA-targeting module thereof, comprises, from N- to C-terminal order: a DNMT3A/L fusion domain set forth in SEQ ID NO: 201, an NLS and/or a linker, a dSpCas9 set forth in SEQ ID NO:207, a linker and/or NLS, and a KRAB domain set forth in SEQ ID NO:290.

In some embodiments, a fusion protein provided herein comprises dCas9, KRAB, and DNMT3A/L. In some embodiments, a fusion protein provided herein comprises dSpCas9-KRAB-DNMT3A/L.

In some embodiments, a fusion protein provided herein comprises the sequence set forth in SEQ ID NO: 278, or an amino acid sequence that has at least 90%, 91%, 92%, 93%, 94%, 95%, 96%, 97%, 98%, or 99% sequence identity to SEQ ID NO:278. In some embodiments, the fusion protein comprises the sequence set forth in SEQ ID NO:278.

In some embodiments, a fusion protein provided herein comprises the sequence set forth in SEQ ID NO: 280, or an amino acid sequence that has at least 90%, 91%, 92%, 93%, 94%, 95%, 96%, 97%, 98%, or 99% sequence identity to SEQ ID NO: 280. In some embodiments, the fusion protein comprises the sequence set forth in SEQ ID NO:280.

In some embodiments, a fusion protein provided herein comprises the sequence set forth in SEQ ID NO: 282, or an amino acid sequence that has at least 90%, 91%, 92%, 93%, 94%, 95%, 96%, 97%, 98%, or 99% sequence identity thereto. In some embodiments, the fusion protein comprises the sequence set forth in SEQ ID NO:282.

II. Polynucleotides, Vectors, and Related Methods for Delivery

In some aspects, provided are polynucleotides encoding any of the DNA-targeting systems described herein or a portion or a component of any of the foregoing. In some aspects, the polynucleotides can encode any of the components of the DNA-targeting systems, and/or any nucleic acid or proteinaceous molecule necessary to carry out aspects of the methods of the disclosure. In particular embodiments, provided are polynucleotides encoding any of the fusion proteins described herein. Also provided herein are polynucleotides encoding any of the gRNAs or combinations of gRNAs described herein.

In some embodiments, provided are polynucleotides comprising the gRNAs described herein. In some embodiments, the gRNA is transcribed from a genetic construct (i.e. vector or plasmid) in the target cell. In some embodiments, the gRNA is produced by in vitro transcription and delivered to the target cell. In some embodiments, the gRNA comprises one or more modified nucleotides for increased stability. In some embodiments, the gRNA is delivered to the target cell pre-complexed as a RNP with the fusion protein.

In some embodiments, a provided polynucleotide encodes a fusion protein as described herein that includes (a) a DNA-binding domain capable of being targeted to a target site of a target gene as described; and (b) at least one effector domain capable of reducing transcription of the gene. In some embodiments, the fusion protein includes a fusion protein of a Cas protein or variant thereof and at least one effector domain capable of reducing transcription of a gene. In a particular example, the Cas is a dCas, such as dCas9. In some embodiments, the dCas9 is a dSpCas9, such as polynucleotide encoding a dSpCas9 set forth in SEQ ID NO: 207. Examples of such domains and fusion proteins include any as described in Section I.

In some embodiments, the polynucleotide comprises a sequence encoding a dCas9-KRAB fusion protein. In some embodiments, the polynucleotide comprises the sequence set forth in SEQ ID NO:208, or a sequence having at least about 80%, 85%, 90%, 91%, 92%, 93%, 94%, 95%, 96%, 97%, 98%, 99%, or 100% sequence identity thereto. In some embodiments, the polynucleotide is set forth in SEQ ID NO:208. In some embodiments, the polynucleotide encodes an amino acid sequence comprising SEQ ID NO:209, or a sequence having at least about 80%, 85%, 90%, 91%, 92%, 93%, 94%, 95%, 96%, 97%, 98%, 99%, or 100% sequence identity thereto. In some embodiments, the polynucleotide encodes the amino acid sequence set forth in SEQ ID NO:209.

In some embodiments, the polynucleotide comprises a sequence encoding a dCas9-KRAB-DNMT3A/L fusion protein. In some embodiments, the polynucleotide comprises the sequence set forth in SEQ ID NO:277, or a sequence having at least about 80%, 85%, 90%, 91%, 92%, 93%, 94%, 95%, 96%, 97%, 98%, 99%, or 100% sequence identity thereto. In some embodiments, the polynucleotide is set forth in SEQ ID NO:277. In some embodiments, the polynucleotide encodes an amino acid sequence comprising SEQ ID NO:278, or a sequence having at least about 80%, 85%, 90%, 91%, 92%, 93%, 94%, 95%, 96%, 97%, 98%, 99%, or 100% sequence identity thereto. In some embodiments, the polynucleotide encodes the amino acid sequence set forth in SEQ ID NO:278.

In some embodiments, the polynucleotide comprises a sequence encoding a dCas9-KRAB-DNMT3A/L fusion protein, such as the sequence set forth in SEQ ID NO:279, or a sequence having at least about 80%, 85%, 90%, 91%, 92%, 93%, 94%, 95%, 96%, 97%, 98%, 99%, or 100% sequence identity thereto. In some embodiments, the polynucleotide is set forth in SEQ ID NO:279. In some embodiments, the polynucleotide encodes an amino acid sequence comprising SEQ ID NO:280, or a sequence having at least about 80%, 85%, 90%, 91%, 92%, 93%, 94%, 95%, 96%, 97%, 98%, 99%, or 100% sequence identity thereto. In some embodiments, the polynucleotide encodes the amino acid sequence set forth in SEQ ID NO:280.

In some embodiments, the polynucleotide comprises a sequence encoding a dCas9-KRAB-DNMT3A/L fusion protein, such as the sequence set forth in SEQ ID NO:281, or a sequence having at least about 80%, 85%, 90%, 91%, 92%, 93%, 94%, 95%, 96%, 97%, 98%, 99%, or 100% sequence identity thereto. In some embodiments, the polynucleotide is set forth in SEQ ID NO:281. In some embodiments, the polynucleotide encodes an amino acid sequence comprising SEQ ID NO:282, or a sequence having at least about 80%, 85%, 90%, 91%, 92%, 93%, 94%, 95%, 96%, 97%, 98%, 99%, or 100% sequence identity thereto. In some embodiments, the polynucleotide encodes the amino acid sequence set forth in SEQ ID NO:282.

In some embodiments, the polynucleotide is an mRNA molecule that comprises a sequence encoding a dCas9-KRAB-DNMT3A/L fusion protein, such as the sequence set forth in SEQ ID NO:395, or a sequence having at least about 80%, 85%, 90%, 91%, 92%, 93%, 94%, 95%, 96%, 97%, 98%, 99%, or 100% sequence identity thereto. In some embodiments, the polynucleotide is set forth in SEQ ID NO:395.

In some embodiments, the polynucleotide is RNA or DNA. In some embodiments, the polynucleotide, such as a polynucleotide encoding a provided fusion protein, is mRNA. In some embodiments, the gRNA is provided as RNA and a polynucleotide encoding the fusion protein is mRNA. The mRNA can be 5' capped and/or 3' polyadenylated. In another embodiment, a polynucleotide provided herein, such as a polynucleotide encoding a provided fusion protein, is DNA. The DNA can be present in a vector.

Also provided herein is a vector that contains any of the provided polynucleotides. In some embodiments, the vector comprises a genetic construct, such as a plasmid or an expression vector.

In some embodiments, the expression vector comprising the sequence encoding the fusion protein of a DNA-targeting system provided herein can further comprise a polynucleotide sequence encoding at least one gRNA. In some embodiments, the expression vector comprises a polynucleotide sequence or combination of polynucleotide sequences encoding two gRNAs. In some embodiments, the expression vector comprises a polynucleotide sequence or combination of polynucleotide sequences encoding three gRNAs. The sequence encoding the gRNA can be operably linked to at least one transcriptional control sequence for expression of the gRNA in the cell. For example, DNA encoding the gRNA can be operably linked to a promoter sequence that is recognized by RNA polymerase III (Pol 111). Examples of suitable Pol III promoters include, but are not limited to, mammalian U6, U3, H1, and 7SL RNA promoters.

An expression vector (such as a DNA or RNA (e.g. mRNA) expression vector) can comprise any number of suitable transcriptional control sequences. For example, transcriptional control sequences may include enhancers, promoters, or untranslated regions (UTRs) such as 3'UTRs or 5'UTRs. In some embodiments, the UTRs are encoded by and/or present in the expression vector (e.g. a DNA vector). In some embodiments, mRNA encoding the fusion protein includes UTRs. In some aspects, different transcriptional control sequences may be selected for use in an expression vector, for example to achieve the appropriate level of expression. For example, in some embodiments, UTRs can be selected that facilitate expression in a specific tissue or cell type (e.g. liver or hepatocyte). In some embodiments, a 5'UTR of the expression vector encodes or comprises the sequence set forth in SEQ ID NO:393. In some embodiments, a 3'UTR of the expression vector encodes or comprises the sequence set forth in SEQ ID NO:394.

In some embodiments, provided is a vector containing a polynucleotide that encodes a fusion protein comprising a DNA-binding domain comprising a dCas and at least one effector domain capable of increasing transcription of a gene, and a polynucleotide or combination of polynucleotides encoding a gRNA, or combination of gRNAs, such as two gRNAs, or three gRNAs. In some embodiments, the dCas is a dCas9, such as dSpCas9. In some embodiments, the polynucleotide encodes a fusion protein that includes a dSpCas9 set forth in SEQ ID NO: 207. In some embodiments, the polynucleotide(s) encodes a gRNA or combination of gRNAs as described in Section II.B.ii. For example, the polynucleotide can encode a combination of gRNAs, each comprising a spacer sequence selected from any one of SEQ ID NOS: 64-126, 318-329, 352-361, or 378-383, or a contiguous portion thereof of at least 14 nt. In some embodiments the polynucleotide(s) encodes a combination of gRNAs that each comprise a sequence set forth in any one of SEQ ID NOS:127-189, 330-341, 362-371, or 384-389.

In some embodiments, the effector domain is KRAB. In some embodiments, the effector domain is DNMT3A/L. In some embodiments, the vector includes a polynucleotide comprising SEQ ID NO:192, SEQ ID NO:277, SEQ ID NO:279, or SEQ ID NO:281, or a sequence having at least about 80%, 85%, 90%, 91%, 92%, 93%, 94%, 95%, 96%, 97%, 98%, 99%, or 100% sequence identity thereto, and a polynucleotide or polynucleotides that encode a gRNA or combination of gRNAs such as any described in Section I.B.ii. In some embodiments, the polynucleotide(s) encodes a combination of gRNAs, each comprising a spacer sequence selected from any one of SEQ ID NOS: 64-126, 318-329, 352-361, or 378-383, or a contiguous portion thereof of at least 14 nt. In some embodiments, each gRNA further comprises the sequence set forth in SEQ ID NO: 191. In some embodiments the polynucleotide(s) encodes a combination of gRNAs that each comprises a sequence set forth in any one of SEQ ID NOS:127-189, 330-341, 362-371, or 384-389.

In some embodiments, the polynucleotide encodes the fusion protein and the combination of gRNAs.

In some embodiments, the polynucleotide as provided herein can be codon optimized for efficient translation into protein in the eukaryotic cell or animal of interest. For example, codons can be optimized for expression in humans, mice, rats, hamsters, cows, pigs, cats, dogs, fish, amphibians, plants, yeast, insects, and so forth. Programs for codon optimization are available as freeware. Commercial codon optimization programs are also available.

In some embodiments, a polynucleotide described herein can comprise one or more transcription and/or translation control elements. Depending on the host/vector system utilized, any of a number of suitable transcription and translation control elements, including constitutive and inducible promoters, transcription enhancer elements, transcription terminators, etc. can be used in the expression vector.

Non-limiting examples of suitable eukaryotic promoters (i.e., promoters functional in a eukaryotic cell) include those from cytomegalovirus (CMV) immediate early, herpes simplex virus (HSV) thymidine kinase, early and late SV40, long terminal repeats (LTRs) from retrovirus, human elongation factor-1 promoter (EF1), a hybrid construct comprising the cytomegalovirus (CMV) enhancer fused to the chicken beta-actin promoter (CAG), murine stem cell virus promoter (MSCV), phosphoglycerate kinase-1 locus promoter (PGK), and mouse metallothionein-I.

For expressing small RNAs, including guide RNAs used in connection with the DNA-targeting systems, various promoters such as RNA polymerase III promoters, including for example U6 and H1, can be advantageous. Descriptions of and parameters for enhancing the use of such promoters are known in the art, and additional information and approaches are regularly being described; see, e.g., Ma, H. et al., Molecular Therapy-Nucleic Acids 3, e161 (2014) doi:10.1038/mtna.2014.12.

The expression vector can also contain a ribosome binding site for translation initiation and a transcription terminator. The expression vector can also comprise appropriate sequences for amplifying expression. The expression vector can also include nucleotide sequences encoding non-native tags (e.g., histidine tag, hemagglutinin tag, green fluorescent protein, etc.) that are fused to the site-directed polypeptide, thus resulting in a fusion protein.

A promoter can be an inducible promoter (e.g., a heat shock promoter, tetracycline-regulated promoter, steroid-regulated promoter, metal-regulated promoter, estrogen receptor-regulated promoter, etc.). The promoter can be a constitutive promoter (e.g., CMV promoter, UBC promoter). In some cases, the promoter can be a spatially restricted and/or temporally restricted promoter (e.g., a tissue specific promoter, a cell type specific promoter (e.g. a hepatocyte specific promoter), etc.).

Expression vectors contemplated include, but are not limited to, viral vectors based on vaccinia virus, poliovirus, adenovirus, adeno-associated virus, SV40, herpes simplex virus, human immunodeficiency virus, retrovirus (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus) and other recombinant vectors. Other vectors contemplated for eukaryotic target cells include, but are not limited to, the vectors pXT1, pSG5, pSVK3, pBPV, pMSG, and pSVLSV40 (Pharmacia). Other vectors can be used so long as they are compatible with the host cell.

In some embodiments, the vector is a viral vector, such as an adeno-associated virus (AAV) vector, a retroviral vector, a lentiviral vector, or a gammaretroviral vector. In some embodiments In some embodiments, the viral vector is an adeno-associated virus (AAV) vector. In some embodiments, the AAV vector is selected from among an AAV1, AAV2, AAV3, AAV4, AAV5, AAV6, AAV7, AAV8, or AAV9 vector. In some embodiments, the vector is a lentiviral vector. In some embodiments, the vector is a non-viral vector, for example a lipid nanoparticle, a liposome, an exosome, or a cell penetrating peptide. In some embodiments, the vector comprises one vector, or two or more vectors.

In some embodiments, a vector described herein is or comprises a lipid nanoparticle (LNP). Among provided embodiments, is a lipid nanoparticle that contains any of the provided polynucleotides for delivery of an epigenetic DNA-targeting system. In some embodiments, the LNP contains a polynucleotide that encodes a fusion protein as provided herein that includes (a) a DNA-binding domain capable of being targeted to a target site of a target gene as described; and (b) at least one effector domain capable of reducing transcription of the gene. In some embodiments, the DNA-binding domain is a Cas (e.g. dCas) and the LNP further includes a gRNA. In some embodiments, the polynucleotide encoding the fusion protein is an mRNA and the gRNA is provided as an RNA.

In some embodiments, any of the epigenetic-modifying DNA-targeting systems, gRNAs, Cas-gRNA combinations, polynucleotides, fusion proteins, or components thereof described herein, are incorporated in lipid nanoparticles (LNPs), such as for delivery. In some embodiments, the lipid nanoparticle is a vector for delivery. In some embodiments, the nanoparticle may comprise at least one lipid. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG and PEGylated lipids. In another aspect, the lipid may be a cationic lipid such as, but not limited to, DLin-DMA, DLin-D-DMA, DLin-MC3-DMA, DLin-KC2-DMA and DODMA. Typically, the LNPs are composed of two or more lipids, such as 3, 4 or 5 lipids. In some embodiments, at least lipid is either ionizable cationic or cationic.

Lipid nanoparticles can be used for the delivery of encapsulated or associated (e.g., complexed) therapeutic agents, including nucleic acids and proteins, such as those encoding and/or comprising CRISPR/Cas systems. See, e.g., U.S. Pat. Nos. 10,723,692, 10,941,395, and WO 2015/035136.

In some embodiments, the provided methods involve use of a lipid nanoparticle (LNP) comprising mRNA, such as mRNA encoding a protein component of any of the provided DNA-targeting systems, for example any of the fusion proteins provided herein. In some embodiments, the mRNA can be produced using methods known in the art such as in vitro transcription. In some embodiments of the method, the mRNA comprises a 5' cap. In some embodiments, the 5' cap is an altered nucleotide on the 5' end of primary transcripts such as messenger RNA. In some aspects, the 5' caps of the mRNA improves one or more of RNA stability and processing, mRNA metabolism, the processing and maturation of an RNA transcript in the nucleus, transport of mRNA from the nucleus to the cytoplasm, mRNA stability, and efficient translation of mRNA to protein. In some embodiments, a 5' cap can be a naturally-occurring 5' cap or one that differs from a naturally-occurring cap of an mRNA. A 5' cap may be any 5' cap known to a skilled artisan. In certain embodiments, the 5' cap is selected from the group consisting of an Anti-Reverse Cap Analog (ARCA) cap, a 7-methyl-guanosine (7 mG) cap, a CleanCap® analog, a vaccinia cap, and analogs thereof. For instance, the 5' cap may include, without limitation, an anti-reverse cap analogs (ARCA) (U.S. Pat. No. 7,074,596), 7-methyl-guanosine, CleanCap® analogs, such as Cap 1 analogs (Trilink; San Diego, CA), or enzymatically capped using, for example, a vaccinia capping enzyme or the like. In some embodiments, the mRNA may be polyadenylated. The mRNA may contain various 5' and 3' untranslated sequence elements to enhance expression of the encoded protein and/or stability of the mRNA itself. Such elements can include, for example, posttranslational regulatory elements such as a woodchuck hepatitis virus post-transcriptional regulatory element (WPRE). In some embodiments, the mRNA comprises at least one nucleoside modification. The mRNA may contain modifications of naturally-occurring nucleosides to nucleoside analogs. Any nucleoside analogs known in the art are envisioned. Such nucleoside analogs can include, for example, those described in U.S. Pat. No. 8,278,036. In certain embodiments of the method, the nucleoside modification is selected from the group consisting of a modification from uridine to pseudouridine and uridine to N1-methyl pseudouridine. In particular embodiments of the method the nucleoside modification is from uridine to pseudouridine.

In some embodiments, the LNP composition comprises a PEG-lipid (e.g., a lipid comprising a polyethylene glycol component). In some embodiments, the described LNP composition comprises two or more PEG-lipids. Exemplary PEG-lipids also include, but are not limited to, PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, the one or more PEG-lipids can comprise PEG-c-DOMG, PEG-DMG, PEG-DLPE, PEG-DMPE, PEG-DPPC, a PEG-DSPE lipid, or a combination thereof. In some embodiments, PEG moiety is an optionally substituted linear or branched polymer of ethylene glycol or ethylene oxide. In some embodiments, the PEG moiety is substituted, e.g., by one or more alkyl, alkoxy, acyl, hydroxy, or aryl groups. In some embodiments, the PEG moiety includes PEG copolymer such as PEG-polyurethane or PEG-polypropylene (see, e.g., j. Milton Harris, Poly(ethylene glycol) chemistry: biotechnical and biomedical applications (1992)). In some embodiments, a PEG-lipid is a PEG-lipid conjugate. In some embodiments, the PEG-lipid comprises from about 0.1 mol % to about 6 mol % of a total lipid content present in said nanoparticle composition. In some embodiments, a number average molecular weight of the PEG-lipid is from about 200 Da to about 5000 Da. In some embodiments, the LNP comprises and/or is conjugated to N-Acetylgalactosamine (GalNAc), an amino sugar derivative of galactose. In some aspects, GalNAc is a sugar molecule that can recognize and bind to a cell surface protein, the asialoglycoprotein receptor (ASGPR). ASGPR is abundantly expressed on liver cells (hepatocytes). In some embodiments, GalNAc conjugation to LNPs can improve delivery to hepatocytes. In some embodiments, the lipid nanoparticle comprises GalNAC-conjugated lipids (e.g. a GalNAc-PEG lipid). In some embodiments, the molar percentage of lipids that are GalNAC-conjugated in a lipid nanoparticle is between about 0% and about 2%. In some embodiments, the molar percentage of lipids that are GalNAC-conjugated in a lipid nanoparticle is at or about 0.1%, at or about 0.2%, at or about 0.3%, at or about 0.4%, at or about 0.5%, at or about 0.6%, at or about 0.7%, at or about 0.8%, at or about 0.9%, at or about 1.0%, at or about 1.1%, at or about 1.2%, at or about 1.3%, at or about 1.4%, at or about 1.5%, at or about 1.6%, at or about 1.7%, at or about 1.8%, at or about 1.9%, at or about 2.0%, or more, or a value in between any of the foregoing.

In some embodiments, LNPs useful for in the present methods comprise a cationic lipid selected from DLin-DMA (1,2-dilinoleyloxy-3-dimethylaminopropane), DLin-MC3-DM A (dilinoleylmethyl-4-dimethylaminobutyrate), DLin-KC2-DMA (2,2-dilinoleyl-4-(2-dimethylaminoethyl)-[1,3]-dioxolane), DODMA (1,2-dioleyloxy-N,N-dimethyl-3-aminopropane), SS-OP (Bis[2-(4-{2-[4-(cis-9 octadecenoyloxy)phenylacetoxy]ethyl}piperidinyl)ethyl] disulfide), and derivatives thereof. DLin-MC3-DMA and derivatives thereof are described, for example, in WO 2010/144740. DODMA and derivatives thereof are described, for example, in U.S. Pat. No. 7,745,651 and Mok et al. (1999), Biochimica et Biophysica Acta, 1419(2): 137-150. DLin-DMA and derivatives thereof are described, for example, in U.S. Pat. No. 7,799,565. DLin-KC2-DMA and derivatives thereof are described, for example, in U.S. Pat. No. 9,139,554. SS-OP (NOF America Corporation, White Plains, NY) is described, for example, at www[dot]nofamerica[dot]com/store/index[dot]php?dispatch=products[dot] view&product_id=962. Additional and non-limiting examples of cationic lipids include methylpyridiyl-dialkyl acid (MPDACA), palmitoyl-oleoyl-nor-arginine (PONA), guanidino-dialkyl acid (GUADACA), 1,2-di-0-octadecenyl-3-trimethylammonium propane (DOTMA), 1,2-dioleoyl-3-trimethylammonium-propane (DOTAP), Bis{2-[N-methyl-N-(a-D-tocopherolhemisuccinatepropyl)amino]ethyl} disulfide (SS-33/3AP05), Bis{2-[4-(a-D-tocopherol-hemisuccinateethyl)piperidyl] ethyl} disulfide (SS33/4PE15), Bis {2-[4-(cis-9-octadecenoateethyl)-1-piperidinyl] ethyl} disulfide (SS18/4PE16), and Bis{2-[4-(cis,cis-9,12-octadecadienoateethyl)-1-piperidinyl] ethyl} disulfide (SS18/4PE13). In further embodiments, the lipid nanoparticles also comprise one or more non-cationic lipids and a lipid conjugate.

In some embodiments, the molar concentration of the cationic lipid is from about 20% to about 80%, from about 30% to about 70%, from about 40% to about 60%, from about 45% to about 55%, or about 20%, about 25%, about 30%, about 35%, about 40%, about 45%, about 50%, about 55%, about 60%, about 65%, about 70%, about 75%, or about 80% of the total lipid molar concentration, wherein the total lipid molar concentration is the sum of the cationic lipid, the non-cationic lipid, and the lipid conjugate molar concentrations. In certain embodiments, the lipid nanoparticles comprise a molar ratio of cationic lipid to any of the polynucleotides of from about 1 to about 20, from about 2 to about 16, from about 4 to about 12, from about 6 to about 10, or about 1, about 2, about 3, about 4, about 5, about 6, about 7, about 8, about 9, about 10, about 11, about 12, about 13, about 14, about 15, about 16, about 17, about 18, about 19, or about 20.

In some embodiments, the lipid nanoparticles can comprise at least one non-cationic lipid. In particular embodiments, the molar concentration of the non-cationic lipids is from about 20% to about 80%, from about 30% to about 70%, from about 40% to about 70%, from about 40% to about 60%, from about 46% to about 50%, or about 20%, about 25%, about 30%, about 35%, about 40%, about 45%, about 48.5%, about 50%, about 55%, about 60%, about 65%, about 70%, about 75%, or about 80% of the total lipid molar concentration. Non-cationic lipids include, in some embodiments, phospholipids and steroids.

In some embodiments, phospholipids useful for the lipid nanoparticles described herein include, but are not limited to, 1,2-Distearoyl-sn-glycero-3-phosphocholine (DSPC), 1,2-Didecanoyl-sn-glycero-3-phosphocholine (DDPC), 1,2-Dierucoyl-sn-glycero-3-phosphate (Sodium Salt) (DEPA-NA), 1,2-Dierucoyl-sn-glycero-3-phosphocholine (DEPC), 1,2-Dierucoyl-sn-glycero-3-phosphoethanolamine (DEPE), 1,2-Dierucoyl-sn-glycero-3[Phospho-rac-(1-glycerol)(Sodium Salt) (DEPG-NA), 1,2-Dilinoleoyl-sn-glycero-3-phosphocholine (DLOPC), 1,2-Dilauroyl-sn-glycero-3-phosphate (Sodium Salt) (DLPA-NA), 1,2-Dilauroyl-sn-glycero-3-phosphocholine (DLPC), 1,2-Dilauroyl-sn-glycero-3-phosphoethanolamine (DLPE), 1,2-Dilauroyl-sn-glycero-3 [Phospho-rac-(1-glycerol . . . )(Sodium Salt) (DLPG-NA), 1,2-Dilauroyl-sn-glycero-3[Phospho-rac-(1-glycerol)(Ammonium Salt) (DLPG-NH4), 1,2-Dilauroyl-sn-glycero-3-phosphoserine (Sodium Salt) (DLPS-NA), 1,2-Dimyristoyl-sn-glycero-3-phosphate (SodiumSalt) (DMPA-NA), 1,2-Dimyristoyl-sn-glycero-3-phosphocholine (DMPC), 1,2-Dimyristoyl-sn-glycero-3-phosphoethanolamine (DMPE), 1,2-Dimyristoyl-sn-glycero-3 [Phospho-rac-(1-glycerol) (Sodium Salt) (DMPG-NA), 1,2-Dimyristoyl-sn-glycero-3 [Phospho-rac-(1-glycerol)(Ammonium Salt) (DMPG-NH4), 1,2-Dimyristoyl-sn-glycero-3[Phospho-rac-(1-glycerol)(Sodium/Ammonium Salt) (DMPG-NH4/NA), 1,2-Dimyristoyl-sn-glycero-3-phosphoserine (Sodium Salt) (DMPS-NA), 1,2-Dioleoyl-sn-glycero-3-phosphate (Sodium Salt) (DOPA-NA), 1,2-Dioleoyl-sn-glycero-3-phosphocholine (DOPC), 1,2-Dioleoyl-sn-glycero-3-phosphoethanolamine (DOPE), 1,2-Dioleoyl-sn-glycero-3[Phospho-rac-(1-glycerol)(Sodium Salt) (DOPG-NA), 1,2-Dioleoyl-sn-glycero-3-phosphoserine (Sodium Salt) (DOPS-NA), 1,2-Dipalmitoyl-sn-glycero-3-phosphate (Sodium Salt) (DPPA-NA), 1,2-Dipalmitoyl-sn-glycero-3-phosphocholine (DPPC), 1,2-Dipalmitoyl-sn-glycero-3-phosphoethanolamine (DPPE), 1,2-Dipalmitoyl-sn-glycero-3 [Phospho-rac-(1-glycerol) (Sodium Salt) (DPPG-NA), 1,2-Dipalmitoyl-sn-glycero-3 [Phospho-rac-(1-glycerol)(Ammonium Salt) (DPPG-NH4), 1,2-Dipalmitoyl-sn-glycero-3-phosphoserine (Sodium Salt) (DPPS-NA), 1,2-Distearoyl-sn-glycero-3-phosphate (Sodium Salt) (DSPA-NA), 1,2-Distearoyl-sn-glycero-3-phosphoethanolamine (DSPE), 1,2-Distearoyl-sn-glycero-3 [Phospho-rac-(1-glycerol)(Sodium Salt) (DSPG-NA), 1,2-Distearoyl-sn-glycero-3[Phospho-rac-(1-glycerol) (Ammonium Salt) (DSPG-NH4), 1,2-Distearoyl-sn-glycero-3-phosphoserine (Sodium Salt) (DSPS-NA), Egg-PC (EPC), Hydrogenated Egg PC (HEPC), Hydrogenated Soy PC (HSPC), 1-Myristoyl-sn-glycero-3-phosphocholine (LY S OPCM YRIS TIC), 1-Palmitoyl-sn-glycero-3-phosphocholine (LYSOPCPALMITIC), 1-Stearoyl-sn-glycero-3-phosphocholine (LYSOPC STEARIC), 1-Myristoyl-2- palmitoyl-sn-glycero3-phosphocholine (MPPC), 1-Myristoyl-2-stearoyl-sn-glycero-3-phosphocholine (MSPC), 1-Palmitoyl-2-myristoyl-sn-glycero-3-phosphocholine (PMPC), 1-Palmitoyl-2-oleoyl-sn-glycero-3-phosphocholine (POPC), 1-Palmitoyl-2-oleoyl-sn-glycero-3-phosphoethanolamine (POPE), 1-Palmitoyl-2-oleoyl-sn-glycero-3[Phospho-rac-(1-glycerol)](Sodium Salt) (POPG-NA), 1-Palmitoyl-2-stearoyl-sn-glycero-3-phosphocholine (PS PC), 1-Stearoyl-2-myristoyl-sn-glycero-3-phosphocholine (SMPC), 1-Stearoyl-2-oleoyl-sn-glycero-3-phosphocholine (SOPC), and 1-Stearoyl-2-palmitoyl-sn-glycero-3-phosphocholine (SPPC). In particular embodiments, the phospholipid is DSPC. In particular embodiments, the phospholipid is DOPE. In particular embodiments, the phospholipid is DOPC.

In some embodiments, the non-cationic lipids comprised by the lipid nanoparticles include one or more steroids. Steroids useful for the lipid nanoparticles described herein include, but are not limited to, cholestanes such as cholesterol, cholanes such as cholic acid, pregnanes such as progesterone, androstanes such as testosterone, and estranes such as estradiol. Further steroids include, but are not limited to, cholesterol (ovine), cholesterol sulfate, desmosterol-d6, cholesterol-d7, lathosterol-d7, desmosterol, stigmasterol, lanosterol, dehydrocholesterol, dihydrolanosterol, zymosterol, lathosterol, zymosterol-d5, 14-demethyl-lanosterol, 14-demethyl-lanosterol-d6, 8(9)-dehydrocholesterol, 8(14)-dehydrocholesterol, diosgenin, DHEA sulfate, DHEA, lanosterol-d6, dihydrolanosterol-d7, campesterol-d6, sitosterol, lanosterol-95, Dihydro FF-MAS-d6, zymostenol-d7, zymostenol, sitostanol, campestanol, campesterol, 7-dehydrodesmosterol, pregnenolone, sitosterol-d7, Dihydro T-MAS, Delta 5-avenasterol, Brassicasterol, Dihydro FF-MAS, 24-methylene cholesterol, cholic acid derivatives, cholesteryl esters, and glycosylated sterols. In particular embodiments, the lipid nanoparticles comprise cholesterol.

In some embodiments, the lipid nanoparticles comprise a lipid conjugate. Such lipid conjugates include, but are not limited to, ceramide PEG derivatives such as C8 PEG2000 ceramide, C16 PEG2000 ceramide, C8 PEG5000 ceramide, C16 PEG5000 ceramide, C8 PEG750 ceramide, and C16 PEG750 ceramide, phosphoethanolamine PEG derivatives such as 16:0 PEG5000PE, 14:0 PEG5000 PE, 18:0 PEG5000 PE, 18:1 PEG5000 PE, 16:0 PEG3000 PE, 14:0 PEG3000 PE, 18:0 PEG3000 PE, 18:1 PEG3000 PE, 16:0 PEG2000 PE, 14:0 PEG2000 PE, 18:0 PEG2000 PE, 18:1 PEG2000 PE 16:0 PEG1000 PE, 14:0 PEG1000 PE, 18:0 PEG1000 PE, 18:1 PEG1000 PE, 16:0 PEG750 PE, 14:0 PEG750 PE, 18:0 PEG750 PE, 18:1 PEG750 PE, 16:0 PEG550 PE, 14:0 PEG550 PE, 18:0 PEG550 PE, 18:1 PEG550 PE, 16:0 PEG350 PE, 14:0 PEG350 PE, 18:0 PEG350 PE, and 18:1 PEG350, sterol PEG derivatives such as Chol-PEG600, and glycerol PEG derivatives such as DMG-PEG5000, DSG-PEG5000, DPG-PEG5000, DMG-PEG3000, DSG-PEG3000, DPG-PEG3000, DMG-PEG2000, DSG-PEG2000, DPG-PEG2000, DMG-PEG1000, DSG-PEG1000, DPG-PEG1000, DMG-PEG750, DSG-PEG750, DPG-PEG750, DMG-PEG550, DSG-PEG550, DPG-PEG550, DMG-PEG350, DSG-PEG350, and DPG-PEG350. In some embodiments, the lipid conjugate is a DMG-PEG. In some particular embodiments, the lipid conjugate is DMG-PEG2000. In some particular embodiments, the lipid conjugate is DMG-PEG5000.

It is within the level of a skilled artisan to select the cationic lipids, non-cationic lipids and/or lipid conjugates which comprise the lipid nanoparticle, as well as the relative molar ratio of such lipids to each other, such as based upon the characteristics of the selected lipid(s), the nature of the delivery to the intended target cells, and the characteristics of the nucleic acids and/or proteins to be delivered. Additional considerations include, for example, the saturation of the alkyl chain, as well as the size, charge, pH, pKa, fusogenicity and toxicity of the selected lipid(s). Thus, the molar ratios of each individual component may be adjusted accordingly.

The lipid nanoparticles for use in the method can be prepared by various techniques which are known to a skilled artisan. Nucleic acid-lipid particles and methods of preparation are disclosed in, for example, U.S. Patent Publication Nos. 20040142025 and 20070042031.

In some embodiments, the lipid nanoparticles will have a size within the range of about 25 to about 500 nm. In some embodiments, the lipid nanoparticles have a size from about 50 nm to about 300 nm, or from about 60 nm to about 120 nm. The size of the lipid nanoparticles may be determined by quasi-electric light scattering (QELS) as described in Bloomfield, Ann. Rev. Biophys. Bioeng., 10:421A150 (1981). A variety of methods are known in the art for producing a population of lipid nanoparticles of particular size ranges, for example, sonication or homogenization. One such method is described in U.S. Pat. No. 4,737,323.

In some embodiments, the lipid nanoparticles comprise a cell targeting molecule such as, for example, a targeting ligand (e.g., antibodies, scFv proteins, DART molecules, peptides, aptamers, and the like) anchored on the surface of the lipid nanoparticle that selectively binds the lipid nanoparticles to the targeted cell, such as any cell described herein, e.g. a hepatocyte.

In some embodiments, the vector exhibits liver cell and/or hepatocyte tropism.

In some aspects, provided herein are pluralities of vectors that comprise any of the vectors described herein, and one or more additional vectors comprising one or more additional polynucleotides encoding an additional portion or an additional component of any of the DNA-targeting systems described herein, any of the gRNAs described herein, any of the fusion proteins described herein, or a portion or a component of any of the foregoing.

Provided are pluralities of vectors, that include: a first vector comprising any of the polynucleotides described herein; a second vector comprising any of the polynucleotides described herein; and optionally one or more additional vectors comprising any of the polynucleotides described herein.

In some aspects, vectors provided herein may be referred to as delivery vehicles. In some aspects, any of the DNA-targeting systems, components thereof, or polynucleotides disclosed herein can be packaged into or on the surface of delivery vehicles for delivery to cells. Delivery vehicles contemplated include, but are not limited to, nanospheres, liposomes, quantum dots, nanoparticles, polyethylene glycol particles, hydrogels, and micelles. As described in the art, a variety of targeting moieties can be used to enhance the preferential interaction of such vehicles with desired cell types or locations.

Methods of introducing a nucleic acid into a host cell are known in the art, and any known method can be used to introduce a nucleic acid (e.g., an expression construct) into a cell. Suitable methods include, include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery, and the like. In some embodiments, the composition may be delivered by mRNA delivery and ribonucleoprotein (RNP) complex delivery. Direct delivery of the RNP complex, including the DNA-binding domain complexed with the sgRNA, can eliminate the need for intracellular transcription and translation and can offer a robust platform for host cells with low transcriptional and translational activity. The RNP complexes can be introduced into the host cell by any of the methods known in the art.

Nucleic acids or RNPs of the disclosure can be incorporated into a host using virus-like particles (VLP). VLPs contain normal viral vector components, such as envelope and capsids, but lack the viral genome. For instance, nucleic acids expressing the Cas and sgRNA can be fused to the viral vector components such as gag and introduced into producer cells. The resulting virus-like particles containing the sgRNA-expressing vectors can infect the host cell for efficient editing.

Introduction of the complexes, polypeptides, and nucleic acids of the disclosure can occur by protein transduction domains (PTDs). PTDs, including the human immunodeficiency virus-1 TAT, herpes simplex virus-1 VP22, Drsophila Antennapedia Antp, and the poluarginines, are peptide sequences that can cross the cell membrane, enter a host cell, and deliver the complexes, polypeptides, and nucleic acids into the cell.

Introduction of the complexes, polypeptides, and nucleic acids of the disclosure into cells can occur by viral or bacteriophage infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like, for example as described in WO 2017/193107, WO 2016/123578, WO 2014/152432, WO 2014/093661, WO 2014/093655, or WO 2021/226555.

Various methods for the introduction of polynucleotides are well known and may be used with the provided methods and compositions. Exemplary methods include those for transfer of polynucleotides encoding the DNA targeting systems provided herein, including via viral, e.g., retroviral or lentiviral, transduction, transposons, and electroporation.

In some embodiments, polynucleotides can be cloned into a suitable vector, such as an expression vector or vectors. The expression vector can be any suitable recombinant expression vector, and can be used to transform or transfect any suitable cell. Suitable vectors include those designed for propagation and expansion or for expression or both, such as plasmids and viruses.

In some embodiments, the vector can be a vector of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). In some embodiments, animal expression vectors include pEUK-Cl, pMAM and pMAMneo (Clontech). In some embodiments, a viral vector is used, such as a lentiviral or retroviral vector. In some embodiments, the recombinant expression vectors can be prepared using standard recombinant DNA techniques. In some embodiments, vectors can contain regulatory sequences, such as transcription and translation initiation and termination codons, which are specific to the type of host into which the vector is to be introduced, as appropriate and taking into consideration whether the vector is DNA- or RNA-based. In some embodiments, the vector can contain a nonnative promoter operably linked to the nucleotide sequence encoding the recombinant receptor. In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other promoters known to a skilled artisan also are contemplated.

In some embodiments, recombinant nucleic acids are transferred into cells using recombinant infectious virus particles, such as, e.g., vectors derived from simian virus 40 (SV40), adenoviruses, or adeno-associated virus (AAV). In some embodiments, recombinant nucleic acids are transferred into cells (e.g. hepatocytes) using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207, 453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3: 102-109.

In some embodiments, the vector is a lentiviral vector. In some embodiments, the lentiviral vector is an integrase-deficient lentiviral vector. In some embodiments, the lentiviral vector is a recombinant lentiviral vector. In some embodiments, the lentivirus is selected or engineered for a desired tropism (e.g. for liver cell or hepatocyte tropism). Methods of lentiviral production, transduction, and engineering are known, for example as described in Kasaraneni, N. et al. Sci. Rep. 8(1):10990 (2018), Ghaleh, H. E. G. et al. Biomed. Pharmacother. 128: 110276 (2020), and Milone, M. C. et al. Leukemia. 32(7):1529-1541 (2018). Additional methods for lentiviral transduction are described, for example in Wang et al. (2012) J. Immunother. 35(9): 689-701; Cooper et al. (2003) Blood. 101: 1637-1644; Verhoeyen et al. (2009) Methods Mol Biol. 506: 97-114; and Cavalieri et al. (2003) Blood. 102(2): 497-505.

In some embodiments, recombinant nucleic acids are transferred into cells (e.g. hepatocytes) via electroporation (see, e.g., Chicaybam et al, (2013) PLoS ONE 8(3): e60298 and Van Tedeloo et al. (2000) Gene Therapy 7(16): 1431-1437). In some embodiments, recombinant nucleic acids are transferred into cells via transposition (see, e.g., Manuri et al. (2010) Hum Gene Ther 21(4): 427-437; Sharma et al.

(2013) Molec Ther Nucl Acids 2, e74; and Huang et al. (2009) Methods Mol Biol 506: 115-126). Other methods of introducing and expressing genetic material into immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

III. Pharmaceutical Compositions and Formulations

In some aspects, provided herein are compositions, such as pharmaceutical compositions and formulations for administration, that include any of the DNA-targeting systems described herein, or any of the polynucleotides or vectors encoding the same. In some aspects, the pharmaceutical composition contains one or more DNA-targeting systems provided herein or a component thereof. In some aspects, the pharmaceutical composition comprises one or more vectors that contain polynucleotides that encode one or more components of the DNA-targeting systems provided herein. Such compositions can be used in accord with the provided methods, and/or with the provided articles of manufacture or compositions, such as in the prevention or treatment of diseases, conditions, and disorders, or in detection, diagnostic, and prognostic methods.

The term "pharmaceutical formulation" refers to a preparation which is in such form as to permit the biological activity of an active ingredient contained therein to be effective, and which contains no additional components which are unacceptably toxic to a subject or a cell to which the formulation would be administered.

In some embodiments, the pharmaceutical composition may further comprise a pharmaceutically acceptable excipient. The pharmaceutically acceptable excipient may be functional molecules as vehicles, adjuvants, carriers, or diluents.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular agent and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

In some embodiments, the pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

In some embodiments, the transfection facilitating agent is a polyanion, polycation, including poly-L-glutamate (LGS), or lipid. In some embodiments, the transfection facilitating agent is poly-L-glutamate. In some embodiments, the transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA vector encoding the DNA-targeting system may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. In some embodiments, the transfection facilitating agent is a polyanion, polycation, including poly-L-glutamate (LGS), or lipid.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the agent in a solvent, such as in admixture with a suitable carrier, diluent, or excipient such as sterile water, physiological saline, glucose, dextrose, or the like. The formulations to be used for in vivo or ex vivo administration or use are generally sterile. Sterility may be readily accomplished, e.g., by filtration through sterile filtration membranes.

The pharmaceutical composition in some embodiments contains components in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

In some embodiments, the composition can be administered to a subject by any suitable means, for example, by bolus infusion or by injection, e.g., by intravenous or subcutaneous injection. In some embodiments, a given dose is administered by a single bolus administration of the composition. In some embodiments, the composition is administered by multiple bolus administrations of the composition, for example, over a period of no more than 3 days, or by continuous infusion administration of the composition. In some embodiments, the composition is administered parenterally, for example by intravenous, intramuscular, subcutaneous, or intraperitoneal administration. In some embodiments, the composition is administered to a subject using peripheral systemic delivery by intravenous, intraperitoneal, or subcutaneous injection.

For the prevention or treatment of disease, the appropriate dosage may depend on the type of disease to be treated, the type of agent or agents, the type of cells or recombinant receptors, the severity and course of the disease, whether the agent or cells are administered for preventive or therapeutic purposes, previous therapy, the subject's clinical history and response to the agent or the cells, and the discretion of the attending physician. The compositions are in some embodiments suitably administered to the subject at one time or over a series of treatments.

IV. Methods of Treatment

Provided herein are methods of treatment, e.g., including administering any of the compositions, such as pharmaceutical compositions described herein. In some aspects, also provided are methods of administering any of the compositions described herein to a subject, such as a subject that has a disease or disorder. The compositions, such as pharmaceutical compositions, described herein are useful in a variety of therapeutic, diagnostic and prophylactic indications. For example, the compositions are useful in treating a variety of diseases and disorders in a subject. Such methods and uses include therapeutic methods and uses, for example, involving administration of the compositions, to a subject having a disease, condition, or disorder, such as cardiovascular disease and/or familial hyperholesterolemia. In some of any of the provided embodiments, the subject has a cardiovascular disease. In some of any of the provided embodiments, the subject has familial hypercholesterolemia. In some embodiments, the compositions are administered in an effective amount to effect treatment of the disease or disorder. Uses include uses of the compositions in such methods and treatments, and in the preparation of a medicament in order to carry out such therapeutic methods. In some embodiments, the methods are carried out by administering the compositions to the subject having or suspected of having the disease or condition. In some embodiments, the methods thereby treat the disease or condition or disorder in the subject. Also provided are therapeutic methods for administering the cells and compositions to subjects, e.g., patients.

In some embodiments, the compositions include a DNA-targeting system provided herein, or a polynucleotide or vector encoding the same, in which delivery of the composition to a subject modulates one or more activities or function of liver cells in a subject to thereby treat a disease or condition. For instance, in some embodiments, the subject has familial hypercholesterolemia, characterized by elevated levels of LDL in the blood. In some embodiments, administration or use of a composition that includes a DNA-targeting system provided herein, or a polynucleotide or vector encoding the same, decreases expression of a combination of genes in a population of cells in the liver, leading to increased capacity of the liver cells to reduce LDL in the blood. Reduced LDL in the blood reduces the risk of adverse effects of familial hypercholesterolemia, including cardiovascular disease.

In some embodiments, the methods of administering a composition containing the DNA-targeting system or a polynucleotide or vector encoding the same to a subject as provided herein are carried out in vivo (i.e. in a subject).

In some embodiments, the methods and uses for administering the DNA-targeting systems results in delivery of the DNA-targeting system to liver cells (e.g. hepatocytes). In some embodiments, the methods of administering the epigenetic-modifying DNA-targeting system (or polynucleotides or vectors for delivery of same to the liver cell(s) or compositions of any of the foregoing) to a subject comprises contacting the DNA-targeting system with a liver cell or a population of liver cells. In some embodiments, the contacting introduces the epigenome-modifying DNA-targeting system (or polynucleotides or vectors for delivery of same to the liver cell or compositions of any of the foregoing) into the liver cell, such as where it is able to translocate or localize to the nucleus of the liver cell. In some embodiments, the methods promote an enhanced LDL-reducing phenotype in the liver cell or one or more liver cells in the population. In some embodiments, the methods increase the percentage of liver cells with the phenotype in the population of liver cells.

In some embodiments, the delivery to liver cells leads to an epigenetic change in the genome of the cell in a gene or regulatory region, or a combination of genes or regulatory regions, that is targeted by the DNA-targeting system. In some embodiments, the epigenetic change comprises a change in at least one of: DNA accessibility, histone methylation, acetylation, phosphorylation, ubiquitylation, sumoylation, ribosylation, citrullination, and DNA methylation. In some embodiments, the epigenetic change is an altered DNA methylation of a target site in a target gene or a regulatory element thereof as described herein. In some embodiments, the epigenetic change is a histone modification of a target site in a target gene or a regulatory element thereof as described herein. In some embodiments, the delivery of the DNA-targeting system to a liver cell (e.g., hepatocyte) results in a reduction of LDL in the liver of the subject.

In some embodiments, provided herein is a liver cell with an epigenetic modification, i.e., a modified liver cell. In some embodiments, the modifications in the epigenome of the liver cell is by targeting a combination of genes as described herein with a provided epigenetic-modifying DNA-targeting system to change the epigenome of the liver cell. In some embodiments, the modified liver cell includes an epigenetic change in a gene selected from the list consisting of: PCSK9, LPA, MYLIP, ANGLPTL3, APOC3, and APOB. In some embodiments, the epigenetic change of any of the above target genes is a change in at least one of: DNA accessibility, histone methylation, acetylation, phosphorylation, ubiquitylation, sumoylation, ribosylation, citrullination, and DNA methylation, compared to a comparable unmodified cell (e.g. liver cell) not subjected to the method, i.e. not contacted or introduced with the DNA-targeting system described herein.

In some embodiments, the administration of the DNA-targeting system modulates expression of a gene or a combination of genes in a liver cell, such as a gene or a combination of target genes as described in Section I.A. In some embodiments, the target gene or combination of target genes, such as the target genes described in Section I.A, is reduced in comparison to a comparable unmodified cell (e.g. liver) not subjected to the method, i.e. not contacted or introduced with the DNA-targeting system described herein. In some embodiments, the expression of the one or more genes is reduced by at least about 1.2-fold, 1.25-fold, 1.3-fold, 1.4-fold, 1.5-fold, 1.6-fold, 1.7-fold, 1.75-fold, 1.8-fold, 1.9-fold, 2-fold, 2.5-fold, 3-fold, 4-fold, 5-fold, 10-fold, 20-fold, 30-fold, 40-fold, 50-fold, 100-fold, 200-fold, 300-fold, 400-fold, 500-fold, 1000-fold or more. In some embodiments, the expression is stably reduced or transiently reduced. In some embodiments, the reduced expression of the combination of genes promotes a phenotype in a liver cell that reduces LDL in a subject. In some embodiments, a liver cell in the subject has been modulated to have reduced expression of a combination of genes selected from the list consisting of: PCSK9, LPA, MYLIP, ANGLPTL3, APOC3, and APOB. In some embodiments, the expression of each gene of the combination of genes in the modified liver cell is reduced by at least 1.5-fold or more compared to the expression of the same gene in a comparable unmodified liver cell, such as reduced by at or about or greater than 2-fold, 3-fold, 4-fold, 5-fold, 6-fold, 7-fold, 8-fold, 9-fold, 10-fold or more.

In some embodiments, the administration of the DNA-targeting system is provided as a single dose infusion to the subject. In some embodiments, the subject is redosed with the same or a higher dose of the DNA-targeting system. In some embodiments, the administration is repeated a plurality of times at regular intervals.

In some embodiments, the disease, condition, or disorder to be treated is elevated levels of low-density lipoprotein in the blood, increased risk of cardiovascular disease, increased risk of early-onset cardiovascular disease, a mutation affecting cholesterol biosynthesis, a loss-of-function mutation in a low-density lipoprotein receptor (LDLR) gene, a loss-of-function mutation in APOB, a gain-of-function mutation in PCSK9, or familial hypercholesterolemia.

In some embodiments, the subject has or is suspected of having elevated levels of low-density lipoprotein in the blood, increased risk of cardiovascular disease, increased risk of early-onset cardiovascular disease, a mutation affecting cholesterol biosynthesis, a loss-of-function mutation in a low-density lipoprotein receptor (LDLR) gene, a loss-of-function mutation in APOB, a gain-of-function mutation in PCSK9, or familial hypercholesterolemia.

In some embodiments, the subject has or is suspected of having familial hypercholesterolemia.

In some embodiments, the disease, condition or disorder to be treated is a cardiovascular disease. In some embodiments, the cardiovascular disease is Familial Hypercholestorlemia (FH). In some embodiments, the cardiovascular disease is artheoscherotic cardiovascular disease (ASCVD).

Once the multiplexed epigenetic-modifying DNA-targeting system is administered to the subject (e.g., human), the biological activity of the modified cell populations in some aspects is measured by any of a number of known methods. Parameters to assess include reduced levels of circulating LDL (e.g. by analysis of blood serum using ELISA), reduced expression of target genes in the liver cells (e.g. ex vivo, by qRT-PCR), increased capacity for LDL uptake (e.g. based on uptake of fluorescently labeled LDL molecules as assessed by flow cytometry), and/or increased expression of LDL-R. In some aspects the biological activity is measured by assessing clinical outcome. Specific thresholds for the parameters can be set to determine the efficacy of the methods of therapy provided herein.

V. Kits and Articles of Manufacture

Also provided are articles of manufacture, systems, apparatuses, and kits useful in performing the provided embodiments. In some embodiments, the provided articles of manufacture or kits contain any of the DNA-targeting systems described herein, any of the gRNAs described herein, any of the fusion proteins described herein, any of the polynucleotides described herein, any of the pluralities of polynucleotides described herein, any of the vectors described herein, any of the pluralities of vectors described herein, or a portion or a component of any of the foregoing, or any combination thereof. In some embodiments, the articles of manufacture or kits include polypeptides, polynucleotides, nucleic acids, vectors, and/or cells useful in performing the provided methods.

In some embodiments, the articles of manufacture or kits include one or more containers, typically a plurality of containers, packaging material, and a label or package insert on or associated with the container or containers and/or packaging, generally including instructions for use, e.g., instructions for introducing or administering.

Also provided are articles of manufacture, systems, apparatuses, and kits useful in administering the provided compositions, e.g., pharmaceutical compositions, e.g., for use in therapy or treatment. In some embodiments, the articles of manufacture or kits provided herein contain vectors and/or plurality of vectors, such as any vectors and/or plurality of vectors described herein. In some aspects, the articles of manufacture or kits provided herein can be used for administration of the vectors and/or plurality of vectors, and can include instructions for use.

The articles of manufacture and/or kits containing compositions for therapy, may include a container and a label or package insert on or associated with the container. Suitable containers include, for example, bottles, vials, syringes, IV solution bags, etc. The containers may be formed from a variety of materials such as glass or plastic. The container in some embodiments holds a composition which is by itself or combined with another composition effective for treating, preventing and/or diagnosing the condition. In some embodiments, the container has a sterile access port. Exemplary containers include an intravenous solution bags, vials, including those with stoppers pierceable by a needle for injection, or bottles or vials for orally administered agents. The label or package insert may indicate that the composition is used for treating a disease or condition. The article of manufacture may further include a package insert indicating that the compositions can be used to treat a particular condition. Alternatively, or additionally, the article of manufacture may further include another or the same container comprising a pharmaceutically-acceptable buffer. It may further include other materials such as other buffers, diluents, filters, needles, and/or syringes.

VI. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known. Reference to "about" a value or parameter herein includes (and describes) embodiments that are directed to that value or parameter per se. For example, description referring to "about X" includes description of "X". In some embodiments, "about" may refer to ±25%, ±20%, ±15%, ±10%, ±5%, or ±1%.

As used herein, recitation that nucleotides or amino acid positions "correspond to" nucleotides or amino acid positions in a disclosed sequence, such as set forth in the Sequence listing, refers to nucleotides or amino acid positions identified upon alignment with the disclosed sequence to maximize identity using a standard alignment algorithm, such as the GAP algorithm. By aligning the sequences, corresponding residues can be identified, for example, using conserved and identical amino acid residues as guides. In general, to identify corresponding positions, the sequences of amino acids are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carrillo et al. (1988) SIAM J Applied Math 48: 1073).

A "gene," includes a DNA region encoding a gene product. Thus, the gene typically refers to coding and/or transcribed sequences. The sequence of a gene is typically present at a fixed chromosomal position or locus on a chromosome in the cell.

A "regulatory element" or "DNA regulatory element," which terms are used interchangeably herein, in reference to a gene refers to DNA regions which regulate the production of a gene product, whether or not such regulatory sequences are adjacent to coding and/or transcribed sequences. Accordingly, a regulatory element includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

As used herein, a "target site" or "target nucleic acid sequence" is a nucleic acid sequence that defines a portion of a nucleic acid to which a binding molecule (e.g. a DNA-binding domain disclosed herein) will bind, provided sufficient conditions for binding exist.

The term "expression" with reference to a gene or "gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or can be a protein produced by translation of an mRNA. For instance, expression includes the transcription and/or translation of a particular nucleotide sequence drive by its promoter. Gene products also include RNAs which are modified, by processes such as capping, polyadenylation, methylation, and editing, and proteins modified by, for example, methylation, acetylation, phosphorylation, ubiquitination, ADP-ribosylation, myristoylation, and glycosylation. Hence, reference to expression or gene expression includes protein (or polypeptide) expression or expression of a transcribable product of or a gene such as mRNA. The protein expression may include intracellular expression or surface expression of a protein. Typically, expression of a gene product, such as mRNA or protein, is at a level that is detectable in the cell.

As used herein, a "detectable" expression level, means a level that is detectable by standard techniques known to a skilled artisan, and include for example, differential display, RT (reverse transcriptase)-coupled polymerase chain reaction (PCR), Northern Blot, and/or RNase protection analyses as well as immunoaffinity-based methods for protein detection, such as flow cytometry, ELISA, or western blot. The degree of expression levels need only be large enough to be visualized or measured via standard characterization techniques.

As used herein, the term "DNA-targeting system" or "epigenetic-modifying DNA-targeting system" refers to a composition comprising a DNA-binding domain (such as any Cas, ZFN, or TALE-based DNA-binding domain described herein) that targets a target site of a target gene. In some embodiments, the DNA-targeting system is engineered to target the target site. In some embodiments, the DNA-targeting system comprises one or more effector domains that modify transcription of the target gene when recruited to the target site by the DNA-targeting system. In some embodiments, the DNA-targeting system is capable of targeting more than one target site (i.e. a plurality of target sites), such as 2, 3, 4, 5, 6, or more target sites.

As used herein, the term "DNA-targeting module" refers to any composition or portion of a DNA-targeting system described herein that targets one target site. For example, an individual DNA-targeting module may comprise a fusion protein comprising a DNA-binding domain (e.g. a ZFN or TALE DNA-binding domain) that targets a target site for a target gene, and a transcriptional repressor domain (e.g. KRAB). In other embodiments, a DNA-targeting module comprises (a) a fusion protein comprising a Cas protein and a transcriptional repressor domain, and (b) a gRNA that targets a target site of a target gene. A DNA-targeting system provided herein may comprise one or more (such as two) DNA-targeting modules.

In some embodiments, two DNA-targeting modules of a DNA-targeting system may comprise separate, (i.e. non-overlapping) components. For example, a DNA-targeting system may comprise two different fusion proteins, each fusion protein targeting and repressing a different gene. For example, the DNA-targeting system may comprise a first DNA-targeting module comprising a first fusion protein comprising a DNA-binding domain (such as a ZFN or TALE DNA-binding domain) that targets a target site for a first gene and a transcriptional repressor domain, and a second DNA-targeting module comprising a second fusion protein comprising a DNA-binding domain that targets a target site for a second gene and a transcriptional repressor domain. In another example, the DNA-targeting system may comprise a first DNA-targeting module comprising a first fusion protein comprising a DNA-binding domain that targets a target site for a first gene (such as a ZFN or TALE DNA-binding domain) and a transcriptional repressor domain, and a second DNA-targeting module comprising (a) a fusion protein comprising a Cas protein and a transcriptional repressor domain and (b) a gRNA that targets a target site for a second gene. In another example, the DNA-targeting system may comprise a first DNA-targeting module comprising a first fusion protein comprising a first Cas protein and a transcriptional repressor domain, and (b) a first gRNA that complexes with the first Cas protein and targets a target site for a first target gene, and a second DNA-targeting module comprising a second fusion protein comprising a second Cas protein that is different from the first Cas protein and a transcriptional repressor domain, and (b) a second gRNA that complexes with the second Cas protein and targets the second Cas protein to a target site for a second target gene. It will be understood that different Cas protein variants (e.g. SpCas9 and SaCas9) are compatible with different gRNA scaffold sequences and PAMs, as described herein. Thus, it is possible to engineer a single DNA-targeting system comprising multiple non-overlapping CRISPR/Cas-based DNA-targeting modules, each targeting a different target site.

In some embodiments, two DNA-targeting modules of a DNA-targeting system may comprise shared (i.e. overlapping) components. For example, a DNA-targeting system may comprise a first DNA-targeting module comprising (a) a fusion protein comprising a Cas protein and a transcriptional repressor domain, and (b) a gRNA that targets a target site for a first gene, and a second DNA-targeting module comprising (a) the fusion protein of the first DNA-targeting module, and (b) a gRNA that targets a target site for a second gene. It will be understood that providing two or more different gRNAs for a given Cas protein allows different molecules of the same Cas protein to be targeted to the target sites of the two or more gRNAs.

As used herein, the term "increased expression", "enhanced expression" or "overexpression" means any form of expression that is additional to the expression in an original or source cell that does not contain the modification for modulating a particular gene expression by a DNA-targeting system, for instance a wild-type expression level (which can be absence of expression or immeasurable expression as well). Reference herein to "increased expression," "enhanced expression" or "overexpression" is taken to mean an increase in gene expression relative to the level in a cell that does not contain the modification, such as the original source cell prior to contacting with, or engineering to introduce, the DNA-targeting system into the cell, such as an unmodified cell or a wild-type cell. The increase in expression can be at least 5%, 10%, 20%, 30%, 40% or 50%, 60%, 70%, 80%, 85%, 90%, or 100% or even more. In some cases, the increase in expression can be at least 2-fold, 5-fold, 10-fold, 20-fold, 30-fold, 40-fold, 50-fold, 60-fold, 70-fold, 80-fold, 90-fold, 100-fold. 200-fold, 300-fold, 400-fold, 500-fold, 1000-fold or more.

As used herein, the term "reduced expression" or "decreased expression" means any form of expression that is lower than the expression in an original or source cell that does not contain the modification for modulating a particular gene expression by a DNA-targeting system, for instance a wild-type expression level (which can be absence of expression or immeasurable expression as well). Reference herein to "reduced expression," or "decreased expression" is taken to mean a decrease in gene expression relative to the level in a cell that does not contain the modification, such as the original source cell prior to contacting with, or engineering to introduce, the DNA-binding system into the cell, such as an unmodified cell or a wild-type cell. The decrease in expression can be at least 5%. 10%, 20%, 30%, 40% or 50%, 60%, 70%, 80%, 85% k, 90%, or 100% or even more. In some cases, the decrease in expression can be at least 2-fold, 5-fold, 10-fold, 20-fold, 30-fold, 40-fold. 50-fold, 60-fold, 70-fold, 80-fold, 90-fold, 100-fold, 200-fold or more.

As used herein, the term "reduced transcription" or "decreased transcription" refers to the level of transcription of a gene that is lower than the transcription of the gene in an original or source cell that does not contain the modification for modulating transcription by a DNA-targeting system, for instance a wild-type transcription level of a gene. Reference to reduced transcription or decreased transcription can refer to reduction in the levels of a transcribable product of a gene such as mRNA. Any of a variety of methods can be used to monitor or quantitate a level of a transcribable product such as mRNA, including but not limited to, real-time quantitative RT (reverse transcriptase)-polymerase chain reaction (qRT-PCR), Northern Blot, microarray analysis, or RNA sequencing (RNA-Seq). The reduction in transcription can be at least 5%, 10%, 20%, 30%, 40% or 50%, 60%, 70%, 80%, 85%, 90%, or 100% or even more. In some cases, the reduction in transcription can be at least 2-fold, 5-fold, 10-fold, 20-fold, 30-fold, 40-fold, 50-fold, 60-fold, 70-fold, 80-fold, 90-fold, 100-fold, 200-fold or more.

As used herein, an "epigenetic modification" refers to changes in the gene expression that are non-genetic modifications, i.e. not caused by changes in the DNA sequences, but are due to epigenetic changes such as events like DNA methylations or histone modifications. An epigenetic modification may result in a heritable change in gene activity and expression that occur without alteration in DNA sequence. For instance, epigenetic modifications include non-genetic modifications such as chemical modifications to the cytosine residues of DNA (DNA methylation) and histone proteins associated with DNA (histone modifications).

As used herein, the term "modification" or "modified" with reference to a cell refers to any change or alteration in a cell that impacts gene expression in the cell. In some embodiments, the modification is an epigenetic modification that directly changes the epigenetic state of a gene or regulatory elements thereof to alter (e.g. reduce or increase) expression of a gene product. In some embodiments, a modification described herein results in reduced expression of a target gene or selected polynucleotide sequence.

As used herein, a "fusion" molecule is a molecule in which two or more subunit molecules are linked, such as covalently. Examples of a fusion molecule include, but are not limited to, fusion proteins (for example, a fusion between a DNA-binding domain such as a ZFP, TALE DNA-binding domain or CRISPR-Cas protein and one or more effector domains, such as a transactivation domain). The fusion molecule also may be part of a system in which a polynucleotide component associates with a polypeptide component to form a functional molecule (e.g., a CRISPR/Cas system in which a single guide RNA associates with a functional domain to modulate gene expression). Fusion molecules also include fusion nucleic acids, for example, a nucleic acid encoding the fusion protein. Expression of a fusion protein in a cell can result from delivery of the fusion protein to the cell or by delivery of a polynucleotide encoding the fusion protein to a cell, where the polynucleotide is transcribed, and the transcript is translated, to generate the fusion protein.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." Among the vectors are viral vectors, such as adenoviral vectors or lentiviral vectors.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include, but are not limited to, cosmids, plasmids (e.g., naked or contained in liposomes) and viruses (e.g., lentiviruses, retroviruses, adenoviruses, and adeno-associated viruses) that incorporate the recombinant polynucleotide.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "polynucleotide" refers to a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomelic nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, "percent (%) amino acid sequence identity" and "percent identity" when used with respect to an amino acid sequence (reference polypeptide sequence) is defined as the percentage of amino acid residues in a candidate sequence (e.g., the subject antibody or fragment) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various known ways, in some embodiments, using publicly available computer software such as BLAST, BLAST-2, ALIGN or Megalign (DNASTAR) software. Appropriate parameters for aligning sequences can be determined, including any algorithms needed to achieve maximal alignment over the full length of the sequences being compared.

In some embodiments, "operably linked" may include the association of components, such as a DNA sequence, (e.g. a heterologous nucleic acid) and a regulatory sequence(s), in such a way as to permit gene expression when the appropriate molecules (e.g. transcriptional activator proteins) are bound to the regulatory sequence. Hence, it means that the components described are in a relationship permitting them to function in their intended manner.

An amino acid substitution may include replacement of one amino acid in a polypeptide with another amino acid. The substitution may be a conservative amino acid substitution or a non-conservative amino acid substitution. Amino acid substitutions may be introduced into a binding molecule, e.g., antibody, of interest and the products screened for a desired activity, e.g., retained/improved antigen binding, decreased immunogenicity, or improved ADCC or CDC.

Amino acids generally can be grouped according to the following common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

In some embodiments, conservative substitutions can involve the exchange of a member of one of these classes for another member of the same class. In some embodiments, non-conservative amino acid substitutions can involve exchanging a member of one of these classes for another class.

As used herein, a composition refers to any mixture of two or more products, substances, or compounds, including cells. It may be a solution, a suspension, liquid, powder, a paste, aqueous, non-aqueous or any combination thereof.

As used herein, a "subject" or an "individual," which are terms that are used interchangeably, is a mammal. In some embodiments, a "mammal" includes humans, non-human primates, domestic and farm animals, and zoo, sports, or pet animals, such as dogs, horses, rabbits, cattle, pigs, hamsters, gerbils, mice, ferrets, rats, cats, monkeys, etc. In some embodiments, the subject or individual is human. In some embodiments, the subject is a patient that is known or suspected of having a disease, disorder or condition.

As used herein, the term "treating" and "treatment" includes administering to a subject an effective amount of a biological molecule, such as a therapeutic agent, so that the subject has a reduction in at least one symptom of the disease or an improvement in the disease, for example, beneficial or desired clinical results. For instance, a biological molecule may include cells (e.g. liver cells), such as cells that have been modified by a DNA-targeting system or polynucleotide(s) encoding the DNA-targeting system described herein. For purposes of this technology, beneficial or desired clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Thus, one of skill in the art realizes that a treatment may improve the disease condition, but may not be a complete cure for the disease. In some embodiments, one or more symptoms of a disease or disorder are alleviated by at least 5%, at least 10%, at least 20%, at least 30%, at least 40%, or at least 50% upon treatment of the disease.

For purposes of this technology, beneficial or desired clinical results of disease treatment include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a biological molecule, such as a compound or cells, that, when administered, is sufficient to prevent development of, or alleviate to some extent, one or more of the signs or symptoms of the disorder or disease being treated. The therapeutically effective amount will vary depending on the biological molecule, the disease and its severity and the age, weight, etc., of the subject to be treated.

VII. Exemplary Embodiments

Among the provided embodiments are:
1. An epigenetic-modifying DNA-targeting system comprising a plurality of DNA-targeting modules for repressing transcription of a plurality of genes that regulate low-density lipoprotein (LDL),
wherein the plurality of DNA-targeting modules comprises a first DNA-targeting module for repressing transcription of a first gene of the plurality of genes, and a second DNA-targeting module for repressing transcription of a second gene of the plurality of genes, and
wherein each DNA-targeting module comprises a fusion protein comprising: (a) a DNA-binding domain for targeting to a target site of one of the plurality of genes, and (b) at least one transcriptional repressor domain.
2. The epigenetic-modifying DNA-targeting system of embodiment 1, wherein the DNA-targeting system does not introduce a genetic disruption or a DNA break.
3. The epigenetic-modifying DNA-targeting system of embodiment 1 or embodiment 2, wherein the fusion protein of each DNA-targeting module comprises a DNA-binding domain selected from: a Clustered Regularly Interspaced Short Palindromic Repeats associated (Cas) protein or a variant thereof; a zinc finger protein (ZFP); a transcription activator-like effector (TALE); a meganuclease; a homing endonuclease; or an I-SceI enzyme or a variant thereof, optionally wherein the DNA-binding domain comprises a catalytically inactive variant of any of the foregoing.
4. The epigenetic-modifying DNA-targeting system of any of embodiments 1-3, wherein:
the fusion protein of the first DNA-targeting module comprises a DNA-binding domain for targeting a target site of the first gene or regulatory DNA element thereof, and at least one transcriptional repressor domain; and
the fusion protein of the second DNA-targeting module comprises a DNA-binding domain for targeting a target site of the second gene or regulatory DNA element thereof, and at least one transcriptional repressor domain.
5. The epigenetic-modifying DNA-targeting system of any of embodiments 1-4, wherein any two or more of the DNA-targeting modules comprise the same fusion protein.
6. The epigenetic-modifying DNA-targeting system of any of embodiments 1-5, wherein the first and second DNA-targeting modules comprise the same fusion protein.
7. The epigenetic-modifying DNA-targeting system of any of embodiments 1-4, wherein any two or more of the DNA-targeting modules comprise different fusion proteins.
8. The epigenetic-modifying DNA-targeting system of any of embodiments 1-4 and 7, wherein the first and second DNA-targeting modules comprise different fusion proteins.
9. An epigenetic-modifying DNA-targeting system comprising a plurality of DNA-targeting modules for repressing transcription of a plurality of genes that regulate low-density lipoprotein (LDL), comprising:
(1) a first DNA-targeting module that reduces transcription of a first gene that regulates low-density lipoprotein (LDL), wherein the first DNA-targeting module comprises a first fusion protein comprising (a) a DNA-binding domain for targeting a target site of the first gene or regulatory DNA element thereof; and (b) at least one transcriptional repressor domain; and (2) a second DNA-targeting module that reduces transcription of a second gene that regulates LDL, wherein the second DNA-targeting module comprises a second fusion protein comprising (a) a DNA-binding domain for targeting a target site of the second gene or regulatory DNA element thereof; and (b) at least one transcriptional repressor domain.

10. The epigenetic-modifying DNA-targeting system of embodiment 5 or 6, wherein the first DNA-targeting module comprises a first targeting polynucleotide for targeting to the target site of the first gene and the second DNA-targeting module comprises a second targeting polynucleotide for targeting to the target site of the second gene, wherein the first and second targeting polynucleotides complex with the DNA-binding domain of the fusion protein.

11. The epigenetic-modifying DNA-targeting system of embodiment 10, wherein the DNA-binding domain is a Clustered Regularly Interspaced Short Palindromic Repeats associated (Cas) protein or variant thereof and the first and second targeting polynucleotides comprise a first gRNA and a second gRNA, respectively.

12. An epigenetic-modifying DNA-targeting system comprising:
(a) a fusion protein comprising a Clustered Regularly Interspaced Short Palindromic Repeats associated (Cas) protein or variant thereof and at least one transcriptional repressor domain; and
(b) a plurality of guide RNAs (gRNAs) comprising at least a first gRNA and a second gRNA, wherein the first gRNA targets a target site of a first gene that regulates low-density lipoprotein (LDL) and the second gRNA targets a target site of a second gene that regulates LDL.

13. The epigenetic-modifying DNA-targeting system of any of embodiments 1-12, wherein the system further comprises a third DNA-targeting module for repressing transcription of a third gene that regulates low-density lipoprotein (LDL).

14. The epigenetic-modifying DNA-targeting system of any of embodiments 11-13, wherein the system further comprises a third gRNA that targets a target site of a third gene that regulates LDL,
optionally wherein the system further comprises a fourth gRNA that targets a target site of a fourth gene that regulates LDL, optionally a fifth gRNA that targets a target site of a fifth gene that regulates LDL, and/or optionally a sixth gRNA that targets a target site of a sixth gene that regulates LDL.

15. The epigenetic-modifying DNA-targeting system of any of embodiments 1-14, wherein the first gene and the second gene are independently selected from the group consisting of PCSK9, LPA, MYLIP, ANGPTL3, APOB, and APOC3.

16. The epigenetic-modifying DNA-targeting system of any of embodiments 1-15, wherein the first gene and the second gene are different.

17. The epigenetic-modifying DNA-targeting system of any of embodiments 1-16, wherein the first gene and the second gene are: PCSK9 and LPA; PCSK9 and MYLIP; PCSK9 and ANGPTL3; PCSK9 and APOC3; PCSK9 and APOB; LPA and MYLIP; LPA and ANGPTL3; LPA and APOC3; LPA and APOB; MYLIP and ANGPTL3; MYLIP and APOC3; MYLIP and APOB; ANGPTL3 and APOC3; ANGPTL3 and APOB; or APOC3 and APOB.

18. The epigenetic-modifying DNA-targeting system of any of embodiments 1-17, wherein the first gene, the second gene, and the third gene are each independently selected from the group consisting of PCSK9, LPA, MYLIP, ANGPTL3, APOC3, and APOB.

19. The epigenetic-modifying DNA-targeting system of any of embodiments 13-18, wherein the first gene, the second gene, and the third gene are different.

20. The epigenetic-modifying DNA-targeting system combination of any of embodiments 13-19, wherein the first gene, the second gene, and the third gene are: PCSK9, LPA, and MYLIP; PCSK9, LPA, and ANGPTL3; PCSK9, LPA, and APOC3; PCSK9, LPA, and APOB; PCSK9, MYLIP, and ANGPTL3; PCSK9, MYLIP, and APOC3; PCSK9, MYLIP, and APOB; PCSK9, ANGPTL3, and APOC3; PCSK9, ANGPTL3, and APOB; PCSK9, APOC3, and APOB; LPA, MYLIP, and ANGPTL3; LPA, MYLIP, and APOC3; LPA, MYLIP, and APOB; LPA, ANGPTL3, and APOC3; LPA, ANGPTL3, and APOB; LPA, APOC3, and APOB; MYLIP, ANGPTL3, and APOC3; MYLIP, ANGPTL3, and APOB; MYLIP, APOC3, and APOB; or ANGPTL3, APOC3, and APOB.

21. The epigenetic-modifying DNA-targeting system of any of embodiments 1-20, wherein at least one gene is PCSK9.

22. The epigenetic-modifying DNA-targeting system of any of embodiments 1-21, wherein at least two genes are PCSK9 and LPA.

23. The epigenetic-modifying DNA-targeting system of any of embodiments 13-22, wherein at least three genes are PCSK9, LPA, and MYLIP.

24. The epigenetic-modifying DNA-targeting system of any of embodiments 1-23, wherein the target site of each of the plurality of genes is in the gene or a regulatory DNA element thereof.

25. The epigenetic-modifying DNA-targeting system of embodiment 24, wherein the regulatory DNA element is an enhancer or a promoter.

26. The epigenetic-modifying DNA-targeting system of any of embodiments 1-25, wherein the target site of the first gene and the second gene are selected from two different members of the group consisting of (a)-(f):
(a) a target site for PCSK9, located within 500 bp of human genome assembly GRCh38 (hg38) genomic coordinates chr1:55,039,548;
(b) a target site for LPA, located within 500 bp of the hg38 genomic coordinates chr6:160,664,275;
(c) a target site for MYLIP, located within 500 bp of the hg38 genomic coordinates chr6:16,129,086;
(d) a target site for ANGPTL3, located within 500 bp of the hg38 genomic coordinates chr1:62,597,520;
(e) a target site for APOC3, located within 500 bp of the hg38 genomic coordinates chr11:116,829,907; and
(f) a target site for APOB, located within 500 bp of the hg38 genomic coordinates chr2:21,044,073.

27. The epigenetic-modifying DNA-targeting system of any of embodiments 1-26, wherein the target site of the first gene and the second gene are selected from two different members of the group consisting of (a)-(f):
(a) a target site located within 500 bp of a transcriptional start site of PCSK9;
(b) a target site located within 500 bp of a transcriptional start site of LPA;
(c) a target site located within 500 bp of a transcriptional start site of MYLIP;
(d) a target site located within 500 bp of a transcriptional start site of ANGPTL3;

(e) a target site located within 500 bp of a transcriptional start site of APOC3; and
(f) a target site located within 500 bp of a transcriptional start site of APOB.

28. The epigenetic-modifying DNA-targeting system of any of embodiments 13-27, wherein the target site of the first gene, the second gene and the third gene are selected from three different members of the group consisting of (a)-(f):
(a) a target site for PCSK9, located within 500 bp of human genome assembly GRCh38 (hg38) genomic coordinates chr1:55,039,548;
(b) a target site for LPA, located within 500 bp of the hg38 genomic coordinates chr6:160,664,275;
(c) a target site for MYLIP, located within 500 bp of the hg38 genomic coordinates chr6:16,129,086;
(d) a target site for ANGPTL3, located within 500 bp of the hg38 genomic coordinates chr1:62,597,520;
(e) a target site for APOC3, located within 500 bp of the hg38 genomic coordinates chr11:116,829,907; and
(f) a target site for APOB, located within 500 bp of the hg38 genomic coordinates chr2:21,044,073.

29. The epigenetic-modifying DNA-targeting system of any of embodiments 13-28, wherein the target site of the first gene, the second gene and the third gene are selected from three different members of the group consisting of (a)-(f):
(a) a target site located within 500 bp of a transcriptional start site of PCSK9;
(b) a target site located within 500 bp of a transcriptional start site of LPA;
(c) a target site located within 500 bp of a transcriptional start site of MYLIP;
(d) a target site located within 500 bp of a transcriptional start site of ANGPTL3;
(e) a target site located within 500 bp of a transcriptional start site of APOC3; and
(f) a target site located within 500 bp of a transcriptional start site of APOB.

30. The epigenetic-modifying DNA-targeting system of any of embodiments 1-29, wherein the target site of the first gene and the second gene are selected from two different members of the group consisting of (a)-(f):
(a) a target site for PCSK9 having the sequence set forth in any one of SEQ ID NOS:1-13 or 306-317, a contiguous portion thereof of at least 14 nucleotides (nt), or a complementary sequence of any of the foregoing, optionally wherein the target site is (i) set forth in SEQ ID NO:3, (ii) has a contiguous portion of SEQ ID NO:3 of at least 14 nucleotides, or (iii) is a complementary sequence of (i) or (ii);
(b) a target site for LPA having the sequence set forth in any one of SEQ ID NOS:14-23, a contiguous portion thereof of at least 14 nucleotides (nt), or a complementary sequence of any of the foregoing;
(c) a target site for MYLIP having the sequence set forth in any one of SEQ ID NOS:24-33 or 342-351, a contiguous portion thereof of at least 14 nucleotides (nt), or a complementary sequence of any of the foregoing;
(d) a target site for ANGPTL3 having the sequence set forth in any one of SEQ ID NOS:34-43, a contiguous portion thereof of at least 14 nucleotides (nt), or a complementary sequence of any of the foregoing;
(e) a target site for APOC3 having the sequence set forth in any one of SEQ ID NOS:44-53, a contiguous portion thereof of at least 14 nucleotides (nt), or a complementary sequence of any of the foregoing; and
(f) a target site for APOB having the sequence set forth in any one of SEQ ID NOS:54-63 or 372-377, a contiguous portion thereof of at least 14 nucleotides (nt), or a complementary sequence of any of the foregoing.

31. The epigenetic-modifying DNA-targeting system combination of any of embodiments 1-30, wherein the target site of the first gene and the second gene are selected from two different members of the group consisting of (a)-(f):
(a) a target site of PCSK9 having the sequence set forth in any one of SEQ ID NOS:1-13 or 306-317, optionally wherein the target site is set forth in SEQ ID NO:3;
(b) a target site of LPA having the sequence set forth in any one of SEQ ID NOS:14-23;
(c) a target site of MYLIP having the sequence set forth in any one of SEQ ID NOS:24-33 or 342-351;
(d) a target site of ANGPTL3 having the sequence set forth in any one of SEQ ID NOS: 34-43;
(e) a target site of APOC3 having the sequence set forth in any one of SEQ ID NOS:44-53; and
(f) a target site of APOB having the sequence set forth in any one of SEQ ID NOS:54-63 or 372-377.

32. The epigenetic-modifying DNA-targeting system combination of any of embodiments 13-31, wherein the target site of the first gene, the second gene and the third gene are selected from three different members of the group consisting of (a)-(f):
(a) a target site of PCSK9 having the sequence set forth in any one of SEQ ID NOS:1-13 or 306-317, a contiguous portion thereof of at least 14 nucleotides (nt), or a complementary sequence of any of the foregoing, optionally wherein the target site is (i) set forth in SEQ ID NO:3, (ii) has a contiguous portion of SEQ ID NO:3 of at least 14 nucleotides, or (iii) is a complementary sequence of (i) or (ii);
(b) a target site of LPA having the sequence set forth in any one of SEQ ID NOS:14-23, a contiguous portion thereof of at least 14 nucleotides (nt), or a complementary sequence of any of the foregoing;
(c) a target site of MYLIP having the sequence set forth in any one of SEQ ID NOS:24-33 or 342-351, a contiguous portion thereof of at least 14 nucleotides (nt), or a complementary sequence of any of the foregoing;
(d) a target site of ANGPTL3 having the sequence set forth in any one of SEQ ID NOS:34-43, a contiguous portion thereof of at least 14 nucleotides (nt), or a complementary sequence of any of the foregoing;
(e) a target site of APOC3 having the sequence set forth in any one of SEQ ID NOS:44-53, a contiguous portion thereof of at least 14 nucleotides (nt), or a complementary sequence of any of the foregoing; and
(f) a target site of APOB having the sequence set forth in any one of SEQ ID NOS:54-63 or 372-377, a contiguous portion thereof of at least 14 nucleotides (nt), or a complementary sequence of any of the foregoing.

33. The epigenetic-modifying DNA-targeting system combination of any of embodiments 13-32, wherein the target site of the first gene, the second gene or the third gene are selected from three different members of the group consisting of (a)-(f):
(a) a target site of PCSK9 having the sequence set forth in any one of SEQ ID NOS:1-13 or 306-317, optionally wherein the target site is set forth in SEQ ID NO:3; (b)

a target site of LPA having the sequence set forth in any one of SEQ ID NOS:14-23;
(c) a target site of MYLIP having the sequence set forth in any one of SEQ ID NOS:24-33 or 342-351;
(d) a target site of ANGPTL3 having the sequence set forth in any one of SEQ ID NOS: 34-43;
(e) a target site of APOC3 having the sequence set forth in any one of SEQ ID NOS:44-53; and
(f) a target site of APOB having the sequence set forth in any one of SEQ ID NOS:54-63 or 372-377.

34. The epigenetic-modifying DNA-targeting system of any of embodiments 11-33, wherein the Cas protein or variant thereof is a variant Cas protein that is a deactivated (dCas) protein.

35. The epigenetic-modifying DNA-targeting system of embodiment 34, wherein the dCas protein lacks nuclease activity.

36. The epigenetic-modifying DNA-targeting system of embodiment 34 or embodiment 35, wherein the dCas protein is a dCas9 protein.

37. The epigenetic-modifying DNA-targeting system of embodiment 34 or embodiment 35, wherein the dCas protein is a dCas12 protein.

38. The epigenetic-modifying DNA-targeting system of embodiment 36, wherein the dCas9 protein is a *Staphylococcus aureus* dCas9 (dSaCas9) protein.

39. The epigenetic-modifying DNA-targeting system of embodiment 38, wherein the dSaCas9 comprises at least one amino acid mutation selected from D10A and N580A, with reference to numbering of positions of SEQ ID NO:204.

40. The epigenetic-modifying DNA-targeting system of embodiment 38 or embodiment 39, wherein the dSaCas9 protein comprises the sequence set forth in SEQ ID NO:205, or an amino acid sequence that has at least 90%, 91%, 92%, 93%, 94%, 95%, 96%, 97%, 98%, or 99% sequence identity thereto.

41. The epigenetic-modifying DNA-targeting system of any of embodiments 38-40, wherein the dSaCas9 is set forth in SEQ ID NO:205.

42. The epigenetic-modifying DNA-targeting system of embodiment 36, wherein the dCas9 protein is a *Streptococcus pyogenes* dCas9 (dSpCas9) protein.

43. The epigenetic-modifying DNA-targeting system of embodiment 42, wherein the dSpCas9 protein comprises at least one amino acid mutation selected from D10A and H840A, with reference to numbering of positions of SEQ ID NO:206.

44. The epigenetic-modifying DNA-targeting system of 42 or embodiment 43, wherein the dSpCas9 comprises the sequence set forth in SEQ ID NO:207, or an amino acid sequence that has at least 90%, 91%, 92%, 93%, 94%, 95%, 96%, 97%, 98%, or 99% sequence identity thereto.

45. The epigenetic-modifying DNA-targeting system of any of embodiments 42-44, wherein the dSpCas9 is set forth in SEQ ID NO:207.

46. The epigenetic-modifying DNA-targeting system of any of embodiments 11-45, wherein each gRNA comprises a gRNA spacer sequence that is complementary to the target site of the respective gene.

47. The epigenetic-modifying DNA-targeting system of any of embodiments 11-46, wherein the first gRNA and the second gRNA are selected from two different members of the group consisting of (a)-(f):
(a) a gRNA targeting a target site of PCSK9 comprising a gRNA spacer sequence comprising the sequence set forth in any one of SEQ ID NOS:64-76 or 318-329, or a contiguous portion thereof of at least 14 nt, optionally wherein the gRNA spacer sequence comprises the sequence set forth in SEQ ID NO:66 or a contiguous portion of at least 14 nt;
(b) a gRNA targeting a target site of LPA comprising a gRNA spacer sequence comprising the sequence set forth in any one of SEQ ID NOS:77-86, or a contiguous portion thereof of at least 14 nt;
(c) a gRNA targeting a target site of MYLIP comprising a gRNA spacer sequence comprising the sequence set forth in any one of SEQ ID NOS:87-96 or 352-361, or a contiguous portion thereof of at least 14 nt;
(d) a gRNA targeting a target site of ANGPTL3 comprising a gRNA spacer sequence comprising the sequence set forth in any one of SEQ ID NOS:97-106, or a contiguous portion thereof of at least 14 nt;
(e) a gRNA targeting a target site of APOC3 comprising a gRNA spacer sequence comprising the sequence set forth in any one of SEQ ID NOS:107-116, or a contiguous portion thereof of at least 14 nt; and
(f) a gRNA targeting a target site of APOB comprising a gRNA spacer sequence comprising the sequence set forth in any one of SEQ ID NOS:117-126 or 378-383, or a contiguous portion thereof of at least 14 nt.

48. The epigenetic-modifying DNA-targeting system of any of embodiments 13-47, wherein the first gRNA, the second gRNA, and the third gRNA are selected from three different members of the group consisting of (a)-(f):
(a) a gRNA targeting a target site of PCSK9 comprising a gRNA spacer sequence comprising the sequence set forth in any one of SEQ ID NOS:64-76 or 318-329, or a contiguous portion thereof of at least 14 nt, optionally wherein the gRNA spacer sequence comprises the sequence set forth in SEQ ID NO:66 or a contiguous portion of at least 14 nt;
(b) a gRNA targeting a target site of LPA comprising a gRNA spacer sequence comprising the sequence set forth in any one of SEQ ID NOS:77-86, or a contiguous portion thereof of at least 14 nt;
(c) a gRNA targeting a target site of MYLIP comprising a gRNA spacer sequence comprising the sequence set forth in any one of SEQ ID NOS:87-96 or 352-361, or a contiguous portion thereof of at least 14 nt;
(d) a gRNA targeting a target site of ANGPTL3 comprising a gRNA spacer sequence comprising the sequence set forth in any one of SEQ ID NOS:97-106, or a contiguous portion thereof of at least 14 nt;
(e) a gRNA targeting a target site of APOC3 comprising a gRNA spacer sequence comprising the sequence set forth in any one of SEQ ID NOS:107-116, or a contiguous portion thereof of at least 14 nt; and
(f) a gRNA targeting a target site of APOB comprising a gRNA spacer sequence comprising the sequence set forth in any one of SEQ ID NOS:117-126 or 378-383, or a contiguous portion thereof of at least 14 nt.

49. The epigenetic-modifying DNA-targeting system of any of embodiments 11-48, wherein each gRNA independently comprises a spacer sequence between 14 nt and 24 nt, or between 16 nt and 22 nt in length.

50. The epigenetic-modifying DNA-targeting system of any of embodiments 11-49, wherein each gRNA independently comprises a spacer sequence that is 18 nt, 19 nt, 20 nt, 21 nt, or 22 nt in length.

51. The epigenetic-modifying DNA-targeting system of any of embodiments 11-50, wherein the first gRNA and the second gRNA are selected from two different members of the group consisting of (a)-(f):
(a) a gRNA targeting a target site of PCSK9 comprising the gRNA spacer sequence set forth in any one of SEQ ID NOS:64-76 or 318-329, optionally wherein the gRNA spacer is set forth in SEQ ID NO:66;
(b) a gRNA targeting a target site in LPA comprising the gRNA spacer sequence set forth in any one of SEQ ID NOS:77-86;
(c) a gRNA targeting a target site in MYLIP comprising the gRNA spacer sequence set forth in any one of SEQ ID NOS:87-96 or 352-361;
(d) a gRNA targeting a target site in ANGPTL3 comprising the gRNA spacer sequence set forth in any one of SEQ ID NOS:97-106;
(e) a gRNA targeting a target site in APOC3 comprising the gRNA spacer sequence set forth in any one of SEQ ID NOS:107-116; and
(f) a gRNA targeting a target site in APOB comprising the gRNA spacer sequence set forth in any one of SEQ ID NOS:117-126 or 378-383.

52. The epigenetic-modifying DNA-targeting system of any of embodiments 43-45, wherein each gRNA further comprises a scaffold sequence set forth in SEQ ID NO:191.

53. The epigenetic-modifying DNA-targeting system of any of embodiments 15-52, wherein the first gRNA and the second gRNA are selected from two different members of the group consisting of (a)-(f):
(a) a gRNA targeting a target site in PCSK9 comprising the sequence set forth in any one of SEQ ID NOS:127-139 or 330-341, optionally wherein the gRNA comprises the sequence set forth in SEQ ID NO:129;
(b) a gRNA targeting a target site in LPA comprising the sequence set forth in any one of SEQ ID NOS:140-149;
(c) a gRNA targeting a target site in MYLIP comprising the sequence set forth in any one of SEQ ID NOS:150-159 or 362-371;
(d) a gRNA targeting a target site in ANGPTL3 comprising the sequence set forth in any one of SEQ ID NOS:160-169;
(e) a gRNA targeting a target site in APOC3 comprising the sequence set forth in any one of SEQ ID NOS:170-179; and
(f) a gRNA targeting a target site in APOB comprising the sequence set forth in any one of SEQ ID NOS:180-189 or 384-389.

54. The epigenetic-modifying DNA-targeting system of any of embodiments 15-53, wherein the first gRNA and the second gRNA are selected from two different members of the group consisting of (a)-(f):
(a) a gRNA targeting a target site in PCSK9 set forth in any one of SEQ ID NOS:127-139 or 330-341, optionally wherein the gRNA is set forth in SEQ ID NO:129;
(b) a gRNA targeting a target site in LPA set forth in any one of SEQ ID NOS:140-149;
(c) a gRNA targeting a target site in MYLIP set forth in any one of SEQ ID NOS:150-159 or 362-371;
(d) a gRNA targeting a target site in ANGPTL3 set forth in any one of SEQ ID NOS:160-169;
(e) a gRNA targeting a target site in APOC3 set forth in any one of SEQ ID NOS:170-179; and
(f) a gRNA targeting a target site in APOB set forth in any one of SEQ ID NOS:180-189 or 384-389.

55. The epigenetic-modifying DNA-targeting combination of any of embodiments 15-54, wherein the first gRNA, the second gRNA, and the third gRNA are selected from three different members of the group consisting of (a)-(f):
(a) a gRNA targeting a target site in PCSK9 comprising the sequence set forth in any one of SEQ ID NOS:127-139 or 330-341, optionally wherein the gRNA comprises the sequence set forth in SEQ ID NO: 129;
(b) a gRNA targeting a target site in LPA comprising the sequence set forth in any one of SEQ ID NOS:140-149;
(c) a gRNA targeting a target site in MYLIP comprising the sequence set forth in any one of SEQ ID NOS:150-159 or 362-371;
(d) a gRNA targeting a target site in ANGPTL3 comprising the sequence set forth in any one of SEQ ID NOS:160-169;
(e) a gRNA targeting a target site in APOC3 comprising the sequence set forth in any one of SEQ ID NOS:170-179; and
(f) a gRNA targeting a target site in APOB comprising the sequence set forth in any one of SEQ ID NOS:180-189 or 384-389.

56. The epigenetic-modifying DNA-targeting combination of any of embodiments 15-55, wherein the first gRNA, the second gRNA, and the third gRNA are selected from three different members of the group consisting of (a)-(f):
(a) a gRNA targeting a target site in PCSK9 set forth in any one of SEQ ID NOS:127-139 or 330-341, optionally wherein the gRNA is set forth in SEQ ID NO:129;
(b) a gRNA targeting a target site in LPA set forth in any one of SEQ ID NOS:140-149;
(c) a gRNA targeting a target site in MYLIP set forth in any one of SEQ ID NOS:150-159 or 362-371;
(d) a gRNA targeting a target site in ANGPTL3 set forth in any one of SEQ ID NOS:160-169;
(e) a gRNA targeting a target site in APOC3 set forth in any one of SEQ ID NOS:170-179; and
(f) a gRNA targeting a target site in APOB set forth in any one of SEQ ID NOS:180-189 or 384-389.

57. The epigenetic-modifying DNA-targeting system of any of embodiments 11-56, wherein at least one gRNA comprises modified nucleotides for increased stability.

58. The epigenetic-modifying DNA-targeting combination of any of embodiments 1-57, wherein the at least one transcriptional repressor domain is capable of reducing transcription of the gene.

59. The epigenetic-modifying DNA-targeting combination of any of embodiments 1-58, wherein the transcriptional repressor domain is selected from the group consisting of a KRAB domain, a DNMT3A domain, a DNMT3L domain, a DNMT3B domain, a DNMT3A-DNMT3L fusion protein domain, an ERF repressor domain, an Mxi1 repressor domain, a SID4X repressor domain, a Mad-SID repressor domain, an LSD1 repressor domain, an EZH2 repressor domain, a SunTag domain, or a variant or portion of any of the foregoing, or a combination of any of the foregoing.

60. The epigenetic-modifying DNA-targeting system of any of embodiments 1-59, wherein the transcriptional repressor domain is a KRAB domain, a DNMT3A domain, or a DNMT3L domain, or a combination of any of the foregoing.

61. The epigenetic-modifying DNA-targeting system of any of embodiments 1-60, wherein the at least one transcriptional repressor domain comprises a KRAB domain or a variant or portion thereof that exhibits transcriptional repressor activity.
62. The epigenetic-modifying DNA-targeting system of any of embodiments 1-60, wherein the at least one transcriptional repressor domain comprises the sequence set forth in SEQ ID NO:193, a portion thereof, or an amino acid sequence that has at least 90%, 91%, 92%, 93%, 94%, 95%, 96%, 97%, 98%, or 99% sequence identity to any of the foregoing.
63. The epigenetic-modifying DNA-targeting system of any of embodiments 1-59, wherein the at least one transcriptional repressor domain comprises a DNMT3A domain or a variant or portion thereof that exhibits transcriptional repressor activity.
64. The epigenetic-modifying DNA-targeting system of any of embodiments 1-59 and 63, wherein the at least one transcriptional repressor domain comprises the sequence set forth in SEQ ID NO:195, a portion thereof, or an amino acid sequence that has at least 90%, 91%, 92%, 93%, 94%, 95%, 96%, 97%, 98%, or 99% sequence identity to any of the foregoing.
65. The epigenetic-modifying DNA-targeting system of any of embodiments 1-59, wherein the at least one transcriptional repressor domain comprises a DNMT3L domain or a variant or portion thereof that exhibits transcriptional repressor activity.
66. The epigenetic-modifying DNA-targeting system of any of embodiments 1-59 and 65, wherein the at least one transcriptional repressor domain comprises the sequence set forth in SEQ ID NO:197, a portion thereof, or an amino acid sequence that has at least 90%, 91%, 92%, 93%, 94%, 95%, 96%, 97%, 98%, or 99% sequence identity to any of the foregoing.
67. The epigenetic-modifying DNA-targeting system of any of embodiments 1-59, wherein the at least one transcriptional repressor domain is a DNMT3A-DNMT3L fusion protein domain or a variant thereof that exhibits transcriptional repressor activity.
68. The epigenetic-modifying DNA-targeting system of any of embodiments 1-59 and 67, wherein the at least one transcriptional repressor domain comprises the sequence set forth in SEQ ID NO:199 or SEQ ID NO:201, a portion thereof, or an amino acid sequence that has at least 90%, 91%, 92%, 93%, 94%, 95%, 96%, 97%, 98%, or 99% sequence identity to any of the foregoing.
69. The epigenetic-modifying DNA-targeting system of any of embodiments 1-59, wherein at least one transcriptional repressor domain comprises a sequence selected from any one of SEQ ID NOS:193, 195, 197, 199, 201, 220-226, and 283, or a domain thereof, a portion thereof, or an amino acid sequence that has at least 90%, 91%, 92%, 93%, 94%, 95%, 96%, 97%, 98%, or 99% sequence identity to any of the foregoing.
70. The epigenetic-modifying DNA-targeting system of any of embodiments 1-69, wherein the at least one transcriptional repressor domain is fused to the N-terminus, the C-terminus, or both the N-terminus and the C-terminus, of the DNA-binding domain.
71. The epigenetic-modifying DNA-targeting system of any of embodiments 1-70, wherein the fusion protein further comprises one or more nuclear localization signals (NLS).
72. The epigenetic-modifying DNA-targeting system of embodiment 71, wherein the fusion protein further comprises one or more linkers connecting two or more of: the DNA-binding domain, the at least one transcriptional repressor domain, and the one or more nuclear localization signals.
73. The epigenetic-modifying DNA-targeting system of any of embodiments 1-107, wherein the fusion protein comprises the sequence set forth in any one of SEQ ID NOS:209, 278, 280, or 282, or an amino acid sequence that has at least 90%, 91%, 92%, 93%, 94%, 95%, 96%, 97%, 98%, or 99% sequence identity thereto, optionally wherein the fusion protein comprises the sequence set forth in SEQ ID NO:280.
74. The epigenetic-modifying DNA-targeting system of any of embodiments 1-108, wherein each of the DNA-targeting modules reduces expression of each of the respective genes by a log 2 fold-change of at or lesser than −1.0.
75. The epigenetic-modifying DNA-targeting system of any of embodiments 1-74, wherein repressed transcription of the plurality of genes in a cell or population of cells leads to a reduction of low-density lipoprotein (LDL).
76. The epigenetic-modifying DNA-targeting system of embodiment 75, wherein the reduction of LDL is greater than the reduction of LDL resulting from comparable repressed transcription of any of the individual genes in the plurality of genes alone.
77. The epigenetic-modifying DNA-targeting system of embodiment 75 or 76, wherein the reduction of LDL occurs extracellularly.
78. The epigenetic-modifying DNA-targeting system of any of embodiments 75-77, wherein the cell or population of cells is a liver cell or comprises liver cells.
79. The epigenetic-modifying DNA-targeting system of any of embodiments 75-78, wherein the cell or population of cells is in a subject.
80. The epigenetic-modifying DNA-targeting system of embodiment 79, wherein the reduction of LDL occurs in the subject or a fluid, tissue, or organ thereof.
81. The epigenetic-modifying DNA-targeting system of any of embodiments 75-80, wherein the reduction of LDL occurs in the blood of a subject.
82. An epigenetic-modifying DNA-targeting system for repressing transcription of a gene that regulates low-density lipoprotein, comprising a fusion protein comprising: (a) a DNA-binding domain for targeting to a target site of a gene, and (b) at least one transcriptional repressor domain.
83. The epigenetic-modifying DNA-targeting system of embodiment 82, wherein the target site of the gene is in the gene or a regulatory DNA element thereof.
84. The epigenetic-modifying DNA-targeting system of embodiment 82 or 83, wherein the DNA-targeting system does not introduce a genetic disruption or a DNA break.
85. The epigenetic-modifying DNA-targeting system of any of embodiments 82-84, wherein the DNA-binding domain is selected from: a Clustered Regularly Interspaced Short Palindromic Repeats associated (Cas) protein or a variant thereof; a zinc finger protein (ZFP); a transcription activator-like effector (TALE); a meganuclease; a homing endonuclease; or an I-SceI enzyme or a variant thereof, optionally wherein the DNA-binding domain comprises a catalytically inactive variant of any of the foregoing.
86. The epigenetic-modifying DNA-targeting system of embodiment 85, wherein the DNA-binding domain is a Clustered Regularly Interspaced Short Palindromic Repeats associated (Cas) protein or variant thereof, and the system further comprises a gRNA for targeting the DNA-binding domain to the target site of the gene.

87. An epigenetic-modifying DNA-targeting system comprising: (a) a fusion protein comprising a Clustered Regularly Interspaced Short Palindromic Repeats associated (Cas) protein or variant thereof and at least one transcriptional repressor domain; and (b) a gRNA that targets a target site of a gene that regulates low-density lipoprotein (LDL).

88. The epigenetic-modifying DNA-targeting system of any of embodiments 82-87, wherein the target site of the gene is in the gene and/or a regulatory DNA element thereof.

89. The epigenetic-modifying DNA-targeting system of embodiment 88, wherein the regulatory DNA element is a promoter or enhancer.

90. The epigenetic-modifying DNA-targeting system of any of embodiments 82-89, wherein the gene is selected from the group consisting of: PCSK9, LPA, MYLIP, ANGPTL3, APOB, and APOC3.

91. The epigenetic-modifying DNA-targeting system of any of embodiments 82-90, wherein the target site is selected from:
(a) a target site for PCSK9, located within 500 bp of human genome assembly GRCh38 (hg38) genomic coordinates chr1:55,039,548;
(b) a target site for LPA, located within 500 bp of the hg38 genomic coordinates chr6:160,664,275;
(c) a target site for MYLIP, located within 500 bp of the hg38 genomic coordinates chr6:16,129,086;
(d) a target site for ANGPTL3, located within 500 bp of the hg38 genomic coordinates chr1:62,597,520;
(e) a target site for APOC3, located within 500 bp of the hg38 genomic coordinates chr11:116,829,907; and
(f) a target site for APOB, located within 500 bp of the hg38 genomic coordinates chr2:21,044,073.

92. The epigenetic-modifying DNA-targeting system of any of embodiments 82-91, wherein the target site is selected from:
(a) a target site located within 500 bp of a transcriptional start site of PCSK9;
(b) a target site located within 500 bp of a transcriptional start site of LPA;
(c) a target site located within 500 bp of a transcriptional start site of MYLIP;
(d) a target site located within 500 bp of a transcriptional start site of ANGPTL3;
(e) a target site located within 500 bp of a transcriptional start site of APOC3; and
(f) a target site located within 500 bp of a transcriptional start site of APOB.

93. The epigenetic-modifying DNA-targeting system of any of embodiments 82-92, wherein the target site is selected from:
(a) a target site for PCSK9 having the sequence set forth in any one of SEQ ID NOS:1-13 or 306-317, a contiguous portion thereof of at least 14 nucleotides (nt), or a complementary sequence of any of the foregoing, optionally wherein the target site has (i) the sequence set forth in SEQ ID NO:3, (ii) a contiguous portion of at least 14 nucleotides set forth in SEQ ID NO:3; or (iii) a complementary sequence of (i) or (ii);
(b) a target site for LPA having the sequence set forth in any one of SEQ ID NOS:14-23, a contiguous portion thereof of at least 14 nucleotides (nt), or a complementary sequence of any of the foregoing;
(c) a target site for MYLIP having the sequence set forth in any one of SEQ ID NOS:24-33 or 342-351, a contiguous portion thereof of at least 14 nucleotides (nt), or a complementary sequence of any of the foregoing;
(d) a target site for ANGPTL3 having the sequence set forth in any one of SEQ ID NOS:34-43, a contiguous portion thereof of at least 14 nucleotides (nt), or a complementary sequence of any of the foregoing;
(e) a target site for APOC3 having the sequence set forth in any one of SEQ ID NOS:44-53, a contiguous portion thereof of at least 14 nucleotides (nt), or a complementary sequence of any of the foregoing; and
(f) a target site for APOB having the sequence set forth in any one of SEQ ID NOS:54-63 or 372-377, a contiguous portion thereof of at least 14 nucleotides (nt), or a complementary sequence of any of the foregoing.

94. The epigenetic-modifying DNA-targeting system of any of embodiments 82-93, wherein the target site is selected from:
(a) a target site of PCSK9 having the sequence set forth in any one of SEQ ID NOS:1-13 or 306-317, optionally wherein the target site has the sequence set forth in SEQ ID NO:3; (b) a target site of LPA having the sequence set forth in any one of SEQ ID NOS:14-23;
(c) a target site of MYLIP having the sequence set forth in any one of SEQ ID NOS:24-33 or 342-351;
(d) a target site of ANGPTL3 having the sequence set forth in any one of SEQ ID NOS: 34-43;
(e) a target site of APOC3 having the sequence set forth in any one of SEQ ID NOS:44-53; and
(f) a target site of APOB having the sequence set forth in any one of SEQ ID NOS:54-63 or 372-377.

95. The epigenetic-modifying DNA-targeting system of any of embodiments 86-94, wherein the Cas protein or variant thereof is a variant Cas protein that is a deactivated (dCas) protein.

96. The epigenetic-modifying DNA-targeting system of embodiment 95, wherein the dCas protein lacks nuclease activity.

97. The epigenetic-modifying DNA-targeting system of embodiment 95 or 96, wherein the dCas protein is a dCas9 protein.

98. The epigenetic-modifying DNA-targeting system of embodiment 95 or 96, wherein the dCas protein is a dCas12 protein.

99. The epigenetic-modifying DNA-targeting system of 97, wherein the dCas9 protein is a *Staphylococcus aureus* dCas9 (dSaCas9) protein.

100. The epigenetic-modifying DNA-targeting system of embodiment 99, wherein the dSaCas9 comprises at least one amino acid mutation selected from D10A and N580A, with reference to numbering of positions of SEQ ID NO:204.

101. The epigenetic-modifying DNA-targeting system of embodiment 99 or embodiment 100, wherein the dSaCas9 protein comprises the sequence set forth in SEQ ID NO:205, or an amino acid sequence that has at least 90%, 91%, 92%, 93%, 94%, 95%, 96%, 97%, 98%, or 99% sequence identity thereto.

102. The epigenetic-modifying DNA-targeting system of any of embodiments 99-101, wherein the dSaCas9 is set forth in SEQ ID NO:205.

103. The epigenetic-modifying DNA-targeting system of embodiment 97, wherein the dCas9 protein is a *Streptococcus pyogenes* dCas9 (dSpCas9) protein.

104. The epigenetic-modifying DNA-targeting system of embodiment 103, wherein the dSpCas9 protein comprises at least one amino acid mutation selected from D10A and H840A, with reference to numbering of positions of SEQ ID NO:206.

105. The epigenetic-modifying DNA-targeting system of 35 or embodiment 104, wherein the dSpCas9 comprises the sequence set forth in SEQ ID NO:207, or an amino acid sequence that has at least 90%, 91%, 92%, 93%, 94%, 95%, 96%, 97%, 98%, or 99% sequence identity thereto.

106. The epigenetic-modifying DNA-targeting system of any of embodiments 103-105, wherein the dSpCas9 is set forth in SEQ ID NO:207.

107. The epigenetic-modifying DNA-targeting system of any of embodiments 86-106, wherein the gRNA comprises a gRNA spacer that is complementary to the target site of the gene.

108. The epigenetic-modifying DNA-targeting system of any of embodiments 86-107, wherein the gRNA is selected from:
(a) a gRNA targeting a target site of PCSK9 comprising a gRNA spacer sequence comprising the sequence set forth in any one of SEQ ID NOS:64-76 or 318-329, or a contiguous portion thereof of at least 14 nt, optionally wherein the gRNA spacer comprises the sequence set forth in SEQ ID NO:66 or a contiguous portion thereof of at least 14 nt;
(b) a gRNA targeting a target site of LPA comprising a gRNA spacer sequence comprising the sequence set forth in any one of SEQ ID NOS:77-86, or a contiguous portion thereof of at least 14 nt;
(c) a gRNA targeting a target site of MYLIP comprising a gRNA spacer sequence comprising the sequence set forth in any one of SEQ ID NOS:87-96 or 352-361, or a contiguous portion thereof of at least 14 nt;
(d) a gRNA targeting a target site of ANGPTL3 comprising a gRNA spacer sequence comprising the sequence set forth in any one of SEQ ID NOS:97-106, or a contiguous portion thereof of at least 14 nt;
(e) a gRNA targeting a target site of APOC3 comprising a gRNA spacer sequence comprising the sequence set forth in any one of SEQ ID NOS:107-116, or a contiguous portion thereof of at least 14 nt; and
(f) a gRNA targeting a target site of APOB comprising a gRNA spacer sequence comprising the sequence set forth in any one of SEQ ID NOS:117-126 or 378-383, or a contiguous portion thereof of at least 14 nt.

109. The epigenetic-modifying DNA-targeting system of any of embodiments 86-108, wherein the gRNA comprises a spacer sequence between 14 nt and 24 nt, or between 16 nt and 22 nt in length.

110. The epigenetic-modifying DNA-targeting system of any of embodiments 86-109, wherein the gRNA comprises a spacer sequence that is 18 nt, 19 nt, 20 nt, 21 nt, or 22 nt in length.

111. The epigenetic-modifying DNA-targeting system of any of embodiments 806-110, wherein the gRNA is selected from:
(a) a gRNA targeting a target site of PCSK9 comprising the gRNA spacer sequence set forth in any one of SEQ ID NOS:64-76 or 318-329, optionally wherein the gRNA spacer sequence is set forth in SEQ ID NO:66;
(b) a gRNA targeting a target site in LPA comprising the gRNA spacer sequence set forth in any one of SEQ ID NOS:77-86;
(c) a gRNA targeting a target site in MYLIP comprising the gRNA spacer sequence set forth in any one of SEQ ID NOS:87-96 or 352-361;
(d) a gRNA targeting a target site in ANGPTL3 comprising the gRNA spacer sequence set forth in any one of SEQ ID NOS:97-106;
(e) a gRNA targeting a target site in APOC3 comprising the gRNA spacer sequence set forth in any one of SEQ ID NOS:107-116; and
(f) a gRNA targeting a target site in APOB comprising the gRNA spacer sequence set forth in any one of SEQ ID NOS:117-126 or 378-383.

112. The epigenetic-modifying DNA-targeting system of any of embodiments 103-111, wherein the gRNA further comprises a scaffold sequence set forth in SEQ ID NO:191.

113. The epigenetic-modifying DNA-targeting system of any of embodiments 103-112, wherein the gRNA is selected from:
(a) a gRNA targeting a target site in PCSK9 comprising the sequence set forth in any one of SEQ ID NOS:127-139 or 330-341, optionally wherein the gRNA comprises the sequence set forth in SEQ ID NO:129;
(b) a gRNA targeting a target site in LPA comprising the sequence set forth in any one of SEQ ID NOS:140-149;
(c) a gRNA targeting a target site in MYLIP comprising the sequence set forth in any one of SEQ ID NOS:150-159 or 362-371;
(d) a gRNA targeting a target site in ANGPTL3 comprising the sequence set forth in any one of SEQ ID NOS:160-169;
(e) a gRNA targeting a target site in APOC3 comprising the sequence set forth in any one of SEQ ID NOS:170-179; and
(f) a gRNA targeting a target site in APOB comprising the sequence set forth in any one of SEQ ID NOS:180-189 or 384-389.

114. The epigenetic-modifying DNA-targeting system of any of embodiments 103-113, wherein the gRNA is selected from:
(a) a gRNA targeting a target site in PCSK9 set forth in any one of SEQ ID NOS:127-139 or 330-341, optionally wherein the gRNA is set forth in SEQ ID NO:129;
(b) a gRNA targeting a target site in LPA set forth in any one of SEQ ID NOS:140-149;
(c) a gRNA targeting a target site in MYLIP set forth in any one of SEQ ID NOS:150-159 or 362-371;
(d) a gRNA targeting a target site in ANGPTL3 set forth in any one of SEQ ID NOS:160-169;
(e) a gRNA targeting a target site in APOC3 set forth in any one of SEQ ID NOS:170-179; and
(f) a gRNA targeting a target site in APOB set forth in any one of SEQ ID NOS:180-189 or 384-389.

115. The epigenetic-modifying DNA-targeting system of any of embodiments 86-114, wherein the gRNA comprises modified nucleotides for increased stability.

116. The epigenetic-modifying DNA-targeting combination of any of embodiments 82-115, wherein the at least one transcriptional repressor domain is capable of reducing transcription of the gene.

117. The epigenetic-modifying DNA-targeting combination of any of embodiments 82-116, wherein the transcriptional repressor domain is selected from the group consisting of a KRAB domain, a DNMT3A domain, a DNMT3L domain, a DNMT3B domain, a DNMT3A-DNMT3L fusion protein domain, an ERF repressor domain, an Mxi1 repressor domain, a SID4X repressor domain, a Mad-SID repressor domain, an LSD1 repressor domain, an EZH2 repressor domain, a SunTag domain, or a variant or portion of any of the foregoing, or a combination of any of the foregoing.
118. The epigenetic-modifying DNA-targeting system of any of embodiments 82-117, wherein the transcriptional repressor domain is a KRAB domain, a DNMT3A domain, or a DNMT3L domain, or a combination of any of the foregoing.
119. The epigenetic-modifying DNA-targeting system of any of embodiments 82-118, wherein the at least one transcriptional repressor domain comprises a KRAB domain or a variant or portion thereof that exhibits transcriptional repressor activity.
120. The epigenetic-modifying DNA-targeting system of any of embodiments 82-119, wherein the at least one transcriptional repressor domain comprises the sequence set forth in SEQ ID NO:193, a portion thereof, or an amino acid sequence that has at least 90%, 91%, 92%, 93%, 94%, 95%, 96%, 97%, 98%, or 99% sequence identity to any of the foregoing.
121. The epigenetic-modifying DNA-targeting system of any of embodiments 82-118, wherein the at least one transcriptional repressor domain comprises a DNMT3A domain or a variant or portion thereof that exhibits transcriptional repressor activity.
122. The epigenetic-modifying DNA-targeting system of any of embodiments 82-118 and 121, wherein the at least one transcriptional repressor domain comprises the sequence set forth in SEQ ID NO:195, a portion thereof, or an amino acid sequence that has at least 90%, 91%, 92%, 93%, 94%, 95%, 96%, 97%, 98%, or 99% sequence identity to any of the foregoing.
123. The epigenetic-modifying DNA-targeting system of any of embodiments 82-118, wherein the at least one transcriptional repressor domain comprises a DNMT3L domain or a variant or portion thereof that exhibits transcriptional repressor activity.
124. The epigenetic-modifying DNA-targeting system of any of embodiments 82-118 and 123, wherein the at least one transcriptional repressor domain comprises the sequence set forth in SEQ ID NO:197, a portion thereof, or an amino acid sequence that has at least 90%, 91%, 92%, 93%, 94%, 95%, 96%, 97%, 98%, or 99% sequence identity to any of the foregoing.
125. The epigenetic-modifying DNA-targeting system of any of embodiments 82-118, wherein the at least one transcriptional repressor domain is a DNMT3A-DNMT3L fusion protein domain or a variant thereof that exhibits transcriptional repressor activity.
126. The epigenetic-modifying DNA-targeting system of any of embodiments 82-118 and 125, wherein the at least one transcriptional repressor domain comprises the sequence set forth in SEQ ID NO:199 or SEQ ID NO:201, a portion thereof, or an amino acid sequence that has at least 90%, 91%, 92%, 93%, 94%, 95%, 96%, 97%, 98%, or 99% sequence identity to any of the foregoing.
127. The epigenetic-modifying DNA-targeting system of any of embodiments 82-117, wherein at least one transcriptional repressor domain comprises a sequence selected from any one of SEQ ID NOS:193, 195, 197, 199, 201, 220-226, and 283, or a domain thereof, a portion thereof, or an amino acid sequence that has at least 90%, 91%, 92%, 93%, 94%, 95%, 96%, 97%, 98%, or 99% sequence identity to any of the foregoing.
128. The epigenetic-modifying DNA-targeting system of any of embodiments 82-127, wherein the at least one transcriptional repressor domain is fused to the N-terminus, the C-terminus, or both the N-terminus and the C-terminus, of the DNA-binding domain.
129. The epigenetic-modifying DNA-targeting system of any of embodiments 82-128, wherein the fusion protein further comprises one or more nuclear localization signals (NLS).
130. The epigenetic-modifying DNA-targeting system of embodiment 129, wherein the fusion protein further comprises one or more linkers connecting two or more of: the DNA-binding domain, the at least one transcriptional repressor domain, and the one or more nuclear localization signals.
131. The epigenetic-modifying DNA-targeting system of any of embodiments 82-130, wherein the fusion protein comprises the sequence set forth in any one of SEQ ID NOS:209, 278, 280, or 282, or an amino acid sequence that has at least 90%, 91%, 92%, 93%, 94%, 95%, 96%, 97%, 98%, or 99% sequence identity thereto, optionally wherein the fusion protein is set forth in SEQ ID NO:280.
132. The epigenetic-modifying DNA-targeting system of any of embodiments 86-131, wherein the fusion protein comprises the sequence set forth in SEQ ID NO:280 or a sequence of amino acids that has at least 90%, 91%, 92%, 93%, 94%, 95%, 96%, 97%, 98%, or 99% sequence identity to SEQ ID NO:280 and a gRNA that targets a target site of PCSK9 comprising the spacer sequence set forth in SEQ ID NO: 66, optionally wherein the gRNA has the sequence set forth in SEQ ID NO:129.
133. The epigenetic-modifying DNA-targeting system of any of embodiments 82-132, wherein each of the DNA-targeting modules reduces expression of each of the respective genes by a log 2 fold-change of at or lesser than −1.0.
134. The epigenetic-modifying DNA-targeting system of any of embodiments 82-133, wherein repressed transcription of the gene in a cell or population of cells leads to a reduction of low-density lipoprotein (LDL), optionally wherein the reduction of LDL occurs extracellularly.
135. The epigenetic-modifying DNA-targeting system of embodiment 133 or 134, wherein the cell or population of cells is a liver cell or comprises liver cells.
136. The epigenetic-modifying DNA-targeting system of any of embodiments 133-135, wherein the cell or population of cells is in a subject.
137. The epigenetic-modifying DNA-targeting system of embodiment 136, wherein the reduction of LDL occurs in the subject or a fluid, tissue, or organ thereof.
138. The epigenetic-modifying DNA-targeting system of any of embodiments 133-137, wherein the reduction of LDL occurs in the blood of a subject.
139. A combination of epigenetic-modifying DNA-targeting systems comprising at least two of the DNA-targeting systems of any of embodiments 82-138, wherein each DNA-targeting system represses transcription of a different gene.
140. The combination of epigenetic-modifying DNA-targeting systems of embodiment 139, wherein each DNA-targeting system represses transcription of a different gene.
141. A guide RNA (gRNA) that targets a target site of a gene that regulates low-density lipoprotein (LDL).

142. The gRNA of embodiment 141, wherein the gene is selected from the group consisting of PCSK9, LPA, MYLIP, ANGPTL3, APOB, and APOC3.

143. the gRNA of embodiment 141-142, wherein the target site of the gene is in the gene or a regulatory DNA element thereof.

144. The gRNA of embodiment 143, wherein the regulatory DNA element is an enhancer or a promoter.

145. The gRNA of any of embodiments 141-144, wherein the target site is selected from the group consisting of:
(a) a target site for PCSK9, located within 500 bp of human genome assembly GRCh38 (hg38) genomic coordinates chr1:55,039,548;
(b) a target site for LPA, located within 500 bp of the hg38 genomic coordinates chr6:160,664,275;
(c) a target site for MYLIP, located within 500 bp of the hg38 genomic coordinates chr6:16,129,086;
(d) a target site for ANGPTL3, located within 500 bp of the hg38 genomic coordinates chr1:62,597,520;
(e) a target site for APOC3, located within 500 bp of the hg38 genomic coordinates chr11:116,829,907; and
(f) a target site for APOB, located within 500 bp of the hg38 genomic coordinates chr2:21,044,073.

146. The gRNA of any of embodiments 141-145, wherein the target site is selected from the group consisting of:
(a) a target site located within 500 bp of a transcriptional start site of PCSK9;
(b) a target site located within 500 bp of a transcriptional start site of LPA;
(c) a target site located within 500 bp of a transcriptional start site of MYLIP;
(d) a target site located within 500 bp of a transcriptional start site of ANGPTL3;
(e) a target site located within 500 bp of a transcriptional start site of APOC3; and
(f) a target site located within 500 bp of a transcriptional start site of APOB.

147. The gRNA of any of embodiments 141-146, wherein the target site is selected from:
(a) a target site for PCSK9 having the sequence set forth in any one of SEQ ID NOS:1-13 or 306-317, a contiguous portion thereof of at least 14 nucleotides (nt), or a complementary sequence of any of the foregoing, optionally wherein the target site has (i) the sequence set forth in SEQ ID NO: 3, (ii) a contiguous portion of SEQ ID NO:3 of at least 14 nt; or (iii) a complementary sequence of (i) or (ii);
(b) a target site for LPA having the sequence set forth in any one of SEQ ID NOS:14-23, a contiguous portion thereof of at least 14 nucleotides (nt), or a complementary sequence of any of the foregoing;
(c) a target site for MYLIP having the sequence set forth in any one of SEQ ID NOS:24-33 or 342-351, a contiguous portion thereof of at least 14 nucleotides (nt), or a complementary sequence of any of the foregoing;
(d) a target site for ANGPTL3 having the sequence set forth in any one of SEQ ID NOS:34-43, a contiguous portion thereof of at least 14 nucleotides (nt), or a complementary sequence of any of the foregoing;
(e) a target site for APOC3 having the sequence set forth in any one of SEQ ID NOS:44-53, a contiguous portion thereof of at least 14 nucleotides (nt), or a complementary sequence of any of the foregoing; and
(f) a target site for APOB having the sequence set forth in any one of SEQ ID NOS:54-63 or 372-377, a contiguous portion thereof of at least 14 nucleotides (nt), or a complementary sequence of any of the foregoing.

148. The gRNA of any of embodiments 141-147, wherein the target site is selected from:
(a) a target site of PCSK9 having the sequence set forth in any one of SEQ ID NOS:1-13 or 306-317, optionally wherein the target site has the sequence set forth in SEQ ID NO:3;
(b) a target site of LPA having the sequence set forth in any one of SEQ ID NOS:14-23;
(c) a target site of MYLIP having the sequence set forth in any one of SEQ ID NOS:24-33 or 342-351;
(d) a target site of ANGPTL3 having the sequence set forth in any one of SEQ ID NOS: 34-43;
(e) a target site of APOC3 having the sequence set forth in any one of SEQ ID NOS:44-53; and
(f) a target site of APOB having the sequence set forth in any one of SEQ ID NOS:54-63 or 372-377.

149. The gRNA of any of embodiments 141-148, wherein the gRNA is selected from:
(a) a gRNA targeting a target site of PCSK9 comprising a gRNA spacer sequence comprising the sequence set forth in any one of SEQ ID NOS:64-76 or 318-329, or a contiguous portion thereof of at least 14 nt, optionally wherein the gRNA spacer sequence comprises the sequence set forth in SEQ ID NO:66 or a contiguous portion thereof of at least 14 nt;
(b) a gRNA targeting a target site of LPA comprising a gRNA spacer sequence comprising the sequence set forth in any one of SEQ ID NOS:77-86, or a contiguous portion thereof of at least 14 nt;
(c) a gRNA targeting a target site of MYLIP comprising a gRNA spacer sequence comprising the sequence set forth in any one of SEQ ID NOS:87-96 or 352-361, or a contiguous portion thereof of at least 14 nt;
(d) a gRNA targeting a target site of ANGPTL3 comprising a gRNA spacer sequence comprising the sequence set forth in any one of SEQ ID NOS:97-106, or a contiguous portion thereof of at least 14 nt;
(e) a gRNA targeting a target site of APOC3 comprising a gRNA spacer sequence comprising the sequence set forth in any one of SEQ ID NOS:107-116, or a contiguous portion thereof of at least 14 nt; and
(f) a gRNA targeting a target site of APOB comprising a gRNA spacer sequence comprising the sequence set forth in any one of SEQ ID NOS:117-126 or 378-383, or a contiguous portion thereof of at least 14 nt.

150. The gRNA of any of embodiments 141-149, wherein the gRNA comprises a spacer sequence between 14 nt and 24 nt, or between 16 nt and 22 nt in length.

151. The gRNA of any of embodiments 141-150, wherein the gRNA comprises a spacer sequence that is 18 nt, 19 nt, 20 nt, 21 nt, or 22 nt in length.

152. The gRNA of any of embodiments 141-151, wherein the gRNA is selected from:
(a) a gRNA targeting a target site of PCSK9 comprising the gRNA spacer sequence set forth in any one of SEQ ID NOS:64-76 or 318-329, optionally wherein the gRNA spacer is set forth in SEQ ID NO: 66;
(b) a gRNA targeting a target site in LPA comprising the gRNA spacer sequence set forth in any one of SEQ ID NOS:77-86;
(c) a gRNA targeting a target site in MYLIP comprising the gRNA spacer sequence set forth in any one of SEQ ID NOS:87-96 or 352-361;

(d) a gRNA targeting a target site in ANGPTL3 comprising the gRNA spacer sequence set forth in any one of SEQ ID NOS:97-106;
(e) a gRNA targeting a target site in APOC3 comprising the gRNA spacer sequence set forth in any one of SEQ ID NOS:107-116; and
(f) a gRNA targeting a target site in APOB comprising the gRNA spacer sequence set forth in any one of SEQ ID NOS:117-126 or 378-383.

153. The gRNA of any of embodiments 141-152, wherein the gRNA further comprises a scaffold sequence set forth in SEQ ID NO:191.

154. The gRNA of any of embodiments 141-153, wherein the gRNA is selected from:
(a) a gRNA targeting a target site in PCSK9 comprising the sequence set forth in any one of SEQ ID NOS:127-139 or 330-341, optionally wherein the gRNA comprises the sequence set forth in SEQ ID NO:129;
(b) a gRNA targeting a target site in LPA comprising the sequence set forth in any one of SEQ ID NOS:140-149;
(c) a gRNA targeting a target site in MYLIP comprising the sequence set forth in any one of SEQ ID NOS:150-159 or 362-371;
(d) a gRNA targeting a target site in ANGPTL3 comprising the sequence set forth in any one of SEQ ID NOS:160-169;
(e) a gRNA targeting a target site in APOC3 comprising the sequence set forth in any one of SEQ ID NOS:170-179; or
(f) a gRNA targeting a target site in APOB comprising the sequence set forth in any one of SEQ ID NOS:180-189 or 384-389.

155. The gRNA of any of embodiments 141-154, wherein the gRNA is selected from:
(a) a gRNA targeting a target site in PCSK9 set forth in any one of SEQ ID NOS:127-139 or 330-341, optionally wherein the gRNA is set forth in SEQ ID NO: 129;
(b) a gRNA targeting a target site in LPA set forth in any one of SEQ ID NOS:140-149;
(c) a gRNA targeting a target site in MYLIP set forth in any one of SEQ ID NOS:150-159 or 362-371;
(d) a gRNA targeting a target site in ANGPTL3 set forth in any one of SEQ ID NOS:160-169;
(e) a gRNA targeting a target site in APOC3 set forth in any one of SEQ ID NOS:170-179; or
(f) a gRNA targeting a target site in APOB set forth in any one of SEQ ID NOS:180-189 or 384-389.

156. The gRNA of any of embodiments 141-155, wherein the gRNA comprises modified nucleotides for increased stability.

157. A plurality of gRNAs comprising at least a first gRNA and a second gRNA, wherein the first gRNA targets a target site of a first gene that regulates low-density lipoprotein (LDL) and the second gRNA targets a target site of a second gene that regulates LDL.

158. The plurality of gRNAs of embodiment 157, comprising a third gRNA that targets a target site of a third gene that regulates LDL, optionally wherein the plurality of gRNAs further comprises a fourth gRNA that targets a target site of a fourth gene that regulates LDL, optionally a fifth gRNA that targets a target site of a fifth gene that regulates LDL, and/or optionally a sixth gRNA that targets a target site of a sixth gene that regulates LDL.

159. The plurality of gRNAs of embodiment 157 or 158, wherein each gRNA is selected from the gRNA of any of embodiments 141-156.

160. The plurality of gRNAs of any of embodiments 157-159, wherein the first gene and the second gene are independently selected from the group consisting of PCSK9, LPA, MYLIP, ANGPTL3, APOB, and APOC3.

161. The plurality of gRNAs of any of embodiments 157-160, wherein the first gene and the second gene are different.

162. The plurality of gRNAs of any of embodiments 157-161, wherein the first gene and the second gene are: PCSK9 and LPA; PCSK9 and MYLIP; PCSK9 and ANGPTL3; PCSK9 and APOC3; PCSK9 and APOB; LPA and MYLIP; LPA and ANGPTL3; LPA and APOC3; LPA and APOB; MYLIP and ANGPTL3; MYLIP and APOC3; MYLIP and APOB; ANGPTL3 and APOC3; ANGPTL3 and APOB; or APOC3 and APOB.

163. The plurality of gRNAs of any of embodiments 158-162, wherein the first gene, the second gene, and the third gene are each independently selected from the group consisting of PCSK9, LPA, MYLIP, ANGPTL3, APOC3, and APOB.

164. The plurality of gRNAs of any of embodiments 158-163, wherein the first gene, the second gene, and the third gene are different.

165. The plurality of gRNAs of any of embodiments 158-164, wherein the first gene, the second gene, and the third gene are: PCSK9, LPA, and MYLIP; PCSK9, LPA, and ANGPTL3; PCSK9, LPA, and APOC3; PCSK9, LPA, and APOB; PCSK9, MYLIP, and ANGPTL3; PCSK9, MYLIP, and APOC3; PCSK9, MYLIP, and APOB; PCSK9, ANGPTL3, and APOC3; PCSK9, ANGPTL3, and APOB; PCSK9, APOC3, and APOB; LPA, MYLIP, and ANGPTL3; LPA, MYLIP, and APOC3; LPA, MYLIP, and APOB; LPA, ANGPTL3, and APOC3; LPA, ANGPTL3, and APOB; LPA, APOC3, and APOB; MYLIP, ANGPTL3, and APOC3; MYLIP, ANGPTL3, and APOB; MYLIP, APOC3, and APOB; or ANGPTL3, APOC3, and APOB.

166. The plurality of gRNAs of any of embodiments 157-165, wherein at least one gene is PCSK9.

167. The plurality of gRNAs of any of embodiments 157-166, wherein at least two genes are PCSK9 and LPA.

168. The plurality of gRNAs of any of embodiments 157-167, wherein at least three genes are PCSK9, LPA, and MYLIP.

169. The plurality of gRNAs of any of embodiments 157-168, wherein the target site of each of the plurality of genes is in the gene or a regulatory DNA element thereof.

170. A Cas-guide RNA (gRNA) combination comprising:
(a) a Clustered Regularly Interspaced Short Palindromic Repeats associated (Cas) protein or variant thereof; and
(b) the gRNA of any of embodiments 141-156 or the plurality of gRNAs of any of embodiments 157-169.

171. The Cas-gRNA combination of embodiment 170, wherein the Cas protein or variant thereof is a variant Cas protein that is a deactivated (dCas) protein.

172. The Cas-gRNA combination of embodiment 171, wherein the dCas protein lacks nuclease activity.

173. The Cas-gRNA combination of embodiment 171 or embodiment 172, wherein the dCas protein is a dCas9 protein.

174. The Cas-gRNA combination of embodiment 171 or embodiment 172, wherein the dCas protein is a dCas12 protein.

175. The Cas-gRNA combination of embodiment 173, wherein the dCas9 protein is a *Staphylococcus aureus* dCas9 (dSaCas9) protein.
176. The Cas-gRNA combination of embodiment 175, wherein the dSaCas9 comprises at least one amino acid mutation selected from D10A and N580A, with reference to numbering of positions of SEQ ID NO:204.
177. The Cas-gRNA combination of embodiment 175 or embodiment 176, wherein the dSaCas9 protein comprises the sequence set forth in SEQ ID NO:205, or an amino acid sequence that has at least 90%, 91%, 92%, 93%, 94%, 95%, 96%, 97%, 98%, or 99% sequence identity thereto.
178. The Cas-gRNA combination of any of embodiments 175-177, wherein the dSaCas9 is set forth in SEQ ID NO:205.
179. The Cas-gRNA combination of embodiment 173, wherein the dCas9 protein is a *Streptococcus pyogenes* dCas9 (dSpCas9) protein.
180. The Cas-gRNA combination of embodiment 179, wherein the dSpCas9 protein comprises at least one amino acid mutation selected from D10A and H840A, with reference to numbering of positions of SEQ ID NO:206.
181. The Cas-gRNA combination of 179 or embodiment 180, wherein the dSpCas9 comprises the sequence set forth in SEQ ID NO:207, or an amino acid sequence that has at least 90%, 91%, 92%, 93%, 94%, 95%, 96%, 97%, 98%, or 99% sequence identity thereto.
182. The Cas-gRNA combination of any of embodiments 179-181, wherein the dSpCas9 is set forth in SEQ ID NO:207.
183. A polynucleotide encoding the epigenetic-modifying DNA-targeting system of any of embodiments 1-138, the combination of epigenetic-modifying DNA-targeting systems of embodiment 139 or 140, the gRNA of any of embodiments 141-156, the plurality of gRNAs of any of embodiments 157-169, the Cas-gRNA combination of any of embodiments 170-182, or a portion or a component of any of the foregoing.
184. A polynucleotide encoding the epigenetic-modifying DNA-targeting system of any of embodiments 1-138.
185. A polynucleotide encoding at least one DNA-targeting module of the epigenetic-modifying DNA-targeting system of any of embodiments 1-11 and 13-81.
186. A polynucleotide encoding the fusion protein and the at least first gRNA and second gRNA of the epigenetic-modifying DNA-targeting system of any of embodiments 11-81.
187. A polynucleotide encoding the fusion protein of the epigenetic-modifying DNA-targeting system of any of embodiments 82-138.
188. A polynucleotide encoding the fusion protein and gRNA of the epigenetic-modifying DNA-targeting system of any of embodiments 86-138.
189. A polynucleotide encoding the combination of epigenetic-modifying DNA-targeting systems of embodiment 139 or 140.
190. A polynucleotide encoding the gRNA of any of embodiments 141-156.
191. A polynucleotide encoding the plurality of gRNAs of any of embodiments 157-169.
192. A polynucleotide encoding the Cas-gRNA combination of any of embodiments 170-182.
193. A plurality of polynucleotides encoding the epigenetic-modifying DNA-targeting system of any of embodiments 1-138, the combination of epigenetic-modifying DNA-targeting systems of embodiment 139 or 140, the plurality of gRNAs of any of embodiments 157-169, the Cas-gRNA combination of any of embodiments 170-182, or a portion or a component of any of the foregoing.
194. A plurality of polynucleotides encoding the epigenetic-modifying DNA-targeting system of any of embodiments 1-138.
195. A plurality of polynucleotides encoding at least one DNA-targeting module of the epigenetic-modifying DNA-targeting system of any of embodiments 1-11 and 13-81.
196. A plurality of polynucleotides encoding the fusion protein and the at least first gRNA and second gRNA of the epigenetic-modifying DNA-targeting system of any of embodiments 11-81.
197. A plurality of polynucleotides encoding the fusion protein of the epigenetic-modifying DNA-targeting system of any of embodiments 82-138.
198. A plurality of polynucleotides encoding the fusion protein and gRNA of the epigenetic-modifying DNA-targeting system of any of embodiments 86-138.
199. A plurality of polynucleotides encoding the combination of epigenetic-modifying DNA-targeting systems of embodiment 139 or 140.
200. A plurality of polynucleotides encoding the plurality of gRNAs of any of embodiments 157-169.
201. A plurality of polynucleotides encoding the Cas-gRNA combination of any of embodiments 170-182.
202. A vector comprising the polynucleotide of any of embodiments 183-192.
203. A vector comprising the plurality of polynucleotides of any of embodiments 193-201.
204. The vector of embodiment 202 or embodiment 203, wherein the vector is a viral vector.
205. The vector of embodiment 204, wherein the vector is an adeno-associated virus (AAV) vector.
206. The vector of embodiment 205, wherein the vector is selected from among AAV1, AAV2, AAV3, AAV4, AAV5, AAV6, AAV7, AAV8, and AAV9.
207. The vector of embodiment 204, wherein the vector is a lentiviral vector.
208. The vector of embodiment 202 or embodiment 203, wherein the vector is a non-viral vector.
209. The vector of embodiment 208, wherein the non-viral vector is selected from: a lipid nanoparticle, a liposome, an exosome, or a cell penetrating peptide.
210. The vector of embodiment 208, wherein the non-viral vector is a lipid nanoparticle.
211. The vector of any of embodiments 202-210, wherein the vector exhibits hepatocyte tropism.
212. A lipid nanoparticle comprising, the polynucleotide of any of embodiments 183-192 or the plurality of polynucleotides of any of embodiments 193-201.
213. A method of decreasing transcription of at least two genes in a cell or population of cells, the method comprising administering to a cell or population of cells the epigenetic-modifying DNA-targeting system of any of embodiments 1-138, the combination of epigenetic-modifying DNA-targeting systems of embodiment 139 or 140, the gRNA of any of embodiments 141-156, the plurality of gRNAs of any of embodiments 157-169, the Cas-gRNA combination of any of embodiments 170-182, the polynucleotide of any of embodiments 183-192, the plurality of polynucleotides of any of embodiments 193-201, the vector of any of embodiments 202-211, or the lipid nanoparticle of embodiment 212, or a portion or a component of any of the foregoing.

214. The method of embodiment 213, wherein the at least two genes are epigenetically modified.

215. The method of embodiment 213 or embodiment 214, wherein the transcription of each of the at least two genes is decreased in comparison to a comparable cell or population of cells not subjected to the method.

216. The method of any of embodiments 213-215, wherein the transcription of each of the at least two genes is reduced by at least about 1.2-fold, 1.25-fold, 1.3-fold, 1.4-fold, 1.5-fold, 1.6-fold, 1.7-fold, 1.75-fold, 1.8-fold, 1.9-fold, 2-fold, 2.5-fold, 3-fold, 4-fold, or 5-fold.

217. The method of any of embodiments 213-216, wherein the reduced transcription of each of the at least two genes leads to a reduction of low-density lipoprotein (LDL).

218. The method of embodiment 217, wherein the reduction of LDL resulting from reduced transcription each of the at least two genes is greater than the reduction of LDL resulting from comparable reduced transcription of any individual gene of the at least two genes alone.

219. A method of reducing LDL, the method comprising introducing into a cell or population of cells the epigenetic-modifying DNA-targeting system of any of embodiments 1-138, the combination of epigenetic-modifying DNA-targeting systems of embodiment 139 or 140, the gRNA of any of embodiments 141-156, the plurality of gRNAs of any of embodiments 157-169, the Cas-gRNA combination of any of embodiments 170-182, the polynucleotide of any of embodiments 183-192, the plurality of polynucleotides of any of embodiments 193-201, the vector of any of embodiments 202-211, or the lipid nanoparticle of embodiment 212, or a portion or a component of any of the foregoing.

220. The method of any of embodiments 213-219, wherein the cell or population of cells is a liver cell or comprises liver cells.

221. The method of any of embodiments 213-220, wherein the cell or population of cells is in a subject and the method is carried out in vivo.

222. The method of embodiment 221, wherein LDL is reduced in the subject or a fluid, tissue, or organ thereof.

223. The method of any of embodiments 213-222, wherein LDL is reduced in the blood of a subject.

224. The method of any of embodiments 221-223, wherein the subject is a human.

225. The method of any of embodiments 221-224, wherein the subject has or is suspected of having a disease, condition, or disorder, optionally wherein the disease, condition or disorder is a cardiovascular disease.

226. The method of any of embodiments 221-225, wherein the subject has or is suspected of having one or more of: elevated levels of low-density lipoprotein in the blood, increased risk of cardiovascular disease, increased risk of early-onset cardiovascular disease, a mutation affecting cholesterol biosynthesis, a loss-of-function mutation in a low-density lipoprotein receptor (LDLR) gene, a loss-of-function mutation in APOB, a gain-of-function mutation in PCSK9, and familial hypercholesterolemia.

227. The method of any of embodiments 221-226, wherein the subject has is or is suspected of having familial hypercholesterolemia.

228. A pharmaceutical composition comprising the epigenetic-modifying DNA-targeting system of any of embodiments 1-138, the combination of epigenetic-modifying DNA-targeting systems of embodiment 139 or 140, the gRNA of any of embodiments 141-156, the plurality of gRNAs of any of embodiments 157-169, the Cas-gRNA combination of any of embodiments 170-182, the polynucleotide of any of embodiments 183-192, the plurality of polynucleotides of any of embodiments 193-201, the vector of any of embodiments 202-211, the lipid nanoparticle of embodiment 212, or a portion or a component of any of the foregoing.

229. The pharmaceutical composition of embodiment 228, for use in treating a disease, condition, or disorder in a subject, optionally wherein the disease, condition or disorder is a cardiovascular disease.

230. Use of the pharmaceutical composition of embodiment 228 in the manufacture of a medicament for treating a disease, condition, or disorder in a subject, optionally wherein the disease, condition or disorder is a cardiovascular disease.

231. The pharmaceutical composition of embodiment 229 or the use of embodiment 230, wherein the subject has or is suspected of having a disease, condition, or disorder, optionally wherein the disease, condition or disorder is a cardiovascular disease.

232. The pharmaceutical composition or use of any of embodiments 229-231, wherein the subject has or is suspected of having one or more of: elevated levels of low-density lipoprotein in the blood, increased risk of cardiovascular disease, increased risk of early-onset cardiovascular disease, a mutation affecting cholesterol biosynthesis, a loss-of-function mutation in a low-density lipoprotein receptor (LDLR) gene, a loss-of-function mutation in APOB, a gain-of-function mutation in PCSK9, and familial hypercholesterolemia.

233. The pharmaceutical composition or use of any of embodiments 229-232, wherein the subject has is or is suspected of having familial hypercholesterolemia.

234. The pharmaceutical composition or use of any of embodiments 229-233, wherein the pharmaceutical composition is to be administered to the subject in vivo.

235. The pharmaceutical composition or use of embodiment 234, wherein the pharmaceutical composition is targeted to, or is to be administered to the liver of the subject.

236. The pharmaceutical composition or use of embodiment 234 or 235, wherein following administration of the pharmaceutical composition, the expression of at least two genes is reduced in cells of the subject.

237. The pharmaceutical composition or use of any of embodiments 234-236, wherein following administration of the pharmaceutical composition, the expression of at least two genes is reduced in liver cells of the subject.

238. The pharmaceutical composition or use of embodiment 236 or 237, wherein the at least two genes are selected from the group consisting of: PCSK9, LPA, MYLIP, ANGPTL3, APOB, and APOC3.

239. A method for treating a disease, condition, or disorder associated with elevated low-density lipoprotein (LDL) in a subject in need thereof, comprising administering to the subject the epigenetic-modifying DNA-targeting system of any of embodiments 1-138, the combination of epigenetic-modifying DNA-targeting systems of embodiment 139 or 140, the gRNA of any of embodiments 141-156, the plurality of gRNAs of any of embodiments 157-169, the Cas-gRNA combination of any of embodiments 170-182, the polynucleotide of any of embodiments 183-192, the plurality of polynucleotides of any of embodiments 193-201, the vector of any of embodiments 202-211, the lipid nanoparticle of emdodiment 212, the pharmaceutical composition of any of embodiments 228-238, or a portion or a component of any of the foregoing.

240. The method of embodiment 239, wherein the disease, condition or disorder associated with elevated LDL is a cardiovascular disease.

241. The method of embodiment 239 or embodiment 240, wherein the subject has or is suspected of having one or more of: elevated levels of low-density lipoprotein in the blood, increased risk of cardiovascular disease, increased risk of early-onset cardiovascular disease, a mutation affecting cholesterol biosynthesis, a loss-of-function mutation in a low-density lipoprotein receptor (LDLR) gene, a loss-of-function mutation in APOB, a gain-of-function mutation in PCSK9, and familial hypercholesterolemia.

242. A method for treating a familial hypercholesterolemia in a subject, comprising administering to the subject the epigenetic-modifying DNA-targeting system of any of embodiments 1-138, the combination of epigenetic-modifying DNA-targeting systems of embodiment 139 or 140, the gRNA of any of embodiments 141-156, the plurality of gRNAs of any of embodiments 157-169, the Cas-gRNA combination of any of embodiments 170-182, the polynucleotide of any of embodiments 183-192, the plurality of polynucleotides of any of embodiments 193-201, the vector of any of embodiments 202-211, the lipid nanoparticle of embodiment 212, the pharmaceutical composition of any of embodiments 228-238, or a portion or a component of any of the foregoing.

243. The method of any of embodiments 213-227 and 239-242, wherein the administration is a single dose infusion to the subject.

244. The method of any of embodiments 213-227 and 239-242, wherein the administration is repeated at least once, optionally a plurality of times at regular intervals.

250. The method of any of embodiments 218-232, 244-247 and 249, wherein the administration is a multiple dose administration comprising at least a first dose and a second dose.

251. The method of embodiment 250, wherein the first dose and the second dose are the same.

252. The method of embodiment 250, wherein the second dose is lower than the first dose, optionally wherein the second dose is 25% to 75% of the first dose (e.g., about 30%, about 40%, about 50%, about 60% or about 70%, or a percentage between any of the foregoing).

253. The method of embodiment 250, wherein the second dose is higher than the first dose, optionally wherein the second dose is 150% to 500% of the first dose (e.g., about 200%, about 300%, about 400% or about 500%, or a percentage between any of the foregoing).

254. The method of any of embodiments 218-232 and 244-253, wherein the lipid nanoparticle of embodiment 212 is administered to the subject.

255. The pharmaceutical composition or use of any of embodiments 233-243, wherein the pharmaceutical compositon is for single dose infusion to the subject.

256. The pharmaceutical composition or use of any of embodiments 233-243, wherein the pharmaceutical composition is for repeated dose administration, optionally a plurality of times at regular intervals.

257. The pharmaceutical composition or use of any of embodiments 233-243 and 256, wherein the administration is a multiple dose administration comprising at least a first dose and a second dose.

258. The pharmaceutical composition or use of embodiment 257, wherein the first dose and the second dose are the same.

259. The pharmaceutical composition or use of embodiment 257, wherein the second dose is lower than the first dose, optionally wherein the second dose is 25% to 75% of the first dose (e.g., about 30%, about 40%, about 50%, about 60% or about 70%, or a percentage between any of the foregoing).

260. The pharmaceutical composition or use of embodiment 257, wherein the second dose is higher than the first dose, optionally wherein the second dose is 150% to 500% of the first dose (e.g., about 200%, about 300%, about 400% or about 500%, or a percentage between any of the foregoing).

261. The pharmaceutical composition or use of any of embodiments 233-243, and 255-260, wherein the pharmaceutical composition comprises the lipid nanoparticle of embodiment 217.

VIII. EXAMPLES

The following examples are included for illustrative purposes only and are not intended to limit the scope of the invention.

Example 1: Transcriptional Repression of Mouse PCSK9 Using an Epigenetic-Modifying DNA-Targteting System DNA-targeting systems comprising an exemplary dCas9-effector fusion protein for transcriptional repression and guide RNAs (gRNAs) targeting the promoter of mouse PCSK9 were tested for the ability to repress PCSK9 in vitro.

gRNAs targeting the promoter of a mouse PCSK9 gene were designed. Target sites were selected according to the protospacer adjacent motif (PAM) sequence for SpCas9 (5'-NGG-3'; SEQ ID NO:202). gRNAs included a scaffold sequence for SpCas9 (SEQ ID NO:191). DNA target site (protospacer) sequences, and gRNA spacer sequences for gRNAs targeting mouse PCSK9 are shown in Table E1. The designed gRNA sequences targeting mouse PSCK9 are set forth in SEQ ID NOs: 268-276.

TABLE E1 gRNAs targeting mouse PCSK9

| gRNA Name | target site (protospacer) sequence | target SEQ ID | gRNA spacer sequence | gRNA spacer SEQ ID |
|---|---|---|---|---|
| mPCSK9-A | GGGAAGGGATACAGGCTGGA | 250 | GGGAAGGGAUACAGGCUGGA | 259 |
| mPCSK9-B | GTCCCGTTTGCAGCCCAATT | 251 | GUCCCGUUUGCAGCCCAAUU | 260 |
| mPCSK9-C | GAGCGTCATTTGACGCTGTC | 252 | GAGCGUCAUUUGACGCUGUC | 261 |
| mPCSK9-D | GGATCTTCCGATGGGGCTCG | 253 | GGAUCUUCCGAUGGGGCUCG | 262 |
| mPCSK9-E | GTGAAGGTGGAAGCCTTCTG | 254 | GUGAAGGUGGAAGCCUUCUG | 263 |
| mPCSK9-F | GTGGACGCGCAGGCTGCCGG | 255 | GUGGACGCGCAGGCUGCCGG | 264 |
| mPCSK9-G | GGGGCGAGGAGAGGTGCGCG | 256 | GGGGCGAGGAGAGGUGCGCG | 265 |
| mPCSK9-H | AGTGGGTGCCCATCGGGGCG | 257 | AGUGGGUGCCCAUCGGGGCG | 266 |
| mPCSK9-I | CTACTGTGCCCCACCGGCGC | 258 | CUACUGUGCCCCACCGGCGC | 267 |

Expression plasmids were constructed, each encoding one of the designed gRNAs, GFP, and dSpCas9-KRAB-DNMT3A/L (SEQ ID NO:278), an exemplary DNA-targeting fusion protein for transcriptional repression of gRNA-targeted genes. A murine liver cell line (AML12) was transiently transfected with the plasmids encoding each gRNA, or encoding a non-targeting gRNA (negative control). One day after transfection, GFP+ cells were sorted to enrich for transfected cells. Three days after enrichment, PCKS9 mRNA levels were assessed by qRT-PCR. As shown in FIG. 1, expression of dSpCas9-KRAB-DNMT3A/L and the PCSK9-targeting gRNAs led to transcriptional repression of PCSK9.

The results showed that a DNA-targeting system comprising a gRNA targeting PCSK9 and a dCas9-effector fusion protein can facilitate transcriptional repression of PCSK9. The results also showed that a DNA-targeting system comprising a dCas9-effector fusion with more than one effector domain can effectively mediate transcriptional repression. The results support the utility of repressing PCSK9 in vivo and for potential treatment of familial hypercholesterolemia and/or cardiovascular disease.

Example 2: Design and Verification of gRNAs Targeting Human Genes Associated with Regulation of Low-Density Lipoprotein (LDL)

gRNAs were designed for targeting human genes associated with regulation of low-density lipoprotein (LDL), including PCSK9, LPA, MYLIP, ANGPTL3, APOC3, and APOB. The designed gRNAs were generated and assessed for the ability to mediate transcriptional repression as part of a DNA-targeting system composed of a designed gRNA and a dCas9-effector fusion protein.

Multiple gRNAs targeting the promoter region of each gene (within 500 base pairs of the transcriptional start site) were designed. Target sites were selected according to the protospacer adjacent motif (PAM) sequence for SpCas9 (5'-NGG-3'; SEQ ID NO:202). Exemplary DNA target site (protospacer) sequences are set forth in SEQ ID NOS:1-63 and gRNA spacer sequences for gRNAs targeting each site are set forth in SEQ ID NOS:64-126. These sequences are listed in Table 3 (Section I.B.). Each gRNA further comprised a scaffold sequence for SpCas9, comprising the sequence: GUUUAAGAGCUAUGCUGGAAACAG-CAUAGCAAGUUUAAAUAAGGCUAGUCCG UUAU-CAACUUGAAAAAGUGGCACCGAGUCGGUGC (SEQ ID NO: 191). The sequences of the designed gRNAs (SEQ ID NOS: 127-189) and their respective DNA target sites (SEQ ID NOS: 1-63) are shown in Table E2 for PCSK9, Table E3 for LPA, Table E4 for MYLIP, Table E5 for ANGPTL3, Table E6 for APOC3, and Table E7 for APOB.

TABLE E2 gRNAs targeting human PCSK9

| gRNA name | target site SEQ ID | target site sequence | gRNA SEQ ID | gRNA sequence |
|---|---|---|---|---|
| PCSK9-A | 1 | GCGCGTAATCTGACGCTGTT | 127 | GCGCGUAAUCUGACGCUGUUGUUU AAGAGCUAUGCUGGAAACAGCAUA GCAAGUUUAAAUAAGGCUAGUCCG UUAUCAACUUGAAAAAGUGGCACC GAGUCGGUGC |
| PCSK9-B | 2 | ATCAGATAGGATCGTCCGAT | 128 | AUCAGAUAGGAUCGUCCGAUGUUU AAGAGCUAUGCUGGAAACAGCAUA GCAAGUUUAAAUAAGGCUAGUCCG |

TABLE E2-continued gRNAs targeting human PCSK9

| gRNA name | target site SEQ ID | target site sequence | gRNA SEQ ID | gRNA sequence |
|---|---|---|---|---|
| | | | | UUAUCAACUUGAAAAAGUGGCACC GAGUCGGUGC |
| PCSK9-C | 3 | AGGTTTCCGCAG CGACGTCG | 129 | AGGUUUCCGCAGCGACGUCGGUUU AAGAGCUAUGCUGGAAACAGCAUA GCAAGUUUAAAUAAGGCUAGUCCG UUAUCAACUUGAAAAAGUGGCACC GAGUCGGUGC |
| PCSK9-D | 4 | GGGCGCCGCCGT TCAGTTCA | 130 | GGGCGCCGCCGUUCAGUUCAGUUU AAGAGCUAUGCUGGAAACAGCAUA GCAAGUUUAAAUAAGGCUAGUCCG UUAUCAACUUGAAAAAGUGGCACC GAGUCGGUGC |
| PCSK9-E | 5 | GGTGCTAGCCTTG CGTTCCG | 131 | GGUGCUAGCCUUGCGUUCCGGUUU AAGAGCUAUGCUGGAAACAGCAUA GCAAGUUUAAAUAAGGCUAGUCCG UUAUCAACUUGAAAAAGUGGCACC GAGUCGGUGC |
| PCSK9-F | 6 | CATTAACGGAAC CCCCGGAC | 132 | CAUUAACGGAACCCCCGGACGUUU AAGAGCUAUGCUGGAAACAGCAUA GCAAGUUUAAAUAAGGCUAGUCCG UUAUCAACUUGAAAAAGUGGCACC GAGUCGGUGC |
| PCSK9-G | 7 | AGGATCGTCCGA TGGGGCTC | 133 | AGGAUCGUCCGAUGGGGCUCGUUU AAGAGCUAUGCUGGAAACAGCAUA GCAAGUUUAAAUAAGGCUAGUCCG UUAUCAACUUGAAAAAGUGGCACC GAGUCGGUGC |
| PCSK9-H | 8 | CCGTTAATGTTTA ATCAGAT | 134 | CCGUUAAUGUUUAAUCAGAUGUUU AAGAGCUAUGCUGGAAACAGCAUA GCAAGUUUAAAUAAGGCUAGUCCG UUAUCAACUUGAAAAAGUGGCACC GAGUCGGUGC |
| PCSK9-I | 9 | CGTAATCTGACG CTGTTTG | 135 | CGUAAUCUGACGCUGUUUGGUUUA AGAGCUAUGCUGGAAACAGCAUAG CAAGUUUAAAUAAGGCUAGUCCGU UAUCAACUUGAAAAAGUGGCACCG AGUCGGUGC |
| PCSK9-J | 10 | GGTGTGGGTGCTT GACGCCT | 136 | GGUGUGGGUGCUUGACGCCUGUUU AAGAGCUAUGCUGGAAACAGCAUA GCAAGUUUAAAUAAGGCUAGUCCG UUAUCAACUUGAAAAAGUGGCACC GAGUCGGUGC |
| PCSK9-K | 11 | ACCCACTGCACG CTGGACAG | 137 | ACCCACUGCACGCUGGACAGGUUU AAGAGCUAUGCUGGAAACAGCAUA GCAAGUUUAAAUAAGGCUAGUCCG UUAUCAACUUGAAAAAGUGGCACC GAGUCGGUGC |
| PCSK9-L | 12 | GCACAGTAACAA CCCCTGGT | 138 | GCACAGUAACAACCCCUGGUGUUU AAGAGCUAUGCUGGAAACAGCAUA GCAAGUUUAAAUAAGGCUAGUCCG UUAUCAACUUGAAAAAGUGGCACC GAGUCGGUGC |
| PCSK9-M | 13 | CCATCCATTCTTT CTCTAGG | 139 | CCAUCCAUUCUUUCUCUAGGGUUU AAGAGCUAUGCUGGAAACAGCAUA GCAAGUUUAAAUAAGGCUAGUCCG UUAUCAACUUGAAAAAGUGGCACC GAGUCGGUGC |

TABLE E3 gRNAs targeting human LPA

| gRNA name | target site SEQ ID | target site sequence | gRNA SEQ ID | gRNA sequence |
|---|---|---|---|---|
| LPA-A | 14 | AAGGAGACATAA AGGCAATG | 140 | AAGGAGACAUAAAGGCAAUGGUUU AAGAGCUAUGCUGGAAACAGCAUA GCAAGUUUAAAUAAGGCUAGUCCG UUAUCAACUUGAAAAAGUGGCACC GAGUCGGUGC |
| LPA-B | 15 | GGCAATGTGGAG CAGCTGAG | 141 | GGCAAUGUGGAGCAGCUGAGGUUU AAGAGCUAUGCUGGAAACAGCAUA GCAAGUUUAAAUAAGGCUAGUCCG UUAUCAACUUGAAAAAGUGGCACC GAGUCGGUGC |
| LPA-C | 16 | GGAGCAGCTGAG GGGGGAAA | 142 | GGAGCAGCUGAGGGGGGAAAGUUU AAGAGCUAUGCUGGAAACAGCAUA GCAAGUUUAAAUAAGGCUAGUCCG UUAUCAACUUGAAAAAGUGGCACC GAGUCGGUGC |
| LPA-D | 17 | TGTCAATAGATG CTGGGAAG | 143 | UGUCAAUAGAUGCUGGGAAGGUUU AAGAGCUAUGCUGGAAACAGCAUA GCAAGUUUAAAUAAGGCUAGUCCG UUAUCAACUUGAAAAAGUGGCACC GAGUCGGUGC |
| LPA-E | 18 | AGTGCAATGTCA ATAGATGC | 144 | AGUGCAAUGUCAAUAGAUGCGUUU AAGAGCUAUGCUGGAAACAGCAUA GCAAGUUUAAAUAAGGCUAGUCCG UUAUCAACUUGAAAAAGUGGCACC GAGUCGGUGC |
| LPA-F | 19 | TTTATAAGACTCT ATATTCA | 145 | UUUAUAAGACUCUAUAUUCAGUUU AAGAGCUAUGCUGGAAACAGCAUA GCAAGUUUAAAUAAGGCUAGUCCG UUAUCAACUUGAAAAAGUGGCACC GAGUCGGUGC |
| LPA-G | 20 | CATGTAAGTCAA CAATGTCC | 146 | CAUGUAAGUCAACAAUGUCCGUUU AAGAGCUAUGCUGGAAACAGCAUA GCAAGUUUAAAUAAGGCUAGUCCG UUAUCAACUUGAAAAAGUGGCACC GAGUCGGUGC |
| LPA-H | 21 | GTCAACAATGTC CTGGGATT | 147 | GUCAACAAUGUCCUGGGAUUGUUU AAGAGCUAUGCUGGAAACAGCAUA GCAAGUUUAAAUAAGGCUAGUCCG UUAUCAACUUGAAAAAGUGGCACC GAGUCGGUGC |
| LPA-I | 22 | CATATACAAGAT TTTGAACT | 148 | CAUAUACAAGAUUUUGAACUGUUU AAGAGCUAUGCUGGAAACAGCAUA GCAAGUUUAAAUAAGGCUAGUCCG UUAUCAACUUGAAAAAGUGGCACC GAGUCGGUGC |
| LPA-J | 23 | GCACCGTGACAG TCTTCACG | 149 | GCACCGUGACAGUCUUCACGGUUU AAGAGCUAUGCUGGAAACAGCAUA GCAAGUUUAAAUAAGGCUAGUCCG UUAUCAACUUGAAAAAGUGGCACC GAGUCGGUGC |

TABLE E4 gRNAs targeting human MYLIP

| gRNA name | target site SEQ ID | target site sequence | gRNA SEQ ID | gRNA sequence |
|---|---|---|---|---|
| MYLIP-A | 24 | TTGGCGGGGACC CGAGCTGA | 150 | UUGGCGGGGACCCGAGCUGAGUUU AAGAGCUAUGCUGGAAACAGCAUA GCAAGUUUAAAUAAGGCUAGUCCG UUAUCAACUUGAAAAAGUGGCACC GAGUCGGUGC |

TABLE E4-continued gRNAs targeting human MYLIP

| gRNA name | target site SEQ ID | target site sequence | gRNA SEQ ID | gRNA sequence |
|---|---|---|---|---|
| MYLIP-B | 25 | CTGTCGCAGCGC AGGCAGTT | 151 | CUGUCGCAGCGCAGGCAGUUGUUU AAGAGCUAUGCUGGAAACAGCAUA GCAAGUUUAAAUAAGGCUAGUCCG UUAUCAACUUGAAAAAGUGGCACC GAGUCGGUGC |
| MYLIP-C | 26 | GCTGGAGTGCGG CGCCACCG | 152 | GCUGGAGUGCGGCGCCACCGGUUU AAGAGCUAUGCUGGAAACAGCAUA GCAAGUUUAAAUAAGGCUAGUCCG UUAUCAACUUGAAAAAGUGGCACC GAGUCGGUGC |
| MYLIP-D | 27 | CGGCGCCACCGC GGAGGACA | 153 | CGGCGCCACCGCGGAGGACAGUUU AAGAGCUAUGCUGGAAACAGCAUA GCAAGUUUAAAUAAGGCUAGUCCG UUAUCAACUUGAAAAAGUGGCACC GAGUCGGUGC |
| MYLIP-E | 28 | CAGCTCTGCGGA CCCTTGTC | 154 | CAGCUCUGCGGACCCUUGUCGUUU AAGAGCUAUGCUGGAAACAGCAUA GCAAGUUUAAAUAAGGCUAGUCCG UUAUCAACUUGAAAAAGUGGCACC GAGUCGGUGC |
| MYLIP-F | 29 | CCCCGCGCACAC CAAAGAGA | 155 | CCCCGCGCACACCAAAGAGAGUUU AAGAGCUAUGCUGGAAACAGCAUA GCAAGUUUAAAUAAGGCUAGUCCG UUAUCAACUUGAAAAAGUGGCACC GAGUCGGUGC |
| MYLIP-G | 30 | CCTCGTCACATAA CACAGCA | 156 | CCUCGUCACAUAACACAGCAGUUU AAGAGCUAUGCUGGAAACAGCAUA GCAAGUUUAAAUAAGGCUAGUCCG UUAUCAACUUGAAAAAGUGGCACC GAGUCGGUGC |
| MYLIP-H | 31 | ACCTCCATCAGC ACCGCGTC | 157 | ACCUCCAUCAGCACCGCGUCGUUU AAGAGCUAUGCUGGAAACAGCAUA GCAAGUUUAAAUAAGGCUAGUCCG UUAUCAACUUGAAAAAGUGGCACC GAGUCGGUGC |
| MYLIP-I | 32 | GGAGGCGAAAGC CAACGGCG | 158 | GGAGGCGAAAGCCAACGGCGGUUU AAGAGCUAUGCUGGAAACAGCAUA GCAAGUUUAAAUAAGGCUAGUCCG UUAUCAACUUGAAAAAGUGGCACC GAGUCGGUGC |
| MYLIP-J | 33 | GTTGAGGCAGTC CTCGCCGT | 159 | GUUGAGGCAGUCCUCGCCGUGUUU AAGAGCUAUGCUGGAAACAGCAUA GCAAGUUUAAAUAAGGCUAGUCCG UUAUCAACUUGAAAAAGUGGCACC GAGUCGGUGC |

TABLE E5 gRNAs targeting human ANGPTL3

| gRNA name | target site SEQ ID | target site sequence | gRNA SEQ ID | gRNA sequence |
|---|---|---|---|---|
| ANGPTL3-A | 34 | TACATTCGTGCAA GTTAACA | 160 | UACAUUCGUGCAAGUUAACAGUUU AAGAGCUAUGCUGGAAACAGCAUA GCAAGUUUAAAUAAGGCUAGUCCG UUAUCAACUUGAAAAAGUGGCACC GAGUCGGUGC |

TABLE E5-continued gRNAs targeting human ANGPTL3

| gRNA name | target site SEQ ID | target site sequence | gRNA SEQ ID | gRNA sequence |
|---|---|---|---|---|
| ANGPTL3-B | 35 | CCTACCAACCTTACCTTTTC | 161 | CCUACCAACCUUACCUUUUCGUUUAAGAGCUAUGCUGGAAACAGCAUAGCAAGUUUAAAUAAGGCUAGUCCGUUAUCAACUUGAAAAAGUGGCACCGAGUCGGUGC |
| ANGPTL3-C | 36 | TATATAGAGTTAAGAAGTCT | 162 | UAUAUAGAGUUAAGAAGUCUGUUUAAGAGCUAUGCUGGAAACAGCAUAGCAAGUUUAAAUAAGGCUAGUCCGUUAUCAACUUGAAAAAGUGGCACCGAGUCGGUGC |
| ANGPTL3-D | 37 | AACGTGGAACTGTTTTCTTC | 163 | AACGUGGAACUGUUUUCUUCGUUUAAGAGCUAUGCUGGAAACAGCAUAGCAAGUUUAAAUAAGGCUAGUCCGUUAUCAACUUGAAAAAGUGGCACCGAGUCGGUGC |
| ANGPTL3-E | 38 | ATTTTCAATTTCAAGCAACG | 164 | AUUUUCAAUUUCAAGCAACGGUUUAAGAGCUAUGCUGGAAACAGCAUAGCAAGUUUAAAUAAGGCUAGUCCGUUAUCAACUUGAAAAAGUGGCACCGAGUCGGUGC |
| ANGPTL3-F | 39 | ATTCTGGAGGAAATAACTAG | 165 | AUUCUGGAGGAAAUAACUAGGUUUAAGAGCUAUGCUGGAAACAGCAUAGCAAGUUUAAAUAAGGCUAGUCCGUUAUCAACUUGAAAAAGUGGCACCGAGUCGGUGC |
| ANGPTL3-G | 40 | GCAAATCTTGATTTTGGCTC | 166 | GCAAAUCUUGAUUUUGGCUCGUUUAAGAGCUAUGCUGGAAACAGCAUAGCAAGUUUAAAUAAGGCUAGUCCGUUAUCAACUUGAAAAAGUGGCACCGAGUCGGUGC |
| ANGPTL3-H | 41 | AGCCAATGGCCTCCTTCAGT | 167 | AGCCAAUGGCCUCCUUCAGUGUUUAAGAGCUAUGCUGGAAACAGCAUAGCAAGUUUAAAUAAGGCUAGUCCGUUAUCAACUUGAAAAAGUGGCACCGAGUCGGUGC |
| ANGPTL3-I | 42 | TAAGACCATGTCCCAACTGA | 168 | UAAGACCAUGUCCCAACUGAGUUUAAGAGCUAUGCUGGAAACAGCAUAGCAAGUUUAAAUAAGGCUAGUCCGUUAUCAACUUGAAAAAGUGGCACCGAGUCGGUGC |
| ANGPTL3-J | 43 | AGACTTTGTCCATAAGACGA | 169 | AGACUUUGUCCAUAAGACGAGUUUAAGAGCUAUGCUGGAAACAGCAUAGCAAGUUUAAAUAAGGCUAGUCCGUUAUCAACUUGAAAAAGUGGCACCGAGUCGGUGC |

TABLE E6 gRNAs targeting human APOC3

| gRNA name | target site SEQ ID | target site sequence | gRNA SEQ ID | gRNA sequence |
|---|---|---|---|---|
| APOC3-A | 44 | GGGGCACCCGTCCAGCTCCG | 170 | GGGGCACCCGUCCAGCUCCGGUUUAAGAGCUAUGCUGGAAACAGCAUAGCAAGUUUAAAUAAGGCUAGUCCGUUAUCAACUUGAAAAAGUGGCACCGAGUCGGUGC |
| APOC3-B | 45 | TGACCTTTGCCCAGCGCCCT | 171 | UGACCUUUGCCCAGCGCCCUGUUUAAGAGCUAUGCUGGAAACAGCAUAGCAAGUUUAAAUAAGGCUAGUCCGUUAUCAACUUGAAAAAGUGGCACCGAGUCGGUGC |

TABLE E6-continued gRNAs targeting human APOC3

| gRNA name | target site SEQ ID | target site sequence | gRNA SEQ ID | gRNA sequence |
|---|---|---|---|---|
| APOC3-C | 46 | TCCAGATGCAGC AAGCGGGC | 172 | UCCAGAUGCAGCAAGCGGGCGUUU AAGAGCUAUGCUGGAAACAGCAUA GCAAGUUUAAAUAAGGCUAGUCCG UUAUCAACUUGAAAAAGUGGCACC GAGUCGGUGC |
| APOC3-D | 47 | TAGGGATGAACT GAGCAGAC | 173 | UAGGGAUGAACUGAGCAGACGUUU AAGAGCUAUGCUGGAAACAGCAUA GCAAGUUUAAAUAAGGCUAGUCCG UUAUCAACUUGAAAAAGUGGCACC GAGUCGGUGC |
| APOC3-E | 48 | AGAAGCACTTGC TAGAGCTA | 174 | AGAAGCACUUGCUAGAGCUAGUUU AAGAGCUAUGCUGGAAACAGCAUA GCAAGUUUAAAUAAGGCUAGUCCG UUAUCAACUUGAAAAAGUGGCACC GAGUCGGUGC |
| APOC3-F | 49 | CTGCTCCAGGTA ATGCCCTC | 175 | CUGCUCCAGGUAAUGCCCUCGUUU AAGAGCUAUGCUGGAAACAGCAUA GCAAGUUUAAAUAAGGCUAGUCCG UUAUCAACUUGAAAAAGUGGCACC GAGUCGGUGC |
| APOC3-G | 50 | GGGAGAGTTGGG AAATCCCT | 176 | GGGAGAGUUGGGAAAUCCCUGUUU AAGAGCUAUGCUGGAAACAGCAUA GCAAGUUUAAAUAAGGCUAGUCCG UUAUCAACUUGAAAAAGUGGCACC GAGUCGGUGC |
| APOC3-H | 51 | AGGAAGCCTCGG AGCTGGAC | 177 | AGGAAGCCUCGGAGCUGGACGUUU AAGAGCUAUGCUGGAAACAGCAUA GCAAGUUUAAAUAAGGCUAGUCCG UUAUCAACUUGAAAAAGUGGCACC GAGUCGGUGC |
| APOC3-I | 52 | CCCTGGAGATGA TATAAAAC | 178 | CCCUGGAGAUGAUAUAAAACGUUU AAGAGCUAUGCUGGAAACAGCAUA GCAAGUUUAAAUAAGGCUAGUCCG UUAUCAACUUGAAAAAGUGGCACC GAGUCGGUGC |
| APOC3-J | 53 | TCATAACCTGAA GAACATGG | 179 | UCAUAACCUGAAGAACAUGGGUUU AAGAGCUAUGCUGGAAACAGCAUA GCAAGUUUAAAUAAGGCUAGUCCG UUAUCAACUUGAAAAAGUGGCACC GAGUCGGUGC |

TABLE E7 gRNAs targeting human APOB

| gRNA name | target site SEQ ID | target site sequence | gRNA SEQ ID | gRNA sequence |
|---|---|---|---|---|
| APOB-A | 54 | GTCCATCGCCAG CTGCGGTG | 180 | GUCCAUCGCCAGCUGCGGUGGUUU AAGAGCUAUGCUGGAAACAGCAUA GCAAGUUUAAAUAAGGCUAGUCCG UUAUCAACUUGAAAAAGUGGCACC GAGUCGGUGC |
| APOB-B | 55 | GGCGCCCGCACC CCATTTAT | 181 | GGCGCCCGCACCCCAUUUAUGUUU AAGAGCUAUGCUGGAAACAGCAUA GCAAGUUUAAAUAAGGCUAGUCCG UUAUCAACUUGAAAAAGUGGCACC GAGUCGGUGC |

TABLE E7-continued gRNAs targeting human APOB

| gRNA name | target site SEQ ID | target site sequence | gRNA SEQ ID | gRNA sequence |
|---|---|---|---|---|
| APOB-C | 56 | CAGAGCGGCCGC GCACTCAC | 182 | CAGAGCGGCCGCGCACUCACGUUU AAGAGCUAUGCUGGAAACAGCAUA GCAAGUUUAAAUAAGGCUAGUCCG UUAUCAACUUGAAAAAGUGGCACC GAGUCGGUGC |
| APOB-D | 57 | CTCAGCGGCAGC AACCGAGA | 183 | CUCAGCGGCAGCAACCGAGAGUUU AAGAGCUAUGCUGGAAACAGCAUA GCAAGUUUAAAUAAGGCUAGUCCG UUAUCAACUUGAAAAAGUGGCACC GAGUCGGUGC |
| APOB-E | 58 | TCCCGGTGGGAA TGCGCGGC | 184 | UCCCGGUGGGAAUGCGCGGCGUUU AAGAGCUAUGCUGGAAACAGCAUA GCAAGUUUAAAUAAGGCUAGUCCG UUAUCAACUUGAAAAAGUGGCACC GAGUCGGUGC |
| APOB-F | 59 | GCATTCCCACCG GGACCTGC | 185 | GCAUUCCCACCGGGACCUGCGUUU AAGAGCUAUGCUGGAAACAGCAUA GCAAGUUUAAAUAAGGCUAGUCCG UUAUCAACUUGAAAAAGUGGCACC GAGUCGGUGC |
| APOB-G | 60 | GCCTCGCGGCCCT GGCTGGC | 186 | GCCUCGCGGCCCUGGCUGGCGUUU AAGAGCUAUGCUGGAAACAGCAUA GCAAGUUUAAAUAAGGCUAGUCCG UUAUCAACUUGAAAAAGUGGCACC GAGUCGGUGC |
| APOB-H | 61 | CCCGGCCAACCT CGTGCCGC | 187 | CCCGGCCAACCUCGUGCCGCGUUU AAGAGCUAUGCUGGAAACAGCAUA GCAAGUUUAAAUAAGGCUAGUCCG UUAUCAACUUGAAAAAGUGGCACC GAGUCGGUGC |
| APOB-I | 62 | AGCGCCAGCAGC GCGGGCCT | 188 | AGCGCCAGCAGCGCGGGCCUGUUU AAGAGCUAUGCUGGAAACAGCAUA GCAAGUUUAAAUAAGGCUAGUCCG UUAUCAACUUGAAAAAGUGGCACC GAGUCGGUGC |
| APOB-J | 63 | CTCCCTCTGCGCC CGCAGAG | 189 | CUCCCUCUGCGCCCGCAGAGGUUU AAGAGCUAUGCUGGAAACAGCAUA GCAAGUUUAAAUAAGGCUAGUCCG UUAUCAACUUGAAAAAGUGGCACC GAGUCGGUGC |

Figure 2:
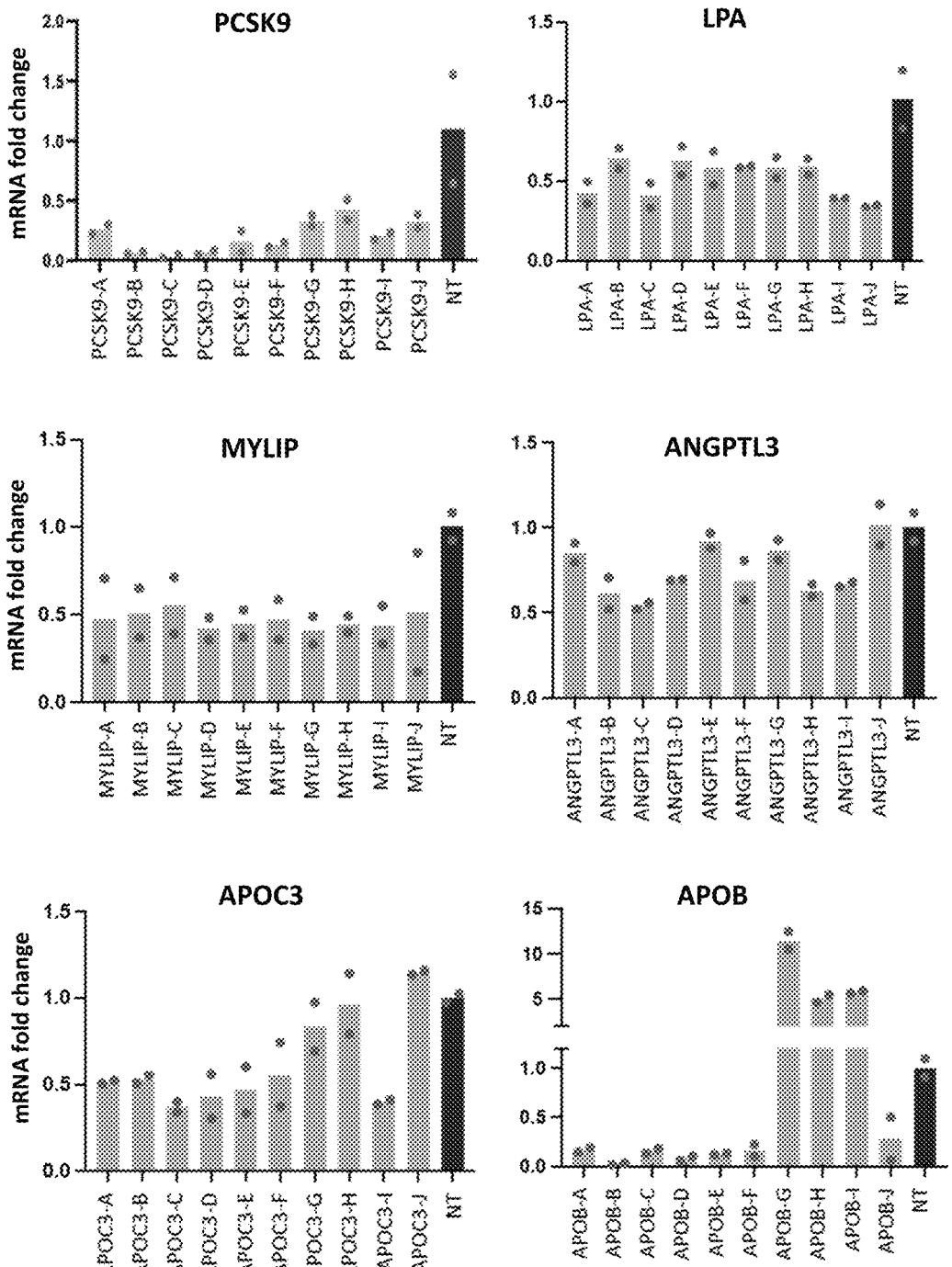
FIG. 2 shows results from qRT-PCR to assess expression of genes associated with regulation of low-density lipoprotein (LDL) in human hepatocellular carcinoma (Huh7) cells transfected with dSpCas9-KRAB-DNMT3A/L and a non-targeting gRNA (NT; negative control) or a gRNA targeting human PCSK9, LPA, MYLIP, ANGPTL3, APOC3, or APOB. Results are shown for 7 days post-transfection. Dots represent expression levels for experimental replicates, bars represent mean of expression from experimental replicates. Expression is shown as fold change with respect to cells expressing the non-targeting gRNA.

Ten gRNAs were tested for each gene. A human hepatocellular carcinoma cell line (Huh7) was transfected with dSpCas9-KRAB-DNMT3A/L in combination with each designed gRNA. mRNA was isolated from the transfected cells seven days after transfection and assessed for knockdown of the target gene by qRT-PCR. As shown in FIG. 2, co-expression of dSpCas9-KRAB-DNMT3A/L and agRNA led to transcriptional repression of the target genes, with the exception of 3 or 4 gRNAs targeting ANGPTL3, APOC3, and APOB.

Figure 3A:
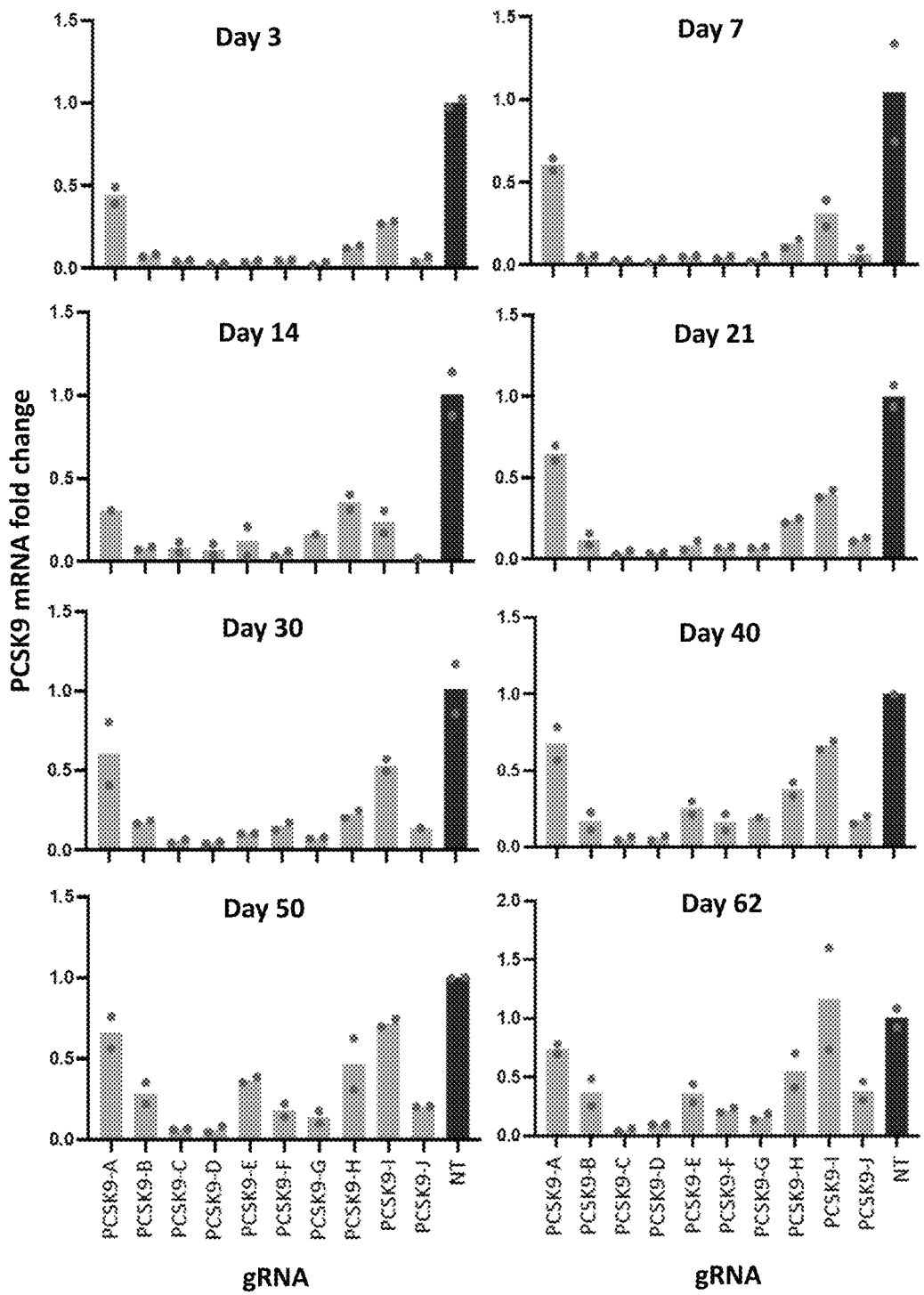
FIG. 3A-3E show PCSK9 mRNA expression levels and PCSK9 CpG methylation in human hepatocellular carcinoma (Huh7) cells transfected with dSpCas9-KRAB-DNMT3A/L and a non-targeting gRNA (NT; negative control) or a PCSK9-targeting gRNA.
Figure 3B:
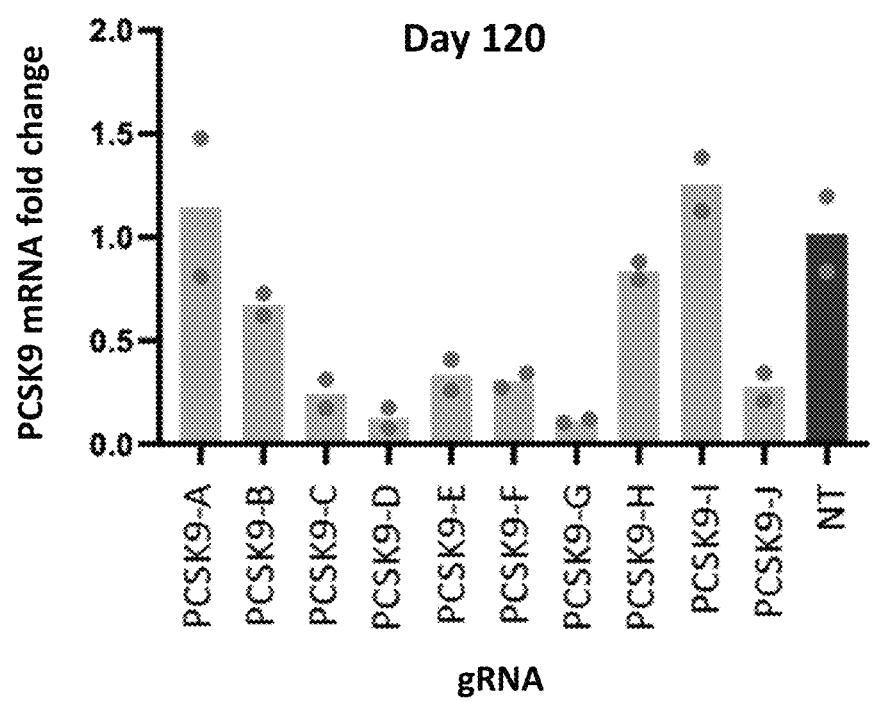
Figure 3C:
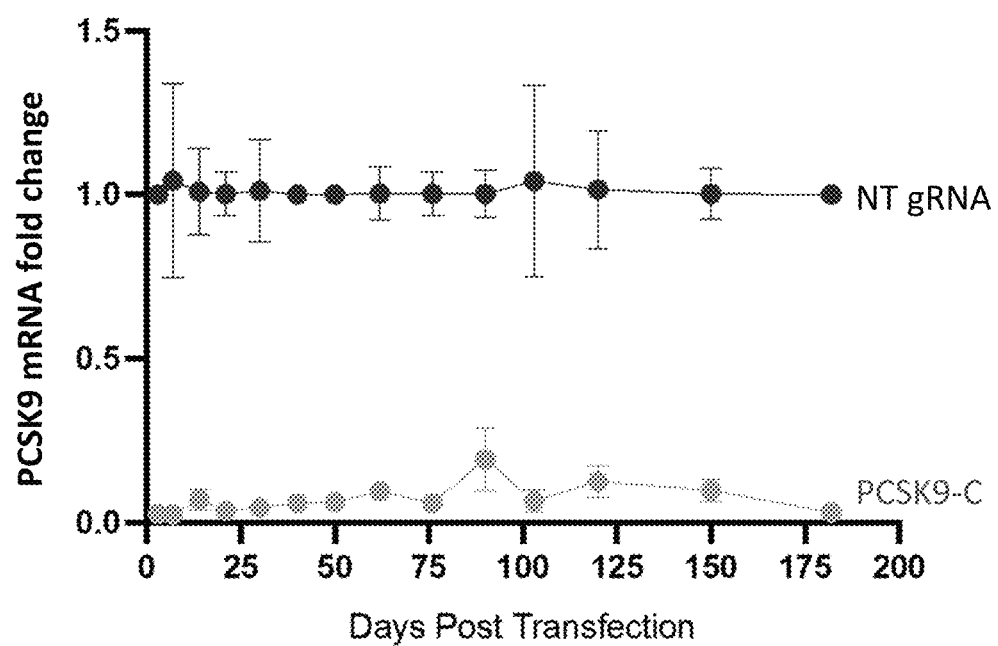

To test the durability of the repression induced by the DNA-targeting systems, PCSK9 mRNA levels were assessed at multiple time points post-transfection with the PCSK9-targeting gRNAs and dSpCas9-KRAB-DNMT3A/L (FIG. 3A). After transfection, cells were passaged approximately every 4-6 days, as necessary. As shown in FIG. 3B, sustained repression of PCSK9 mRNA post-transfection was observed 120 days post-transfection with 8/10 of the gRNAs tested in comparison to a non-targeting gRNA. Analysis at subsequent timepoints demonstrated stable repression of PCSK9 mRNA was sustained for six months after the single transient exposure of liver cells to dSpCas9-KRAB-DNMT3A/L (SEQ ID NO: 278) and gRNA PCSK9-C(SEQ ID NO:129) (FIG. 3C).

Figure 3D:
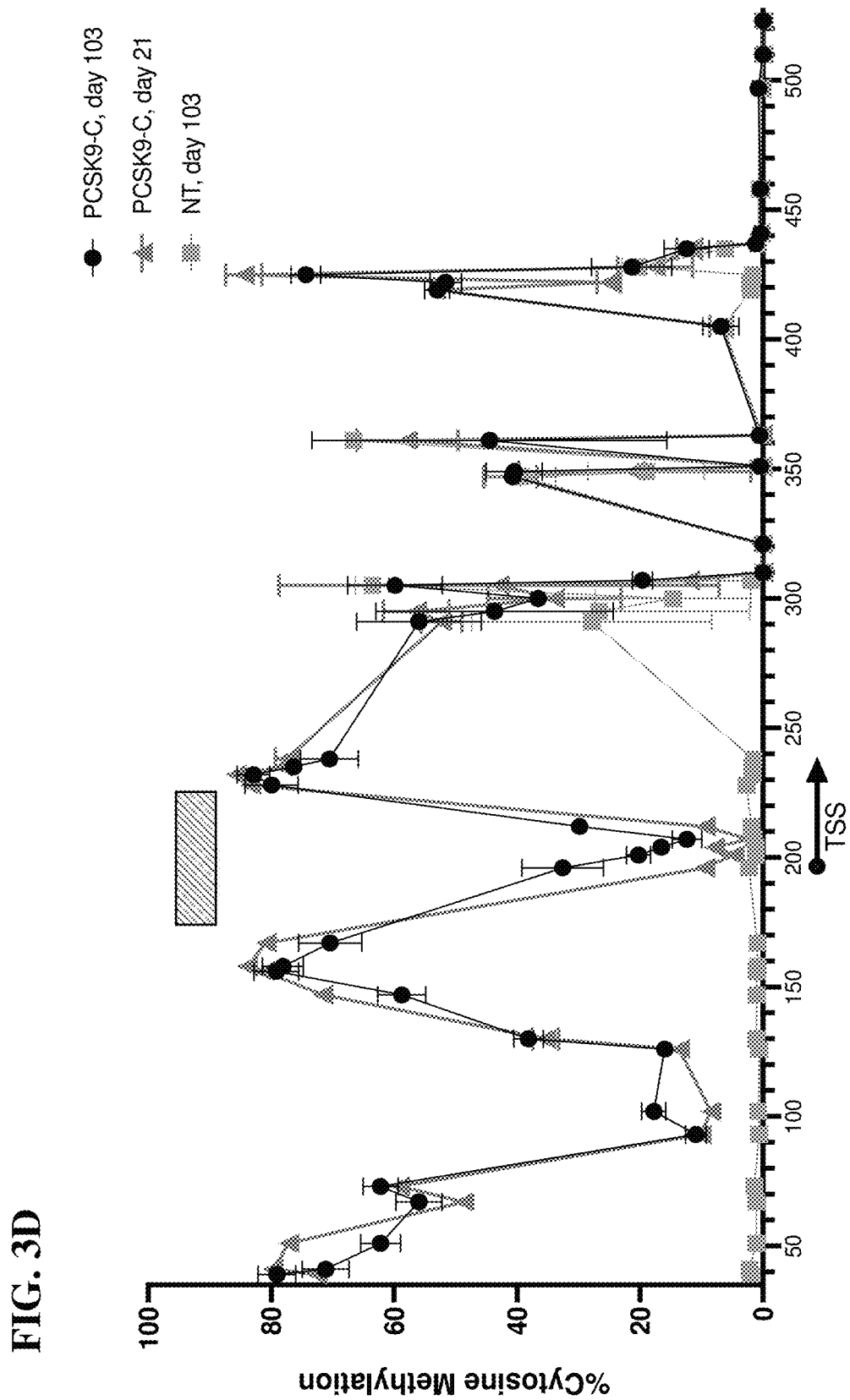
Figure 3E:
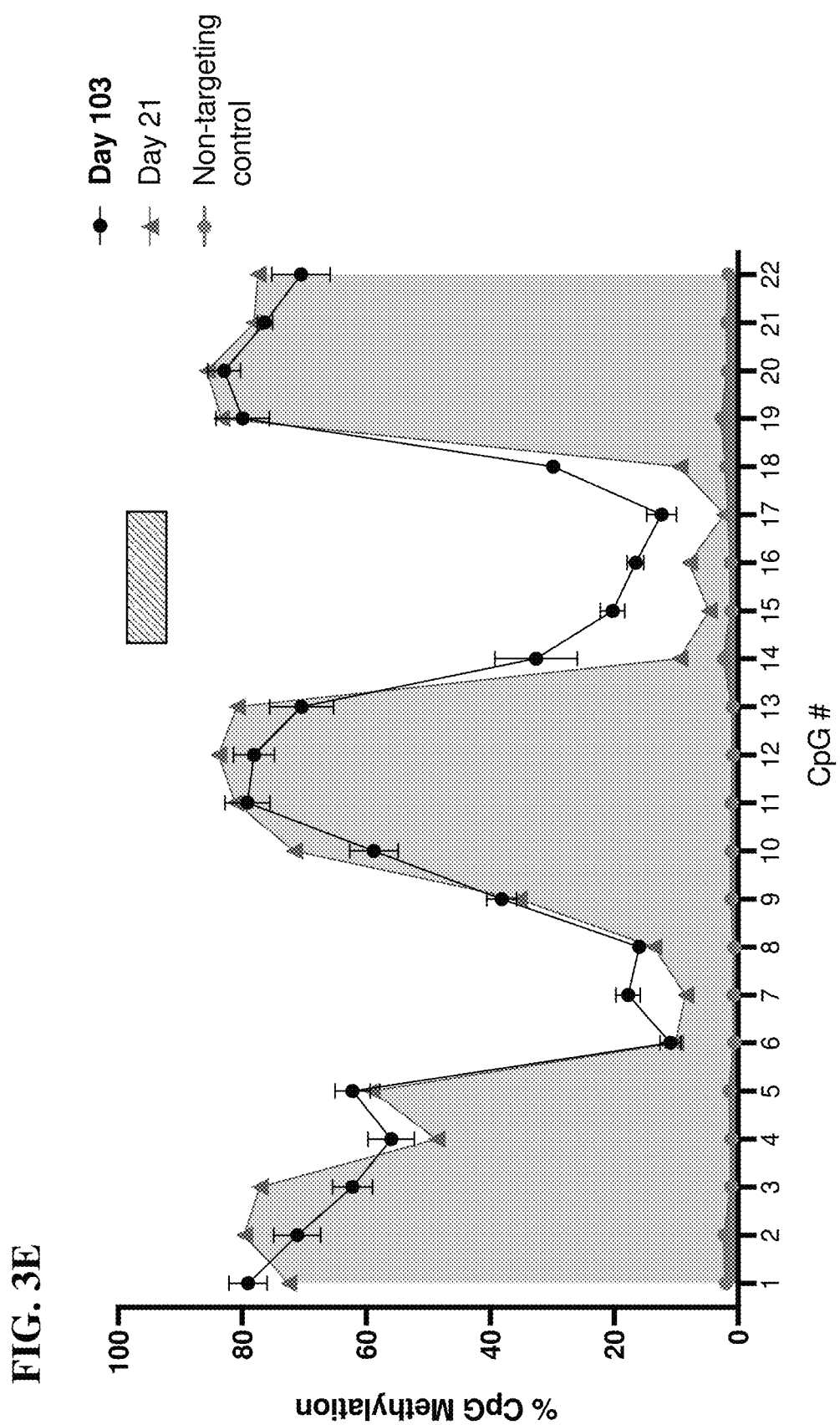

To assess if the observed repression of PCSK9 mRNA was due to increased CpG methylation at or near the PCSK9 promoter, DNA was extracted from Huh7 cells transfected with dSpCas9-KRAB-DNMT3A/L (SEQ ID NO: 278) and gRNA PCSK9-C(SEQ ID NO:129) or a non-targeting (NT) gRNA for sequencing analysis and quantification of differential CpG methylation. As shown in FIG. 3D, increased methylation of CpGs at the PCSK9 promoter was observed at day 21 (triangles) and day 103 (circles) post-transfection with gRNA PCSK9-C as compared to the non-targeting control (squares), particularly in the region surrounding the PSCK9-C target site (FIG. 3E). These results are consistent with stable methylation around the target site facilitated by the epigenetic-modifying DNA-targeting system in human liver cells.

The results showed that a DNA-targeting system comprising a designed gRNA and a dCas9-effector fusion protein can facilitate durable transcriptional repression of targeted genes and increase CpG methylation around gRNA target sites in human cells. The results further support the utility of repressing PCSK9 and other genes associated with regulation of LDL in vivo for potential treatment of familial hypercholesterolemia and/or cardiovascular disease.

Example 3: Multiplexed Targeted Transcriptional Repression for Reducing LDL

DNA-targeting systems comprising different combinations of the gRNAs identified in Example 2 are screened to identify conditions in which multiplexed targeted transcriptional repression of at least two genes promotes cellular phenotypes that could reduce LDL in vivo.

DNA-targeting systems comprising gRNAs and a dSpCas9-effector are transiently transfected into Huh7 cells. gRNAs are transfected individually, or in combinations of two gRNAs or three gRNAs, with each gRNA targeting a different gene.

In one example, a combination of two gRNAs comprises a first gRNA targeting one of PCSK9, LPA, MYLIP, ANGLPTL3, APOC3, and APOB, and a second gRNA targeting one of PCSK9, LPA, MYLIP, ANGLPTL3, APOC3, and APOB, wherein the first and second gRNA target different genes. In another example, a combination of two gRNAs comprises a first gRNA targeting PCSK9 and a second gRNA targeting one of LPA, MYLIP, ANGLPTL3, APOC3, and APOB. In another example, a combination of two gRNAs comprises a first gRNA targeting PCSK9 and a second gRNA targeting LPA.

In another example, a combination of three gRNAs comprises a first gRNA targeting one of PCSK9, LPA, MYLIP, ANGLPTL3, APOC3, and APOB, a second gRNA targeting one of PCSK9, LPA, MYLIP, ANGLPTL3, APOC3, and APOB, and a third gRNA targeting one of PCSK9, LPA, MYLIP, ANGLPTL3, APOC3, and APOB, wherein the first, second, and third gRNA each target a different gene. In another example, a combination of three gRNAs comprises a first gRNA targeting PCSK9, a second gRNA targeting one of LPA, MYLIP, ANGLPTL3, APOC3, and APOB, and a third gRNA targeting one of LPA, MYLIP, ANGLPTL3, APOC3, and APOB, wherein the second and third gRNA each target a different gene. In another example, a combination of three gRNAs comprises a first gRNA targeting PCSK9, a second gRNA targeting LPA, and a third gRNA targeting one of MYLIP, ANGLPTL3, APOC3, and APOB.

Following transfection, cells are assessed for phenotypes that could promote reduction of LDL in vivo. Specifically, cells are assessed for increased LDL uptake or increased cell-surface expression of LDL receptor (LDL-R).

To assess LDL uptake, fluorescently labeled LDL (BODIPY-LDL; ThermoFisher #L3483) is added to the cell media, and cells are incubated for 2 hours. Cells are then washed and assessed by flow cytometry for LDL uptake based on fluorescence of BODIPY-LDL. Conditions resulting in increased LDL uptake in comparison to control cells (e.g., cells not transfected with a gRNA) are identified. In addition, conditions are identified in which multiplexed targeted repression of a combination of genes (e.g., PCSK9 and LPA) leads to greater LDL uptake than targeted repression of any individual gene of the combination alone (e.g., PCSK9 alone or LPA alone).

Cells are assessed for cell-surface expression of LDL-R by flow cytometry, using a fluorescently labeled anti-LDL-R antibody (R&D Biosystems #FAB2148P. Conditions resulting in increased expression of LDL-R in comparison to control cells are identified. In addition, conditions are identified in which multiplexed targeted repression of a combination of genes (e.g., PCSK9 and LPA) leads to greater LDL-R expression than targeted repression of any individual gene of the combination alone (e.g., PCSK9 alone or LPA alone).

DNA-targeting systems with combinations of gRNAs are identified that mediate multiplexed targeted transcriptional repression of at least two genes to promote LDL reduction.

Example 4: In Vivo Targeted Transcriptional Repression for Reducing LDL in a Humanized Mouse Model DNA-targeting systems comprising a gRNA identified in Example 2 or combinations of gRNAs for multiplexed targeted transcriptional repression identified in Example 3, are assessed for efficacy in vivo using a liver-humanized mouse model. Liver-humanized mice are Fah/Rag2/Il2rg triple mutants (FRG KO) in which the liver is repopulated with human hepatocytes, for example as described in Azuma et al., Nat Biotechnol. 25(8):903-910 (2007).

The identified gRNA or gRNA combinations are delivered with a dSpCas9-effector fusion protein for targeted gene repression (e.g., dSpCas9-KRAB or dSpCas9-KRAB-DNMT3A/L). Lipid nanoparticles (LNPs) comprising the gRNAs and fusion protein (or nucleic acids encoding either component) are formulated for the delivery. In one example, the LNPs include the gRNAs and mRNA encoding the fusion protein. LNPs are delivered systemically via injection (e.g. into the tail vein). Levels of circulating cholesterol, including LDL, and target protein knockdown are assessed based on analysis of blood serum using enzyme-linked immunoassay (ELISA).

Decreased levels of circulating LDL support the utility of repressing genes associated with regulation of LDL in vivo, including with the multiplexed epigenetic-modifying DNA-targeting systems provided herein, for potential treatment of familial hypercholesterolemia and/or cardiovascular disease.

Example 5: Identification of gRNAs that Repress Target Genes Associated with Regulation of LDL Using FlowFISH A library of gRNAs were designed for targeting human genes associated with regulation of low-density lipoprotein (LDL), including PCSK9, MYLIP, and APOB. The designed gRNAs were assessed using FlowFISH for their ability to mediate transcriptional repression as part of a DNA-targeting system composed of a gRNA and a dCas9-effector fusion protein. FlowFISH is a flow cytometry-based fluorescent in situ hybridization technique for assessing gene expression by measuring fluorescently labeled RNA. The FlowFISH technique provides a more direct analysis of gRNA effects by staining for mRNA expression and is a useful alternative to antibody staining since the gene targets include those that encode cell-secretable proteins.

gRNAs were designed that target an area surrounding the transcriptional start site of each target gene, ~5 kb upstream and downstream for each gene, as well as open chromatin and possible enhancer regions lying outside of this 10 kb region, up to 30 kb in either direction. Target regions were selected based on DNase hypersensitive regions and H3k27ac ChIP called peaks in human liver tissue identified in ENCODE data. Target sites were selected according to the protospacer adjacent motif (PAM) sequence for SpCas9

(5'-NGG-3'; SEQ ID NO:202). Each gRNA further comprised a scaffold sequence for SpCas9, set forth in SEQ ID NO: 191.

Huh7 cells were transduced with lentivirus vector comprising a gRNA and transiently transfected with mRNA encoding dSpCas9-KRAB-DNMT3A/L (SEQ ID NO:278) fusion protein. Transfected cells were collected at day 28, fixed, permeabilized, and stained with fluorescently labeled probes that bind the mRNA of the target genesto enable gene expression anlysuis using FlowFISH.

gRNAs that repressed PCSK9, MYLIP, and APOB were identified and are listed in Table E8 (PCSK9), Table E9 (MYLIP) and Table E10 (APOB). The DNA target site (protospacer) sequences are set forth in SEQ ID NOS:3, 4, 29, 54, 57, 306-317, 342-351 and 372-377 and gRNA spacer sequences for gRNAs targeting each site are set forth in SEQ ID NOS: 66, 67, 92, 117, 120, 318-329, 352-361, and 378-383. These sequences are listed in Table 3 (Section I.B.). In some cases, the identified gRNAs had the same or similar sequences to gRNAs identified in Example 2 above.

TABLE E8 gRNAs targeting human PCSK9

| gRNA name | target site SEQ ID | target site sequence | gRNA SEQ ID | gRNA sequence |
|---|---|---|---|---|
| PCSK9-N | 306 | GTCGAGGCGCTC ATGGTTGC | 330 | GUCGAGGCGCUCAUGGUUGCGUUU AAGAGCUAUGCUGGAAACAGCAUA GCAAGUUUAAAUAAGGCUAGUCCG UUAUCAACUUGAAAAAGUGGCACC GAGUCGGUGC |
| PCSK9-C | 3 | AGGTTTCCGCAG CGACGTCG | 129 | AGGUUUCCGCAGCGACGUCGGUUU AAGAGCUAUGCUGGAAACAGCAUA GCAAGUUUAAAUAAGGCUAGUCCG UUAUCAACUUGAAAAAGUGGCACC GAGUCGGUGC |
| PCSK9-O | 307 | TTCCAGCCCAGTT AGGATTT | 331 | UUCCAGCCCAGUUAGGAUUUGUUU AAGAGCUAUGCUGGAAACAGCAUA GCAAGUUUAAAUAAGGCUAGUCCG UUAUCAACUUGAAAAAGUGGCACC GAGUCGGUGC |
| PCSK9-P | 308 | TCCTAACTGGGCT GGAAGGC | 332 | UCCUAACUGGGCUGGAAGGCGUUU AAGAGCUAUGCUGGAAACAGCAUA GCAAGUUUAAAUAAGGCUAGUCCG UUAUCAACUUGAAAAAGUGGCACC GAGUCGGUGC |
| PCSK9-Q | 309 | TCAGGAGCAGGG CGCGTGAA | 333 | UCAGGAGCAGGGCGCGUGAAGUUU AAGAGCUAUGCUGGAAACAGCAUA GCAAGUUUAAAUAAGGCUAGUCCG UUAUCAACUUGAAAAAGUGGCACC GAGUCGGUGC |
| PCSK9-R | 310 | CAGCGACGTCGA GGCGCTCA | 334 | CAGCGACGUCGAGGCGCUCAGUUU AAGAGCUAUGCUGGAAACAGCAUA GCAAGUUUAAAUAAGGCUAGUCCG UUAUCAACUUGAAAAAGUGGCACC GAGUCGGUGC |
| PCSK9-S | 311 | CCGTCAGCTCCA GGCGGTCC | 335 | CCGUCAGCUCCAGGCGGUCCGUUU AAGAGCUAUGCUGGAAACAGCAUA GCAAGUUUAAAUAAGGCUAGUCCG UUAUCAACUUGAAAAAGUGGCACC GAGUCGGUGC |
| PCSK9-T | 312 | AACCTGATCCTCC AGTCCGG | 336 | AACCUGAUCCUCCAGUCCGGGUUU AAGAGCUAUGCUGGAAACAGCAUA GCAAGUUUAAAUAAGGCUAGUCCG UUAUCAACUUGAAAAAGUGGCACC GAGUCGGUGC |
| PCSK9-U | 313 | TCATGGGCACCG TCAGCTCC | 337 | UCAUGGGCACCGUCAGCUCCGUUU AAGAGCUAUGCUGGAAACAGCAUA GCAAGUUUAAAUAAGGCUAGUCCG UUAUCAACUUGAAAAAGUGGCACC GAGUCGGUGC |
| PCSK9-V | 314 | CCGCCGGCGTGG ACCGCGCA | 338 | CCGCCGGCGUGGACCGCGCAGUUU AAGAGCUAUGCUGGAAACAGCAUA GCAAGUUUAAAUAAGGCUAGUCCG UUAUCAACUUGAAAAAGUGGCACC GAGUCGGUGC |

TABLE E8-continued gRNAs targeting human PCSK9

| gRNA name | target site SEQ ID | target site sequence | gRNA SEQ ID | gRNA sequence |
|---|---|---|---|---|
| PCSK9-W | 315 | GAAGGCAGGCCG GCGCCCTA | 339 | GAAGGCAGGCCGGCGCCCUAGUUU AAGAGCUAUGCUGGAAACAGCAUA GCAAGUUUAAAUAAGGCUAGUCCG UUAUCAACUUGAAAAAGUGGCACC GAGUCGGUGC |
| PCSK9-X | 316 | GCGCCTTGAGCCT TGCGGTG | 340 | GCGCCUUGAGCCUUGCGGUGGUUU AAGAGCUAUGCUGGAAACAGCAUA GCAAGUUUAAAUAAGGCUAGUCCG UUAUCAACUUGAAAAAGUGGCACC GAGUCGGUGC |
| PCSK9-D | 4 | GGGCGCCGCCGT TCAGTTCA | 130 | GGGCGCCGCCGUUCAGUUCAGUUU AAGAGCUAUGCUGGAAACAGCAUA GCAAGUUUAAAUAAGGCUAGUCCG UUAUCAACUUGAAAAAGUGGCACC GAGUCGGUGC |
| PCSK9-Y | 317 | CCCGCACCTTGGC GCAGCGG | 341 | CCCGCACCUUGGCGCAGCGGGUUU AAGAGCUAUGCUGGAAACAGCAUA GCAAGUUUAAAUAAGGCUAGUCCG UUAUCAACUUGAAAAAGUGGCACC GAGUCGGUGC |

TABLE E9 gRNAs targeting human MYLIP

| gRNA name | target site SEQ ID | target site sequence | gRNA SEQ ID | gRNA sequence |
|---|---|---|---|---|
| MYLIP-K | 342 | GCACTGCGGCGG CAGCCGGG | 362 | GCACUGCGGCGGCAGCCGGGGUUU AAGAGCUAUGCUGGAAACAGCAUA GCAAGUUUAAAUAAGGCUAGUCCG UUAUCAACUUGAAAAAGUGGCACC GAGUCGGUGC |
| MYLIP-L | 343 | GGCGCCACCGCG GAGGACAG | 363 | GGCGCCACCGCGGAGGACAGGUUU AAGAGCUAUGCUGGAAACAGCAUA GCAAGUUUAAAUAAGGCUAGUCCG UUAUCAACUUGAAAAAGUGGCACC GAGUCGGUGC |
| MYLIP-M | 344 | ATGCTCATAGGA TGTATTCA | 364 | AUGCUCAUAGGAUGUAUUCAGUUU AAGAGCUAUGCUGGAAACAGCAUA GCAAGUUUAAAUAAGGCUAGUCCG UUAUCAACUUGAAAAAGUGGCACC GAGUCGGUGC |
| MYLIP-N | 345 | CCACAATAAACA CATGGTCT | 365 | CCACAAUAAACACAUGGUCUGUUU AAGAGCUAUGCUGGAAACAGCAUA GCAAGUUUAAAUAAGGCUAGUCCG UUAUCAACUUGAAAAAGUGGCACC GAGUCGGUGC |
| MYLIP-O | 346 | GGGTCCCACCAG TGACAAGG | 366 | GGGUCCCACCAGUGACAAGGGUUU AAGAGCUAUGCUGGAAACAGCAUA GCAAGUUUAAAUAAGGCUAGUCCG UUAUCAACUUGAAAAAGUGGCACC GAGUCGGUGC |
| MYLIP-P | 347 | GGACTGCCTCAA CCAGGTGA | 367 | GGACUGCCUCAACCAGGUGAGUUU AAGAGCUAUGCUGGAAACAGCAUA GCAAGUUUAAAUAAGGCUAGUCCG UUAUCAACUUGAAAAAGUGGCACC GAGUCGGUGC |
| MYLIP-Q | 348 | CAGAGTCCCTGTC GCAGCGC | 368 | CAGAGUCCCUGUCGCAGCGCGUUU AAGAGCUAUGCUGGAAACAGCAUA GCAAGUUUAAAUAAGGCUAGUCCG UUAUCAACUUGAAAAAGUGGCACC GAGUCGGUGC |

TABLE E9-continued gRNAs targeting human MYLIP

| gRNA name | target site SEQ ID | target site sequence | gRNA SEQ ID | gRNA sequence |
|---|---|---|---|---|
| MYLIP-R | 349 | CTCAGAGTGAGC GATCGCCC | 369 | CUCAGAGUGAGCGAUCGCCCGUUU AAGAGCUAUGCUGGAAACAGCAUA GCAAGUUUAAAUAAGGCUAGUCCG UUAUCAACUUGAAAAAGUGGCACC GAGUCGGUGC |
| MYLIP-F | 29 | CCCCGCGCACAC CAAAGAGA | 155 | CCCCGCGCACACCAAAGAGAGUUU AAGAGCUAUGCUGGAAACAGCAUA GCAAGUUUAAAUAAGGCUAGUCCG UUAUCAACUUGAAAAAGUGGCACC GAGUCGGUGC |
| MYLIP-S | 350 | CTGAGTTTCCCTG GCCGCCC | 370 | CUGAGUUUCCCUGGCCGCCCGUUU AAGAGCUAUGCUGGAAACAGCAUA GCAAGUUUAAAUAAGGCUAGUCCG UUAUCAACUUGAAAAAGUGGCACC GAGUCGGUGC |
| MYLIP-T | 351 | GTTTCCCTGGCCG CCCCGGG | 371 | GUUUCCCUGGCCGCCCCGGGGUUU AAGAGCUAUGCUGGAAACAGCAUA GCAAGUUUAAAUAAGGCUAGUCCG UUAUCAACUUGAAAAAGUGGCACC GAGUCGGUGC |

TABLE E10 gRNAs targeting human APOB

| gRNA name | target site SEQ ID | target site sequence | gRNA SEQ ID | gRNA sequence |
|---|---|---|---|---|
| APOB-A | 54 | GTCCATCGCCAG CTGCGGTG | 180 | GUCCAUCGCCAGCUGCGGUGGUUU AAGAGCUAUGCUGGAAACAGCAUA GCAAGUUUAAAUAAGGCUAGUCCG UUAUCAACUUGAAAAAGUGGCACC GAGUCGGUGC |
| APOB-K | 372 | TGAGGGCCTCCC ACTCTACA | 384 | UGAGGGCCUCCCACUCUACAGUUU AAGAGCUAUGCUGGAAACAGCAUA GCAAGUUUAAAUAAGGCUAGUCCG UUAUCAACUUGAAAAAGUGGCACC GAGUCGGUGC |
| APOB-L | 373 | CCAGAGCACTGA AGACGCTT | 385 | CCAGAGCACUGAAGACGCUUGUUU AAGAGCUAUGCUGGAAACAGCAUA GCAAGUUUAAAUAAGGCUAGUCCG UUAUCAACUUGAAAAAGUGGCACC GAGUCGGUGC |
| APOB-M | 374 | ACTGGAGGAAAC CTAGAAGC | 386 | ACUGGAGGAAACCUAGAAGCGUUU AAGAGCUAUGCUGGAAACAGCAUA GCAAGUUUAAAUAAGGCUAGUCCG UUAUCAACUUGAAAAAGUGGCACC GAGUCGGUGC |
| APOB-D | 57 | CTCAGCGGCAGC AACCGAGA | 183 | CUCAGCGGCAGCAACCGAGAGUUU AAGAGCUAUGCUGGAAACAGCAUA GCAAGUUUAAAUAAGGCUAGUCCG UUAUCAACUUGAAAAAGUGGCACC GAGUCGGUGC |
| APOB-N | 375 | CACTGAAGACGC TTGGGGAA | 387 | CACUGAAGACGCUUGGGGAAGUUU AAGAGCUAUGCUGGAAACAGCAUA GCAAGUUUAAAUAAGGCUAGUCCG UUAUCAACUUGAAAAAGUGGCACC GAGUCGGUGC |
| APOB-O | 376 | TGAAGAAGGCAC CCCTGGTC | 388 | UGAAGAAGGCACCCCUGGUCGUUU AAGAGCUAUGCUGGAAACAGCAUA GCAAGUUUAAAUAAGGCUAGUCCG |

TABLE E10-continued gRNAs targeting human APOB

| gRNA name | target site SEQ ID | target site sequence | gRNA SEQ ID | gRNA sequence |
|---|---|---|---|---|
| | | | | UUAUCAACUUGAAAAAGUGGCACC GAGUCGGUGC |
| APOB-P | 377 | TGAGTGCGCGGC CGCTCTGC | 389 | UGAGUGCGCGGCCGCUCUGCGUUU AAGAGCUAUGCUGGAAACAGCAUA GCAAGUUUAAAUAAGGCUAGUCCG UUAUCAACUUGAAAAAGUGGCACC GAGUCGGUGC |

Example 6: In Vivo Targeted PCSK9 Repression in a Non-Human Primate

DNA-targeting systems comprising an exemplary dCas9-effector fusion protein for transcriptional repression and a PCSK9 targeting guide RNA were assessed in vivo using a non-human primate model (NHP).

Figure 4A:
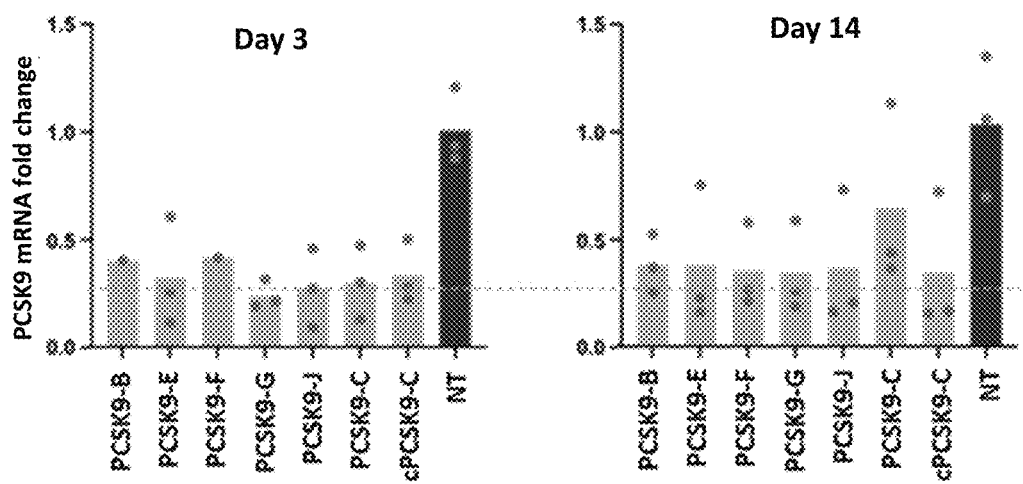
FIG. 4A-4B show PCSK9 mRNA and protein levels in Cynomolgus macaque primary hepatocytes transfected with dSpCas9-KRAB-DNMT3A/L and a non-targeting gRNA (NT), a human PCSK9-targeting gRNA, or a cynomolgus-specific PCSK9-gRNA (cPCSK9-C).
Figure 4B:
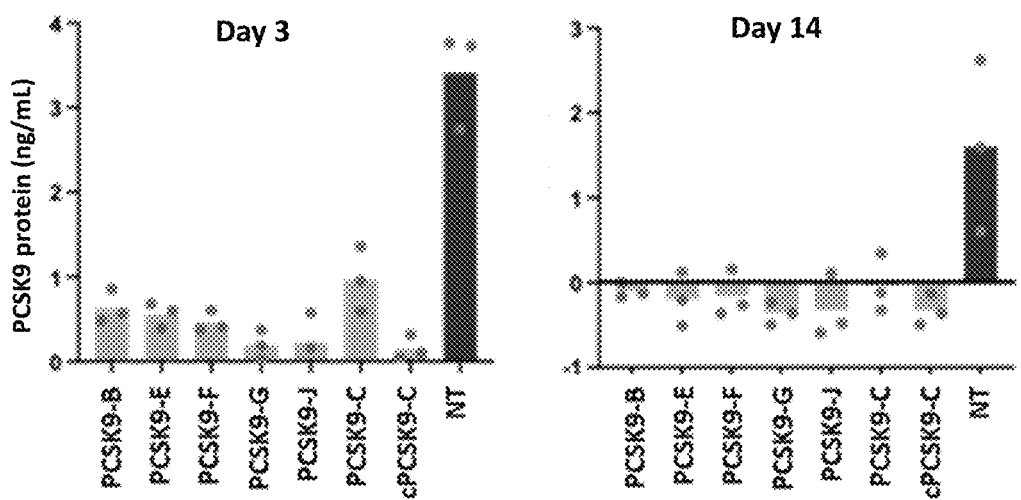

To ensure targeting of Cynomolgus macaque PCSK9, primary hepatocytes from a Cynomolgus macaque donor were transfected with a PCSK9 targeting gRNA and dSpCas9-KRAB-DNMT3A/L. mRNA was isolated from the transfected cells 3 days and 14 days after transfection and assessed for knockdown of the target gene by qRT-PCR. PCSK9 target protein knockdown was also assessed in supernatant using enzyme-linked immunoassay (ELISA). The gRNAs included those targeting target sites: PCSK9-B (SEQ ID NO:2; gRNA SEQ ID NO:128), PCSK9-E (SEQ ID NO:5; gRNA SEQ ID NO:131), PCSK9-F (SEQ ID NO:6; gRNA SEQ ID NO:132), PCSK9-G (SEQ ID NO:7; gRNA SEQ ID NO:133), PCSK9-J (SEQ ID NO:10; gRNA SEQ ID NO:136), and PCSK9-C(SEQ ID NO:3; gRNA SEQ ID NO:129), as well as a cynomolgus-specific version of PCSK9-C(cPCSK9-C) targeting the DNA target site set forth in SEQ ID NO:390. The corresponding gRNA spacer sequence is set forth in SEQ ID NO:391 and the full cPCSK9-C gRNA sequence is set forth in SEQ ID NO:392. As shown in FIGS. 4A and 4B, co-expression of dSpCas9-KRAB-DNMT3A/L and the respective PCSK9 gRNA led to transcriptional repression of PCSK9 at day 3 and 14 post-transfection, as shown by reduced levels of both mRNA (FIG. 4A) and protein (FIG. 4B). After a single administration, PCSK9 mRNA was repressed by about 93% and protein expression dropped below the limit of assay detection 14 days after transfection, which is the approximate lifespan of primary hepatocytes in culture.

To test targeted PCSK9 repression in vivo, ten cynomolgus macaques were divided into four treatment groups: a) PBS-treated control (n=2); b) High dose treatment: 3.0 mg/kg (n=3); c) Low dose treatment: 1.0 mg/kg (n=3); and d) Low dose treatment: 1.0 mg/kg (n=2) for assessing biodistribution. The treatment group for each NHP is listed in Table E11.

TABLE E11

NHP study design for PCSK9-targeting system

| Subject | Treatment Group |
|---|---|
| NHP1 | High dose (3.0 mg/kg) |
| NHP2 | High dose (3.0 mg/kg) |
| NHP3 | High dose (3.0 mg/kg) |
| NHP4 | Low dose (1.0 mg/kg) |
| NHP5 | Low dose (1.0 mg/kg) |
| NHP6 | Low dose (1.0 mg/kg) |
| NHP7 | PBS control |
| NHP8 | PBS control |
| NHP9 | Low dose (1.0 mg/kg) |
| NHP10 | Low dose (1.0 mg/kg) |

Lipid nanoparticles (LNPs) containing gRNA cPCSK9-C(SEQ ID:392) and dSpCas9-KRAB-DNMT3A/L (SEQ ID NO:280) were formulated and delivered systemically via intravenous infusion. Levels of circulating cholesterol (i.e., LDL-C), liver enzymes (i.e., alanine transaminase (ALT) and aspartate aminotransferase (AST)), and PCSK9 protein knockdown were assessed at multiple time-points post-infusion based on blood serum samples analyzed using enzyme-linked immunoassay (ELISA).

Figure 5:
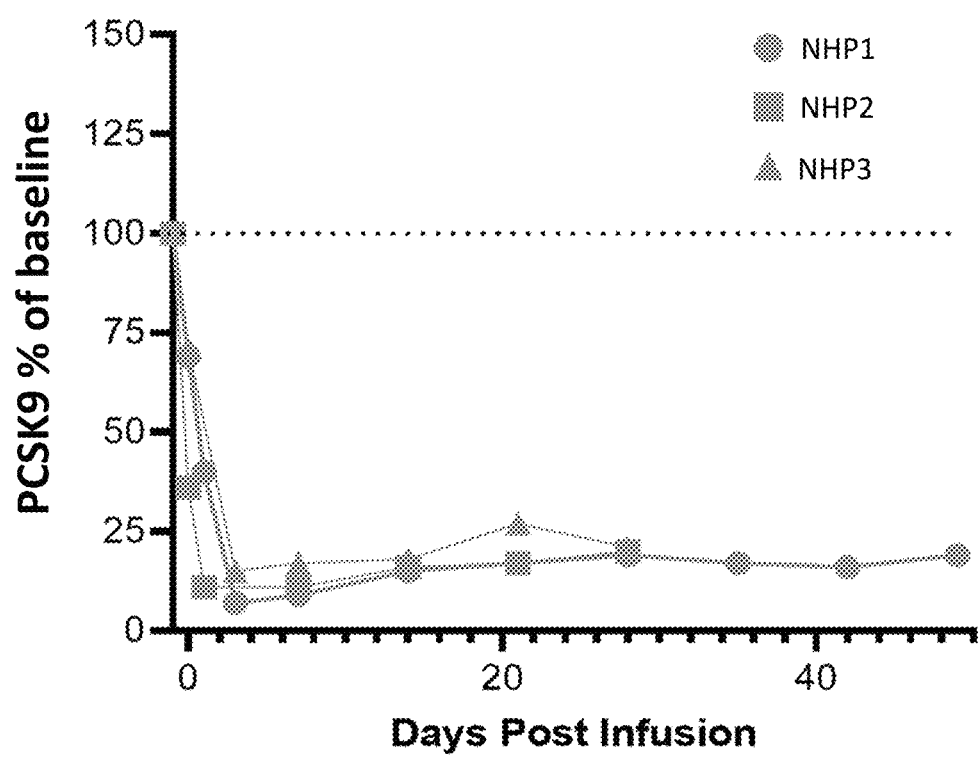
FIG. 5 shows blood PCSK9 protein levels from three individual Cynomolgus macaques (NHP1, NHP2, and NHP3) intravenously infused with a high dose (3.0 mg/kg) of dSpCas9-KRAB-DNMT3A/L and gRNA cPCSK9-C. Protein levels are shown as % change from baseline at numerous time points spanning 49 days post-infusion for NHP1 and 28 days post-infusion for NHP2 and NHP3.
Figure 6:
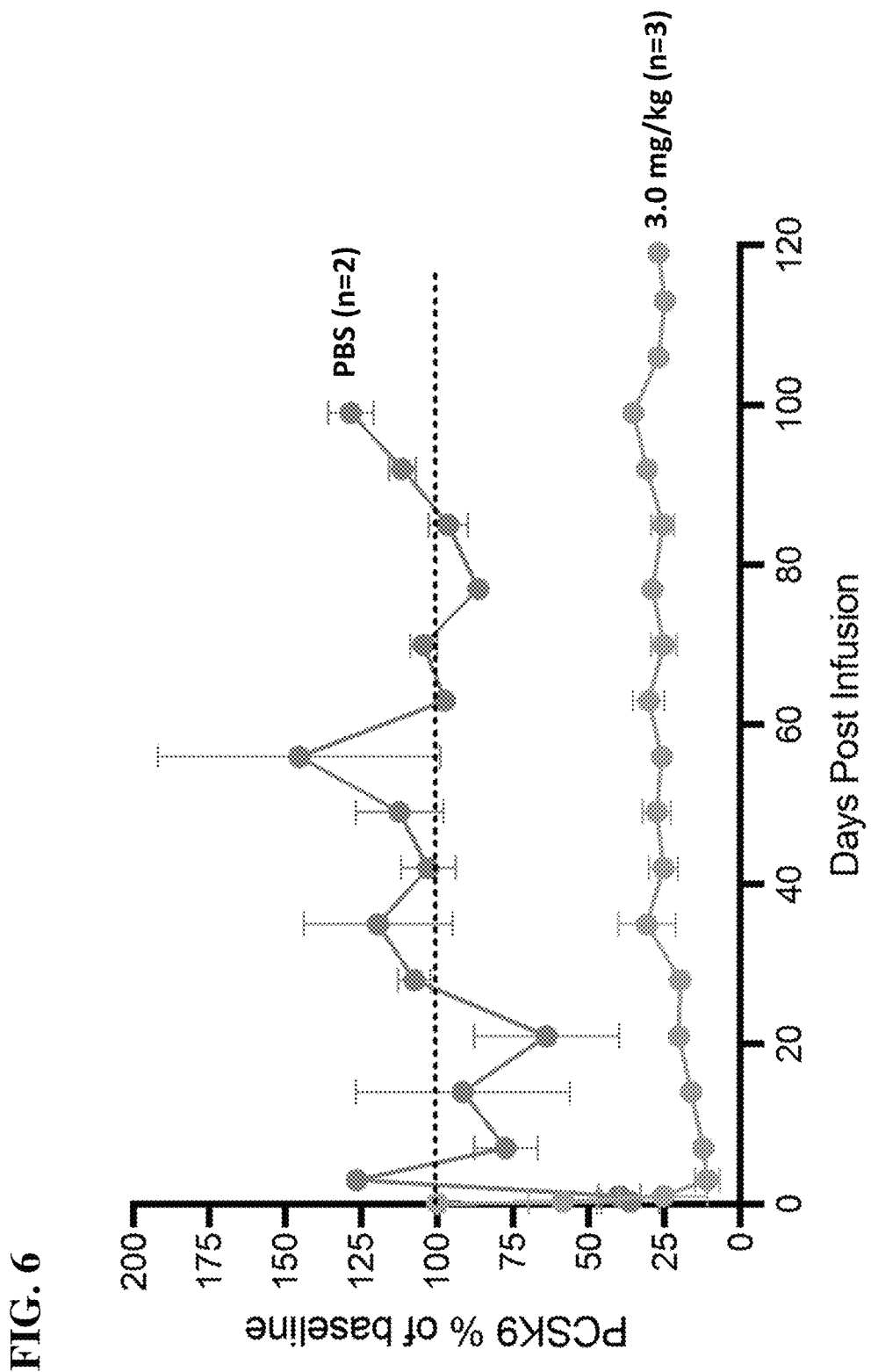
FIG. 6 shows average blood PCSK9 protein levels from Cynomolgus macaques intravenously infused with a high dose (3.0 mg/kg, n=3) of dSpCas9-KRAB-DNMT3A/L and gRNA cPCSK9-C as compared to a PBS control dose (n=2). Protein levels are shown as % change from baseline at numerous time points spanning 100 days post-infusion for the PBS treated group and 120 days post-infusion for high dose treated group. Dots represent individual time points and error bars represent mean of expression from experimental replicates.
Figure 7:
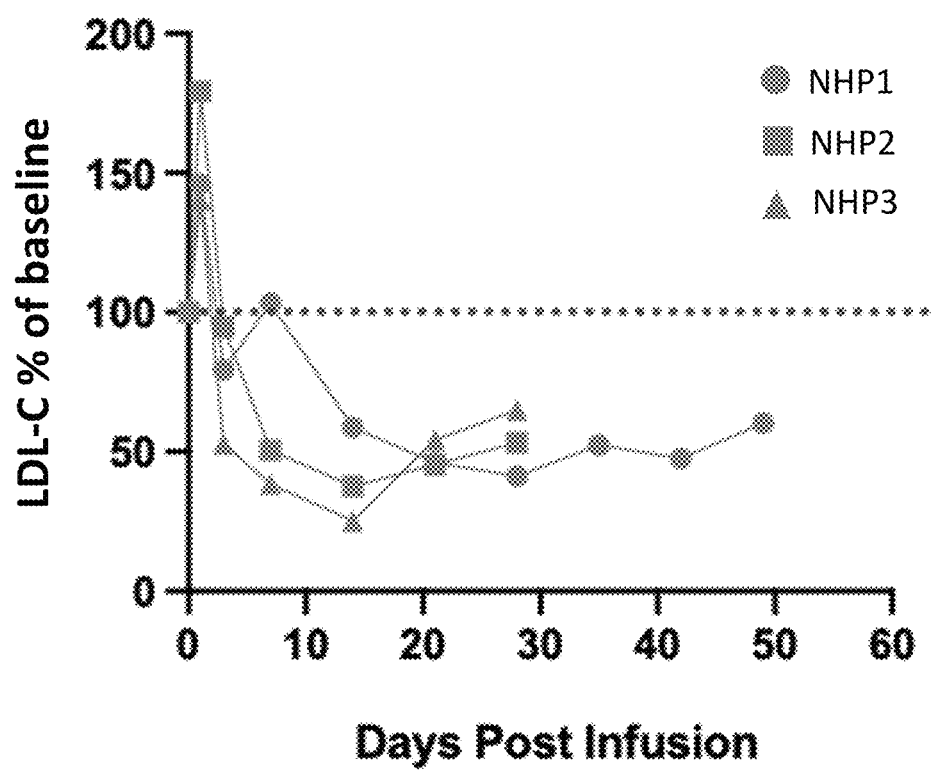
FIG. 7 shows LDL-C measurements from three individual Cynomolgus macaques (NHP1, NHP2, and NHP3) intravenously infused with a high dose (3.0 mg/kg) of dSpCas9-KRAB-DNMT3A/L and gRNA cPCSK9-C. Blood LDL-C levels are shown as % of baseline at numerous time points spanning 49 days post-infusion for NHP1 and 28 days post-infusion for NHP2 and NHP3.
Figure 8:
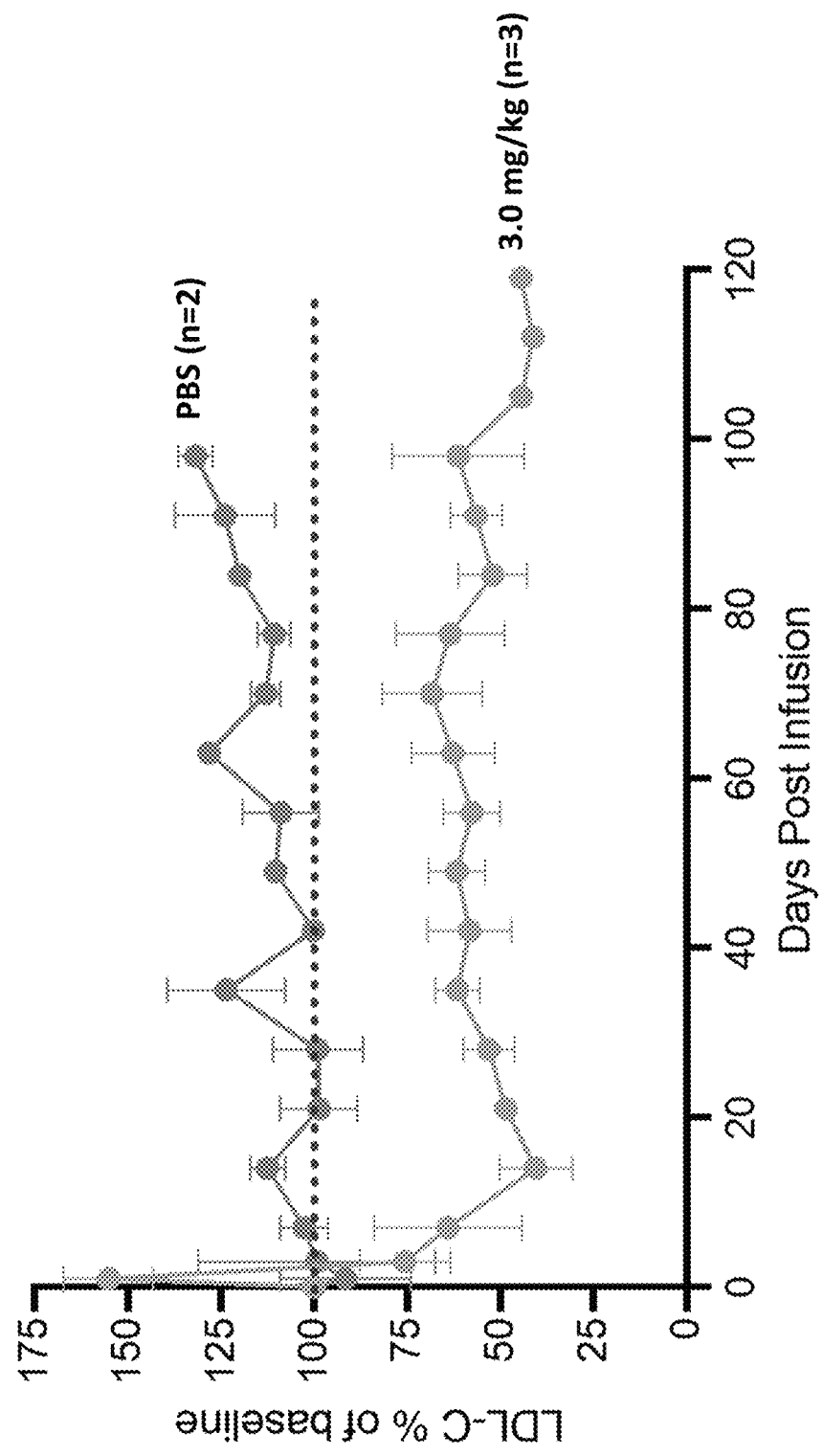
FIG. 8 shows average LDL-C levels from Cynomolgus macaques intravenously infused with a high dose (3.0 mg/kg, n=3) of dSpCas9-KRAB-DNMT3A/L and gRNA cPCSK9-C as compared to a PBS control dose (n=2). Blood LDL-C levels are shown as % change from baseline at numerous time points spanning 100 days post-infusion for the PBS treated group and 120 days post-infusion for high dose treated group. Dots represent individual time points and error bars represent mean of expression from experimental replicates.
Figure 9A:
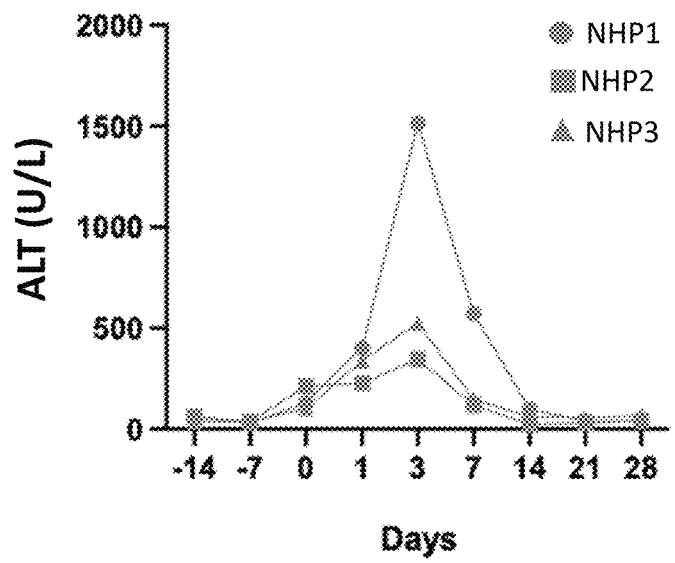
FIG. 9A-9B show alanine transaminase (ALT) and aspartate aminotransferase (AST) measurements from three individual Cynomolgus macaques (NHP1, NHP2, and NHP3) intravenously infused with a high dose (3.0 mg/kg) of dSpCas9-KRAB-DNMT3A/L and gRNA cPCSK9-C.
Figure 9B:
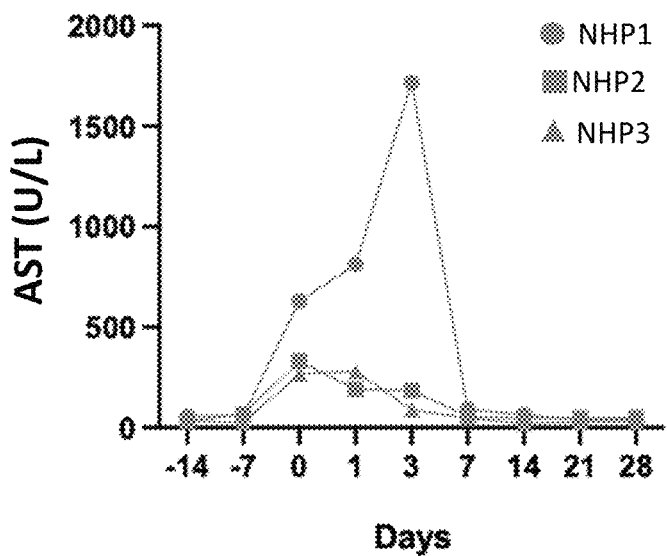
Figure 10A:
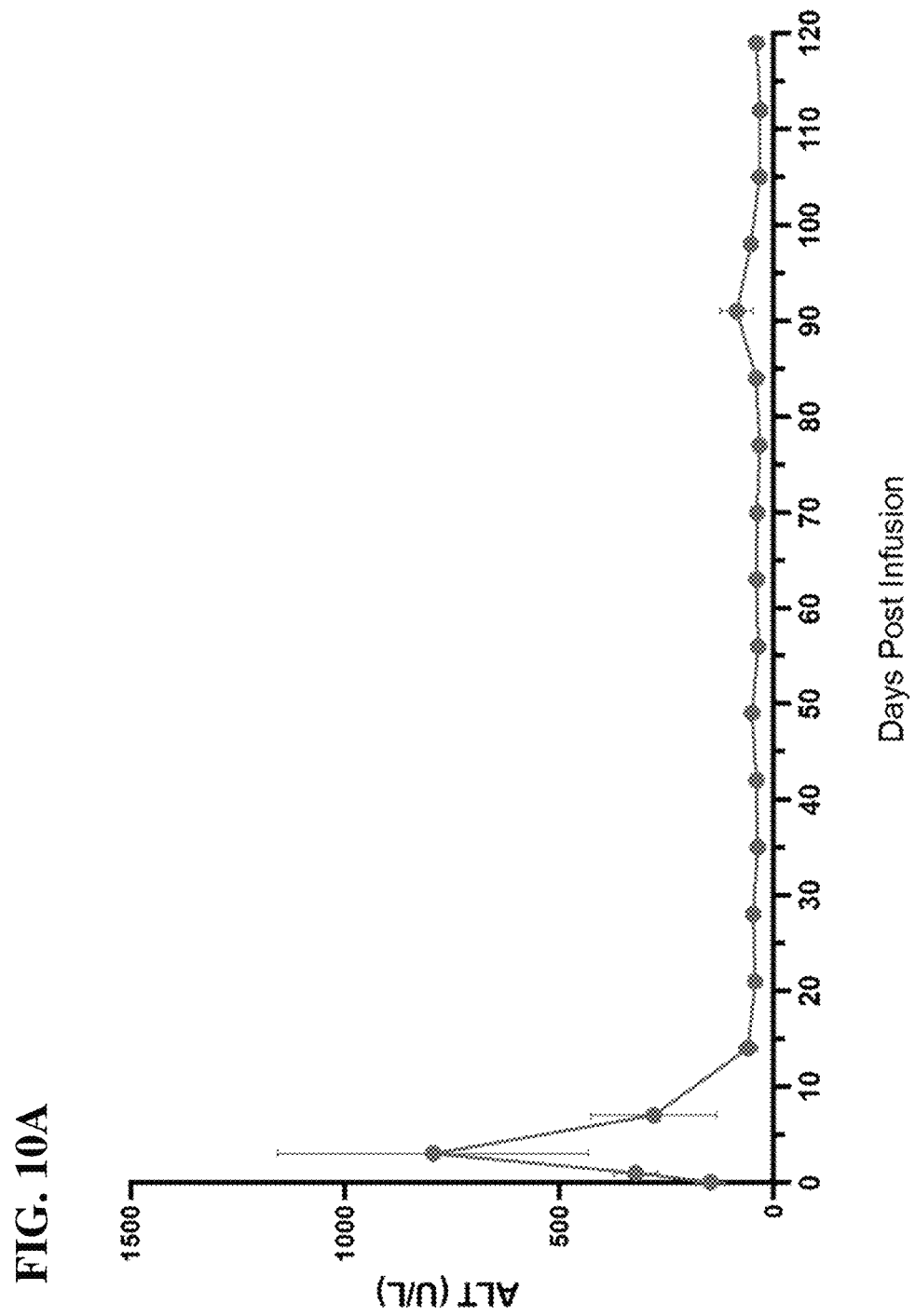
FIG. 10A-10B show average alanine transaminase (ALT) and asparate aminotransferase (AST) measurements from Cynomolgus macaques intravenously infused with a high dose (3.0 mg/kg, n=3) of dSpCas9-KRAB-DNMT3A/L and gRNA cPCSK9-C.
Figure 10B:
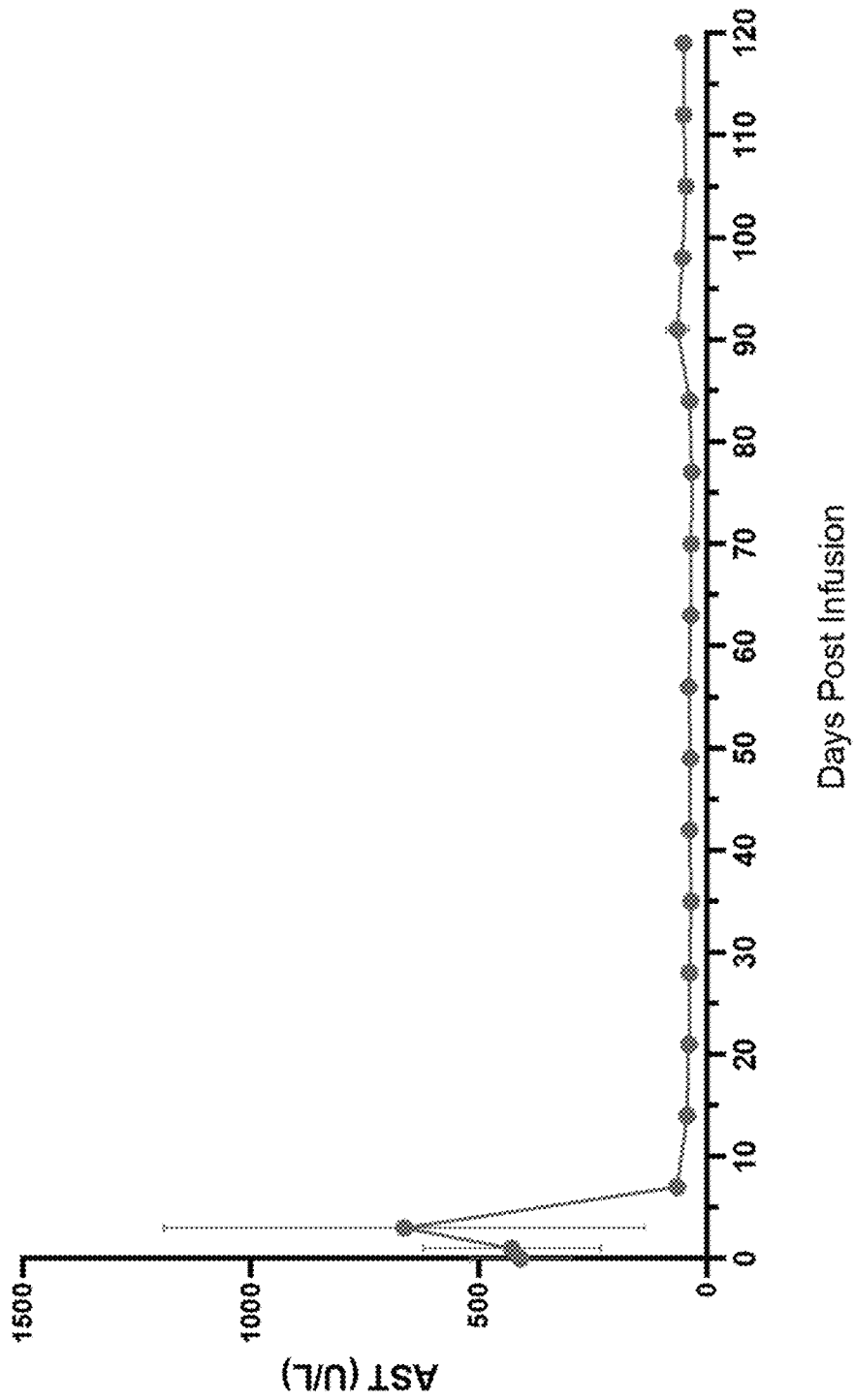

Blood PCSK9 protein levels for the high dose (3.0 mg/kg, n=3) group dropped substantially by day 3 post-infusion and the repression from the single intravenous dose was maintained throughout the measured time points. FIG. 5 shows results for data collected through day 49 post-infusion for NHP 1 (circles) and through day 28 post-infusion for NHP 2 (squares) and NHP3 (triangles). At day 28 post-infusion, all three subjects exhibited a reduction of blood PCSK9 levels of ~80%. FIG. 6 shows sustained PCSK9 repression of ~80% out to 120 days post-infusion FIG. 7 shows that the high dose treatment also resulted in a downward trend of LDL-C levels, with a stable reduction of ~50% for all three subjects at day 28 post-infusion. FIG. 8 shows sustained LDL-C repression of ~50% out to 120 days post-infusion. FIGS. 9A and 9B show a transient spike in ALT and AST liver enzyme levels at day 3 post-infusion with the high dose treatment that normalized to baseline levels within 1-2 weeks and remained at baseline through day 120 (FIGS. 10A and 10B). Otherwise, the animals were observed to be healthy and normal without any adverse clinical symptoms throughout the treatment.

Figure 11:
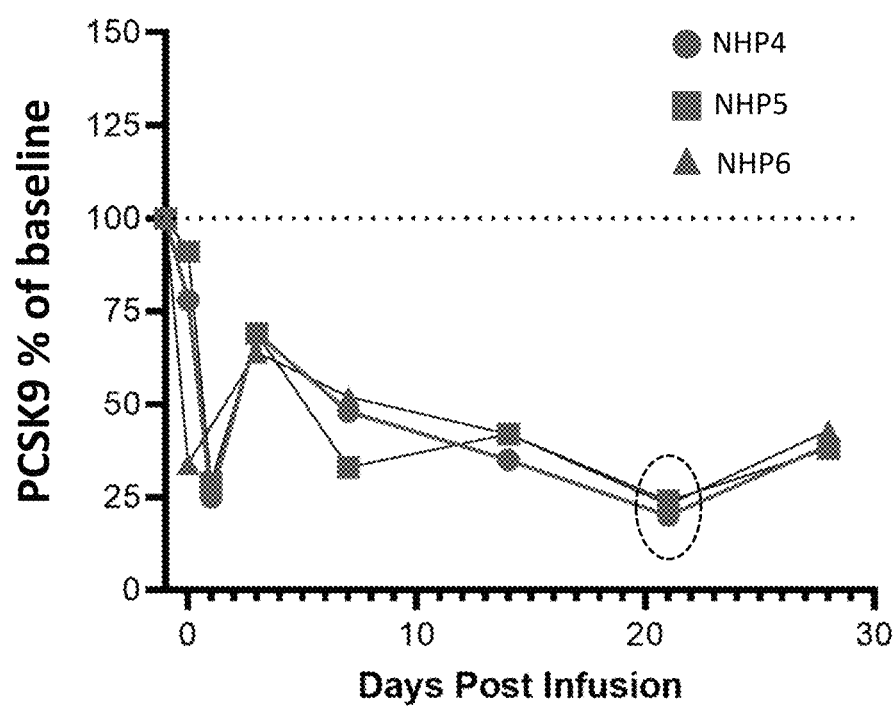
FIG. 11 shows blood PCSK9 protein levels from three individual Cynomolgus macaques (NHP4, NHP5, and NHP6) intravenously infused with a low dose (1.0 mg/mL) of dSpCas9-KRAB-DNMT3A/L and gRNA cPCSK9-C and re-dosed at 1.0 mg/kg 21 days after the initial infusion. A dashed oval marks the re-dose time point. Protein levels are shown as % change from baseline at numerous time points spanning 28 days after the initial infusion.
Figure 12A:
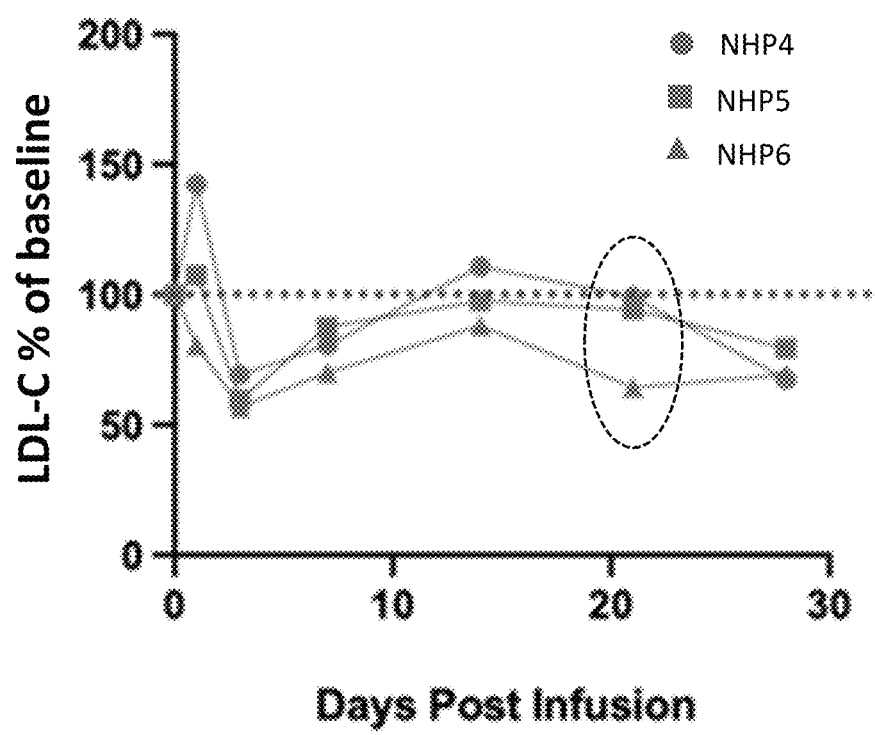
FIG. 12A-C show LDL-C, alanine transaminase (ALT), and asparate aminotransferase (AST) measurements from three individual Cynomolgus macaques (NHP4, NHP5, and NHP6) intravenously infused with a low dose (1.0 mg/kg) of dSpCas9-KRAB-DNMT3A/L and gRNA cPCSK9-C and re-dosed at 1.0 mg/kg 21 days after the initial infusion. A dashed oval marks the re-dose time point.
Figure 12B:
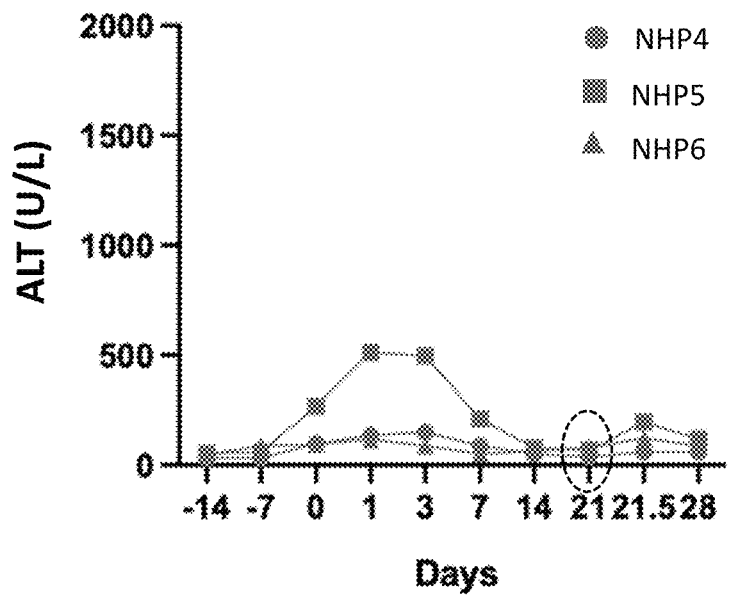
Figure 12C:
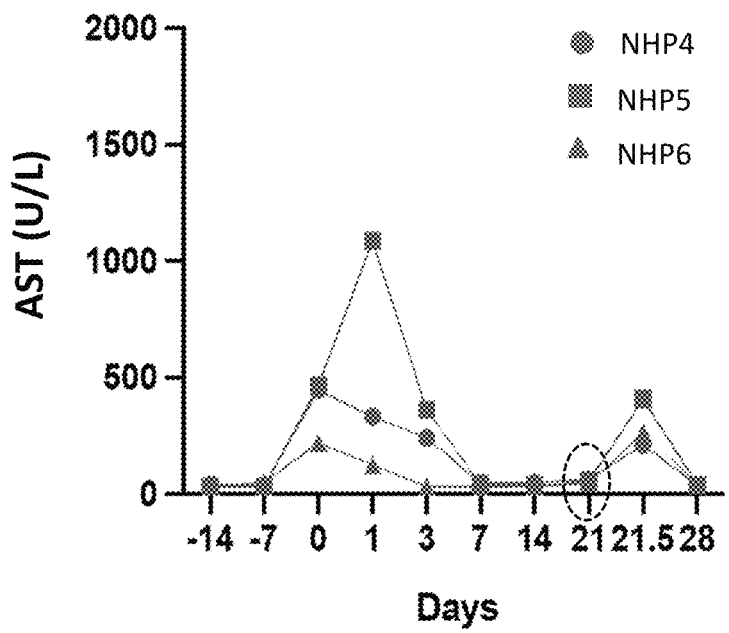

As shown in FIG. 11, blood PCSK9 protein levels for the low dose (1.0 mg/kg, n=3) group decreased ~60% by day 7. Each NHP in the low dose group was re-dosed at 1.0 mg/kg at day 21 post-infusion and data was collected for an additional 7 days. FIG. 12A shows that LDL-C levels decreased modestly after the administration of the re-dose. FIGS. 12B and 12C show that ALT and AST liver enzyme levels spiked after the initial infusion but returned to baseline by day 7 and that a second smaller spike occurred after the re-dose at day 21 but returned to baseline by day 28.

Figure 13:
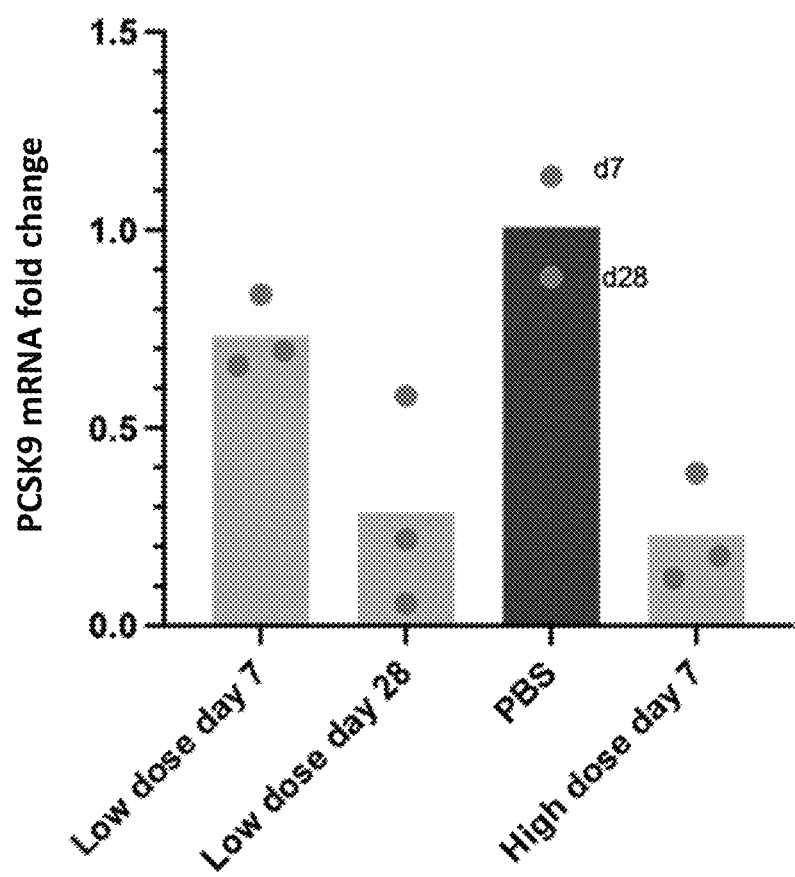
FIG. 13 shows PCSK9 mRNA levels measured from liver biopsies of Cynomolgus macaques intravenously infused with a PBS control, a high dose (3.0 mg/kg) of dSpCas9-KRAB-DNMT3A/L and gRNA cPCSK9-C, or a low dose (1.0 mg/kg) of dSpCas9-KRAB-DNMT3A/L and gRNA cPCSK9-C. Relative mRNA levels are shown from liver biopsies performed on day 7 post-infusion for each treatment group and biopsies performed on day 28 post-infusion for the low dose (1.0 mg/kg) and PBS treatment groups. mRNA levels are shown as fold change relative to the PBS controls. Dots represent values for experimental replicates, bars represent mean values for experimental replicates.

To assess the tissue-specific efficacy of the DNA-targeting system, liver biopsies were performed at day 7 for the low dose (1.0 mg/kg, n=3), high dose (3.0 mg/kg, n=3), and control (PBS, n=2) treatment groups. To determine the impact of the re-dose at day 21 post-infusion, a second liver biopsy was performed for the low dose and PBS control groups 7 days after the low dose group was re-dosed at 1.0 mg/kg. As shown in FIG. 13, the low dose group exhibited a modest reduction in PCSK9 mRNA at day 7 and a further reduction at day 28 that approached the strong reduction of PCSK9 mRNA observed in the high dose group at day 7. These results indicate that a re-dose of a dCas9-effector fusion and PCSK9 gRNA can further decrease PCSK9 mRNA levels in a tissue-specific manner.

Figure 14:
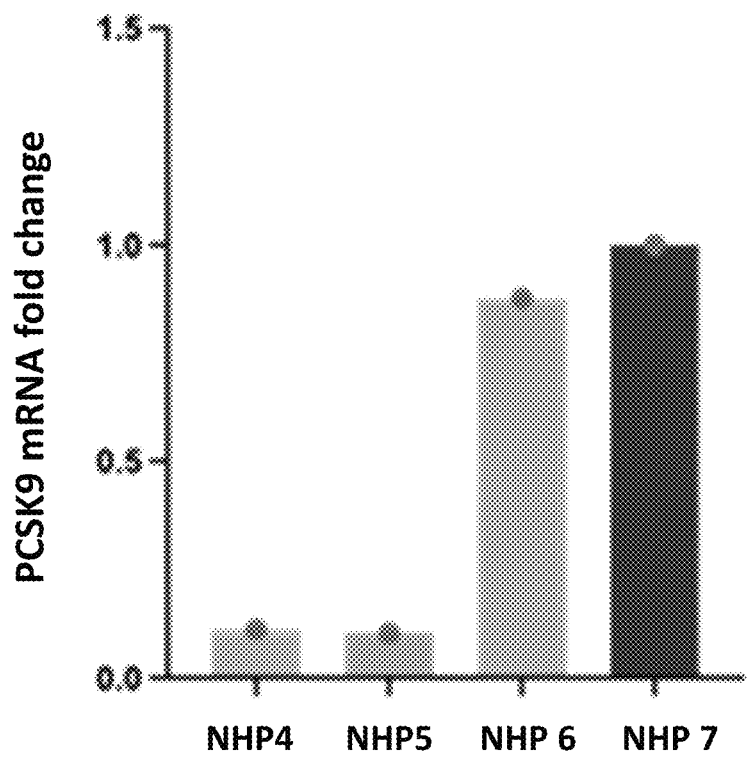
FIG. 14. shows PCSK9 mRNA levels measured from liver biopsies of three individual Cynomolgus macaques (NHP4, NHP5, and NHP6) following a third intravenous infusion of KRAB-DNMT3A/L and gRNA cPCSK9-C at varying doses 126 days after the initial infusion compared to a PBS control (NHP7). NHP4 and NHP5 were redosed at 3.0 mg/kg and NHP6 was redosed at 1.0 mg/kg. Relative mRNA levels are shown from liver biopsies performed on day 140 post-infusion for NHP4, NHP6, and NHP7 and a biopsy performed on day 129 post-infusion for NHP5. mRNA levels are shown as fold change relative to the PBS controls.

To assess the efficacy of redosing at a higher dose, 126 days after the initial infusion NHP4 and NHP5 from the low dose group were redosed at 3.0 mg/kg and NHP6 was redosed at 1.0 mg/kg. NHP5 experienced an adverse event after the redose. PCSK9 mRNA levels were assessed from liver biopsies performed at day 129 for NHP5 and day 140 for NHP4, NHP6, and NHP7 from the PBS control group. As shown in FIG. 14, the 3.0 mg/kg redose for NHP4 and NHP5 resulted in a substantial drop in PCSK9 mRNA levels compared to NHP6 which exhibited only a modest reduction compared to the PBS control (NHP7).

Figure 15:
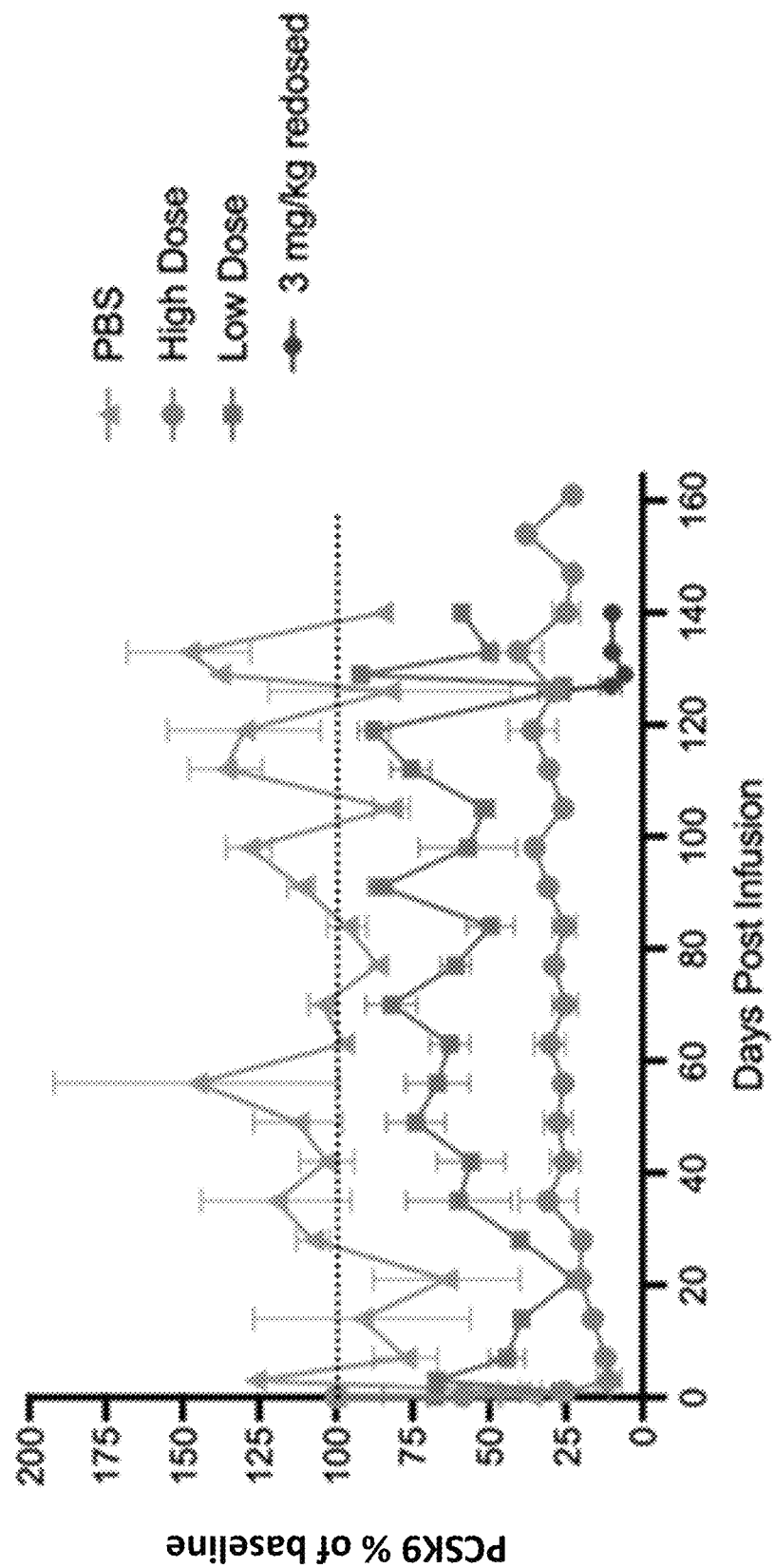
FIG. 15 shows average blood PCSK9 protein levels from Cynomolgus macaques intravenously infused with dSp-Cas9-KRAB-DNMT3A/L and gRNA cPCSK9-C at a high dose (3.0 mg/kg, n=3) and a low dose (1.0 mg/kg, n=3) as compared to a PBS control dose (n=2). 126 days after the initial infusion, NHP4 and NHP5 from the low dose group were redosed at 3.0 mg/kg and NHP6 was redosed at 1.0 mg/kg. Protein levels are shown as % change from baseline at numerous time points spanning 160 days post-infusion for the high dose treated group and 140 days post-infusion for the low dose and PBS treated groups. Dots represent individual time points and error bars represent mean of expression from experimental replicates.
Figure 16:
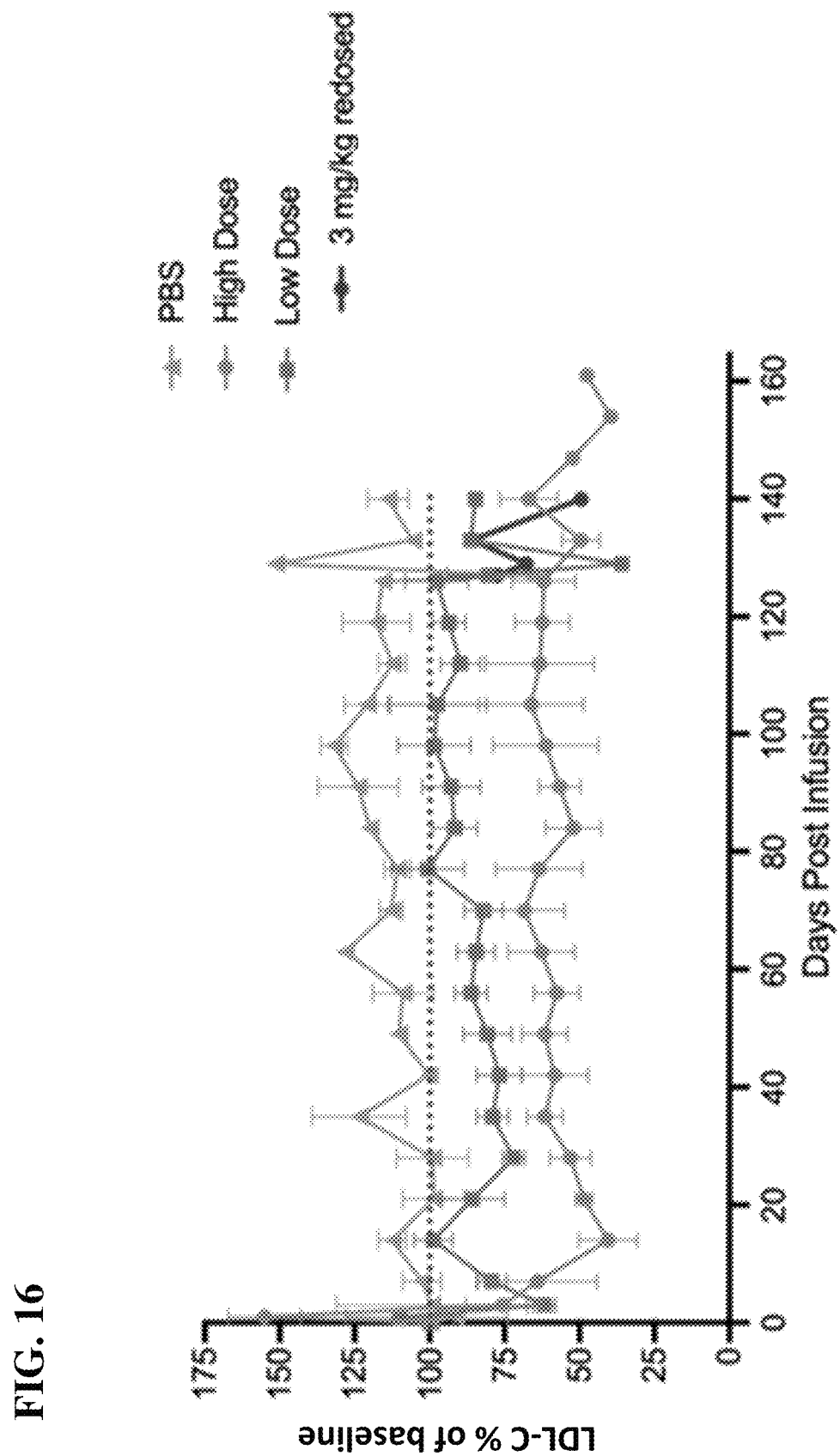
FIG. 16 shows average LDL-C levels from Cynomolgus macaques intravenously infused with dSpCas9-KRAB-DNMT3A/L and gRNA cPCSK9-C at a high dose (3.0 mg/kg, n=3) and a low dose (1.0 mg/kg, n=3) as compared to a PBS control dose (n=2). 126 days after the initial infusion, NHP4 and NHP5 from the low dose group were redosed at 3.0 mg/kg and NHP6 was redosed at 1.0 mg/kg. Blood LDL-C levels are shown as % change from baseline at numerous time points spanning 160 days post-infusion for the high dose treated group and 140 days post-infusion for the low dose and PBS treated groups. Dots represent individual time points and error bars represent mean of expression from experimental replicates.

FIG. 15 shows results for blood PCSK9 protein levels through day 160 post-infusion for the high dose group (circles) and through day 140 post-infusion for the low dose group (squares) and the PBS-treated group (triangles). The high dose group continued to maintain stable repression of blood PCSK9 levels through day 160. The 3.0 mg/kg redose for NHP4 at day 126 resulted in a drop in blood PCSK9 levels below the levels observed for the high dose group that was sustained through day 140. FIG. 16 shows results for LDL-C levels through day 160 post-infusion for the high dose group (circles) and through day 140 post-infusion for the low dose group (squares) and the PBS-treated group (triangles). The high dose group continued to maintain stable repression of LDL-C levels through day 160. The 3.0 mg/kg redose for NHP4 at day 126 resulted in a downward trend of LDL-C levels that reached the levels observed for the high dose group. These results indicate that a higher re-dose of a dCas9-effector fusion and PCSK9 gRNA can further decrease PCSK9 protein and LDL-C levels in vivo.

Figure 17:
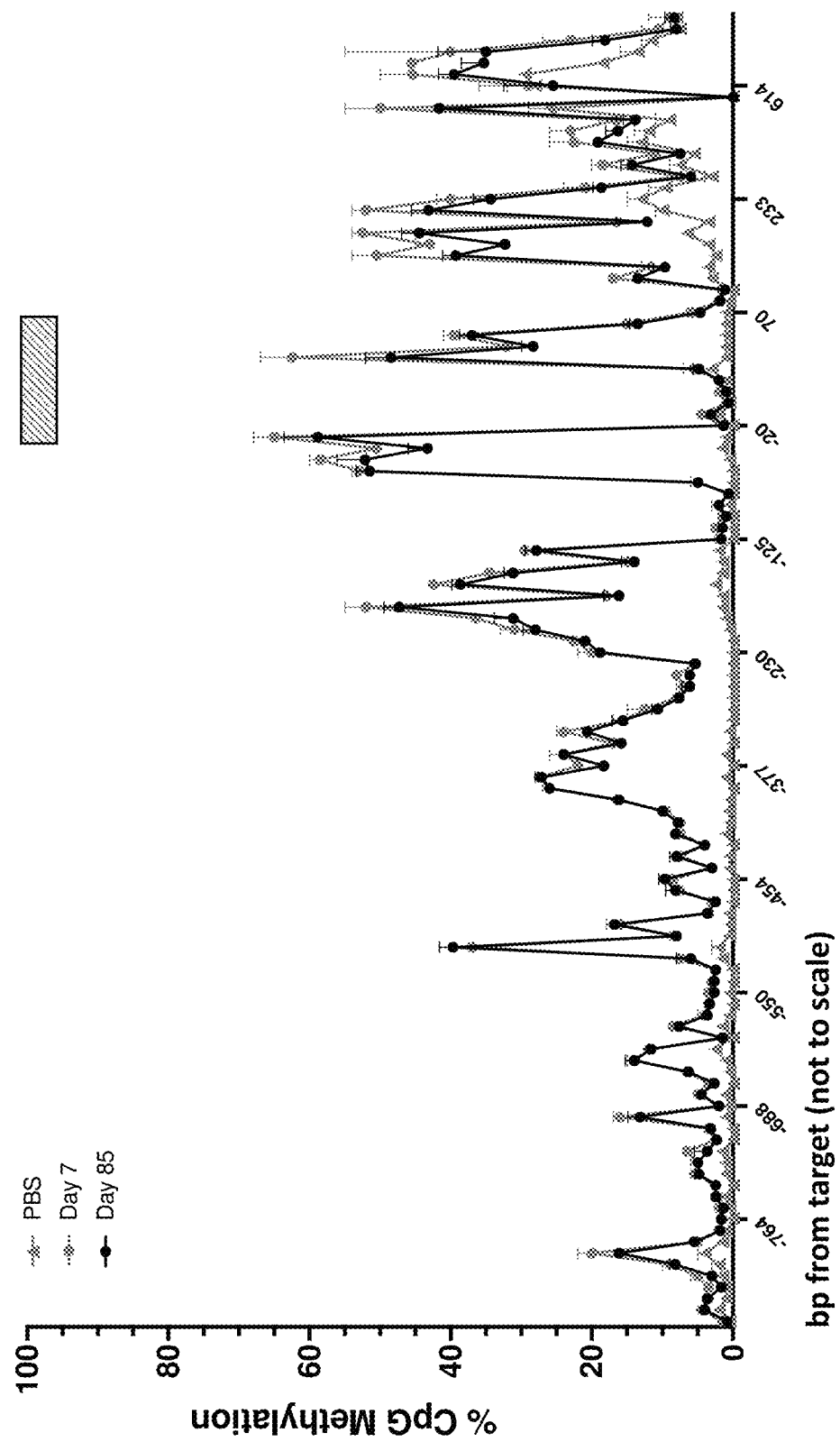
FIG. 17 shows the % methylation of CpGs in the PCSK9 promoter of DNA extracted from liver biopsies of Cynomolgus macaques intravenously infused with a PBS control (n=2) or a high dose (3.0 mg/kg, n=3) of dSpCas9-KRAB-DNMT3A/L and gRNA cPCSK9-C. Liver biopsies were performed at day 7 and day 85 post-infusion. The shaded bar indicates the location of the target site for gRNA cPCSK9-C in the cPCSK9 promoter.
Figure 18:
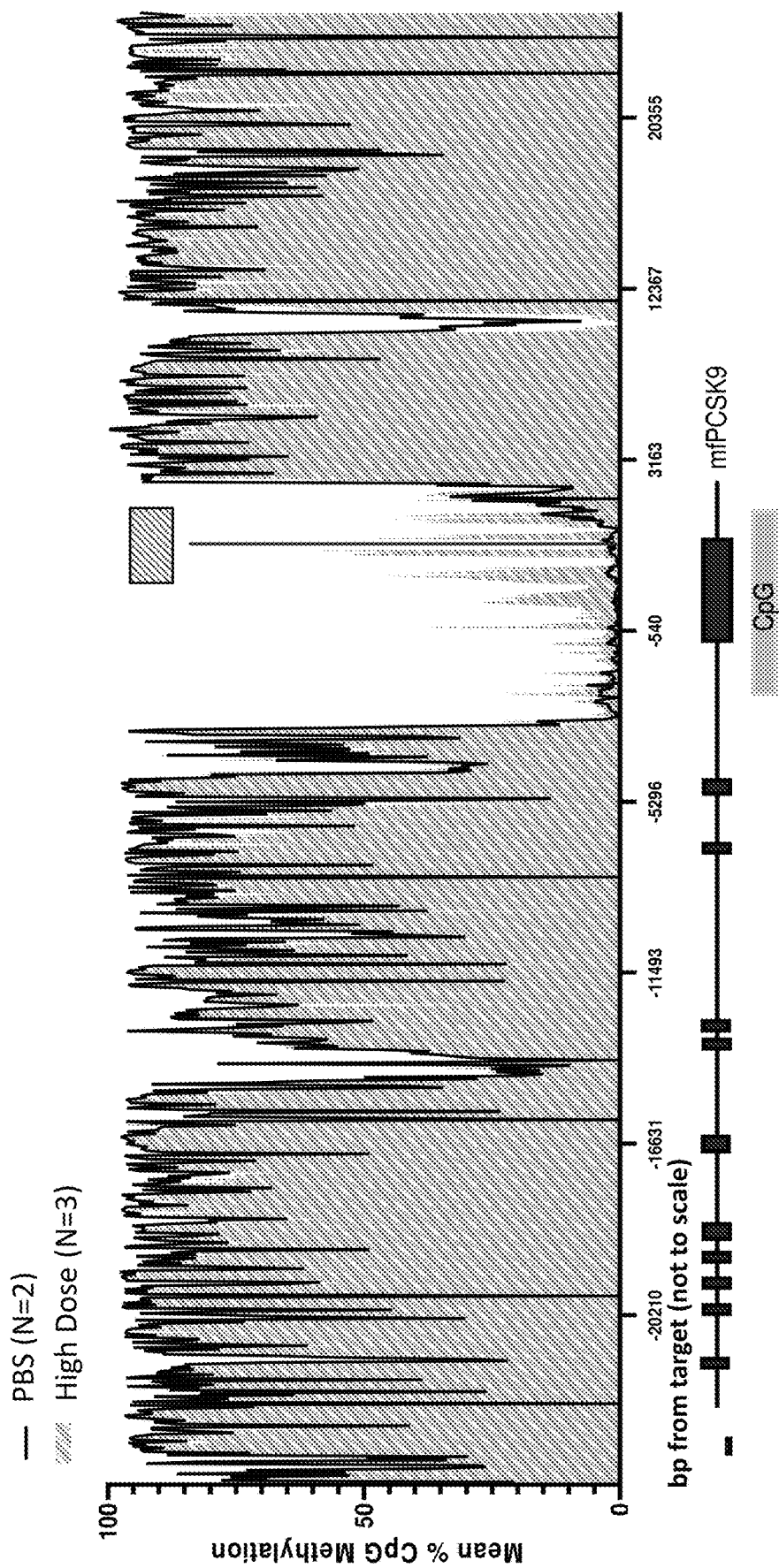
FIG. 18 shows the methylation signature surrounding the CpGs in the PCSK9 promoter for Cynomolgus macaques intravenously infused with a PBS control (n=2) or a high dose (3.0 mg/kg, n=3) of dSpCas9-KRAB-DNMT3A/L and gRNA cPCSK9-C at day 85 post-infusion. The shaded bar indicates the location of the target site for gRNA cPCSK9-C in the cPCSK9 promoter.

To investigate the mechanistic basis for the observed reductions in PCSK9, DNA was extracted from the high dose and control liver biopsies performed at day 7 post-infusion for targeted methylation sequencing. A 50 kb region surrounding the gRNA target site was sequenced and differential CpG methylation was quantified. As shown in FIG. 17, at day 7 (light circles) the high dose (3.0 mg/kg) subjects exhibited peak methylation in the region surrounding the gRNA target site (e.g., −500 bp), with up to 68% CpG methylation at certain residues compared to ~1% in PBS controls (triangles). To assess the durability of the treatment, liver biopsies for the high dose and control groups were performed at day 85 post-infusion and DNA was extracted for targeted methylation sequencing. Notably, methylation levels at day 85 (dark circles) were similar to levels measured at day 7 (FIG. 17). The spread of methylation at day 85 post LNP administration was limited to a ~2 kb region surrounding the PCSK9 CpG island (FIG. 18).

Figure 19:
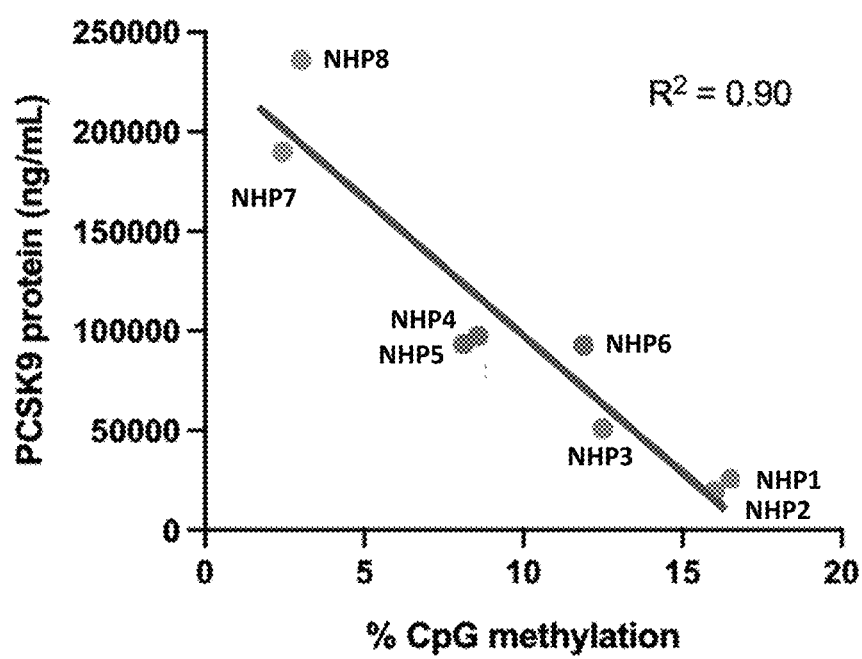
FIG. 19 shows PCSK9 protein levels plotted against the average % CpG methylation across the 2.2 kB PCSK9 promoter region for individual Cynomolgus macaques intravenously infused with a PBS control (NHP7 and NHP8), a low dose (1.0 mg/kg) of dSpCas9-KRAB-DNMT3A/L and gRNA cPCSK9-C (NHP4, NHP5, and NHP6), or a high dose (3.0 mg/kg) of dSpCas9-KRAB-DNMT3A/L and gRNA cPCSK9-C (NHP1, NHP2, and NHP3). Measurements were taken on day 7 post-infusion.

FIG. 19 shows that PCSK9 protein levels decrease as CpG methylation increases across the three treatment groups. Specifically, PCSK9 protein levels were plotted against the average % CpG methylation across the 2.2 kB PCSK9 promoter region for each individual NHP in the three treatment groups. The PBS-treated control group, NHP7 and NHP8, show high levels of PCSK9 and minimal CpG methylation. The low dose (1.0 mg/kg) group, NHP 4, NHP5, and NHP 6, exhibited ~60% reduction in PCSK9 levels compared to the PBS control group, which corresponded to ~7-12% average CpG methylation. The high dose group exhibited a strong reduction in PCSK9 levels (~80%), which corresponded to ~13-17% average CpG methylation. The calculated $R^2$ value (coefficient of determination) for these data was 0.90, indicating that 90% of the variance in PCSK9 protein levels can be predicted by % CpG methylation of the PCSK9 promoter.

The results demonstrated that a DNA-targeting system composed of a PCSK9 targeting gRNA and a dCas9-effector fusion protein can substantially and stably reduce PCSK9 blood protein and LDL-C levels in a non-human primate by increasing CpG methylation of the PCSK9 promoter. Notably, increased methylation of the PCSK9 promoter reduces PSCK9 and LDL-C levels without altering genomic DNA sequences, minimizes off-target effects that can occur from gene editing, and is more durable than RNAi. The results further support the utility of targeted repression of PCSK9 in vivo for potential treatment of familial hypercholesterolemia and/or cardiovascular disease, such as atherosclerotic cardiovascular disease (ASCVD).

Example 7: In Vitro Targeted PCSK9 Repression in Human Hepatocytes

DNA-targeting systems comprising an exemplary dCas9-effector fusion protein for transcriptional repression and a PCSK9 targeting guide RNA were assessed in primary human hepatocytes.

Figure 20:
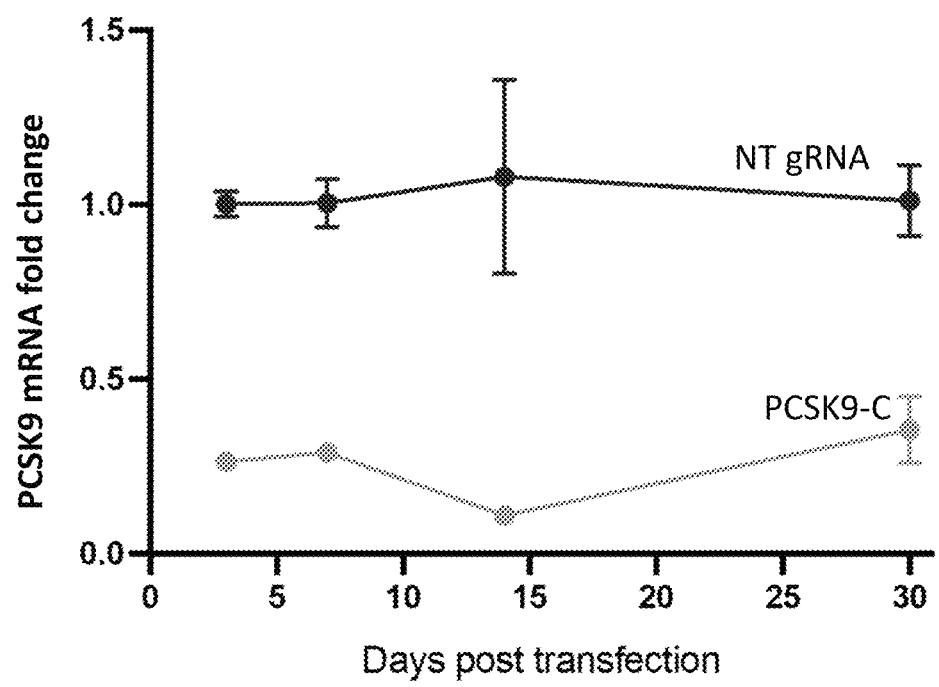
FIG. 20 shows results from qRT-PCR to assess PCSK9 mRNA expression levels in primary human hepatocytes transfected with dSpCas9-KRAB-DNMT3A/L and a non-targeting gRNA (NT) or gRNA PCSK9-C from day 3 through day 30 post-transfection. Dots represent individual time points and error bars represent mean of expression from experimental replicates.

Primary human hepatocytes were transfected with PCSK9-C gRNA (SEQ ID NO: 129; target site SEQ ID NO:3) and dSpCas9-KRAB-DNMT3A/L. mRNA was isolated from the transfected cells at day 3, 7, 14 and 30 post-transfection and assessed for knockdown of the target gene by qRT-PCR. As shown in FIG. 20, co-expression of dSpCas9-KRAB-DNMT3A/L and PCSK9-C gRNA led to transcriptional repression of PCSK9 at every time point as shown by reduced levels of PCSK9 mRNA. After a single administration, there was substantial PCSK9 mRNA repression through day 30 post-transfection.

The results demonstrated that a DNA-targeting system composed of a PCSK9 targeting gRNA and a dCas9-effector fusion protein can substantially and stably reduce PCSK9 mRNA levels in primary human hepatocytes.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

| SEQ ID NO. | Sequence | Annotation |
|---|---|---|
| 190 | GTTTAAGAGCTATGCTGGAAACAGCATAGCAAGTTTAAATAAGGCTAGTCCGTTA<br>TCAACTTGAAAAAGTGGCACCGAGTCGGTGC | SpCas9 gRNA scaffold (DNA) |
| 191 | GUUUAAGAGCUAUGCUGGAAACAGCAUAGCAAGUUUAAAUAAGGCUAGUCCGU<br>UAUCAACUUGAAAAAGUGGCACCGAGUCGGUGC | SpCas9 gRNA scaffold (RNA) |
| 192 | CGGACACTGGTGACCTTCAAGGATGTGTTTGTGGACTTCACCAGGGAGGAGTGGA<br>AGCTGCTGGACACTGCTCAGCAGATCCTGTACAGAAATGTGATGCTGGAGAACTA<br>TAAGAACCTGGTTTCCTTGGGTTATCAGCTTACTAAGCCAGATGTGATCCTCCGGT<br>TGGAGAAGGGAGAAGAGCCCTGGCTGGTG | KRAB (nt) |
| 193 | RTLVTFKDVFVDFTREEWKLLDTAQQILYRNVMLENYKNLVSLGYQLTKPDVILRLE<br>KGEEPWLV | KRAB (AA) |
| 194 | ACCTACGGGCTGCTGCGGCGGCGAGAGGACTGGCCCTCCCGGCTCCAGATGTTCT<br>TCGCTAATAACCACGACCAGGAATTTGACCCTCCAAAGGTTTACCCACCTGTCCCA<br>GCTGAGAAGAGGAAGCCCATCCGGGTGCTGTCTCTCTTTGATGGAATCGCTACAG<br>GGCTCCTGGTGCTGAAGGACTTGGGCATTCAGGTGGACCGCTACATTGCCTCGGA<br>GGTGTGTGAGGACTCCATCACGGTGGGCATGGTGCGGCACCAGGGGAAGATCATG<br>TACGTCGGGGACGTCCGCAGCGTCACACAGAAGCATATCCAGGAGTGGGGCCCAT<br>TCGATCTGGTGATTGGGGGCAGTCCCTGCAATGACCTCTCCATCGTCAACCCTGCT<br>CGCAAGGGCCTCTACGAGGGCACTGGCCGGCTCTTCTTTGAGTTCTACCGCCTCCT<br>GCATGATGCGCGGCCCAAGGAGGGAGATGATCGCCCCTTCTTCTGGCTCTTTGAG<br>AATGTGGTGGCCATGGGCGTTAGTGACAAGAGGGACATCTCGCGATTTCTCGAGT<br>CCAACCCTGTGATGATTGATGCAAAGAAGTGTCAGCTGCACACAGGGCCCGCTA<br>CTTCTGGGGTAACCTTCCCGGTATGAACAGGCCGTTGGCATCCACTGTGAATGATA<br>AGCTGGAGCTGCAGGAGTGTCTGGAGCATGGCAGGATAGCCAAGTTCAGCAAAGT<br>GAGGACCATTACTACGAGGTCAAACTCCATAAAGCAGGGCAAAGACCAGCATTTT<br>CCTGTCTTCATGAATGAGAAAGAGGACATCTTATGGTGCACTGAAATGGAAGGG<br>TATTTGGTTTCCCAGTCCACTATACTGACGTATCCAACATGAGCCGCTTGGCGAGG<br>CAGAGACTGCTGGGCCGGTCATGGAGCGTGCCAGTCATCCGCCACCTCTTCGCTCC<br>GCTGAAGGAGTATTTTGCGTGTGTG | DNMT3A (nt) |
| 195 | TYGLLRRREDWPSRLQMFFANNHDQEFDPPKVYPPVPAEKRKPIRVLSLFDGIATGLL<br>VLKDLGIQVDRYIASEVCEDSITVGMVRHQGKIMYVGDVRSVTQKHIQEWGPFDLVI<br>GGSPCNDLSIVNPARKGLYEGTGRLFFEFYRLLHDARPKEGDDRPFFWLFENVVAMG<br>VSDKRDISRFLESNPVMIDAKEVSAAHRARYFWGNLPGMNRPLASTVNDKLELQECL<br>EHGRIAKFSKVRTITTRSNSIKQGKDQHFPVFMNEKEDILWCTEMERVFGFPVHYTDV<br>SNMSRLARQRLLGRSWSVPVIRHLFAPLKEYFACV | DNMT3A (AA) |
| 196 | ATGGCGGCCATCCCAGCCCTGGACCCAGAGGCCGAGCCCAGCATGGACGTGATTT<br>TGGTGGGATCCAGTGAGCTCTCAAGCTCCGTTTCACCCGGGACAGGCAGAGATCT<br>TATTGCATATGAAGTCAAGGCTAACCAGCGAAATATAGAAGACATCTGCATCTGC<br>TGCGGAAGTCTCCAGGTTCACACACAGCACCCTCTGTTTGAGGGAGGGATCTGCG<br>CCCCCATGTAAGGACAAGTTCCTGGATGCCCTCTTCCTGTACGACGATGACGGGTAC<br>CAATCCTACTGCTCCATCTGCTGCTCCGGAGAAACGCTGCTCATCTGCGGAAACCC<br>TGATTGCACCCGATGCTACTGCTTCGAGTGTGTGGATAGCCTGGTCGGCCCCGGGA<br>CCTCGGGGAAGGTGCACGCCATGAGCAACTGGGTGTGCTACCTGTGCCTGCCGTC<br>CTCCCGAAGCGGGCTGCTGCAGCGTCGGAGGAAGTGGCGCAGCCAGCTCAAGGCC<br>TTCTACGACCGAGAGTCGGAGAATCCCCTTGAGATGTTCGAAACCGTGCCTGTGT<br>GGAGGAGACAGCCAGTCCGGGTGCTGTCCCTTTTTGAAGACATCAAGAAAGAGCT<br>GACGAGTTTGGGCTTTTTGGAAAGTGGTTCTGACCCGGGACAACTGAAGCATGTG<br>GTTGATGTCACAGACACAGTGAGGAAGGATGTGGAGGAGTGGGGACCCTTCGATC<br>TTGTGTACGGCGCCACACCTCCCCTGGGCCACACCTGTGACCGTCCTCCCAGCTGG<br>TACCTGTTCCAGTTCCACCGGCTCCTGCAGTACGCACGGCCCAAGCCAGGCAGCC<br>CCAGGCCCTTCTTCTGGATGTTCGTGGACAATCTGGTGCTGAACAAGGAAGACCT<br>GGACGTCGCATCTCGCTTCCTGGAGATGGAGCCAGTCACCATCCCAGATGTCCAC<br>GGCGGATCCTTGCAGAATGCTGTCCGCGTGTGGAGCAACATCCCAGCCATAAGGA<br>GCAGGCACTGGGCTCTGGTTTCGGAAGAAGAATTGTCCCTGCTGGCCCAGAACAA<br>GCAGAGCTCGAAGCTCGCGGCCAAGTGGCCCACCAAGCTGGTGAAGAACTGCTTT<br>CTCCCCCTAAGAGAATATTTCAAGTATTTTTCAACAGAACTCACTTCCTCTTTA | DNMT3L (nt) |
| 197 | MAAIPALDPEAEPSMDVILVGSSELSSSVSPGTGRDLIAYEVKANQRNIEDICICCGSLQ<br>VHTQHPLFEGGICAPCKDKFLDALFLYDDDGYQSYCSICCSGETLLICGNPDCTRCYCF<br>ECVVDSLVGPGTSGKVHAMSNWVCYLCLPSSRSGLLQRRRKWRSQLKAFYDRESENPL<br>EMFETVPVWRRQPVRVLSLFEDIKKELTSLGFLESGSDPGQLKHVVDVTDTVRKDVE<br>EWGPFDLVYGATPPLGHTCDRPPSWYLFQFHRLLQYARPKPGSPRPFFWMFVDNLVL<br>NKEDLDVASRFLEMEPVTIPDVHGGSLQNAVRVWSNIPAIRSRHWALVSEEELSLLAQ<br>NKQSSKLAAKWPTKLVKNCFLPLREYFKYFSTELTSSL | DNMT3L (AA) |

| SEQ ID NO. | Sequence | Annotation |
|---|---|---|
| 198 | AACCATGACCAGGAATTTGACCCCCCAAAGGTTTACCCACCTGTGCCAGCTGAGA<br>AGAGGAAGCCCATCCGCGTGCTGTCTCTCTTTGATGGGATTGCTACAGGGCTCCTG<br>GTGCTGAAGGACCTGGGCATCCAAGTGGACCGCTACATTGCCTCCGAGGTGTGT<br>GAGGACTCCATCACGGTGGGCATGGTGCGGCACCAGGGAAAGATCATGTACGTCGG<br>GGACGTCCGCAGCGTCACACAGAAGCATATCCAGGAGTGGGGCCCATTCGACCTG<br>GTGATTGGAGGCAGTCCCTGCAATGACCTCTCCATTGTCAACCCTGCCCGCAAGG<br>GACTTTATGAGGGTACTGGCCGCCTCTTCTTTGAGTTCTACCGCCTCCTGCATGAT<br>GCGCGGCCCAAGGAGGGAGATGATCGCCCCTTCTTCTGGCTCTTTGAGAATGTGG<br>TGGCCATGGGCGTTAGTGACAAGAGGGACATCTCGCGATTTCTTGAGTCTAACCC<br>CGTGATGATTGACGCCAAAGAAGTGTCTGCTGCACACAGGGCCCGTTACTTCTGG<br>GGTAACCTTCCTGGCATGAACAGGCCTTTGGCATCCACTGTGAATGATAAGCTGG<br>AGCTGCAAGAGTGTCTGGAGCACGGGCAGAATAGCCAAGTTCAGCAAAGTGAGGA<br>CCATTACCACCAGGTCAAACTCTATAAAGCAGGGCAAAGACCAGCATTTCCCCGT<br>CTTCATGAACGAGAAGGAGGACATCCTGTGGTGCACTGAAATGGAAAGGGTGTTT<br>GGCTTCCCCGTCCACTACACAGACGTCTCCAACATGAGCCGCTTGGCGAGGCAGA<br>GACTGCTGGGCCGATCGTGGAGCGTGCCGGTCATCCGCCACCTCTTCGCTCCGCTG<br>AAGGAATATTTTGCTTGTGTGTCTAGCGGCAATAGTAACGCTAACAGCCGCGGGC<br>CGAGCTTCAGCAGCGGCCTGGTGCCGTTAAGCTTGCGCGGCAGCCATATGGGCCC<br>TATGGAGATATACAAGACAGTGTCTGCATGGAAGAGACAGCCAGTGCGGGTACTG<br>AGCCTCTTCAGAAACATCGACAAGGTACTAAAGAGTTTGGGCTTCTTGGAAAGCG<br>GTTCTGGTTCTGGGGGAGGAACGCTGAAGTACGTGGAAGATGTCACAAATGTCGT<br>GAGGAGAGACGTGGAGAAATGGGGCCCCTTTGACCTGGTGTACGGCTCGACGCAG<br>CCCCTAGGCAGCTCTTGTGATCGCTGTCCCGGCTGGTACATGTTCCAGTTCCACCG<br>GATCCTGCAGTATGCGCTGCCTCGCCAGGAGAGTCAGCGGCCCTTCTTCTGGATAT<br>TCATGGACAATCTGCTGCTGACTGAGGATGACCAAGAGACAACTACCCGCTTCCT<br>TCAGACAGAGGCTGTGACCCTCCAGGATGTCCGTGGCAGAGACTACCAGAATGCT<br>ATGCGGGTGTGGAGCAACATTCCAGGGCTGAAGAGCAAGCATGCGCCCCTGACCC<br>CAAAGGAAGAAGAGTATCTGCAAGCCCAAGTCAGAAGCAGGAGCAAGCTGGACG<br>CCCCGAAAGTTGACCTCCTGGTGAAGAACTGCCTTCTCCCGCTGAGAGAGTACTTC<br>AAGTATTTTTCTCAAAACTCACTTCCTCTT | DNMT3A/<br>L v1 (nt) |
| 199 | NHDQEFDPPKVYPPVPAEKRKPIRVLSLFDGIATGLLVLKDLGIQVDRYIASEVCEDSIT<br>VGMVRHQGKIMYVGDVRSVTQKHIQEWGPFDLVIGGSPCNDLSIVNPARKGLYEGTG<br>RLFFEFYRLLHDARPKEGDDRPFFWLFENVVAMGVSDKRDISRFLESNPVMIDAKEVS<br>AAHRARYFWGNLPGMNRPLASTVNDKLELQECLEHGRIAKFSKVRTITTRSNSIKQGK<br>DQHFPVFMNEKEDILWCTEMERVFGFPVHYTDVSNMSRLARQRLLGRSWSVPVIRHL<br>FAPLKEYFACVSSGNSNANSRGPSFSSGLVPLSLRGSHMGPMEIYKTVSAWKRQPVRV<br>LSLFRNIDKVLKSLGFLESGSGSGGGTLKYVEDVTNVVRRDVEKWGPFDLVYGSTQP<br>LGSSCDRCPGWYMFQFHRILQY ALPRQESQRPFFWIFMDNLLLTEDDQETTTRFLQTE<br>AVTLQDVRGRDYQNAMR VWSNIPGLKSKHAPLTPKEEEYLQAQVRSRSKLDAPKVD<br>LLVKNCLLPLREYFKYFSQNSLPL | DNMT3A/<br>L v1 (AA) |
| 200 | AACCACGATCAGGAGTTTGACCCCCCTAAGGTGTACCCACCCGTGCCAGCCGAGA<br>AGAGGAAGCCCATCCGCGTGCTGTCCCTGTTCGACGGCATCGCCACAGGCCTGCT<br>GGTGCTGAAGGATCTGGGCATCCAGGTGGACAGATATATCGCCTCCGAGGTGTGC<br>GAGGATTCTATCACCGTGGGCATGGTGAGGCACCAGGGCAAGATCATGTACGTGG<br>GCGACGTGCGCAGCGTGACACAGAAGCACATCCAGGAGTGGGGACCCTTCGACCT<br>GGTCATCGGAGGCAGCCCCTGTAATGACCTGTCCATCGTGAACCCTGCAAGGAAG<br>GGCCTGTATGAGGGAACCGGCAGACTGTTCTTTGAGTTCTACAGGCTGCTGCACG<br>ACGCCCGCCCTAAGGAGGGCGATGACAGGCCATTCTTTTGGCTGTTTGAGAACGT<br>GGTGGCCATGGGCGTGAGCGACAAGCGGGATATCTCCAGATTCCTGGAGTCTAAT<br>CCCGTGATGATCGATGCAAAGGAGGTGTCTGCCGCACACAGGGCAAGGTACTTTT<br>GGGGAAATCTGCCTGGCATGAACCGCCCACTGGCCAGCACCGTGAACGACAAGCT<br>GGAGCTGCAGGAGTGCCTGGAGCACGGAAGGATCGCCAAGTTCTCCAAGGTGCG<br>GACAATCACCACAAGATCTAACAGCATCAAGCAGGGCAAGGATCAGCACTTCCCC<br>GTGTTCATGAATGAGAAGGAGGACATCCTGTGGTGTACCGAGATGGAGCGCGTGT<br>TCGGCTTTCCAGTGCACTATACAGACGTGAGCAATATGAGCCGGCTGGCAAGGCA<br>GAGACTGCTGGGCCGGTCCTGGTCTGTGCCAGTGATCAGACACCTGTTCGCCCCCC<br>TGAAGGAGTACTTTGCCTGCGTGTCTAGCGGCAACTCTAATGCCAACAGCAGAGG<br>CCCTTCCTTTTCCTCTGGCCTGGTGCCACTGTCTCTGAGGGGCAGCCACATGGGCC<br>CCATGGAGATCTACAAGACCGTGTCCGCCTGGAAGAGGCAGCCTGTGCGCGTGCT<br>GTCTCTGTTCCGCAACATCGACAAGGTGCTGAAGAGCCTGGGCTTTCTGGAGAGC<br>GGATCCGGATCTGGAGGAGGCACCCTGAAGTATGTGGAGGATGTGACAAATGTGG<br>TGCGGAGAGATGTGGAGAAGTGGGGCCCCTTCGATCTGGTGTACGGATCCACCCA<br>GCCACTGGGAAGCTCCTGCGATAGGTGTCCAGGATGGTATATGTTCCAGTTTCACA<br>GAATCCTGCAGTACGCACTGCCAAGGCAGGAGAGCCAGCGCCCTTCTTTTGGAT<br>CTTTATGGACAACCTGCTGCTGACAGAGGATGACCAGGAGACAACAACCCGCTTC<br>CTGCAGACAGAGGCAGTGACCCTGCAGGATGTGAGGGGACGCGACTATCAGAAT<br>GCCATGCGGGTGTGGTCTAACATCCCTGGCCTGAAGAGCAAGCACGCCCCCCTGA<br>CCCCTAAGGAGGAGGAGTACCTGCAGGCCCAGGTGCGGAGCAGATCCAAGCTGG<br>ATGCCCCTAAGGTGGACCTGCTGGTGAAGAATTGTCTGCTGCCACTGCGGGAGTA<br>CTTCAAGTACTTTAGTCAGAATAGCCTGCCACTG | DNMT3A/<br>L v2 (nt) |

-continued

| SEQ ID NO. | Sequence | Annotation |
|---|---|---|
| 201 | NHDQEFDPPKVYPPVPAEKRKPIRVLSLFDGIATGLLVLKDLGIQVDRYIASEVCEDSIT VGMVRHQGKIMYVGDVRSVTQKHIQEWGPFDLVIGGSPCNDLSIVNPARKGLYEGTG RLFFEFYRLLHDARPKEGDDRPFFWLFENVVAMGVSDKRDISRFLESNPVMIDAKEVS AAHRARYFWGNLPGMNRPLASTVNDKLELQECLEHGRIAKFSKVRTITTTRSNSIKQGK DQHFPVFMNEKEDILWCTEMERVFGFPVHYTDVSNMSRLARQRLLGRSWSVPVIRHL FAPLKEYFACVSSGNSNANSRGPSFSSGLVPLSLRGSHMGPMEIYKTVSAWKRQPVRV LSLFRNIDKVLKSLGFLESGSGSGGGTLKYVEDVTNVVRRDVEKWGPFDLVYGSTQP LGSSCDRCPGWYMFQFHRILQYALPRQESQRPFFWIFMDNLLLTEDDQETTTRFLQTE AVTLQDVRGRDYQNAMRVWSNIPGLKSKHAPLTPKEEEYLQAQVRSRSKLDAPKVD LLVKNCLLPLREYFKYFSQNSLPL | DNMT3A/L v2 (AA) |
| 202 | NGG | PAM-SpCas9 |
| 203 | NNGRRT | PAM-SaCas9 |
| 204 | MKRNYILGLDIGITSVGYGIIDYETRDVIDAGVRLFKEANVENNEGRRSKRGARRLKR RRRHRIQRVKKLLFDYNLLTDHSELSGINPYEARVKGLSQKLSEEEFSAALLHLAKRR GVHNVNEVEEDTGNELSTKEQISRNSKALEEKYVAELQLERLKKDGEVRGSINRFKTS DYVKEAKQLLKVQKAYHQLDQSFIDTYIDLLETRRTYYEGPGEGSPFGWKDIKEWYE MLMGHCTYFPEELRSVKYAYNADLYNALNDLNNLVITRDENEKLEYYEKFQIIENVF KQKKKPTLKQIAKEILVNEEDIKGYRVTSTGKPEFTNLKVYHDIKDITARKEIIENAELL DQIAKILTIYQSSEDIQEELTNLNSELTQEEIEQISNLKGYTGTHNLSLKAINLILDELWH TNDNQIAIFNRLKLVPKKVDLSQQKEIPTTLVDDFILSPVVKRSFIQSIKVINAIIKKYGL PNDIIIELAREKNSKDAQKMINEMQKRNRQTNERIEEIIRTTGKENAKYLIEKIKLHDM QEGKCLYSLEAIPLEDLLNNPFNYEVDHIIPRSVSFDNSFNNKVLVKQEENSKKGNRTP FQYLSSSDSKISYETFKKHILNLAKGKGRISKTKKEYLLEERDINRFSVQKDFINRNLVD TRYATRGLMNLLRSYFRVNNLDVKVKSINGGFTSFLRRKWKFKKERNKGYKHHAED ALIIANADFIFKEWKKLDKAKKVMENQMFEEKQAESMPEIETEQEYKEIFITPHQIKHI KDFKDYKYSHRVDKKPNRELINDTLYSTRKDDKGNTLIVNNLNGLYDKDNDKLKKLI NKSPEKLLMYHHDPQTYQKLKLIMEQYGDEKNPLYKYYEETGNYLTKYSKKDNGPV IKKIKYYGNKLNAHLDITDDYPNSRNKVVKLSLKPYRFDVYLDNGVYKFVTVKNLDV IKKENYYEVNSKCYEEAKKLKKISNQAEFIASFYNNDLIKINGELYRVIGVNNDLLNRI EVNMIDITYREYLENMNDKRPPRIIKTIASKTQSIKKYSTDILGNLYEVKSKKHPQIIKK G | SaCas9 (AA) |
| 205 | KRNYILGLAIGITSVGYGIIDYETRDVIDAGVRLFKEANVENNEGRRSKRGARRLKRRR RHRIQRVKKLLFDYNLLTDHSELSGINPYEARVKGLSQKLSEEEFSAALLHLAKRRGV HNVNEVEEDTGNELSTKEQISRNSKALEEKYVAELQLERLKKDGEVRGSINRFKTSDY VKEAKQLLKVQKAYHQLDQSFIDTYIDLLETRRTYYEGPGEGSPFGWKDIKEWYEML MGHCTYFPEELRSVKYAYNADLYNALNDLNNLVITRDENEKLEYYEKFQIIENVFKQ KKKPTLKQIAKEILVNEEDIKGYRVTSTGKPEFTNLKVYHDIKDITARKEIIENAELLDQ IAKILTIYQSSEDIQEELTNLNSELTQEEIEQISNLKGYTGTHNLSLKAINLILDELWHTN DNQIAIFNRLKLVPKKVDLSQQKEIPTTLVDDFILSPVVKRSFIQSIKVINAIIKKYGLPN DIIIELAREKNSKDAQKMINEMQKRNRQTNERIEEIIRTTGKENAKYLIEKIKLHDMQE GKCLYSLEAIPLEDLLNNPFNYEVDHIIPRSVSFDNSFNNKVLVKQEEASKKGNRTPFQ YLSSSDSKISYETFKKHILNLAKGKGRISKTKKEYLLEERDINRFSVQKDFINRNLVDTR YATRGLMNLLRSYFRVNNLDVKVKSINGGFTSFLRRKWKFKKERNKGYKHHAEDAL IIANADFIFKEWKKLDKAKKVMENQMFEEKQAESMPEIETEQEYKEIFITPHQIKHIKD FKDYKYSHRVDKKPNRELINDTLYSTRKDDKGNTLIVNNLNGLYDKDNDKLKKLINK SPEKLLMYHHDPQTYQKLKLIMEQYGDEKNPLYKYYEETGNYLTKYSKKDNGPVIK KIKYYGNKLNAHLDITDDYPNSRNKVVKLSLKPYRFDVYLDNGVYKFVTVKNLDVIK KENYYEVNSKCYEEAKKLKKISNQAEFIASFYNNDLIKINGELYRVIGVNNDLLNRIEV NMIDITYREYLENMNDKRPPRIIKTIASKTQSIKKYSTDILGNLYEVKSKKHPQIIKKG | dSaCas9 (AA) |
| 206 | MDKKYSIGLDIGTNSVGWAVITDEYKVPSKKFKVLGNTDRHSIKKNLIGALLFDSGET AEATRLKRTARRRYTRRKNRICYLQEIFSNEMAKVDDSFFHRLEESFLVEEDKKHERH PIFGNIVDEVAYHEKYPTIYHLRKKLVDSTDKADLRLIYLALAHMIKFRGHFLIEGDLN PDNSDVDKLFIQLVQTYNQLFEENPINASGVDAKAILSARLSKSRRLENLIAQLPGEKK NGLFGNLIALSLGLTPNFKSNFDLAEDAKLQLSKDTYDDDLDNLLAQIGDQYADLFLA AKNLSDAILLSDILRVNTEITKAPLSASMIKRYDEHHQDLTLLKALVRQQLPEKYKEIF FDQSKNGYAGYIDGGASQEEFYKFIKPILEKMDGTEELLVKLNREDLLRKQRTFDNGS IPHQIHLGELHAILRRQEDFYPFLKDNREKIEKILTFRIPYYVGPLARGNSRFAWMTRKS EETITPWNFEEVVDKGASAQSFIERMTNFDKNLPNEKVLPKHSLLYEYFTVYNELTKV KYVTEGMRKPAFLSGEQKKAIVDLLFKTNRKVTVKQLKEDYFKKIECFDSVEISGVED RFNASLGTYHDLLKIIKDKDFLDNEENEDILEDIVLTLTLFEDREMIEERLKTYAHLFD DKVMKQLKRRRYTGWGRLSRKLINGIRDKQSGKTILDFLKSDGFANRNFMQLIHDDS LTFKEDIQKAQVSGQGDSLHEHIANLAGSPAIKKGILQTVKVVDELVKVMGRHKPENI VIEMARENQTTQKGQKNSRERMKRIEEGIKELGSQILKEHPVENTQLQNEKLYLYYLQ NGRDMYVDQELDINRLSDYDVDHIVPQSFLKDDSIDNKVLTRSDKNRGKSDNVPSEE VVKKMKNYWRQLLNAKLITQRKFDNLTKAERGGLSELDKAGFIKRQLVETRQITKHV AQILDSRMNTKYDENDKLIREVKVITLKSKLVSDFRKDFQFYKVREINNYHHAHDAY | SpCas9 (AA) |

| SEQ ID NO. | Sequence | Annotation |
|---|---|---|
| | LNAVVGTALIKKYPKLESEFVYGDYKVYDVRKMIAKSEQEIGKATAKYFFYSNIMNF<br>FKTEITLANGEIRKRPLIETNGETEIVWDKGRDFATVRKVLSMPQVNIVKKTEVTG<br>GFSKESILPKRNSDKLIARKKDWDPKKYGGFDSPTVAYSVLVVAKVEKGKSKKLKSV<br>KELLGITIMERSSFEKNPIDFLEAKGYKEVKKDLIIKLPKYSLFELENGRKRMLASAGEL<br>QKGNELALPSKYVNFLYLASHYEKLKGSPEDNEQKQLFVEQHKHYLDEIIEQISEFSKR<br>VILADANLDKVLSAYNKHRDKPIREQAENIIHLFTLTNLGAPAAFKYFDTTIDRKRYTS<br>TKEVLDATLIHQSITGLYETRIDLSQLGGD | |
| 207 | DKKYSIGLAIGTNSVGWAVITDEYKVPSKKFKVLGNTDRHSIKKNLIGALLFDSGETA<br>EATRLKRTARRRYTRRKNRICYLQEIFSNEMAKVDDSFFHRLEESFLVEEDKKHERHPI<br>FGNIVDEVAYHEKYPTIYHLRKKLVDSTDKADLRLIYLALAHMIKFRGHFLIEGDLNP<br>DNSDVDKLFIQLVQTYNQLFEENPINASGVDAKAILSARLSKSRRLENLIAQLPGEKKN<br>GLFGNLIALSLGLTPNFKSNFDLAEDAKLQLSKDTYDDDLDNLLAQIGDQYADLFLAA<br>KNLSDAILLSDILRVNTEITKAPLSASMIKRYDEHHQDLTLLKALVRQQLPEKYKEIFF<br>DQSKNGYAGYIDGGASQEEFYKFIKPILEKMDGTEELLVKLNREDLLRKQRTFDNGSI<br>PHQIHLGELHAILRRQEDFYPFLKDNREKIEKILTFRIPYYVGPLARGNSRFAWMTRKS<br>EETITPWNFEEVVDKGASAQSFIERMTNFDKNLPNEKVLPKHSLLYEYFTVYNELTKV<br>KYVTEGMRKPAFLSGEQKKAIVDLLFKTNRKVTVKQLKEDYFKKIECFDSVEISGVED<br>RFNASLGTYHDLLKIIKDKDFLDNEENEDILEDIVLTLTLFEDREMIEERLKTYAHLFD<br>DKVMKQLKRRRYTGWGRLSRKLINGIRDKQSGKTILDFLKSDGFANRNFMQLIHDDS<br>LTFKEDIQKAQVSGQGDSLHEHIANLAGSPAIKKGILQTVKVVDELVKVMGRHKPENI<br>VIEMARENQTTQKGQKNSRERMKRIEEGIKELGSQILKEHPVENTQLQNEKLYLYYLQ<br>NGRDMYVDQELDINRLSDYDVDAIVPQSFLKDDSIDNKVLTRSDKNRGKSDNVPSEE<br>VVKKMKNYWRQLLNAKLITQRKFDNLTKAERGGLSELDKAGFIKRQLVETRQITKHV<br>AQILDSRMNTKYDENDKLIREVKVITLKSKLVSDFRKDFQFYKVREINNYHHAHDAY<br>LNAVVGTALIKKYPKLESEFVYGDYKVYDVRKMIAKSEQEIGKATAKYFFYSNIMNF<br>FKTEITLANGEIRKRPLIETNGETEIVWDKGRDFATVRKVLSMPQVNIVKKTEVTG<br>GFSKESILPKRNSDKLIARKKDWDPKKYGGFDSPTVAYSVLVVAKVEKGKSKKLKSV<br>KELLGITIMERSSFEKNPIDFLEAKGYKEVKKDLIIKLPKYSLFELENGRKRMLASAGEL<br>QKGNELALPSKYVNFLYLASHYEKLKGSPEDNEQKQLFVEQHKHYLDEIIEQISEFSKR<br>VILADANLDKVLSAYNKHRDKPIREQAENIIHLFTLTNLGAPAAFKYFDTTIDRKRYTS<br>TKEVLDATLIHQSITGLYETRIDLSQLGGD | dSpCas9 (AA) |
| 208 | CCAAAGAAGAAGCGGAAGGTCGGTATCCACGGAGTCCCAGCAGCCGACAAGAAG<br>TACTCCATTGGGCTCGCCATCGGCACAAACAGCGTCGGCTGGGCCGTCATTACGG<br>ACGAGTACAAGGTGCCGAGCAAAAAATTCAAAGTTCTGGGCAATACCGATCGCCA<br>CAGCATAAAGAAGAACCTCATTGGCGCCCTCCTGTTCGACTCCGGGGAAACCGCC<br>GAAGCCACGCGGCTCAAAAGAACAGCACGGCGCAGATATACCGCAGAAAGAAT<br>CGGATCTGCTACCtgcaGGAGATCTTTAGTAATGAGATGGCTAAGGTGGATGACTCT<br>TTCTTCCATAGGCTGGAGGAGTCCTTTTTGGTGGAGGAGGATAAAAAGCACGAGC<br>GCCACCCAATCTTTGGCAATATCGTGGACGAGGTGGCGTACCATGAAAAGTACCC<br>AACCATATATCATCTGAGGAAGAAGCTTGTAGACAGTACTGATAAGGCTGACTTG<br>CGGTTGATCTATCTCGCGCTGGCGCATATGATCAAATTTCGGGGACACTTCCTCAT<br>CGAGGGGGACCTGAACCCAGACAACAGCGATGTCGACAAACTCTTTATCCAACTG<br>GTTCAGACTTACAATCAGCTTTTCGAAGAGAACCCGATCAACGCATCCGGAGTTG<br>ACGCCAAAGCAATCCTGAGCGCTAGGCTGTCCAAATCCCGGCGGCTCGAAAACCT<br>CATCGCACAGCTCCCTGGGGAGAAGAAGAACGGCCTGTTTGGTAATCTTATCGCC<br>CTGTCACTCGGGCTGACCCCCAACTTTAAATCTAACTTCGACCTGGCCGAAGATGC<br>CAAGCTTCAACTGAGCAAAGACACCTACGATGATGATCTCGACAATCTGCTGGCC<br>CAGATCGGCGACCAGTACGCAGACCTTTTTTTGGCGGCAAAGAACCTGTCAGACG<br>CCATTCTGCTGAGTGATATTCTGCGAGTGAACACGGAGATCACCAAAGCTCCGCT<br>GAGCGCTAGTATGATCAAGCGCTATGATGAGCACCACCAAGACTTGACTTTGCTG<br>AAGGCCCTTGTCAGACAGCAACTGCCTGAGAAGTACAAGGAAATTTTCTTCGATC<br>AGTCTAAAAATGGCTACGCCGGATACATTGACGGCGGAGCAAGCCAGGAGGAAT<br>TTTACAAATTTATTAAGCCCATCTTGGAAAAAATGGACGGCACCGAGGAGCTGCT<br>GGTAAAGCTTAACAGAGAAGATCTGTTGCGCAAACAGCGCACTTTCGACAATGGA<br>AGCATCCCCCACCAGATTCACCTGGGCGAACTGCACGCTATCCTCAGGCGGCAAG<br>AGGATTTCTACCCCTTTTTGAAAGATAACAGGGAAAAGATTGAGAAAATCCTCAC<br>ATTTCGGATACCCTACTATGTAGGCCCCCTCGCCCGGGGAAATTCAGATTCGCGT<br>GGATGACTCGCAAATCAGAAGAGACCATCACTCCCTGGAACTTCGAGGAAGTCGT<br>GGATAAGGGGGCCTCTGCCCAGTCCTTCATCGAAAGGATGACTAACTTTGATAAA<br>AATCTGCCTAACGAAAAGGTGCTTCCTAAACACTCTCTGCTGTACGAGTACTTCAC<br>AGTTTATAACGAGCTCACCAAGGTCAAATACGTCACAGAAGGGATGAGAAAGCC<br>AGCATTCCTGTCTGGAGAGCAGAAGAAAGCTATCGTGGACCTCCTCTTCAAGACG<br>AACCGGAAGTTACCGTGAAACAGCTCAAAGAAGACTATTTCAAAAAGATTGAAT<br>GTTTCGACTCTGTTGAAATCAGCGGAGTGGAGGATCGCTTCAACGCATCCCTGGG<br>AACGTATCACGATCTCCTGAAAATCATTAAAGACAAGGACTTCCTGGACAATGAG<br>GAGAACGAGGACATTCTTGAGGACATTGTCCTCACCCTTACGTTGTTTGAAGATAG<br>GGAGATGATTGAAGAACGCTTGAAAACTTACGCTCATCTCTTCGACGACAAAGTC<br>ATGAAACAGCTCAAGAGGCGCCGATATACAGGATGGGGCGGCTGTCAAGAAAA<br>CTGATCAATGGgatcCGAGACAAGCAGAGTGGAAAGACAATCCTGGATTTTCTTAA<br>GTCCGATGGATTTGCCAACCGGAACTTCATGCAGTTGATCCATGATGACTCTCTCA<br>CCTTTAAGGAGGACATCCAGAAAGCACAAGTTTCTGGCCAGGGGGACAGTCTTCA | dSpCas9-KRAB (nt) |

-continued

| SEQ ID NO. | Sequence | Annotation |
|---|---|---|
| | CGAGCACATCGCTAATCTTGCAGGTAGCCCAGCTATCAAAAAGGGAATACTGCAG<br>ACCGTTAAGGTCGTGGATGAACTCGTCAAAGTAATGGGAAGGCATAAGCCCGAGA<br>ATATCGTTATCGAGATGGCCCGAGAGAACCAAACTACCCAGAAGGGACAGAAGA<br>ACAGTAGGGAAAGGATGAAGAGGATTGAAGAGGGTATAAAAGAACTGGGGTCCC<br>AAATCCTTAAGGAACACCCAGTTGAAAACACCCAGCTTCAGAATGAGAAGCTCTA<br>CCTGTACTACCTGCAGAACGGCAGGGACATGTACGTGGATCAGGAACTGGACATC<br>AATCGGCTCTCCGACTACGACGTGGATGCCATCGTGCCCCAGTCTTTTCTCAAAGA<br>TGATTCTATTGATAATAAAGTGTTGACAAGATCCGATAAAAATAGAGGGAAGAGT<br>GATAACGTCCCCTCAGAAGAAGTTGTCAAGAAAATGAAAAATTATTGGCGGCAGC<br>TGCTGAACGCCAAACTGATCACACAACGGAAGTTCGATAATCTGACTAAGGCTGA<br>ACGAGGTGGCCTGTCTGAGTTGGATAAAGCCGGCTTCATCAAAAGGCAGCTTGTT<br>GAGACACGCCAGATCACCAAgcacGTGGCCCAAATTCTCGATTCACGCATGAACAC<br>CAAGTACGATGAAAATGACAAACTGATTCGAGAGGTGAAAGTTATTACTCTGAAG<br>TCTAAGCTGGTCTCAGATTTCAGAAAGGACTTTCAGTTTTATAAGGTGAGAGAGAT<br>CAACAATTACCACCATGCGCATGATGCCTACCTGAATGCAGTGGTAGGCACTGCA<br>CTTATCAAAAAATATCCCAAGCTTGAATCTGAATTTGTTTACGGAGACTATAAGT<br>GTACGATGTTAGGAAAATGATCGCAAAGTCTGAGCAGGAAATAGGCAAGGCCAC<br>CGCTAAGTACTTCTTTTACAGCAATATTATGAATTTTTTCAAGACCGAGATTACAC<br>TGGCCAATGGAGAGATTCGGAAGCGACCACTTATCGAAACAAACGGAGAAACAG<br>GAGAAATCGTGTGGGACAAGGGTAGGGATTTCGCGACAGTCCGGAAGGTCCTGTC<br>CATGCCGCAGGTGAACATCGTTAAAAAGACCGAAGTACAGACCGGAGGCTTCTCC<br>AAGGAAAGTATCCTCCCGAAAAGGAACAGCGACAAGCTGATCGCACGCAAAAAA<br>GATTGGGACCCCAAGAAATACGCGGATTCGATTCTCCTACAGTCGCTTACAGTG<br>TACTGGTTGTGGCCAAAGTGGAGAAAGGGAAGTCTAAAAAACTCAAAAGCGTCA<br>AGGAACTGCTGGGCATCACAATCATGGAGCGATCAAGCTTCGAAAAAAACCCCAT<br>CGACTTTCTCGAGGCGAAAGGATATAAGAGGTCAAAAAAGACCTCATCATTAAG<br>CTTCCCAAGTACTCTCTCTTTGAGCTTGAAAACGGCCGGAAACGAATGCTCGCTAG<br>TGCGGGCGAGCTGCAGAAAGGTAACGAGCTGGCACTGCCCTCTAAATACGTTAAT<br>TTCTTGTATCTGGCCAGCCACTATGAAAAGCTCAAAGGGTCTCCCGAAGATAATG<br>AGCAGAAGCAGCTGTTCGTGGAACAACACAAACACTACCTTGATGAGATCATCGA<br>GCAAATAAGCGAATTCTCCAAAAGAGTGATCCTCGCCGACGCTAACCTCGATAAG<br>GTGCTTTCTGCTTACAATAAGCACAGGGATAAGCCCATCAGGGAGCAGGCAGAAA<br>ACATTATCCACTTGTTTACTCTGACCAACTTGGGCGCGCCTGCAGCCTTCAAGTAC<br>TTCGACACCACCATAGACAGAAAGCGGTACACCTCTACAAAGGAGGTCCTGGACG<br>CCACACTGATTCATCAGTCAATTACGGGCTCTATGAAACAAGAATCGACCTCTCT<br>CAGCTCGGTGGAGACAAAAGGCCGGCGGCCACGAAAAAGGCCGGCCAGGCAAAA<br>AAGAAAAAGGctagCgatgctaagtcactgactgcctggtcccggacactggtgaccttcaaggatgtgtttgtg<br>gacttcaccagggaggagtggaagctgctggacactgctcagcagatcctgtacagaaatgtgatgctggagaac<br>tataagaacctggtttcctttgggttatcagcttactaagcagatgtgatcctccggttggagaagggagaagag<br>ccctggctggtggagagagaaattcaccaagagacccatcctgattcagagactgcatttgaaatcaaatca<br>tcagttCCGAAAAAGAAACGCAAAGTT | |
| 209 | PKKKRKVGIHGVPAADKKYSIGLAIGTNSVGWAVITDEYKVPSKKFKVLGNTDRHSIK<br>KNLIGALLFDSGETAEATRLKRTARRRYTRRKNRICYLQEIFSNEMAKVDDSFFHRLE<br>ESPFLVEEDKKHERHPIFGNIVDEVAYHEKYPTIYHLRKKLVDSTDKADLRLIYLALAH<br>MIKFRGHFLIEGDLNPDNSDVDKLFIQLVQTYNQLFEENPINASGVDAKAILSARLSKS<br>RRLENLIAQLPGEKKNGLFGNLIALSLGLTPNFKSNFDLAEDAKLQLSKDTYDDDLDN<br>LLAQIGDQYADLFLAAKNLSDAILLSDILRVNTEITKAPLSASMIKRYDEHHQDLTLLK<br>ALVRQQLPEKYKEIFFDQSKNGYAGYIDGASQEEFYKFIKPILEKMDGTEELLVKLN<br>REDLLRKQRTFDNGSIPHQIHLGELHAILRRQEDFYPFLKDNREKIEKILTFRIPYYVGP<br>LARGNSRFAWMTRKSEETITPWNFEEVVDKGASAQSFIERMTNFDKNLPNEKVLPKH<br>SLLYEYFTVYNELTKVKYVTEGMRKPAFLSGEQKKAIVDLLFKTNRKVTVKQLKEDY<br>FKKIECFDSVEISGVEDRFNASLGTYHDLLKIIKDKDFLDNEENEDILEDIVLTLTLFED<br>REMIEERLKTYAHLFDDKVMKQLKRRRYTGWGRLSRKLINGIRDKQSGKTILDFLKS<br>DGFANRNFMQLIHDDSLTFKEDIQKAQVSGQGDSLHEHIANLAGSPAIKKGILQTVKV<br>VDELVKVMGRHKPENIVIEMARENQTTQKGQKNSRERMKRIEEGIKELGSQILKEHPV<br>ENTQLQNEKLYLYYLQNGRDMYVDQELDINRLSDYDVDAIVPQSFLKDDSIDNKVLT<br>RSDKNRGKSDNVPSEEVVKKMKNYWRQLLNAKLITQRKFDNLTKAERGGLSELDKA<br>GFIKRQLVETRQITKHVAQILDSRMNTKYDENDKLIREVKVITLKSKLVSDFRKDFQFY<br>KVREINNYHHAHDAYLNAVVGTALIKKYPKLESEFVYGDYKVYDVRKMIAKSEQEIG<br>KATAKYFFYSNIMNFFKTEITLANGEIRKRPLIETNGETGEIVWDKGRDFATVRKVLS<br>MPQVNIVKKTEVQTGGFSKESILPKRNSDKLIARKKDWDPKKYGGFDSPTVAYSVLV<br>VAKVEKGKSKKLKSVKELLGITIMERSSFEKNPIDFLEAKGYKEVKKDLIIKLPKYSLF<br>ELENGRKRMLASAGELQKGNELALPSKYVNFLYLASHYEKLKGSPEDNEQKQLFVEQ<br>HKHYLDEIIEQISEFSKRVILADANLDKVLSAYNKHRDKPIREQAENIIHLFTLTNLGAP<br>AAFKYFDTTIDRKRYTSTKEVLDATLIHQSITGLYETRIDLSQLGGDKRPAATKKAGQ<br>AKKKKASDAKSLTAWSRTLVTFKDVFVDFTREEWKLLDTAQQILYRNVMLENYKNL<br>VSLGYQLTKPDVILRLEKGEEPWLVEREIHQETHPDSETAFEIKSSVPKKKRKV | dSpCas9-<br>KRAB<br>(AA) |
| 210 | NNNNGATT | PAM-*N. meningitidis* Cas9 |

| SEQ ID NO. | Sequence | Annotation |
|---|---|---|
| 211 | NNNNRYAC | PAM-*C. jejuni* Cas9 |
| 212 | NNAGAAW | PAM-*S. thermophilus* |
| 213 | NGG | PAM-*F. Novicida* |
| 214 | NAAAAC | PAM-*T. denticola* |
| 215 | TTTV | PAM-Cas12a/Cpf1 |
| 216 | NGAN | Variant PAM-SpCas9 variant |
| 217 | NGNG | Variant PAM-SpCas9 variant |
| 218 | NGAG | Variant PAM-SpCas9 variant |
| 219 | NGCG | Variant PAM-SpCas9 variant |
| 220 | MKTPADTGFAFPDWAYKPESSPGSRQIQLWHFILELLRKEEYQGVIAWQGDYGEFVIK DPDEVARLWGVRKCKPQMNYDKLSRALRYYYNKRILHKTKGKRFTYKFNFNKLVLV NYPFIDVGLAGGAVPQSAPPVPSGGSHFRFPPSTPSEVLSPTEDPRSPPACSSSSSSLFSA VVARRLGRGSVSDCSDGTSELEEPLGEDPRARPPGPPDLGAFRGPPLARLPHDPGVFR VYPRPRGGPEPLSPFPVSPLAGPGSLLPPQLSPALPMTPTHLAYTPSPTLSPMYPSGGGG PSGSGGGSHFSFSPEDMKRYLQAHTQSVYNYHLSPRAFLHYPGLVVPQPQRPDKCPLP PMAPETPPVPSSASSSSSSSSSPPFKFKLQPPPLGRRQRAAGEKAVAGADKSGGSAGGLA EGAGALAPPPPPPQIKVEPISEGESEEVEVTDISDEDEEDGEVFKTPRAPPAPPKPEPGEA PGASQCMPLKLRFKRRWSEDCRLEGGGGPAGGFEDEGEDKKVRGEGPGEAGGPLTP RRVSSDLQHATAQLSLEHRDS | ERF domain (AA) |
| 221 | MERVKMINVQRLLEAAEFLERRERECEHGYASSFPSMPSPRLQHSKPPRRLSRAQKHS SGSSNTSTANRSTHNELEKNRRAHLRLCLERLKVLIPLGPDCTRHTTLGLLNKAKAHI KKLEEAERKSQHQLENLEREQRFLKWRLEQLQGPQEMERIRMDSIGSTISSDRSDSERE EIEVDVESTEFSHGEVDNISTTSISDIDDHSSLPSIGSDEGYSSASVKLSFTS | MXI1 domain (AA) |
| 222 | ASPKKKRKVEASGSGMNIQMLLEAADYLERREREAEHGYASMLPGSGMNIQMLLEA ADYLERREREAEHGYASMLPGSGMNIQMLLEAADYLERREREAEHGYASMLPSRSR | SID4X domain (AA) |
| 223 | MAAAVRMNIQMLLEAADYLERREREAEHGYASMLPYNNKDRDALKRRNKSKKNNS SSRST HNEMEKNRRAHLRLCLEKLKGLVPLGPESSRHTTLSLLTKAKLHIKKLEDCDRKAVH QID QLQREQRHLKRQLEKLGIERIRMDSIGSTVSSERSDSDREEIDVDVESTDYLTGDLDWS S SSVSDSDERGSMQSLGSDEGYSSTSIKRIKLQDSHKACLG | MAD-SID domain (AA) |
| 224 | MKGDTRHLNGEEDAGGREDSILVNGACSDQSSDSPPILEAIRTPEIRGRRSSSRLSKRE VSSLLSYTQDLTGDGDEDGDGSDTPVMPKLFRETRTRSESPAVRTRNNNSVSSRERH RPSPRSTRGRQGRNHVDESPVEFPATRSLRRRATASAGTPWPSPPSSYLTIDLTDDTED THGTPQSSSTPYARLAQDSQQGMESPQVEADSGDGDSSEYQDGKEFGIGDLVWGKI KGFSWWPAMVVSWKATSKRQAMSGMRWVQWFGDGKFSEVSADKLVALGLFSQHF NLATFNKLVSYRKAMYHALEKARVRAGKTFPSSPGDSLEDQLKPMLEWAHGGFKPT GIEGLKPNNTQPVVNKSKVRRAGSRKLESRKYENKTRRRTADDSATSDYCPAPKRLK TNCYNNGKDRGDEDQSREQMASDVANNKSSLEDGCLSCGRKNPVSFHPLFEGGLCQ TCRDRFLELFYMDDDGYQSYCTVCCEGRELLLCSNTSCCRCFCVECLEVLVGTGTA AEAKLQEPWSCYMCLPQRCHGVLRRRKDWNVRLQAFFTSDTGLEYEAPKLYPAIPA | DNMT3B (AA) |

| SEQ ID NO. | Sequence | Annotation |
|---|---|---|
| | ARRRPIRVLSLFDGIATGYLVLKELGIKVGKYVASEVCEESIAVGTVKHEGNIKYVND VRNITKKNIEEWGPFDLVIGGSPCNDLSNVNPARKGLYEGTGRLFFEFYHLLNYSRPK EGDDRPFFWMFENVVAMKVGDKRDISRFLECNPVMIDAIKVSAAHRARYFWGNLPG MNRPVIASKNDKLELQDCLEYNRIAKLKKVQTITTKSNSIKQGKNQLFPVVMNGKED VLWCTELERIFGFPVHYTDVSNMGRGARQKLLGRSWSVPVIRHLFAPLKDYFACE | |
| 225 | MLSGKKAAAAAAAAAAAATGTEAGPGTAGGSENGSEVAAQPAGLSGPAEVGPGAV GERTPRKKEPPRASPPGGLAEPPGSAGPQAGPTVVPGSATPMETGIAETPEGRRTSRRK RAKVEYREMDESLANLSEDEYYSEEERNAKAEKEKKLPPPPPQAPPEEENESEPEEPSG VEGAAFQSRLPHDRMTSQEAACFPDIISGPQQTQKVFLFIRNRTLQLWLDNPKIQLTFE ATLQQLEAPYNSDTVLVHRVHSYLERHGLINFGIYKRIKPLPTKKTGKVIIGSGVSGLA AARQLQSFGMDVTLLEARDRVGGRVATFRKGNYVADLGAMVVTGLGGNPMAVVS KQVNMELAKIKQKCPLYEANGQAVPKEKDEMVEQEFNRLLEATSYLSHQLDFNVLN NKPVSLGQALEVVIQLQEKHVKDEQIEHWKKIVKTQEELKELLNKMVNLKEKIKELH QQYKEASEVKPPRDITAEFLVKSKHRDLTALCKEYDELAETQGKLEEKLQELEANPPS DVYLSSRDRQILDWHFANLEFANATPLSTLSLKHWDQDDDFEFTGSHLTVRNGYSCV PVALAEGLDIKLNTAVRQVRYTASGCEVIAVNTRSTSQTFIYKCDAVLCTLPLGVLKQ QPPAVQFVPPLPEWKTSAVQRMGFGNLNKVVLCFDRVFWDPSVNLFGHVGSTTASR GELFLFWNLYKAPILLALVAGEAAGIMENISDDVIVGRCLAILKGIFGSSAVPQPKETV VSRWRADPWARGSYSYVAAGSSGNDYDLMAQPITPGPSIPGAPQPIPRLFFAGEHTIR NYPATVHGALLSGLREAGRIADQFLGAMYTLPRQATPGVPAQQSPSM | LSD1 (AA) |
| 226 | LLPKNYHLENEVARLKKLVGER | SunTag GCN4 peptide (AA) |
| 227 | GGSGG | GGSGG linker (AA) |
| 228 | GGGGS | GGGGS linker (AA) |
| 229 | GGGGG | GGGGG linker (AA) |
| 230 | GGAGG | GGAGG linker (AA) |
| 231 | GGGGSSS | GGGGSSS linker (AA) |
| 232 | GGGGAAA | GGGGAAA linker (AA) |
| 233 | GGPSSGAPPPSGGSPAGSPTSTEEGTSESATPESGPGTSTEPSEGSAPGSPAGSPTSTEEG TSTEPSEGSAPGTSTEPSE | XTEN80 (aa) |
| 234 | PKKKRKV | NLS-SV40 (AA) |
| 235 | PAAKRVKLD | NLS-cMyc (AA) |
| 236 | RQRRNELKRSP | NLS-cMyc (AA) |
| 237 | NQSSNFGPMKGGNFGGRSSGPYGGGGQYFAKPRNQGGY | NLS-hRNPA1 M9 (AA) |
| 238 | RMRIZFKNKGKDTAELRRRRVEVSVELRKAKKDEQILKRRNV | NLS-IBB domain importin-alpha (AA) |
| 239 | VSRKRPRP | NLS-myoma T protein (AA) |

-continued

| SEQ ID NO. | Sequence | Annotation |
|---|---|---|
| 240 | PPKKARED | NLS-myoma T protein (AA) |
| 241 | PQPKKKPL | NLS-human p53 (AA) |
| 242 | SALIKKKKKMAP | NLS-mouse c-abl IV (AA) |
| 243 | DRLRR | NLS-influenza NS1 (AA) |
| 244 | PKQKKRK | NLS-influenza NS1 (AA) |
| 245 | RKLKKKIKKL | NLS-hepatitis delta antigen (AA) |
| 246 | REKKKFLKRR | NLS-mouse Mx1 (AA) |
| 247 | KRKGDEVDGVDEVAKKKSKK | NLS-human poly(ADP-ribose) polymerase (AA) |
| 248 | RKCLQAGMNLEARKTKK | NLS-gluco-corticoid (AA) |
| 249 | KRPAATKKAGQAKKKK | NLS-nucleo-plasmin (AA) |
| 250 | GGGAAGGGATACAGGCTGGA | gRNA-mousePCSK9-A spacer DNA |
| 251 | GTCCCGTTTGCAGCCCAATT | gRNA-mousePCSK9-B spacer DNA |
| 252 | GAGCGTCATTTGACGCTGTC | gRNA-mousePCSK9-C spacer DNA |
| 253 | GGATCTTCCGATGGGGCTCG | gRNA-mousePCSK9-D spacer DNA |

-continued

Sequences

| SEQ ID NO. | Sequence | Annotation |
|---|---|---|
| 254 | GTGAAGGTGGAAGCCTTCTG | gRNA-mousePCSK9-E spacer DNA |
| 255 | GTGGACGCGCAGGCTGCCGG | gRNA-mousePCSK9-F spacer DNA |
| 256 | GGGGCGAGGAGAGGTGCGCG | gRNA-mousePCSK9-G spacer DNA |
| 257 | AGTGGGTGCCCATCGGGGCG | gRNA-mousePCSK9-H spacer DNA |
| 258 | CTACTGTGCCCCACCGGCGC | gRNA-mousePCSK9-I spacer DNA |
| 259 | GGGAAGGGAUACAGGCUGGA | gRNA-mousePCSK9-A spacer RNA |
| 260 | GUCCCGUUUGCAGCCCAAUU | gRNA-mousePCSK9-B spacer RNA |
| 261 | GAGCGUCAUUUGACGCUGUC | gRNA-mousePCSK9-C spacer RNA |
| 262 | GGAUCUUCCGAUGGGCUCG | gRNA-mousePCSK9-D spacer RNA |
| 263 | GUGAAGGUGGAAGCCUUCUG | gRNA-mousePCSK9-E spacer RNA |
| 264 | GUGGACGCGCAGGCUGCCGG | gRNA-mousePCSK9-F spacer RNA |
| 265 | GGGGCGAGGAGAGGUGCGCG | gRNA-mousePCSK9-G spacer RNA |

-continued

Sequences

| SEQ ID NO. | Sequence | Annotation |
|---|---|---|
| 266 | AGUGGGUGCCCAUCGGGGCG | gRNA-mousePCSK9-H spacer RNA |
| 267 | CUACUGUGCCCCACCGGCGC | gRNA-mousePCSK9-I spacer RNA |
| 268 | GGGAAGGGAUACAGGCUGGAGUUUAAGAGCUAUGCUGGAAACAGCAUAGCAAG UUUAAAUAAGGCUAGUCCGUUAUCAACUUGAAAAAGUGGCACCGAGUCGGUGC | gRNA-mousePCSK9-A gRNA |
| 269 | GUCCCGUUUGCAGCCCAAUUGUUUAAGAGCUAUGCUGGAAACAGCAUAGCAAG UUUAAAUAAGGCUAGUCCGUUAUCAACUUGAAAAAGUGGCACCGAGUCGGUGC | gRNA-mousePCSK9-B gRNA |
| 270 | GAGCGUCAUUUGACGCUGUCGUUUAAGAGCUAUGCUGGAAACAGCAUAGCAAG UUUAAAUAAGGCUAGUCCGUUAUCAACUUGAAAAAGUGGCACCGAGUCGGUGC | gRNA-mousePCSK9-C gRNA |
| 271 | GGAUCUUCCGAUGGGGCUCGGUUUAAGAGCUAUGCUGGAAACAGCAUAGCAAG UUUAAAUAAGGCUAGUCCGUUAUCAACUUGAAAAAGUGGCACCGAGUCGGUGC | gRNA-mousePCSK9-D gRNA |
| 272 | GUGAAGGUGGAAGCCUUCUGGUUUAAGAGCUAUGCUGGAAACAGCAUAGCAAG UUUAAAUAAGGCUAGUCCGUUAUCAACUUGAAAAAGUGGCACCGAGUCGGUGC | gRNA-mousePCSK9-E gRNA |
| 273 | GUGGACGCGCAGGCUGCCGGGUUUAAGAGCUAUGCUGGAAACAGCAUAGCAAG UUUAAAUAAGGCUAGUCCGUUAUCAACUUGAAAAAGUGGCACCGAGUCGGUGC | gRNA-mousePCSK9-F gRNA |
| 274 | GGGGCGAGGAGAGGUGCGCGGUUUAAGAGCUAUGCUGGAAACAGCAUAGCAAG UUUAAAUAAGGCUAGUCCGUUAUCAACUUGAAAAAGUGGCACCGAGUCGGUGC | gRNA-mousePCSK9-G gRNA |
| 275 | AGUGGGUGCCCAUCGGGGCGGUUUAAGAGCUAUGCUGGAAACAGCAUAGCAAG UUUAAAUAAGGCUAGUCCGUUAUCAACUUGAAAAAGUGGCACCGAGUCGGUGC | gRNA-mousePCSK9-H gRNA |
| 276 | CUACUGUGCCCCACCGGCGCGUUUAAGAGCUAUGCUGGAAACAGCAUAGCAAG UUUAAAUAAGGCUAGUCCGUUAUCAACUUGAAAAAGUGGCACCGAGUCGGUGC | gRNA-mousePCSK9-I gRNA |
| 277 | AACcacgatcaggagtttgacccccctaaggtgtacccacccgtgccagccgagaagaggaagcccatccgcgt gctgtccctgttcgacggcatcgccacaggcctgctggtgctgaaggatctgggcatccaggtggacagatata tcgcctccgaggtgtgcgaggattctatcaccgtgggcatggtgaggcaccagggcaagatcatgtacgtgggc gacgtgcgcagcgtgacacagaagcacatccaggagtggggaccctcgacctggtcatcggaggcagcccctg taatgacctgtccatcgtgaaccctgcaaggaagggcctgtatgagggaaccggcagactgttctttgagttct acaggctgctgcacgacgcccgccctaaggagggcgatgacaggccattcttttggctgtttgagaacgtggtg gccatgggcgtgagcgacaagcgggatatctccagattcctggagtctaatccgtgatgatcgatgcaaagga ggtgtctgccgcacacagggcaaggtactttgggaaatctgcctggcatgaaccgcccactggccagcaccg tgaacgacaagctggagctgcaggagtgcctggagcacggaaggatcgccaagttctccaaggtgcggacaatc accacaagatctaacagcatcaagcagggcaaggatcagcacttccccgtgttcatgaatgagaaggaggacat cctgtggtgtaccgagatggagcgcgtgttcggctttccagtgcactatacgacgtgagcaatatgagccggc tggcaaggcagagactgctgggccggtcctggtctgtgccagtgatcagacacctgttcgccccctgaaggag tactttgcctgcgtgtcgtagcggaactctaatgccaacagcagagccctttccttttcctctggcctggtgcc actgtctctgagggcagccacatgggcccatggagatctacaagaccgtgtccgcctggaagaggcagcctg tgcgcgtgctgtctgttccgcaacatcgacaaggtgctgaagagctgggcttctggagagcggatccga tctggaggaggcaccctgaagtatgtggaggatgtgacaaatgtggtgcgagagatgtggagaagtggggccc cttcgatctggtgtacggatccacccagccactgggaagctcctgcgataggtgtccaggatggtatatgttcc agtttcacagaatcctgcagtacgcactgccaaggcaggagagccagcgccctttcttttggatctttatggac | dSpCas9-KRAB-DNTM3A/L (nt) |

| SEQ ID NO. | Sequence | Annotation |
|---|---|---|
| | aacctgctgctgacagaggatgaccaggagacaacaacccgcttcctgcagacagaggcagtgaccctgcagga<br>tgtgaggggacgcgactatcagaatgccatgcgggtgtggtctaacatccctggcctgaagagcaagcacgccc<br>ccctgacccctaaggaggaggagtacctgcaggcccaggtgcggagcagatccaagctggatgcccctaaggtg<br>gacctgctggtgaagaattgtctgctgccactgcgggagtacttcaagtactttagtcagaatagcctgccact<br>ggaggcaagcggatccggaagggcatctcctggaatcccaggaagcacccgcAACCCCAAGAAGAAGCGGAAGG<br>TGGGCATCCACGGCGTGCCCGCCGCCGACAAGAAGTACAGCATCGGCCTGGCCATCGGCACCAACAGCGTGGGC<br>TGGGCCGTGATCACCGACGAGTACAAGGTGCCCAGCAAGAAGTTCAAGGTGCTGGGCAACACCG<br>ACCGGCACAGCATCAAGAAGAACCTGATCGGCGCCCTGCTGTTCGACAGCGGCGA<br>GACCGCCGAGGCCACCCGGCTGAAGCGGACCGCCCGGCGGCGGTACACCCGGCG<br>GAAGAACCGGATCTGCTACCTGCAGGAGATCTTCAGCAACGAGATGGCCAAGGTG<br>GACGACAGCTTCTTCCACCGGCTGGAGGAGAGCTTCCTGGTGGAGGAGGACAAGA<br>AGCACGAGCGGCACCCCATCTTCGGCAACATCGTGGACGAGGTGGCCTACCACGA<br>GAAGTACCCCACCATCTACCACCTGCGGAAGAAGCTGGTGGACAGCACCGACAAG<br>GCCGACCTGCGGCTGATCTACCTGGCCCTGGCCCACATGATCAAGTTCCGGGGCC<br>ACTTCCTGATCGAGGGCGACCTGAACCCCGACAACAGCGACGTGGACAAGCTGTT<br>CATCCAGCTGGTGCAGACCTACAACCAGCTGTTCGAGGAGAACCCCATCAACGCC<br>AGCGGCGTGGACGCCAAGGCCATCCTGAGCGCCCGGCTGAGCAAGAGCCGGCGG<br>CTGGAGAACCTGATCGCCCAGCTGCCCGGCGAGAAGAAGAACGGCCTGTTCGGCA<br>ACCTGATCGCCCTGAGCCTGGGCCTGACCCCCAACTTCAAGAGCAACTTCGACCT<br>GGCCGAGGACGCCAAGCTGCAGCTGAGCAAGGACACCTACGACGACGACCTGGA<br>CAACCTGCTGGCCCAGATCGGCGACCAGTACGCCGACCTGTTCCTGGCCGCCAAG<br>AACCTGAGCGACGCCATCCTGCTGAGCGACATCCTGCGGGTGAACACCGAGATCA<br>CCAAGGCCCCCCTGAGCGCCAGCATGATCAAGCGGTACGACGAGCACCACCAGG<br>ACCTGACCCTGCTGAAGGCCCTGGTGCGGCAGCAGCTGCCCGAGAAGTACAAGGA<br>GATCTTCTTCGACCAGAGCAAGAACGGCTACGCCGGCTACATCGACGGCGGCGCC<br>AGCCAGGAGGAGTTCTACAAGTTCATCAAGCCCATCCTGGAGAAGATGGACGGCA<br>CCGAGGAGCTGCTGGTGAAGCTGAACCGGGAGGACCTGCTGCGGAAGCAGCGGA<br>CCTTCGACAACGGCAGCATCCCCCACCAGATCCACCTGGGCGAGCTGCACGCCAT<br>CCTGCGGCGGCAGGAGGACTTCTACCCCTTCCTGAAGGACAACCGGGAGAAGATC<br>GAGAAGATCCTGACCTTCCGGATCCCCTACTACGTGGGCCCCCTGGCCCGGGGCA<br>ACAGCCGGTTCGCCTGGATGACCCGGAAGAGCGAGGAGACCATCACCCCCTGGAA<br>CTTCGAGGAGGTGGTGGACAAGGGCGCCAGCGCCCAGAGCTTCATCGAGCGGATG<br>ACCAACTTCGACAAGAACCTGCCCAACGAGAAGGTGCTGCCCAAGCACAGCCTGC<br>TGTACGAGTACTTCACCGTGTACAACGAGCTGACCAAGGTGAAGTACGTGACCGA<br>GGGCATGCGGAAGCCCGCCTTCCTGAGCGGCGAGCAGAAGAAGGCCATCGTGGA<br>CCTGCTGTTCAAGACCAACCGGAAGGTGACCGTGAAGCAGCTGAAGGAGGACTAC<br>TTCAAGAAGATCGAGTGCTTCGACAGCGTGGAGATCAGCGGCGTGGAGGACCGGT<br>TCAACGCCAGCCTGGGCACCTACCACGACCTGCTGAAGATCATCAAGGACAAGGA<br>CTTCCTGGACAACGAGGAGAACGAGGACATCCTGGAGGACATCGTGCTGACCCTG<br>ACCCTGTTCGAGGACCGGGAGATGATCGAGGAGCGGCTGAAGACCTACGCCCACC<br>TGTTCGACGACAAGGTGATGAAGCAGCTGAAGCGGCGGCGGTACACCGGCTGGG<br>GCCGGCTGAGCCGGAAGCTGATCAACGGCATCCGGGACAAGCAGAGCGGCAAGA<br>CCATCCTGGACTTCCTGAAGAGCGACGGCTTCGCCAACCGGAACTTCATGCAGCT<br>GATCCACGACGACAGCCTGACCTTCAAGGAGGACATCCAGAAGGCCCAGGTGAG<br>CGGCCAGGGCGACAGCCTGCACGAGCACATCGCCAACCTGGCCGGCAGCCCCGCC<br>ATCAAGAAGGGCATCCTGCAGACCGTGAAGGTGGTGGACGAGCTGGTGAAGGTG<br>ATGGGCCGGCACAAGCCCGAGAACATCGTGATCGAGATGGCCCGGGAGAACCAG<br>ACCACCCAGAAGGGCCAGAAGAACAGCCGGGAGCGGATGAAGCGGATCGAGGAG<br>GGCATCAAGGAGCTGGGCAGCCAGATCCTGAAGGAGCACCCCGTGGAGAACACC<br>CAGCTGCAGAACGAGAAGCTGTACCTGTACTACCTGCAGAACGGCCGGGACATGT<br>ACGTGGACCAGGAGCTGGACATCAACCGGCTGAGCGACTACGACGTGGACGCCAT<br>CGTGCCCCAGAGCTTCCTGAAGGACGACAGCATCGACAACAAGGTGCTGACCCGG<br>AGCGACAAGAACCGGGGCAAGAGCGACAACGTGCCCAGCGAGGAGGTGGTGAAG<br>AAGATGAAGAACTACTGGCGGCAGCTGCTGAACGCCAAGCTGATCACCCAGCGG<br>AAGTTCGACAACCTGACCAAGGCCGAGCGGGGCGGCCTGAGCGAGCTGGACAAG<br>GCCGGCTTCATCAAGCGGCAGCTGGTGGAGACCCGGCAGATCACCAAGCACGTGG<br>CCCAGATCCTGGACAGCCGGATGAACACCAAGTACGACGAGAACGACAAGCTGA<br>TCCGGGAGGTGAAGGTGATCACCCTGAAGAGCAAGCTGGTGAGCGACTTCCGGAA<br>GGACTTCCAGTTCTACAAGGTGCGGGAGATCAACAACTACCACCACGCCCACGAC<br>GCCTACCTGAACGCCGTGGTGGGCACCGCCCTGATCAAGAAGTACCCCAAGCTGG<br>AGAGCGAGTTCGTGTACGGCGACTACAAGGTGTACGACGTGCGGAAGATGATCGC<br>CAAGAGCGAGCAGGAGATCGGCAAGGCCACCGCCAAGTACTTCTTCTACAGCAAC<br>ATCATGAACTTCTTCAAGACCGAGATCACCCTGGCCAACGGCGAGATCCGGAAGC<br>GGCCCCTGATCGAGACCAACGGCGAGACCGGCGAGATCGTGTGGGACAAGGGCC<br>GGGACTTCGCCACCGTGCGGAAGGTGCTGAGCATGCCCCAGGTGAACATCGTGAA<br>GAAGACCGAGGTGCAGACCGGCGGCTTCAGCAAGGAGAGCATCCTGCCCAAGCG<br>GAACAGCGACAAGCTGATCGCCCGGAAGAAGGACTGGGACCCCAAGAAGTACGG<br>CGGCTTCGACAGCCCCACCGTGGCCTACAGCGTGCTGGTGGTGGCCAAGGTGGAG<br>AAGGGCAAGAGCAAGAAGCTGAAGAGCGTGAAGGAGCTGCTGGGCATCACCATC<br>ATGGAGCGGAGCAGCTTCGAGAAGAACCCCATCGACTTCCTGGAGGCCAAGGGCT<br>ACAAGGAGGTGAAGAAGGACCTGATCATCAAGCTGCCCAAGTACAGCCTGTTCGA<br>GCTGGAGAACGGCCGGAAGCGGATGCTGGCCAGCGCCGGCGAGCTGCAGAAGGG<br>CAACGAGCTGGCCCTGCCCAGCAAGTACGTGAACTTCCTGTACCTGGCCAGCCAC | |

| SEQ ID NO. | Sequence | Annotation |
|---|---|---|
| | TACGAGAAGCTGAAGGGCAGCCCCGAGGACAACGAGCAGAAGCAGCTGTTCGTG<br>GAGCAGCACAAGCACTACCTGGACGAGATCATCGAGCAGATCAGCGAGTTCAGC<br>AAGCGGGTGATCCTGGCCGACGCCAACCTGGACAAGGTGCTGAGCGCCTACAACA<br>AGCACCGGGACAAGCCCATCCGGGAGCAGGCCGAGAACATCATCCACCTGTTCAC<br>CCTGACCAACCTGGGCGCCCCCGCCGCCTTCAAGTACTTCGACACCACCATCGACC<br>GGAAGCGGTACACCAGCACCAAGGAGGTGCTGGACGCCACCCTGATCCACCAGA<br>GCATCACCGGCCTGTACGAGACCCGGATCGACCTGAGCCAGCTGGGCGGCGACAG<br>CGGCGGCAAGCGGCCCGCCGCCACCAAGAAGGCCGGCCAGGCCAAGAAGAAGAA<br>GGctagCgatgCtaagtcactgactgcctggtcccggacactggtgaccttcaaggatgtgtttgtggactt<br>caccagggaggagtggaagctgctggacactgctcagcagatcctgtacagaaatgtgatgctggagaacta<br>taagaacctggtttccttgggttatcagcttactaagccagatgtgatcctccggttggagaagggagaaga<br>gccctggctggtggagagagaaattcaccaagagacccatcctgattcagagactgcatttgaaatcaaatc<br>atcagttCCGAAAAAGAAACGCAAAGTTTAG | |
| 278 | NHDQEFDPPKVYPPVPAEKRKPIRVLSLFDGIATGLLVLKDLGIQVDRYIASEVCEDSIT<br>VGMVRHQGKIMYVGDVRSVTQKHIQEWGPFDLVIGGSPCNDLSIVNPARKGLYEGTG<br>RLFFEFYRLLHDARPKEGDDRPFFWLFENVVAMGVSDKRDISRFLESNPVMIDAKEVS<br>AAHRARYFWGNLPGMNRPLASTVNDKLELQECLEHGRIAKFSKVRTITTRSNSIKQGK<br>DQHFPVFMNEKEDILWCTEMERVFGFPVHYTDVSNMSRLARQRLLGRSWSVPVIRHL<br>FAPLKEYFACVSSGNSNANSRGPSFSSGLVPLSLRGSHMGPMEIYKTVSAWKRQPVRV<br>LSLFRNIDKVLKSLGFLESGSGSGGGTLKYVEDVTNVVRRDVEKWGPFDLVYGSTQP<br>LGSSCDRCPGWYMFQFHRILQYALPRQESQRPFFWIFMDNLLLTEDDQETTTRFLQTE<br>AVTLQDVRGRDYQNAMRVWSNIPGLKSKHAPLTPKEEEYLQAQVRSRSKLDAPKVD<br>LLVKNCLLPLREYFKYFSQNSLPLEASGSGRASPGIPGSTRNPKKKRKVGIHGVPAAD<br>KKYSIGLAIGTNSVGWAVITDEYKVPSKKFKVLGNTDRHSIKKNLIGALLFDSGETAE<br>ATRLKRTARRRYTRRKNRICYLQEIFSNEMAKVDDSFFHRLEESFLVEEDKKHERHPIF<br>GNIVDEVAYHEKYPTIYHLRKKLVDSTDKADLRLIYLALAHMIKFRGHFLIEGDLNPD<br>NSDVDKLFIQLVQTYNQLFEENPINASGVDAKAILSARLSKSRRLENLIAQLPGEKKNG<br>LFGNLIALSLGLTPNFKSNFDLAEDAKLQLSKDTYDDDLDNLLAQIGDQYADLFLAAK<br>NLSDAILLSDILRVNTEITKAPLSASMIKRYDEHHQDLTLLKALVRQQLPEKYKEIFFD<br>QSKNGYAGYIDGGASQEEFYKFIKPILEKMDGTEELLVKLNREDLLRKQRTFDNGSIP<br>HQIHLGELHAILRRQEDFYPFLKDNREKIEKILTFRIPYYVGPLARGNSRFAWMTRKSE<br>ETITPWNFEEVVDKGASAQSFIERMTNFDKNLPNEKVLPKHSLLYEYFTVYNELTKVK<br>YVTEGMRKPAFLSGEQKKAIVDLLFKTNRKVTVKQLKEDYFKKIECFDSVEISGVEDR<br>FNASLGTYHDLLKIIKDKDFLDNEENEDILEDIVLTLTLFEDREMIEERLKTYAHLFDD<br>KVMKQLKRRRYTGWGRLSRKLINGIRDKQSGKTILDFLKSDGFANRNFMQLIHDDSL<br>TFKEDIQKAQVSGQGDSLHEHIANLAGSPAIKKGILQTVKVVDELVKVMGRHKPENIV<br>IEMARENQTTQKGQKNSRERMKRIEEGIKELGSQILKEHPVENTQLQNEKLYLYYLQN<br>GRDMYVDQELDINRLSDYDVDAIVPQSFLKDDSIDNKVLTRSDKNRGKSDNVPSEEV<br>VKKKMKNYWRQLLNAKLITQRKFDNLTKAERGGLSELDKAGFIKRQLVETRQITKHVA<br>QILDSRMNTKYDENDKLIREVKVITLKSKLVSDFRKDFQFYKVREINNYHHAHDAYL<br>NAVVGTALIKKYPKLESEFVYGDYKVYDVRKMIAKSEQEIGKATAKYFFYSNIMNFF<br>KTEITLANGEIRKRPLIETNGETGEIVWDKGRDFATVRKVLSMPQVNIVKKTEVQTGG<br>FSKESILPKRNSDKLIARKKDWDPKKYGGFDSPTVAYSVLVVAKVEKGKSKKLKSVK<br>ELLGITIMERSSFEKNPIDFLEAKGYKEVKKDLIIKLPKYSLFELENGRKRMLASAGELQ<br>KGNELALPSKYVNFLYLASHYEKLKGSPEDNEQKQLFVEQHKHYLDEIIEQISEFSKRV<br>ILADANLDKVLSAYNKHRDKPIREQAENIIHLFTLTNLGAPAAFKYFDTTIDRKRYTST<br>KEVLDATLIHQSITGLYETRIDLSQLGGDSGGKRPAATKKAGQAKKKKASDAKSLTA<br>WSRTLVTFKDVFVDFTREEWKLLDTAQQILYRNVMLENYKNLVSLGYQLTKPDVILR<br>LEKGEEPWLVEREIHQETHPDSETAFEIKSSVPKKKRKV | dSpCas9-<br>KRAB-<br>DNTM3A/<br>L (AA) |
| 279 | ATGAACCACGATCAGGAGTTTGACCCCCCTAAGGTGTACCCACCCGTGCCAGCCG<br>AGAAGAGGAAGCCCATCCGCGTGCTGTCCCTGTTCGACGGCATCGCCACAGGCCT<br>GCTGGTGCTGAAGGATCTGGGCATCCAGGTGGACAGATATATCGCCTCCGAGGTG<br>TGCGAGGATTCTATCACCGTGGGCATGGTGAGGCACCAGGGCAAGATCATGTACG<br>TGGGCGACGTGCGCAGCGTGACACAGAAGCACATCCAGGAGTGGGGACCCTTCG<br>ACCTGGTCATCGGAGGCAGCCCCTGTAATGACCTGTCCATCGTGAACCCTGCAAG<br>GAAGGGCCTGTATGAGGGAACCGGCAGACTGTTCTTTGAGTTCTACAGGCTGCTG<br>CACGACGCCCGCCCTAAGGAGGGCGATGACAGGCCATTCTTTTGGCTGTTTGAGA<br>ACGTGGTGGCCATGGGCGTGAGCGACAAGCGGGATATCTCCAGATTCCTGGAGTC<br>TAATCCCGTGATGATCGATGCAAAGGAGGTGTCTGCCGCACACAGGGCAAGGTAC<br>TTTTGGGGAAATCTGCCTGGCATGAACCGCCCACTGGCCAGCACCGTGAACGACA<br>AGCTGGAGCTGCAGGAGTGCCTGGAGCACGGAAGGATCGCCAAGTTCTCCAAGGT<br>GCGGACAATCACCACAAGATCTAACAGCATCAAGCAGGGCAAGGATCAGCACTTC<br>CCCGTGTTCATGAATGAGAAGGAGGACATCCTGTGGTGTACCGAGATGGAGCGCG<br>TGTTCGGCTTTCCAGTGCACTATACAGACGTGAGCAATATGAGCCGGCTGGCAAG<br>GCAGAGACTGCTGGGCCGGTCCTGGTCTGTGCCAGTGATCAGACACCTGTTCGCC<br>CCCCTGAAGGAGTACTTTGCCTGCGTGTCTAGCGGCAACTCTAATGCCAACAGCA<br>GAGGCCCTTCCTTTTCCTCTGGCCTGGTGCCACTGTCTCTGAGGGGCAGCCACATG<br>GGCCCCATGGAGATCTACAAGACCGTGTCCGCCTGGAAGAGGCAGCCTGTGCGCG<br>TGCTGTCTCTGTTCCGCAACATCGACAAGGTGCTGAAGAGCCTGGGCTTTCTGGAG<br>AGCGGATCCGGATCTGGAGGAGGCACCCTGAAGTATGTGGAGGATGTGACAAAT<br>GTGGTGCGGAGAGATGTGGAGAAGTGGGGCCCCTTCGATCTGGTGTACGGATCCA | DNMT3A/<br>L-<br>XTEN80-<br>dSpCas9-<br>KRAB (nt) |

Sequences

| SEQ ID NO. | Sequence | Annotation |
|---|---|---|
| | CCCAGCCACTGGGAAGCTCCTGCGATAGGTGTCCAGGATGGTATATGTTCCAGTTT<br>CACAGAATCCTGCAGTACGCACTGCCAAGGCAGGAGAGCCAGCGCCCTTTCTTTT<br>GGATCTTTATGGACAACCTGCTGCTGACAGAGGATGACCAGGAGACAACAACCCG<br>CTTCCTGCAGACAGAGGCAGTGACCCTGCAGGATGTGAGGGGACGCGACTATCAG<br>AATGCCATGCGGGTGTGGTCTAACATCCCTGGCCTGAAGAGCAAGCACGCCCCCC<br>TGACCCCTAAGGAGGAGGAGTACCTGCAGGCCCAGGTGCGGAGCAGATCCAAGC<br>TGGATGCCCCTAAGGTGGACCTGCTGGTGAAGAATTGTCTGCTGCCACTGCGGGA<br>GTACTTCAAGTACTTTAGTCAGAATAGCCTGCCACTGGGAGGGCCGAGCTCTGGC<br>GCACCCCCACCAAGTGGAGGGTCTCCTGCCGGGTCCCCAACATCTACTGAAGAAG<br>GCACCAGCGAATCCGCAACGCCCGAGTCAGGCCCTGGTACCTCCACAGAACCATC<br>TGAAGGTAGTGCGCCTGGTTCCCCAGCTGGAAGCCCTACTTCCACCGAAGAAGGC<br>ACGTCAACCGAACCAAGTGAAGGATCTGCCCCTGGGACCAGCACTGAACCATCTG<br>AGGTTAACCCCAAGAAGAAGCGGAAGGTGGGCATCCACGGCGTGCCCGCCGCCG<br>ACAAGAAGTACAGCATCGGCCTGGCCATCGGCACCAACAGCGTGGGCTGGGCCGT<br>GATCACCGACGAGTACAAGGTGCCCAGCAAGAAGTTCAAGGTGCTGGGCAACAC<br>CGACCGGCACAGCATCAAGAAGAACCTGATCGGCGCCCTGCTGTTCGACAGCGGC<br>GAGACCGCCGAGGCCACCCGGCTGAAGCGGACCGCCCGGCGGCGGTACACCCGG<br>CGGAAGAACCGGATCTGCTACCTGCAGGAGATCTTCAGCAACGAGATGGCCAAGG<br>TGGACGACAGCTTCTTCCACCGGCTGGAGGAGAGCTTCCTGGTGGAGGAGGACAA<br>GAAGCACGAGCGGCACCCCATCTTCGGCAACATCGTGGACGAGGTGGCCTACCAC<br>GAGAAGTACCCCACCATCTACCACCTGCGCAAGAAGCTGGTGGACAGCACCGACA<br>AGGCCGACCTGCGGCTGATCTACCTGGCCCTGGCCCACATGATCAAGTTCCGGGG<br>CCACTTCCTGATCGAGGGCGACCTGAACCCCGACAACAGCGACGTGGACAAGCTG<br>TTCATCCAGCTGGTGCAGACCTACAACCAGCTGTTCGAGGAGAACCCCATCAACG<br>CCAGCGGCGTGGACGCCAAGGCCATCCTGAGCGCCCGGCTGAGCAAGAGCCGGC<br>GGCTGGAGAACCTGATCGCCCAGCTGCCCGGCGAGAAGAAGAACGGCCTGTTCGG<br>CAACCTGATCGCCCTGAGCCTGGGCCTGACCCCCAACTTCAAGAGCAACTTCGAC<br>CTGGCCGAGGACGCCAAGCTGCAGCTGAGCAAGGACACCTACGACGACGACCTG<br>GACAACCTGCTGGCCCAGATCGGCGACCAGTACGCCGACCTGTTCCTGGCCGCCA<br>AGAACCTGAGCGACGCCATCCTGCTGAGCGACATCCTGCGGGTGAACACCGAGAT<br>CACCAAGGCCCCCCTGAGCGCCAGCATGATCAAGCGGTACGACGAGCACCACCAG<br>GACCTGACCCTGCTGAAGGCCCTGGTGCGGCAGCAGCTGCCCGAGAAGTACAAGG<br>AGATCTTCTTCGACCAGAGCAAGAACGGCTACGCCGGCTACATCGACGGCGGCGC<br>CAGCCAGGAGGAGTTCTACAAGTTCATCAAGCCCATCCTGGAGAAGATGGACGGC<br>ACCGAGGAGCTGCTGGTGAAGCTGAACCGGGAGGACCTGCTGCGGAAGCAGCGG<br>ACCTTCGACAACGGCAGCATCCCCCACCAGATCCACCTGGGCGAGCTGCACGCCA<br>TCCTGCGGCGGCAGGAGGACTTCTACCCCTTCCTGAAGGACAACCGGGAGAAGAT<br>CGAGAAGATCCTGACCTTCCGGATCCCCTACTACGTGGGCCCCCTGGCCCGGGGC<br>AACAGCCGGTTCGCCTGGATGACCCGGAAGAGCGAGGAGACCATCACCCCCTGGA<br>ACTTCGAGGAGGTGGTGGACAAGGGCGCCAGCGCCCAGAGCTTCATCGAGCGGAT<br>GACCAACTTCGACAAGAACCTGCCCAACGAGAAGGTGCTGCCCAAGCACAGCCTG<br>CTGTACGAGTACTTCACCGTGTACAACGAGCTGACCAAGGTGAAGTACGTGACCG<br>AGGGCATGCGGAAGCCCGCCTTCCTGAGCGGCGAGCAGAAGAAGGCCATCGTGG<br>ACCTGCTGTTCAAGACCAACCGGAAGGTGACCGTGAAGCAGCTGAAGGAGGACT<br>ACTTCAAGAAGATCGAGTGCTTCGACAGCGTGGAGATCAGCGGCGTGGAGGACCG<br>GTTCAACGCCAGCCTGGGCACCTACCACGACCTGCTGAAGATCATCAAGGACAAG<br>GACTTCCTGGACAACGAGGAGAACGAGGACATCCTGGAGGACATCGTGCTGACCC<br>TGACCCTGTTCGAGGACCGGGAGATGATCGAGGAGCGGCTGAAGACCTACGCCCA<br>CCTGTTCGACGACAAGGTGATGAAGCAGCTGAAGCGGCGGCGGTACACCGGCTGG<br>GGCCGGCTGAGCCGGAAGCTGATCAACGGCATCCGGGACAAGCAGAGCGGCAAG<br>ACCATCCTGGACTTCCTGAAGAGCGACGGCTTCGCCAACCGGAACTTCATGCAGC<br>TGATCCACGACGACAGCCTGACCTTCAAGGAGGACATCCAGAAGGCCCAGGTGAG<br>CGGCCAGGGCGACAGCCTGCACGAGCACATCGCCAACCTGGCCGGCAGCCCCGCC<br>ATCAAGAAGGGCATCCTGCAGACCGTGAAGGTGGTGGACGAGCTGGTGAAGGTG<br>ATGGGCCGGCACAAGCCCGAGAACATCGTGATCGAGATGGCCCGGGAGAACCAG<br>ACCACCCAGAAGGGCCAGAAGAACAGCCGGGAGCGGATGAAGCGGATCGAGGAG<br>GGCATCAAGGAGCTGGGCAGCCAGATCCTGAAGGAGCACCCCGTGGAGAACACC<br>CAGCTGCAGAACGAGAAGCTGTACCTGTACTACCTGCAGAACGGCCGGGACATGT<br>ACGTGGACCAGGAGCTGGACATCAACCGGCTGAGCGACTACGACGTGGACGCCAT<br>CGTGCCCCAGAGCTTCCTGAAGGACGACAGCATCGACAACAAGGTGCTGACCCGG<br>AGCGACAAGAACCGGGGCAAGAGCGACAACGTGCCCAGCGAGGAGGTGGTGAAG<br>AAGATGAAGAACTACTGGCGGCAGCTGCTGAACGCCAAGCTGATCACCCAGCGG<br>AAGTTCGACAACCTGACCAAGGCCGAGCGGGGCGGCCTGAGCGAGCTGGACAAG<br>GCCGGCTTCATCAAGCGGCAGCTGGTGGAGACCCGGCAGATCACCAAGCACGTGG<br>CCCAGATCCTGGACAGCCGGATGAACACCAAGTACGACGAGAACGACAAGCTGA<br>TCCGGGAGGTGAAGGTGATCACCCTGAAGAGCAAGCTGGTGAGCGACTTCCGGAA<br>GGACTTCCAGTTCTACAAGGTGCGGGAGATCAACAACTACCACCACGCCCACGAC<br>GCCTACCTGAACGCCGTGGTGGGCACCGCCCTGATCAAGAAGTACCCCAAGCTGG<br>AGAGCGAGTTCGTGTACGGCGACTACAAGGTGTACGACGTGCGGAAGATGATCGC<br>CAAGAGCGAGCAGGAGATCGGCAAGGCCACCGCCAAGTACTTCTTCTACAGCAAC<br>ATCATGAACTTCTTCAAGACCGAGATCACCCTGGCCAACGGCGAGATCCGGAAGC<br>GGCCCCTGATCGAGACCAACGGCGAGACCGGCGAGATCGTGTGGGACAAGGGCC<br>GGGACTTCGCCACCGTGCGGAAGGTGCTGAGCATGCCCCAGGTGAACATCGTGAA | |

| SEQ ID NO. | Sequence | Annotation |
|---|---|---|
| | GAAGACCGAGGTGCAGACCGGCGGCTTCAGCAAGGAGAGCATCCTGCCCAAGCG<br>GAACAGCGACAAGCTGATCGCCCGGAAGAAGGACTGGGACCCCAAGAAGTACGG<br>CGGCTTCGACAGCCCCACCGTGGCCTACAGCGTGCTGGTGGTGGCCAAGGTGGAG<br>AAGGGCAAGAGCAAGAAGCTGAAGAGCGTGAAGGAGCTGCTGGGCATCACCATC<br>ATGGAGCGGAGCAGCTTCGAGAAGAACCCCATCGACTTCCTGGAGGCCAAGGGCT<br>ACAAGGAGGTGAAGAAGGACCTGATCATCAAGCTGCCCAAGTACAGCCTGTTCGA<br>GCTGGAGAACGGCCGGAAGCGGATGCTGGCCAGCGCCGGCGAGCTGCAGAAGGG<br>CAACGAGCTGGCCCTGCCCAGCAAGTACGTGAACTTCCTGTACCTGGCCAGCCAC<br>TACGAGAAGCTGAAGGGCAGCCCCGAGGACAACGAGCAGAAGCAGCTGTTCGTG<br>GAGCAGCACAAGCACTACCTGGACGAGATCATCGAGCAGATCAGCGAGTTCAGC<br>AAGCGGGTGATCCTGGCCGACGCCAACCTGGACAAGGTGCTGAGCGCCTACAACA<br>AGCACCGGGACAAGCCCATCCGGGAGCAGGCCGAGAACATCATCCACCTGTTCAC<br>CCTGACCAACCTGGGCGCCCCCGCCGCCTTCAAGTACTTCGACACCACCATCGACC<br>GGAAGCGGTACACCAGCACCAAGGAGGTGCTGGACGCCACCCTGATCCACCAGA<br>GCATCACCGGCCTGTACGAGACCCGGATCGACCTGAGCCAGCTGGGCGGCGACAG<br>CGGCGGCAAGCGGCCCGCCGCCACCAAGAAGGCCGGCCAGGCCAAGAAGAAGAA<br>GGctagCgatgctaagtcactgactgcctggtcccggacactggtgaccttcaaggatgtgtttgtggacttc<br>accagggaggagtggaagctgctggacactgctcagcagatcctgtacagaaatgtgatgctggagaactata<br>agaacctggtttccttgggttatcagcttactaagccagatgtgatcctccggttggagaagggagaagagcc<br>ctggctggtggagagagaaattcaccaagagacccatcctgattcagagactgcatttgaaatcaaatcatca<br>gttCCGAAAAAGAAACGCAAAGTTTAG | |
| 280 | MNHDQEFDPPKVYPPVPAEKRKPIRVLSLFDGIATGLLVLKDLGIQVDRYIASEVCEDS<br>ITVGMVRHQGKIMYVGDVRSVTQKHIQEWGPFDLVIGGSPCNDLSIVNPARKGLYEG<br>TGRLFFEFYRLLHDARPKEGDDRPFFWLFENVVAMGVSDKRDISRFLESNPVMIDAKE<br>VSAAHRARYFWGNLPGMNRPLASTVNDKLELQECLEHGRIAKFSKVRTITTRSNSIKQ<br>GKDQHFPVFMNEKEDILWCTEMERVFGFPVHYTDVSNMSRLARQRLLGRSWSVPIR<br>HLFAPLKEYFACVSSGNSNANSRGPSFSSGLVPLSLRGSHMGPMEIYKTVSAWKRQPV<br>RVLSLFRNIDKVLKSLGFLESGSGSGGGTLKYVEDVTNVVRRDVEKWGPFDLVYGST<br>QPLGSSCDRCPGWYMFQFHRILQYALPRQESQRPFFWIFMDNLLLTEDDQETTRFLQ<br>TEAVTLQDVRGRDYQNAMRVWSNIPGLKSKHAPLTPKEEEYLQAQVRSRSKLDAPK<br>VDLLVKNCLLPLREYFKYFSQNSLPLGGPSSGAPPPSGGSPAGSPTSTEEGTSESATPES<br>GPGTSTEPSEGSAPGSPAGSPTSTEEGTSTEPSEGSAPGTSTEPSEVNPKKKRKVGIHGV<br>PAADKKYSIGLAIGTNSVGWAVITDEYKVPSKKFKVLGNTDRHSIKKNLIGALLFDSG<br>ETAEATRLKRTARRRYTRRKNRICYLQEIFSNEMAKVDDSFFHRLEESFLVEEDKKHE<br>RHPIFGNIVDEVAYHEKYPTIYHLRKKLVDSTDKADLRLIYLALAHMIKFRGHFLIEGD<br>LNPDNSDVDKLFIQLVQTYNQLFEENPINASGVDAKAILSARLSKSRRLENLIAQLPGE<br>KKNGLFGNLIALSLGLTPNFKSNFDLAEDAKLQLSKDTYDDDLDNLLAQIGDQYADL<br>FLAAKNLSDAILLSDILRVNTEITKAPLSASMIKRYDEHHQDLTLLKALVRQQLPEKYK<br>EIFFDQSKNGYAGYIDGGASQEEFYKFIKPILEKMDGTEELLVKLNREDLLRKQRTFDN<br>GSIPHQIHLGELHAILRRQEDFYPFLKDNREKIEKILTFRIPYYVGPLARGNSRFAWMTR<br>KSEETITPWNFEEVVDKGASAQSFIERMTNFDKNLPNEKVLPKHSLLYEYFTVYNELT<br>KVKYVTEGMRKPAFLSGEQKKAIVDLLFKTNRKVTVKQLKEDYFKKIECFDSVEISGV<br>EDRFNASLGTYHDLLKIIKDKDFLDNEENEDILEDIVLTLTLFEDREMIEERLKTYAHLF<br>DDKVMKQLKRRRYTGWGRLSRKLINGIRDKQSGKTILDFLKSDGFANRNFMQLIHDD<br>SLTFKEDIQKAQVSGQGDSLHEHIANLAGSPAIKKGILQTVKVVDELVKVMGRHKPEN<br>IVIEMARENQTTQKGQKNSRERMKRIEEGIKELGSQILKEHPVENTQLQNEKLYLYYL<br>QNGRDMYVDQELDINRLSDYDVDAIVPQSFLKDDSIDNKVLTRSDKNRGKSDNVPSE<br>EVVKKMKNYWRQLLNAKLITQRKFDNLTKAERGGLSELDKAGFIKRQLVETRQITKH<br>VAQILDSRMNTKYDENDKLIREVKVITLKSKLVSDFRKDFQFYKVREINNYHHAHDA<br>YLNAVVGTALIKKYPKLESEFVYGDYKVYDVRKMIAKSEQEIGKATAKYFFYSNIMN<br>FFKTEITLANGEIRKRPLIETNGETGEIVWDKGRDFATVRKVLSMPQVNIVKKTEVQTG<br>GFSKESILPKRNSDKLIARKKDWDPKKYGGFDSPTVAYSVLVVAKVEKGKSKKLKSV<br>KELLGITIMERSSFEKNPIDFLEAKGYKEVKKDLIIKLPKYSLFELENGRKRMLASAGEL<br>QKGNELALPSKYVNFLYLASHYEKLKGSPEDNEQKQLFVEQHKHYLDEIIEQISEFSKR<br>VILADANLDKVLSAYNKHRDKPIREQAENIIHLFTLTNLGAPAAFKYFDTTIDRKRYTS<br>TKEVLDATLIHQSITGLYETRIDLSQLGGDSGGKRPAATKKAGQAKKKKASDAKSLTA<br>WSRTLVTFKDVFVDFTREEWKLLDTAQQILYRNVMLENYKNLVSLGYQLTKPDVILR<br>LEKGEEPWLVEREIHQETHPDSETAFEIKSSVPKKKRKV | DNMT3A/<br>L-<br>XTEN80-<br>dSpCas9-<br>KRAB<br>(AA) |
| 281 | AGTAACCATGACCAGGAATTTGACCCCCCAAAGGTTTACCCACCTGTGCCAGCTG<br>AGAAGAGGAAGCCCATCCGCGTGCTGTCTCTCTTTGATGGGATTGCTACAGGGCT<br>CCTGGTGCTGAAGGACCTGGGCATCCAAGTGGACCGCTACATTGCCTCCGAGGTG<br>TGTGAGGACTCCATCACGGTGGGCATGGTGCGGCACCAGGGAAAGATCATGTACG<br>TCGGGGACGTCCGCAGCGTCACACAGAAGCATATCCAGGAGTGGGGCCCATTCGA<br>CCTGGTGATTGGAGGCAGTCCCTGCAATGACCTCTCCATTGTCAACCCTGCCCGCA<br>AGGGACTTTATGAGGGTACTGGCCGCCTCTTCTTTGAGTTCTACCGCCTCCTGCAT<br>GATGCGCGGCCCAAGGAGGGAGATGATCGCCCCTTCTTCTGGCTCTTTGAGAATG<br>TGGTGGCCATGGGCGTTAGTGACAAGAGGGACATCTCGCGATTTCTTGAGTCTAA<br>CCCCGTGATGATTGACGCCAAAGAAGTGTCTGCTGCACACAGGGCCCGTTACTTCT<br>GGGGTAACCTTCCTGGCATGAACAGGCCTTTGGCATCCACTGTGAATGATAAGCT<br>GGAGCTGCAAGAGTGTCTGGAGCACGGCAGAATAGCCAAGTTCAGCAAAGTGAG<br>GACCATTACCACCAGGTCAAACTCTATAAAGCAGGGCAAAGACCAGCATTTCCCC | DNMT3A/<br>L (CRISPR<br>OFF)-<br>XTEN80-<br>dSpCas9-<br>KRAB (nt) |

-continued

| SEQ ID NO. | Sequence | Annotation |
|---|---|---|
| | GTCTTCATGAACGAGAAGGAGGACATCCTGTGGTGCACTGAAATGGAAAGGGTGT<br>TTGGCTTCCCCGTCCACTACACAGACGTCTCCAACATGAGCCGCTTGGCGAGGCA<br>GAGACTGCTGGGCCGATCGTGGAGCGTGCCGGTCATCCGCCACCTCTTCGCTCCGC<br>TGAAGGAATATTTTGCTTGTGTGTCTAGCGGCAATAGTAACGCTAACAGCCGCGG<br>GCCGAGCTTCAGCAGCGGCCTGGTGCCGTTAAGCTTGCGCGGCAGCCATATGGGC<br>CCTATGGAGATATACAAGACAGTGTCTGCATGGAAGAGACAGCCAGTGCGGGTAC<br>TGAGCCTCTTCAGAAACATCGACAAGGTACTAAAGAGTTTGGGCTTCTTGGAAAG<br>CGGTTCTGGTTCTGGGGGAGGAACGCTGAAGTACGTGGAAGATGTCACAAATGTC<br>GTGAGGAGAGACGTGGAGAAATGGGGCCCCTTTGACCTGGTGTACGGCTCGACGC<br>AGCCCCTAGGCAGCTCTTGTGATCGCTGTCCCGGCTGGTACATGTTCCAGTTCCAC<br>CGGATCCTGCAGTATGCGCTGCCTCGCCAGGAGAGTCAGCGGCCCTTCTTCTGGAT<br>ATTCATGGACAATCTGCTGCTGACTGAGGATGACCAAGAGACAACTACCCGCTTC<br>CTTCAGACAGAGGCTGTGACCCTCCAGGATGTCCGTGGCAGAGACTACCAGAATG<br>CTATGCGGGTGTGGAGCAACATTCCAGGGCTGAAGAGCAAGCATGCGCCCCTGAC<br>CCCAAAGGAAGAAGAGTATCTGCAAGCCCAAGTCAGAAGCAGGAGCAAGCTGGA<br>CGCCCCGAAAGTTGACCTCCTGGTGAAGAACTGCCTTCTCCCGCTGAGAGAGTAC<br>TTCAAGTATTTTTCTCAAAACTCACTTCCTCTTGGAGGGCCGAGCTCTGGCGCACC<br>CCCACCAAGTGGAGGGTCTCCTGCCGGGTCCCCAACATCTACTGAAGAAGGCACC<br>AGCGAATCCGCAACGCCCGAGTCAGGCCCTGGTACCTCCACAGAACCATCTGAAG<br>GTAGTGCGCCTGGTTCCCCAGCTGGAAGCCCTACTTCCACCGAAGAAGGCACGTC<br>AACCGAACCAAGTGAAGGATCTGCCCCTGGGACCAGCACTGAACCATCTGAGGTT<br>AACCCCAAGAAGAAGCGGAAGGTGGGCATCCACGGCGTGCCCGCCGCCGACAAG<br>AAGTACAGCATCGGCCTGGCCATCGGCACCAACAGCGTGGGCTGGGCCGTGATCA<br>CCGACGAGTACAAGGTGCCCAGCAAGAAGTTCAAGGTGCTGGGCAACACCGACC<br>GGCACAGCATCAAGAAGAACCTGATCGGCGCCCTGCTGTTCGACAGCGGCGAGAC<br>CGCCGAGGCCACCCGGCTGAAGCGGACCGCCCGGCGGCGGTACACCCGGCGGAA<br>GAACCGGATCTGCTACCTGCAGGAGATCTTCAGCAACGAGATGGCCAAGGTGGAC<br>GACAGCTTCTTCCACCGGCTGGAGGAAGAGCTTCCTGGTGGAGGAGGACAAGAAGC<br>ACGAGCGGCACCCCATCTTCGGCAACATCGTGGACGAGGTGGCCTACCACGAGAA<br>GTACCCCACCATCTACCACCTGCGGAAGAAGCTGGTGGACAGCACCGACAAGGCC<br>GACCTGCGGCTGATCTACCTGGCCCTGGCCCACATGATCAAGTTCCGGGGCCACTT<br>CCTGATCGAGGGCGACCTGAACCCCGACAACAGCGACGTGGACAAGCTGTTCATC<br>CAGCTGGTGCAGACCTACAACCAGCTGTTCGAGGAGAACCCCATCAACGCCAGCG<br>GCGTGGACGCCAAGGCCATCCTGAGCGCCCGGCTGAGCAAGAGCCGGCGGCTGG<br>AGAACCTGATCGCCCAGCTGCCCGGCGAGAAGAAGAACGGCCTGTTCGGCAACCT<br>GATCGCCCTGAGCCTGGGCCTGACCCCCAACTTCAAGAGCAACTTCGACCTGGCC<br>GAGGACGCCAAGCTGCAGCTGAGCAAGGACACCTACGACGACGACCTGGACAAC<br>CTGCTGGCCCAGATCGGCGACCAGTACGCCGACCTGTTCCTGGCCGCCAAGAACC<br>TGAGCGACGCCATCCTGCTGAGCGACATCCTGCGGGTGAACACCGAGATCACCAA<br>GGCCCCCCTGAGCGCCAGCATGATCAAGCGGTACGACGAGCACCACCAGGACCTG<br>ACCCTGCTGAAGGCCCTGGTGCGGCAGCAGCTGCCCGAGAAGTACAAGGAGATCT<br>TCTTCGACCAGAGCAAGAACGGCTACGCCGGCTACATCGACGGCGGCGCCAGCCA<br>GGAGGAGTTCTACAAGTTCATCAAGCCCATCCTGGAGAAGATGGACGGCACCGAG<br>GAGCTGCTGGTGAAGCTGAACCGGGAGGACCTGCTGCGGAAGCAGCGGACCTTCG<br>ACAACGGCAGCATCCCCCACCAGATCCACCTGGGCGAGCTGCACGCCATCCTGCG<br>GCGGCAGGAGGACTTCTACCCCTTCCTGAAGGACAACCGGGAGAAGATCGAGAA<br>GATCCTGACCTTCCGGATCCCCTACTACGTGGGCCCCCTGGCCCGGGGCAACAGC<br>CGGTTCGCCTGGATGACCCGGAAGAGCGAGGAGACCATCACCCCCTGGAACTTCG<br>AGGAGGTGGTGGACAAGGGCGCCAGCGCCCAGAGCTTCATCGAGCGGATGACCA<br>ACTTCGACAAGAACCTGCCCAACGAGAAGGTGCTGCCCAAGCACAGCCTGCTGTA<br>CGAGTACTTCACCGTGTACAACGAGCTGACCAAGGTGAAGTACGTGACCGAGGGC<br>ATGCGGAAGCCCGCCTTCCTGAGCGGCGAGCAGAAGAAGGCCATCGTGGACCTGC<br>TGTTCAAGACCAACCGGAAGGTGACCGTGAAGCAGCTGAAGGAGGACTACTTCAA<br>GAAGATCGAGTGCTTCGACAGCGTGGAGATCAGCGGCGTGGAGGACCGGTTCAAC<br>GCCAGCCTGGGCACCTACCACGACCTGCTGAAGATCATCAAGGACAAGGACTTCC<br>TGGACAACGAGGAGAACGAGGACATCCTGGAGGACATCGTGCTGACCCTGACCCT<br>GTTCGAGGACCGGGAGATGATCGAGGAGCGGCTGAAGACCTACGCCCACCTGTTC<br>GACGACAAGGTGATGAAGCAGCTGAAGCGGCGGCGGTACACCGGCTGGGGCCGG<br>CTGAGCCGGAAGCTGATCAACGGCATCCGGGACAAGCAGAGCGGCAAGACCATC<br>CTGGACTTCCTGAAGAGCGACGGCTTCGCCAACCGGAACTTCATGCAGCTGATCC<br>ACGACGACAGCCTGACCTTCAAGGAGGACATCCAGAAGGCCCAGGTGAGCGGCC<br>AGGGCGACAGCCTGCACGAGCACATCGCCAACCTGGCCGGCAGCCCCGCCATCAA<br>GAAGGGCATCCTGCAGACCGTGAAGGTGGTGGACGAGCTGGTGAAGGTGATGGG<br>CCGGCACAAGCCCGAGAACATCGTGATCGAGATGGCCCGGGAGAACCAGACCAC<br>CCAGAAGGGCCAGAAGAACAGCCGGGAGCGGATGAAGCGGATCGAGGAGGGCAT<br>CAAGGAGCTGGGCAGCCAGATCCTGAAGGAGCACCCCGTGGAGAACACCCAGCT<br>GCAGAACGAGAAGCTGTACCTGTACTACCTGCAGAACGGCCGGGACATGTACGTG<br>GACCAGGAGCTGGACATCAACCGGCTGAGCGACTACGACGTGGACGCCATCGTGC<br>CCCAGAGCTTCCTGAAGGACGACAGCATCGACAACAAGGTGCTGACCCGGAGCG<br>ACAAGAACCGGGGCAAGAGCGACAACGTGCCCAGCGAGGAGGTGGTGAAGAAGA<br>TGAAGAACTACTGGCGGCAGCTGCTGAACGCCAAGCTGATCACCCAGCGGAAGTT<br>CGACAACCTGACCAAGGCCGAGCGGGGCGGCCTGAGCGAGCTGGACAAGGCCGG<br>CTTCATCAAGCGGCAGCTGGTGGAGACCCGGCAGATCACCAAGCACGTGGCCCAG | |

| SEQ ID NO. | Sequence | Annotation |
|---|---|---|
| | ATCCTGGACAGCCGGATGAACACCAAGTACGACGAGAACGACAAGCTGATCCGG<br>GAGGTGAAGGTGATCACCCTGAAGAGCAAGCTGGTGAGCGACTTCCGGAAGGAC<br>TTCCAGTTCTACAAGGTGCGGGAGATCAACAACTACCACCACGCCCACGACGCCT<br>ACCTGAACGCCGTGGTGGGCACCGCCCTGATCAAGAAGTACCCCAAGCTGGAGAG<br>CGAGTTCGTGTACGGCGACTACAAGGTGTACGACGTGCGGAAGATGATCGCCAAG<br>AGCGAGCAGGAGATCGGCAAGGCCACCGCCAAGTACTTCTTCTACAGCAACATCA<br>TGAACTTCTTCAAGACCGAGATCACCCTGGCCAACGGCGAGATCCGGAAGCGGCC<br>CCTGATCGAGACCAACGGCGAGACCGGCGAGATCGTGTGGGACAAGGGCCGGGA<br>CTTCGCCACCGTGCGGAAGGTGCTGAGCATGCCCCAGGTGAACATCGTGAAGAAG<br>ACCGAGGTGCAGACCGGCGGCTTCAGCAAGGAGAGCATCCTGCCCAAGCGGAAC<br>AGCGACAAGCTGATCGCCCGGAAGAAGGACTGGGACCCCAAGAAGTACGGCGGC<br>TTCGACAGCCCCACCGTGGCCTACAGCGTGCTGGTGGTGGCCAAGGTGGAGAAGG<br>GCAAGAGCAAGAAGCTGAAGAGCGTGAAGGAGCTGCTGGGCATCACCATCATGG<br>AGCGGAGCAGCTTCGAGAAGAACCCCATCGACTTCCTGGAGGCCAAGGGCTACAA<br>GGAGGTGAAGAAGGACCTGATCATCAAGCTGCCCAAGTACAGCCTGTTCGAGCTG<br>GAGAACGGCCGGAAGCGGATGCTGGCCAGCGCCGGCGAGCTGCAGAAGGGCAAC<br>GAGCTGGCCCTGCCCAGCAAGTACGTGAACTTCCTGTACCTGGCCAGCCACTACG<br>AGAAGCTGAAGGGCAGCCCCGAGGACAACGAGCAGAAGCAGCTGTTCGTGGAGC<br>AGCACAAGCACTACCTGGACGAGATCATCGAGCAGATCAGCGAGTTCAGCAAGC<br>GGGTGATCCTGGCCGACGCCAACCTGGACAAGGTGCTGAGCGCCTACAACAAGCA<br>CCGGGACAAGCCCATCCGGGAGCAGGCCGAGAACATCATCCACCTGTTCACCCTG<br>ACCAACCTGGGCGCCCCCGCCGCCTTCAAGTACTTCGACACCACCATCGACCGGA<br>AGCGGTACACCAGCACCAAGGAGGTGCTGGACGCCACCCTGATCCACCAGAGCAT<br>CACCGGCCTGTACGAGACCCGGATCGACCTGAGCCAGCTGGGCGGCGACAGCGGC<br>GGCAAGCGGCCCGCCGCCACCAAGAAGGCCGGCCAGGCCAAGAAGAAGAAGGcta<br>gCgatgctaagtcactgactgcctggtcccggacactggtgaccttcaaggatgtgtttgtggacttcacca<br>gggaggagtggaagctgctggacactgctcagcagatcctgtacagaaatgtgatgctggagaactataaga<br>acctggtttccttgggttatcagcttactaagccagatgtgatcctccggttggagaagggagaagagccct<br>ggctggtggagagagaaattcaccaagagacccatcctgattcagagactgcatttgaaatcaaatcatcag<br>ttCCGAAAAAGAAACGCAAAGTTTAG | |
| 282 | SNHDQEFDPPKVYPPVPAEKRKPIRVLSLFDGIATGLLVLKDLGIQVDRYIASEVCEDSI<br>TVGMVRHQGKIMYVGDVRSVTQKHIQEWGPFDLVIGGSPCNDLSIVNPARKGLYEGT<br>GRLFFEFYRLLHDARPKEGDDRPFFWLFENVVAMGVSDKRDISRFLESNPVMIDAKEV<br>SAAHRARYFWGNLPGMNRPLASTVNDKLELQECLEHGRIAKFSKVRTITTRSNSIKQG<br>KDQHFPVFMNEKEDILWCTEMERVFGFPVHYTDVSNMSRLARQRLLGRSWSVPVIRH<br>LFAPLKEYFACVSSGNSNANSRGPSFSSGLVPLSLRGSHMGPMEIYKTVSAWKRQPVR<br>VLSLFRNIDKVLKSLGFLESGSGSGGGTLKYVEDVTNVVRRDVEKWGPFDLVYGSTQ<br>PLGSSCDRCPGWYMFQFHRILQYALPRQESQRPFFWIFMDNLLLTEDDQETTTRFLQT<br>EAVTLQDVRGRDYQNAMRVWSNIPGLKSKHAPLTPKEEEYLQAQVRSRSKLDAPKV<br>DLLVKNCLLPLREYFKYFSQNSLPLGGPSSGAPPPSGGSPAGSPTSTEEGTSESATPESG<br>PGTSTEPSEGSAPGSPAGSPTSTEEGTSTEPSEGSAPGTSTEPSEVNPKKKRKVGIHGVP<br>AADKKYSIGLAIGTNSVGWAVITDEYKVPSKKFKVLGNTDRHSIKKNLIGALLFDSGE<br>TAEATRLKRTARRRYTRRKNRICYLQEIFSNEMAKVDDSFFHRLEESFLVEEDKKHER<br>HPIFGNIVDEVAYHEKYPTIYHLRKKLVDSTDKADLRLIYLALAHMIKFRGHFLIEGDL<br>NPDNSDVDKLFIQLVQTYNQLFEENPINASGVDAKAILSARLSKSRRLENLIAQLPGEK<br>KNGLFGNLIALSLGLTPNFKSNFDLAEDAKLQLSKDTYDDDLDNLLAQIGDQYADLFL<br>AAKNLSDAILLSDILRVNTEITKAPLSASMIKRYDEHHQDLTLLKALVRQQLPEKYKEI<br>FFDQSKNGYAGYIDGGASQEEFYKFIKPILEKMDGTEELLVKLNREDLLRKQRTFDNG<br>SIPHQIHLGELHAILRRQEDFYPFLKDNREKIEKILTFRIPYYVGPLARGNSRFAWMTRK<br>SEETITPWNFEEVVDKGASAQSFIERMTNFDKNLPNEKVLPKHSLLYEYFTVYNELTK<br>VKYVTEGMRKPAFLSGEQKKAIVDLLFKTNRKVTVKQLKEDYFKKIECFDSVEISGVE<br>DRFNASLGTYHDLLKIIKDKDFLDNEENEDILEDIVLTLTLFEDREMIEERLKTYAHLF<br>DDKVMKQLKRRRYTGWGRLSRKLINGIRDKQSGKTILDFLKSDGFANRNFMQLIHDD<br>SLTFKEDIQKAQVSGQGDSLHEHIANLAGSPAIKKGILQTVKVVDELVKVMGRHKPEN<br>IVIEMARENQTTQKGQKNSRERMKRIEEGIKELGSQILKEHPVENTQLQNEKLYLYYL<br>QNGRDMYVDQELDINRLSDYDVDAIVPQSFLKDDSIDNKVLTRSDKNRGKSDNVPSE<br>EVVKKMKNYWRQLLNAKLITQRKFDNLTKAERGGLSELDKAGFIKRQLVETRQITKH<br>VAQILDSRMNTKYDENDKLIREVKVITLKSKLVSDFRKDFQFYKVREINNYHHAHDA<br>YLNAVVGTALIKKYPKLESEFVYGDYKVYDVRKMIAKSEQEIGKATAKYFFYSNIMN<br>FFKTEITLANGEIRKRPLIETNGETGEIVWDKGRDFATVRKVLSMPQVNIVKKTEVQTG<br>GFSKESILPKRNSDKLIARKKDWDPKKYGGFDSPTVAYSVLVVAKVEKGKSKKLKSV<br>KELLGITIMERSSFEKNPIDFLEAKGYKEVKKDLIIKLPKYSLFELENGRKRMLASAGEL<br>QKGNELALPSKYVNFLYLASHYEKLKGSPEDNEQKQLFVEQHKHYLDEIIEQISEFSKR<br>VILADANLDKVLSAYNKHRDKPIREQAENIIHLFTLTNLGAPAAFKYFDTTIDRKRYTS<br>TKEVLDATLIHQSITGLYETRIDLSQLGGDSGGKRPAATKKAGQAKKKKASDAKSLTA<br>WSRTLVTFKDVFVDFTREEWKLLDTAQQILYRNVMLENYKNLVSLGYQLTKPDVILR<br>LEKGEEPWLVEREIHQETHPDSETAFEIKSSVPKKKRKV | DNMT3A/<br>L (CRISPR<br>OFF)-<br>XTEN80-<br>dSpCas9-<br>KRAB<br>(AA) |
| 283 | MGQTGKKSEKGPVCWRKRVKSEYMRLRQLKRFRRADEVKTMFSSNRQKILERTETL<br>NQEWKQRRIQPVHIMTSVSSLRGTRECSVTSDLDFPAQVIPLKTLNAVASVPIMYSWS<br>PLQQNFMVEDETVLHNIPYMGDEVLDQDGTFIEELIKNYDGKVHGDRECGFINDEIFV<br>ELVNALGQYNDDDDDDGDDPDEREEKQKDLEDNRDDKETCPPRKFPADKIFEAISS | EZH2 (AA) |

| SEQ ID NO. | Sequence | Annotation |
|---|---|---|
|  | MFPDKGTAEELKEKYKELTEQQLPGALPPECTPNIDGPNAKSVQREQSLHSFHTLFCR RCFKYDCFLHPFHATPNTYKRKNTETALDNKPCGPQCYQHLEGAKEFAAALTAERIK TPPKRPGGRRRGRLPNNSSRPSTPTISVLESKDTDSDREAGTETGGENNDKEEEEKKDE TSSSSEANSRCQTPIKMKPNIEPPENVEWSGAEASMFRVLIGTYYDNFCAIARLIGTKT CRQVYEFRVKESSIIAPVPTEDVDTPPRKKKRKHRLWAAHCRKIQLKKDGSSNHVYN YQPCDHPRQPCDSSCPCVIAQNFCEKFCQCSSECQNRFPGCRCKAQCNTKQCPCYLAV RECDPDLCLTCGAADHWDSKNVSCKNCSIQRGSKKHLLLAPSDVAGWGIFIKDPVQK NEFISEYCGEIISQDEADRRGKVYDKYMCSFLFNLNNDFVVDATRKGNKIRFANHSVN PNCYAKVMMVNGDHRIGIFAKRAIQTGEELFFDYRYSQADALKYVGIEREMEIP |  |
| 284 | MPAMPSSGPGDTSSSAAEREEDRKDGEEQEEPRGKEERQEPSTTARKVGRPG RKRKHPPVESGDTPKDPAVISKSPSMAQDSGASELLPNGDLEKRSEPQPEEGS PAGGQKGGAPAEGEGAAETLPEASRAVENGCCTPKEGRGAPAEAGKEQKET NIESMKMEGSRGRLRGGLGWESSLRQRPMPRLTFQAGDPYYISKRKRDEWL ARWKREAEKKAKVIAGMNAVEENQGPGESQKVEEASPPAVQQPTDPASPTV ATTPEPVGSDAGDKNATKAGDDEPEYEDGRGFGIGELVWGKLRGFSWWPGR IVSWWMTGRSRAAEGTRWVMWFGDGKFSVVCVEKLMPLSSFCSAFHQATY NKQPMYRKAIYEVLQVASSRAGKLFPVCHDSDESDTAKAVEVQNKPMIEWA LGGFQPSGPKGLEPPEEEKNPYKEVYTDMWVEPEAAAYAPPPPAKKPRKSTA EKPKVKEIIDERTRERLVYEVRQKCRNIEDICISCGSLNVTLEHPLFVGGMCQN CKNCFLECAYQYDDDGYQSYCTICCGGREVLMCGNNNCCRCFCVECVDLLV GPGAAQAAIKEDPWNCYMCGHKGTYGLLRRREDWPSRLQMFFANNHDQEF DPPKVYPPVPAEKRKPIRVLSLFDGIATGLLVLKDLGIQVDRYIASEVCEDSIT VGMVRHQGKIMYVGDVRSVTQKHIQEWGPFDLVIGGSPCNDLSIVNPARKG LYEGTGRLFFEFYRLLHDARPKEGDDRPFFWLFENVVAMGVSDKRDISRFLE SNPVMIDAKEVSAAHRARYFWGNLPGMNRPLASTVNDKLELQECLEHGRIA KFSKVRTITTRSNSIKQGKDQHFPVFMNEKEDILWCTEMERVFGFPVHYTDVS NMSRLARQRLLGRSWSVPVIRHLFAPLKEYFA | DNMT3A (AA) |
| 285 | NHDQEFDPPKVYPPVPAEKRKPIRVLSLFDGIATGLLVLKDLGIQVDRYIASEV CEDSITVGMVRHQGKIMYVGDVRSVTQKHIQEWGPFDLVIGGSPCNDLSIVN PARKGLYEGTGRLFFEFYRLLHDARPKEGDDRPFFWLFENVVAMGVSDKRDI SRFLESNPVMIDAKEVSAAHRARYFWGNLPGMNRPLASTVNDKLELQECLE HGRIAKFSKVRTITTRSNSIKQGKDQHFPVFMNEKEDILWCTEMERVFGFPVH YTDVSNMSRLARQRLLGRSWSVPVIRHLFAPLKEYFACV | Human DNMT3A |
| 286 | MGPMEIYKTVSAWKRQPVRVLSLFRNIDKVLKSLGFLESGSGSGGTLKYVE DVTNVVRRDVEKWGPFDLVYGSTQPLGSSCDRCPGWYMFQFHRILQYALPR QESQRPFFWIFMDNLLLTEDDQETTTRFLQTEAVTLQDVRGRDYQNAMRVW SNIPGLKSKHAPLTPKEEEYLQAVRSRSKLDAPKVDLLVKNCLLPLREYFKY FSQNSLPL | Murine DNMT3L |
| 287 | MNPLEMFETVPVWRRQPVRVLSLFEDIKKELTSLGFLESGSDPGQLKHVVDV TDTVRKDVEEWGPFDL VYGATPPLGHTCDRPPSWYLFQFHRLLQYARPKPGSPRPFFWMFVDNLVLNK EDLDVASR FLEMEPVTIPDVHGGSLQNAVRVWSNIPAIRSRHWALVSEEELSLLAQNKQSS KLAAKWP TKLVKNCFLPLREYFKYFSTELTSSL | C-terminal human DNM3L |
| 288 | SSGNSNANSRGPSFSSGLVPLSLRGSH | Linker |
| 289 | MGSRETPSSCSKTLETLDLETSDSSSPDADSPLEEQWLKSSPALKEDSVDVVL EDCKEPL SPSSPPTGREMIRYEVKVNRRSIEDICLCCGTLQVYTRHPLFEGGLCAPCKDKF LESLFL YDDDGHQSYCTICCSGGTLFICESPDCTRCYCFECVDILVGPGTSERINAMAC WVCFLCL PFSRSGLLQRRKRWRHQLKAFHDQEGAGPMEIYKTVSAWKRQPVRVLSLFR NIDKVLKSL GFLESGSGSGGGTLKYVEDVTNVVRRDVEKWGPFDLVYGSTQPLGSSCDRCP GWYMFQFH RILQYALPRQESQRPFFWIFMDNLLLTEDDQETTTRFLQTEAVTLQDVRGRDY QNAMRVW SNIPGLKSKHAPLTPKEEEYLQAVRSRSKLDAPKVDLLVKNCLLPLREYFKY FSQNSLP L | Murine DNMT3L |
| 290 | RTLVTFKDVFVDFTREEWKLLDTAQQILYRNVMLENYKNLVSLGYQL TKPDVILRLEKGEEPWLVEREIHQETHPDSETAFEIKSSV | KRAB |
| 291 | PKKKRKVGIHGVPAA | NLS and linker |

| SEQ ID NO. | Sequence | Annotation |
|---|---|---|
| 292 | DYKDDDDK | Flag tag |
| 293 | EASGSGRASPGIPGSTR | Linker |
| 294 | GIHGVPAA | Linker |
| 295 | MDYKDHDGDYKDHDI DYKDDDDK | 3 x Flag peptide |
| 296 | YPYDVPDYA | HA tag |
| 297 | HHHHHH | poly-histidine tag |
| 298 | KRPAATKKAGQAKKKKASDAKSLTAWS | Linker |
| 299 | SGSETPGTSESATPES | Linke (aa) |
| 300 | CLSYETEILTVEYGLLPIGKIVEKRIECTVYSVDNNGNIYTQPVAQWHDRGEQ EVFEYCLEDGSLIRATKDHKFMTVDGQMLPID | N term Npu Intein (aa) |
| 301 | ATCAAGATTGCTACACGGAAATACCTGGGAAAGCAGAACGTGTACGACAT CGGCGTGGAGCGGGATCACAACTTCGCCCTGAAGAATGGCTTTATCGCCA GCAAT | C term Npu Intein (nt) |
| 302 | IKIATRKYLGKQNVYDIGVERDHNFALKNGFIASN | C term Npu Intein (aa) |
| 303 | ATGAAACGGACAGCCGACGGAAGCGAGTTCGAGTCACCAAAGAAGAAGC GGAAAGTCATCAAGATTGCTACACGGAAATACCTGGGAAAGCAGAACGT GTACGACATCGGCGTGGAGCGGGATCACAACTTCGCCCTGAAGAATGGCT TTATCGCCAGCAATTGTTTCGACTCTGTTGAAATCAGCGGAGTGGAGGATC GCTTCAACGCATCCCTGGGAACGTATCACGATCTCCTGAAATCATTAAA GACAAGGACTTCCTGGACAATGAGGAGAACGAGGACATTCTTGAGGACA TTGTCCTCACCCTTACGTTGTTTGAAGATAGGGAGATGATTGAAGAACGCT TGAAAACTTACGCTCATCTCTTCGACGACAAAGTCATGAAACAGCTCAAG AGGCGCCGATATACAGGATGGGGCGGCTGTCAAGAAAACTGATCAATG GgatcCGAGACAAGCAGAGTGGAAAGACAATCCTGGATTTTCTTAAGTCCG ATGGATTTGCCAACCGGAACTTCATGCAGTTGATCCATGATGACTCTCTCA CCTTTAAGGAGGACATCCAGAAAGCACAAGTTTCTGGCCAGGGGGACAGT CTTCACGAGCACATCGCTAATCTTGCAGGTAGCCCAGCTATCAAAAAGGG AATACTGCAGACCGTTAAGGTCGTGGATGAACTCGTCAAAGTAATGGGAA GGCATAAGCCCGAGAATATCGTTATCGAGATGGCCCGAGAGAACCAAACT ACCCAGAAGGGACAGAAGAACAGTAGGGAAAGGATGAAGAGGATTGAA GAGGGTATAAAAGAACTGGGGTCCCAAATCCTTAAGGAACACCCAGTTGA AAACACCCAGCTTCAGAATGAGAAGCTCTACCTGTACTACCTGCAGAACG GCAGGGACATGTACGTGGATCAGGAACTGGACATCAATCGGCTCTCCGAC TACGACGTGGATGCCATCGTGCCCCAGTCTTTTCTCAAAGATGATTCTATT GATAATAAAGTGTTGACAAGATCCGATAAAAATAGAGGGAAGAGTGATA ACGTCCCCTCAGAAGAAGTTGTCAAGAAAATGAAAAATTATTGGCGGCAG CTGCTGAACGCCAAACTGATCACACAACGGAAGTTCGATAATCTGACTAA GGCTGAACGAGGTGGCCTGTCTGAGTTGGATAAAGCCGGCTTCATCAAAA GGCAGCTTGTTGAGACACGCCAGATCACCAAgcacGTGGCCCAAATTCTCG ATTCACGCATGAACACCAAGTACGATGAAAATGACAAACTGATTCGAGAG GTGAAAGTTATTACTCTGAAGTCTAAGCTGGTCTCAGATTTCAGAAAGGA CTTTCAGTTTTATAAGGTGAGAGAGATCAACAATTACCACCATGCGCATG ATGCCTACCTGAATGCAGTGGTAGGCACTGCACTTATCAAAAAATATCCC AAGCTTGAATCTGAATTTGTTTACGGAGACTATAAAGTGTACGATGTTAG GAAAATGATCGCAAAGTCTGAGCAGGAAATAGGCAAGGCCACCGCTAAG TACTTCTTTTACAGCAATATTATGAATTTTTTCAAGACCGAGATTACACTG GCCAATGGAGAGATTCGGAAGCGACCACTTATCGAAACAAACGGAGAAA CAGGAGAAATCGTGTGGGACAAGGGTAGGGATTTCGCGACAGTCCGGAA GGTCCTGTCCATGCCGCAGGTGAACATCGTTAAAAAGACCGAAGTACAGA CCGGAGGCTTCTCCAAGGAAAGTATCCTCCCGAAAAGGAACAGCGACAA GCTGATCGCACGCAAAAAGATTGGGACCCAAGAAATACGGCGGATTC GATTCTCCTACAGTCGCTTACAGTGTACTGGTTGTGGCCAAAGTGGAGAA AAGGAAGTCTAAAAAACTCAAAAGCGTCAAGGAACTGCTGGGCATCACA ATCATGGAGCGATCAAGCTTCGAAAAAACCCCATCGACTTTCTCGAGGC | dSpCas9-573-C Intein (nt) |

| SEQ ID NO. | Sequence | Annotation |
|---|---|---|
| | GAAAGGATATAAAGAGGTCAAAAAAGACCTCATCATTAAGCTTCCCAAGT<br>ACTCTCTCTTTGAGCTTGAAAACGGCCGGAAACGAATGCTCGCTAGTGCG<br>GGCGAGCTGCAGAAAGGTAACGAGCTGGCACTGCCCTCTAAATACGTTAA<br>TTTCTTGTATCTGGCCAGCCACTATGAAAAGCTCAAAGGGTCTCCCGAAG<br>ATAATGAGCAGAAGCAGCTGTTCGTGGAACAACACAAACACTACCTTGAT<br>GAGATCATCGAGCAAATAAGCGAATTCTCCAAAAGAGTGATCCTCGCCGA<br>CGCTAACCTCGATAAGGTGCTTTCTGCTTACAATAAGCACAGGGATAAGC<br>CCATCAGGGAGCAGGCAGAAAACATTATCCACTTGTTTACTCTGACCAAC<br>TTGGGCGCGCCTGCAGCCTTCAAGTACTTCGACACCACCATAGACAGAAA<br>GCGGTACACCTCTACAAAGGAGGTCCTGGACGCCACACTGATTCATCAGT<br>CAATTACGGGGCTCTATGAAACAAGAATCGACCTCTCTCAGCTCGGTGGA<br>GACAAAAGGCCGGCGGCCACGAAAAAGGCCGGCCAGGCAAAAAGAAA<br>AAGTGA | |
| 304 | MKRTADGSEFESPKKKRKVIKIATRKYLGKQNVYDIGVERDHNFALKNGFIA<br>SNCFDSVEISGVEDRFNASLGTYHDLLKIIKDKDFLDNEENEDILEDIVLTLTLF<br>EDREMIEERLKTYAHLFDDKVMKQLKRRRYTGWGRLSRKLINGIRDKQSGK<br>TILDFLKSDGFANRNFMQLIHDDSLTFKEDIQKAQVSGQGDSLHEHIANLAGS<br>PAIKKGILQTVKVVDELVKVMGRHKPENIVIEMARENQTTQKGQKNSRERM<br>KRIEEGIKELGSQILKEHPVENTQLQNEKLYLYYLQNGRDMYVDQELDINRLS<br>DYDVDAIVPQSFLKDDSIDNKVLTRSDKNRGKSDNVPSEEVVKKMKNYWRQ<br>LLNAKLITQRKFDNLTKAERGGLSELDKAGFIKRQLVETRQITKHVAQILDSR<br>MNTKYDENDKLIREVKVITLKSKLVSDFRKDFQFYKVREINNYHHAHDAYLN<br>AVVGTALIKKYPKLESEFVYGDYKVYDVRKMIAKSEQEIGKATAKYFFYSNI<br>MNFFKTEITLANGEIRKRPLIETNGETGEIVWDKGRDFATVRKVLSMPQVNIV<br>KKTEVQTGGFSKESILPKRNSDKLIARKKDWDPKKYGGFDSPTVAYSVLVVA<br>KVEKGKSKKLKSVKELLGITIMERSSFEKNPIDFLEAKGYKEVKKDLIIKLPKY<br>SLFELENGRKRMLASAGELQKGNELALPSKYVNFLYLASHYEKLKGSPEDNE<br>QKQLFVEQHKHYLDEIIEQISEFSKRVILADANLDKVLSAYNKHRDKPIREQA<br>ENIIHLFTLTNLGAPAAFKYFDTTIDRKRYTSTKEVLDATLIHQSITGLYETRID<br>LSQLGGDKRPAATKKAGQAKKKK | dSpCas9-573-C Intein (aa) |
| 305 | TGCCTGTCCTACGAGACAGAGATCCTGACAGTGGAGTATGGCCTGCTGCC<br>AATCGGCAAGATCGTGGAGAAGAGGATCGAGTGTACCGTGTACTCTGTGG<br>ATAACAATGGCAACATCTATACACAGCCCGTGGCACAGTGGCACGATAGG<br>GGGAGAGCAGGAGGTGTTCGAGTATTGCCTGGAGGACGGCAGCCTGATCA<br>GGGCAACCAAGGACCACAAGTTCATGACAGTGGATGGCCAGATGCTGCCC<br>ATCGAC | N term Npu Intein (nt) |
| 390 | AGGTTTCCGCAGCGGCGTCG | cPCSK9-C gRNA target site |
| 391 | AGGUUUCCGCAGCGGCGUCG | cPCSK9-C gRNA spacer |
| 392 | AGGUUUCCGCAGCGGCGUCGGUUUUAGAGCUAGAAAUAGCAAGU<br>UAAAAUAAGGCUAGUCCGUUAUCAACUUGAAAAAGUGGCACCGA<br>GUCGGUGCUUUU | cPCSK9-C full length gRNA |
| 393 | ggagcaauugaccgggaagcucagaauaaacgcucaacuuuggccggaucuucuagagccacc | 5' UTR (5U4) |
| 394 | uaguaagaauucaaagaaaguuucuucacauucucucgagcguacg | 3' UTR (3U2) |
| 395 | ggagcaauugaccgggaagcucagaauaaacgcucaacuuuggccggaucuucuagagccaccauga<br>accacgaucaggaguuugaccccccuaaggguguacccaccgugccagccgagaagaggaagcccauc<br>cgcgugcugucccuguucgacggcaucgccacaggccugcugguucugaaggaucugggcauccag<br>guggacagauauaucgccucgagguguggcgaggacugucuacaccgugggcauggugaggcaccag<br>ggcaagaucuacguggugcgcgcagcguggacacaaggagugggggaacccu<br>ucgaccuggucaucggaggcagccccguaaugaccugccaucgugaacccugcaaggaagggccu<br>guaugaggaaccggcagacuguucuuugaguucuacaggcugcugcacgacgcccgcccuaaggag<br>ggcgaugacaggccauucuuuuggcuguuugagaacguggucgccaugggcgugagcgacaagcgg<br>gauaucuccagauccuggagucuaaucccgugaugaucgaucaaaggagggugcucgccacaca<br>gggcaaguacuuuugggaaauugccuggcaugaaccgccgcaccggagaacgacaa<br>gcuggagcugcaggagugccuggagcacgaaggaucgccaaguucuccaaggugcggacaaucacc<br>acaagaucuaacagcaucaagcagggcaaggaucagcacuucccguguucaugaaugagaaggagg<br>acauccuguggguguaccgagauggagcgcguguucggcuuccagugcacuauacagacgugagca<br>auaugagccggcuggcaaggcagagacugcugggccgguccuggucuguguccagugaucagacacc<br>guuccgccccccugaaggaguacuuugccugcgugucuagcggcaacucuaaugccaacagcagagg | dCas9-KRAB-DNMT3A/L mRNA |

Sequences

| SEQ ID NO. | Sequence | Annotation |
|---|---|---|
| | cccuuccuuuuccucuggccuggugccacugucucugaggggcagccacaugggccccauggagauc<br>uacaagaccguguccgccuggaagaggcagccguggcgugcugucucuguuccgcaacaucgaca<br>aggugcucaagagccugggcuuucuggagagcggauccggaucuggaggaggcacccugaaguaug<br>uggaggaugugacaaaugggugcggagagauguggagaaguggggccccuucgaucggugguacg<br>gauccacccagccacugggaagcuccugcgauaggugaccaggauggauaugucacaguucacag<br>aauccugcaguacgcacugccaaggcaggagagccagcgcccuuucuuuuggaucuuuauggacaac<br>cugcugcugacagaggaugaccaggagacaacaacccgcuuccugcagacagaggcagugacccugc<br>aggaugugagggacgcgacuaucagaaugccaugcggguguggucuaacaucccuggccugaaaa<br>gcaagcacgccccccugaccccuaaggaggaggaguaccugcaggcccaggugcggagcagauccaa<br>gcuggaugcccuaagguggaccugcuggugaagaauugucugcugccacugcgggaguacuucaa<br>guacuuuagucagaauagccugccacuggaggcaagcggauccggaagggcauccccuggaauccca<br>ggaagcacccgcaaccccaagaagaagcggaaggugggcauccacggcgugcccgccgccgacaagaa<br>guacagcaucggccuggccaucggcaccaacagcguggucugggccgugaucaccgacgaguacaag<br>gugcccagcaagaaguucaaggugcugggcaacaccgaccggcacagcaucaagaagaaccugaucg<br>gcgcccugcucuuucgacagcggcgagaccgccgaggccaccggcugaagcggaccgcccggcggcg<br>guacacccggcggaagaaccgaucugcuaccggcaggagaacuucagcaacgagauggccaaggug<br>gacgacagcuucuuccaccggcuggaggagagcuuccuggggaggaggacaagaagcacgagcggc<br>accccaucuucggcaacaucguggacgagguggccuaccacgagaaguacccaccaucuaccaccug<br>cggaagaagcugguggacagccccgacaaggccgaccugcggcugaucuaccugccccuggccacaa<br>ugaucaaguucggggccacuuccugaucgagggcgaccguggacaacagcgacguggacaa<br>gcuguucauccagcuggugcagaccuacaaccagcuguucgaggagaaccccaucaacgccagcggc<br>guggacgccaaggccauccugaucgccccggcugagcaagagccggcggcuggagaaccugaucgccc<br>agcugcccggcgagaagaagaacggccuguucggcaaccugaucgcccugagccugggccugaccccc<br>caacuucaagagcaacuucgaccuggccgaggacgccaagcugcagcuaaguaccaccuacgacg<br>acgaccuggacaaccugcugccccagaucggcgaccaguacgccgaccuguuccuggccgccaagaac<br>cugagcgacgccauccugcugagcgacauccugcgggugaacaccgagaucaccaaggccccccuga<br>gcgccagcaugaucaagcggacgacgagcaccaccaggaccugacccugcugaaggcccuggugcg<br>gcagcagcugcccgagaaguacaaggagaucuucuucgaccagagcaagaacggcuacgccggcuac<br>aucgacggcggcgccagccaggaggaguucuacaaguucaucaagcccauccuggagaagauggacg<br>gcaccgaggagcugcuggugaagcugaaccggaggaccugcugcggaagcagcggaccuucgacaa<br>cggcagcauccccaccagauccaccugggcgagcugcacgccauccugcggggcaggaggacuuc<br>uacccccuuccugaaggacaaccgggagaagaucgagaagauccugaccuuccggaucccuacuacg<br>ugggccccuggcccggggcaacagccgguucgccuggaugacccggaaaagcgaggagaccaucac<br>ccccuggaacuucgaggagguguggacaagggcgccagcgcccagagcuucaucgagcggaugacc<br>aacuucgacaagaaccugccaacgagaaggugcugcccaagcacagccugcuguacgaguacuucac<br>cguguacaacgagcugaccaaggugaaguacgugaccgagggcaugcggaagcccgccuuccugagc<br>ggcgagcagaagaaggccaucguggaccugcguucaagaccagccggaaguugcccggaccggugaagcgc<br>ugaaggaggacuacuucaagaagaucgagugcuucgacagcguggagaucagcggcguggaggacc<br>gguucaacgccagccugggcaccuaccacgaccugcugaagaucaucaaggacaaggacuuccugga<br>caacgaggagaacgaggacauccuggaggacaucgugcugacccugacccuguucgaggacgggag<br>augaucgaggagcggcugaagaccuacgcccaccuguucgacaaggugaugaagcagcugaagc<br>ggcggcguacaccggcuggggccggcugagccggaagcugaucaacggcauccgggacaagcagag<br>cggcaagaccauccuggacuuccugaaaagcgacggcuucgccaaccggaacuucaugcagcugauc<br>cacgacgacagccugaccuucaaggaggacauccagaaggcccaggugagcggccagggcgacagcc<br>ugcacgagcacaucgccaaccugcggcggcagcccccgccaucaagaagggcauccugcagacccgugaag<br>guggaggacgagcugguaagguggaugggccggcacaagcccgagaacaucgugaucgauggcc<br>cgggagaaccagaccaccagaagggccagaagaacagccgggagcggaugaagcggaucgaggagg<br>gcaucaaggagcugggcagccagauccugaaggagcacccgguggagaacacccagcugcagaacga<br>gaagcuguaccuguacuaccugcagaacgggccgggacauguacgggaccaggucgacaucaac<br>cggcugagcgacuacgacguggacgccauccugccccagagcuuccugaaggacgacagcaucgaca<br>acaaggugcugaccggagcgacaagaaccggggcaagagcgacaacgugcccagcgaggagguggu<br>gaagaagaugaagaacuacuggcggcagcugcuaacgccaagcugaucacccagcggaaguucgac<br>aaccugaccaaggccgagggggcggccugagcgagcuggacaaggccggccuugcagcaucaagcggcagc<br>ugguggaccccggcagaucaccaagcacguggcccagauccuggacagccggaugaacaccaagua<br>cgacgagaacgacaagcugauccgggaggugaaggugaucacccugaaaagcaagcuggugagcgac<br>uuccggaaggacuucuacaguucuacaaggugcgggagaucaacaacuaccaccacgcccacgacgccua<br>ccugaacgccguggugggcaccgcccugaucaagaaguacccaagcuggagagcgaguucguguac<br>ggcgacuacaaggugaucggcgaaugaucgccaagagcgagaugaucgcaaggcca<br>ccgccaaguacuucuucuacagcaacaucaugaacuucuucaagaccgagaucacccuggccaacggc<br>gagauccggaagcggccccugaucgagaccaacggcgagaccggcgagaucguguggacaagggcc<br>gggacuucgccaccgugcggaaggugcugagcaugcccaggugaacaucgugaagaagaccgaggu<br>gcagacggccggcuucagcaaggagagcaucccccaagcggaacagcgacaagcugaucgcccgg<br>aagaaggacuggaccccaagaguacggcggcuucgauagccccaccgugcuacagcgugcugg<br>ugguggcaagguggagaagggcaagagcaagaagcugaaaagcgugaaggagcugcugcaucac<br>caucauggagcggagcagcuucgagaagaaccccaucgacuuccuggaggcaaagggcuacaaggag<br>gugaagaaggaccugaucaagcugcccaaguacagccuguucgagcuggagaacggccggaagc<br>ggaugcuggccagcgccggcgagcugcagaagggcaacgagcugccccugcccagcaaguacgugaa<br>cuuccuguaccuggccagccacuacgagaaguugaagggcagcccgaggacaacgagcagaagcagc<br>uguucguggagcagcacaagcacuaccuggacgagaucaucgagcagaucagcgaguucagcaagcg<br>ggugauccuggccgacgccaaccuggacaaggugcugagcgccuacaacaagcaccggacaagccca<br>uccgggagcaggccgagaacaucauccaccuguucacccugaccaaccuggggccccgccgccuuc<br>aaguacuucgacaccaccaucgaccggaagcgguacaccagcaccaaggaggugcuggacgccacccu<br>gauccaccagagcaucaccggccuguacgagacccggaucgaccugagccagcuggggcgacagc | |

| | Sequences | |
|---|---|---|
| SEQ ID NO. | Sequence | Annotation |
| | ggcggcaagcggcccgccgccaccaagaaggccggccaggccaagaagaagaaggcuagcgaugcuaa gucacugacugccugguccccggacacuggugaccuucaaggaugucuuugugacuucaccaggga ggaguggaagcugcuggacacugcucagcagauccuguacagaaaugugaugcuggagaacuauaag aaccugguuuccuuggguuaucagcuuacuaagccagaugugauccuccgguuggagaagggagag gaacccuggcugguggagagagaaauuucaccaagagacccauccugauucagagacugcauuugaaa ucaaaucaucaguuccgaaaaagaaacgcaaaguuuaguaagaauucaaagaaaguuucuucacauuc ucucgagcguacgaaaaaaaaaaaaaaaaaaaaaaaaaaaaaaaaaaaaaaaaaaaaaaaaaaaaa aaaaaaaaaaaaaaaaaaaaaaaaaaaaaaaaaaaaaaaaaaaaaaaaaa | |

The invention claimed is:

1. An epigenetic-modifying DNA-targeting system comprising
   (a) a fusion protein comprising, in the following order from the N-to C-terminus:
      (i) a DNA-methyltransferase (DNMT) 3A/L domain comprising the amino acid sequence set forth in SEQ ID NO: 199;
      (ii) a dead *Streptococcus pyogenes* Clustered Regularly Interspaced Short Palindromic Repeats associated protein 9 (dSpCas9) comprising the amino acid sequence set forth in SEQ ID NO: 207, and
      (iii) a Krüppel associated box (KRAB) domain comprising the amino acid sequence set forth in SEQ ID NO:290,
   wherein the fusion protein comprises one or more nuclear localization signals (NLS), wherein an NLS is between the DNMT3A/L domain and the dSpCas9 protein, and an NLS is between the SpCas9 protein and the KRAB domain; and
   (b) a gRNA comprising the sequence set forth in SEQ ID NO: 66.

2. The epigenetic-modifying DNA-targeting system of claim 1, wherein the NLS between the DNMT3A/L domain and the dSpCas9 protein has the amino acid sequence PKKKRKV (SEQ ID NO: 234).

3. The epigenetic-modifying DNA-targeting system of claim 1, wherein the NLS between the dSpCas9 protein and the KRAB domain has the amino acid sequence KRPAATKKAGQAKKKK (SEQ ID NO: 249).

4. The epigenetic-modifying DNA-targeting system of claim 1, further comprising an NLS at the C-terminus of the fusion protein.

5. The epigenetic-modifying DNA-targeting system of claim 4, wherein the NLS at the C-terminus of the fusion protein has the amino acid sequence PKKKRKV (SEQ ID NO: 234).

6. An epigenetic-modifying DNA-targeting system comprising
   (a) a fusion protein comprising the amino acid sequence set forth in SEQ ID NO: 278; and
   (b) a gRNA comprising the sequence set forth in SEQ ID NO:66.

7. The epigenetic-modifying DNA-targeting system of claim 6, wherein the gRNA comprises the sequence set forth in SEQ ID NO:129.

8. The epigenetic-modifying DNA-targeting system of claim 1, wherein the gRNA comprises the sequence set forth in SEQ ID NO:129.

* * * * *